United States Patent
Ribeiro Lemos Pereira et al.

(10) Patent No.: US 11,345,891 B2
(45) Date of Patent: May 31, 2022

(54) COMPOSITIONS FOR REPROGRAMMING CELLS INTO DENDRITIC CELLS OR ANTIGEN PRESENTING CELLS, METHODS AND USES THEREOF

(71) Applicant: Asgard Therapeutics AB, Lund (SE)

(72) Inventors: Carlos Filipe Ribeiro Lemos Pereira, Moledo (PT); Cristiana Ferreira Pires, Palhaca (PT); Fabio Alexandre Fiuza Rosa, Leiria (PT)

(73) Assignee: Asgard Therapeutics AB, Lund (SE)

( * ) Notice: Subject to any disclaimer, the term of this patent is extended or adjusted under 35 U.S.C. 154(b) by 231 days.

(21) Appl. No.: 16/342,803

(22) PCT Filed: Apr. 5, 2018

(86) PCT No.: PCT/IB2018/052378
§ 371 (c)(1),
(2) Date: Apr. 17, 2019

(87) PCT Pub. No.: WO2018/185709
PCT Pub. Date: Oct. 11, 2018

(65) Prior Publication Data
US 2020/0017832 A1    Jan. 16, 2020

(30) Foreign Application Priority Data

Apr. 5, 2017 (PT) ........................ 110012
May 15, 2017 (EP) ..................... 17171166
Aug. 24, 2017 (PT) ........................ 110263
Aug. 25, 2017 (PT) ........................ 110267

(51) Int. Cl.
*C12N 5/0784* (2010.01)
*A61K 35/15* (2015.01)
*A61K 45/06* (2006.01)
*C12N 15/86* (2006.01)

(52) U.S. Cl.
CPC .......... *C12N 5/0639* (2013.01); *A61K 35/15* (2013.01); *A61K 45/06* (2013.01); *C12N 15/86* (2013.01); *C12N 2501/22* (2013.01); *C12N 2501/23* (2013.01); *C12N 2501/26* (2013.01); *C12N 2501/60* (2013.01); *C12N 2506/1307* (2013.01)

(58) Field of Classification Search
CPC .................................................. C12N 5/0639
See application file for complete search history.

(56) References Cited

U.S. PATENT DOCUMENTS

| 2012/0142094 A1* | 6/2012 | Duan | C12N 5/0696 |
| | | | 435/366 |
| 2014/0170752 A1* | 6/2014 | Pulst | C12N 5/0696 |
| | | | 435/456 |
| 2014/0309177 A1 | 10/2014 | Perez-Pinera et al. | |

FOREIGN PATENT DOCUMENTS

| WO | 2013036829 A1 | 3/2013 |
| WO | 2014197748 A2 | 12/2014 |
| WO | 2021/087234 A1 | 5/2021 |

OTHER PUBLICATIONS

Rosa et al., Sci. Immunol. 3, eaau4292 (2018) Dec. 7, 2018) (Year: 2018).*
Tamura et al. (J Immunol 2005; 174:2573-2581) (Year: 2005).*
Belz et al. (Nature Reviews. Immunology. Feb. 2012. 12:101-113) (Year: 2012).*
Carotta, et al., The Transcription Factor PU.1 Controls Dendritic Cell Development and Flt3 Cytokine Receptor Expression in a Dose-Dependent Manner, Immunity, 32: 628-641, 2010.
Jaiswal, et al., Batf3 and Id2 Have a Synergistic Effect on Irf8-Directed Classical CD8a+ Dendritic Cell Development, The Journal of Immunology, 191:5993-6001, 2013.
Bretou, M. et al., "Lysosome signaling controls the migration of dendritic cells", Science Immunology, vol. 2, No. 16, pp. 1-11, 2017.
Datta, J. et al., "Optimizing dendritic cell-based approaches for cancer immunotherapy", Yale Journal of Biology and Medicine, vol. 87, No. 4, pp. 491-518, 2014.
Delamarre, L. et al., "Presentation of Exogenous Antigens on Major Histocompatibility Complex (MHC) Class I and MHC Class II Molecules Is Differentially Regulated during Dendritic Cell Maturation", The Journal of Experimental Medicine, vol. 198, No. 1, 111-122, 2003.
Dunand-Sauthier, I. et al., "Silencing of c-Fos expression by microRNA-155 is critical for dendritic cell maturation and function", Blood, vol. 117, No. 17, pp. 4490-4500, 2011.
Edelson, B. T. et al., "Peripheral CD103+ dendritic cells form a unified subset developmentally related to CD8a+ conventional dendritic cells", The Journal of Experimental Medicine, 207, No. 4, p. 823, 2010.

(Continued)

*Primary Examiner* — Scott Long
(74) *Attorney, Agent, or Firm* — Dinsmore & Shohl LLP; Weston R. Gould

(57) ABSTRACT

The present disclosure relates to compositions, nucleic acid constructs, methods and kits thereof for cell induction or reprogramming cells to the dendritic cell state or antigen presenting cell state, based, in part, on the surprisingly effect described herein of novel use and combinations of transcription factors that permit induction or reprogramming of differentiated or undifferentiated cells into dendritic cells or antigen presenting cells. Such compositions, nucleic acid constructs, methods and kits can be used for inducing dendritic cells in vitro, ex vivo, or in vivo, and these induced dendritic cells or antigen presenting cells can be used for immunotherapy applications.

6 Claims, 26 Drawing Sheets
Specification includes a Sequence Listing.

(56) References Cited

OTHER PUBLICATIONS

Grajales-Reyes, G. E. et al., "Batf3 maintains autoactivation of Irf8 for commitment of a CD8alpha+ conventional DC clonogenic progenitor", Nature Immunology, vol. 16, No. 7, 708-717, 2015.

Han, S. M. et al., "TCF4-Targeting miR-124 is Differentially Expressed amongst Dendritic Cell Subsets", Immune Network, vol. 16, No. 1, pp. 61-74, 2016.

Helft, J. et al., "GM-CSF Mouse Bone Marrow Cultures Comprise a Heterogeneous Population of CD11c+MHCII+ Macrophages and Dendritic Cells", Immunity, vol. 42, 1197-1211, 2015.

Hogquist, K.A. et al., "T cell receptor antagonist peptides induce positive selection", Cell, vol. 76, No. 1, pp. 17-27, 1994.

Kitamura, N. et al., "Role of PU.1 in MHC class II expression through transcriptional regulation of class II transactivator ol in dendritic cells", Journal of Allergy and Clinical Immunology, vol. 129, No. 3, pp. 814-824, 2012.

Kobayashi, K. S. et al., "NLRC5: a key regulator of MHC class I-dependent immune responses", Nature Reviews Immunology, vol. 12, p. 813-820, 2012.

Laiosa, C.V. et al., "Reprogramming of Comitted T Cell Progenitors to Macrophages and Dendritic Cells by C/EBP [alpha] and PU.1 Transcription Factors", Immunity, vol. 25, No. 5, pp. 731-744, 2006.

Merad, M. et al., "The dendritic cell lineage: ontogeny and function of dendritic cells and their subsets in the steady state and the inflamed setting", Annual Review of Immunology, vol. 31, pp. 563-604, 2013.

Onai, N. et al., "A Clonogenic Progenitor with Prominent Plasmacytoid Dendritic Cell Developmental Potential", Immunity, vol. 38, No. 5, pp. 943-957, 2013.

Pereira, C.-F. et al., "Reprogramming cell fates: insights from combinatorial approaches", Annals of the New York Academy of Sciences, vol. 1266, No. 1, pp. 7-17, 2012.

Pereira, C.-F. et al., "Hematopoietic Reprogramming In Vitro Informs In Vivo Identification of Hemogenic Precursors to Definitive Hematopoietic Stem Cells", Developmental Cell, vol. 36, No. 5, pp. 525-539, 2016.

Pereira, C.-F. et al., "Induction of a hemogenic program in mouse fibroblasts", Cell Stem Cell, vol. 13, No. 2, pp. 205-218, 2013.

Reith, W. et al., "Regulation of MHC class II gene expression by the class II transactivator", Nature Reviews Immunology, vol. 5, No. 10, pp. 793-806, 2005.

Schlitzer, A. et al., "Identification of CCR9—murine plasmacytoid DC precursors with plasticity to differentiate into conventional DCs", Blood, vol. 117, No. 24, pp. 6562-6570, 2011.

Schlitzer, A. et al., "Identification of cDC1- and cDC2-committed DC progenitors reveals early lineage priming at the common DC progenitor stage in the bone marrow", Nature Immunology, vol. 16, No. 7, pp. 718-728, 2015.

Schraml, B.U. et al., "Genetic tracing via DNGR-1 expression history defines dendritic cells as a hematopoietic lineage", Cell, vol. 154, No. 4, pp. 843-858, 2013.

Schulz, O. et al., "Cross-presentation of cell-associated antigens by CD8a+ dendritic cells is attributable to their ability to internalize dead cells", Immunology, vol. 107, pp. 183-189, 2002.

Senju, S. et al., "Generation and genetic modification of dendritic cells derived from mouse embryonic stem cells", Blood, vol. 101, No. 9, pp. 3501-3508, 2003.

Shinkai, Y. et al., "RAG-2—deficient mice lack mature lymphocytes owing to inability to initiate V(D)J rearrangement", Cell, vol. 68, No. 5, pp. 855-867, 1992.

Smith, M.A. et al., "Positive regulatory domain I (PRDM1) and IRF8/PU.1 counter-regulate MHC class II transactivator (CIITA) expression during dendritic cell maturation", Journal of Biological Chemistry, vol. 286, No. 10, pp. 7893-7904, 2011.

Subklewe, M. et al., "New generation dendritic cell vaccine for immunotherapy of acute myeloid leukemia", Cancer Immunol Immunother, vol. 63, No. 10, pp. 1093-1103, 2014.

Takahashi, K. et al., "Induction of pluripotent stem cells from mouse embryonic and adult fibroblast cultures by defined factors", Cell., vol. 126, No. 4, pp. 663-676, 2006.

Takahashi, K. et al., "Induction of pluripotent stem cells from adult human fibroblasts by defined factors", Cell., vol. 131, No. 5, pp. 861-872, 2007.

Van der Stoep, N. et al., "E47, IRF-4, and PU.1 synergize to induce B-cell-specific activation of the class II transactivator promoter III (CIITA-PIII)", Blood, vol. 104, No. 9, pp. 2849-2857, 2004.

Xie, H. et al., "Stepwise reprogramming of B cells into macrophages", Cell, vol. 117, No. 5, pp. 663-676, 2004.

Xu, J. et al., "Direct lineage reprogramming: strategies, mechanisms, and applications", Cell Stem Cell, vol. 16, No. 2, pp. 119-134, 2015.

Yáñez, A. et al., "Interferon regulatory factor 8 and the regulation of neutrophil, monocyte, and dendritic cell production", Current Opinion in Hematology, vol. 23, No. 1, pp. 11-17, 2016.

\* cited by examiner

A

B

C

A

B

C

SEQUENCE LISTING

<160> NUMBER OF SEQ ID NOS: 74

<210> SEQ ID NO 1
<211> LENGTH: 992
<212> TYPE: DNA
<213> ORGANISM: Homo sapiens
<220> FEATURE:
<223> OTHER INFORMATION: Human BATF3 (NM_018664.2)

<400> SEQUENCE: 1

```
ggggcagacg tgggacggga aggacggctg ccgggactgg cgcgcgggga cactgggccg      60
acgcgtggag tagcggggag agcgggaagc ctgaggggc ggggccggcg cgaggccgtg      120
ggtgcggcac gaggatgccg gcggcgggac agcgcccgta ggcagcccca cgggcagggc      180
gcgcgggcgg ggcggggcgg gccgggccag aggagcgccc ggcatgtcgc aagggctccc      240
ggccgccggc agcgtcctgc agaggagcgt cgcgcgcccc gggaaccagc cgcagccgca      300
gccgcagcag cagagccctg aggatgatga caggaaggtc cgaaggagag aaaaaaaccg      360
agttgctgct cagagaagtc ggaagaagca gacccagaag gctgacaagc tccatgagga      420
atatgagagc ctggagcaag aaaacaccat gctgcggaga gagatcggga agctgacaga      480
ggagctgaag cacctgacag aggcactgaa ggagcacgag aagatgtgcc cgctgctgct      540
ctgccctatg aactttgtgc cagtgcctcc ccggccggac cctgtggccg gctgcttgcc      600
ccgatgaagc cggggacact cctctgccca gcaaggagcc ttggtcattt tcatacctgg      660
gaggaaggct tttccttcac aattgtatac aggggcacc tgtggccagg cctcctcctg      720
ggagctccag gaccagccag ctgtgttccc tgcagactgg gctcagcccg acatccaaca      780
ggcgccaaac tcacagagcc cttgtgcaga tccagcatgg aggccaccct caggagtgac      840
ttctcatcca ccctggcagc tagtaggttc tgctgttatg cagagccatt tcctctagaa      900
```

| | |
|---|---|
| tttggataat aaagatgctt attgtctctc ccttctccag ttctgggaat ttacaggcac | 960 |
| aatacacttc cttttcctgg aaaaaaaaaa aa | 992 |

<210> SEQ ID NO 2
<211> LENGTH: 712
<212> TYPE: DNA
<213> ORGANISM: Mus <mouse, genus>
<220> FEATURE:
<223> OTHER INFORMATION: Mouse Batf3 (NM_030060.2)

<400> SEQUENCE: 2

| | |
|---|---|
| agcagagccc cacgttcagg gcgccccgtg tggcgagcgc gcggcatgtc gcaagggccc | 60 |
| cccgcggtca gcgtgctgca gagaagcgtg gatgcgcccg gaaccagcc gcagagcccc | 120 |
| aaggacgatg acaggaaagt tcgaaggaga gagaaaaacc gggttgcagc tcagaggagc | 180 |
| cggaagaagc agacccagaa ggctgacaag ctccacgagg agcacgagag cctggagcag | 240 |
| gagaactctg tgctgcgcag ggagatttcg aagctgaagg aggagctgcg tcacctgagc | 300 |
| gaggtgctga aggagcacga aagatgtgc ccgctgctgc tgtgtcctat gaactttgtg | 360 |
| cagcttcggt cagaccccgt ggccagctgt ctaccacgat gacaccccag ctcactcctc | 420 |
| cttttgtccgg ctcggaacct tggtttgcac actcaggagt ttccctacac acctgtgtcc | 480 |
| aggggtacat gtggctgtgc ccttccaggg agctctgggg ccagcctggg ctcagcatcg | 540 |
| tgctctgggg catctgactt ccggcccctg ccttccggcc ccaggacaga ggatccagag | 600 |
| gccccagcaa gaaggccctt tgagtcgttc ctctctcact ttggcagcta gccggtgctg | 660 |
| tcctttggca ggatcttttc gtctagaact tggaaaataa agatagttac ct | 712 |

<210> SEQ ID NO 3
<211> LENGTH: 3537
<212> TYPE: DNA
<213> ORGANISM: Homo sapiens
<220> FEATURE:
<223> OTHER INFORMATION: Human SPIB (NM_003121.4)

<400> SEQUENCE: 3

| | |
|---|---|
| ggcaaacagc ccgcccggca ccaccatgct cgccctggag gctgcacagc tcgacgggcc | 60 |
| acacttcagc tgtctgtacc cagatggcgt cttctatgac ctggacagct gcaagcattc | 120 |
| cagctaccct gattcagagg gggctcctga ctccctgtgg gactggactg tggccccacc | 180 |
| tgtcccagcc accccctatg aagccttcga cccggcagca gccgctttta gccaccccca | 240 |
| ggctgcccag ctctgctacg aaccccccac ctacagccct gcagggaacc tcgaactggc | 300 |
| ccccagcctg gaggccccgg ggcctggcct cccgcatac cccacggaga acttcgctag | 360 |
| ccagaccctg gttccccgg catatgcccc gtaccccagc cctgtgctat cagaggagga | 420 |
| agacttaccg ttggacagcc ctgccctgga ggtctcggac agcgagtcgg atgaggccct | 480 |
| cgtggctggc cccgaggga agggatccga ggcaggggact cgcaagaagc tgcgcctgta | 540 |
| ccagttcctg ctggggctac tgacgcgcgg ggacatgcgt gagtgcgtgt ggtgggtgga | 600 |
| gccaggcgcc ggcgtcttcc agttctcctc caagcacaag gaactcctgg cgcgccgctg | 660 |
| gggccagcag aaggggaacc gcaagcgcat gacctaccag aagctggcgc gcgccctccg | 720 |
| aaactacgcc aagacggcg agatccgcaa ggtcaagcgc aagctcacct accagttcga | 780 |
| cagcgcgctg ctgcctgcag tccgccgggc ctgagcacac ccgaggctcc cacctgcgga | 840 |
| gccgctgggg gacctcacgt cccagccagg atcccctgg aagaaaaagg gcgtccccac | 900 |

```
actctaggtg ataggactta cgcatcccca ccttttgggg taaggggagt gctgccctgc      960
cataatcccc aagcccagcc cgggcctgtc tgggattccc cacttgtgcc tggggtccct     1020
ctgggatttc tttgtcatgt acagactccc tgggatcctc atgttttggg tgacaggacc     1080
tatgaccac tatactcggg gaggcagggt agcagttctt ccagaatccc aagagcttct      1140
ctgggatttt cttgtgatat ctgattcccc agtgaggcct gggacgtttt taagatcgct     1200
gtgtgtctgt aaaccctgaa tctcatctgg gtgggggcc ctgctggcaa ccctgagccc      1260
tgtccaaggt tccctcttgt cagatctgag atttcctagt tatgtctggg gccctctggg     1320
agctgttatc atctcagatc tcttcgccca tctatggctg tgttgtcaca tctgtcccct     1380
cattttgag atcccccaat tctctggaac tattctgctg cccctttta tgtgtctgga      1440
gttccccaat cacatctagg gctcctccaa gatccttttg tcatgtctga aatcactctt     1500
gagaggtctg gggtggagga tggggagtca gtgaaatgtg tcatgtctgg gccctgtcag     1560
ggacacccctt gttatatctg ggatcctcca atcacatctg agacctccta ggctctccat    1620
ctgatatgcc ctttcaggga ccccacaaag actgagttct catggggatc ctacccttcc     1680
tagtgccact ccctatggcc atgctgaaga ccactctggc cacgcgactg attttgggtg     1740
atcatggcag ctccccaccc atgtcatttc taaccagaag tctcaaggtc gtcaccccc      1800
tgccccccaa ccgaggcccc ggtcgctggt ggtggtctct ttagtgcact gtagcacttg     1860
gtggtggagg tgtgagggat ccacattaac agcaggccat cagctgggca atggctcaca    1920
cctgtaatcc cagcactttg ggaggcgagg caggggaat ggcttgaacc caggcattca      1980
agaccagcct gggcaacata tgagacctc gtctctacaa aacataacaa aaacaattag      2040
ccgagcgtgg gggtgaacac ctgtggtccc agctgctcag gaggctgagg tgggaggatc     2100
tcttgagccc aggaagtagg aggctgtagt gagctgtaat cgtgccactg cactccagcc     2160
tgggcgacag agtgagacac cgtcttaaaa acaaaaacaa ggccgggcac ggtggctcat     2220
gcctgttgtc ccagcacttt gggaggccga ggcaggcgga tcacgaggtc gagagatcga    2280
gaccatcctg gccaacatgg tgaaaccctg tctctactaa aaatacagaa attagctggg     2340
cgtggtggca cgtgcctgta gtcccagcta ctcgggaggc tgaggcaaga gaatcgcttg    2400
aacgtgggag gcagaggttg cagtgagcct agattgtgcc actgcactcc agcctggggg    2460
acagagcgag actccgtctg aaaataaaaa caacaaaaac agcagaccat tcaaaatagg    2520
gagactttgc ataatccaga tttctgcctt cacttaaaac tttggacggt ctggagagag    2580
tcggccagtt ttcggtgggg ggtggggagc tggaacagga cagtagcctt tcctaatgag    2640
gcatttgttc tccaatctgc cccagtcgct gccatcctg gctatctcac cctagcagct     2700
tctcaagcct gttggcttta gaccactgta taaacccagc tggaactgaa gcctgggtgg    2760
actatggagc cctggttggg acccccaggg agtcaaaggc tgcgggccaa gaggccagag    2820
gtccttgagc ctgggtgggc aggtggatct agggtgcatg acttgctgct tcccaacctt    2880
agtttgtccc ttctgtgaaa aagggagaga aggaggagga agatctcaaa aagactttcc    2940
agcccagtgc ggtggctcac gcctgtaatc ccagcacttt gggaggccga tgcaggtgga    3000
tcacctgagg taggagttca agaccagcct gaccaacata tgaagcccc ttctctacta     3060
aaaatacaaa attagctggg cgtggtggca tgtgcctgta ctcccagcta cttgggaggc    3120
tgaggcagga gaatcgcttg aacctggag gcggaggttg tagtgagctg agatcacacc     3180
actgcacacc agcctgggcg acaagagcga aactccgtct caaaaaaaaa aaactgttgc    3240
agccccgttg agcctttgac accgcctgaa atccacccca ctcccaggag gaggaggagg    3300
```

```
aaggaatgcc aatgacctag agacacgaga agtccatgtg gaggcacaca gcagctgatg    3360
gcagagccca ggctgggacc tgcccttaag agaatgagtg ggaagggggga gggaggaagg    3420 gcaggtaaaa cgtcctcccc agggccccct gcaacgggga aggtactttt tacaaaagct    3480
atcattgtca ccctaaatgt ggaataaaat aagatgcatc gacgtagaca aaaaaaa        3537
```

<210> SEQ ID NO 4
<211> LENGTH: 2786
<212> TYPE: DNA
<213> ORGANISM: Mus <mouse, genus>
<220> FEATURE:
<223> OTHER INFORMATION: Mouse SpiB (NM_019866.1)

<400> SEQUENCE: 4

```
agcctgctct gaaccaccat gcttgctctg gaggctgcac agctggatgg cccacactta      60
agctgtttgt acccagaagg agtcttctac gacctggaca gctgcaagcc cttcagttac     120
ccagattcag atgggggcct tgactctaca tggggctgga cagaggcccc gcctgctcct     180
gccatcgctc cctatgaagc cttcgatcct gctactgctg cctttagcca ctcccaaact     240
gttcagctct gttatagcca tggtcctaac ccctccacct atagccccat ggggacccct    300
gacccagccc ccagcttgga ggccccaggg cctggcctcc aggtgtaccc cccagaggac     360
ttcaccagcc agaccctggg ctccttggct tatgctccgt accccagccc tgtgctatca     420
gaggaagaag acattatgct ggacagcccc gccctggagg tctcggacag tgagtcagac     480
gaggccctct tggctggctc cgaggggagg ggatctgagg caggtgcacg caagaagctg     540
cgcctgtacc agttcttgct ggggttgctc ctacgcgggg acatgcgcga gtgcgtgtgg     600
tgggtggagc caggtgccgg cgtcttccag ttctcctcca agcacaagga gttgttggct     660
cgccgctggg gccagcagaa gggcaaccgc aagcgcatga cgtatcagaa gctggcccga     720
gcgctgcgca actatgccaa gacaggcgaa atccgcaagg tcaaacgcaa actcacctac     780
cagtttgaca gcgcgctgct gccagcctcc cggcatgtct gagcactccg ctaaggaccc     840
ctttctggcc cctaagtccc atggagcccc atatgagggc agtcagggtt ctcagctctc     900
cctagagcct cccccagagtt tcctgtgccg tgtataggat tccaatctag gatggtcgtg    960
tttgagggag cactggccat tctacacggt tcagaatgg caggtttctc ggggggggg   1020 gggatggggg agccctgatg tcgtctacgg ttccagaaac cgcagttctt gcgagtcctg     1080
tgagctcaca tgacatctca ccagcaggtg gcgctgtcta cagcccccccc caaacccttg     1140 ttttgttggc cagataggtc ggtccctctg tactccccct gaagcccttg ttagatctga     1200
ggtctagtta tgtttggagc tctctgagaa ccctgtgcca cctgtgtgtg acttttctct     1260
gcgtccgttt atgactttg tttgtttgag acagggtctc attatgtagc tcaggctggc     1320
cccccaactt ttaacaatcg tcctgcctcg gcctcctgag tgctgggatg acaagggtgc     1380
accatcacac caggtttttt ccttttttga gagattttac tatgtaaccc gggctgggct     1440
attctcaagc tagtggcagt cctcttgcct caggctcctc ttgcctcagg cacccccttgg    1500 gaccctctgg gacctatgtc cgagatgaat ggctgggtaa ggtagggtgg gaggttcagt     1560
gaaccttata ggttgggccc ttccttctgg gatcccttga tcatatggga agttctctag     1620
gctctcagca gccctgcatt cacacactga ctgaggcgcg acctgtatgt tgtgtttgag     1680
ggggatgtgt ggcagaggta tggctgtggc aaggccggtg ccttttattc ttgagattga     1740
gtcttatgta gctcaggctg gtcttgaact cactctcact gtgtagctag ggaagacctt     1800
```

| | |
|---|---|
| gagcccttgc ctcagccaga atgctcagat gtcaggcagc gcaccacgtg actgtttctt | 1860 |
| tccattgtct tgtctttttg ttgttgttgt tttcgagaca gggtttctct gtgtagccct | 1920 |
| ggccgttctg gaactcactc tgtagaccag gctggcctta aactcagaaa tccacctgcc | 1980 |
| tctgcctctc aaatgctggg attaaaggcg tgcaccacca cgcccttttt ccttttttctt | 2040 |
| aagtcaaggt ctatttgtgt agcccaggct ggcttcaagc tcatgacact cttcctgcct | 2100 |
| ctgcgtctgg aactatgaac ataccttact actctgtgct tacccacgcc atgggtagac | 2160 |
| agacttctag acttggtcaa cccccaccca caaggcaggc aaattaagtc cctgcaggtg | 2220 |
| cttctttggg aggaaagccc gctttcatag tgatctgtca agctagaaag cactcccgcc | 2280 |
| acccagatat ctaagtgtga atctttggac aactggtgac ttctggccag cttttctggg | 2340 |
| gccggcctct gtccaggtgt ctgcccagga ccctgctcag tgcctgtctg tctcacacca | 2400 |
| gtgacttcct cacacccgcc tgttcaggcc cagtcttttc cgttcaagtg ctacaggcca | 2460 |
| agtaggctca aactgtgggt ttgtcttggg catccacagc agaatcagaa cccagagctt | 2520 |
| tgaagcctga gtgaggggag gggggcactc aggcttccgt ctctctgaga aacagacgat | 2580 |
| gaagaggccc ttaaaactct ttgcaacccc atgagcctcc ccaatgagcc tgtgacacac | 2640 |
| cggaactcac ctctgtgggt ggccgggagg gggaacaggg tcatgaagga tccagatgtc | 2700 |
| catgtggtca aggctaaact gtactaaata aaattatttc tcatcaccac tatacatgca | 2760 |
| taataaaataa agtgtacatc aaaatt | 2786 |

<210> SEQ ID NO 5
<211> LENGTH: 2678
<212> TYPE: DNA
<213> ORGANISM: Homo sapiens
<220> FEATURE:
<223> OTHER INFORMATION: Human IRF8 (NM_002163.2)

<400> SEQUENCE: 5

| | |
|---|---|
| agcgcggcag caagcgtggg aacgcgggcg gcgagacggc ggcaggacgg cggcaggatg | 60 |
| tgtgaccgga atggtggtcg gcggcttcga cagtggctga tcgagcagat tgacagtagc | 120 |
| atgtatccag gactgatttg ggagaatgag gagaagagca tgttccggat cccttggaaa | 180 |
| cacgctggca agcaagatta taatcaggaa gtggatgcct ccattttta aggcctgggca | 240 |
| gttttttaaag ggaagtttaa agaagggac aaagctgaac cagccacttg gaagacgagg | 300 |
| ttacgctgtg cctttgaataa gagcccagat tttgaggaag tgacggaccg gtcccaactg | 360 |
| gacatttccg agccatacaa agtttaccga attgttcctg aggaagagca aaaatgcaaa | 420 |
| ctaggcgtgg caactgctgg ctgcgtgaat gaagttacag agatggagtg cggtcgctct | 480 |
| gaaatcgacg agctgatcaa ggagccttct gtggacgatt acatggggat gatcaaaagg | 540 |
| agcccttccc cgccggaggc ctgtcggagt cagctccttc cagactggtg ggcgcagcag | 600 |
| cccagcacag gcgtgccgct ggtgacgggg tacaccaccc tcgacgcgca ccattcagca | 660 |
| ttctcccaga tggtgatcag cttctactat gggggcaagc tggtgggcca ggccaccacc | 720 |
| acctgccccg agggctgccg cctgtccctg agccagcctg gctgccccgg caccaagctg | 780 |
| tatgggcccg agggcctgga gctggtgcgc ttcccgccgg ccgacgccat ccccagcgag | 840 |
| cgacagaggc aggtgacgcg gaagctgttc gggcacctgg agcgggggt gctgctgcac | 900 |
| agcagccggc agggcgtgtt cgtcaagcgg ctgtgccagg gccgcgtgtt ctgcagcggc | 960 |
| aacgccgtgg tgtgcaaagg caggcccaac aagctggagc gtgatgaggt ggtccaggtc | 1020 |
| ttcgacacca gccagttctt ccgagagctg cagcagttct ataacagcca gggccggctt | 1080 |

```
cctgacggca gggtggtgct gtgctttggg aagagtttc cggatatggc cccttgcgc    1140 tccaaactca ttctcgtgca gattgagcag ctgtatgtcc ggcaactggc agaagaggct    1200
gggaagagct gtggagccgg ctctgtgatg caggccccg aggagccgcc gccagaccag    1260
gtcttccgga tgtttccaga tatttgtgcc tcacaccaga gatcattttt cagagaaaac    1320
caacagatca ccgtctaagt gcgtcgcttg ggcgccccac cccgtctgcg tcctgcatcc    1380
atctccctgt tacagtggcc cgcatcatga ttaaagaatg tggatccctc tgtctggggt    1440
gggatgcctt actttgcact taatttaata agggcattct cggaggagta gacgtttaat    1500
acgaagtggc ggcatagccc tgccgagatg tcggtgatgg cctggatgct gtaaccacaa    1560
cctgtggcta aaaattttat tttctatcct tacccgtca ttatcattag ttgctatgat    1620
tctttctgca ttttcggtta actatcattt ccaaagactt gtcattcagt aatattagca    1680
gatagctgct tcgataaagg aatttggagt ttaaaaatca acttgtgaaa acaaggttgt    1740
ttttgtcttt atcgtttgtt agagttatag atttatgatt tcataggctt gattctatgt    1800
gaaatatctt tttacttta tgcattttaa taagatttaa aaatatttag attaaagccc    1860
cctttaatga gtacaagaaa aactcttggc ttgttagaag aaagtatatt ctttctagaa    1920
tttggtgcag gaatatgtgt tcatatccag gcaaacgggt gtgtttttat cttcagacaa    1980
tgaaaccttc tcctctgggg cttgttgcc aggaagatta gaactaaatt tatttttttc    2040
atttctgtca tgaaatcatt ccagatacct ctttctttct ttccaaatgg ttttcacatg    2100
tgtttgaaat atttgtactt cgaattgtcg gatttccat gtcctccttt ctcctttgtg    2160
cccagcctga gtcagcacca atcccgcatt cagaacctcc cagtgaaagg gcagccttca    2220
ttttgagaag gtggaaggtg ttaggtttg ggagacagct catccaatct cccaagtctc    2280
atggtggatt tgtgactgtg agagtttccg gtttaaaatc tgaaaagcca gatatgcctg    2340
tttccttttc ccagcaccat gcctgtggag gggacagtca gacccagagg tcctttacgt    2400
gtggatggag ttcacaggcg aatagaggag aggaccaggg gacgtggctt gtcccttttg    2460
tccaacaaag cattatattt ttaagaatgg cagacctgtt tgctgaagtg ttcataagat    2520
aacaataggc ttgaatctcc aattcaaatg aatgtcaaag cacatatctt taatatgctg    2580
aatgaatatt tattttgta tccattaaaa cagtatattg atctctttta ttctttatta    2640
aaataaaatg ctctttttta aaaaaaaaa aaaaaaa                              2678
```

<210> SEQ ID NO 6
<211> LENGTH: 3391
<212> TYPE: DNA
<213> ORGANISM: Mus <mouse, genus>
<220> FEATURE:
<223> OTHER INFORMATION: Mouse Irf8 (NM_001301811.1)

<400> SEQUENCE: 6

```
ttccaagccc actggtggca gttagggctg ctgtgtggct aaaaccagcc ctggagagac      60
ctcatctccc tcctctcagg ctgctgccgt cttttcctgg cccactacca cctgcaagcg     120
gcctggagtt tctgaccctc aggcctcttt ccagcaatcc tgactttgtg gacatgctg     180 gctctggatg tgactatgtt cttggggata tcttgacttc tcactgatga taacttcttt     240
tttttttttt tttccctacc ccaagaggtc atttttagttg gaagactaga agtgctgtgt     300
tctggttttc agggtgggcg tctgtccaac tgctttgggg atttccaggc tgttctagta     360
aatgctggct gcaagtccct gtgcacaaat gccctctctc cccacgctgt aggaaaagca     420
```

-continued

```
gacccgagag tgtccaagtg tgccattagg tgtctgggga tggcgggcct ggatatggag      480
tccctgagct ggctttgtac tgtcccttg ttctcactga gggctgattg taagagggac      540
```

```
gacccgagag tgtccaagtg tgccattagg tgtctgggga tggcgggcct ggatatggag      480
tccctgagct ggctttgtac tgtccctttg ttctcactga gggctgattg taagagggac      540
tccctgtgtt gttggaggag tcctctagga tacaggctct gattgcagga tgtgtgaccg      600
gaacggcggg cggcggctgc ggcagtggct gatcgaacag atcgacagca gcatgtaccc      660
ggggctgatc tgggaaaatg atgagaagac catgttccgt atccctggaa agcatgccgg      720
caagcaggat tacaatcagg aggtggatgc ttccatcttc aaggcctggg cagttttaa      780
agggaagttt aaagagggag acaaagctga accagccacg tggaagacga ggttacgctg      840
tgctctgaac aagagcccag attttgaaga agtgactgac cggtcccagc tggacatttc      900
tgagccatat aaagtttacc gaattgtccc cgaggaagaa caaaaatgca agctgggcgt      960
ggcacctgca ggctgcatga gcgaagttcc tgagatggag tgtggccgct cagagattga     1020
ggagctgatc aaggaacctt ctgtggatga gtacatgggt atgaccaaga ggagcccatc     1080
cccaccagag gcctgcagga gccagatcct ccctgactgg tgggtccagc agcccagtgc     1140
aggcctgcca ctggtgaccg gatatgccgc ctatgacaca caccattcag ctttctccca     1200
gatggtcatc agcttctact acgggggcaa gctggtgggc caggccacca ccacctgcct     1260
tgaaggctgc cgtctctccc tgagccagcc ggggctgcct aagttgtatg gccggatgg     1320
cctggaaccc gtgtgctttc cgacggccga caccatcccc agtgagcgga gaggcaggt     1380
gacccggaag ctgtttgggc acctggaacg tggcgtgcta ctgcacagca accgcaaggg     1440
cgtgttcgtg aagcggctgt gccagggccg cgtgttctgc agcggcaacg cggtggtgtg     1500
caagggcagg cccaacaagc tggagcggga cgaggtggtg caggtctttg acaccaacca     1560
gttcatccga gagctgcagc aattctacgc cacccagagc cgcctacctg acagcagggt     1620
ggtcctgtgc ttcggggagg agtttccgga cactgtgccc ttgcgctcca aactcattct     1680
ggtgcaggta gagcagctgt atgccaggca gctggtggag aagcgggca agagctgcgg     1740
tgctggctcc ctgatgccag ccctggagga gccccagccg gaccaggctt ccgcatgtt     1800
tccggatatc tgtacctcac accagagacc cttttttaga gaaaatcaac agatcaccgt     1860
ctaagcctca gtccgggcac cccacctcgc ctgagctcaa gcttcaagag tctgtgacta     1920
agagaattcc gaaaggatgt ggagccctct gactggggtg ggcgggtgtc ctccaagggg     1980
cctccggaag cccacagagg gatgcgctcc tgctcaggca ggtgtcagaa gcttgcaggg     2040
gctgtggccg caacctgtga ttaaagcatt cctttcctgc gtttcccct tcaccactaa     2100
tggctggcct ttctgtgtgc tgaggtcttt cgacagttca aatcatctgg tggcagcaga     2160
ctcgcctttg cccttctgcg gccgagggcg gagatttatg actttctctg cttggttgga     2220
gaagaagaat ctttactatt cagcttcttt tcttttttggc cagaactctg aaaaaaaaaa     2280
aaactctttt taagacaata tttgtattct cacaggctca gctgtcaatc acttgagacc     2340
ttccctgtaa agtggggcag atttttaaata tgggtgtaga tactgcttgc agccttcgca     2400
ggaattttgg ttgtggttca ttgattcaca cagactctgt gtcagctgac agggctgtgt     2460
ggggcatcaa aggaggacca ggcactgtgg agaagaccca ttcactggca tctcacccgtt     2520
ccttgtccag ctccataccc agtcctaaga cccagtgaaa agccacgtcc aaactgtgct     2580
ctgggctcat cagtgcccac ccacgtacca gggaaaggca cacccctac ccagtgggca     2640
cagagcggaa tgtcccccta ccgcaccatt tgcgcccca atctggctgt ccaacctagt     2700
ttgtaagtaa tctaaatcag tgactatagc cccgcctaag ggacacttcc cggaggaggg     2760
agccgctgaa aaggagttag tttgagggtc agtacacaac aggggcagaa agccaagcag     2820
```

| | |
|---|---|
| atgtggggc agggagagtc atcatctgct tttgtctgag agaaggagag cttctccgtt | 2880 |
| tgttcaactt tgtaacaagc tgggttacat gctccacgca gctagagaag cctaggtgct | 2940 |
| ctgcattccc tggggaactg caggaaagcc ttacctgctg actgttgctc tggggaaaag | 3000 |
| cctgagggtc cagagcagct acaagctaca ggccatacct tacaacctga aaagctaagg | 3060 |
| accacggtga ccttcccggc tactgtgtga aggtgctggg tggggcctgc tcaacagaca | 3120 |
| gggtcgacag agtgtgtgat acatgcaaac agaatccttg gagtgtgtga tacatgcaaa | 3180 |
| cagaatcctg ggcccctgct tctcccctc agtcaaagca ggagtgtccc ttccgaagcc | 3240 |
| aggacaacct gttcacaagg cccttgtca catgtcacct tccacctgcc tcaaggagtg | 3300 |
| ctagtgtcca atatttatt tttgtattct cttaagaagt attgatttca tcctttatta | 3360 |
| aaaaaagttg ctctttcaca aaaaaaaaaa a | 3391 |

<210> SEQ ID NO 7
<211> LENGTH: 1426
<212> TYPE: DNA
<213> ORGANISM: Homo sapiens
<220> FEATURE:
<223> OTHER INFORMATION: Human PU.1 (NM_001080547.1)

<400> SEQUENCE: 7

| | |
|---|---|
| gactatctcc cagcggcagg cccttcgata aaatcaggaa cttgtgctgg ccctgcaatg | 60 |
| tcaagggagg gggctcaccc agggctcctg tagctcaggg ggcaggcctg agccctgcac | 120 |
| ccgccccacg accgtccagc ccctgacggg gcaccccatc ctgaggggct ctgcattggc | 180 |
| ccccaccgag gcagggatc tgaccgactc ggagcccggc tggatgttac aggcgtgcaa | 240 |
| aatggaaggg tttcccctcg tcccccctca gccatcagaa gacctggtgc cctatgacac | 300 |
| ggatctatac caacgccaaa cgcacgagta ttacccctat ctcagcagtg atggggagag | 360 |
| ccatagcgac cattactggg acttccaccc ccaccgtg cacagcgagt tcgagagctt | 420 |
| cgccgagaac aacttcacgg agctccagag cgtgcagccc ccgcagctgc agcagctcta | 480 |
| ccgcccacatg gagctggagc agatgcacgt cctcgatacc cccatggtgc caccccatcc | 540 |
| cagtcttggc caccaggtct cctacctgcc ccggatgtgc ctccagtacc catccctgtc | 600 |
| cccagcccag cccagctcag atgaggagga gggcgagcgg cagagccccc cactggaggt | 660 |
| gtctgacggc gaggcggatg gcctggagcc cgggcctggg ctcctgcctg ggagacagg | 720 |
| cagcaagaag aagatccgcc tgtaccagtt cctgttggac ctgctccgca gcggcgacat | 780 |
| gaaggacagc atctggtggg tggacaagga caagggcacc ttccagttct cgtccaagca | 840 |
| caaggaggcg ctggcgcacc gctggggcat ccagaagggc aaccgcaaga gatgaccta | 900 |
| ccagaagatg cgcgcgcgc tgcgcaacta cggcaagacg ggcgaggtca agaaggtgaa | 960 |
| gaagaagctc acctaccagt tcagcggcga agtgctgggc cgcggggcc tggccgagcg | 1020 |
| gcgccacccg ccccactgag cccgcagccc ccgccgggcc ccgccaggcc tccccgctgg | 1080 |
| ccatagcatt aagccctcgc ccggcccgga cacagggagg acgctcccgg ggcccagagg | 1140 |
| caggactgtg gcgggccggg cctcgcctca cccgcccct ccccactc caggcccct | 1200 |
| ccacatcccg cttcgcctcc ctccaggact ccaccccggc tccggacgc cagctgggcg | 1260 |
| tcagacccca ccggggcaac cttgcagagg acgacccggg gtactgcctt gggagtctca | 1320 |
| agtccgtatg taaatcagat ctcccctctc accctccca cccattaacc tcctcccaaa | 1380 |
| aaacaagtaa agttattctc aatccatcaa aaaaaaaaaa aaaaaa | 1426 |

<210> SEQ ID NO 8
<211> LENGTH: 1473
<212> TYPE: DNA
<213> ORGANISM: Mus <mouse, genus>
<220> FEATURE:
<223> OTHER INFORMATION: Mouse Pu.1 (NM_011355.2)

<400> SEQUENCE: 8

| | | | | | |
|---|---|---|---|---|---|
| aagagattta | tgcaaacggg | ctggggcggt | gatgtcaccc | caaggggact | atctcccagt | 60 |
| ggcaggccct | tcgataaaat | caggaacttg | tgctggccct | gcaatgtcaa | gggaggggc | 120 |
| tcacccaggg | ctcctgtagc | tcaggggca | ggcctgagcc | ctgcgtctga | cccacgaccg | 180 |
| tccagtcccc | cgacggggca | cctggtcctg | aggggatcc | gccttgatcc | ccaccgaagc | 240 |
| aggggatctg | accaacctgg | agctcagctg | gatgttacag | gcgtgcaaaa | tggaagggtt | 300 |
| ttccctcacc | gccctccat | cggatgactt | ggttacttac | gattcagagc | tataccaacg | 360 |
| tccaatgcat | gactactact | ccttcgtggg | cagcgatgga | gaaagccata | gcgatcacta | 420 |
| ctgggatttc | tccgcacacc | atgtccacaa | caacgagttt | gagaacttcc | ctgagaacca | 480 |
| cttcacagag | ctgcagagtg | tgcagccccc | gcagctacag | cagctctatc | gccacatgga | 540 |
| gctggaacag | atgcacgtcc | tcgatactcc | catggtgcca | ccccacaccg | gcctcagtca | 600 |
| ccaggtttcc | tacatgcccc | ggatgtgctt | cccttatcaa | accttgtccc | cagcccacca | 660 |
| gcagagctca | gatgaggagg | agggtgagag | gcagagccct | ccctggagg | tgtctgatgg | 720 |
| agaagctgat | ggcttggagc | ctgggccagg | tcttctgcac | ggggagacag | gcagcaagaa | 780 |
| aaagattcgc | ctgtaccagt | tcctgctgga | cctgctgcgc | agcggcgaca | tgaaggacag | 840 |
| catctggtgg | gtggacaagg | acaaaggtac | cttccagttc | tcgtccaagc | acaaggaggc | 900 |
| gctggcgcac | cgctggggca | tccagaaggg | caaccgcaag | aagatgacct | accagaagat | 960 |
| ggcgcgcgcg | ctgcgcaact | acggcaagac | aggcgaggtg | aagaaagtca | agaagaagct | 1020 |
| cacctaccag | ttcagcggcg | aggtgctggg | ccgtggggc | ctggccgagc | ggcgcctccc | 1080 |
| gccccactga | tcgcccgcag | agaccgccag | gctcctggac | cccgccggcc | atagcattaa | 1140 |
| cccgtcgccc | ggcccggaca | cagggaggac | attcccaggg | ccgaggcagg | actggggcc | 1200 |
| cggcctcgcc | ctcccatgcc | cggcctggcc | cgccccaccc | gctttgcctc | ccaccaggac | 1260 |
| tctagcccgc | tccaagggcc | gcctgggcct | cggacctcaa | ccgagggtca | gcctggctta | 1320 |
| gtggccacgg | tgcttccttg | ggagtctggc | gctggcacct | ttttgtatat | tgaatgcttt | 1380 |
| ttaaaaagct | cttcctcccc | accccctcat | tagtcactaa | agacaagtaa | aattattgac | 1440 |
| agctattctc | ccagaaaaaa | aaaaaaaaaa | aaa | | | 1473 |

<210> SEQ ID NO 9
<211> LENGTH: 5332
<212> TYPE: DNA
<213> ORGANISM: Homo sapiens
<220> FEATURE:
<223> OTHER INFORMATION: Human IRF4 (NM_002460.3)

<400> SEQUENCE: 9

| | | | | | |
|---|---|---|---|---|---|
| acctcgcact | ctcagtttca | ccgctcgatc | ttgggaccca | ccgctgccct | cagctccgag | 60 |
| tccagggcga | gtgcagagca | gagcgggcgg | aggaccccgg | gcgcgggcgc | ggacggcacg | 120 |
| cggggcatga | acctggaggg | cggcggccga | ggcggagagt | tcggcatgag | cgcggtgagc | 180 |
| tgcggcaacg | ggaagctccg | ccagtggctg | atcgaccaga | tcgacagcgg | caagtacccc | 240 |
| gggctggtgt | gggagaacga | ggagaagagc | atcttccgca | tccctggaa | gcacgcgggc | 300 |

```
aagcaggact acaaccgcga ggaggacgcc gcgctcttca aggcttgggc actgtttaaa      360
ggaaagttcc gagaaggcat cgacaagccg gaccctccca cctggaagac gcgcctgcgg      420
tgcgctttga acaagagcaa tgactttgag gaactggttg agcggagcca gctggacatc      480
tcagacccgt acaaagtgta caggattgtt cctgagggag ccaaaaaagg agccaagcag      540
ctcaccctgg aggacccgca gatgtccatg agccacccct acaccatgac aacgccttac      600
ccttcgctcc cagcccagca ggttcacaac tacatgatgc cacccctcga ccgaagctgg      660
agggactacg tcccggatca gccacacccg gaaatcccgt accaatgtcc catgacgttt      720
ggaccccgcg gccaccactg gcaaggccca gcttgtgaaa atggttgcca ggtgacagga      780
accttttatg cttgtgcccc acctgagtcc caggctcccg gagtccccac agagccaagc      840
ataaggtctg ccgaagcctt ggcgttctca gactgccggc tgcacatctg cctgtactac      900
cgggaaatcc tcgtgaagga gctgaccacg tccagccccg agggctgccg gatctcccat      960
ggacatacgt atgacgccag caacctggac caggtcctgt tcccctaccc agaggacaat     1020
ggccagagga aaaacattga aagctgctg agccacctgg agagggcgt ggtcctctgg       1080 atggcccccg acgggctcta tgcgaaaaga ctgtgccaga gcaggatcta ctgggacggg     1140
cccctggcgc tgtgcaacga ccggcccaac aaactggaga gagaccagac ctgcaagctc     1200
tttgacacac agcagttctt gtcagagctg caagcgtttg ctcaccacgg ccgctccctg     1260
ccaagattcc aggtgactct atgctttgga gaggagtttc cagaccctca gaggcaaaga     1320
aagctcatca cagctcacgt agaacctctg ctagccagac aactatatta ttttgctcaa     1380
caaaacagtg gacatttcct gagggggctac gatttaccag aacacatcag caatccagaa     1440
gattaccaca gatctatccg ccattcctct attcaagaat gaaaaatgtc aagatgagtg     1500
gttttctttt tccttttttt tttttttttt ttgatacggg gatacggggt cttgctctgt     1560
ctcccaggct ggagtgcagt gacacaatct cagctcactg tgacctccgc ctcctgggtt     1620
caagagactc tcctgcctca gcctcctgg tagctgggat tacaggtgtg agccactgca      1680
cccacccaag acaagtgatt ttcattgtaa atatttgact ttagtgaaag cgtccaattg     1740
actgccctct tactgttttg aggaattcag aagtggagat ttcagttcag cggttgagga     1800
gaattgcggc gagacaagca tggaaaatca gtgacatctg attggcagat gagcttattt     1860
caaaaggaag ggtggctttg catttcttgt gttctgtaga ctgccatcat tgatgatcac     1920
tgtgaaaatt gaccaagtga tgtgtttaca tttactgaaa tgcgctcttt aatttgttgt     1980
agattaggtc ttgctggaag acagagaaaa cttgcctttc agtattgaca ctgactagag     2040
tgatgactgc ttgtaggtat gtctgtgcca tttctcaggg aagtaagatg taaattgaag     2100
aagcctcaca cgtaaaagaa atgtattaat gtatgtagga gctgcagttc ttgtggaaga    2160
cacttgctga gtgaaggaaa tgaatctttg actgaagccg tgcctgtagc cttggggagg     2220
cccatccccc acctgccagc ggtttcctgg tgtgggtccc tctgcccgc cctccttccc      2280 attggctttc tctccttggc cttctggaa agccagttag taaacttcct attttcttga     2340
gtcaaaaaac atgagcgcta ctcttggatg ggacattttt gtctgtccta caatctagta    2400
atgtctaagt aatggttaag ttttcttgtt tctgcatctt tttgaccctc attctttaga    2460
gatgctaaaa ttcttcgcat aaagaagaag aaattaagga acataaatct taatacttga    2520
actgttgccc ttctgtccaa gtacttaact atctgttccc ttcctctgtg ccacgctcct    2580
ctgtttgttt ggctgtccag cgatcagcca tggcgacact aaaggaggag gagccgggga   2640
```

```
ctcccaggct ggagagcact gccaggaccc accactggaa gcaggatgga gctgactacg  2700
gaactgcaca ctcagtgggc tgtttctgct tatttcatct gttctatgct tcctcgtgcc  2760
aattatagtt tgacagggcc ttaaaattac ttggctttt ccaaatgctt ctatttatag    2820
aatcccaaag acctccactt gcttaagtat acctatcact tacatttttg tggttttgag  2880
aaagtacagc agtagactgg ggcgtcacct ccaggccgtt tctcatacta caggatattt  2940
actattactc ccaggatcag cagaagattg cgtagctctc aaatgtgtgt tcctgctttt  3000
ctaatggata tttaaattc attcaacaag cacctagtaa gtgcctgctg tatccctaca   3060
ttacacagtt cagcctttat caagcttagt gagcagtgag cactgaaaca tttttttta   3120 atgtttaaaa agtttctaat attaaagtca gaatattaat acaattaata ttaatattaa  3180
ctacagaaaa gacaaacagt agagaacagc aaaaaaataa aaaggatctc cttttttccc  3240
agcccaaatt ctcctctcta aaagtgtcca caagaagggg tgtttattct tccaacacat  3300
ttcacttttc tgtaaatata cataaactta aaaagaaaac ctcatggagt catcttgcac  3360
acactttcat gcagtgctct ttgtagctaa cagtgaagat ttacctcgtt ctgctcagag  3420
gccttgctgt ggagctccac tgccatgtac ccagtagggt ttgacatttc attagccatg  3480
caacatggat atgtattggg cagcagactg tgtttcgtga actgcagtga tgtatacatc  3540
ttatagatgc aaagtatttt ggggtatatt atcctaaggg aagataaaga tgatattaag  3600
aactgctgtt tcacggggcc cttacctgtg accctctttg ctgaagaata tttaaccca    3660 cacagcactt caaagaagct gtcttggaag tctgtctcag gagcaccctg tcttcttaat  3720
tctccaagcg gatgctccat ttcaattgct ttgtgacttc ttcttctttg ttttttaaa    3780 tattatgctg ctttaacagt ggagctgaat tttctggaaa atgcttcttg gctggggcca  3840
ctacctcctt tcctatcttt acatctatgt gtatgttgac ttttaaaat tctgagtgat   3900 ccagggtatg acctagggaa tgaactagct atgaaatact cagggttagg aatcctagca  3960
cttgtctcag gactctgaaa aggaacggct tcctcattcc ttgtcttgat aaagtggaat  4020
tggcaaacta gaatttagtt tgtactcagt ggacagtgct gttgaagatt tgaggacttg  4080
ttaaagagca ctgggtcata tggaaaaaat gtatgtgtct cccaggtgca tttcttggtt  4140
tatgtcttgt tcttgagatt ttgtatattt aggaaaacct caagcagtaa ttaatatctc  4200
ctggaacact atagagaacc aagtgaccga ctcatttaca actgaaacct aggaagcccc  4260
tgagtcctga gcgaaaacag gagagttagt cgccctacag aaaacccagc tagactattg  4320
ggtatgaact aaaagagac tgtgccatgg tgagaaaaat gtaaatcct acagtgaaat     4380 gagcagccct tacagtattg ttaccaccaa gggcaggtag gtattagtgt ttgaaaaagc  4440
tggtctttga gcgagggcat aaatacagct agccccaggg gtggaacaac tctgggagtc  4500
ttgggtactc gcacctcttg gctttgttga tgctccgcca ggaaggccac ttgtgtgtgc  4560
gtgtcagtta cttttttagt aacaattcag atccagtgta aacttccgtt cattgctctc  4620
cagtcacatg cccccacttc cccacaggtg aaagttttc tgaaagtgtt gggattggtt   4680
aaggtcttta tttgtattac gtatctcccc aagtcctctg tggccagctg catctgtctg  4740
aatggtgcgt gaaggctctc agaccttaca caccattttg taagttatgt tttacatgcc  4800
ccgtttttga gactgatctc gatgcaggtg gatctccttg agatcctgat agcctgttac  4860
aggaatgaag taaggtcag ttttttttg tattgatttt cacagctttg aggaacatgc     4920
ataagaaatg tagctgaagt agaggggacg tgagagaagg gccaggccgg caggccaacc  4980
ctcctccaat ggaaattccc gtgttgcttc aaactgagac agatgggact taacaggcaa  5040
```

| | |
|---|---|
| tggggtccac ttcccctct tcagcatccc ccgtacccca ctttctgctg aaagaactgc | 5100 |
| cagcaggtag gaccccagag gcccccaaat gaaagcttga atttcccta ctggctctgc | 5160 |
| gttttgctga gatctgtagg aaaggatgct tcacaaactg aggtagataa tgctatgctg | 5220 |
| tcgttggtat acatcatgaa tttttatgta aattgctctg caaagcaaat tgatatgttt | 5280 |
| gataaattta tgttttagg taaataaaaa cttttaaaaa tttgttaaaa aa | 5332 |

<210> SEQ ID NO 10
<211> LENGTH: 4762
<212> TYPE: DNA
<213> ORGANISM: Mus <mouse, genus>
<220> FEATURE:
<223> OTHER INFORMATION: Mouse Irf4 (NM_013674.2)

<400> SEQUENCE: 10

| | |
|---|---|
| tttcctagtt tcaccacttg aacttgggac cctttgctgc cctcagctaa gagtgcgggt | 60 |
| gagcgcacaa gcccaggagg aggtccgcac gcgtcatgaa cttggagacg ggcagccggg | 120 |
| gctcagagtt cggcatgagc gcagtgagct gcggcaatgg gaaactccga cagtggttga | 180 |
| tcgaccagat cgacagcggc aagtaccccg ggctggtgtg ggagaacgag gagaagagcg | 240 |
| tcttccgcat cccgtggaaa cacgcgggca agcaggacta caatcgtgag gaggacgctg | 300 |
| ccctcttcaa ggcttgggca ttgtttaaag gcaagttccg agaagggatc gacaagccag | 360 |
| atcctcctac ttggaagaca agattacgat gtgctctgaa caagagcaat gactttgagg | 420 |
| aattggtcga gaggagccag ctggatatct ctgacccata caaggtgtac aggattgttc | 480 |
| cagagggagc caaaaaagga gcaaagcagc tcactttgga tgacacacag atggccatgg | 540 |
| gccaccccta ccccatgaca gcaccttatg gctctctgcc agcccagcag gttcataact | 600 |
| acatgatgcc accccatgac aggagctgga gggattatgc ccctgaccag tcacacccag | 660 |
| aaatcccata tcaatgtcct gtgacgtttg gcccacgagg ccaccactgg caaggcccat | 720 |
| cttgtgaaaa tggttgccag gtgacaggaa ccttttatgc ttgtgcccca cctgagtccc | 780 |
| aggctcctgg aatccccatt gagccaagca taaggtctgc tgaagccttg gcgctctcag | 840 |
| actgccggct gcatatctgc ctgtattacc gggacatcct cgtgaaagag ctgaccacga | 900 |
| cgagccctga aggctgccgg atctcccacg gacacaccta tgatgttagc aacctggacc | 960 |
| aggtcctgtt tccctacccg gacgacaatg gacagaggaa gaacattgag aagttgctga | 1020 |
| gccacctgga gagggactg gtcctctgga tggctccaga tgggcttat gccaaaagac | 1080 |
| tctgccagag taggatctac tgggatgggc cctggcact gtgcagcgat cggcccaaca | 1140 |
| agctagaaag agaccagact tgcaagctct ttgacacaca gcagtttcta tcagagctgc | 1200 |
| aagtgtttgc tcaccatggc cggccagcac cgagattcca ggtgactctg tgctttggtg | 1260 |
| aggagtttcc agaccctcag agacagagga agctcatcac agctcatgtg gaacctctgc | 1320 |
| tagccagaca actgtattac tttgctcaac aaaacactgg acatttcctg aggggctacg | 1380 |
| agttacctga acacgttacc actccagatt accaccgctc cctccgtcat tcttccatcc | 1440 |
| aagagtgaga agaaatactc tgacagggca gccggctgct gccctttctc tttggaagag | 1500 |
| ctaagaagtg agtgggtttc cacttgaaga caacaacagg gctttgtgag gaaaaacagc | 1560 |
| tgtatctgct caacagagga gcttccccca aagagtgcc tgtcatccag gtcttgacaa | 1620 |
| gtgccaggac ttgggtgact gtgccctggc ttataactgt gaaacttgat cagtgttgtg | 1680 |
| tttacatgta cttgaatgct ggctttagcc tggtatagat ggacttttgc ttgaagactg | 1740 |

```
aaaacctgtg ccagcatgaa tccctgacaa gagaagacat acgtattatt ggtccatttc   1800
tcagggaagt aaagtctaga ctagagacta cgctgtccac tcacagagaa acgcattcct   1860
ggatagagga gctgtaggtt gcccagatca tgtccactga gtgaagggac ttggttctta   1920
ggtccagtct aggctatcat gtcctgatcc tgcactctct ctgagtagac cctacatcct   1980
gtttgctccc tcttcttgcc cttccctaaa agccagctgg tggactcttg ttgccacata   2040
cttgagccaa aaaccatca gggacatata agatgagaca tgtttgcatc tcctctgatc   2100
taacaacggc tacaaagttt tttgttgttg ttgtctcccc tttctgtttt gcctctcatt   2160
ctttagaatt gttgcttttt tgtaaagaaa ggaagagaga gagaccgaat atactagaga   2220 tagatttta aaattctgtg ccatttcccc ttctatttgt tttgttggcc atcagtggtc   2280
cccatggcaa cactggaagg gcggagcctt tgagcaggtt gggaactgtc ccggacacca   2340
gtggttcagt gtacagctgt agactcagtg agctgtttct gcttattttg tatattagat   2400
gcttccttgt gccaataata gtttgacaga gtctcaaagc taccgggctt cttttccaac   2460
aacacattct ttcacagaat cccaaagagt ctcacttgcc ttcacaaccg tctgatcctt   2520
tattgttact gttttgttta ggtggctttg ccatgctctg ggattttct cctaccacaa   2580 catcattcct gactctttcg ggctcagaaa gagttaagcg ctcttgcaca cttggcactt   2640
acttcttttt aattttttt ttaacatgcc actcttaata tttcttctta agtctttcag   2700
cagcatacat tcaataagca atggaccatt gggtgtctca tttcattgtt ttattttaa   2760 aaaggaacct ttgacaaata atacacatta cagaaaatgg aagcattttt catagagaag   2820
gtaagaactg aaatgcattt tatgttcgaa tcctccttgc tagtattagc cccaagagtt   2880
cagtctgtcc tttaagcatg ttttagtttt caatacatat atatgaagtt gccctttctt   2940
agagagagag agagagatat gtgatgacac tcttatgtac ccaactatac agatttacct   3000
catcttttga gtggcatgtg gacttccact gctatgtgcc taggtgcagt ttagacatct   3060
tcttagctac ccatcccagc agccactga gtctcgtgaa ctaaagtcac ttatacatct   3120
tatagatgca aaacattctg gggtatatta tcccaaggga agatgaaggc aaaatcggga   3180
agcactcttc ctgaggcccc aagccacagc tgtcctcctg gagtatctta accatatctg   3240
gcacttcacc aaggtcccctt gcctggtcct gtatgaccat gactcttcag tccataagca   3300
gatgctttgt ctcaattgcc atgtgaagtc ttttggtttt tggttttttt ccttaatgtt   3360
aagctgtttt aacagtgaag ctgaatttc tggaaaatgc tgtatggttc gagccccag   3420 ttcatgtttc actttacagc catgcatgct gatgccttcc atcttgacaa atggaatgat   3480
gggtaaacac tcctgacaca aagaggaaca ccttcctcgt cccttgctga aacaaagtgc   3540
aatgcacaca gtagaattta gtttgcttgc actggaagat gccgttgaag aggtaggctg   3600
aggaacactg tatcctaggg agaaaatatg caagtctcac gggtgctttc tgttggcttg   3660
tttctggtcc ttgagcaggc ttaagtatct agtttcaaac tagaagcccc aaagccctca   3720
gtcgttgtcc tggacagagt tggtagaccc cacctgtaga aatccagatg cactctggga   3780
ttggagcaca gagaggcttg ctctatcgtg agaatgccca gcctgcagag gcccaggtgc   3840
ggtgcctgag tggctgtatg ccagacacag gaacgccagc aggctgagtg tggtgactga   3900
tatgtgaggt gcccttgccc tgcagacagg ctgaatgtga gccccagcag cagaggattc   3960
tgagagtcag ggtggtgtca tgtcctacac aggaagagcc ttcaatatta cttttaaac   4020 gaactttccc attgctgata ttttgataaa aacccacaca aggtttaatt acatgccccc   4080
tcatccctct ccacacagtc ttgcccatcc cactggtgaa ttgttgttgt tcttgttgtt   4140
```

| | | | | |
|---|---|---|---|---|
| gtttttttgtt | attggtgaaa | attgtgaaat | tgttaaggtc | tctgttttgg ttatttatct | 4200 |
| ccctaaatca | catggctgct | gcatacattg | caatgttgcc | ctaccacatg tatgtttttg | 4260 |
| caagttgctt | cttcactcat | tgaagaagcc | tgcaccgtaa | gtgaaactca cttagtcctt | 4320 |
| gctaattgct | gctcactgtc | acgtgaacgc | agagaaggct | gattttcctg acccatttt | 4380 |
| cagtgctttg | aggaacatga | gtccagagta | tattgaagta | aagacagtg tttggcaagc | 4440 |
| cagttcttat | tagacactgc | tacaggcttc | acaatcttca | aggtggaccc acctcatgtg | 4500 |
| gaagggcatc | attgcccctc | tgctcccatg | cgctgtgcac | cccttcaca gtgaaagacc | 4560 |
| tgctggggac | caggactcag | agatctctgg | cttcgagctc | atatcttggc ttcctgtcat | 4620 |
| gtctaagccc | gacaggaaag | tgtggcacca | tcctgcctgc | ggcgttggat ggataggcca | 4680 |
| tggattttgc | tgtaaacttg | cttcacaagg | aaagctgtgt | gttttaaaat atttgataaa | 4740 |
| taaaggattt | ctagaaagat | tg | | | 4762 |

<210> SEQ ID NO 11
<211> LENGTH: 4978
<212> TYPE: DNA
<213> ORGANISM: Homo sapiens
<220> FEATURE:
<223> OTHER INFORMATION: Human STAT3 (NM_139276.2)

<400> SEQUENCE: 11

| | | | | |
|---|---|---|---|---|
| ggtttccgga | gctgcggcgg | cgcagactgg | gaggggagc | cggggttcc gacgtcgcag | 60 |
| ccgagggaac | aagccccaac | cggatcctgg | acaggcaccc | cggcttggcg ctgtctctcc | 120 |
| ccctcggctc | ggagaggccc | ttcggcctga | gggagcctcg | ccgcccgtcc ccggcacacg | 180 |
| cgcagccccg | gcctctcggc | ctctgccgga | gaaacagttg | gaccccctga ttttagcagg | 240 |
| atggcccaat | ggaatcagct | acagcagctt | gacacacggt | acctggagca gctccatcag | 300 |
| ctctacagtg | acagcttccc | aatggagctg | cggcagtttc | tggccccttg gattgagagt | 360 |
| caagattggg | catatgcggc | cagcaaagaa | tcacatgcca | ctttggtgtt tcataatctc | 420 |
| ctgggagaga | ttgaccagca | gtatagccgc | ttcctgcaag | agtcgaatgt tctctatcag | 480 |
| cacaatctac | gaagaatcaa | gcagtttctt | cagagcaggt | atcttgagaa gccaatggag | 540 |
| attgcccgga | ttgtggcccg | gtgcctgtgg | gaagaatcac | gccttctaca gactgcagcc | 600 |
| actgcggccc | agcaaggggg | ccaggccaac | caccccacag | cagccgtggt gacggagaag | 660 |
| cagcagatgc | tggagcagca | ccttcaggat | gtccggaaga | gagtgcagga tctagaacag | 720 |
| aaaatgaaag | tggtagagaa | tctccaggat | gactttgatt | tcaactataa aaccctcaag | 780 |
| agtcaaggag | acatgcaaga | tctgaatgga | aacaaccagt | cagtgaccag gcagaagatg | 840 |
| cagcagctga | aacagatgct | cactgcgctg | gaccagatgc | ggagaagcat cgtgagtgag | 900 |
| ctggcgggc | ttttgtcagc | gatggagtac | gtgcagaaaa | ctctcacgga cgaggagctg | 960 |
| gctgactgga | gaggcggca | acagattgcc | tgcattggag | gccgcccaa catctgccta | 1020 |
| gatcggctag | aaaactggat | aacgtcatta | gcagaatctc | aacttcagac ccgtcaacaa | 1080 |
| attaagaaac | tggaggagtt | gcagcaaaaa | gtttcctaca | aggggaccc cattgtacag | 1140 |
| caccggccga | tgctggagga | gagaatcgtg | gagctgttta | gaaacttaat gaaaagtgcc | 1200 |
| tttgtggtgg | agcggcagcc | ctgcatgccc | atgcatcctg | accggcccct cgtcatcaag | 1260 |
| accggcgtcc | agttcactac | taaagtcagg | ttgctggtca | aattccctga gttgaattat | 1320 |
| cagcttaaaa | ttaaagtgtg | cattgacaaa | gactctgggg | acgttgcagc tctcagagga | 1380 |

```
tcccggaaat ttaacattct gggcacaaac acaaaagtga tgaacatgga agaatccaac    1440
aacggcagcc tctctgcaga attcaaacac ttgaccctga gggagcagag atgtgggaat    1500
gggggccgag ccaattgtga tgcttccctg attgtgactg aggagctgca cctgatcacc    1560
tttgagaccg aggtgtatca ccaaggcctc aagattgacc tagagaccca ctccttgcca    1620
gttgtggtga tctccaacat ctgtcagatg ccaaatgcct gggcgtccat cctgtggtac    1680
aacatgctga ccaacaatcc caagaatgta aactttttta ccaagccccc aattggaacc    1740
tgggatcaag tggccgaggt cctgagctgg cagttctcct ccaccaccaa gcgaggactg    1800
agcatcgagc agctgactac actggcgaga aaactcttgg gacctggtgt gaattattca    1860
gggtgtcaga tcacatgggc taaattttgc aaagaaaaca tggctggcaa gggcttctcc    1920
ttctgggtct ggctgacaa tatcattgac cttgtgaaaa agtacatcct ggcccttggg    1980
aacgaagggt acatcatggg ctttatcagt aaggagcggg agcgggccat cttgagcact    2040
aagcctccag gcaccttcct gctaagattc agtgaaagca gcaaagaagg aggcgtcact    2100
ttcacttggg tggagaagga catcagcggt aagacccaga tccagtccgt ggaaccatac    2160
acaaagcagc agctgaacaa catgtcattt gctgaaatca tcatgggcta taagatcatg    2220
gatgctacca atatcctggt gtctccactg gtctatctct atcctgacat tcccaaggag    2280
gaggcattcg aaagtattg tcggccagag agccaggagc atcctgaagc tgacccaggt    2340
agcgctgccc catacctgaa gaccaagttt atctgtgtga caccaacgac ctgcagcaat    2400
accattgacc tgccgatgtc cccccgcact ttagattcat tgatgcagtt tggaaataat    2460
ggtgaaggtg ctgaaccctc agcaggaggg cagtttgagt ccctcacctt tgacatggag    2520
ttgacctcgg agtgcgctac ctcccccatg tgaggagctg agaacggaag ctgcagaaag    2580
atacgactga ggcgcctacc tgcattctgc caccccctcac acagccaaac cccagatcat    2640
ctgaaactac taactttgtg gttccagatt ttttttaatc tcctacttct gctatctttg    2700
agcaatctgg gcactttaa aaatagagaa atgagtgaat gtgggtgatc tgcttttatc    2760
taaatgcaaa taaggatgtg ttctctgaga cccatgatca ggggatgtgg cggggggtgg    2820
ctagagggag aaaaaggaaa tgtcttgtgt tgttttgttc ccctgccctc ctttctcagc    2880 agcttttgt tattgttgtt gttgttctta gacaagtgcc tcctggtgcc tgcggcatcc    2940
ttctgcctgt ttctgtaagc aaatgccaca ggccacctat agctacatac tcctggcatt    3000 gcactttta accttgctga catccaaata gaagatagga ctatctaagc cctaggtttc    3060
tttttaaatt aagaaataat aacaattaaa gggcaaaaaa cactgtatca gcatagcctt    3120
tctgtattta agaaacttaa gcagccgggc atggtggctc acgcctgtaa tcccagcact    3180
ttgggaggcc gaggcggatc ataaggtcag gagatcaaga ccatcctggc taacacggtg    3240
aaaccccgtc tctactaaaa gtacaaaaaa ttagctgggt gtggtggtgg gcgcctgtag    3300
tcccagctac tcgggaggct gaggcaggag aatcgcttga acctgagagg cggaggttgc    3360
agtgagccaa aattgcacca ctgcacactg cactccatcc tgggcgacag tctgagactc    3420
tgtctcaaaa aaaaaaaaaa aaaaagaaa cttcagttaa cagcctcctt ggtgctttaa    3480
gcattcagct tccttcaggc tggtaattta tataatccct gaaacgggct tcaggtcaaa    3540
cccttaagac atctgaagct gcaacctggc ctttggtgtt gaaataggaa ggtttaagga    3600
gaatctaagc attttagact ttttttttata aatagactta ttttcctttg taatgtattg    3660 gcctttagt gagtaaggct gggcagaggg tgcttacaac cttgactccc tttctccctg    3720
gacttgatct gctgtttcag aggctaggtt gtttctgtgg gtgccttatc agggctggga    3780
```

```
tacttctgat tctggcttcc ttcctgcccc accctcccga ccccagtccc cctgatcctg    3840
ctagaggcat gtctccttgc gtgtctaaag gtccctcatc ctgtttgttt taggaatcct    3900
ggtctcagga cctcatggaa gaagaggggg agagagttac aggttggaca tgatgcacac    3960 tatgggccc cagcgacgtg tctggttgag ctcaggaat atggttctta gccagtttct    4020
tggtgatatc cagtggcact tgtaatggcg tcttcattca gttcatgcag ggcaaaggct    4080
tactgataaa cttgagtctg ccctcgtatg agggtgtata cctggcctcc ctctgaggct    4140
ggtgactcct ccctgctggg gccccacagg tgaggcagaa cagctagagg gcctccccgc    4200
ctgcccgcct ggctggcta gctcgcctct cctgtgcgta tgggaacacc tagcacgtgc    4260
tggatgggct gcctctgact cagaggcatg gccggatttg gcaactcaaa accaccttgc    4320
ctcagctgat cagagtttct gtggaattct gtttgttaaa tcaaattagc tggtctctga    4380
attaaggggg agacgacctt ctctaagatg aacagggttc gccccagtcc tcctgcctgg    4440
agacagttga tgtgtcatgc agagctctta cttctccagc aacactcttc agtacataat    4500
aagcttaact gataaacaga atatttagaa aggtgagact tgggcttacc attgggttta    4560
aatcataggg acctagggcg agggttcagg gcttctctgg agcagatatt gtcaagttca    4620
tggccttagg tagcatgtat ctggtcttaa ctctgattgt agcaaaagtt ctgagaggag    4680
ctgagccctg ttgtgggcca ttaaagaaca gggtcctcag gccctgcccg cttcctgtcc    4740 actgcccct cccatcccc agcccagccg agggaatccc gtgggttgct tacctaccta    4800
taaggtggtt tataagctgc tgtcctggcc actgcattca aattccaatg tgtacttcat    4860
agtgtaaaaa tttatattat tgtgaggttt tttgtctttt tttttttttt ttttttttgg    4920
tatattgctg tatctacttt aacttccaga aataaacgtt atataggaac cgtaaaaa     4978

<210> SEQ ID NO 12
<211> LENGTH: 4520
<212> TYPE: DNA
<213> ORGANISM: Mus <mouse, genus>
<220> FEATURE:
<223> OTHER INFORMATION: Mouse Stat3 (NM_213659.3)

<400> SEQUENCE: 12
aattatgcat ggaggcgtgt cttggccagt ggcggctggg tggggattgg ctggagggc      60 tgtaattcag cggtttccgg agctgcagtg tagacaggga gggggaacct ggggttccga    120
cgtcgcggcg gagggaacga gccctaaccg gatcgctgag gtacaacccc gctcggtgtc    180
gcctgaccgc gtcggctagg agaggccagg cggcctcgg gagcccagca gctcgcgcct    240
ggagtcagcg caggccggcc agtcgggcct cagccccgga gacagtcgag acccctgact    300
gcagcaggat ggctcagtgg aaccagctgc agcagctgga cacacgctac ctggagcagc    360
tgcaccagct gtacagcgac agcttcccca tggagctgcg gcagttcctg gcaccttgga    420
ttgagagtca agactgggca tatgcagcca gcaaagagtc acatgccacg ttggtgtttc    480
ataatctctt gggtgaaatt gaccagcaat atagccgatt cctgcaagag tccaatgtcc    540
tctatcagca caaccttcga agaatcaagc agtttctgca gagcaggtat cttgagaagc    600
caatggaaat tgcccggatc gtggcccgat gcctgtggga agagtctcgc ctcctccaga    660
cggcagccac ggcagcccag caaggggcc aggccaacca cccaacagcc gccgtagtga    720
cagagaagca gcagatgttg gagcagcatc ttcaggatgt ccggaagcga gtgcaggatc    780
tagaacagaa aatgaaggtg gtggagaacc tccaggacga ctttgattc aactacaaaa    840
```

```
ccctcaagag ccaaggagac atgcaggatc tgaatggaaa caaccagtct gtgaccagac    900
agaagatgca gcagctggaa cagatgctca cagccctgga ccagatgcgg agaagcattg    960
tgagtgagct ggcggggctc ttgtcagcaa tggagtacgt gcagaagaca ctgactgatg   1020
aagagctggc tgactggaag aggcggcagc agatcgcgtg catcggaggc cctcccaaca   1080
tctgcctgga ccgtctggaa aactggataa cttcattagc agaatctcaa cttcagaccc   1140
gccaacaaat taagaaactg gaggagctgc agcagaaagt gtcctacaag ggcgacccta   1200
tcgtgcagca ccggcccatg ctggaggaga ggatcgtgga gctgttcaga aacttaatga   1260
agagtgcctt cgtggtggag cggcagccct gcatgcccat gcacccggac cggcccttag   1320
tcatcaagac tggtgtccag tttaccacga aagtcaggtt gctggtcaaa tttcctgagt   1380
tgaattatca gcttaaaatt aaagtgtgca ttgataaaga ctctggggat gttgctgccc   1440
tcagagggtc tcggaaattt aacattctgg gcacgaacac aaaagtgatg aacatggagg   1500
agtctaacaa cggcagcctg tctgcagagt tcaagcacct gacccttagg gagcagagat   1560
gtgggaatgg aggccgtgcc aattgtgatg cctccttgat cgtgactgag gagctgcacc   1620
tgatcacctt cgagactgag gtgtaccacc aaggcctcaa gattgaccta gagacccact   1680
ccttgccagt tgtggtgatc tccaacatct gtcagatgcc aaatgcttgg gcatcaatcc   1740
tgtggtataa catgctgacc aataacccca gaacgtgaa cttcttcact aagccgccaa   1800
ttggaacctg gaccaagtg gccgaggtgc tcagctggca gttctcgtcc accaccaagc   1860
gggggctgag catcgagcag ctgacaacgc tggctgagaa gctcctaggg cctggtgtga   1920
actactcagg gtgtcagatc acatgggcta aattctgcaa agaaaacatg gctggcaagg   1980
gcttctcctt ctgggtctgg ctagacaata tcatcgacct tgtgaaaaag tatatcttgg   2040
ccctttggaa tgaagggtac atcatggggt tcatcagcaa ggagcgggag cgggccatcc   2100
taagcacaaa gccccgggc accttcctac tgcgcttcag cgagagcagc aaagaaggag   2160
gggtcacttt cacttgggtg aaaaggaca tcagtggcaa gacccagatc cagtctgtag   2220
agccatacac caagcagcag ctgaacaaca tgtcatttgc tgaaatcatc atgggctata   2280
agatcatgga tgcgaccaac atcctggtgt ctccacttgt ctacctctac cccgacattc   2340
ccaaggagga ggcatttgga aagtactgta ggcccgagag ccaggagcac cccgaagccg   2400
acccaggtag tgctgccccg tacctgaaga ccaagttcat ctgtgtgaca ccaacgacct   2460
gcagcaatac cattgacctg ccgatgtccc cccgcacttt agattcattg atgcagtttg   2520
gaaataacgg tgaaggtgct gagccctcag caggagggca gtttgagtcg ctcacgtttg   2580
acatggatct gacctcggag tgtgctacct ccccatgtg aggagctgaa accagaagct   2640
gcagagacgt gacttgagac acctgccccg tgctccaccc ctaagcagcc gaaccccata   2700
tcgtctgaaa ctcctaactt tgtggttcca gattttttt tttaatttcc tacttctgct   2760
atctttgggc aatctgggca ctttttaaaa tagagaaatg agtgagtgtg ggtgataaac   2820
tgttatgtaa agaggagagc acctctgagt ctggggatgg ggctgagagc agaagggagc   2880
aaggggaaca cctcctgtcc tgcccgcctg ccctcctttt tcagcagctc ggggttggtt   2940
gttagacaag tgcctcctgg tgcccatggc atcctgttgc cccactctgt gagctgatac   3000
cccaggctgg gaactcctgg ctctgcactt tcaaccttgc taatatccac atagaagcta   3060
ggactaagcc cagaggttcc tctttaaatt aaaaaaaaaa aaaataagaa ttaagggca   3120
aaacacactg acacagcata gccttttcat atcaaggaat actcagttaa cagcctctcc   3180
agcgctgtct tcaggctgat catctatata aaccctggaa tggttgcaga tcaaatctgt   3240
```

-continued

| | | | |
|---|---|---|---|
| aaaagagatc | cgagagctgt | ggcttggcct | ctggttcaaa | cacaaaggct | agagagaacc | 3300 |
| tagatatccc | tgggttttgt | ttacccagta | tgcttgtcgg | ttggaggtgt | gaggtaggcc | 3360 |
| aagggcactg | gaaagccttt | gtcatcaccc | tactccctcc | ccaacccaga | ctccagaccc | 3420 |
| tgtttcaggg | tcagcctgcc | ctgtgggtgc | cttactgggc | ctagggtcaa | cctgccttcc | 3480 |
| tttcccactt | gaccttgctg | gtagtatgtc | cccttcccat | gtccaaaggc | cctctgtcct | 3540 |
| gcttctattg | ggaatccctg | cctcaggacc | ttgtgtcgag | agggattgcc | ttacaggttt | 3600 |
| gaacctgcct | cagactacag | gccctcagca | aagctcaggg | agtatggtcc | ttattctatg | 3660 |
| cgcttggttc | ccagggatat | ctgtaaccac | agggcaaaag | ctgacatata | ctccaggtct | 3720 |
| gccctcatat | gagtggtgta | ttcttggcct | ccctgagac | tggcaactgt | ctgctcccca | 3780 |
| ttgggtctcc | caggtgaggt | ggaacacagt | tcctgcacct | actgtggcct | ccatgtcgct | 3840 |
| tgcttgcttc | gctcactcag | cttactggaa | cactgagtgt | tcaaggcaag | cctttcctga | 3900 |
| cagaggcatg | gctagattca | gtgactcaaa | gccacctcat | tcagctgatc | agtgtctgtg | 3960 |
| gaattgtttc | cttccagtta | accagtgtct | gaattaaggg | cagtgaggac | attgtctcca | 4020 |
| agacgaactg | cttgccttga | ccaccccagc | cttctgcttc | gagacagtta | ctgctctccc | 4080 |
| accccatcaa | tgttctttag | ttatacaata | agctgaactt | ataaactgaa | agggtattta | 4140 |
| ggaaggcaag | gcttgggcat | ttttatggct | ttcaatcctg | ggacccagg | aacaaggtga | 4200 |
| gggcttctct | ggggctggtg | ttgtacctca | ggggctctgg | gaagtctgtg | tgcctgggtt | 4260 |
| aaccacccat | agtgagcccc | tggaactgcc | cactttccct | ctccttggcc | ccacttggcc | 4320 |
| ccagcctcac | ccagcctgca | gactgcttag | cctttcagtg | cagtggcttg | tgttctggcc | 4380 |
| actgcactca | gattccaatg | taaactttct | agtgtaaaaa | tttatattat | tgtgggttgt | 4440 |
| tttttgttgt | tgtttgtttt | tgtatattgc | tgtaactact | ttaacttcca | gaaataaaga | 4500 |
| ttatatagga | actgtctggc | | | | | 4520 |

<210> SEQ ID NO 13
<211> LENGTH: 8332
<212> TYPE: DNA
<213> ORGANISM: Homo sapiens
<220> FEATURE:
<223> OTHER INFORMATION: Human TCF4 (NM_001083962.1)

<400> SEQUENCE: 13

| | | | |
|---|---|---|---|
| gtgtgtggat | gtgtgagtga | gagggaacga | gagtaagaga | aagaaagaag | tgaggggatg | 60 |
| taaactcgaa | taaatttcaa | agtgcctccg | agggatgcaa | cgggcaaaaa | ctgaactgtt | 120 |
| caggcttcag | attgtaactg | acgatctgag | gaaaaatgag | gtgctcgatg | aattttcgtt | 180 |
| tgtatttttt | ggcgaggcgg | gggaggtgtt | gagatttttt | ttttttcccc | tcggggtggg | 240 |
| tgcgaggggg | atgcatccta | gcctgcccga | cccggagcaa | gtcgcgtctc | cccgccggag | 300 |
| ccccccacc | catttctttg | ctgaacttgc | aattccgtgc | gcctcggcgt | gtttcccct | 360 |
| cccccttcc | ctccgtcccc | tcccctcccc | ggagaagaga | gttggtgtta | agagtcaggg | 420 |
| atcttggctg | tgtgtctgcg | gatctgtagt | ggcggcggcg | gcggcggcgg | cggggaggca | 480 |
| gcaggcgcgg | gagcgggcgc | aggagcaggc | ggcggcggtg | gcggcggcgg | ttagacatga | 540 |
| acgccgcctc | ggcgccggcg | gtgcacggag | agcccttct | cgcgcgcggg | cggtttgtgt | 600 |
| gattttgcta | aaatgcatca | ccaacagcga | atggctgcct | tagggacgga | caaagagctg | 660 |
| agtgatttac | tggatttcag | tgcgatgttt | tcacctcctg | tgagcagtgg | gaaaaatgga | 720 |

```
ccaacttctt tggcaagtgg acattttact ggctcaaatg tagaagacag aagtagctca    780
gggtcctggg ggaatggagg acatccaagc ccgtccagga actatggaga tgggactccc    840
tatgaccaca tgaccagcag ggaccttggg tcacatgaca atctctctcc acctttgtc    900 aattccagaa tacaaagtaa aacagaaagg ggctcatact catcttatgg gagagaatca    960
aacttacagg gttgccacca gcagagtctc cttggaggtg acatggatat gggcaaccca   1020 ggaaccettt cgcccaccaa acctggttcc cagtactatc agtattctag caataatccc   1080
cgaaggaggc ctcttcacag tagtgccatg gaggtacaga caaagaaagt tcgaaaagtt   1140
cctccaggtt tgccatcttc agtctatgct ccatcagcaa gcactgccga ctacaatagg   1200
gactcgccag gctatccttc ctccaaacca gcaaccagca ctttccctag ctccttcttc   1260
atgcaagatg ccatcacag cagtgaccct tggagctcct ccagtgggat gaatcagcct   1320
ggctatgcag gaatgttggg caactcttct catattccac agtccagcag ctactgtagc   1380
ctgcatccac atgaacgttt gagctatcca tcacactcct cagcagacat caattccagt   1440
cttcctccga tgtccacttt ccatcgtagt ggtacaaacc attacagcac ctcttcctgt   1500
acgcctcctg ccaacgggac agacagtata atggcaaata gaggaagcgg ggcagccggc   1560
agctcccaga ctgagatgc tctggggaaa gcacttgctt cgatctattc tccagatcac   1620
actaacaaca gcttttcatc aaaccettca actcctgttg gctctcctcc atctctctca   1680
gcaggcacag ctgtttggtc tagaaatgga ggacaggcct catcgtctcc taattatgaa   1740
ggacccttac actctttgca aagccgaatt gaagatcgtt tagaaagact ggatgatgct   1800
attcatgttc tccggaacca tgcagtgggc ccatccacag ctatgcctgg tggtcatggg   1860
gacatgcatg gaatcattgg accttctcat aatggagcca tgggtggtct gggctcaggg   1920 tatgaaccg gccttctttc agccaacaga cattcactca tggtggggac ccatcgtgaa   1980
gatggcgtgg ccctgagagg cagccattct cttctgccaa accaggttcc ggttccacag   2040
cttcctgtcc agtctgcgac ttcccctgac ctgaacccac cccaggaccc ttacagaggc   2100
atgccaccag gactacaggg gcagagtgtc tcctctggca gctctgagat caaatccgat   2160
gacgagggtc atgagaacct gcaagacacg aaatcttcgg aggacaagaa attagatgac   2220
gacaagaagg atatcaaatc aattactagg tcaagatcta gcaataatga cgatgaggac   2280
ctgacaccag agcagaaggc agagcgtgag aaggagcgga ggatggccaa caatgcccga   2340
gagcgtctgc gggtccgtga catcaacgag gctttcaaag agctcggccg catggtgcag   2400
ctccacctca agagtgacaa gccccagacc aagctcctga tcctccacca ggcggtggcc   2460
gtcatcctca gtctggagca gcaagtccga gaaaggaatc tgaatccgaa agctgcgtgt   2520
ctgaaaagaa gggaggaaga gaaggtgtcc tcagagcctc cccctctctc cttggccggc   2580
ccacaccctg gaatgggaga cgcatcgaat cacatgggac agatgtaaaa gggtccaagt   2640
tgccacattg cttcattaaa acaagagacc acttccttaa cagctgtatt atcttaaacc   2700
cacataaaca cttctcctta accccatttt ttgtaatata agacaagtct gagtagttat   2760
gaatcgcaga cgcaagaggt ttcagcattc ccaattatca aaaacagaa aaacaaaaaa   2820 aagaaagaaa aaagtgcaac ttgagggacg actttcttta acatatcatt cagaatgtgc   2880
aaagcagtat gtacaggctg agacacagcc cagagactga acggcaatct ttccacactg   2940
tggaacaatg catttgtgcc taaacttctt ttggaaaaaa aaaatataat taatttgtaa   3000
gtctgaaaaa aaaatattta atttaaaaaa aattgtaaac ttgcaataat gaaaagtgt   3060 acttctgaag aaaactacat gaacgttttt gttggtattc aagtcagcta gtgtttataa   3120
```

-continued

```
ttactggata ttgaattagg ggaagctcgg ctgccctagt aacaaaacca gcaaacgtcc    3180
tgatgacaac gaagtgatga cattagccat tccttagggt aggaggaaca gatggatctt    3240
atagacctat gacaaatata tatataaata tatatataaa tatatattaa aaatttagtg    3300
actatggtaa gcttttgttc atttgtttca gactttttc tcctgtaaaa aaatagtact    3360 gattaactt tttaaaagaa agattttact gtaaatatgg atttttttt ttttggtctt    3420 atttctgtcc ctttccctgg tttgttatcg taacctgtag tgccaactct gcttccagag    3480
gggtagtgca ggatgaaatg ctgaccctga tgttgcttct cattcataaa taagtagaaa    3540
gttgtttctc cagtctttg ggaacacagg acttaaaagt cacatcatgt gtagatatta    3600
caagcagcat taccaagaca tggcaaaaag agtttgtctg aattgtaatg ttgcgtttgt    3660
gaacctattc tgggattttc agaggtacaa ggttagaatg ctacaatgtt accactgtgc    3720
cttccaatgt ttatatcatc ggaaacataa cataatcaaa gtggctgtga tttaacaaaa    3780
tgattaaagt gttacctacc tgtgtagccg aagtagtgtg cagtgaggcg tttctgaata    3840
catggtcaga ttttggaaa aaaacaaaaa caaaaaaaac aagtaaagtt caaaaaccgt    3900
caaatgagaa aattgcaagt agtgtgacag agctgattga ttttgttgct ttcttgattt    3960
tttttttcaa aatgggttta ctaaaatgta gatgacttaa ctgcctcctc cttcgtctga    4020
aaaatgccaa tattcaatca tcatgcagca ttataacaag ccttataagt cctaaagcat    4080
taagttgcac ttttttgagg aggggtagtg cagtatttct ctggccagta tgaatgaagt    4140
ttatacttac catatttgat agaaacatag atcaagctat ggcacagcga ctcatcagat    4200
agctagcttt gacgtctggg cacaattgaa ccaacttcca tcgtgaatct ttataatgat    4260
tgactttggt gtatagtgca gtaaacaaat agtgctccta gttaagtatt tgtcagcatc    4320
cttttgtctc taacttgttt ctattttac agccacacaa ttcttggcat gtattaagaa    4380
aaaaaaaaat ccctgttcaa gtagtttttc cacctatcag cactgagtaa atgccataaa    4440
tccattgaaa tggtctaaat gttccatctg ttctcctgtt ttgccagtta tatagtaatg    4500
aaatacattt gtaaatttta tgcaacaaat ggcaaacgta tcattatttt gaaattgtgt    4560
atgtaaaagt tatatttta catgtagact cttgttatta tgtgttttaa tacattgtat    4620
cagtttttgt tttttttaa aaactgtggt ttaaaagaa gtctcattta aatgaaatag    4680
ctacaagaat cagaatttta tgttcatttc tgaaatgta agaacaaata agatagttac    4740
cacgtggtca tcttttacaa acccataaac attttgatta gctgtgtgtg tgttgaaaaa    4800
ctgtaaatat gttcagtagc gataaaacta aaataacttt gatttgttga taagttccta    4860
aaatgtggag gtggattaaa accttaggag aatagcagaa atcaaacttc atgaaaagtt    4920
attttggggc tttcctgtga aatgtatgaa caaagaggct cagagaagga catgaaagac    4980
aataatgtat actctctcct cctccctgaa taatgaaaac catgtgtatt tgttccctcc    5040
gtatgttaaa gatttccttt tagtggtaca ttctgcactc attttgtata gtctaccaag    5100
gcgggtatcc ctaggaacaa tattatatag gaagcaggta tactctgatc acattcagga    5160
taagtgtaca gaagaaaata cggtgtttac tctttaggga actggaaaca ctccctgcat    5220
tgatgtacat tttaagaatg gcacttttga tacatgttat cataaggtg cttaatagag    5280 ctgaattaaa gttttcaaa tctgtaaaca aagcaaaaaa gtaaattgta gtcatttgat    5340
tattttttaa attggtgctt tatatttgt tctcactcag agtaaaagct gcaatttatt    5400
gttcaccagc tttgatgtat tcattactca gtaatgcaat acctctattg ttgaattccc    5460
```

```
tttggaaata agtgaaaatt ctaacggcca ctgaaagctg ctcgctaggt tttgcttggt      5520
ggagaaacat aatctgcacc tatccatatt aattgggttg tatccccatt aaaaaagaaa      5580 aaagggaat gtggccttttt tagtgtgttt tttattgttg ttgttttgta attatcaaac      5640
ccaggtaaga tattggtatc ctgcactgga ttttcaaatg aagttcagca gaagacagtt      5700
aagattaaag tactatacaa aaatttcaaa agggtccata ctacgctatc tgtatgacga      5760
cacttaggct ggggatctct ttcagaaact cggactttaa aagcaacttg gagcagttga      5820
tccacctcca cattcaagta atttatgaat atgcagaata gggatctgtt catctagaaa      5880
tttttaccat ttgtcttctg tgtagctgca aggaacacta atgtttatac aactgtcagt      5940
ccacccagtg gtgcaactgg ttctgattca gtcttccgat tccttttat ttttcacttt       6000 ttcctatttc tgaatttttt tttttatttg tgatcttgat tttgatgagg ggttggggag      6060
tggggaggga gtcgaaccaa gacttggagt taagaggatt ttcatctttt gcatccaaca      6120
ggcagaatat gatctgtgtc caaaagtgaa cttgagtcag gaatgaatca atttcagcat      6180
aaacaagcac aaaaatttag tctgctggct gactggaagc aaaaaagtca agatggaata      6240
tgatgaattc caacacaatg gggcaccaag gcctttaggc ctctcttttt attttgcttt      6300
ggttttgttt gttttttctt agagacatgc tctttctcat gggacttgaa gtggactcat      6360
ctttgtgcag tgctggtttt gccatactca tttcaagtat tatagacata tgtaatggtg      6420
aaaatatatg aactgtggcc ttttcattc ttgttacttg tgatgcaatt aagtgaagat       6480 aagaaaaaa aaaaaaaagc agagatttac catgtatcag tgcctggctt tttgttataa      6540
agctttgttt gtctagtgct cttttgctat aaaatagact gtagtacacc ctagtaggaa      6600 aaaaaaaaa ctaaatttaa aaataaaaaa tatatttggc ttattttttcg caggagcaat      6660 ccttttatac catgaatatt acaaaaaaat tgtcagattc tgaatatttc ttctttgtag      6720 attttttggaa tcattatgag taaaagtttg ttactttatt ttactatttta aagatgtta    6780 ttttaccatg tgttaccaag atgaaactgt atgggtagct tttttgtttg ttttttgttt      6840 tgttttttgtt tttgtttttg ttttagttg taggtcgcag cggggaaatt ttttgcgact      6900
gtacacatag ctgcagcatt aaaaacttaa aaaaattgtt aaaaaaaaaa aagggaaaa      6960 catttcaaaa aaaaaaaaa agataaacag ttacaccttg ttttcaatgt gtggctgagt      7020
gcctcgattt tttcatgttt ttggtgtatt tctgatttgt agaagtgtcc aaacaggttg      7080
tgtgctggag ttccttcaag acaaaaacaa acccagcttg gtcaaggcca ttacctgttt      7140
cccatctgta gttattcgat gaagtcatgt acatgaccgt tctgtagcaa taaatgtgcc      7200 attttttataa actgtttctg acacttgttt catttcattt tgcattgtcc atatagctat      7260
gattctcttc tgtaagtaaa acgcatctat atttcattt ccaagtgttg gaggtattga       7320
cagcttaaca aacaaaacat acaaaaaaaa tcacaaaaac aaattgaaaa gcaaagcaca      7380
tgattgatca aggaagagat gcccttaatg aaaatggaac gggatgcatg caaaacaaaa      7440
agaaaactgt ctagaggatt aactaattga aggaatataa ttaatgtgtg tgtaacactg      7500
aagctatgca tttgaagagc tctgaactgc accagtgttt tcggttgtgc tgcaggttgc      7560
taagtcaagt cagccttaac cttttgcacc agttggtcgg ctgtttggca gaacattctc      7620
agatcttttc agtcaaaaat ctaagatgat ttattttgta tcactttgtt aaaagctgaa      7680
tattgttaac tacagttaat attaacactg tatttatact ttctcaaact acatccgccc      7740
caccacttct ggttgcctct gttgactatt aatccagatg taaacaacca gatgtttttt      7800
tctaacttgt acaaactgac gtgtgtcaac tatcatggaa ggaaaaaaat gtacagatta      7860
```

| | |
|---|---|
| aaattattca gtgttatgta ctgtaagtta atattttgt agaatggaca tcaatctact | 7920 |
| ttgcaaaatt tggaggctat ttcaacattg cactgtagaa atgtaaagta atgtatgcaa | 7980 |
| tgtaaaggaa agcccgcggt agctgagcgc ttcataacag aatgttctaa tcaagtacgt | 8040 |
| ggtatttggg gatgtctcca atattgctct tgtattcttt ctaattgggt ttagtgacta | 8100 |
| gttgaaggaa aatgttataa cgccatttgg ttcacatgtg aagtgccctc catagccaaa | 8160 |
| tgttgggatt ttttttttt tcgttttgg ttggactgtt tgcagatatt taaattttat | 8220 |
| gaaatttcca agatttgg ttgataaccc ccttttacct tctaaatgat ttgagatgtt | 8280 |
| cttatgttct tactgtgtgt tttaaatata tataaaagag ccacaagcat tt | 8332 |

<210> SEQ ID NO 14
<211> LENGTH: 7462
<212> TYPE: DNA
<213> ORGANISM: Mus <mouse, genus>
<220> FEATURE:
<223> OTHER INFORMATION: Mouse Tcf4 (NM_013685.2)

<400> SEQUENCE: 14

| | |
|---|---|
| ggagcagccg cggccgcagc gccttctctt tataagccgc agtgcccgga tgtgaatgga | 60 |
| ttacaatgta tctttcaggg aaacctatta ttatcaatgt gactcctcgg gggagtcaat | 120 |
| gatggtgttg gggaggagga tgatgatgag acgcctctaa acttggaaca agtttaggac | 180 |
| tttgaaagag aagagaaaaa aaatacaac caacaagacc gaagaacaat tataactatc | 240 |
| cagtgttgat tatttttata aacaatacga aaaagttgtc ggatttttt ttttaatgat | 300 |
| tacttttgg ggggagggaa ttttgttaca gtttgatgat ggaaaatgca aaaaccgagc | 360 |
| caggtgcata atcttgtaat ctgtggctaa ccctggaaca ggactgactt ctatttaaaa | 420 |
| tactctttg ggggaacact catgtgagac actaagttct tgcagaagat ttttgtctct | 480 |
| ctttttaaag tctctttcct tggaatattg tgagcatatt tgtggccatt gaaggtttgt | 540 |
| gtgattttgc taaaatgcat caccaacagc gaatggctgc cttagggacg acaaagagc | 600 |
| tgagtgattt actggatttc agtgcgatgt tttcgcctcc tgtaagcagt gggaaaaatg | 660 |
| gaccaacttc tttggcgagt ggacatttca ctggctcaaa tgtagaagac agaagtagct | 720 |
| cagggtcctg gggaactgga ggccatccaa gcccgtccag gaactatgga gatgggactc | 780 |
| cctatgacca catgactagc agggatcttg ggtcacatga caatctctct ccacctttg | 840 |
| tcaattccag aatacaaagt aaaacagaaa ggggctcata ctcatcttat gggagagaaa | 900 |
| acgttcaggg ttgccaccag cagagtctcc tcggagggga catggatatg gcaatccag | 960 |
| gaacccttc gcccaccaaa cctggctccc agtactatca gtattcaagc aataatgccc | 1020 |
| gccggaggcc tcttcacagt agtgccatgg aggtacagac aaagaaagtc cgaaaagttc | 1080 |
| ctccgggttt gccgtcttca gtctacgctc cttcagccag cactgccgac tacaacaggg | 1140 |
| actcgccagg ctatccttcc tccaagccag cagccagcac tttccctagc tccttcttca | 1200 |
| tgcaagatgg ccatcacagc agcgaccctt ggagctcctc cagcgggatg aatcagcccg | 1260 |
| gctacgagg gatgctgggc aattcttctc atatcccaca gtccagcagc tactgtagcc | 1320 |
| tgcatccaca tgaacgtttg agctatccat cccactcctc ggcagacatc aactccagtc | 1380 |
| ttcctccgat gtccacgttc catcgtagtg gcacaaacca ttacagcacc tcttcctgca | 1440 |
| cacccctgc caacggaaca gacagtataa tggcaaacag aggaactggg gcagcaggca | 1500 |
| gctcgcagac tggagacgct ctagggaaag ccctagcttc gatctattct cctgaccaca | 1560 |

```
cgaacaacag cttttcctcc aatccttcaa ctcctgtggg ctcccctcct tcactctcag    1620
caggcacagc tgtttggtct agaaatggag gacaggcctc gtcatctccc aattatgaag    1680
gacccttgca ctcactgcaa agccgaatcg aagaccgttt ggaaagactg gacgatgcga    1740
ttcatgttct ccggaaccac gcagtgggcc cgtccacagc tgtgcctggt ggccatgggg    1800
acatgcatgg gatcatggga ccctcccaca acggagcgat gggtagcctg ggctcagggt    1860
acggaactag tcttctctca gccaacagac actcgctcat ggttggggcc caccgtgaag    1920
atggcgtggc tctgagaggc agccattctc tcctgccaaa ccaggttccg gtcccacaac    1980
ttccggtcca gtctgcaact tcccctgact gaacccacc ccaagaccct tacagaggga     2040
tgccaccagg cctccagggc cagagcgtgt cttctggtag ctctgagatc aaatccgacg    2100
acgagggcga tgagaacctg caagacacaa aatcttctga ggacaagaaa ttagatgacg    2160
acaagaagga tatcaaatca attactaggt caagatctag caataacgat gatgaggacc    2220
tgaccccaga gcagaaggct gagcgcgaga aggaacggag gatggccaat aatgcccgtg    2280
agcgcctgag ggtccgagat atcaacgagg ctttcaagga gcttggccgt atggtgcagc    2340
tccacctgaa gagcgacaag ccccagacca agctcctgat tctccaccag gccgtggctg    2400
tcatcctcag cctggagcag caagttcgag aaaggaatct gaacccgaaa gctgcctgtc    2460
tgaaaagaag ggaggaagag aaggtgtcct cagagcctcc cccactctcc ttggctggcc    2520
cacaccctgg gatgggagac gcagcgaatc acatgggaca gatgtgaaaa ggtccaagtt    2580
gctaccttgc ttcattaaac aagagaccac ttccttaaca gctgtattac cctaaaccca    2640
cataaacact gctccttaac cccgtttttt tttgtaatat aagacaagtc tgagtagtta    2700
tgaatcgcag acgcaagagg tttcagcatt cccaattatc aaaaaacaga aaaacaaaca    2760
aaaaaatgaa tgaagaaag aaagaaagaa aaaatgcaa cttgagggac gacttctta     2820 acatatcact ctgaatgtgc gaagcggtat gtacaggctg agacacagcc cagagactga    2880
atggcaatcc tcccacactg tggagcaatg catttgtgcc taaacttctt ttggaaaaaa    2940
aaaatataat taatttgtaa gtctgaaaaa aatatttaat ttaaaaaaaa attgtaaact    3000
tgcaataatg aaaaagtgta cttctgaaga aaacgacatg aacgttttg ttggtattca     3060 cgtcagctag tgtttctaat taccggatat tgaataggg aagcccggct gccctcgtaa     3120 caaaccagc aaacgtcctg atggcaacga agtgatgaca ttagccattc cttagggtag    3180
gagggacaga tggatgttat agacctatga caaatatata tataaatata tatataaata    3240
tatattaaaa atttagtgac tatggtaagc ttttgttgat ttgtttcaga cttttttctc    3300
ctgtaaaaaa atagtactga ttaacttttt taaaagaaag attttactgt aaatatggat    3360
tttttttttt gtctgatttt tgtcccttcc cccggtttgt tatcgtaacc tgtagtgcca    3420
actctgcttc cggaggggca gtgcaggacg aaatgctgac cctgaagttg cttctcattc    3480
acaaatagta aaaagttgtt tctccagtct tttgggaaca caggacttaa aagtcacatc    3540
atgtgtagga attacatgca gcattgcccg ggcgaggcaa aaagcgtttg tctggcttgt    3600
ggcgctgccc ttgttaccct cccctgggat tttcagaggt acacggttag aatgctacaa    3660
tgttaccact gtgccttcca atgtttatat catcggaaac ataacataat caaagtggct    3720
gtgatttaac aaaaaaaacg attcaagtgt tacctacctg tgtagccgaa gtagtgtgca    3780
gtgaccgaga cgtttctgaa tacatggtca gatttttttt ggaaaaaata caaaaattaa    3840 aaaaaaaaa aaaaagaaa aaagaaaaa aaaactaaaa aagaaagtca agttcaaaaa     3900
ccgtcaaatg agaaaattgc aaggagtgtg acagagctga ttgattttg ttgctttctt    3960
```

```
gatttttttt tcaaaatggg tttactaaaa agtagatgac ttacctgcct cctccttcgt    4020
ctgaaaaaaa aaaaaaatgc caaccaatca tgcagcatta taacaagcct tataagcccc    4080
aaagcattaa gttgcacttt tgtgaggagg ggtaacgcag tattctctct ggccagtatg    4140
agtgaagttt atacttaaca tttgatagaa acatagatca aactacggca cagcaactca    4200
tcagatagct agcgttgact ctgggcacaa ttgaaccaat tcccatcgta agtctttcca    4260
acaatggact ttggtgtgta gtgcagtgaa cacataggac tcctacgtaa gcatttgtca    4320 gcatccttt  gtctctaact cggttctgtt ttgacagcca cacaatcttg gcatgtatta    4380
aggaaaaaaa aaatccctgt tgaagtagtt tttccaccta tcagcactga gtaaatgcca    4440
taactccgcg gaaatggtct aaataccca  tttgttgtcc tgaactacca gttacatagt    4500
gacgaaacac atctgtaaat tttatgcaac caatggcaaa cctatcatta ttttgaaact    4560
gtgtatgtaa aagttatatt tttacatgta gactcttgtt attatgtgtt ttaatacatt    4620
gtatcagttt tttgttttt  tttaaactgt gtggttttaa aaagtcattt aaatgaaata    4680
gtgagctaca agaatctgaa atttatgttc atttctgaaa atgtaagaac aaataagata    4740
gttaccacgt ggtcaccttt tacaaaccca tgaacatttt gattagctgt gtgcatgtgt    4800
gtgcgtgtgt gctcttgcgc gtgtgtgtgt gtgtgtgtgt gtgtgtatgt gtgtgtgttg    4860
aaaattgtaa atatgttcag tagcgataaa actaaaatgc tttgatttgt tgagaagttc    4920
ctaaaatgtg gaggtggatt gaaaatgtag gggaatagca ggaatcaaat ctcataaaaa    4980
gttcttcggg gactttgctg tgatgcggtg gcacaaaggt gctccaagaa gggcaaagaa    5040
gaaagacagt aacttcccct cctccctgaa cgatggaaaa catgtgtacg tggtctctca    5100
ccatgttaaa gatttctttt ccgtgataca ttctgcactc attttgtata gtctgccaag    5160
gcgggtatcc ctaggaacaa tattattata taggaaacag gtatcgtccg atcacattca    5220
ggagaagcgt atagaaaaga atatggtgtt tactctttag ggaactggaa atcctcccg    5280 cattgatgga tatcttcaga gtggcacttt tgatacatgt tatcataaag gtgcttacta    5340
aagcagaatc aaagtttttc aactctgtaa acaaagcaaa aaattaaatt tttaaattaa    5400
atcatttgag atttttttt  tcaattggtg ctttatatt  ttgttctcac tcggacagag    5460
aaaaagctgc aatttcatgt tctcaccagc tttgatgtat tcattacttg gtaatgtaat    5520
atggctattg tcaaattcct tttggaaata agcaaaagac tccccaaagg ccagcagcag    5580
ctgctggcta ctttctgctt ggtgcggaaa cctgatctga ccctctttgt agtaatcagg    5640
tgtatctcca gttttaaaaa gaaggagaaa ggaaatgtgg ccgttttaac gtgttggttt    5700
tgttttgttt tgttttgttt tgttttcctt gttgttattt tgtaattatc aaacccaggt    5760
aagatattgg tattcctgca ctggattttt gaaagaaact tagcagaagt caggattaaa    5820
atactacaca aacatttcat aagtgttcat cctatactag acatacacga aggcggtgag    5880
gcttaggtgc aggatcggtt taagagactt tgaaagcaac ttggaacagt tgatccacct    5940
ccacattaaa gtaaattatg aatatgcaga attagggatc tgtccatctt ggagttgtta    6000
ctctttttgt cttctgtatg gcagtgatga acactaatgc tttgacagct ttcagcccac    6060
ccagtggtcc aactgattcc aattcagtct tccgattcct ggttttgttt tgtctttcca    6120
cttttttttt cctatcttga ttttattgtt attgttattg ttattattat tattattatt    6180
attattaata ttcatgatgt ttgttttgat gagggattgg gaagtgggag ggagtcgaac    6240
tgagactagg ggctgagagg atttttttt  ttccatcttt gcatccaaca ggcagaatat    6300
```

| | |
|---|---|
| ggtctgtgtc caaaacggaa cttaagtcag gaaggaaacc attcagcata acaagcaca | 6360 |
| acatgtagtc tgccggctga ctggaagcat aaataaataa ataaataaca catacggagg | 6420 |
| tgaagatgga atgtgctgga ttccaagaca atggggcacc aaggcctgag ggcctcctct | 6480 |
| tgactttgct ttggttatgt ttgttttctt tagagatgtc ttttctcatg ggacttgaag | 6540 |
| tgactcatct ctgtgcagta ctggtttcgc catatgctca tttcaagtat tatagacata | 6600 |
| tgtaatggtg aaatatatga actgtggcct ttttcattct tgttacttgt gatgcaatta | 6660 |
| agtgaagata agaaaaaaaa aaagcagaga tttaccatgt atcagtgcct ggcttttttgt | 6720 |
| tataaagctt cgtctgtcta gtgctctttt tgctataaaa aatagactgt agtacaccct | 6780 |
| agtaggaaaa aaaaactaaa tttaaaaata aaaaatata tttggcttat ttttcgcagg | 6840 |
| agtaatcctt ttataccatg gatattcaa aaaaaatgt cagattctga gtatttcttc | 6900 |
| tttgtagatt tttggaatca ttatgagtaa agtttgtta ctttattttg ctatttaaaa | 6960 |
| gatgttattt taccatgtgt tactgaaagg aaactgtatg gtagagcttc tgtttgtttt | 7020 |
| tgttttcagg ttttttttgt ttgtttgttt ttagttgtag gtcgcagtat gaactttttt | 7080 |
| tttgtttctc gttatgtttt gttttgtttt tgcgactgta cacatagctg cagcattaaa | 7140 |
| aacttttaaa aaattgttta aaaaaaaaga aaaaagggga aaacgttta aaaaaaaaga | 7200 |
| taaacagtta caccttgttt tcaatgtgtg gctgagtgcc tcaattttt catgtttttg | 7260 |
| gtgtatttct gatttgtaga agtgtccaaa caggttgtgt gccggacttc cttcaagagg | 7320 |
| cccacagccc agcttggtct agacctgttc ccatctgtag ttactcgatg aagtcatgta | 7380 |
| catgaccgtt ctgtagcaat aaatgtgcca tttttataaa ctgtctctga cactttttttc | 7440 |
| atttcacctc tcgtgcacat ag | 7462 |

<210> SEQ ID NO 15
<211> LENGTH: 6317
<212> TYPE: DNA
<213> ORGANISM: Homo sapiens
<220> FEATURE:
<223> OTHER INFORMATION: Human IKZF1 (NM_006060.5)

<400> SEQUENCE: 15

| | |
|---|---|
| attgtgaaag aaagctggga agagctccgc ggccaagtta gcaggacact ctaacaagtg | 60 |
| actgcgcggc ccgcgcccgg ggcggtgact gcggcaagcc ccctgggtcc ccgcgcggcg | 120 |
| catcccagcc tgggcgggac gctcggccgc ggcgaggcgg gcaagcctgg cagggcagag | 180 |
| ggagccccgg ctccgaggtt gctcttcgca cccgaggatc agtcttggcc ccaaagcgcg | 240 |
| acgcacaaat ccacataacc tgaggaccat ggatgctgat gagggtcaag acatgtccca | 300 |
| agtttcaggg aaggaaagcc cccctgtaag cgatactcca gatgagggcg atgagcccat | 360 |
| gccgatcccc gaggacctct ccaccacctc gggaggacag caaagctcca gagtgacag | 420 |
| agtcgtggcc agtaatgtta agtagagac tcagagtgat gaagagaatg gcgtgcctg | 480 |
| tgaaatgaat ggggaagaat gtgcggagga tttacgaatg cttgatgcct cgggagagaa | 540 |
| aatgaatggc tcccacaggg accaaggcag ctcggctttg tcgggagttg gaggcattcg | 600 |
| acttcctaac ggaaaactaa agtgtgatat ctgtgggatc atttgcatcg ggcccaatgt | 660 |
| gctcatggtt cacaaaagaa gccacactgg agaacggccc ttccagtgca atcagtgcgg | 720 |
| ggcctcattc acccagaagg gcaacctgct ccggcacatc aagctgcatt ccggggagaa | 780 |
| gcccttcaaa tgccacctct gcaactacgc ctgccgccgg agggacgccc tcactggcca | 840 |
| cctgaggacg cactccgttg gtaaaccctca caaatgtgga tattgtggcc gaagctataa | 900 |

```
acagcgaagc tctttagagg aacataaaga gcgctgccac aactacttgg aaagcatggg      960
ccttccgggc acactgtacc cagtcattaa agaagaaact aatcacagtg aaatggcaga     1020
agacctgtgc aagataggat cagagagatc tctcgtgctg acagactag caagtaacgt      1080
cgccaaacgt aagagctcta tgcctcagaa atttcttggg acaagggcc tgtccgacac      1140
gccctacgac agcagcgcca gctacgagaa ggagaacgaa atgatgaagt cccacgtgat     1200
ggaccaagcc atcaacaacg ccatcaacta cctgggggcc gagtccctgc gcccgctggt     1260
gcagacgccc ccgggcggtt ccgaggtggt cccggtcatc agcccgatgt accagctgca     1320
caagccgctc gcggagggca ccccgcgctc caaccactcg gcccaggaca gcgccgtgga     1380
gaacctgctg ctgctctcca aggccaagtt ggtgccctcg gagcgcgagg cgtccccgag     1440
caacagctgc caagactcca cggacaccga gagcaacaac gaggagcagc gcagcggtct     1500
catctacctg accaaccaca tcgccccgca cgcgcgcaac gggctgtcgc tcaaggagga     1560
gcaccgcgcc tacgacctgc tgcgcgccgc ctccgagaac tcgcaggacg cgctccgcgt     1620
ggtcagcacc agcggggagc agatgaaggt gtacaagtgc gaacactgcc gggtgctctt     1680
cctggatcac gtcatgtaca ccatccacat gggctgccac ggcttccgtg atccttttga     1740
gtgcaacatg tgcggctacc acagccagga ccggtacgag ttctcgtcgc acataacgcg     1800
aggggagcac cgcttccaca tgagctaaag ccctcccgcg ccccaccccc agaccccgag     1860
ccacccagg aaaagcacaa ggactgccgc cttctcgctc ccgccagcag catagactgg     1920
actgaccag acaatgttgt gtttggattt gtaactgttt tttgtttttt gtttgagttg      1980
gttgattggg gtttgatttg cttttgaaaa gatttttatt tttagaggca gggctgcatt    2040
gggagcatcc agaactgcta ccttcctaga tgtttcccca gaccgctggc tgagattccc     2100
tcacctgtcg cttcctagaa tccccttctc caaacgatta gtctaaattt tcagagagaa     2160
atagataaaa cacgccacag cctgggaagg agcgtgctct accctgtgct aagcacgggg     2220
ttcgcgcacc aggtgtcttt ttccagtccc cagaagcaga gagcacagcc cctgctgtgt     2280
gggtctgcag gtgagcagac aggacaggtg tgccgccacc caagtgccaa gacacagcag     2340
ggccaacaac ctgtgcccag ccagcttcg agctacatgc atctagggcg agagagctgc      2400
acttgtgaga gaaatactac ttttcaagtca tattctgcgt aggaaaatga attggttggg    2460
gaaagtcgtg tctgtcagac tgccctgggt ggagggagac gccgggctag agcctttggg     2520
atcgtcctgg attcactggc tttgcggagg ctgctcagat ggcctgagcc tcccgaggct     2580
tgctgccccg taggaggaga ctgtcttccc gtgggcatat ctggggagcc ctgttccccg     2640
ctttttcact cccatacctt taatggcccc caaaatctgt cactacaatt taaacaccag     2700
tcccgaaatt tggatcttct ttcttttga atctctcaaa cggcaacatt cctcagaaac      2760
caaagcttta tttcaaatct cttccttccc tggctggttc catctagtac cagaggcctc    2820
ttttcctgaa gaaatccaat cctagccctc attttaatta tgtacatctg tttgtagcca    2880
caagcctgaa tttctcagtg ttggtaagtt tctttaccta ccctcactat atattattct    2940
cgttttaaaa cccataaagg agtgatttag aacagtcatt aattttcaac tcaatgaaat    3000
atgtgaagcc cagcatctct gttgctaaca cacagagctc acctgtttga aaccaagctt     3060
tcaaacatgt tgaagctctt tactgtaaag gcaagccagc atgtgtgtcc acacatacat     3120
aggatggctg gctctgcacc tgtaggatat tggaatgcac agggcaattg agggactgag    3180
ccagaccttc ggagagtaat gccaccagat cccctaggaa agaggaggca aatggcactg    3240
```

```
caggtgagaa ccccgcccat ccgtgctatg acatggaggc actgaagccc gaggaaggtg      3300
tgtggagatt ctaatcccaa caagcaaggg tctccttcaa gattaatgct atcaatcatt      3360
aaggtcatta ctctcaacca cctaggcaat gaagaatata ccatttcaaa tatttacagt      3420
acttgtcttc accaacactg tcccaaggtg aaatgaagca acagagagga aattgtacat      3480
aagtacctca gcatttaatc caaacagggg ttcttagtct cagcactatg acattttggg      3540
ctgactactt atttgttagg cgggagctct cctgtgcatt gtaggataat tagcagtatc      3600
cctggtggct acccaataga cgccagtagc accccgaatt gacaacccaa actctccaga      3660
catcaccaac tgtcccctgc gaggagaaat cactcctggg ggagaaccac tgacccaaat      3720
gaattctaaa ccaatcaaat gtctgggaag ccctccaaga aaaaaatag aaaagcactt       3780 gaagaatatt cccaatattc ccggtcagca gtatcaaggc tgacttgtgt tcatgtggag      3840
tcattataaa ttctataaat caattattcc ccttcggtct taaaaatata tttcctcata      3900
aacatttgag ttttgttgaa agatggagt ttacaaagat accattcttg agtcatggat       3960
ttctctgctc acagaagggt gtggcatttg gaaacgggaa taaacaaaat tgctgcacca     4020
atgcactgag tgaaggaaga gagacagagg atcaagggct ttagacagca ctccttcaat     4080
atgcaatcac agagaaagat gcgccttatc caagttaata tctctaaggt gagagccttc     4140
ttagagtcag tttgttgcaa atttcaccta ctctgttctt ttccatccat cccctgagt     4200 cagttggttg aagggagtta ttttttcaag tggaattcaa acaaagctca aaccagaact     4260
gtaaatagtg attgcaggaa ttcttttcta aactgctttg cccttttcctc tcactgcctt    4320 ttatagccaa tataaatgtc tctttgcaca ccttttgttg tggttttata ttgtaacacc     4380
atttttcttt gaaactattg tatttaaagt aaggtttcat attatgtcag caagtaatta    4440
acttatgttt aaaaggtggc catatcatgt accaaaagtt gctgaagttt ctcttctagc    4500
tggtaaagta ggagtttgca tgacttcaca ctttttttgc gtagtttctt ctgttgtatg    4560
atggcgtgag tgtgtgtctt gggtaccgct gtgtactact gtgtgcctag attccatgca    4620
ctctcgttgt gtttgaagta aatattggag accggagggt aacaggttgg cctgttgatt    4680
acagctagta atcgctgtgt cttgttccgc ccctcccctg acaccccagc ttcccaggat    4740
gtggaaagcc tggatctcag ctccttgccc catatccctt ctgtaatttg tacctaaaga    4800
gtgtgattat cctaattcaa gagtcactaa aactcatcac attatcattg catatcagca    4860
aagggtaaag tcctagcacc aattgcttca cataccagca tgttccattt ccaatttaga    4920
attagccaca taataaaatc ttagaatctt ccttgagaaa gagctgcctg agatgtagtt    4980
ttgttatatg gttccccacc gaccattttt gtgcttttt cttgttttgt tttgttttga     5040
ctgcactgtg agttttgtag tgtcctcttc ttgccaaaac aaacgcgaga tgaactggac    5100
ttatgtagac aaatcgtgat gccagtgtat ccttccttc ttcagttcca gcaataatga    5160
atggtcaact tttttaaaat ctagatctct ctcattcatt tcaatgtatt tttactttaa    5220
gatgaaccaa aattattaga cttatttaag atgtacaggc atcagaaaaa agaagcacat    5280
aatgcttttg gtgcgatggc actcactgtg aacatgtgta accacatatt aatatgcaat    5340
attgttccca atactttcta atacagtttt ttataatgtt gtgtgtggtg attgttcagg    5400
tcgaatctgt tgtatccagt acagctttag gtcttcagct gcccttctgg cgagtacatg    5460
cacaggattg taaatgagaa atgcagtcat atttccagtc tgcctctatg atgatgttaa    5520
attattgctg tttagctgtg aacaagggat gtaccactgg aggaatagag tatcctttg    5580 tacacatttt gaaatgcttc ttctgtagtg atagaacaaa taaatgcaac gaatactctg    5640
```

| | |
|---|---|
| tctgccctat cccgtgaagt ccacactggc gtaagagaag gcccagcaga gcaggaatct | 5700 |
| gcctagactt tctcccaatg agatcccaat atgagaggga gaagagatgg gcctcaggac | 5760 |
| agctgcaata ccacttggga acacatgtgg tgtcttgatg tggccagcgc agcagttcag | 5820 |
| cacaacgtac ctcccatcta caacagtgct ggacgtggga attctaagtc ccagtcttga | 5880 |
| gggtgggtgg agatggaggg caacaagaga tacatttcca gttctccact gcagcatgct | 5940 |
| tcagtcattc tgtgagtggc cgggcccagg gccctcacaa tttcactacc ttgtcttta | 6000 |
| catagtcata agaattatcc tcaacatagc cttttgacgc tgtaaatctt gagtattcat | 6060 |
| ttaccctttt ctgatctcct ggaaacagct gcctgcctgc attgcacttc tcttcccgag | 6120 |
| gagtggggta aatttaaaag tcaagttata gtttggatgt tagtatagaa ttttgaaatt | 6180 |
| gggaattaaa aatcaggact ggggactggg agaccaaaaa tttctgatcc catttctgat | 6240 |
| ggatgtgtca cacctttct gtcaaaataa aatgtcttgg aggttatgac tccttggtga | 6300 |
| aaaaaaaaaa aaaaaaa | 6317 |

<210> SEQ ID NO 16
<211> LENGTH: 5451
<212> TYPE: DNA
<213> ORGANISM: Mus <mouse, genus>
<220> FEATURE:
<223> OTHER INFORMATION: Mouse Ikzf1 (NM_001025597.2)

<400> SEQUENCE: 16

| | |
|---|---|
| gtcagggtcc cgaagccgcg tgccgtgcgc gcaggccggg tgggctgtgg gacaagccga | 60 |
| gcgggaggcg agtcgcaagc gccaacccaa agtttgcacg gtgcggggcg aggggcgcgc | 120 |
| gctccgggct gccgcaggtg gcggcgcggt gagcccgggc caggtgcccc ggcagcgggg | 180 |
| cggcgctgtc gtgcgggaca gccgggctgc caggggctcg gagccgggtc ggagcccgcg | 240 |
| gggggcgggg agtgtggcga gaaatgggga caatgcgag tgagcaactt gaggaagtca | 300 |
| ttgtgaaaga aagctgggaa ttgctccgca gccaacttag cagggcactc taacaagtgc | 360 |
| ctgcgcggcc gcgcccgggc cggggacagg ggcagcccgg cgcagtacag cccatcccgg | 420 |
| gacgctcggc cgcggctgcc ggagaccccgg taggtcccgc ggggtgcagg agcccccaga | 480 |
| tccccggctg ctcttcgcgc cccaggatca ttcttggccc ccaaagcgcg gcgcacaaat | 540 |
| ccacataacc tgaagacaat ggatgtcgat gagggtcaag acatgtccca agtttcagga | 600 |
| aaggagagcc ccccagtcag tgacactcca gatgaagggg atgagcccat gcctgtccct | 660 |
| gaggacctgt ccactacctc tggagcacag cagaactcca agagtgatcg aggcatggcc | 720 |
| agtaatgtta agtagagac tcagagtgat gaagagaatg ggcgtgcctg tgaaatgaat | 780 |
| ggggaagaat gtgcagagga tttacgaatg cttgatgcct cggagagaa aatgaatggc | 840 |
| tcccacaggg accaaggcag ctcggctttg tcaggagttg gaggcattcg acttcctaac | 900 |
| ggaaaactaa agtgtgatat ctgtgggatc gtttgcatcg gcccaatgt gctcatggtt | 960 |
| cacaaaagaa gtcatactgg tgaacggcct ttccagtgca accagtgtgg ggcctccttt | 1020 |
| acccagaaag gcaacctcct gcggcacatc aagctgcact cgggtgagaa gcccttcaaa | 1080 |
| tgccatcttt gcaactatgc ctgccgccgg agggacgccc tcaccggcca cctgaggacg | 1140 |
| cactccgttg gtaagcctca caaatgtgga tattgtggcc ggagctataa acagcgaagc | 1200 |
| tctttagagg agcataaaga gcgatgccac aactacttgg aaagcatggg ccttccgggc | 1260 |
| atgtacccag tcattaagga agaaactaac cacaacgaga tggcagaaga cctgtgcaag | 1320 |

```
ataggagcag agaggtccct tgtcctggac aggctggcaa gcaatgtcgc caaacgtaag    1380
agctctatgc ctcagaaatt tcttggagac aagtgcctgt cagacatgcc ctatgacagt    1440
gccaactatg agaaggagga tatgatgaca tcccacgtga tggaccaggc catcaacaat    1500
gccatcaact acctggggc tgagtccctg cgcccattgg tgcagacacc cccggtagc     1560
tccgaggtgg tgccagtcat cagctccatg taccagctgc acaagccccc ctcagatggc    1620
cccccacgt ccaaccattc agcacaggac gccgtggata acttgctgct gctgtccaag    1680
gccaagtctg tgtcatcgga gcgagaggcc tccccgagca cagctgcca agactccaca    1740
gatacagaga gcaacgcgga ggaacagcgc agcggcctta tctacctaac caaccacatc    1800
aacccgcatg cacgcaatgg gctggctctc aaggaggagc agcgcgccta cgaggtgctg    1860
agggcggcct cagagaactc gcaggatgcc ttccgtgtgg tcagcacgag tggcgagcag    1920
ctgaaggtgt acaagtgcga acactgccgc gtgctcttcc tggatcacgt catgtatacc    1980
attcacatgg gctgccatgg ctttcgggat ccctttgagt gtaacatgtg tggttatcac    2040
agccaggaca ggtacgagtt ctcatcccat atcacgcggg gggagcatcg ttaccacctg    2100
agctaaaccc agccaggccc cactgaagca caaagatagc tggttatgcc tccttcccgg    2160
cagctggacc cacagcggac aatgttggga gtggatttgc aggcagcatt tgttcttta    2220
tgttggttgt ttggcgtttg atttgcgttg aagataagt ttttaatgtt agtgacagga    2280
ttgcattgca tcaggaacat tcacaacatc catccttcta gccagttttg ttcactggta    2340
gctgaggttt cccggatatg tggcttccta acactctccc cacccacccc acccccaaa    2400
acagagcctg aatcttcatg aagtgaataa aacaattatc caagaaggag taaggtggat    2460
cttgccctaa gcagagttta tgccacaaag attctccaaa tcccccaaga cagcacagcc    2520
actgggttg agccatctca gggagctctg caggtgagcc agaggaccag atataaggca    2580
gctggggagg agcagggaca tcagcctgtg cagagaccaa ggccaaaggt tgaactttga    2640
aagactatta agtcatatat tgtatggcaa tatggtgtct ggacaagttg tgcaatgtgc    2700
tgaagggaag ggattggaga gccttgaaga ctcttcttca tttgcctgat caacccgacc    2760
tccagagggt tgttgcccca gtaagacgag ctcagtgctc ttgtgatcat ttttctctta    2820
tcgtttccat gccgttgatg gccctgaagc tcatcactgc attttagaac ccaatcctga    2880
aattgggacc ttttttttaa acttctgata ctgtaaaact tcttggaagc caaagctttc    2940
ttccaagccc catcctcagt tatcctggtt cctgttcttc cccgagctga tagtaccagg    3000
acctgttatt ccacaaaagc acaggcatcc gtcacttcaa ttcaatccct gttcagatta    3060
tagatatgga ctttgctatc ttgataaatg tcttctctat gttattttgt ctgaaaaacc    3120
tataaaacca ttattaagaa tgaccatttt tagatggaag aaatgagccc agcatctcag    3180
tggctaaaac acaaaatatc catgctttta aacaaaattg ttaaatattc cgaagctctc    3240
tagtataaac accaagtagc atgtgttttc acataaagaa gacaggggcc atgcaacctt    3300
tatcaagtgg aggtattaga atgttgtaat gtttggagac acagtgtgac cagtacaggt    3360
tcccagagag gaatgcccac catatcacag aaaggtagag gtgggatctg gtatagccag    3420
accaagacag ggatgtcacg ctgaagccaa gtcagttagc tgaagattct caacaggaag    3480
gcctctctta agagtcagta atagggttgt taccatccac cacctcaaca aaacaaaaag    3540
cttataattg taaatgttta cagcactgtc ttcgcagaaa ctttctgagg tgattccaaa    3600
gaactagagg ggagatggtc tataacagct cttgaagtaa acgaggttct tagtctcagc    3660
tctcctgaca tatagggctt gatcattact ggtagggatt gttctgtgaa ttgcttacta    3720
```

```
ctacccctgg tctctcccca gtagatgcca ggaacattct agctgatacc taactgtctt    3780
cccaggtgtt cgagggagca aaccactgat ctaaactcta aacgctgaag tacgcaggtt    3840
ttctaaaaat gacaagccct tgaaaccttt cccagtaggc agcctcgagc tggacttgtg    3900
tctttggaat gctgatgaat tctatagatc agcattgcaa atacacttca aatacgtctg    3960
agttcaagtg cagggactga gttcaccaag gtgtgaaatg tgctcaaaaa gttcaaaagt    4020 gtgtgttct ttgtttctaa acattgtgg catcttttc atttgttct aaacttttt         4080 ttttagaaac aaatgaagca cttggaaagt gaaagtaaaa ttacaaatat aaggatttac    4140
actgaagaga gaaaaatttt aggaactata gctgtgaaaa gattttgttc aaaaggcagg    4200
ctagccttac ccaaattcat atatggcagg tgtcaacctc ccaagcttac agttagcagg    4260
cagcttttgc tcactcatcc ttagccatga gagccattaa gtgtggtcca agaaagatgg    4320
ctccaaaccc taccccgac ccaccagtgg tattcagaga ttaaagcaga attgtaaata    4380
gtggcttcag gagctcttt ttagaatgct ttgccccttc ctctcactgc ctttttagc    4440 caatataaat gtcaatttgc acaccttttg ttgtggtttt atattgtaac agcattttt    4500 tgaaactatt gtatttaaga taaggtttca tattatgtcc acaagtaatt aaattatgtt    4560
tgaaggtggc tatatgctgt atcagaagtt gatgatgttt ttcttagct ggtaaaggag    4620 ggttttgcat gacctcactg tttgttctgt ggttgttct gttgtatgat gtgtgtcttg    4680
agttttgctg tgtgatgaag tgcgctgaga ttccagtgcc ctcaagttgt gtttttaagta    4740 gctatcagag gcaagagggt tcctaagagc aggttgacct gttggcgaca gatggcaatc    4800
accatttctc attccttctt ctccctgtta ccccagcttc ctgtcccagg tcccttctgt    4860
gattcttacc ttagtgtgca tgtgtgtctg tcctggtgag agtcaggagc atcgatatgt    4920
tatcattgca ttatcaccaa gggcacgcac agcctagcac ctgttgcttc agataccgtc    4980
acactctgtt tccaatttag atacaaccac ataataaaat gttagagtct tcaatgggaa    5040
gcagaggtgc ttgttataaa gatgggggct tatgcttgtg tcacattttg tgttcttttc    5100
ttcttttgtt tggttttaac ttaattgtga cccttgtaac atcatcttgc caaaaaaaaa    5160 aaaaagttg aactggattt atgtagacat gtcaagacgt actatctatt tctttgtcag    5220
ttatagcaat aagagtggat aaactctaaa atccagatct cccacaatga acatccgtgt    5280
tctttctatg atttttcttt ctttatggtg agccacaatt aaacttgaga tgtacagcca    5340
cccaaaccca ggaagctcat gtgcatctgg tgctatggca ctcactgtga ataagtgtga    5400
ccagatatta atatgcaata ttgtttccaa tcctttctaa tacattttt c              5451
```

<210> SEQ ID NO 17
<211> LENGTH: 1402
<212> TYPE: DNA
<213> ORGANISM: Homo sapiens
<220> FEATURE:
<223> OTHER INFORMATION: Human ID2 (NM_002166.4)

<400> SEQUENCE: 17

```
ggggacgaag ggaagctcca gcgtgtggcc ccggcgagtg cggataaaag ccgccccgcc      60
gggctcgggc ttcattctga gccgagcccg gtgccaagcg cagctagctc agcaggcggc     120
agcggcggcc tgagcttcag ggcagccagc tccctcccgg tctcgccttc cctcgcggtc     180
agcatgaaag ccttcagtcc cgtgaggtcc gttaggaaaa acagcctgtc ggaccacagc     240
ctgggcatct cccggagcaa aacccctgtg gacgacccga tgagcctgct atacaacatg     300
```

| | |
|---|---|
| aacgactgct actccaagct caaggagctg gtgcccagca tcccccagaa caagaaggtg | 360 |
| agcaagatgg aaatcctgca gcacgtcatc gactacatct tggacctgca gatcgccctg | 420 |
| gactcgcatc ccactattgt cagcctgcat caccagagac ccgggcagaa ccaggcgtcc | 480 |
| aggacgccgc tgaccaccct caacacggat atcagcatcc tgtccttgca ggcttctgaa | 540 |
| ttcccttctg agttaatgtc aaatgacagc aaagcactgt gtggctgaat aagcggtgtt | 600 |
| catgatttct tttattcttt gcacaacaac aacaacaaca aattcacgga atcttttaag | 660 |
| tgctgaactt attttttcaac catttcacaa ggaggacaag ttgaatggac cttttttaaaa | 720 |
| agaaaaaaaa aatggaagga aaactaagaa tgatcatctt cccagggtgt tctcttactt | 780 |
| ggactgtgat attcgttatt tatgaaaaag acttttaaat gccctttctg cagttggaag | 840 |
| gttttctttta tatactattc ccaccatggg gagcgaaaac gttaaaatca caggaattg | 900 |
| cccaatctaa gcagactttg cctttttttca aggtggagc gtgaataccca gaaggatcca | 960 |
| gtattcagtc acttaaatga agtctttttgg tcagaaatta cctttttgac acaagcctac | 1020 |
| tgaatgctgt gtatatattt atatataaat atatctattt gagtgaaacc ttgtgaactc | 1080 |
| tttaattaga gttttcttgt atagtggcag agatgtctat ttctgcattc aaaagtgtaa | 1140 |
| tgatgtactt attcatgcta aactttttat aaaagtttag ttgtaaactt aaccctttta | 1200 |
| tacaaaataa atcaagtgtg tttattgaat ggtgattgcc tgcttttatttt cagaggacca | 1260 |
| gtgctttgat ttttattatg ctatgttata actgaaccca aataaataca agttcaaatt | 1320 |
| tatgtagact gtataagatt ataataaaac atgtctgaag tcaaaaaaaa aaaaaaaaa | 1380 |
| aaaaaaaaaa aaaaaaaaaaa aa | 1402 |

<210> SEQ ID NO 18
<211> LENGTH: 1289
<212> TYPE: DNA
<213> ORGANISM: Mus <mouse, genus>
<220> FEATURE:
<223> OTHER INFORMATION: Mouse Id2 (NM_010496.3)

<400> SEQUENCE: 18

| | |
|---|---|
| tcattctgaa ccgagcctgg tgccgcgcag tcagctcagc cccctgtggc ggctccctcc | 60 |
| cggtcttcct cctacgagca gcatgaaagc cttcagtccg gtgaggtccg ttaggaaaaa | 120 |
| cagcctgtcg gaccacagct tgggcatctc ccggagcaaa accccggtgg acgacccgat | 180 |
| gagtctgctc tacaacatga cgactgcta ctccaagctc aaggaactgg tgcccagcat | 240 |
| ccccccagaac aagaaggtga ccaagatgga aatcctgcag cacgtcatcg attacatctt | 300 |
| ggacctgcag atcgccctgg actcgcatcc cactatcgtc agcctgcatc accagagacc | 360 |
| tggacagaac caggcgtcca ggacgccgct gaccaccctg aacacggaca tcagcatcct | 420 |
| gtccttgcag gcatctgaat tcccttctga gcttatgtcg aatgatagca aagtactctg | 480 |
| tggctaaata aatggcattt ggggacttttt ttttttcttt ttactttctc ttttttcttttt | 540 |
| gcacaagaag aagtctacaa gatcttttaa gacttttgtt atcagccatt tcaccaggag | 600 |
| aacacgttga atggaccttt ttaaaaagaa agcggaagga aaactaagga tgatcgtctt | 660 |
| gcccaggtgt cgttctccgg cctggactgt gataccgtta tttatgagag actttcagtg | 720 |
| ccctttctac agttggaagg ttttctttat atactattcc caccatgggg agcgaaaacg | 780 |
| ttaaaaaaaa aagaaaaaaaa tcacaaggaa ttgcccaatg taagcagact ttgccttttc | 840 |
| acaaggtgg agcgtgaata ccagaaggac ccagtattcg gttacttaaa tgaagtcttc | 900 |
| ggtcagaaat ggcctttttg acacgagcct actgaatgct gtgtatatat ttatatataa | 960 |

```
atatatatat attgagtgaa ccttgtggac tctttaatta gagttttctt gtatagtggc    1020
agaaataacc tatttctgca ttaaaatgta atgacgtact tatgctaaac ttttataaa     1080 agtttagttg taaacttaac cctttttatac aaaataaatc aagtgtgttt attgaatgtt   1140
gattgcttgc tttatttcag acaaccagtg ctttgatttt ttttatgcta tgttataact   1200
gaacccaaat aaataccagt tcaaatttat gtagactgta ttaagattat aataaaatgt   1260
gtctgacatc aaaaaaaaaa aaaaaaaa                                       1289
```

<210> SEQ ID NO 19
<211> LENGTH: 5946
<212> TYPE: DNA
<213> ORGANISM: Homo sapiens
<220> FEATURE:
<223> OTHER INFORMATION: Human BCL11A (NM_022893.3)

<400> SEQUENCE: 19

```
tttttttttt tttttgctt  aaaaaaaagc catgacggct ctcccacaat tcatcttccc    60
tgcgccatct ttgtattatt tctaatttat tttggatgtc aaaaggcact gatgaagata   120
ttttctctgg agtctccttc tttctaaccc ggctctcccg atgtgaaccg agccgtcgtc   180
cgcccgccgc cgccgccgcc gccgccgccg cccgccccgc agcccaccat gtctcgccgc   240
aagcaaggca acccccagca cttaagcaaa cgggaattct cgcccgagcc tcttgaagcc   300
attcttacag atgatgaacc agaccacggc ccgttgggag ctccagaagg ggatcatgac   360
ctcctcacct gtgggcagtg ccagatgaac ttcccattgg gggacattct tatttttatc   420
gagcacaaac ggaaacaatg caatggcagc ctctgcttag aaaaagctgt ggataagcca   480 ccttccccctt caccaatcga gatgaaaaaa gcatccaatc ccgtggaggt tggcatccag   540
gtcacgccag aggatgacga ttgtttatca acgtcatcta gaggaatttg ccccaaacag   600
gaacacatag cagataaact tctgcactgg aggggcctct cctcccctcg ttctgcacat   660
ggagctctaa tccccacgcc tgggatgagt gcagaatatg ccccgcaggg tatttgtaaa   720
gatgagccca gcagctacac atgtacaact tgcaaacagc cattcaccag tgcatggttt   780
ctcttgcaac acgcacagaa cactcatgga ttaagaatct acttagaaag cgaacacgga   840
agtcccctga ccccgcgggt tggtatccct tcaggactag gtgcagaatg tccttcccag   900
ccacctctcc atgggattca tattgcagac aataacccct taacctgct aagaatacca    960 ggatcagtat cgagagaggc ttccggcctg gcagaagggc gctttccacc cactccccc   1020 ctgtttagtc caccaccgag acatcacttg gaccccacc gcatagagcg cctggggggcg   1080 gaagagatgg ccctggccac ccatcacccg agtgcctttg caggggtgct gcggttgaat   1140
ccaatggcta tggagcctcc cgccatggat ttctctagga gacttagaga gctggcaggg   1200
aacacgtcta gcccaccgct gtccccaggc cggcccagcc ctatgcaaag gttactgcaa   1260
ccattccagc caggtagcaa gccgccttc ctggcgacgc cccccctccc tcctctgcaa   1320
tccgcccctc ctccctccca gccccggtc aagtccaagt catgcgagtt ctgcggcaag   1380
acgttcaaat tcagagcaa cctggtggtg caccggcgca gccacacggg cgagaagccc   1440
tacaagtgca acctgtgcga ccacgcgtgc acccaggcca gcaagctgaa gcgccacatg   1500
aagacgcaca tgcacaaatc gtcccccatg acggtcaagt ccgacgacgg tctctccacc   1560
gccagctccc cggaacccgg caccagcgac ttggtgggca gcgccagcag cgcgctcaag   1620
tccgtggtgg ccaagttcaa gagcgagaac gaccccaacc tgatcccgga gaacgggggac   1680
```

```
gaggaggaag aggaggacga cgaggaagag gaagaagagg aggaagagga ggaggaggag    1740
ctgacggaga gcgagagggt ggactacggc ttcgggctga gcctggaggc ggcgcgccac    1800
cacgagaaca gctcgcgggg cgcggtcgtg ggcgtgggcg acgagagccg cgccctgccc    1860
gacgtcatgc agggcatggt gctcagctcc atgcagcact tcagcgaggc cttccaccag    1920
gtcctgggcg agaagcataa gcgcggccac ctggccgagg ccgagggcca cagggacact    1980
tgcgacgaag actcggtggc cggcgagtcg gaccgcatag acgatggcac tgttaatggc    2040
cgcggctgct ccccgggcga gtcggcctcg gggggcctgt ccaaaaagct gctgctgggc    2100
agccccagct cgctgagccc cttctctaag cgcatcaagc tcgagaagga gttcgacctg    2160
cccccggccg cgatgcccaa cacggagaac gtgtactcgc agtggctcgc cggctacgcg    2220
gcctccaggc agctcaaaga tcccttcctt agcttcggag actccagaca atcgccttt    2280 gcctcctcgt cggagcactc ctcggagaac gggagtttgc gcttctccac accgcccggg    2340
gagctggacg gagggatctc ggggcgcagc ggcacgggaa gtggagggag cacgcccat    2400 attagtggtc cgggcccggg caggcccagc tcaaaagagg gcagacgcag cgacacttgt    2460
gagtactgtg ggaaagtctt caagaactgt agcaatctca ctgtccacag gagaagccac    2520
acgggcgaaa ggccttataa atgcgagctg tgcaactatg cctgtgccca gagtagcaag    2580
ctcaccaggc acatgaaaac gcatggccag gtggggaagg acgtttacaa atgtgaaatt    2640
tgtaagatgc ctttagcgt gtacagtacc ctggagaaac acatgaaaaa atggcacagt    2700
gatcgagtgt tgaataatga tataaaaact gaatagaggt atattaatac ccctccctca    2760
ctcccacctg acacccccctt tttcaccact cccttcccc atcgccctcc agccccactc    2820
cctgtaggat ttttttctag tcccatgtga tttaaacaaa caaacaaaca aacagaagta    2880
acgaagctaa gaatatgaga gtgccttgtca ccagcacacc tgttttttt cttttcttt    2940 ttctttttc ttttccttt tttttttt tcctttatgt tctcaccgtt tgaatgcatg    3000
atctgtatgg ggcaatacta ttgcatttta cgcaaacttt gagccttct cttgtgcaat    3060 aatttacatg ttgtgtatgt tttttttaa acttagacag catgtatggt atgttatggc    3120 tatttaaat tgtccctaat tcgttgctga gcaaacatgt tgctgtttcc agttccgttc    3180
tgagagaaaa agagagagag agagaaaaag accatgctgc atacattctg taatacatat    3240
catgtacagt tttattttat aacgtgagga ggaaaaacag tctttggatt aaccctctat    3300
agacagaata gatagcactg aaaaaaaatc tctatgagct aaatgtctgt ctctaagggg    3360
ttaaatgtat caattggaaa ggaagaaaaa aggccttgaa ttgacaaatt aacagaaaaa    3420
cagaacaagt ttattctatc atttggtttt aaaatatgag tgccttggat ctattaaaac    3480
cacatcgatg gttctttcta cttgttataa acttgtagct taattcagca ttgggtgagg    3540
taataaacct taggaactag catataattc tatattgtat ttctcacaac aatggctacc    3600 taaaagatg acccattatg tcctagttaa tcatcatttt tcctttagtt taattttata    3660
aacaaaactg attataccag tataaaagct actttgctcc tggtgagagc ttaaagaaa    3720 tgggctgttt tgcccaaagt tttatttttt ttaaacaatg attaaattga atgtgtaatg    3780
tgcaaaagcc ctgaacgca attaaataca ctagtaagga gttcatttta tgaagatatt    3840
tgctttaata atgtcttttt aaaaatactg gcaccaaaag aaatagatcc agatctactt    3900
ggttgtcaag tggacaatca aatgataaac tttaagacct tgtataccat attgaaagga    3960
agaggctgac aataaggttt gacagagggg aacagaagaa aataatatga tttattagca    4020
caacgtggta ctatttgcca tttaaaacta gaacaggtat ataagctaat attgatacaa    4080
```

| | |
|---|---|
| tgatgattaa ctatgaattc ttaagacttg catttaaatg tgacattctt aaaaaaagaa | 4140 |
| gagaaagaat tttaagagta gcagtatata tgtctgtgct ccctaaaagt tgtacttcat | 4200 |
| ttcttttcca tacactgtgt gctatttgtg ttaacatgga agaggattca ttgtttttat | 4260 |
| ttttatttt ttaattttt ctttttatt aagctagcat ctgccccagt tggtgttcaa | 4320 |
| atagcacttg actctgcctg tgatatctgt atcttttctc taatcagaga tacagaggtt | 4380 |
| gagtataaaa taaacctgct cagataggac aattaagtgc actgtacaat tttcccagtt | 4440 |
| tacaggtcta tacttaaggg aaaagttgca agaatgctga aaaaaattg aacacaatct | 4500 |
| cattgaggag catttttaa aaactaaaaa aaaaaaaact ttgccagcca tttacttgac | 4560 |
| tattgagctt acttacttgg acgcaacatt gcaagcgctg tgaatggaaa cagaatacac | 4620 |
| ttaacataga aatgaatgat tgctttcgct tctacagtgc aaggatttt ttgtacaaaa | 4680 |
| ctttttaaa tataaatgtt aagaaaaatt tttttaaaa aacacttcat tatgtttagg | 4740 |
| ggggaactgc atttagggt tccattgtct tggtggtgtt acaagacttg ttatccattt | 4800 |
| aaaaatggta gtggaaattc tatgccttgg atacacaccg ctcttcaggt tgtaaaaaaa | 4860 |
| aaaaacatac attggggaaa ggtttaagat tatatagtac ttaaatatag gaaaatgcac | 4920 |
| actcatgttg attcctatgc taaaatacat ttatggtctt ttttctgtat ttctagaatg | 4980 |
| gtatttgaat taaatgttca tctagtgtta ggcactatag tatttatatt gaagcttgta | 5040 |
| tttttaactg ttgcttgttc tcttaaaagg tatcaatgta cctttttgg tagtggaaaa | 5100 |
| aaaaaagaca ggctgccaca gtatatttt ttaatttggc aggataatat agtgcaaatt | 5160 |
| atttgtatgc ttcaaaaaaa aaaaaagag agaaacaaaa aagtgtgaca ttacagatga | 5220 |
| gaagccatat aatggcggtt tgggggagcc tgctagaatg tcacatggat ggctgtcata | 5280 |
| ggggttgtac atatccttt ttgttccttt ttcctgctgc catactgtat gcagtactgc | 5340 |
| aagctaataa cgttgtttg ttatgtagtg tgcttttgt cccttccctt ctatcaccct | 5400 |
| acattccagc atcttacctt catatgcagt aaaagaaaga aagaaaaaaa aaggaaaaaa | 5460 |
| aaaaaaaaac caatgttttg cagttttttt cattgccaaa aactaaatgg tgctttatat | 5520 |
| ttagattgga aagaatttca tatgcaaagc atattaaaga gaaagcccgc tttagtcaat | 5580 |
| acttttttgt aaatggcaat gcagaatatt ttgttattgg cctttctat tcctgtaatg | 5640 |
| aaagctgttt gtcgtaactt gaaatttat cttttactat gggagtcact atttattatt | 5700 |
| gcttatgtgc cctgttcaaa acagaggcac ttaatttgat cttttatttt tctttgtttt | 5760 |
| tattttttt tttatttaga tgaccaaagg tcattacaac ctggcttttt attgtatttg | 5820 |
| tttctggtct tgttaagtt ctattggaaa accactgtc tgtgtttttt tggcagttgt | 5880 |
| ctgcattaac ctgttcatac acccattttg tcccttatt gaaaaaataa aaaaaattaa | 5940 |
| agtaca | 5946 |

<210> SEQ ID NO 20
<211> LENGTH: 3425
<212> TYPE: DNA
<213> ORGANISM: Mus <mouse, genus>
<220> FEATURE:
<223> OTHER INFORMATION: Mouse Bcl11a (NM_016707.3)

<400> SEQUENCE: 20

| | |
|---|---|
| gacgttcaag ttcgcaggga cgtcacgtcc gcacttgaac ttgcagctca gggggggcttt | 60 |
| tgccatttt ttcatctctc tctctccctc tatccctctt ctctcttcct ctctctcttt | 120 |

-continued

| | |
|---|---|
| tttttcctta aaaaaaaaaa agccatgacg gctctcccac aattcatctt ccctgcgcca | 180 |
| tctttgtatt atttctaatt tattttggat gtcaaaaggc actgatgaag atattttctc | 240 |
| tggagtctcc ttctttctaa cccggctctc ccgatgtgaa ccgagccgtc gtccgcacgc | 300 |
| cgccgccgcc gccgccgccc gccccgcagc ccaccatgtc tcgccgcaag caaggcaaac | 360 |
| cccagcactt aagcaaacgg gaattctcgc ccgaacctct tgaagccatt cttacagatg | 420 |
| atgaaccaga ccatggcccg ttgggagctc cagaagggga ccacgacctt ctcacctgtg | 480 |
| ggcagtgcca gatgaatttc ccactggggg acattcttat ttttatcgag cacaaacgga | 540 |
| aacaatgcaa tggcagcctc tgcttagaaa aaggtgtgga taagccgcct tccccttctc | 600 |
| ccatcgagat gaaaaaggca tccaatcctg tggaggttgg catccaggtc acgccagagg | 660 |
| atgacgattg tttatcaacg tcatctagag gaatttgccc caaacaggaa cacatagcag | 720 |
| ataaacttct gcactggagg ggcctgtcct ctcctcggtc tgcacacgga gctctaatcc | 780 |
| ccacgcccgg gatgagtgca gaatatgccc cgcagggtat ttgtaaagat gagcccagca | 840 |
| gctacacatg tacaacttgc aaacagccat tcaccagtgc atggtttctc ttgcaacacg | 900 |
| cacagaacac tcatggatta agaatctact tagaaagtga acacggaagt cccctgaccc | 960 |
| cgcgggttgg tatcccttca ggactaggtg cagaatgtcc ttcccagcca cctctccatg | 1020 |
| ggattcatat tgcagacaat aaccccttta acctgctaag aataccagga tcagtatcga | 1080 |
| gagaggcttc cggcctggca aagggcgct ttccacccac tccccccctg tttagtccac | 1140 |
| caccgagaca tcacttggac ccccaccgca tagagcgcct gggggcggaa gagatggccc | 1200 |
| tggccaccca tcacccgagt gccttttgaca gggtgctgcg gttgaatcca atggctatgg | 1260 |
| agcctcccgc catggatttc tctaggagac ttagagagct ggcagggaac acgtctagtc | 1320 |
| caccgctgtc cccaggccgg cccagtccta tgcaaaggtt actgcaacca ttccagccag | 1380 |
| gtagcaagcc acccttcctg gcgacgcccc cctccctcc tctgcaatcc gccctcctc | 1440 |
| cctcccaacc cccggtcaag tccaagtcat gcgagttctg cggcaagacg ttcaaatttc | 1500 |
| agagcaactt ggtggttcac cgacgcagcc atactggtga aagccctat aagtgcaacc | 1560 |
| tgtgcgacca cgcgtgcaca caggccagca agctgaagcg tcacatgaag acacacatgc | 1620 |
| acaaatcgtc ccccatgaca gtcaagtccg acgatggcct ctccacagcc agctccccgg | 1680 |
| aacctggtac cagcgacctg gtgggcagcg ccagcagtgc gctcaagtca gtggtggcca | 1740 |
| agttcaagag tgagaacgac cccaacttga tcccagagaa cggggatgag gaggaagagg | 1800 |
| aggacgacga ggaagaagaa gaagaggagg aagaggagga ggaggagctg acggagagcg | 1860 |
| agagggtgga ctacggcttc gggctgagcc tggaggctgc acgccaccat gagaacagct | 1920 |
| ctcggggcgc agtggtgggc gtgggcgacg agggccgcgc cctgcccgat gtcatgcagg | 1980 |
| gcatggtgct cagctccatg cagcacttca gcgaggcctt ccaccaggtc ctgggcgaaa | 2040 |
| agcataagcg tagccacctg gccgaggccg agggccatag ggacacttgt gatgaagact | 2100 |
| cggtggccgg tgagtcagac cgcatagacg atggcactgt taatggtcgt ggctgctccc | 2160 |
| ccggcgaatc ggcttcgggg ggtctgtcca aaaagctgct gctgggtagc cccagctcgc | 2220 |
| tgagccccett ctccaagcgc atcaagctgg agaaggagtt tgacctgccc ccggccgcga | 2280 |
| tgcctaacac ggagaacgtg tattcgcagt ggctcgctgg ctatgcggcc tccaggcagc | 2340 |
| tcaaagatcc cttccttact ttcggagact ccagacaatc gccttttgcc tcctcatcag | 2400 |
| agcactcctc ggagaacggg agcttgcgct ctctccacacc gccgggggag ctggacggag | 2460 |
| ggatctcagg gcgcagcggc acaggaagtg gagggagcac gccccatatt agtggtccgg | 2520 |

```
gcccgggcag gcccagctca aaagagggca gacgcagcga cacttgtcct tcacacaccc   2580
ccgttcggcg tagtaccccg cgagctcaag atgtgtggca gttttcggat ggaagctcaa   2640
gaacccttaa gttctgagaa actttgaagc ccccaagggc ggggcggaca tgcgccgccc   2700
agccgacgtc aacgtgctcc gttatcctgc tagattgtga tgttttctga cagtagcctc   2760
caagaagaca agagtcctgc cgagtcctcc cagcctgggc ctgcagtgcc atttattta    2820 tattttttaa taaaacgtaa aaacaaaaaa aaccagaccc acattggaac agtgaacccg   2880
tcccatccag agggccctag gactgccgca gttggagcga cgtccaaccc ttttgaaacc   2940
agccaaccta attacccgta ctgtggaaat gagcatgacc cctgaccct  tgtttctata   3000 cattctatgt tgtcttttaa aaagtgtgct taacattgac ataataaatg ttggagcttt   3060
aggcggtgtg tgcttgtttt ttaattttta atgctcgtaa gacaatgtgg ctgcttcagg   3120
ctttatgtct gtgtactttt tttccttcag aagctcatag ggtgagcaga aggaccagac   3180
tcaagtgcca ggcaggagac ctagaaaagg aagtaggctt ttcagatggc atacattttc   3240
aaagaaaatc aaaatgcaaa gctaggggat aaatcatagt aatatcataa ttaatgtagt   3300
agtattgctg tttattaatg ctgacgtgtg ttttcctct  ctgacttata atttgcatac   3360
cattaaataa tgcataaata tggcacactg aatccttttt caaatacacg cttttggtga   3420
ctacc                                                              3425

<210> SEQ ID NO 21
<211> LENGTH: 2297
<212> TYPE: DNA
<213> ORGANISM: Homo sapiens
<220> FEATURE:
<223> OTHER INFORMATION: Human RELB (NM_006509.3)

<400> SEQUENCE: 21
ggccccgcgc cccgcgcagc cccgggcgcc gcgcgtcctg cccggcctgc ggccccagcc     60
cttgcgccgc tcgtccgacc cgcgatcgtc caccagaccg tgcctcccgg ccgcccggcc    120
ggcccgcgtg catgcttcgg tctgggccag cctctgggcc gtccgtcccc actggccggg    180
ccatgccgag tcgccgcgtc gccagaccgc cggctgcgcc ggagctgggg gccttagggt    240
cccccgacct ctcctcactc tcgctcgccg tttccaggag cacagatgaa ttggagatca    300
tcgacgagta catcaaggag aacggcttcg gcctggacgg gggacagccg ggcccggggcg   360 aggggctgcc acgcctggtg tctcgcgggg ctgcgtccct gagcacggtc accctgggcc    420
ctgtggcgcc cccagccacg ccgccgcctt ggggctgccc cctgggccga ctagtgtccc    480
cagcgccggg cccgggcccg cagccgcacc tggtcatcac ggagcagccc aagcagcgcg    540
gcatgcgctt ccgctacgag tgcgagggcc gctcggccgg cagcatcctt ggggagagca    600
gcaccgaggc cagcaagacg ctgcccgcca tcgagctccg ggattgtgga gggctgcggg    660
aggtggaggt gactgcctgc ctggtgtgga aggactggcc tcaccgagtc cacccccaca    720
gcctcgtggg gaaagactgc accgacggca tctgcagggt gcggctccgg cctcacgtca    780
gcccccggca cagttttaac aacctgggca tccagtgtgt gaggaagaag gagattgagg    840
ctgccattga gcggaagatt caactgggca ttgacccta  caacgctggg tccctgaaga    900
accatcagga agtagacatg aatgtggtga ggatctgctt ccaggcctca tatcgggacc    960
agcagggaca gatgcgccgg atggatcctg tgctttccga gcccgtctat gacaagaaat   1020
ccacaaacac atcagagctg cggatttgcc gaattaacaa ggaaagcggg ccgtgcaccg   1080
```

| | |
|---|---|
| gtggcgagga gctctacttg ctctgcgaca aggtgcagaa agaggacata tcagtggtgt | 1140 |
| tcagcagggc ctcctgggaa ggtcgggctg acttctccca ggccgacgtg caccgccaga | 1200 |
| ttgccattgt gttcaagacg ccgccctacg aggacctgga gattgtcgag cccgtgacag | 1260 |
| tcaacgtctt cctgcagcgg ctcaccgatg gggtctgcag cgagccattg cctttcacgt | 1320 |
| acctgcctcg cgaccatgac agctacggcg tggacaagaa gcggaaacgg gggatgcccg | 1380 |
| acgtccttgg ggagctgaac agctctgacc cccatggcat cgagagcaaa cggcggaaga | 1440 |
| aaaagccggc catcctggac cacttcctgc ccaaccacgg ctcaggcccg ttcctcccgc | 1500 |
| cgtcagccct gctgccagac cctgacttct tctctggcac cgtgtccctg cccggcctgg | 1560 |
| agccccctgg cgggcctgac ctcctggacg atggctttgc ctacgaccct acggccccca | 1620 |
| cactcttcac catgctggac ctgctgcccc cggcaccgcc acacgctagc gctgttgtgt | 1680 |
| gcagcggagg tgccggggcc gtggttgggg agaccccggg ccctgaacca ctgacactgg | 1740 |
| actcgtacca ggccccgggc cccggggatg gaggcaccgc cagccttgtg ggcagcaaca | 1800 |
| tgttccccaa tcattaccgc gaggcggcct ttggggggcgg cctcctatcc ccggggcctg | 1860 |
| aagccacgta gccccgcgat gccagaggag gggcactggg tggggaggga ggtggaggag | 1920 |
| ccgtgcaatc ccaaccagga tgtctagcac ccccatcccc ttggcccttc ctcatgcttc | 1980 |
| tgaagtggac atattcagcc ttggcgagaa gctccgttgc acgggtttcc ccttgagccc | 2040 |
| attttacaga tgaggaaact gagtccggag aggaaaaggg acatggctcc cgtgcactag | 2100 |
| cttgttacag ctgcctctgt ccccacatgt gggggcacct tctccagtag gattcggaaa | 2160 |
| agattgtaca tatgggagga gggggcagat tcctggccct ccctccccag acttgaaggt | 2220 |
| ggggggtagg ttggttgttc agagtcttcc caataaagat gagttttttga gcctccggga | 2280 |
| aaaaaaaaaa aaaaaaa | 2297 |

<210> SEQ ID NO 22
<211> LENGTH: 2218
<212> TYPE: DNA
<213> ORGANISM: Mus <mouse, genus>
<220> FEATURE:
<223> OTHER INFORMATION: Mouse RelB (NM_009046.2)

<400> SEQUENCE: 22

| | |
|---|---|
| gcccgccgcc cgctcggccc ggcgcccccc gcagccccgg gcgccgtgcg tccagcccgg | 60 |
| ccttcggccc tagccttgca ccgcttgccc ggccggtgat cgtcccagcc gaccgggctg | 120 |
| tccgactgcc cggcttgccc tcgtgtgcgc tcgccctgag ctggccttcg ggctgtcggt | 180 |
| ccctacgggc cgggccatgc cgagtcgccg cgctgccaga gagtccgcgc ccgagctagg | 240 |
| ggccttgggt tccagtgacc tctcttccct gtcactaacg gtctccagga ccacagatga | 300 |
| attggaaatc atcgacgaat acattaagga gaacggcttt ggcctggacg ggacacagct | 360 |
| gagtgagatg ccgcgcctgg tgccccgcgg gccgcctca ctgagcagcg tcacgctggg | 420 |
| ccctgctgca ccaccgcctc cggccacgcc gtcctggagc tgcacactgg gcaggctggt | 480 |
| gtcacccggc ccgtgcccac ggccgtacct ggtcatcaca gagcagccaa agcagcgtgg | 540 |
| catgcgcttc cgctacgagt gcgagggccg ctcggccggc agcatcctcg gggagagcag | 600 |
| caccgaagcc agcaagaccc tgcccgccat cgagcttcga gactgtggcg ggctgcggga | 660 |
| ggtggaggtg acggcgtgcc tggtgtggaa ggactggcca caccgggtac acccacatag | 720 |
| cctcgtgggg aaagactgca cggacggcgt ctgcaggggtg cggctgcggc ctcacgtcag | 780 |
| cccccggcac agctttaaca acctgggcat ccagtgtgtt aggaagaagg aaattgaagc | 840 |

-continued

```
tgccattgag cggaagatcc agctgggaat tgaccoctac aatgctggct ccctgaagaa      900
ccatcaggag gtcgacatga atgtcgtcag gatctgcttc caggcctcct atcgggacca      960
gcagggacat ctgcaccgca tggacoccat cctctctgag cctgtctacg acaagaagtc     1020
caccaacaca tcggagctgc ggatttgccg aatcaacaag gagagcgggc cgtgcacagg     1080
tggtgaggag ctgtacttgc tctgtgacaa ggtgcaaaaa gaggacatat ccgtggtgtt     1140
cagcacagct tcctgggaag gccgtgccga cttctctcaa gctgatgtgc accggcagat     1200
cgccattgtg ttcaaaacgc caccctacga ggacctggag atctcagagc ccgtgactgt     1260
caatgtgttc ttgcagcggc tcacggatgg ggtgtgcagc gagccgctgc ccttcacgta     1320
cctgcctcgg gatcatgaca gctacggtgt ggacaagaag cgaaagcggg gactgcctga     1380
tgtccttgga gagttgagca gctctgatcc acatggaatc gagagcaaac gaaggaaaaa     1440
gaaaccagtg ttcttggacc acttcctgcc tggccacagc tcaggcctgt tcctcccacc     1500
atcggctctg cagccggcag actctgattt cttccctgct tccatatccc ttcctgggct     1560
ggagcctcct ggtggacccg atctcctgga cgatggcttt gcctatgatc cttctgcccc     1620
cacgctcttc actatgttgg acctgctgcc cccagcacca ccacttgcca gtgctgtggt     1680
gggtagcggg ggtgcagggg ccaccgttgt ggagtcttct ggcccagagc ccctatcact     1740
ggactctttt gcagcgccgg gccccgggga tgttggtact gctagccttg tgggcagcaa     1800
catgtttccc aaccagtacc gagaggcagc tttcgggggt ggcctcctat ctccagggcc     1860
tgaagccacg tagcctctga ggtaacagag gaggcactgg gtgaggtatg tggtatagca     1920
ctccattccg aagccaacct tgatcagtct tccagcttcc tcatcctgaa tcggacatct     1980
gcagcgctgg tgggaagatg gggagcactc cggttctctt tgagcccatt ttacagaatg     2040
ctgagtccga agaggaaaag gggctcctgc agatggaccc cttctcagga cagattctca     2100
gagattgtac ataggggagg agggagcagg tccccagcct tctcccctaa tcctgaagaa     2160
ggcagtggat tgttcagttt tcccaataaa aattagtttt tgaaaaaaaa aaaaaaaa     2218
```

<210> SEQ ID NO 23
<211> LENGTH: 5233
<212> TYPE: DNA
<213> ORGANISM: Homo sapiens
<220> FEATURE:
<223> OTHER INFORMATION: Human ZBTB46 (NM_025224.3)

<400> SEQUENCE: 23

```
tgaccttctc tcctccctgt gtctttttt ttcctttaga gatgggggtc ttgctctgtc       60
actccagcta gagcacagtg gtgcaatcgg agctcactga ctgcagcctg caactcctgg      120
gctcaagtga ttctgccgcc tcagcctctc aacgtgctgc gattagagag tctgtagaag      180
aggcgacacc agggcttcca aatgaacaac cgaaaggaag atatggaaat cacgtcccac      240
taccggcacc tgctgcggga gctcaacgag cagaggcagc acggcgtcct gtgcgacgtc      300
tgcgtggtcg tggagggcaa ggtcttcaag gcgcacaaga acgtcctgct gggcagcagc      360
cgctacttca agacgctcta ctgccaggtg cagaagacgt cggagcaggc cacggtcacg      420
cacctggaca tcgtcacggc ccagggcttc aaggccatca tcgacttcat gtactcagcg      480
cacctggcgc tcaccagcag gaacgtcatc gaggtgatgt cagccgccag cttcctgcag      540
atgacggaca tcgtgcaagc ctgccacgac ttcatcaagg cggcgctgga catcagcatc      600
aagtcggacg cctcagatga gcttgcggag ttcgagatcg gcgcctcgtc cagcagcagc      660
```

```
acggaagctc tcatctcggc cgtgatggct gggaggagca tctccccgtg gctggcacgg    720
cgaacgagtc ctgccaattc ttccggagac tcggccatcg ccagctgtca cgacggaggg    780
agcagctacg ggaaagagga tcaggagccc aaggccgatg ccctgatga tgtttcttca    840
cagcctctat ggcctggaga cgtgggctac gggcctctgc gcatcaagga agagcaggtt    900
tcaccgtctc agtacggagg gagcgagctg ccttctgcca aggacggtgc agtacagaac    960
tcttttctcag agcagagtgc tggtgatgcc tggcagccca cgggccgaag gaagaatcgg   1020
aaaaacaaag agaccgtccg gcacatcaca cagcaggtgg aagatgacag ccgggccagc   1080
tccccggtgc cgtccttcct gccgacgtcg gggtggccgt tcagcagccg agactcaaat   1140
gcggacctgt ccgtcaccga agccagcagc tccgacagcc gaggagagag ggccgagctc   1200
tatgcacagg tggaggaggg tctcctggga ggagaagcca gctatctggg ccctccccctc  1260
accccagaga aggacgacgc cctgcatcag gccaccgcgg tggccaacct gcgcgcggcg   1320
ctcatgagta agaacagcct gctgtcgctg aaggccgacg tgctggggga tgacggctcc   1380
ctgctgttcg agtacctgcc cagagggggcc cactcgctgt ccctgaatga gttcacggtg   1440
atcaggaaga agttcaagtg tccgtactgc agcttctcgg ccatgcacca gtgcatcctc   1500
aagcgacaca tgcgctcgca cacggagag cggcctacc cctgcgagat ctgcgggaag   1560
aagttcacgc ggcgcgagca catgaagcgc cacacgctgg tccacagcaa ggacaagaag   1620
tatgtgtgca aggtgtgcag ccgcgtcttc atgtccgccg ccagcgtggg catcaggcat   1680
ggctccaggc gccacggtgt gtgcaccgac tgtgctggcc gcggcatggc cgggcccctg   1740
gaccatggcg gcggaggcgg cgagggctct ccagaggcgc tgttcccagg cgacgggccc   1800
tatctggagg accctgagga cccacgaggg gaggcggagg agctgggcga ggacgacgag   1860
ggcctggccc ctgaggatgc gctgttggcg gacgacaagg atgaggaaga ctcgccgcgg   1920
ccgcgcagcc ccccaggagg ccctgacaag gacttcgcct ggctctccta ggccccgcccg   1980
ccggcagggt cggtgctgc ctcgctccgt ccacccgtgt gtgtgtccgg tgggtctcca   2040
ctgcggggcc agggccacgc tcacccctct cgcggcccct cctctgcttc ccctgaacc   2100
caccccccac ggaaaccagc cctgcgggct aagcaggtgc gacccagca agagggggtgc  2160
tctgggacca gacatgaagt gagttggggg agggcacagg gtgggtttga gtgaagggag   2220
agcacggtcc taagtcccca gcaggtggtg cgggtgtgtg agtggcccct gtgatggcca   2280
gcctggcttg gacacgtgat gggcctgtgg ccgggtccag tgggcactgg gcggggtggt   2340
gtgttcggcc cagaggcccc tggcctgagc aggtgcagag ttttacagac acccggtcag   2400
cccggctgga gcccgccctc ccctcccta gcagccaggt cactgcctgt ggctgcagcc   2460
gtggcccgtg gtgcagccgt ggcccatggc agcctgtaga atccaggtgc acagagagcc   2520
ctgccaccgt cttacctctg ggctttggtg cttaacacac aacacagctg cagaccctgc   2580
tggaggccga gggctccagg tgctatctta ggtggacaca gccctggggg ctccttccag   2640
gaggggaccc tcagccctgt gcccccccacc acttcaggcc acaccaggtt ccctctgcaa   2700
gggcctcggc tcagtcgtgt gcacttcctc ggagagcctt gggctgccac gtccaccccg   2760
ggctctgccc gtcctgttct gcccatggcc cagcccggcc gctcctgctg accctcctg    2820
gacgggctgg agctgggctc ctgcctttgc tgctaacact ggaggcggtg ttcctaactg   2880
cagtgtgctg cttacacctc cccgcgtggg taaccaaatt tttaagtagt cagagacata   2940
tcgaggtagt tacataaaat tattttgttt ggcattattt ttctcactcg aagaaactat   3000
atagggttgt ttttccttta gcttgtgctc aagtcctctt gctgtgtttt cagaagcact   3060
```

```
cacatgttct ttcttttcct gagtgaaaag caaaggtccc acggtgtgtg ctgtggtgca    3120
ccgcctggct ttgggggtcc cggaggcagg ctgcctagac tcacagcctc gggaccgttg    3180
ccacggcctg tcttctcgtt caggcctgcc tctgacagca ctcaccatga ggacattcca    3240
tccttcaccc cctcctctgg cacaggccac cactgcggtg ctgtgccttc agatgggagg    3300
tgggcgcggt ggcctcctcc ttccctccag gacctgcccg tgtgaagacc ccccggagtg    3360
ctgagcttca gggctgcgtg gaaagagttt ttactctctt tttctagcct gtataccagg    3420
cttttcccca cattgtcagg tagagcacca gcttccctga ccgctgctgc tcggggaggg    3480
ctggggctgg ccgggggtcc tgtggaggag tacatggagg actccaggta cagcgcagga    3540
gtcacggctt ttgttttttg acattggccc ccggttctac caatgacagg gtgccctggc    3600
tggagctgtc atcacacaca cccctcagct cggaggctgt gggctcctca agctggaga    3660
aagaggccaa gattttttctg cacacggagt gtggggatag gagccgggcc aagcgctggc    3720
ccctcagcgg tgagccctgc ccactcttac cgagcaaggt gggtggctct ggcacgagtc    3780
ccccaggggg agagcatggc taccagggag ctgcagcgga gccctccagc cctcaccca    3840
ggccagcccc accccggcct cttttgagaat tctcagaact ttgtaccttt ccctgattt    3900
ttaaacccctt tttctaaaca gactgacttt cttacaaaat gcatttggaa accagacctt    3960
tgctacccac caatgtctct gggttttgta ccagtccctg ctctcaggcc accctgccca    4020
ggacccaggc ccgcctcccc ctccacactc aggatgtcct gctccatctg gccggctcac    4080
tccgtgtggc ctgcctttgc tgaccgtttt ggggttcccc gccggagcta caggggcatt    4140
ttcttcccta aaaccaacag tgtcccactg acctccccaa gtgtttgctg cgtggcagat    4200
ttcctgttct tgttcgcagt ttgccgactg aagagtgtgg gatttccgag gcccaggtga    4260
gcacgtccat ctcaggaggc gtggagggaa aagacatgtc atgaagggtt ttttttatgt    4320
gactgatttt ttttttaaatc gatgttcaaa ctaataaata tttttttatg aagaggaaaa    4380
atgtgtagat tacatttcac attttgtatt tttgtttgtg tctgtttgta ttttggtgtt    4440
tacaacacca aagtgggaaa tacagtccat tggggatggt gttatttggg ggcggggagg    4500
gggcagggac accacgattt ttctgtcaag ctctggatcc tgaccaggtt gtacactggg    4560
gctctctgag ctttgggaca caggacactg ccagggctac gtaggaact gactcagaag    4620
acgcagctta ctgcttccaa ctttgcacat cttcctcttt aaaaaactga gaaaatgcaa    4680
aaactggaac ttttttgcaat attataaaag aagtaatctt attttagctc attctgtgac    4740
atgtgcgact cttaagaaag ccatacttaa tggtggtggt ttttttttaga tcttatattg    4800
tgttttgtat gcagcccttt tagaactact tgtagtgagg gtgctgtgtg tgcttttctt    4860
aaatatttat ttttttcaac atgctttcaa cctgtcaaca aaaacaaaac acacaaaaaa    4920
agggcagtgt ttgaagattg ttgatttttt tctggggata atctatatta tattgacttc    4980
ctattactta ttataaacct gtgtttgtat tggagatgtg tctactattg ggggaagagg    5040
ttctcgtaat cgctcggtgg gaaatcatgg ctctgccgtc ctgcctctct gtggccgtgg    5100
gttcacgtgg cctctgcggt gagtctccaa gtttctgcct aggcgcctgt gcgtttcctt    5160
tctgtgacgg gattagctta gacatccttg caaagcgatc actttcaata aattgggaaa    5220
ttgctgctcc agc    5233
```

<210> SEQ ID NO 24
<211> LENGTH: 2014
<212> TYPE: DNA

<213> ORGANISM: Mus <mouse, genus>
<220> FEATURE:
<223> OTHER INFORMATION: Mouse Zbtb46 (NM_027656.2)

<400> SEQUENCE: 24

```
agtctataga agacacagca gcaagactcc cagatgaaca accgaaagga agatatggaa      60
atcacttctc actaccggca tctgcttcga gagctcaatg agcagaggca gcacggagtc     120
ctctgtgatg cgtgcgtcgt ggtggagggc aaggtcttca aggcacataa gaacgtcttg     180
cttgggagca gccgctactt taagacgctc tactgccagg tacagaagac atctgaccag     240
gccaccgtca ctcacttgga cattgttaca gcccagggct tcaaggccat tattgacttc     300
atgtactccg cccatctggc tctcactagt aggaatgtca tcgaggtgat gtcagctgcc     360
agcttcctac agatgactga cattgtgcag gcctgccatg atttcatcaa ggctgcactg     420
gacatcagca taaagtcaga tgcctccgat gaactctcag aatttgagat tggcacccca     480
gccagcaaca gtacagaggc gttgatctca gctgtgatgg ctggaaggag tatctcccca     540
tggttggctc ggagaacaag tcctgccaat tcttctggaa actctgccat tgccagctgt     600
catgaaggag gaagcagcta tgggaaggag gaccaggaac ccaaagctga tggccctgat     660
gacgtttctt cacagtcttt gtggcctgga gatgtaggct atgggtctct gcgcatcaag     720
gaagaacaga tttcaccatc acattatgga gggagtgagc ttccatcttc caaggacact     780
gcaatacaga attctttatc agaacagggt tctggggatg gctggcagcc cacaggccgg     840
aggaagaatc ggaaaaacaa agagactgtc cgacacatca cccagcaggt ggaggaggac     900
agccaggctg gctctccagt accttcattc ctacccacat cgggatggcc tttcagcagc     960
cgagactcaa atgtagacct gacggtcact gaggccagca gcttggacag ccgaggcgag    1020
agagcagagc tctatgctca catcgatgag ggcctactag gaggagaaac cagctacttg    1080
ggcccacccc tcaccccaga aaggaagaa gcactacacc aggctactgc agtggccaat    1140
cttcgtgctg cactcatgag taagaacagt ctgctgtcac tcaaggctga cgtgctcggt    1200
gatgatggct cacttctgtt cgagtacctg cccaaaggtg cccactcact gtctctgaac    1260
gaattcacgg tgatcaggaa gaagttcaag tgcccctact gcagcttctc agccatgcac    1320
cagtgcatcc ttaagcgaca catgcgctca catactggag agcggcccta cccttgtgag    1380
atctgtggca agaagttcac taggagagag cacatgaagc gacatactct ggtccacagc    1440
aaggacaaga agtacgtgtg caaagtgtgc agccgtgtgt tcatgtctgc agccagcgtg    1500
ggcattaagc acggctctcg tcgccatggg gtgtgtgcag actgtgctgg ccggggtgtg    1560
ggcacgccac tggaccatgg tggaggtggc gagggctccc ctgaggcgct gtttgctggt    1620
gaagggccgt acctggagga cccggatgat ccacgagggg aggctgagga ggagctggtt    1680
gaggatgagg atgaggacgt ggccaagtgg aaggatgacg tgggcttggc ccatgaggat    1740
gcactgctgg gggatgacaa ggatgatgaa gactctccac agggcctca cagcccctct    1800
ggggagcccg ataaagactt tgcctggatc tcctagggc tctgctctag tgggcaggt    1860
gagtgatggc tgaatcgctt tgtccacctg tgtgtgtgtc ttagtggatc tttacttacc    1920
caggagcagg gctatgctta ctccttgaag ctcctcctaa aggcctctcc tccatgctat    1980
acccctctcc attacagaaa ctggtcctgt gagc                                2014
```

<210> SEQ ID NO 25
<211> LENGTH: 4340
<212> TYPE: DNA
<213> ORGANISM: Homo sapiens
<220> FEATURE:
<223> OTHER INFORMATION: Human RUNX3 (NM_001031680.2)

<400> SEQUENCE: 25

```
attcattcat tccccgtggc actggaggcg gcccactctg ctctgtcagc ttcggagctc      60
ctccaccctg gctgccgaaa gccccttccc gccatctaat gatacactct gcatacgctt     120
ctgttgagaa tttgtggcta gacattcctg tgggaccggg aatccaaatt cttgggtaca     180
aacagaaact tactttcctt ggggattttt ttctctctct cactcacaca cactctcgcg     240
ttctttcctt ttttcttttt cgtagcagca gggggaaaa aagagacaaa aacaaaacaa     300
aaacaacaa aaagcaacac ccccccttt tattttcaaa agtagctaga ggaaaaaaaa     360
ataaaacaac agccaaccaa gtgaatccca acccaacccc ctgaagggct gaaaattctc     420
gccttcttca gagcggggca tggcatcgaa cagcatcttc gactccttcc cgacctactc     480
gccgaccttc atccgcgacc caagcaccag ccgccgcttc acacctccct ccccggcctt     540
cccctgcggc ggcggcggcg gcaagatggg cgagaacagc ggcgcgctga gcgcgcaggc     600
ggccgtgggg cccggagggc gcgcccggcc cgaggtgcgc tcgatggtgg acgtgctggc     660
ggaccacgca ggcgagctcg tgcgcaccga cagccccaac ttcctctgct ccgtgctgcc     720
ctcgcactgg cgctgcaaca gacgctgcc cgtcgccttc aaggtggtgg cattggggga     780
cgtgccggat ggtacggtgg tgactgtgat ggcaggcaat gacgagaact actccgctga     840
gctgcgcaat gcctcggccg tcatgaagaa ccaggtggcc aggttcaacg accttcgctt     900
cgtgggccgc agtgggcgag ggaagagttt caccctgacc atcactgtgt tcaccaaccc     960
cacccaagtg gcgacctacc accgagccat caaggtgacc gtggacggac cccgggagcc    1020
cagacggcac cggcagaagc tggaggacca gaccaagccg ttccctgacc gctttgggga    1080
cctggaacgg ctgcgcatgc gggtgacacc gagcacaccc agccccgag gctcactcag    1140
caccacaagc cacttcagca gccagccca gaccccaatc caaggcacct cggaactgaa    1200
cccattctcc gaccccgcc agtttgaccg ctccttcccc acgctgccaa ccctcacgga    1260
gagccgcttc ccagacccca ggatgcatta tcccgggggcc atgtcagctg ccttcccccta   1320
cagcgccacg ccctcgggca cgagcatcag cagcctcagc gtggcgggca tgccggccac    1380
cagccgcttc caccatacct acctcccgcc accctaccg ggggccccgc agaaccagag    1440
cgggccctcc caggccaacc cgtcccccta ccacctctac tacggggacat cctctggctc    1500
ctaccagttc tccatggtgg ccggcagcag cagtgggggc gaccgctcac ctacccgcat    1560
gctggcctct tgcaccagca gcgctgcctc tgtcgccgcc ggcaacctca tgaaccccag    1620
cctgggcggc cagagtgatg gcgtggaggc cgacggcagc cacagcaact cacccacggc    1680
cctgagcacg ccaggccgca tggatgaggc cgtgtggcgg ccctactgac cgccctggtg    1740
gactcctccc gctggaggcg gggaccctaa caaccttcaa gaccagtgat gggccggctc    1800
cgaggctccg ggcgggaatg ggacctgcgc tccaggtgg tctcggtccc agggtggtcc    1860
cagctggtgg gagcctctgg ctgcatctgt gcagccacat ccttgtacag aggcataggt    1920
taccaccccc acccccggccc gggatactgc ccccggccca gatcctggcc gtctcatccc    1980
atacttctgt ggggaatcag cctcctgcca cccccccgga aggacctcac tgtctccagc    2040
tatgcccagt gctgcatggg acccatgtct cctgggacag aggccatctc tcttccagag    2100
agaggcagca ttggcccaca ggataagcct caggccctgg gaaacctccc gacccctgca    2160
ccttcgttgg agcccctgca tccctgggt ccagcccct ctgcatttac acagatttga    2220
```

| | |
|---|---|
| gtcagaactg gaaagtgtcc cccaccccca ccaccctcga gcggggttcc cctcattgta | 2280 |
| cagatggggc aggacccagc acgctgctgg cagagatggt ttgagaacac atccaagcca | 2340 |
| gtcccccag cccagcttcc cctccgttcc taactgttgg ctttcccca gccgcacggg | 2400 |
| tcccaggccc cagagaagat gagtctatgg catcaggttc ttaaacccag gaaagcacct | 2460 |
| acagaccggc tcctccatgc actttaccag ctcaacgcat ccactctctg ttctcttggc | 2520 |
| agggcggggg agggggata ggaggtcccc tttcccctag gtggtctcat aattccattt | 2580 |
| gtggagagaa caggagggcc agatagatag gtcctagcag aaggcattga ggtgagggat | 2640 |
| cattttgggt cagacatcaa tgtccctgtc cccctgggt ccagccaagc tgtgccccat | 2700 |
| ccccaagcc tcctgggagg atccagccaa atcttgcgac tcctggcaca cacctgtctg | 2760 |
| taacctgttt tgtgctctga agcaaatag tcctgagcaa aaaaaaaaa aaaacaaaaa | 2820 |
| aacaaaaaaa aaacaaaaca gtttttaaaa ctgattttag aaaagaagc ttaatctaac | 2880 |
| gttttcaaac acaaggtctc ttacaggtat agttccgtga ttatgatagc tctgtgatta | 2940 |
| taagcaacat ccccgccccc tctcccccc gcggacccc agctgcctcc tgagggtgtg | 3000 |
| gggttattag ggtctcaata ctttctcaag gggctacact ccccatcagg cagcatccca | 3060 |
| ccagcctgca ccacaggctc ccctgggagg acgagggaaa cgctgatgag acgctgggca | 3120 |
| tctctcctct gtggctctag gacatctgtc caggaggctg ggcggaggtg ggcaggatgt | 3180 |
| gagaggtggg gagtactggc tgtgcgtggc aggacagaag cactgtaaag ggctctccag | 3240 |
| ccgcagctca gctgcactgc gttccgaggt gaagtcttgc ccctgaattt tgcaaaatgg | 3300 |
| gaaagtgggc gcttgcccaa gggccaggct gcatggattc tcacatcaga gttctctggc | 3360 |
| cctagaaagg cttagaaaag gcgtaaggga actcataaag gctagcagca tgcggtattt | 3420 |
| taactttctg cctcggcctc tgtggatgca gaaatctgcc ctacaaaatg ctcttcattg | 3480 |
| gttgtctctg tgagagcact gtccccaccc aacctgtcac aacggccaga accatacacc | 3540 |
| agagacacac tggcaggtta ggcagtcctt ctggtgatcc tattccattc cctcctgctg | 3600 |
| cggtttctct tggcctgtcc tcactggaaa aacagtctcc atctcctcaa aatagttgct | 3660 |
| gactccctgc acccaagggg cctctccatg ccttcttagg aagcagctat gaatccattg | 3720 |
| tccttgtagt ttcttccctc ctgttctctg gttatagctg gtcccaggtc agcgtgggag | 3780 |
| gcacctttgg gttcccagtg cccagcactt tgtagtctca tcccagatta ctaacccttc | 3840 |
| ctgatcctgg agaggcaggg atagtaaata aattgctctt cctaccccat cccccatccc | 3900 |
| ctgacaaaaa gtgacggcag ccgtactgag tctgtaaggc ccaaagtggg tacagacagc | 3960 |
| ctgggctggt aaaagtaggt ccttatttac aaggctgcgt taaagttgta ctaggcaaac | 4020 |
| acactgatgt aggaagcacg aggaaaggaa gacgttttga tatagtgtta ctgtgagcct | 4080 |
| gtcagtagtg ggtaccaatc ttttgtgaca tattgtcatg ctgaggtgtg acacctgctg | 4140 |
| cactcatctg atgtaaaacc atcccagagc tggcgagagg atggagctgg gtggaaactg | 4200 |
| ctttgcacta tcgtttgctt ggtgtttgtt tttaacgcac aacttgcttg tacagtaaac | 4260 |
| tgtcttctgt actatttaac tgtaaaatgg aattttgact gatttgttac aataatataa | 4320 |
| ctctgagatg tgtggaagga | 4340 |

```
<210> SEQ ID NO 26
<211> LENGTH: 3891
<212> TYPE: DNA
<213> ORGANISM: Mus <mouse, genus>
<220> FEATURE:
<223> OTHER INFORMATION: Mouse Runx3 (NM_019732.2)
```

<400> SEQUENCE: 26

```
attcattcat tcatccaggc tgctgagtct ggactggctg ctgcagcccc gggctcctcc      60
gccctgactg cccagagccc cttcccacca tttaatgata ctctgcacat agtgctgttg     120
aaaatttgtg gctagacatt cctgtgggac tgggaagcca aattcttggg tacaaaccga     180
aactttcttt ccttggagat tttcttctct ctcgcccaca gacgctctcg cgttctttcc     240
ccatttttt tctttctctt ctttttttc tttttttt tttttttgta gcagcagggg        300
gagaaaaaa gaaaccaaac tttaaaaaaa aaagtcaac acctccct ttttattttc        360
gaaagcaact tgaaaaaata tataacaa aacagcagcc aaccaagtgg gtctgaaccc       420
aaccccctga ggccgagtcc ttgccactgt cagcgtgcga catggcttcc aacagcatct     480
ttgactcctt ccccaactat acaccaacct tcatacgaga cccgagcacc agccgccgct     540
tcactccccc ctccacggcc ttcccctgcg gcggcggcgg cggcggcaag atgggcgaga     600
acagcggcgc gctaagcgcg caggcaaccg cgggccccgg cggccgcacc cggcccgaag     660
tgcgctcgat ggtggacgtg ctggccgacc acgcgggaga gctcgtgcgc accgacagcc     720
ccaacttcct ctgctccgtg ctgccctcgc actggcgctg caacaagacg ctgccggtcg     780
ccttcaaggt ggtggccctg ggggatgtgc cggatggaac ggtggtgacc gtgatggccg     840
gcaatgatga gaactactcc gccgagctgc gcaacgcttc cgctgtcatg aagaaccaag     900
tggccaggtt caacgacctt cgattcgtgg gccgcagtgg gcgagggaag agtttcacgc     960
tcacaatcac cgtgttcacc aaccctaccc aagtggctac ctaccaccga gccatcaagg    1020
tcactgtgga tggaccccgg gaaccccgac ggcaccggca gaagatagaa gaccagacca    1080
aggccttccc cgaccgcttt ggagacctgc gcatgcgtgt aacaccaagc acacccagcc    1140
cccgtggctc tctcagcacc acgagccact tcagcagcca ggcccagacc ccaatccaag    1200
gctcctcaga cctgaacccc ttctccgacc ccgccagtt tgaccgctcc ttccctacgc    1260
tgcagagcct cacagagagc cgcttcccgg accccaggat gcactaccccg ggagccatgt    1320
ctgccgcctt cccctacagc gccacaccat cgggcaccag cctgggcagc ctgagcgtgg    1380
cgggcatgcc ggccagcagc cgcttccacc acacctacct ccctccgccc tacccggggg    1440
ccccacagag ccagagcggg cccttttcagg ccaaccccgc gccctaccac ctcttttacg    1500
gcgcctcctc cggctcctac cagttctcca tggcagccgc ggaggtggt gagcgctcgc     1560
ccacccgcat gctgacctcc tgccccagcg gcgcttcggt gtcagcaggc aacctcatga    1620
accccagcct gggccaggct gatggcgtgg aagccgacgg cagccacagc aactcgccca    1680
cggccctgag cacgccgggc cgcatggacg aggccgtgtg gcggccctac taagcaccct    1740
ggagactctc gggccagccg aatccttccc tccagcccga gactacaaga agaaacagac    1800
tttggcctgg tcccaggggc cagagctggc agtggctccc agagctctgt ccagccacaa    1860
gtttgagcag aggatgtggg gacctccac aggacactgc tccaacccaa atcaatgtcc    1920
tctctagctg tgcatcccaa acccacctct tgtctccagc catgcccagg atcaattcta    1980
gaatcagagg ctacccctgc ctgtgtgggg agggcctttg ctggcaagag aagctcaggc    2040
tcagagatgt ctggactttc tctccctccc tctctctctc tctctctctc tctctctctc    2100
tctctctctc tctctctctc acacacacac acacacacac acacacacac acacacacac    2160
actgccctgg ggaccatcca tgcccatcaa accaaaggga aactcaaacc cctgggaagg    2220
tttcactccc ctgaagagag agaggagcca tatctctctt tcacatacac acacacacac    2280
```

| | |
|---|---:|
| acacacacac acacacacac acacgtcccc aacttgactt cccccctggtc ccaggccagc | 2340 |
| agccccctgat cagtcctaac ttacctgaaa acaccaggcc ccagagcaga ctcatccggg | 2400 |
| gtggcaggtc cctaaagcaa ggaaggcctc acactgtcca gcatactcca gcctgaattg | 2460 |
| cctactgggt tctcaggggg cagacaggtc ctggccgaaa gtcttaccat ggggatcgat | 2520 |
| agggtggtta gccctgcgca ctaggtccag ccaatctgtg ctctgggcct tgcctcccag | 2580 |
| gccacagtcc tgctcccaac ttgtttgtcc ctagaagcag acaactttga accaaaagca | 2640 |
| tctcagtcaa gcatctaaaa caggggggcag tctgtgtata caagagccca cctcctgctg | 2700 |
| tgtgatgtca tcaggacacc cccaccctca ccccaccacc agggtcctga cttcacattc | 2760 |
| ttcacagaag gggacaagac ctccaggagg ccctgtggag tctctggtga ggtgtgcgat | 2820 |
| ggcagagcag catccaagca gagatcagat gtcctcttca gtctgtgggc gggcgattgt | 2880 |
| cagtgggatt ggttaaaaag ctcttaccag agctggctgg cccacggctg ttttttcaaa | 2940 |
| ctgagtgagc cccgtagtga tggcctctgc cttgtgcttg gccttcccca ttgcctgcac | 3000 |
| ctgaaacagc cacccacata cacactctgg taggtcaggg ggtccccgac aatcctggac | 3060 |
| aatcctgagc agaataccctc ctgttacagt gtctcttgtc ccacccttac tggaggaaaa | 3120 |
| aaaaaaaaaa aactctatct cttggaagta gctgaggtaa ccttccagct ccctgcaccc | 3180 |
| agagggggcc ttctcacctc ttctcaggaa gcagctacga cccattgccc tcctacctgc | 3240 |
| ttcgctactg gtccatggta cagactgttc cagatcacca agaaaggtac tttcaggatc | 3300 |
| ccagtgccta gcactgggta agctaccccca gacaactagc cttccttata cccaaacgct | 3360 |
| ggtcggtgga aatagaaagt caccccctccc ccatcgcctc tttctcatcc ctgattaaca | 3420 |
| gtgaagtttg agtcttgtcg tgagtcctac agtgagcaca ggcagctggg gctaataaaa | 3480 |
| aaagaagaag aagaagaaaa aggagaggag agaaaaaaaa caaaaatgaa aggaaaaggg | 3540 |
| tccttatttg caaggctact ttaaagtgct acttgaaagc acaggctaga cagaaagcac | 3600 |
| aaggaaccta gggggttgat acaatgttac tgtaattgtg tgggtgggtg tcatcctttg | 3660 |
| tgacattgtt accctgaggt atactccctg cagtgagctg gtcttcctga agtgggcctg | 3720 |
| cttttgcacta taggctgctt gtatgtttgg tttgttgttt ttgttttttt gtttttttta | 3780 |
| atgcacaact tgcttgtaca ggtcaactgt ccatcttggg tactatttaa ctgtcaaaca | 3840 |
| gaggaatctg tgtttgttac aataatataa cagatgcctt gaaggacccg c | 3891 |

```
<210> SEQ ID NO 27
<211> LENGTH: 2802
<212> TYPE: DNA
<213> ORGANISM: Homo sapiens
<220> FEATURE:
<223> OTHER INFORMATION: Human GFI1 (NM_005263.3)

<400> SEQUENCE: 27
```

| | |
|---|---:|
| gagggtgcgc ccaccggtcc cgccgggcgc ccgcggacg cgccgccagg gccctctccg | 60 |
| ccgggggctc ggcgctcgcc cacctcttcc aaatttaacc attacctaaa tccgaaggga | 120 |
| aatgagcaaa cctctcggat tgggtgtcaa ggtctcctcc gggctggggc tgagcaagcc | 180 |
| ctcggagtga ccgtgggtga cagcggctcc agggactctt ggggcgcagt ggggaaagtg | 240 |
| ccggaccacc atgccgcgct catttctcgt caaaagcaag aaggctcaca gctaccacca | 300 |
| gccgcgctcc ccaggaccag actattccct ccgtttagag aatgtaccgg cgcctagccg | 360 |
| agcagacagc acttcaaatg caggcggggc gaaggcggag ccccgggacc gtttgtcccc | 420 |
| cgaatcgcag ctgaccgaag ccccagacag agcctccgca tccccagaca gctgcgaagg | 480 |

```
cagcgtctgc gaacggagct cggagtttga ggacttctgg aggcccccgt caccctccgc    540
gtctccagcc tcggagaagt caatgtgccc atcgctggac gaagcccagc ccttcccect    600 gcctttcaaa ccgtactcat ggagcggcct ggcgggttct gacctgcggc acctggtgca    660
gagctaccga ccgtgtgggg ccctggagcg tggcgctggc ctgggcctct ctgcgaacc     720 cgccccggag cctggccacc cggccgcgct gtacggcccg aagcgggctg ccggcggcgc    780
gggggccggg gcgccaggga gctgcagcgc aggggccggt gccaccgctg ccctggcct     840 agggctctac ggcgacttcg ggtctgcggc agccgggctg tatgagaggc ccacggcagc    900
ggcgggcttg ctgtaccccg agcgtggcca cgggctgcac gcagacaagg gcgctggcgt    960
caaggtggag tcggagctgc tgtgcacccg cctgctgctg ggcggcggct cctacaagtg   1020
catcaagtgc agcaaggtgt ctccacgcc gcacgggctc gaggtgcacg tgcgcaggtc    1080
ccacagcggt accagaccct tgcctgcga gatgtgcggc aagaccttcg gcacgcggt    1140 gagcctggag cagcacaaag ccgtgcactc gcaggaacgg agctttgact gtaagatctg   1200
tgggaagagc ttcaagaggt catccacact gtccacacac ctgcttatcc actcagacac   1260
tcggccctac ccctgtcagt actgtggcaa gaggttccac cagaagtcag acatgaagaa   1320
acacactttc atccacactg gtgagaagcc tcacaagtgc caggtgtgcg gcaaggcatt   1380
cagccagagc tccaacctca tcacccacag ccgcaaacac acaggcttca gcccttcgg   1440 ctgcgacctc tgtgggaagg gtttccagag gaaggtggac ctccgaaggc accgggagac   1500
gcagcatggg ctcaaatgag caccctggct ggctgcaagc agcagctaca caacactaca   1560
gagggcagcc tccctgcttg ccaccactct gctccctgct tgcctccact cccttctgac   1620
tttccagacc ccaggtccag tctgcagatc ctaccaggtt gctcctcctt cgccttacct   1680
cctggagctg ccagaagaaa tgaggtacct tttcaaagtg cagccgagag tgagaaccaa   1740
gtgactctct aggcttcgga cacaaatagg ctcctctaca cctgaagaca aggcaaagt    1800 caaatgggga ccagaataaa tcttagaccc cacagtcctt cccatttcca gccctaatct   1860
acagacagga atgcccttca ggtttcttcc ctccccctc ttgacctacc ccagatattt    1920
gtgtggaaga ggaggaatca ccatttacaa ggtggacaaa tgctaatatt tttatctaga   1980
aagaagagtg agtgttaact tttattttt tccttctggg gggtctgttg actccttct     2040 tttgggtgct gcctataaat cttggaggaa tcatttctcc tcctcaaaaa ctgattcaga   2100
aactgacttg gggaaggaat ttaatacttt gaagtcatga gatgcaccat cgaggctacc   2160
cccaagaaga agcagaagag aagttggtaa tgagagggga ttagaggtcc tcccttcagt   2220
agggctgtga aacctcatc actggaggta aaagcacaag caatgcctgt ggacaagatg    2280
tcattcattc actcagcaaa tgttcatgga tcaccggcta ccaaggtacc aggcaccatg   2340
ctaggtattg gggaagagag actgaagtca caacccctga ctgctcctca aaagctaacg   2400
gttgcacctc caagtggctg ggtctgttct tactcttgga gggaattctg agaagacagc   2460
acagaattgt aaaccttccc ttttgacct tttggatttt atcaggtgta aacaaaaagc     2520
tgaacagtta cttcaaagat atgtgtgtat attcagtttt ttattgttaa gctgatattt   2580
taaagatttc tgagctagca ggcatgtggg aaggaaggct ctgtcttcaa ctctttgacc   2640
ctccatgtgt accatagagg ggggaaaggt ggtattttca ctttgatgag gttggtaaat   2700 gttttttagat cttctggtaa gcattatgtt tgttaataca tatttattag agtgatgttt   2760
taagttaata aagtattaag agtattaaaa aaaaaaaaa aa                       2802
```

<210> SEQ ID NO 28
<211> LENGTH: 2862
<212> TYPE: DNA
<213> ORGANISM: Mus <mouse, genus>
<220> FEATURE:
<223> OTHER INFORMATION: Mouse GFI1 (NM_010278.2)

<400> SEQUENCE: 28

| | | | | | |
|---|---|---|---|---|---|
| ctccaagccc | cttccgggtc | ccaaacactg | atgcccctg | actggctaaa | ctaagccacg | 60 |
| catccctggc | gtgagccaca | acccagaagg | gagcaggtgg | gcttgcaggg | ttgacttggg | 120 |
| ataacggacc | agttgtggac | tactgctctc | aggagagtga | tgatctagct | ttggtaggga | 180 |
| aggggagggg | ctgaggcgtg | ggcagggcag | agcaaaggga | ccagagccag | agcctgggga | 240 |
| caggttttac | cactgagctg | ttgcagtggc | ggcggaggcc | gggattcgtg | ccacctgtcc | 300 |
| gagtgccacc | tggtgagcgt | ggcgcctggg | tccaggcccc | tcctcccgcg | gcttccctct | 360 |
| ctcctccctg | gcccacactc | ttccttggcc | tgggaaccta | ccacaaccgc | catcggtgct | 420 |
| gaccctcgtt | tccacccaat | tttcccccctt | ctctcagaac | tcagagtatc | cgagggtcca | 480 |
| aacattcgtc | cagcggctga | ccaccatgcc | gcgctcattc | ctggtcaaga | gcaagaaggc | 540 |
| gcacagctat | caccagccgc | gttctccggg | gccggactac | tccctgcgcc | tggagaccgt | 600 |
| gcctgcgccg | ggcagagcag | agggcggcgc | tgtgagtgca | ggcgagtcga | aaatggagcc | 660 |
| ccgagagcgt | ttgtcccccg | actctcagct | taccgaggct | cccgacaggg | cctccgcgtc | 720 |
| ccccaacagc | tgcgaaggca | gcgtttgtga | cccctgctcc | gagttcgagg | acttttggag | 780 |
| gccccttct | ccctccgtgt | ctccagcgtc | ggagaagtca | ctgtgccgct | ctctggacga | 840 |
| agcccagccc | tacacgctgc | ctttcaagcc | ctatgcatgg | agcggtcttg | ctgggtctga | 900 |
| cctgcggcac | ctggtgcaga | gctatcggca | gtgcagcgcg | ctggagcgca | gcgcgggcct | 960 |
| gagcctcttc | tgcgagcgcg | gctcggagcc | gggccgcccg | gcagcgcgct | acggccccga | 1020 |
| gcaggctgcg | ggcggagccg | gtgcgggaca | gccaggagc | tgcggggtcg | ccgggggcgc | 1080 |
| caccagcgct | gcgggcctgg | ggctctacgg | cgacttcgcg | cctgcggcgg | ccgggctgta | 1140 |
| cgagcggccg | agcacagcag | caggccggct | gtaccaagat | catggccacg | agctgcacgc | 1200 |
| ggacaagagc | gtgggcgtca | aggtggagtc | ggagctgctt | tgcacccgtc | tgctgctggg | 1260 |
| cggcggctcc | tacaaatgca | tcaaatgcag | caaggtgttc | tccacaccgc | acgggctgga | 1320 |
| ggtgcacgtg | cgccggtccc | acagcggcac | aagacccttt | gcgtgcgaga | tgtgcggcaa | 1380 |
| gaccttcggg | cacgcggtga | gcctggcaga | acacaaggca | gtgcactccc | aggaacgcag | 1440 |
| ctttgactgt | aagatctgtg | gcaagagctt | caaggagtca | tccacgctgt | ccacacatct | 1500 |
| gctcattcac | tcggacaccc | ggccctatcc | ctgtcagtac | tgtggcaaaa | gattccacca | 1560 |
| gaagtcagat | atgaagaaac | acaccttcat | ccacacaggt | gagaagcccc | acaaatgcca | 1620 |
| ggtgtgcggc | aaagccttca | gtcagagctc | caacctcatc | actcatagca | gaaagcacac | 1680 |
| aggcttcaag | ccctttggct | gtgacctgtg | tgggaagggc | ttccagagga | aggtggatct | 1740 |
| caggaggcac | cgagagactc | agcatggact | caaatgagta | ccctggcagc | cgcaacacc | 1800 |
| agctgtgtaa | cactaccgtg | agggatgtct | tccctgcctc | cctccagccc | cttctcaggc | 1860 |
| cctgagtcca | gtgtgcaaag | ctcatcatgg | ttagtcccct | tcaccttcct | tcccggagct | 1920 |
| gctggaggag | atgaactccc | gtttctaagg | tcaacccaga | gtgggaaccg | cagcagcagc | 1980 |
| agcagtcgtc | tgtgctttgg | gcttcccta c| agctgaagat | ggggatcaaa | tgagatcttg | 2040 |
| cacctcccag | ttcttccctt | ttttgctgtc | tcacaggcca | gaatgaactc | tgggcagctg | 2100 |

```
ctacaagagg aggcatcacc tcttaagctt tgagcgccac tgatgcattt attgagaacg    2160
aatgaacatt aattttctct tctggggaga ctgctgactc ctttatcctc caccagactc    2220
tggtttaggg aaggaacctc gttcctttga aatcatcaga tgcaccatca agcctgccac    2280
gagaagaagg ggacttggtg atgagaggga gtcagaggtc ctgtggtgcc atcagaggag    2340
gtgaagctgt ggagcagctc cggggaacag ggtcttcact tactcagcga gtgattattg    2400
gccgcaggtt atcagagtaa ggaactgtgc taggtatggg agagccagag attaaagtca    2460
taggccctaa cccccaaaag ctatcagttg gacttcaaca tagctagagc ctgtgttctg    2520
tgcttccaag ggagttctga agaaggccac acaaacattg ggacttcttt ttgacactta    2580
cggagttttt caagtgtaaa caaataggaa ctggaggatt atttctaaag ttcatgagta    2640
aatccagctt ttattgttag gtgggacttt attagatgcc tgcgctggga gatgtggggt    2700
gaaggctatg gcctcagctc ctgcccctta tcatcttagg aacaacttat ttttcctgtg    2760
agggttgtag acgttcctaa atcttcttga gtgcattatg tattagcata atcatattta    2820
ttagaatgtt gttttaactt aataaagtat taagattatt ac                       2862
```

<210> SEQ ID NO 29
<211> LENGTH: 2302
<212> TYPE: DNA
<213> ORGANISM: Homo sapiens
<220> FEATURE:
<223> OTHER INFORMATION: Human IRF2 (NM_002199.3)

<400> SEQUENCE: 29

```
agccgcggct cttcgcagtt tcctctcctt gttttgcttt cgatctggac tgttctcagg     60
caagccgggg agtaactttt agttttgctc ctgcgattat tcaactgacg ggctttcatt    120
tccatttcac atacccctagc aacacttata ccttgcggaa ttgtattggt agcgtgaaaa   180
aagcacactg agagggcacc atgccggtgg aaaggatgcg catgcgcccg tggctggagg    240
agcagataaa ctccaacacg atcccggggc tcaagtggct taacaaggaa aagaagattt    300
ttcagatccc ctggatgcat gcggctagac atgggtggga tgtggaaaaa gatgcaccac    360
tctttagaaa ctgggcaatc catacaggaa agcatcaacc aggagtagat aaacctgatc    420
ccaaaacatg gaaggcgaat ttcagatgcg ccatgaattc cttgcctgat attgaagaag    480
tcaaggataa aagcataaag aaaggaaata atgccttcag ggtctaccga atgctgcccc    540
tatcagaacg gccttctaag aaaggaaaga accaaagac agaaaaagaa gacaaagtta     600
agcacatcaa gcaagaacca gttgagtcat ctctggggct tagtaatgga gtaagtgatc    660
tttctcctga gtatgcggtc ctgacttcaa ctataaaaaa tgaagtggat agtacggtga    720
acatcatagt tgtaggacag tcccatctgg acagcaacat tgagaatcaa gagattgtca    780
ccaatccgcc agacatttgc caagttgtag aggtgaccac tgagagcgac gagcagccgg    840
tcagcatgag cgagctctac cctctgcaga tctcccccgt gtcttcctat gcagaaagcg    900
aaacgactga tagtgtgccc agcgatgaag agagtgccga ggggcggcca cactggcgga    960
agaggaatat tgaaggcaaa cagtacctca gcaacatggg gactcgaggc tcctacctgc   1020
tgcccggcat ggcgtccttc gtcacttcca acaaaccggga cctccaggtc accatcaaag   1080
aggagagcaa tccggtgcct tacaacagct cctggcccc ttttcaagac ctcccccttt    1140
cttcctccat gacccccagca tccagcagca gtcggccaga ccgggagacc cgggccagcg   1200
tcatcaagaa aacatcggat atcacccagg cccgcgtcaa gagctgttaa gcctctgact    1260
```

```
ctccgcggtg gttgttgggg cttcttggct ttgttttgtt gtttgtttgt atttatttt      1320
tttctctctg acacctattt tagacaaatc taagggaaaa agccttgaca atagaacatt      1380
gattgctgtg tccaactcca gtactggagc ttctctttaa ctcaggactc cagcccattg      1440
gtagacgtgt gtttctagag cctgctggat ctcccagggc tactcactca agttcaagga      1500
ccaacaaggg cagtggaggt gctgcattgc ctgcggtcaa ggccagcaag gtggagtgga      1560
tgcctcagaa cggacgagat aatgtgaact agctggaatt ttttattctt gtgaatatgt      1620
acataggcag cactagcgac attgcagtct gcttctgcac cttatcttaa agcacttaca      1680
gataggcctt cttgtgatct tgctctatct cacagcacac tcagcacccc cttctctgcc      1740
cattccccag cctctcttcc tatcccatcc catcccatcc catcccatcc catcccatcc      1800
cgctcttttc ctacttttcc ttccctcaaa gcttccattc cacatccgga ggagaagaag      1860
gaaatgaatt tctctacaga tgtcccattt tcagactgct ttaaaaaaaa tccttctaat      1920
ctgctatgct tgaatgccac gcggtacaaa ggaaaaagta tcatggaaat attatgcaaa      1980
ttcccagatt tgaagacaaa aatactctaa ttctaaccag agcaagcttt tttattttt       2040
atacagggga atattttatt caaggtaaaa ttctaaataa aatataattg ttttttatct      2100
tttctacagc aaatttataa ttttaagatt ccttttcttg tttatcagca gttgttatta      2160
catccttgtg gcacattttt ttttttaatt ttgtaaaggt gaaaaaagct tttatgagct      2220
catgtagcaa tcagattttc ctgtggattg ataataaatg aatatgatat atagttaaat      2280
ttttaaaaaa aaaaaaaaaa aa                                               2302

<210> SEQ ID NO 30
<211> LENGTH: 2484
<212> TYPE: DNA
<213> ORGANISM: Mus <mouse, genus>
<220> FEATURE:
<223> OTHER INFORMATION: Mouse Irf2 (NM_008391.4)

<400> SEQUENCE: 30
gctcctcgca gtttcctctc cttgttttgc tttcgatctg gactgttctc aggcaagccg        60
gggactaact tttagttttg ctcctgcgat tattcaactg acgggctttc atttccattt       120
tacacaccct aacaacactc acaccttgcg ggattgtatt ggtagcgtgg aaaaaaaaaa       180
gcacattgag agggtaccat gccggtggaa cggatgcgaa tgcgcccgtg gctggaggag       240
cagataaatt ccaatacgat accagggcta aagtggctga acaaggagaa gaagattttc       300
cagatcccct ggatgcatgc ggctcggcac ggatgggacg tggaaaagga tgctccgctc       360
ttcagaaact gggcgatcca tacaggaaag catcaaccag gaatagataa accagatcca       420
aaaacatgga agcaaatttt cgatgtgcc atgaattccc tgcccgacat tgaggaagtg       480
aaggacagaa gcataaagaa aggaaacaac gccttcagag tctaccggat gctgccctta       540
tccgaacgac cttccaagaa aggaaagaaa ccaaagacag aaaaagaaga gagagttaag       600
cacatcaagc aagaaccagt tgagtcatct ttggggctta gtaatggagt aagtggcttt       660
tctcctgagt atgcggtcct gacttcagct ataaaaatg aagtggatag tacggtgaac        720
atcatagttg taggacagtc ccatctggac agcaacattg aagatcaaga gatcgtcact       780
aacccgccag acatctgcca ggttgtagaa gtgaccactg agagtgatga ccagccagtc       840
agcatgagtg agctctaccc tctacagatt tctcctgtgt cttcctacgc agaaaagcgaa       900
actaccgaca gtgtggccag tgatgaagag aacgcagagg ggagaccaca ctggaggaag       960
aggagcatcg aaggcaagca gtacctcagc aacatgggga cacggaacac ctatctgctg      1020
```

```
cccagcatgg cgacctttgt cacctccaac aagccagatc tgcaggtcac catcaaagag    1080
gatagctgtc cgatgcctta caacagctcc tggcccccat ttacagacct tccccttcct    1140
gccccagtga cccccacgcc cagcagcagt cggccagacc gggagacccg ggccagtgtc    1200
atcaagaaga catctgatat cacccaggcc cgtgtcaaga gctgttaagc ctttgactct    1260
ccctggtggt tgtttgggatt tcttagcttt gtgttgttct ttgtttgtat tatattattt    1320
tttttctcta tgatacctat cttagacaca tctaagggag aaagccttga cgatagatta    1380
ttgattgctg tgtccaactc cagagctgga gcttcttctt aactcaggac tccagccccc    1440
cccccccctc ggtagatgcg tatctctaga acctgctgga tctgccaggg ctactccctc    1500
aagttcaagg accaacagcc acacgggcag tggaggtgct gcgttgccta cggtcaaggc    1560
cagcatggtg gagtggatgc ctcagaacgg aggagaaaat gtgaactagc tggaatttt    1620 ttattcttgt gaatatgtac atagggcagt acgagcaatg tcgcgggctg cttctgcacc    1680
ttatcttgaa gcacttacaa taggccttct tgtaatcttg ctctccttca cagcacactc    1740
ggcgacccct tctgtgtcca ctaccccact acccacccct ccctcctcaa cccctccatc    1800
ccggtcctct atgcgcccct tcccccccaac caatcccatc acaacctctt acctatcctt    1860
tccctcccaa cccccttctat cccagcccac cacctacccc actcctcccc aactcctcca    1920
ttctagccca ttaccacgc ctctctcctc agcccagcct accccatccc accctgttcc    1980
tttcctccag tttcctctcc tcaaaggcaa ggctctacat cttggaggag gaggaggaga    2040
agaaaatgag tttcttcacc gctgtcccat tttaagactg cttgaataat aaaaaaaaaa    2100
tctttctaat ctgctatgct tgaatggcac gcggtacaaa ggaaaactgt catggaaata    2160
ttatgcaaat tcccagatct gaagacggaa aatactctaa ttctaaccag agcaagcttt    2220
tttatttttt tatacaaggg gaatatttta ttcaaggtaa aaaaattcta aataaaatat    2280
aattgttttt tatcttttct acagcaaatt tataatttta agattccttt tcctgttcat    2340
cagcagttgt tattacatcc cttgtggcac atttttttt taattttgta aaggtgaaaa    2400 aaaaacttt atgagctcat gtagcaatca aattatcctg tggattgata ataaatgaat    2460
atggtatata gttaaagatt ttaa                                            2484

<210> SEQ ID NO 31
<211> LENGTH: 2247
<212> TYPE: DNA
<213> ORGANISM: Homo sapiens
<220> FEATURE:
<223> OTHER INFORMATION: Human NFIL3 (NM_001289999.1)

<400> SEQUENCE: 31
aattgtgcag ggggcggtgt ttgtgcgtgg agctttccct cccggctccg ggccgtcgcg     60
gctctcggga gaggcgccgg gacatttaa tcgctgcctc cgccgcgcag ccctgcgcag    120
ctgcccggcc gcgccaaccc cttccccgcc gcagcgcgcc ccgagtgttg gcagcttgcc    180
agccgccacc ccccgccttc cctcctgccc acccccaaggt agagggctcc tctcgggagt    240
gtgcggggaa ggggaggccg aggtccgggc cacgcccggg tagccgcaac ccgcagtgct    300
cagtcggcaa caggtagccc agcaggctgc ggctctcagg aagacaaaaa gcgcctctgc    360
gagcaaataa cgaaggaggc ccaacttcat tcaataagga gcctgacgga tttatcccag    420
acggtagaac aaaaggaaga atattgatgg attttaaacc agagttttta aagagcttga    480
gaatacgggg aaattaattt gttctcctac acacatagat agggtaaggt tgtttctgat    540
```

```
gcagctgaga aaaatgcaga ccgtcaaaaa ggagcaggcg tctcttgatg ccagtagcaa      600
tgtggacaag atgatggtcc ttaattctgc tttaacggaa gtgtcagaag actccacaac      660
aggtgaggag ctgcttctca gtgaaggaag tgtggggaag aacaaatctt ctgcatgtcg      720
gaggaaacgg gaattcattc ctgatgaaaa gaaagatgct atgtattggg aaaaaaggcg      780
gaaaaataat gaagctgcca aaagatctcg tgagaagcgt cgactgaatg acctggtttt      840
agagaacaaa ctaattgcac tgggagaaga aaacgccact ttaaaagctg agctgctttc      900
actaaaatta agtttggtt taattagctc cacagcatat gctcaagaga ttcagaaact       960
cagtaattct acagctgtgt actttcaaga ttaccagact tccaaatcca atgtgagttc     1020
atttgtggac gagcacgaac cctcgatggt gtcaagtagt tgtatttctg tcattaaaca     1080
ctctccacaa agctcgctgt ccgatgtttc agaagtgtcc tcagtagaac acacgcagga     1140
gagctctgtg cagggaagct gcagaagtcc tgaaaacaag ttccagatta tcaagcaaga     1200
gccgatggaa ttagagagct acacaaggga gccaagagat gaccgaggct cttacacagc     1260
gtccatctat caaaactata tggggaattc tttctctggg tactcacact ctcccccact     1320
actgcaagtc aaccgatcct ccagcaactc cccgagaacg tcggaaactg atgatggtgt     1380
ggtaggaaag tcatctgatg gagaagacga gcaacaggtc cccaagggcc ccatccattc     1440
tccagttgaa ctcaagcatg tgcatgcaac tgtggttaaa gttccagaag tgaattcctc     1500
tgccttgcca cacaagctcc ggatcaaagc caaagccatg cagatcaaag tagaagcctt     1560
tgataatgaa tttgaggcca cgcaaaaact ttcctcacct attgacatga catctaaaag     1620
acatttcgaa ctcgaaaagc atagtgcccc aagtatggta cattcttctc ttactccttt     1680
ctcagtgcaa gtgactaaca ttcaagattg gtctctcaaa tcggagcact ggcatcaaaa     1740
agaactgagt ggcaaaactc agaatagttt caaaactgga gttgttgaaa tgaaagacag     1800
tggctacaaa gtttctgacc cagagaactt gtatttgaag caggggatag caaacttatc     1860
tgcagaggtt gtctcactca agagacttat agccacacaa ccaatctctg cttcagactc     1920
tgggtaaatt actactgagt aagagctggg catttagaaa gatgtcattt gcaatagagc     1980
agtccatttt gtattatgct gaattttcac tggacctgtg atgtcatttc actgtgatgt     2040
gcacatgttg tctgtttggt gtctttttgt gcacagatta tgatgaagat tagattgtgt     2100
tatcactctg cctgtgtata gtcagatagt ccatgcgaag gctgtatata ttgaacatta     2160 ttttgttgt tctattataa agtgtgtaag ttaccagttt caataaagga ttggtgacaa      2220
acacagaaaa aaaaaaaaaa aaaaaaa                                         2247
```

<210> SEQ ID NO 32
<211> LENGTH: 2019
<212> TYPE: DNA
<213> ORGANISM: Mus <mouse, genus>
<220> FEATURE:
<223> OTHER INFORMATION: Mouse Nfil3 (NM_017373.3)

<400> SEQUENCE: 32

```
acacatctct cggcgcggcc acggcgcccg cggacccggc gcgcccgctc gtctcccgcg       60
ccgcgccctc gccaccgccc gctgagggcc cggcggagct tgaatcgcgc cccggcgccg      120
ccagcccggt tacagccgcc ctttcttttc cccctcacgg accagggagc agaaccacga      180
taacccatga aaggctcctg acagatttac cctgtgccgg acaacagaag gacccattga      240
tggatgagag gctgaagtcc ttaagacctg aaagaagact ggggaagtga tttgtctcct      300
ccatccggtc tgtaggacga ggaggtcctt tctgatgcag ctgagaaaaa tgcagaccat      360
```

-continued

```
caaaaaggag cccgcacccc tagatcctac cagcagctca gacaagatgc tgctgctgaa      420
ctctgcctta gctgaggtgg ccgaggacct agcctcaggt gaagatttgc tcctgaacga      480
agggagcatg gggaaaaaca atcctcggc gtgtcggaga aaacgggaat tcattccgga       540
cgagaagaaa gacgccatgt attgggagaa acggcgaaa acaacgaag ctgccaaaag       600 atctcgggag aagcgccgcc tcaatgacct ggttttggag aacaagctga tcgccctggg      660
agaagaaaat gccactttaa aagctgagct gctctccctg aaattaaagt ttggtttaat      720
tagctccacg gcgtatgccc aagaaatcca gaaactcagt aattccacag ctgtctactt      780
tcaggactac cagacatcca aggctgccgt gagctctttt gtggacgagc atgagcctgc      840
gatggtagcc ggaagttgca tctcagtcat caagcactct ccccagagct cgctctccga      900
tgtgtcagag gtgtcctcgg tggagcacac tcaggaaagc cccgcacagg gaggctgccg      960
gagccctgag aacaagttcc ctgtgatcaa gcaggagccc gtggagttgg agagctttgc     1020
cagggaggcc agggaggagc ggggcacgta ttccacctcc atctaccaga gctacatggg     1080
aagctctttc tccacttact cccactcccc acccctcttg caggtccatg ggtccactag     1140
caactcccca agaacctcag aggccgatga gggtgtagtg ggcaagtctt ctgatgggga     1200
agacgaacaa caggtcccta agggcccat ccattctcca gtggagctgc aacgggtcca     1260
cgccacggtg gtgaaggttc cggaagtgaa cccttctgcc ttaccgcaca gcttcggat    1320 taaagccaag gccatgcagg tcaaagtgga ggctttggac agcgagtttg aaggcatgca     1380
gaaactctct tcacccgccg atgcgatcgc caaaagacat tttgacctgg agaaacatgg     1440
aacctcgggt atggcccatt cctccctccc tcctttctca gtgcaggtga cgaacattca     1500
agattggtcc ctcaaatcgg aacactggca tcacaaagaa ctgagcagca aaactcagag     1560
tagcttcaaa acaggtgtgg tggaagtcaa agacggtggc tataaggttt ccgaagctga     1620
gaatttgtat ttgaagcagg aatagcaaa cttatctgca gaggtggtct cgctcaagag     1680
attcatagcc acacaaccga tctcggcttc ggactccagg taaatggctg ctgaccgagc     1740
tatgcatgga ggaggaggct gttggtacca tactgaattt ccactggacc tctaaagtca     1800
tttcactgta gtgtgcacaa cggcgtctgt ctgggtgtcc ttgtgtgcac gcgctgaaga     1860
cttgatgccc tcactctgcc tggcgtgtag tcagatagcc ccccacagag gctgtacata     1920
ctgaacgtta tttttgctct attataaagt gtgtatgttg ccagtttcaa taaaggattg     1980
gtggcaagca aaaaaaaaa aaaaaaaaa aaaaaaaa                                2019
```

<210> SEQ ID NO 33
<211> LENGTH: 3575
<212> TYPE: DNA
<213> ORGANISM: Homo sapiens
<220> FEATURE:
<223> OTHER INFORMATION: Human BCL6 (NM_001706.4)

<400> SEQUENCE: 33

```
accatcgtct tgggcccggg gagggagagc caccttcagg cccctcgagc ctcgaaccgg       60
aacctccaaa tccgagacgc tctgcttatg aggacctcga aatatgccgg ccagtgaaaa      120
aatcttgtgg ctttgagggc ttttggttgg ccaggggcag taaaaatctc ggagagctga      180
caccaagtcc tcccctgcca cgtagcagtg gtaaagtccg aagctcaaat tccgagaatt      240
gagctctgtt gattcttaga actggggttc ttagaagtgg tgatgcaaga agtttctagg      300
aaaggccgga caccaggttt tgagcaaaat tttggactgt gaagcaaggc attggtgaag      360
```

-continued

| | |
|---|---|
| acaaaatggc ctcgccggct gacagctgta tccagttcac ccgccatgcc agtgatgttc | 420 |
| ttctcaacct taatcgtctc cggagtcgag acatcttgac tgatgttgtc attgttgtga | 480 |
| gccgtgagca gtttagagcc cataaaacgg tcctcatggc ctgcagtggc ctgttctata | 540 |
| gcatctttac agaccagttg aaatgcaacc ttagtgtgat caatctagat cctgagatca | 600 |
| accctgaggg attctgcatc ctcctggact tcatgtacac atctcggctc aatttgcggg | 660 |
| agggcaacat catggctgtg atggccacgg ctatgtacct gcagatggag catgttgtgg | 720 |
| acacttgccg gaagtttatt aaggccagtg aagcagagat ggtttctgcc atcaagcctc | 780 |
| ctcgtgaaga gttcctcaac agccggatgc tgatgcccca agacatcatg gcctatcggg | 840 |
| gtcgtgaggt ggtggagaac aacctgccac tgaggagcgc ccctgggtgt gagagcagag | 900 |
| cctttgcccc cagcctgtac agtggcctgt ccacaccgcc agcctcttat tccatgtaca | 960 |
| gccacctccc tgtcagcagc ctcctcttct ccgatgagga gtttcgggat gtccggatgc | 1020 |
| ctgtggccaa cccettcccc aaggagcggg cactcccatg tgatagtgcc aggccagtcc | 1080 |
| ctggtgagta cagccggccg actttggagg tgtcccccaa tgtgtgccac agcaatatct | 1140 |
| attcacccaa ggaaacaatc ccagaagagg cacgaagtga tatgcactac agtgtggctg | 1200 |
| agggcctcaa acctgctgcc ccctcagccc gaaatgcccc ctacttccct tgtgacaagg | 1260 |
| ccagcaaaga agaagagaga ccctcctcgg aagatgagat tgccctgcat ttcgagcccc | 1320 |
| ccaatgcacc cctgaaccgg aagggtctgg ttagtccaca gagcccccag aaatctgact | 1380 |
| gccagcccaa ctcgcccaca gagtcctgca gcagtaagaa tgcctgcatc ctccaggctt | 1440 |
| ctggctcccc tccagccaag agccccactg accccaaagc ctgcaactgg aagaaataca | 1500 |
| agttcatcgt gctcaacagc ctcaaccaga atgccaaacc agaggggcct gagcaggctg | 1560 |
| agctgggccg cctttcccca cgagcctaca cggcccacc tgcctgccag ccacccatgg | 1620 |
| agcctgagaa ccttgacctc cagtccccaa ccaagctgag tgccagcggg gaggactcca | 1680 |
| ccatcccaca agccagccgg ctcaataaca tcgttaacag gtccatgacg ggctctcccc | 1740 |
| gcagcagcag cgagagccac tcaccactct acatgcaccc cccgaagtgc acgtcctgcg | 1800 |
| gctctcagtc cccacagcat gcagagatgt gcctccacac cgctggcccc acgttccctg | 1860 |
| aggagatggg agagacccag tctgagtact cagattctag ctgtgagaac ggggccttct | 1920 |
| tctgcaatga gtgtgactgc cgcttctctg aggaggcctc actcaagagg cacacgctgc | 1980 |
| agacccacag tgacaaaccc tacaagtgtg accgctgcca ggcctccttc gctacaaagg | 2040 |
| gcaacctcgc cagccacaag accgtccata ccggtgagaa accctatcgt tgcaacatct | 2100 |
| gtggggccca gttcaaccgg ccagccaacc tgaaaaccca cactcgaatt cactctggag | 2160 |
| agaagcccta caaatgcgaa acctgcggag ccagatttgt acaggtggcc cacctccgtg | 2220 |
| cccatgtgct tatccacact ggtgagaagc cctatccctg tgaaatctgt ggcacccgtt | 2280 |
| tccggcacct tcagactctg aagagccacc tgcgaatcca cacaggagag aaaccttacc | 2340 |
| attgtgagaa gtgtaacctg catttccgtc acaaaagcca gctgcgactt cacttgcgcc | 2400 |
| agaagcatgg cgccatcacc aacaccaagg tgcaataccg cgtgtcagcc actgacctgc | 2460 |
| ctccggagct ccccaaagcc tgctgaagca tggagtgttg atgctttcgt ctccagcccc | 2520 |
| ttctcagaat ctacccaaag gatactgtaa cactttacaa tgttcatccc atgatgtagt | 2580 |
| gcctctttca tccactagtg caaatcatag ctggggttg ggggtggtgg ggtcggggc | 2640 |
| ctggggact gggagccgca gcagctcccc ctcccccact gccataaaac attaagaaaa | 2700 |
| tcatattgct tcttctccta tgtgtaaggt gaaccatgtc agcaaaaagc aaaatcatt | 2760 |

| | |
|---|---|
| tatatgtcaa agcagggag tatgcaaaag ttctgacttg actttagtct gcaaaatgag | 2820 |
| gaatgtatat gttttgtggg aacagatgtt tcttttgtat gtaaatgtgc attcttttaa | 2880 |
| aagacaagac ttcagtatgt tgtcaaagag agggctttaa ttttttttaac caaaggtgaa | 2940 |
| ggaatatatg gcagagttgt aaatatataa atatatatat atataaaata aatatatata | 3000 |
| aacctaaaaa agatatatta aaaatataaa actgcgttaa aggctcgatt ttgtatctgc | 3060 |
| aggcagacac ggatctgaga atctttattg agaaagagca cttaagagaa tattttaagt | 3120 |
| attgcatctg tataagtaag aaaatatttt gtctaaaatg cctcagtgta tttgtatttt | 3180 |
| tttgcaagtg aaggtttaca atttacaaag tgtgtattaa aaaaaacaaa aagaacaaaa | 3240 |
| aaatctgcag aaggaaaaat gtgtaatttt gttctagttt tcagtttgta tacccgta | 3300 |
| caacgtgtcc tcacggtgcc ttttttcacg gaagttttca atgatgggcg agcgtgcacc | 3360 |
| atcccttttt gaagtgtagg cagacacagg gacttgaagt tgttactaac taaactctct | 3420 |
| ttgggaatgt ttgtctcatc ccattctgcg tcatgcttgt gttataacta ctccggagac | 3480 |
| agggtttggc tgtgtctaaa ctgcattacc gcgttgtaaa atatagctgt acaaatataa | 3540 |
| gaataaaatg ttgaaaagtc aaactggaaa aaaaa | 3575 |

<210> SEQ ID NO 34
<211> LENGTH: 3527
<212> TYPE: DNA
<213> ORGANISM: Mus <mouse, genus>
<220> FEATURE:
<223> OTHER INFORMATION: Mouse Bcl6 (NM_009744.4)

<400> SEQUENCE: 34

| | |
|---|---|
| gtagccgcgc gcgcccgcct cgggaccccc ggtgttccgg gcggcggtgc tgcgggaacc | 60 |
| acgatccgca ctatagggcg gcgagcggcg cggccccgag gcattctgcc ggccgggagg | 120 |
| gcgctgcgga gcgcgccgct gccaccgagt cctcccctgc tgcggagcaa tggtaaagcc | 180 |
| cgcagctcaa attccgagaa ttgagctctg ttgattctta gaactggggt tcttagaagt | 240 |
| ggtgatgcaa gaagtttcta ggaaaggccg acaccagtt ttaaagcaaa attttggact | 300 |
| gtgaagcaag gcactgggca aacacaacat ggcctccccg gctgacagct gtatccagtt | 360 |
| tacccggcac gctagtgatg ttcttctcaa ccttaatcgc ctccggagtc gggacatctt | 420 |
| gacgacgtt gtcatcgtgg tgagccgtga gcagtttaga gcccataaga cagtgctcat | 480 |
| ggcctgcagc ggcctgttct acagtatctt cactgaccag ttgaaatgca accttagtgt | 540 |
| aatcaatcta gatcctgaaa tcagccctga ggggttttgc atcctcctgg acttcatgta | 600 |
| cacatctagg ctcaacctga gggaaggcaa tatcatggcg gtgatgacca cagccatgta | 660 |
| cctgcagatg gagcatgttg tcgacacatg caggaagttc atcaaggcca gtgaagcaga | 720 |
| aatggccccct gcacttaaac ctccccgtga agagttcctg aacagccgga tgctgatgcc | 780 |
| ccatgacatc atggcctacc gaggtcgtga ggtcgtggag aacaatatgc cactgagaaa | 840 |
| tactcccggg tgtgagagca gagcttttgc tcctcctctg tacagtggcc tgtcaacacc | 900 |
| accagcctct tatcccatgt acagccatct cccgctcagc accttcctct tctctgatga | 960 |
| ggagctccga gatgccccc gaatgcctgt ggccaaccct tttcccaagg agcgtgccct | 1020 |
| cccctgcgac agtgccaggc aagtccctaa tgagtatagc aggccagcca tggaggtgtc | 1080 |
| ccccagtttg tgtcacagca acatctactc gcccaaggag gcagtcccag aggaggctcg | 1140 |
| gagtgacata cactacagtg tgcctgaggg ccccaagcct gctgtccctt ctgctcggaa | 1200 |

```
tgctccatac ttcccctgtg acaaagccag caaagaagaa gagagacctt cttcggagga   1260
tgagattgcc ctgcatttcg agccccccaa tgcacccttg aaccggaagg gtctggttag   1320
tccccagagt ccccagaaat ccgactgcca gcccaactca cccacagagt cctgcagcag   1380
caagaacgcc tgcatccttc aggcctctgg ctctccgcca gccaagagcc ccactgaccc   1440
gaaagcctgc aactggaaga agtataagtt catcgttctc aacagcctca atcagaatgc   1500
caaacccgag ggctctgagc aggcagagct gggtcgcctc tcccctcgag cctaccctgc   1560
accgcccgct tgccagccgc ctatggagcc cgcgaacctt gatctccagt ccccgaccaa   1620
gctcagtgcc agtggggagg actctaccat cccccaagcc agccggctca ataatctcgt   1680
gaacaggtcc ctggcaggct ccccccgaag cagcagtgag agtcactcac cactctacat   1740 gcaccccccca aagtgcacat cctgcggctc tcagtcccca cagcatacag agatgtgcct   1800
ccatactgct gggcccacgt tcccggagga gatgggggaa acccagtcag agtattcgga   1860
ttctagctgt gagaatggga ccttcttctg caacgaatgt gactgccgtt tctctgagga   1920
ggcctcgctc aagaggcaca cgctgcagac gcacagtgac aaaccataca aatgtgatcg   1980
ctgccaggcc tccttccgct acaagggcaa cctcgccagc acaagactg tccacacggg   2040 tgagaaaccc tatcgctgta acatttgtgg agcgcagttc aatcggccag ccaacctgaa   2100
gacccacact cgaattcact ctggagaaaa gccctacaaa tgtgaaacct gtggggccag   2160
gtttgttcag gtgccccacc tccgtgccca cgtgctcatc cacactggag agaagccgta   2220
cccctgtgaa atctgtggca ctcgcttccg gcaccttcag actctgaaga gccatctgcg   2280
catccacaca ggagagaaac cttaccattg tgagaagtgt aacctgcact tcgtcacaa   2340 aagccaactg cgacttcatt tgcgccagaa gcacggcgcc atcaccaaca ccaaggtgca   2400
ataccgcgtg tcggccgctg acctgcctcc ggagctcccc aaagcctgct gaatgaagca   2460
tggagtgttc ctcgcccttt cctctccagc cccttctcag aatctaccca aaggatgctg   2520 taacactta tacaaaggtc atcccatgat gtagtgcctc tctcatccac tagtgcaaat   2580
catagttggg gtgggggtgg gggtggggtt tgcgggaccg ggagccaagg cagctcccct   2640
tcccacactg ccataaaaca ttaagaaaat actattgctt cttctcctat gtgtaaggca   2700
aaccctgtca gcaaaaagca aattcatttt ctatatcaaa gtaggggaga atgcagaagt   2760
tctgacttga caggttgcaa ccgaggaatg taaatgatgt gtgggaacag aggtctcttt   2820
tgtatgtaaa tgtgtattgt tttaaaagac aagacttcag tatgctgtca aagagaaggc   2880
tttaattttt ttaaccaaag gtgaaggaat atatggcaga gttgtaaata tataaatata   2940
tatatatata atataaatat ataaacctaa aagatatat tgaaaatata aaactgtgtt   3000
aaaggctcga ttttgtatct gcaggcagac acggatctga gaatctttat tgagaaagag   3060
cacttaagag actattttaa gtattgcgtc tgtataagta agaaaatatt ttgtctaaaa   3120
tgcctccgtg tatttgtatt tttttgcaag tgaaggttta caaatttaca aagtgtgtat   3180
taaaaacaaa aagaacaaaa aaaaaagctg cagaaggaga aatgtatact tttgttccag   3240
ttttcagttt gtacatacct gtaatgtgtc ctcacggtgc cttttacac ggaagttttc   3300 aatgatggac gggtgtgcgc catcccttt tgaagtgtag gcagacacag ggacttgaag   3360
ttgtcactaa ctaaactctc tttgggaatg tttgactcct cccacattct gcgtcatgct   3420 tgtcgtttata attactccgg agacagggtt tggctgtgtc taaactgcat tagtgcgttg   3480
taaaatagag ctgtacaaaa cataagaata aacattgaa aagtcga               3527
```

<210> SEQ ID NO 35
<211> LENGTH: 3623
<212> TYPE: DNA
<213> ORGANISM: Homo sapiens
<220> FEATURE:
<223> OTHER INFORMATION: Human L-MYC (NM_001033081.2)

<400> SEQUENCE: 35

| | | | | | |
|---|---|---|---|---|---|
| aatgcgcctg | cagctcgcgc | tcccgcgccg | atcccgagag | cgtccgggcc | gccgtgcgcg | 60 |
| agcgagggag | ggcgcgcgcg | cggggggggc | gcgcttgtga | gtgcgggccg | cgctctcggc | 120 |
| ggcgcgcatg | tgcgtgtgtg | ctggctgccg | ggctgccccg | agccggcggg | gagccggtcc | 180 |
| gctccaggtg | gcgggcggct | ggagcgaggg | aggctgcggg | tggccagggc | acgggcgcgg | 240 |
| gtcccgcggt | gcgggctggc | tgcaggctgc | cttctgggca | cggcgcgccc | ccgcccggcc | 300 |
| ccgccgggcc | ctgggagctg | cgctccgggc | ggcgctggca | aagtttgctt | tgaactcgct | 360 |
| gcccacagtc | gggtccgcgc | gctgcgattg | gcttccccta | ccactctgac | ccggggcccg | 420 |
| gcttcccggg | acgcgaggac | tgggcgcagg | ctgcaagctg | gtggggttgg | ggaggaacga | 480 |
| gagcccggca | gccgactgtg | ccgagggacc | cggggacacc | tccttcgccc | ggccggcacc | 540 |
| cggtcagcac | gtcccccctt | ccctcccgca | gggagcggac | atggactacg | actcgtacca | 600 |
| gcactatttc | tacgactatg | actgcgggga | ggatttctac | cgctccacgg | cgcccagcga | 660 |
| ggacatctgg | aagaaattcg | agctggtgcc | atcgcccccc | acgtcgccgc | cctgggcttt | 720 |
| gggtcccggc | gcagggacc | cggccccgg | gattggtccc | ccggagccgt | ggcccggagg | 780 |
| gtgcaccgga | gacgaagcgg | aatcccgggg | ccactcgaaa | ggctggggca | ggaactacgc | 840 |
| ctccatcata | cgccgtgact | gcatgtggag | cggcttctcg | gcccgggaac | ggctggagag | 900 |
| agctgtgagc | gaccggctcg | ctcctggcgc | gccccggggg | aacccgccca | aggcgtccgc | 960 |
| cgccccggac | tgcactccca | gcctcgaagc | cggcaacccg | gcgcccgccg | cccctgtcc | 1020 |
| gctgggcgaa | cccaagaccc | aggcctgctc | cgggtccgag | agcccaagcg | actcggagaa | 1080 |
| tgaagaaatt | gatgttgtga | cagtagagaa | gaggcagtct | ctgggtattc | ggaagccggt | 1140 |
| caccatcacg | gtgcgagcag | accccctgga | tccctgcatg | aagcatttcc | acatctccat | 1200 |
| ccatcagcaa | cagcacaact | atgctgcccg | ttttcctcca | gaaagctgct | cccaagaaga | 1260 |
| ggcttcagag | aggggtcccc | aagaagaggt | tctggagaga | gatgctgcag | gggaaaagga | 1320 |
| agatgaggag | gatgaagaga | ttgtgagtcc | cccacctgta | gaaagtgagg | ctgcccagtc | 1380 |
| ctgccacccc | aaacctgtca | gttctgatac | tgaggatgtg | accaagagga | gaatcacaa | 1440 |
| cttcctggag | cgcaagaggc | ggaatgacct | gcgttcgcga | ttcttggcgc | tgagggacca | 1500 |
| ggtgcccacc | ctggccagct | gctccaaggc | ccccaaagta | gtgatcctaa | gcaaggcctt | 1560 |
| ggaatacttg | caagccctgg | tggggctga | aagaggatg | gctacagaga | aaagacagct | 1620 |
| ccgatgccgg | cagcagcagt | tgcagaaaag | aattgcatac | ctcactggct | actaactgac | 1680 |
| caaaaagcct | gacagttctg | tcttacgaag | acacaagttt | atttttttaac | ctccctctcc | 1740 |
| cctttagtaa | tttgcacatt | ttggttatgg | tgggacagtc | tggacagtag | atcccagaat | 1800 |
| gcattgcagc | cggtgcacac | acaataaagg | cttgcattct | tggaaaccctt | gaaacccagc | 1860 |
| tctccctctt | ccctgactca | tgggagtgct | gtatgttctc | tggcgccttt | ggcttcccag | 1920 |
| caggcagctg | actgaggagc | cttgggggtct | gcctagctca | ctagctctga | agaaaaggct | 1980 |
| gacagatgct | atgcaacagg | tggtggatgt | tgtcaggggc | tccagcctgc | atgaaatctc | 2040 |
| acactctgca | tgagctttag | gctaggaaag | gatgctccca | actggtgtct | ctggggtgat | 2100 |

| | |
|---|---:|
| gcaaggacag ctgggcctgg atgctctccc tgaggctcct ttttccagaa gacacacgag | 2160 |
| ctgtcttggg tgaagacaag cttgcagact tgatcaacat tgaccattac ctcactgtca | 2220 |
| gacactttac agtagccaag gagttggaaa cctttatata ttatgatgtt agctgacccc | 2280 |
| cttcctccca ctcccaatgc tgcgaccctg gaacactta aaaagcttgg cctctagatt | 2340 |
| ctttgtctca gagccctctg gctctctcc tctgagggag ggacctttct ttcctcacaa | 2400 |
| gggactttt tgttccatta tgccttgtta tgcaatgggc tctacagcac cctttcccac | 2460 |
| aggtcagaaa tatttcccca agacacaggg aaatcggtcc tagcctgggg cctggggata | 2520 |
| gcttggagtc ctggcccatg aacttgatcc ctgcccaggt gttttccgag ggcacttga | 2580 |
| ggcccagtct tttctcaagg caggtgtaag acacctcaga gggagaactg tactgctgcc | 2640 |
| tctttcccac ctgcctcatc tcaatccttg agcggcaagt ttgaagttct ctggaacca | 2700 |
| tgcaaatctg tcctcctcat gcaattccaa ggagcttgct ggctctgcag ccaccccttgg | 2760 |
| gccccttcca gcctgccatg aatcagatat ctttcccaga atctgggcgt ttctgaagtt | 2820 |
| ttggggagag ctgttgggac tcatccagtg ctccagaagg tggacttgct tctggtgggt | 2880 |
| tttaaaggag cctccaggag atatgcttag ccaaccatga tggattttac cccagctgga | 2940 |
| ctcggcagct ccaagtggaa tccacgtgca gcttctagtc tgggaaagtc acccaaccta | 3000 |
| gcagttgtca tgtgggtaac ctcaggcacc tctaagcctg tcctggaaga aggaccagca | 3060 |
| gccctccag aactctgccc aggacagcag gtgcctgctg gctctgggtt tggaagttgg | 3120 |
| ggtgggtagg gggtggtaag tactatatat ggctctggaa accagctgc tacttccaaa | 3180 |
| tctattgtcc ataatggttt ctttctgagg ttgcttcttg gctcagagg accccagggg | 3240 |
| atgtttggaa atagcctctc taccccttctg gagcatggtt tacaaaagcc agctgacttc | 3300 |
| tggaattgtc tatggaggac agtttgggtg taggttactg atgtctcaac tgaatagctt | 3360 |
| gtgttttata agctgctgtt ggctattatg ctggggagt cttttttttt tatattgtat | 3420 |
| ttttgtatgc cttttgcaaa gtggtgttaa ctgttttgt acaaggaaaa aaactcttgg | 3480 |
| ggcaatttcc tgttgcaagg gtctgattta ttttgaaagg caagttcacc tgaaattttg | 3540 |
| tatttagttg tgattactga ttgcctgatt ttaaaatgtt gccttctggg acatcttcta | 3600 |
| ataaaagatt tctcaaacat gtc | 3623 |

<210> SEQ ID NO 36
<211> LENGTH: 3686
<212> TYPE: DNA
<213> ORGANISM: Mus <mouse, genus>
<220> FEATURE:
<223> OTHER INFORMATION: Mouse L-myc (NM_008506.3)

<400> SEQUENCE: 36

| | |
|---|---:|
| agtcgggaaa caatgcgcct gcagatcgcg ctcccgcgtc gatcccggga gcgtcctggc | 60 |
| tgccgtgtgc gagcgaggcg gggggcgcgc gcacgggggg cgcgctcgtg agtgcgggc | 120 |
| cgcgcgctcg gtggcgcgca tgtgtgtgtg tgcgggctgc cgggcttccc cgagccggcg | 180 |
| gggagccgct ccgctccagg tggcgggcgg cgggagcgag gtgaggctgc gggtggcccg | 240 |
| ggcagggtc cccaggggac tggcgggctg caaggctgca gactgccttc gagacagcgc | 300 |
| gccccgccc ggccctgctg tgccccgga gctgagctcc gggcggtgct ggcaaagttt | 360 |
| gctttgaact cgctccccctc agcctggtcg gccgttgcg agctgccctg agcgagctga | 420 |
| ccccaggcca ggcttcccag gagcaggac caggcgcgg gctgcaagct ggtgggcctg | 480 |
| gggagagacc agagccccgc agccagctgc agcgagggac tcggagccgc ctcttccctc | 540 |

-continued

```
ggcgggcacc gcagtcagct cgtctccccc ttccctcccg cagggagcgg acatggactt      600
cgactcgtat cagcactatt tctacgacta tgactgcgga gaggatttct accgctccac      660
ggcgcccagc gaggacatct ggaagaaatt cgagctggtg ccgtcgcccc ccacgtcgcc      720
gccctggggc tccggtcccg cgccgtggac cccagcctct gggattaatc ccggggagcc      780
gtggcctgga gggggtgccg gggacgaggc ggaatctcgg ggccattcga aagcctgggg      840
caggaattat gcttccatca ttcgccgtga ctgcatgtgg agcggcttct ccgcccgaga      900
acggctggag agagtggtga gcgacaggct ggccccaggc gcgccccggg ggaacccgcc      960
caaagcgccc gctaccccgg acggcactcc tagtctggaa gccagtaacc cggcgcccgc     1020
cacccaatgt cagctgggcg agcccaagac tcaggcctgc tccgggtccg agagcccag      1080 cgattctgaa ggtgaagaga ttgacgtggt gaccgtggag aagaggcgat ctctggacat     1140
ccgaaagcca gtcaccatca cggtgcgagc agaccccctg gaccccctgca tgaagcactt     1200 ccatatctct atccaccaac agcagcataa ctatgctgcc cgttttcctc cagaaagttg     1260
ctctcaagag ggggatcctg agccaggtcc ccaggaagag gctccggaga tagaagctcc     1320
caaggagaaa gaggaggagg aagaggaaga ggaggaagaa gagattgtga gcccccccacc    1380 tgtcggaagt gaggctcccc agtcctgcca ccccaaacct gtcagttctg acactgagga     1440
cgtgaccaag aggaagaacc ataacttctt ggaacgaaaa aggaggaatg acctccgctc     1500
ccggttccta gccctgcggg accaggttcc caccctggcc agctgctcta aggcccccaa     1560
agtcgtgatc ctcagcaagg cgttagaata cttgcaggct ttggtggggg ctgaaaagaa     1620
aatggctaca gagaaaaggc agctccggtg tcggcaacag caactgcaaa agagaatcgc     1680
gtacctcagt ggctactaac cgaccagaac gcctgacttc ttggtctcac agacacaagc     1740
ttattgttta acctctctct cccttttagt aatttgcaca ttttggttac agcggggggg     1800
gcagtctgga cagtagatcc cagaatgcat tgcagccggt gtgcgcacac aataagggct     1860
tgcattcttg gtaacctcga aacccaattc tccctcttcc ccgaccgact catgggaatg     1920
ctgtccttct ctggcgcctt tggcttctca gcaggcagct actgaggaga tttggggtct     1980
gcttagctca ctagctcctg acgaaaggct gacagatgct atgcaacagg tggtggacgt     2040
tgttggggct gcagcctacg tgaaatctca cactgtgctg gggcttcagg ctaggaaagg     2100
atgctgctct cactgctgtc tctggggatg atctgaggac agctgggcct ggatactgtc     2160
ccccaggctc cgttttccag gaggcaagcg agctgtcccg ggcgaagaca agctcgcaga    2220
cttgatcagc atggagcatt acctcaccgt cagacacttt acagtagctg tggagtggaa     2280
acctttaaga tagatttgga tggtaggcca caccttccc tgcacgctca atgctatgac      2340
tttgagaaag gcttggcct ctatgtagag tctttgtctc agagttctct gggccttctc      2400
agagagggac ctttctatcc tcacaaggga cctttttgtt tcttcctgcc tttgttatgc     2460 aatgccacc acagcaccct ttcacaccga ccagaaatat ttccccagga catagggaaa     2520
tgggtcacag cccaggacct ggggaagcct tggcatcccc actcatgacc aacggtcctt     2580
gcccaggttt tctgcagggc tatttgaggc ccagcttgga accttttctc gaggcagata     2640
gttacaaggt gcctctgaag acaagcccct atcgcttcct cttcccacc tgcctctctg      2700 tcagatcttg actctgtcta caatctgctg gaacagtgca aacctgtcct tctcgagcaa     2760 cttttgctggc tctgcagcca ccatcctgat tctctgccgg cctgagtcac atccctttccc   2820 ctggaatctg ggccttacag agagattcag aggggcaccg cttgcattca cctgatgccc    2880
```

| | |
|---|---|
| ccagaaggta aacttacttc ctggtgggtt gtcagtgtac ctctaggaac gctactcagc | 2940 |
| caacaaggag agtttgctcc agctgtgttc tgcaactccc tgtggaatca aagtacagcc | 3000 |
| ctctatcctg ggaaagtcac caagctagca gccgtcacgt gagcatcttt caggagatcc | 3060 |
| taagctttgc ctgaaagaag agccagcctt tccagaactc tacccaggaa agcagatctg | 3120 |
| ttcctgctgg ccctgggctt ggaagtaggg gtacagtgtg ggggacagac agtaagtaac | 3180 |
| aacatgtggc tctcaaaaac cagctaccac ttccaaattg ctcccaact gtgatggcct | 3240 |
| ccaattactt cctggcctca agtcctagag gaagcttcgg aagttgctgt tgtacctgtt | 3300 |
| ggggcaggac ttctaggcac caagggactc ctggaactat cttgggagga caagtggtga | 3360 |
| acaggctaaa gtctcatctg aatggcttgt gttttataag ctgctgcggg gttgtatgct | 3420 |
| gtgggcgtct tttgttttg ttttgctt ttttaat actgtatttt tgtatgcttt | 3480 |
| tttgcaaagt ggtgttaact gttttgtat aagaaaaaca aaaacaaaa accctcctgt | 3540 |
| tgcaagggtc tggtttattt tgaaaggtgc atttacctga aattttgtat ttagttgtaa | 3600 |
| tcattaattg cttgatttta aactgttgcc ttctgggaca tcttctaata aaagatttc | 3660 |
| tcaaaaaaaa aaaaaaaaa aaaaaa | 3686 |

<210> SEQ ID NO 37
<211> LENGTH: 5635
<212> TYPE: DNA
<213> ORGANISM: Homo sapiens
<220> FEATURE:
<223> OTHER INFORMATION: Human NR4A3 (NM_006981.3)

<400> SEQUENCE: 37

| | |
|---|---|
| ataaatgacg tgccgagaga gcgagcgaac gcgcagccgg gagagcggag tctcctgcct | 60 |
| cccgccccc accctccag ctcctgctcc tcctccgctc cccatacaca gacgcgctca | 120 |
| cacccgctcc ctcactcgca cacagaca caagcgcgca cacaggctcc gcacacacac | 180 |
| ttcgctctcc cgcgcgctca caccctcttt gccctgagcc cttgccggtg cagcgcggcg | 240 |
| ccgcagctgg acgcccctcc cgggctcact ttgcaacgct gacggtgccg gcagtggccg | 300 |
| tggaggtggg aacagcggcg gcatcctccc ccctggtcac agcccaagcc aggacgcccg | 360 |
| cggaacctct cggctgtgct ctcccatgag tcgggatcgc agcatccccc accagccgct | 420 |
| caccgcctcc gggagccgct gggcttgtac accgcagccc ttccgggaca gcagctgtga | 480 |
| ctcccccca gtgcagattt cgggacagct ctctagaaac tcgctctaaa gacggaaccg | 540 |
| ccacagcact caaagcccac tgcggaagag ggcagcccgg caagcccggg ccctgagcct | 600 |
| ggaccccttag cggtgccggg cagcactgcc ggcgcttcgc ctcgccggac gtccgctcct | 660 |
| cctacactct cagcctccgc tggagagacc cccagcccca ccattcagcg cgcaagatac | 720 |
| cctccagata tgccctgcgt ccaagcccaa tatagcccctt cccctccagg ttccagttat | 780 |
| gcggcgcaga catacagctc ggaatacacc acggagatca tgaacccga ctacaccaag | 840 |
| ctgaccatgg accttggcag cactgagatc acggctacag ccaccacgtc cctgcccagc | 900 |
| atcagtacct tcgtggaggg ctactcgagc aactacgaac tcaagccttc ctgcgtgtac | 960 |
| caaatgcagc ggccccttgat caaagtggag gaggggcggg cgcccagcta ccatcaccat | 1020 |
| caccaccacc accaccacca ccaccaccat caccagcagc agcatcagca gccatccatt | 1080 |
| cctccagcct ccagcccgga ggacgaggtg ctgccagca cctccatgta cttcaagcag | 1140 |
| tccccaccgt ccaccccac cacgccgcc ttccccgc aggcgggggc gttatgggac | 1200 |
| gaggcactgc cctcggcgcc cggctgcatc gcacccggcc cgctgctgga cccgccgatg | 1260 |

```
aaggcggtcc ccacggtggc cggcgcgcgc ttcccgctct tccacttcaa gccctcgccg    1320
ccgcatcccc ccgcgcccag cccggccggc ggccaccacc tcggctacga cccgacggcc    1380
gctgccgcgc tcagcctgcc gctgggagcc gcagccgccg cgggcagcca ggccgccgcg    1440
cttgagagcc acccgtacgg gctgccgctg gccaagaggg cggccccgct ggccttcccg    1500
cctctcggcc tcacgccctc ccctaccgcg tccagcctgc tgggcgagag tcccagcctg    1560
ccgtcgccgc ccagcaggag ctcgtcgtct ggcgagggca cgtgtgccgt gtgcggggac    1620
aacgccgcct gccagcacta cggcgtgcga acctgcgagg gctgcaaggg cttttttcaag   1680
agaacagtgc agaaaaatgc aaaatatgtt tgcctggcaa ataaaaactg cccagtagac    1740
aagagacgtc gaaaccgatg tcagtactgt cgatttcaga agtgtctcag tgttggaatg    1800
gtaaaagaag ttgtccgtac agatagtctg aaagggagga gaggtcgtct gccttccaaa    1860
ccaaagagcc cattacaaca ggaaccttct cagccctctc caccttctcc tccaatctgc    1920
atgatgaatg cccttgtccg agctttaaca gactcaacac ccagagatct tgattattcc    1980
agatactgtc ccactgacca ggctgctgca ggcacagatg ctgagcatgt gcaacaattc    2040
tacaacctcc tgacagcctc cattgatgta tccagaagct gggcagaaaa gattccggga    2100
tttactgatc tccccaaaga agatcagaca ttacttattg aatcagcctt tttggagctg    2160
tttgtcctca gactttccat caggtcaaac actgctgaag ataagtttgt gttctgcaat    2220
ggacttgtcc tgcatcgact tcagtgcctt cgtggatttg gggagtggct cgactctatt    2280
aaagactttt ccttaaattt gcagagcctg aaccttgata tccaagcctt agcctgcctg    2340
tcagcactga gcatgatcac agaaagacat gggttaaaag aaccaaagag agtcgaagag    2400
ctatgcaaca agatcacaag cagtttaaaa gaccaccaga gtaagggaca ggctctggag    2460
cccaccgagt ccaaggtcct gggtgccctg gtagaactga ggaagatctg caccctgggc    2520
ctccagcgca tcttctacct gaagctggaa gacttggtgt ctccaccttc catcattgac    2580
aagctcttcc tggacaccct acctttctaa tcaggagcag tggagcagtg agctgcctcc    2640
tctcctagca cctgcttgct acgcagcaaa gggataggtt tggaaaccta tcatttcctg    2700
tccttcctta agaggaaaag cagctcctgt agaaagcaaa gactttcttt tttttctggc    2760
tcttttcctt acaacctaaa gccagaaaac ttgcagagta ttgtgttggg gttgtgtttt    2820
atatttaggc attgggggat ggggtgggag ggggttatag ttcatgaggg ttttctaaga    2880
aattgctaac aaagcacttt tggacaatgc tatcccagca ggaaaaaaaa ggataatata    2940
actgttttaa aactctttct ggggaatcca attatagttg ctttgtattt aaaaacaaga    3000
acagccaagg gttgttcgcc agggtaggat gtgtcttaaa gattggtccc ttgaaaatat    3060
gcttcctgta tcaaaggtac gtatgtggtg caaacaaggc agaaacttcc ttttaatttc    3120
cttcttcctt tattttaaca aatggtgaaa gatggaggat tacctacaaa tcagacatgg    3180
caaaacaata atggctgttt gcttccataa acaagtgcaa ttttttaaag tgctgtctta    3240
ctaagtcttg tttattaact ctcctttatt ctatatggaa ataaaaagga ggcagtcatg    3300
ttagcaaatg acacgttaat atccctagca gaggctgtgt tcaccttccc tgtcgatccc    3360
ttctgaggta tggcccatcc aagacttta ggccattctt gatggaacca gatccctgcc     3420
ctgactgtcc agctatcctg aaagtggatc agattataaa ctggattaca tgtaactgtt    3480
ttggttgtgt tctatcaacc ccaccagagt tccctaaact tgcttcagtt atagtaactg    3540
actggtatat tcattcagaa gcgccataag tcagttgagt atttgatccc tagataagaa    3600
```

```
catgcaaatc agcaggaact ggtcatacag ggtaagcacc agggacaata aggattttta    3660
tagatataat ttaattttg ttattggtta aggagacaat tttggagagc aagcaaatct    3720
ttttaaaaaa tagtatgaat gtgaatacta gaaaagattt aaaaaatagt atgagtgtga    3780
gtactaggaa ggattagtgg gctgcgtttc aacattccgt gttcgtactc ccttttgtat    3840
gtttctactg ttaatgccat attactatga gataatttgt tgcatagtgt ccttatttgt    3900
ataaacattt gtatgcacgt tatattgtaa tagcttttgcc tgtatttatt gcaagaccac    3960
cagctcctgg aagctgagtt acagagtaat taaatggggt gttcacagtg acttggatac    4020
accaattaga aattaaataa gcaaatatat atatatatat aaatatagca ggttacatat    4080
atatatttat aatgtgtctt tttattaacc atttgtacaa taaatgtcac ttcccatgcc    4140
gttattttat ggttcatttg cagtgacttt taaggcagta ctgtttagca ctttgatatt    4200
aaaattttgc ttatgttttg ctaaattcga ataatgtttg aagattttta ggtctaaaag    4260
tctttatatt atatactctg tatcaagtca aaatatcttt ggccattttg ctaagaaaca    4320
aactttgaat gtcaaactga tgtcacagta gttttgtta gctttaaatc attttgctt    4380
tagtcttttt aaaggaaaat aacaaaacta tgctgtttat attgtcatta aattatacaa    4440
tcaaacaaat gccaaatgaa ttgcctaatt gctgcaaagt ataacccaga taggaaatca    4500
tatgttttt tccaagagtc attctaatat ttgattatgt tatgtgtgct tttatgaaag    4560
attgttattt ttatatatca agatgataga acctggaatg ttaggatttt gaatgttag    4620
acttggaagg ggcctggtct gtcaactagt ccaaccctt aaaattcata gaggagcaaa    4680
ctggggccca ttgaagggtg aagagttact caaggtcaaa cagctggtaa cagaatcaag    4740
actaagacct aatttacctt tccatactct ttttttttct caacttcatc tatataaat    4800
caggcttta aacataacca ctaatattta cctgaagata accatgagta aagtatactt    4860
ttgcattaat tttttgagct tatatgcaaa cataataaat attattaaat atcaggaaag    4920
ctaacatttc atacaagata gcttcagacc aaattcaaat tgaatttgaa taaattagaa    4980
atactgtgca tacataacct tcttgtgcac catgagtatt tggaaagtta atccttgttt    5040
ttgtcgtgtc tataaaggaa gaacaaaaca aaataaaaac agagccctag agaaatgctg    5100
ttacttttta ttttacacc catcagattt aaggaaaaga cttttttagcc attataatct    5160
agtggttgga aggaatgaag aagctttttt agtaataggt ccagatatga gtgctaaaaa    5220
taaagatgat agcatgttct tctgtcttcc atagttatta caactatgag agcctcccaa    5280
gtcatcttat caactcaact cccttttttt tgtcttaatg ttgcacataa gtttatacag    5340
agtggatgac cacactagca cagaagagaa caacatgtat taaagcaggt gattcctccc    5400
cttggcggga gagctctctc agtgtgaaca tgccttctgt gggcggaaat caggaagcca    5460
ccagctgtta atggagagtg ccttgctttt atttcagaca gcagagtttt ccaaagtttc    5520
tctgctcctc taacagcatt gctctttagt gtgtgttaac ctgtggtttg aaagaaatgc    5580
tcttgtacat taacaatgta aatttaaatg attaaattac atttatcaa tggca          5635
```

<210> SEQ ID NO 38
<211> LENGTH: 5573
<212> TYPE: DNA
<213> ORGANISM: Mus <mouse, genus>
<220> FEATURE:
<223> OTHER INFORMATION: Mouse Nr4a3 (NM_015743.3)

<400> SEQUENCE: 38

```
cacacgcgcg ctcacacgct ccgcacacac actccactct ctcccgcgcg ctcacacccc    60
```

```
tctcacccgg ctccctcgcc agtgtcgcgc cgcgccgcgc cgcagccgga cgccctcca     120
gggctcactt tgcaacgctg acagagcccg cagtgtccgt ggaggtggga aacgtggcga     180
catcctaccc cctggtcgca gccggagact ggatgcctgc ggaacctctc ggcggcgctc     240
tcccatgagt tgggatcgca gcatccccg ccagccgctc accgcctctg ggagccgctg      300
ggtttgtgca ccgcagccct tccgggacag cagctgtgac tctcccccaa tccagatttc     360
ggggtcgctc tctagaaact cgctctaaag acggaaccgc cacagcaccc aaagcccact     420
gcgggagagc gcagcccgac aagcccgggc gctgagcctg gaccctcagc agagcgggcc     480
agcacagcgg ctgctgcttc gcctatcccg acgtccccgc ctcctacact ctcagcctcc     540
gctggagaga cccccagccc caccattcag cgcgcaagat accctccaga tatgccctgc     600
gtgcaagccc agtatagccc ttcacctccg ggtccacttt acgccacgca gacttatggc     660
tcggaataca ccacagaaat catgaacccc gactacacca agctgaccat ggacctcggt     720
agcacgggga tcatggccac cgccactaca tccctgccca gcttcagtac cttcatggag     780
ggctacccca gcagctgcga actcaagccc tcctgcctgt accaaatgcc gccttctggg     840
cctcggcctt tgatcaagat ggaagagggt cgcgagcatg gctaccacca ccaccatcac     900
catcaccatc atcaccacca ccaccagcaa cagcagccgt ccattcctcc tccctccggc     960
cccgaggacg aggtactgcc cagcacctcc atgtacttca agcagtctcc gccttctaca    1020
ccgaccactc caggcttccc cccgcaggcg ggggcgctgt gggacgacga gctgccctct    1080
gcgcctggct gcatcgctcc gggaccgctg ctggacccgc agatgaaggc ggtacccccc    1140
atggccgctg ctgcgcgctt cccgatcttc ttcaagccct caccgccaca ccctcccgcg    1200
cccagtccag ccggcggcca ccacctcggc tatgacccca cggccgcagc tgcactcagt    1260
ctgcccctgg gagccgcggc cgcagcaggc agccaagctg ctgcgctcga gggccaccca    1320
tacgggctcc cgctggccaa gaggacggcc acgctgacct tccctccgct gggcctcaca    1380
gcctccccca ccgcgtccag cctgctggga gagagcccca gcctcccatc gccacccaat    1440
aggagctcat catctgggga aggcacatgt gccgtgtgcg gcgacaacgc tgcctgccag    1500
cactacggag tccgcacctg cgagggctgc aagggcttct tcaagagaac ggtgcagaaa    1560
aatgcaaaat atgtttgcct ggcaaataaa aactgcccag tggacaagag acgccgaaac    1620
cgatgtcagt actgcagatt tcagaagtgt ctcagtgtcg ggatggttaa ggaagttgtg    1680
cgtacagaca gtctgaaagg gaggagaggt cgtctgcctt ccaaaccaaa gagcccacta    1740
caacaggagc cctcgcagcc ctccccgcca tctcctccga tctgtatgat gaatgccctt    1800
gtccgagctt taacagatgc aacacccaga gatcttgatt attccagata ctgtcccacc    1860
gaccaggcca ctgcaggcac agatgctgag cacgtgcaac agttctacaa ccttctgacg    1920
gcctccattg acgtgtccag aagctgggca gaaaagatcc caggattcac tgatctcccc    1980
aaagaagatc agacgttact tatagaatca gccttttgg agctgtttgt tcttagactt     2040
tccatcaggt caaacactgc tgaagataag tttgtgttct gcaatggact tgtcctgcat    2100
cgacttcagt gccttcgagg atttgggag tggctcgact ccattaaaga ctttcttta      2160
aacttgcaga gcctgaacct tgatatccaa gcctagcct gcctgtcagc actgagtatg     2220
atcacagagc gacatgggtt aaaagaacca agagagtgg aggagctatg caccaagatc     2280
acaagcagct taaggacca ccagaggaag ggacaggctc tggagccctc ggagcctaag     2340
gtcctgcgcg cgctggtaga actgagaaag atctgtaccc agggcctcca gcgcatcttc    2400
```

```
tacctgaagc tagaggactt ggtacctcca ccttctgtca tcgacaagct cttccttgac    2460
accctgcctt tctgagcagg ggaagcctga gcagagagct acttgctctg ctggcacctg    2520
atcattaagt gagcaaaaga atgggtttga acaccttcca cactcactgt ccttccttca    2580
ggggaaaagc agctcccgta gaaagcaaag actttttttt cttttcctgg caccttttcct   2640 tacaacctaa agccagaaac cttgcagagt atcgtgttgg ggttgtgttt tatatttagg    2700 cttttggtggg tgggttggga gggggtaaat agttcatgag gcttttctaa gaaattgctg   2760
acaaagcact tttggatgat gctatcccag cagtggggtg gggagaaagg ataatataac    2820
tgttttgttt ttgttttttgt ttttgttttt aaaaaaaaac tctttctggg gaatatgatt   2880
atggttgctt tgtatttaaa aataagaaca gccaagggct gttcaccagg gtagggctgt    2940
gtcctacgac ggatcccttt aggatatact tcctgtgtca agggtagata cgtggtgcaa    3000
atgaggcaga aaattcccctt ttcttcattt ctttcttaaa aaaatggcaa aagatgaaag   3060
attatctaca aatcagactt agcaaaaatg ataatggcta tttgcttcca tatacaagtg    3120 caattttttta gagtgctgtc ttactaagtc ttgtttgtga actccccctt attttacatg   3180
aaaataagaa ggaggcagtc atgctatgaa atggcgcgct cattttccta gctaaggctt    3240
gatccacctg cccctgtagaa cccttcggag gtgtggcccct tctaagactt tcaggccatt   3300
ctcgatggaa ttcgacccct gatgactatc cagccatcct gaagggggat cgggttataa    3360
agtggattgc atacaactgt cttcgctgtg ttttgtcaac ctggacagag ttctctaaac    3420
ctacttcagt tgtagcaagt tcctgattca tccactcaga agcccaatga gcactggttg    3480
actcaatcaa gtgttaaccc taggagaaca agcaaataag taggaactgg gtcatacagg    3540
gtaaacacca gagatgataa ggatatatat atatatatat atatatatat atatatatat    3600
atgtatatgt atatatatat acatattaat ttttgttatt ggttagagac aattttggaa    3660
agcaagagaa tcatcttttt ttaaaaaaga gagaagaaga agaagaaaag atagtattaa    3720
cgtgagttct agagaaggtt agtgggttgc ggttcaaaat tccgtgtttg tgccccccttt   3780 tatatgtttc tactgttgat gccatattat tatgaaatga tttgttgcat agtgtccttaa   3840 tttgtatgaa catttgtatg cacgttatat tgtaatagct ttgcctgtat ttattgcaag    3900
accaccagct cctggaggct gagatacaga gtaatcaaat ggggtgttcg tggtgacttg    3960
gatacaccaa ttagaaatta aataagcata tatatatata aacatagccg gttacatata    4020
tatttataat gtgtcttttt attaaccatt tgtacaagaa atgtcacttc ccacgcagtt    4080
actttaccct tcacttgcag tgaccttttaa ggcagcactg tttagcactt tgatatgaaa   4140
tttttgctta tgttttgcta aattctaata atgtttgaag attttaaggt ctaaaagtct    4200
ttatattata tactctgtat caagtcaaga tcccttggc cgttttgcta agactcaaaa    4260
actttgaatg tcaaactgat gtcacagtag cttttgttag cttttaatca tttttgcttt    4320 agttttttttt ttaaaaaaaa taacaaacta tactgtttat attgtcatta aattatacaa   4380
tcaaacaaat gccaaatgaa ttgcctaatt gctgcaaagt gtaacccaga taacaaatca    4440
tattctctcc tcttttttgca actcattcag atgtttgatc ttgtgttttg tttgtataaa   4500
gattgtatga actatatcac cttcctatca aggtgacagg gcttgagatg ttaagatttt    4560
tgaacttcag acttggaagg ggcctggctc atcatctggt cagatctatt aaaattcaca    4620
aaggagaaaa gtgggggccc gttgcagggc aaacagctag caacaggata aaggctcaga    4680
cttaattcac cttcccttag tctccccccac atcttactgc atctgtagga aaataaactt    4740
ttaaacatag tcacgcatac taacacttta ccagcagaca gccttgaata aagtagtact    4800
```

```
ttggcattaa tttgttgagc ttatatgcaa acataataaa cattattaaa tatcaggaaa      4860
gctaacattt cacacgagat cgcttcagac caaattcaat ttgaatttga ataaattaga      4920
agtactgagc gtacgtaacc ttcttgtgca ccttgagtat tgcaaagttg ctccttggtt      4980
gttggttttt tttgttgttt cttttcgtcc tgtctgaaag gcaaagcaaa acagcagcac      5040
ggtgctctgg gaaatgctgt tccccttct gtcctcacac ccacagattg aagggaaaga       5100
actgtctaag catctatctg ctggtttgaa gaatgatgaa gccgttttag ttaagggcca      5160
gacactagtg ctgaaagaaa agactataca gccagtgttc ttctgtcttc catagttatc      5220
acaactatga gagcctctta ggtcatcatt ttgaaatgtt gacacccaag tgtacccaga      5280
gtggaaggca cactagctct gcagaggaca agcattaatg caggtgattc ctcccgctga      5340
ctggagtgca gtctcagtgt gaacccgccc tcagcaggaa atgggaatcc acttgctgtt      5400
cctggagagt gccttgcttt tgtttcaaat ggccgagtct cccaagccct tctcctctaa      5460
cagcattgct tttagtaag tgtgtgttaa cctgtggttt gaaagaaatg ctcttgtaca       5520
ttaacaatgt aaatttaaat gattaaatta aattacattt taccaatgga aaa            5573

<210> SEQ ID NO 39
<211> LENGTH: 5989
<212> TYPE: DNA
<213> ORGANISM: Homo sapiens
<220> FEATURE:
<223> OTHER INFORMATION: Human ETV6 (NM_001987.4)

<400> SEQUENCE: 39
gcgtcccggg tcccgcgcc gcgccgcgac ctgcagaccc cgccgccgcg ctcgggcccg         60
tctcccacgc ccccgccgcc ccgcgcgccc aactccgccg gccgccccgc ccgccccgc        120 gcgctccaga ccccgggc ggctgccggg agagatgctg gaagaaactt cttaaatgac         180
cgcgtctggc tggccgtgga gccttttctgg gttggggaga ggaaaggaaa gtggaaaaaa      240
cctgagaact tcctgatctc tctcgctgtg agacatgtct gagactcctg ctcagtgtag        300
cattaagcag gaacgaattt catatacacc tccagagagc ccagtgccga gttacgcttc        360
ctcgacgcca cttcatgttc cagtgcctcg agcgctcagg atggaggaag actcgatccg        420
cctgcctgcg cacctgcgct tgcagccaat ttactggagc agggatgacg tagcccagtg        480
gctcaagtgg gctgaaaatg agttttcttt aaggccaatt gacagcaaca cgtttgaaat        540
gaatggcaaa gctctcctgc tgctgaccaa agaggacttt cgctatcgat ctcctcattc        600
aggtgatgtg ctctatgaac tccttcagca tattctgaag cagaggaaac ctcggattct        660 ttttcacca ttcttccacc ctggaaactc tatacacaca cagccggagg tcatactgca         720
tcagaaccat gaagaagata actgtgtcca gaggaccccc aggccatccg tggataatgt        780
gcaccataac cctcccacca ttgaactgtt gcaccgctcc aggtcaccta tcacgacaaa        840
tcaccggcct tctcctgacc ccgagcagcg ccccctccgg tccccctgg acaacatgat         900 ccgccgcctc tcccggctg agagagctca gggacccagg ccgcaccagg agaacaacca        960
ccaggagtcc tacctctgt cagtgtctcc catggagaat aatcactgcc cagcgtcctc        1020
cgagtcccac ccgaagccat ccagcccccg gcaggagagc acgcgtgtga tccagctgat       1080
gcccagcccc atcatgcacc ctctgatcct gaaccccggg cactccgtgg atttcaaaca       1140
gtccaggctc tccgaggacg ggctgcatag ggaagggaag cccatcaacc tctctcatcg       1200
ggaagacctg gcttacatga accacatcat ggtctctgtc tccccgcctg aagagcacgc       1260
```

```
catgcccatt gggagaatag cagactgtag actgctttgg gattacgtct atcagttgct    1320
ttctgacagc cggtacgaaa acttcatccg atgggaggac aaagaatcca aaatattccg    1380
gatagtggat cccaacggac tggctcgact gtggggaaac cataagaaca gaacaaacat    1440
gacctatgag aaaatgtcca gagccctgcg ccactactac aaactaaaca ttatcaggaa    1500
ggagccagga caaaggcttt tgttcaggtt tatgaaaacc ccagatgaaa tcatgagtgg    1560
ccgaacagac cgtctggagc acctagagtc ccaggagctg gatgaacaaa tataccaaga    1620
agatgaatgc tgaaggaacc aacagtccac ctcagcgggc cagcagccca gggaacccct    1680
gcccaccagg attgctggaa gtgtgacgga gcaggcgggc tgaggagagt ggaaaaggaa    1740
gcgacccaga aatggcaggg acacttctct tgcagaccaa gagggaccct ggagcacctt    1800
agacaaacta cccagcacag gcggggctgg aattctggcg gagggcatga gcctgggact    1860
ccatgtcacg tttccttctg atttggaatc tctccatctg taattcctca ccctcaccct    1920
tccaccgttg ttagtatcat ggtgttttttg tttttgtttt tgttttaaga acctgcagtt    1980
tgactcttca tcgttcatct agggggaagac atctgatgtt gttttcctat ggaaatatat    2040
atctattata tatatatttt ttgcaaatct cacaaagtgc ggcaagccca gctggtcagg    2100
aaagagaata cttgcagagg ggttcaggtt cctcttttc ctgccacgtg gatcaggtct    2160
gttcctgtta ctgttgggtc ttggctgaaa aaaaaaatg cttttaaaaa agataaaatg    2220
aaaaggagag ctctctttt ctctctcttg ctctgttctt cccttggtcc cctctgtcct    2280
cccgccctgc ctgcagttga gattcagatg ccttctgaca gagttcagcc tcttggagag    2340
tcttggggat tgttggcacc taaacagaat cagtgacccg ggtgctttgt ggccagcagc    2400
acagaatcaa acccgcatcc cagcattggg ccacccatct gagggaggcc aaaatcatca    2460
cagatgctgc tgtgctgcag acagatacat gctagtccag agagccgccc ctagatggc    2520 tgtgagaacc atgtgtctaa ggcgtaagat aaggatggaa ggctgtccaa gttatttgga    2580
aggcctcggc agcttgggat tagcttggga gcgcagcgct gcaaagtgga aaatatgaaa    2640
agaccacaca ggcccagcag tccagaaact gggcaaaaat attctgcagt ggggatttat    2700
ttttccaaag caggtaacag aggctagtga gaaagaaaag ctcctctctg ctccattcca    2760
aaggccatct tgtggtcagt tcatgccct cacctgattt tttttttttt tttttttttt    2820
caattcctaa cctttttaa agtttcctgg tctccactgg acacagagct ttggagacgg    2880
aggatcccag agggcagtct cagttgcaat cagtgtgtgc ccagcctggg cagacaggaa    2940
attcctcgga tacattattt tttctttctt tcatagctgt gtctcagaaa ggacccattt    3000
gtggctcttt ttcacctcaa aataagatcg atggtatctt gtaaaatgag ggtagtgcca    3060
cttcttagta tttttgaaag ctgttttaga ttttttttt ttttccttt ctagccatct    3120 aaattgactc ttccaatata ggtctcagaa atccaatatt tggagtacaa tttcttttaa    3180
tccagattac acctgcctta caaagcaccc cctccttgtt cccctctgtt tcctctactc    3240
agttggggga gaaactcaca gctcctccgg gatacatatg tgccctcagc agcagctccc    3300
aggtgaagtt accagacccc tgggcttctc cccagctttt tctgagttga gtcagacatg    3360
tagagtttgg gtcacacagg caagaggaat ttccctcgg ccttactgac aaggacacca    3420
acctagggtg caaacagatg gactatggtt caaggacact ggaattgagg agctgatcaa    3480
ggctctcttc agccttgctc tgtccctgcc tcttatcaga gcacaggtag acacacgggc    3540
atagccagcc cactcctact gtcacaggcg ccccaccatt caaccttccg ggaggtcagg    3600
gaccttctat atgaggcgag tgggtctcag tctgcttgaa tggtgatgag attctgctgg    3660
```

```
atctcagcac gctgcaggtg tcttttgaga gcattcagta ggacatggtg atccctattt    3720
cagcctctaa gatgactggt attctatctg aaatgcagag attaagccaa atacctgatg    3780
tattgtgaaa gccactgatt ttaagaatgg agagaaaggg attttttact gcatccctct    3840
gtatgaatat gaaatcagag accagggcat gatgttgcta ggattagagc ctctcagtct    3900
ggcctcttca cccaagtgca agaactcagt ctcttactgt tcaaagaatc ttaacagttg    3960
aattatggag ggaaattccc ttttgcccca agcattccta tatttaaagc aatatcccag    4020
gagaatatgt tagacttagg atgatacctt cagccacttg aagaagaaat agaaggcgct    4080
cattccaata tagtctttat ttcccattca gatacaggtt gagcatccct aatctgaaca    4140
gttaaaaccc ccaaatgccc caaaatccaa accttcctga acgctatgac accatgagtg    4200
gaaaattcca cacctaacaa acacatttgc tttcttatgg ttcaatgtac acaaactgtt    4260
ttatatagaa aatgatttca aatatcataa aattaccttc aggctatgtg tataaagtat    4320
atatgagcca taaatgaatt ttgtgtttag actttgtgtc catccccaag atctctcatt    4380
ttatatatat atatatatat atatatatat atatatatat atatatatac acacacacac    4440
acatacacaa atattccagg atacaaaaaa aaacatttaa aaatccgaga cccagaacac    4500
ttctggtccc aagcatttca gataagggat atcaatctgt actaccaata aggatttcgt    4560
aattcccta actgcaaatg tcctcttcat ttgttctttta tgagaaaacc cgggtagtgc    4620
cagcacctgg atacagtatt tacaccctgc agaccctaaa gatttcagat tcagttagca    4680
aaccttgatg aagcacctgc tggacactga gggacccaaa gctcaatcag ccataatccc    4740
tgctttcaga gtttatattg tacctgccta atccacccgg cgtgactcat ttcaacacta    4800
agtactaggg gtgttgtcag gagacaaatc tgaagtcagg agaggaaaat gcaaaggagc    4860
cctgccgtgt gatggatgtg cattctcact tgggtcttga agttctcatt cctacatctc    4920
aagctagcca ggcagtctcc tctctatcag aagaaagcac tggtaattgg ctagactggc    4980
tatgttgaag gtaacatgaa ctctaagatc ttgacccagg gcgacttggt tttgcttaag    5040
gtggcatcac caatgttcca aatcctttag ggagatgagg gtatcccac agaaaaagag    5100
gaataataga ccaatggatt ttctcctttc accagtatgt ttggaaccct ctgatccaat    5160
gtcttttgat actgatctct tgtccaaatg agaatgtcgc tttagctgaa attcaaatgg    5220
ctgtgacaat ttaccgaaat gatgaagtaa ccaccattcc cacctttcac tgcctaggct    5280
ccaagtctga atacatttt gaaataggaa ctcccttttg caaaaagaa acctgggtgt    5340
cagggaggtg aagtgacttg ccctaggagc agacagcatg ccaagaatgg aattaggctc    5400
aggatccagc ctgggctcac cctgtgtggc tcattcccac ccaggaaact gaagataaaa    5460
gatttgggaa aacacaccaa gaaaaagggg cagttttctt tgcccaagca tttggtgcta    5520
gttagaggct gttcactctc tcctgctcct cttcggagta gaaataaagg ctgtgacaca    5580
aggaagccag tggggtggga gggaggcacc ataatccctc cctaaaaccc acagaagact    5640
aacctgatac tcttttgacc caactgcatc aacactaaac agctgcagac cccctgaatc    5700
tttcacacat gccaagtgaa cattcttgat gatttctctt tgtgaccgca accacctgca    5760
aaccagaacg actctagaat ttccttcccc gccccccttt ttgtttagtt tctaatctct    5820
tgtttatgag gtgtggggtt tataagggac tgaatcaaat gaatgtaaca aaaagaaaa    5880
aaaaaacaaa aaaaaatgcc ttttctcagg gccagtgagt tgcaaataat ttttaaagaa    5940
aagcctataa ttacatcatc tcaataaatt ttttataaaa aaaaaaaa                 5989
```

<210> SEQ ID NO 40
<211> LENGTH: 5548
<212> TYPE: DNA
<213> ORGANISM: Mus <mouse, genus>
<220> FEATURE:
<223> OTHER INFORMATION: Mouse ETV6 (NM_007961.4)

<400> SEQUENCE: 40

| | | | | | |
|---|---|---|---|---|---|
| ttctgccttt | cagtttctct | cttccaggaa | ggaaaacatt | cgagaaagag | agagggaggg | 60 |
| agggagcgag | ggagcgagag | agcgagcgag | cgagcgccgc | gggagggcgg | gcgcgccggc | 120 |
| cgcgggtggg | aggagacacg | ccaggccggc | ctgctgcgcc | cggtcgccg | cgccgcgacc | 180 |
| cgcacacccc | acgccgtgct | cgccggctcc | tacgcccccg | cacctcgcgc | ccaatccgcg | 240 |
| cgttgagaag | agccccccct | cccctcgggg | cggccgccgc | cagcgatgct | gcaagaaact | 300 |
| tcttaaacga | ccgcatcccg | ctgccccgcc | gagcgtttct | gggttgggga | gaggaaagga | 360 |
| aagtggaaaa | aaactgagaa | cttcctgatc | cctttcgctg | tgagacatgt | ctgagactcc | 420 |
| tgctcagtct | agcattaagc | aggaacgaat | ttcatacacg | cccccagaga | gtccagtggc | 480 |
| aagccaccgt | tcctcgactc | cgcttcatgt | tcacacagtg | cctcgagcgc | tcaggatgga | 540 |
| ggaagactcg | atccacctgc | caacacacct | gcgtttgcag | ccgatttact | ggagcagaga | 600 |
| tgacgtagcc | cagtggctca | agtgggcaga | aaatgagttt | tctttaaggc | ccattgagag | 660 |
| caacaagttc | gaaatgaatg | gcaaggccct | cctgctgctg | accaagaggg | atttccgcta | 720 |
| ccgatctcct | cattcaggcg | acgtgctcta | tgaactcctt | cagcatatcc | tgaagcagag | 780 |
| gaaatctcga | atgctcttct | caccattctt | ccccctggg | gactctatcc | acaccaagcc | 840 |
| agaggtcctc | ctgcatcaga | accatgacga | agataactgt | gtccagagga | cacccaggac | 900 |
| gcccgcggag | agcgtgcacc | acaaccctcc | caccatcgaa | ctcttacatc | gccctaggtc | 960 |
| acccatcacc | acaaaccaca | ggccttctcc | tgaccccgaa | cagcagcggc | cccagcggtc | 1020 |
| cccctagac | aacatgagcc | gccgcctctc | gccagtggaa | aaagcccagg | ggcccaggct | 1080 |
| acagcaggag | aacaaccacc | aggaaacgta | ccccctgtca | gtgtctcctg | tcgagaataa | 1140 |
| tcactgcctg | ccctcaagcc | cctggcagga | gagcactcga | gtgatccagc | tgatgcccag | 1200 |
| ccccatcatg | cacccttga | tcctgaaccc | ccggcactcg | cactcggtgg | acttcaaaca | 1260 |
| gtcccggcac | tccaggatg | ggatgaatcg | ggaagggaag | cccatcaacc | tgtctcatcg | 1320 |
| ggaggacctg | gcttacttga | accacatcat | ggtctctatg | tccccaccgg | aagagcacgc | 1380 |
| catgcccatt | gggagaatag | cagactgtag | actgcttgg | gattatgtct | atcagttgct | 1440 |
| gtctgacagc | cggtacgaaa | acttcatccg | atgggaggac | aaagaatcca | aatattccg | 1500 |
| gatagtggat | cccaacggac | tggctcgact | ctggggaaac | cataagaaca | gaacaaacat | 1560 |
| gacctatgag | aaaatgtcca | gagccctgcg | ccactactac | aaactaaaca | ttatcaggaa | 1620 |
| ggagcccgga | caaggctttt | tgttcaggtt | catgaaaacc | ccagatgaga | tcatgagtgg | 1680 |
| ccggacagac | cgtctagaac | acctcgagtc | tcaagtgctg | gatgaacaaa | cgtaccaaga | 1740 |
| ggatgaacct | accatagcct | caccggtggg | ctggccaaga | ggaaacctgc | ccacggggac | 1800 |
| cgcaggaggc | gtgatggaag | caggcgagct | agggtggct | gtaaaggaag | agacccggga | 1860 |
| atagcaggga | cacttctcct | gccgatcaag | agggacccag | agcaccttag | acaagccacc | 1920 |
| gagcaatggc | agggctgaag | ttctggcgga | gggcacaagc | ctgagactca | cacgtcacgt | 1980 |
| tcgcttctcc | ttctgatctc | ttgtctgtaa | ctctcaccct | ctcccttccc | ctacacctgt | 2040 |
| tgtagtctca | tggtgtttct | ggtttcgttt | tttgttttg | tttttaaga | acatgcagtt | 2100 |

```
tgactattca ttgttcatac agggaagaca tcacatgttg ttttcctatg gaaatatatc    2160
tattatatat atattattaa ttttttttgtt gttgttgcaa atctcaccaa gtacggccag   2220
cttggctggt caggaaagag aaaacttgca gaaggaatca ggttcctctt tttcctgcca    2280
catagatctg gtgtgtcctg tccaagtcag gtcttagatg agaaaggaaa acaaaatgag    2340
agagatactt tcaaacaatg gaaaagaaga gttctgtctc catctccctc tctcgccgct    2400
catccccgcc cctttctcct tccccttct ctgcctgcta tgcacttcac aggcttttca     2460
tcagagctag cctcactagc acctgaacta cacagtgacc cggctgctct gtgacagtca    2520 gacccctt gg gcacccatct gaggaaggcc agacatctcc ccccaccaaa tgctgctgta   2580
ttctagaaag aacaatggga ggatcgagca taagatagga cagagggtgg ccacaggatt    2640
tgcaaggccc aggcagtttg ggattgtcct gaaagtgcta cacattagga aaatatgaga    2700
gaccacacag gcctggtagt ttaggagcaa gaacaggtca ccaatgttgt cccaagacat    2760
catgcccttg tgggattgtc accaccccac acacacactc caagtcctag ccttttttctt   2820 ctatgctggt cctcatggaa cacagaacac acatgaggga ggatgctgga atttagtctc    2880
aggcacagcc ggtatttgcg cagacaggaa attcctcaga tttagacttt ttcctttttt    2940
ccgtctgtca tggctgtatt tcaggaggac atatctgtgg ctcttctcca cctcgacata    3000
aggtcagtag catcttccaa gatgagggta atgctattcc ttaggatttt tgatagcagg    3060
gattttattt tatttattta tttattttg ggatttttt ttttgagaca gggttttttct     3120 gtgtatccct ggaattcact ctgtagacca gactaggact cagagatcta cctgcctctg    3180
cctcccaagc actgagatta aggtgtgcg ccccccatgct tagcttttttt tccttttcta    3240 gccatctaag tggactcttt gaagttcact gttttaaaac ccagataatg aggcctgcct    3300
ttcaaaacca ccccttgtcc ttcctgtgtt ctcccacatc atggaatgag cctctcccag    3360
ccctcctggg tgtgtctctg cttggtcaga cgcaggacac aggtgaggct gacagaccag    3420
agctgaccta caactactcc taagtggggc acatagaggc taggaggacc tggacaagtc    3480
actctcccga cgtcagctca caggcggact gtggttcaca gacactggaa ttgagttgac    3540
tgggtatctt tagtcttgct gtgacttccc cgtgcctccc ccacaaccca caatctgcct    3600
tcaaagaggt cagtgacctg ggtgagggt tccctcttaa tattcatggg gaatgatgag    3660
agtcacgtgc tatgtgtttc ttgaaagcat gacagggggt tccttttttg gcctctaaaa    3720
atgactggta ccttatatca aatggggaga ttaagccaaa tacttgtgtt gtatgagcca    3780
ctgggaggaa gagcaagtga gaaagggtgt gcttttttgtt ttttgtttga ctgaggtcct    3840
ttgtgtgaat ataaaatgag aaactacaac acttcatact ggccactttg cccatgcgta    3900
gaactcagtc ctttaactgc ccaaagaatt gtccatatga actgtgtaag gaaattcctc    3960
tgttccctaa ggagtcttgg atgacagctt tggccactta cgttagaaat gctcatggca    4020
gtgccgtctt tatttcacac ctggtgttgc cataattgat ttccttgatt ctcttacctg    4080
caaaagccct tgtttgtttt ttggagagaa aatatggcca gggttgtctg ggttgtcagg    4140
gttgtgcagt gctctcaggc ttcagactca cagaatttag atttagccaa tcagaccttg    4200
gaggaaacac cacaatgggg gtcctgtttt gtcttttgg ttttttgagtt ttggtttttt     4260 gtttgtttgt ttttttacaa tcaactatga tcttctagat cgacattaaa gcgacattaa    4320
gttcaagagt tgatagaagg aatctaaaag ctccttagt ggccttttc tgcagccatt      4380 gtgggttgag tcaggaaagg aatttgcagg gaagcattgc catgtggagg atgggcattg    4440
```

| | |
|---|---|
| ccacctaggt cctgggattc tgtcctgagt cctcggccgg gctgtcttca ggtctccttc | 4500 |
| agcagaaacc aggggcagct ggtcagatgt tgacagcagc ttctcttccg ataatttca | 4560 |
| tccaaggcca cttagtgcca cttggagaca gggtccctga tgtcccatat ctggttttgg | 4620 |
| aaagagaatg gtcctcataa gaaaagaaca aaacaggctt cttgcctagt acattcaggt | 4680 |
| ccctctgatc cagcatcttt ttacactaat accttgtcca gataagaatg tcactccagc | 4740 |
| tgacatctag atgtctgtga ggagtccctg gaatgaccac tcttgtcttt tcacactgtt | 4800 |
| cgggatccaa ccataaacac agtttggccc attcactgtt gttggcagaa gacaacctga | 4860 |
| gagaggtcgt gtcactttcc gtgggagcag acagcatgac acacagttgg gatcagtatc | 4920 |
| tagccggcct gcacttagca gcaggataag cgttcagaag gcagttagaa attattctgg | 4980 |
| tttaaacccc catttgatcc atccccggca aagagacgaa agatgccaag ggtggttttt | 5040 |
| actgcccagt cattcggtgc tagttagagc tgctgtgcgt tctcagcctg ctcctcttct | 5100 |
| gaacagaaac caaaattgga cgtcatgaga acccagtgg agcaggggta cagagggaca | 5160 |
| ccccagaacc ctgcctatca acaaggcaca cgggactcac ccagcactct tttgccccca | 5220 |
| tccgcatcaa cactaaacaa cttcaaatgc gcccgactct tttcacccct acaggtgaac | 5280 |
| cctcttctgg agacttctct ttgtgacggc acccacctgc aagccagatg aatctagaat | 5340 |
| gactttttgt tgttgttgtt gtttagtttc taatctcttg tttatgaggt gtggggttta | 5400 |
| taagggactg aatcaaatga atgtaacaaa aaagaaaaa aaaacaaaca aaaatgcct | 5460 |
| tttctcaggg ccagtgagtt gcaaataatt tttaaagaaa aacctataat tacatcatct | 5520 |
| caataaattt tttataaaaa aaaaaaaa | 5548 |

<210> SEQ ID NO 41
<211> LENGTH: 5967
<212> TYPE: DNA
<213> ORGANISM: Homo sapiens
<220> FEATURE:
<223> OTHER INFORMATION: Human RUNX1 (NM_001754.4)

<400> SEQUENCE: 41

| | |
|---|---|
| ctttgggcct cataaacaac cacagaacca caagttgggt agcctggcag tgtcagaagt | 60 |
| ctgaacccag catagtggtc agcaggcagg acgaatcaca ctgaatgcaa accacagggt | 120 |
| ttcgcagcgt ggtaaaagaa atcattgagt ccccgcctt cagaagaggg tgcattttca | 180 |
| ggaggaagcg atggcttcag acagcatatt tgagtcattt ccttcgtacc cacagtgctt | 240 |
| catgagagaa tgcatacttg gaatgaatcc ttctagagac gtccacgatg ccagcacgag | 300 |
| ccgccgcttc acgccgcctt ccaccgcgct gagcccaggc aagatgagcg aggcgttgcc | 360 |
| gctgggcgcc ccggacgccg cgctgcccct ggccggcaag ctgaggagcg cgaccgcag | 420 |
| catggtggag gtgctggccg accacccggg cgagctggtg cgcaccgaca gccccaactt | 480 |
| cctctgctcc gtgctgccta cgcactggcg ctgcaacaag accctgccca tcgctttcaa | 540 |
| ggtggtggcc ctaggggatg ttccagatgg cactctggtc actgtgatgg ctggcaatga | 600 |
| tgaaaactac tcggctgagc tgagaaatgc taccgcagcc atgaagaacc aggttgcaag | 660 |
| atttaatgac ctcaggtttg tcggtcgaag tggaagaggg aaaagcttca ctctgaccat | 720 |
| cactgtcttc acaaacccac cgcaagtcgc cacctaccac agagccatca aaatcacagt | 780 |
| ggatgggccc cgagaacctc gaagacatcg gcagaaacta gatgatcaga ccaagcccgg | 840 |
| gagcttgtcc ttttccgagc ggctcagtga actggagcag ctgcggcgca cagccatgag | 900 |
| ggtcagccca caccacccag ccccacgcc caaccctcgt gcctccctga accactccac | 960 |

```
tgcctttaac cctcagcctc agagtcagat gcaggataca aggcagatcc aaccatcccc    1020
accgtggtcc tacgatcagt cctaccaata cctgggatcc attgcctctc cttctgtgca    1080
cccagcaacg cccatttcac ctggacgtgc cagcggcatg acaaccctct ctgcagaact    1140
ttccagtcga ctctcaacgg cacccgacct gacagcgttc agcgacccgc gccagttccc    1200
cgcgctgccc tccatctccg accccgcat gcactatcca ggcgccttca cctactcccc     1260
gacgccggtc acctcgggca tcggcatcgg catgtcggcc atgggctcgg ccacgcgcta    1320
ccacacctac ctgccgccgc cctaccccgg ctcgtcgcaa gcgcagggag gcccgttcca    1380
agccagctcg ccctcctacc acctgtacta cggcgcctcg gccggctcct accagttctc    1440
catggtgggc ggcgagcgct cgccgccgcg catcctgccg ccctgcacca acgcctccac    1500
cggctccgcg ctgctcaacc ccagcctccc gaaccagagc gacgtggtgg aggccgaggg    1560
cagccacagc aactccccca ccaacatggc gccctccgcg cgcctggagg aggccgtgtg    1620
gaggccctac tgaggcgcca ggcctggccc ggctgggccc cgcggcccgc cgccttcgcc    1680
tccgggcgcg cgggcctcct gttcgcgaca agcccgccgg gatcccgggc cctgggcccg    1740
gccaccgtcc tggggccgag ggcgcccgac ggccaggatc tcgctgtagg tcaggcccgc    1800
gcagcctcct gcgcccagaa gcccacgccg ccgccgtctg ctggcgcccc ggccctcgcg    1860
gaggtgtccg aggcgacgca cctcgagggt gtccgccggc cccagcaccc aggggacgcg    1920
ctggaaagca acaggaaga ttcccggagg gaaactgtga atgcttctga tttagcaatg      1980
ctgtgaataa aaagaaagat tttataccct tgacttaact tttaaccaa gttgtttatt     2040 ccaaagagtg tggaattttg gttggggtgg ggggagagga gggatgcaac tcgccctgtt    2100
tggcatctaa ttcttatttt taattttcc gcaccttatc aattgcaaaa tgcgtatttg     2160
catttgggtg gttttatttt ttatatacgt ttatataaat atatataaat tgagcttgct    2220
tctttcttgc tttgaccatg gaaagaaata tgattcccctt ttctttaagt tttattttaac  2280 ttttcttttg gacttttggg tagttgtttt tttttgtttt gttttgtttt tttgagaaac    2340
agctacagct ttgggtcatt tttaactact gtattcccac aaggaatccc cagatattta    2400
tgtatcttga tgttcagaca tttatgtgtt gataattttt taattattta aatgtactta    2460
tattaagaaa aatatcaagt actacatttt cttttgttct tgatagtagc caaagttaaa    2520
tgtatcacat tgaagaaggc tagaaaaaaa gaatgagtaa tgtgatcgct tggttatcca    2580
gaagtattgt ttacattaaa ctcccttttca tgttaatcaa acaagtgagt agctcacgca    2640
gcaacgtttt taataggatt tttagacact gagggtcact ccaaggatca gaagtatgga    2700
attttctgcc aggctcaaca agggtctcat atctaacttc ctccttaaaa cagagaaggt    2760
caatctagtt ccgagggtt gaggcaggtg ccaataatta catctttgga gaggatttga     2820
tttctgccca gggatttgct caccccaagg tcatctgata atttcacaga tgctgtgtaa    2880
cagaacacag ccaaagtaaa ctgtgtaggg agccacatt tacataggaa ccaaatcaat     2940
gaatttaggg gttacgatta tagcaattta agggcccacc agaagcaggc ctcgaggagt    3000
caatttgcct ctgtgtgcct cagtgggagac aagtgggaaa acatggtccc acctgtgcga   3060 gacccctgt cctgtgctgc tcactcaaca acatctttgt gttgctttca ccaggctgag     3120
accctaccct atgggtata tgggctttta cctgtgcacc agtgtgacag gaaagattca     3180
tgtcactact gtccgtggct acaattcaaa ggtatccaat gtcgctgtaa attttatggc    3240 actatttta ttggaggatt tggtcagaat gcagttgttg tacaactcat aaatactaac     3300
```

```
tgctgatttt gacacatgtg tgctccaaat gatctggtgg ttatttaacg tacctcttaa    3360
aattcgttga aacgatttca ggtcaactct gaagagtatt tgaaagcagg acttcagaac    3420
agtgtttgat ttttatttta taaatttaag cattcaaatt aggcaaatct ttggctgcag    3480
gcagcaaaaa cagctggact tatttaaaac aacttgtttt tgagttttct tatatatata    3540
ttgattattt gttttacaca catgcagtag cactttggta agagttaaag agtaaagcag    3600
cttatgttgt caggtcgttc ttatctagag aagagctata gcagatctcg gacaaactca    3660
gaatatattc actttcattt ttgacaggat tccctccaca actcagtttc atatattatt    3720
ccgtattaca tttttgcagc taaattacca taaaatgtca gcaaatgtaa aaatttaatt    3780
tctgaaaagc accattagcc catttccccc aaattaaacg taaatgtttt ttttcagcac    3840
atgttaccat gtctgacctg caaaaatgct ggagaaaaat gaaggaaaaa attatgtttt    3900
tcagtttaat tctgttaact gaagatattc caactcaaaa ccagcctcat gctctgatta    3960
gataatcttt tacattgaac ctttactctc aaagccatgt gtggagggggg cttgtcacta    4020
ttgtaggctc actggattgg tcatttagag tttcacagac tcttaccagc atatatagta    4080
tttaattgtt tcaaaaaaaa tcaaactgta gttgttttgg cgataggtct cacgcaacac    4140
attttttgtat gtgtgtgtgt gtgcgtgtgt gtgtgtgtgt gtgaaaaatt gcattcattg    4200
acttcaggta gattaaggta tcttttttatt cattgccctc aggaaagtta aggtatcaat    4260
gagaccctta agccaatcat gtaataactg catgtgtctg gtccaggaga agtattgaat    4320
aagccatttc tactgcttac tcatgtccct atttatgatt tcaacatgga tacatatttc    4380
agttcttttct ttttctcact atctgaaaat acatttccct ccctctcttc cccccaatat    4440
ctccctttt ttctctcttc ctctatcttc caaaccccac tttctccctc ctccttttcc    4500
tgtgttctct taagcagata gcacataccc ccacccagta ccaaatttca gaacacaaga    4560
aggtccagtt cttccccctt cacataaagg aacatggttt gtcagccttt ctcctgttta    4620
tgggtttctt ccagcagaac agagacattg ccaaccatat tggatctgct tgctgtccaa    4680
accagcaaac tttcctgggc aaatcacaat cagtgagtaa atagacagcc tttctgctgc    4740
cttgggtttc tgtgcagata aacagaaatg ctctgattag aaaggaaatg aatggttcca    4800
ctcaaatgtc ctgcaattta ggattgcaga tttctgcctt gaaatacctg tttctttggg    4860
acattccgtc ctgatgattt ttatttttgt tggttttat ttttgggggg aatgacatgt    4920
ttgggtctttt tatacatgaa aatttgtttg acaataatct cacaaaacat attttacatc    4980
tgaacaaaat gcctttttgt ttaccgtagc gtatacattt gttttgggat ttttgtgtgt    5040
ttgttgggaa ttttgttttt agccaggtca gtattgatga ggctgatcat ttggctcttt    5100
ttttccttcc agaagagttg catcaacaaa gttaattgta tttatgtatg taaatagatt    5160
ttaagcttca ttataaaata ttgttaatgc ctataacttt ttttcaattt ttttgtgtgt    5220
gtttctaagg acttttttctt aggtttgcta aatactgtag ggaaaaaaat gcttctttct    5280
actttgttta ttttagactt taaaatgagc tacttcttat tcacttttgt aaacagctaa    5340
tagcatggtt ccaattttttt ttaagttcac tttttttgtt ctaggggaaa tgaatgtgca    5400
aaaaagaaa aagaactgtt ggttatttgt gttattctgg atgtataaaa atcaatggaa    5460
aaaaataaac tttcaaattg aaatgacggt ataacacatc tactgaaaaa gcaacgggaa    5520
atgtggtcct atttaagcca gcccccacct agggtctatt tgtgtggcag ttattgggtt    5580
tggtcacaaa acatcctgaa aattcgtgcg tgggcttctt tctccctggt acaaacgtat    5640
ggaatgcttc ttaaagggga actgtcaagc tggtgtcttc agccagatga catgagagaa    5700
```

| | | |
|---|---|---|
| tatcccagaa ccctctctcc aaggtgtttc tagatagcac aggagagcag gcactgcact | 5760 | |
| gtccacagtc cacggtacac agtcgggtgg gccgcctccc ctctcctggg agcattcgtc | 5820 | |
| gtgcccagcc tgagcagggc agctggactg ctgctgttca ggagccacca gagccttcct | 5880 | |
| ctctttgtac cacagtttct tctgtaaatc cagtgttaca atcagtgtga atggcaaata | 5940 | |
| aacagtttga caagtacata caccata | 5967 | |

<210> SEQ ID NO 42
<211> LENGTH: 5803
<212> TYPE: DNA
<213> ORGANISM: Mus <mouse, genus>
<220> FEATURE:
<223> OTHER INFORMATION: Mouse Runx1 (NM_001111021.2)

<400> SEQUENCE: 42

| | | |
|---|---|---|
| gtgaaaactt ctttggacct cataaacaac cacagaacca caagttgggt agcctggcag | 60 | |
| tgtcagaagt gtaagcccag cacagtggtc agcaggcagg acgaatcaca ctgaatgcaa | 120 | |
| accacaggct ttcgcagagc ggtgaaagaa attatagaat cccccgcctt caggagaggt | 180 | |
| gcgttttcga aaggaaacga tggcttcaga cagcattttt gagtcatttc cttcatatcc | 240 | |
| acagtgcttc atgagagatg ccagcacgag ccgccgcttc acgccgcctt ccaccgcgct | 300 | |
| gagccccggc aagatgagcg aggcgctgcc gctgggcgcc ccggatggcg cgccgcccct | 360 | |
| ggccagcaag ctgaggagcg cgaccgcag catggtggag gtactagctg accaccctgg | 420 | |
| cgagctagtg cgcaccgaca gccccaactt cctctgctcc gtgctaccca ctcactggcg | 480 | |
| ctgcaacaag accctgccca tcgctttcaa ggtggtggca ctggggacg tcccggatgg | 540 | |
| cactctggtc accgtcatgg caggcaacga tgaaaactac tcggcagaac tgagaaatgc | 600 | |
| taccgcggcc atgaagaacc aggtagcgag attcaacgac ctcaggtttg tcgggcggag | 660 | |
| cggtagaggc aagagcttca ctctgaccat caccgtcttt acaaatccgc cacaagttgc | 720 | |
| cacctaccat agagccatca aaatcacagt ggacggcccc cgagaacccc gaagacatcg | 780 | |
| gcagaaacta gatgatcaga ccaagcccgg gagtttgtcc ttttccgagc ggctcagtga | 840 | |
| attggagcag ctgcggcgca cggccatgag ggtcagcccg caccacccag cccccacgcc | 900 | |
| caaccctcgg gcctccttga ccactccac tgcctttaac cctcagcctc aaagtcagat | 960 | |
| gcaggatgcc aggcagatcc agccatcccc accgtggtcc tatgaccagt cctaccagta | 1020 | |
| cctgggatcc atcacctctt cctctgtcca cccagcgaca cccatttcac ccggccgtgc | 1080 | |
| cagcggcatg accagcctct ctgcagaact ttccagtcga ctctcaacgg ctccggacct | 1140 | |
| gaccgccttc ggcgacccac gccagttccc tactctgccg tccatctccg acccgcgcat | 1200 | |
| gcactaccca ggcgccttca cctactcgcc gcccgtcacg tcgggcatcg gcatcggcat | 1260 | |
| gtcagccatg agctcggcct ctcgctacca cacctacctg ccgccgcct accccggctc | 1320 | |
| atcacaggcg caggccgggc cttccagac cggctcgccc tcctaccatc tatactacgg | 1380 | |
| cgcctcggcc ggttcctacc agttctccat ggtgggcgga gagagatcgc cccgcgcat | 1440 | |
| cctgccgccc tgcaccaacg catccaccgg cgccgcgctg ctcaacccca gcctccccag | 1500 | |
| ccagagcgac gtggtggaga ccgagggcag ccatagcaac tcgcccacca acatgccccc | 1560 | |
| cgcgcgcctg gaggaggccg tgtggcggcc ctactgagct gagcgccatc gccatcgagg | 1620 | |
| gactgggcct gccgtccatg cacagacccc gccaggaggg cccttggagg ccaccaggaa | 1680 | |
| gaatcccgga gggaaactgt gaatgcttct gatttagcaa tgctgtgaat aaaagaaaga | 1740 | |

-continued

```
ttttatacccc ttgacttcac ttttttaacca cgttgtttat tccaaagagt gtggaatgtt      1800
ttcggttcgg ggtggggaag acgcagccca tcctgtttgg catctatttc ttatttcgga      1860
gttttctttt ccgcacctta tcgattgcaa aaatgcctgt ttgcatctgg gtggtcattt      1920 attttttaagt gtgtatagat ttgagcttgc ttttttttct tcctttgacc aactcaaaga      1980
aataaaattc ccttctctgt aaggtttatt taacttttag actttcatgt agctggggt      2040 tttatttgtg tttggttttt gttttttattt ttaaagagac agctacagct ttgggtcatt      2100
ttttaactac tgtatttcca caaagaaatc cctagatatt tatgtatctt gatgtttgaa      2160
catttacata tgtgttgata cttttttaat tatttaaatg tacttatatt aagaaagata      2220
tcaagtacta cattttttctt tataatagcc aaagttaaat attattgcgt tgaagatgtc      2280
tggaaaaaaa agagatcgct tggttaacta gaaatattgt ttacattaaa ctcccttat      2340 gttattcaaa caagttggta ggtaacgcag caatgttttt aattggattg tagacactga      2400
gggtcactcc aaggtcagaa gtacaaaatt ttctgctagg ctcaacaaat agtctcatac      2460
ctggctcctt cccttcaaaa agagaggcaa actctgtcct gaaagggttc agagaggtgc      2520
caaggatttg ctctgaagag gatttcattt tggcctggag atatacttgc cccaaggcct      2580
cctcattctg gcatgcttta tcacagagct caaccaagta agctgttggt caggggttta      2640
cttacatagt atttacatag acccaaacca ctgaatgtga tttttaaatt gccttccatt      2700
aatagtaccc gttcattgat gaaaaccaaa acttgaggct gtaccccaaa gatccaaata      2760
gaagagttaa gaccaggtgt ctttgaggcc taaaggctga gttttaagag agtgtacccc      2820
aaaagtctga aggagccggt ttccttctcc cagtcttagt ggaatcagtc atgggaggca      2880
gatgccacgc ccacctgtgc aggatgctcc tcagaagctg ccccttcacc agcatcttct      2940
cccaccaggc cgagccctg accttgggg tgcatcagtg tgatagatcc tggtctctgc      3000
agtccgccat ggctacggtt cagatgtgca tcgtgtcact gtaaatgtaa tggtactgtt      3060
gttacagtgg aggacttggt caaaatccag ttgttctaca acgtatgaag cctaaccgct      3120
ggttctgaca tacatgtgct caaaatgatc tggttgtttg gattttttctt ttgttgtttt      3180 gttttttaat gtacctctta aattagttga agtgatgtca ggtcaactcc gaagagcgtt      3240
tgaaagcagg acttcagcac agtgtttgat ttttttatta ttattaatat tattttataa      3300
atttaagcat tcagattaga tctttggctg caggcagcaa aaacggctgg acttatttaa      3360
aaaaaataca gcttgttttt tgagttatct atatctatat ctatatgttg attctttgtc      3420
ttacatagag cagcagcact ttggtaacct gtgataccag gttgctcttg tctggagaag      3480
agcgctagca ggattcagag aaactcagaa tagatcttca tatcagccat accttcctcc      3540
tccatccggt ctccactcag ttattccaca gaacactttg acagtgtgt tgtcagaaaa      3600 ataaaaaaaa atttaatttc tcaaaaggag tttgtttctc caacattaga tgttcctctt      3660
accataggct gccgtatctg gcctgagaaa acggtaggga aggacgaagg aaagagattt      3720 ctatttttc atattaattt tgatatctaa agatacgcta gccctcagag gagcagataa      3780
tctcacacat tgaattttcg ccctgggcac catgcatcaa gaaggcttgt cactgtgtta      3840
gagccattta gtgcttccta aacttttatc aacataggca gtatttagtc tcagagaaaa      3900
aaaaatccat caggcacatg tagtcttgga gatagattcc acggggcagg tatttctcta      3960
cctgagaaat tgtgttcatt gccttcgggt gcttccagcg gtctcctcat tcgctgtctt      4020
caaggaagac ccataagcca attctgagat aatggagctg ttgggaatac tggtccagag      4080
aaagaaaaat gggataagcc attcttactg cttattcaag cccctatta taattttaac      4140
```

| | |
|---|---|
| acactttcca ttccttctgg ttttctcgcc gtctatatcc tcccaatagc ccttctcact | 4200 |
| tttcttttcc ctcctgcaaa cacacacaca cacacacaca cacacacaca taaggcacac | 4260 |
| acacacacat cctctccccc ataccaagtg tccagaacac agaaagtcca gttcttctcc | 4320 |
| gtttattaaa gaacagggtg agtcagccat tctcttgctc acgggttttt ttccccaaca | 4380 |
| gaacagaggc gttgccagcc attttgggtc tgctttctgt ccagatactg cagcaaaaac | 4440 |
| tcttgaggat cacaacccgt tggctgagca gctgtgctgc tgcccaaacg tcctgcgcag | 4500 |
| acaaacgcac gctgggaccg aaggggtgt ctctccttct gcctcttttc tttcatacgt | 4560 |
| ttctctcgaa aggcctcaac tgaggactgc aaatttcttt cttgaaataa ctttcccca | 4620 |
| gggacattcg tcttaggga ttttttggtt ttgatgggtt ttgttttgtt ttggtttttt | 4680 |
| tggttcttct cattttcttt gtaggagaag gcatgagatg ttgagggtct ttcatacatg | 4740 |
| aaaataaata gtttgacagc aatctcagaa tatattttt ccttatttga acaaagtact | 4800 |
| gttttgttta ctctacagta cacctttatt tggtgggttt ggctgttggt cggaaatgcc | 4860 |
| ttccctcttt cagccaggtc ggtatagcca aagctgatca tttgtctgtt ttttctttt | 4920 |
| tttcctcaga agagttgtat ccacaaactc aattgtattt atgtatgtaa atagatttca | 4980 |
| tgcttcatta taaatattg ttaatgcctg taataacttt tttcacattt tgtgtgtgtt | 5040 |
| tctaaggact ttttcttatg ttcgctaaat attgtagaag aaaatgctt ctcttaactt | 5100 |
| gtttatttta gatttaaaa aaaccaagct acttcttact cacttttata aacataataa | 5160 |
| acaagcatgg ttccaatggg tttttttaa gttcaccta tgttctagga gaatgaatg | 5220 |
| tgcaaaaaaa aaaatcaatc ttcaaatgaa ctgttgggta tttctgttac tctggatgga | 5280 |
| aaagatcaa tggaaaacaa aaaacaaaaa aacaaacttc caaattgaaa tagcagtaaa | 5340 |
| acacatgtat tgggggtaaa aaaaaaaaaa aaaaacacac ctcagaaaat gcagttctcc | 5400 |
| agcctccagc tactgcccac acatgtggca agtgttagat gtggtcgtga ggaatcccaa | 5460 |
| aatcagtgcc cgggccttttt ccttcctggt actaacatta agaacacctc ctaaggggca | 5520 |
| ctgtcaggct caggtcttaa agcacataga taagagagaa tgtcccagaa cgattctcag | 5580 |
| tagcccaggc cagcaggtac tcacggcact gcacctgctc actgcacaca gtcgctgagg | 5640 |
| cagacccctc tcctgggggc catgcagagc cagggcaggg cagccctaag ctactgatgt | 5700 |
| tttcttttcct ttgtactatg gtcttttctg taactccaat attcaaaccc atgtgaatgg | 5760 |
| caaataaaca atttgacaag cacctaaaaa aaaaaaaaa aaa | 5803 |

<210> SEQ ID NO 43
<211> LENGTH: 2475
<212> TYPE: DNA
<213> ORGANISM: Homo sapiens
<220> FEATURE:
<223> OTHER INFORMATION: Human GFI-1B (NM_004188.6)

<400> SEQUENCE: 43

| | |
|---|---|
| ctttattgcg aggctgagta tgatgggctc catccagcac gaacacaaag ccctgtgaga | 60 |
| ggaggcagag tgagatgaag tcgaactgtg ggatatgaaa ggcattttga aggagtaggc | 120 |
| atcaggctgg ttttgttcg aggaaagcta ctcaggagct tgggaggatt gcttgagacc | 180 |
| aggagttcaa gaccagcctg ggctacagag caagacccca tcttttgaa acttcctgca | 240 |
| actcgcatct ggaaaagtgc tgttatttga aagggtgccg acattgtgaa aaacacggag | 300 |
| tattgatctc tgaagctgag attttgtcc taaagaatac tcaagatgtg tccctggctg | 360 |

```
ggcacagcag ctcgtgcctg taatcccagc actttgggag gctgaggcag gaggatcgct   420
tgaggccagg agttcaagac cagcctattg tgaatagtac cactataaat agagaaagcg   480
tgccgctcca agtgtcgagg gttagaaatg agaattcgaa gtcttgtgtc ctggaaagtt   540
ttgataagca aatacggctg agctcccgcg ctctcttcat tggctgcttg ttcaccgcca   600
gattttgaca caaataatca gattgaaaat cagggagggg aacagaagag gaaaaacaca   660
cagagagaca gagcaaaaag gagaagtatc tatttgtgca aagagtcaca cagttgacag   720
agtggaggcc agtcccgaga gaggctttgc agttcccacc tcgggaagct ccggcagaac   780
ccaggcgagg gacagctccg gacaggtgtg gggtgcacac tgaaaatgcc acgctccttc   840
ctggtgaaga gcaagaaggc tcacacctac caccagcccc gtgtgcagga agatgaaccg   900
ctctggcctc ctgcccttac cccggtgccc agagaccagg ctccaagcaa cagccctgtc   960
cttagcactc tattcccaaa ccagtgcctg gactggacca acctcaaacg agagccggag  1020
ctggagcagg accagaactt ggccaggatg gccccggcac cagagggccc cattgtgctg  1080
tcccgacccc aggatgggga ctctccactg tccgactcac ccccattcta caagcctagc  1140
ttctcctggg acaccttggc cacaacctat ggccacagct accggcaggc cccctccacc  1200
atgcagtcag ccttcctgga gcactccgtc agcctgtacg gcagtcctct tgtgcccagc  1260
actgagcccg ccttggactt cagcctccgc tactccccag gcatggatgc gtaccactgt  1320
gtgaagtgca acaaggtctt ctccaccct cacgggctcg aagtgcatgt gcgacgctcc  1380
catagtggga cccggccctt cgcctgtgac atctgcggca aaaccttcgg ccacgctgtg  1440
agcctggagc agcacacgca cgtccactcc caggagcgca gcttcgagtg ccgcatgtgc  1500
ggcaaggcct tcagcgcctc gtccacgctg tccacccacc tgctcatcca ctcagacacg  1560
cggccctacc cctgccagtt ctgcggcaag cgtttccacc agaagtccga catgaagaag  1620
cacacctaca tccacacagg tgagaagccg cacaagtgcc aggtgtgcgg aaaggccttc  1680
agccagagct ccaacctcat cacccacagc cgcaagcaca caggcttcaa gcccttcagc  1740
tgtgagctgt gcaccaaagg cttccagcgc aaggtggacc tgcggcggca ccgcgagagc  1800
cagcacaatc tcaagtgagg ctgcgccggc tcccagctcc tggccagcct gcctgcggt   1860 cctgtcacct ggaggccagc ctcacatgcc caaatctcca gtctcctgga ggtgggactg  1920
gacaggagtc taccagcttg ttttgagact catgaaattg ctgtgtgacc ttgggcaagt  1980
cacttaccct gtctggatca acatttctcc tgctgccaag tgtgggagcc tggctgggtc  2040
tttctcagca gaagttgttt ccaggtgtgc tcaagtgcct tcctctagca gagcacagaa  2100
agctagaata cccccaggga gacagggatg ccaagagtag accagagctg ggacccacag  2160
acagaacctc cacctgcctg ctgcccactg agctgggacc tggtcacctt ggattttagc  2220
cggcctcttt ctggctataa caggcagagt cggagctgcc tcccacccca gtcagaagcc  2280
tggcaccccc tctgcttcgg ccagatgtgc tggctgactc cgacttccga ccagcactca  2340
gctggcctct ggggattcta gctccacaac caggccgtga ggctggagaa actggcagtt  2400
attgctgtca aaagcctgtt ctctcaactg ctgtcaataa aattaaagat acagatttgc  2460
tgccaaaaaa aaaaa                                                   2475
```

<210> SEQ ID NO 44
<211> LENGTH: 1724
<212> TYPE: DNA
<213> ORGANISM: Mus <mouse, genus>
<220> FEATURE:
<223> OTHER INFORMATION: Mouse Gfi-1b (NM_008114.3)

<400> SEQUENCE: 44

```
cacagaaacg aaaaggagaa gtgtctgtct gtgcagagac tcataacgtt gaccgagccg      60
agagcagtcc ccagggacag tgtggaggtt cgtggctctc gggcagaact cagaagaggg     120
acagctccct gacggtgtgg cgtgcacgca gaaaaatgcc acggtccttt ctagtgaaga     180
gtaagaaggc acacacttac caccagcccc gggcacaggg tgatgagctg gtctggcctc     240
ctgctgtaat tcctgtggca aaagagcata gccagagtgc cagccctctt ctcagcacac     300
cgcttccaag ccagaccttg gactggaaca caatcaaaca ggagcgggag atgttgctga     360
accagagcct tcccaagatg gcctcagccc cagggggcc tctcgtgaca ccccaacccc      420
aggatgggga atcaccactc tctgagtcac ccccttcta caagcccagc ttctcctggg      480
ataccttggc ctcctcctac agccacagct acacacagac ccctccacc atgcagtccg      540
ccttcctgga gcgctccgtg aggctgtacg gcagccccct cgtgcccagc acagagtctc     600
ccttggactt ccgcctccgc tactctccag gcatggacac ttaccactgt gtcaagtgca     660
acaaggtgtt ctccaccct catgggctag aagtgcatgt ccgccgctct cacagcggaa     720
cccggcccctt tgcctgtgat gtctgtggca aaacctttgg ccacgctgtg agcttggagc    780
agcatactca cgtccactca caggagcgaa gcttcgagtg ccggatgtgt ggcaaagcct     840
tcaagcgttc atccaccctg tccacccacc tgctcatcca ctcggacact cggccctacc     900
cctgccagtt ctgtgggaag cgcttccacc agaagtcgga catgaagaaa cacacctaca     960
tccacacagg tgagaagccc acaagtgcc aggtgtgtgg gaaagccttc agccagagct     1020
ccaacctcat cacccacagc cgcaagcaca caggcttcaa gccgttcagc tgtgagctgt    1080
gcaccaaggg cttccagcgc aaggtggacc tgcgacgtca ccgtgagagt caacacaatc    1140
tcaagtgaga cggttggccg cctgctttag tgtgtctcgc ctgaaggcca gcctctcctt    1200
tccaatcctg atcccagtcc tcctggaagc agcattgccc atgagcctct ctgcttcttt    1260
tgagactgga tgacctcaac caagccacac tcctcctctg accacagctg atgtgggagt    1320
cagttcgggc cttctgaac tgaggcagtc acagacatgc tctggtctca ttcaatgcca    1380
gagcacagac agctacaaag ccctcgtgga catggcaaaa ccaggcaaga gccaggatcc    1440
acagagaaac cctcttgctt gcttctctgg gtctagtgac tgaattttta gggattctct    1500
ttttggctgc cacagtcaga gttgtcccct ggcctagagg tctggcgccc ctctgcttcg    1560
gccagatgtg ctctctgtcc cccacctctc accacatcca tccgcccact gggagtcagg    1620
ctcctgaggt gagccacgag gctatgaaat cagccatgat agtagaagcc tgctcctatc    1680
agttgatgta aatgtaaata aaggtgggtt tatttacatg tgaa                     1724
```

<210> SEQ ID NO 45
<211> LENGTH: 2076
<212> TYPE: DNA
<213> ORGANISM: Homo sapiens
<220> FEATURE:
<223> OTHER INFORMATION: Human HOX-A9 (NM_152739.3)

<400> SEQUENCE: 45

```
agttgttaca tgaaatctgc agtttcataa tttccgtggg tcgggccggg cgggccaggc      60
gctgggcacg gtgatggcca ccactggggc cctgggcaac tactacgtgg actcgttcct     120
gctgggcgcc gacgccgcgg atgagctgag cgttggccgc tatgcgccgg ggaccctggg     180
ccagcctccc cggcaggcgg cgacgctggc cgagcacccc gacttcagcc cgtgcagctt     240
```

-continued

| | |
|---|---|
| ccagtccaag gcgacggtgt ttggcgcctc gtggaaccca gtgcacgcgg cgggcgccaa | 300 |
| cgctgtaccc gctgcggtgt accaccacca tcaccaccac ccctacgtgc accccaggc | 360 |
| gcccgtggcg gcggcggcgc cggacggcag gtacatgcgc tcctggctgg agcccacgcc | 420 |
| cggtgcgctc tccttcgcgg gcttgccctc cagccggcct tatggcatta aacctgaacc | 480 |
| gctgtcggcc agaaggggtg actgtcccac gcttgacact cacactttgt ccctgactga | 540 |
| ctatgcttgt ggttctcctc cagttgatag agaaaaacaa cccagcgaag gcgccttctc | 600 |
| tgaaaacaat gctgagaatg agagcggcgg agacaagccc ccatcgatc ccaataaccc | 660 |
| agcagccaac tggcttcatg cgcgctccac tcggaaaaag cggtgcccct atacaaaaca | 720 |
| ccagaccctg gaactggaga agagtttct gttcaacatg tacctcacca gggaccgcag | 780 |
| gtacgaggtg gctcgactgc tcaacctcac cgagaggcag gtcaagatct ggttccagaa | 840 |
| ccgcaggatg aaaatgaaga aaatcaacaa agaccgagca aaagacgagt gatgccattt | 900 |
| gggcttattt agaaaaaagg gtaagctaga gagaaaaaga aagaactgtc cgtccccctt | 960 |
| ccgccttctc ccttctctca cccccaccct agcctccacc atcccgcac aaagcggctc | 1020 |
| taaacctcag gccacatctt ttccaaggca aaccctgttc aggctggctc gtaggcctgc | 1080 |
| cgctttgatg gaggaggtat tgtaagcttt ccatttcta taagaaaaag gaaagttga | 1140 |
| ggggggggca ttagtgctga tagctgtgtg tgttagcttg tatatatatt tttaaaaatc | 1200 |
| tacctgttcc tgacttaaaa caaaaggaaa gaaactacct ttttataatg cacaactgtt | 1260 |
| gatggtaggc tgtatagttt ttagtctgtg tagttaattt aatttgcagt ttgtgcggca | 1320 |
| gattgctctg ccaagatact tgaacactgt gttttattgt ggtaattatg tttttgtgatt | 1380 |
| caaacttctg tgtactgggt gatgcaccca ttgtgattgt ggaagataga attcaatttg | 1440 |
| aactcaggtt gtttatgagg ggaaaaaaac agttgcatag agtatagctc tgtagtggaa | 1500 |
| tatgtcttct gtataactag gctgttaacc tatgattgta aagtagctgt aagaatttcc | 1560 |
| cagtgaaata aaaaaaaatt ttaagtgttc tcggggatgc atagattcat cattttctcc | 1620 |
| accttaaaaa tgcgggcatt taagtctgtc cattatctat atagtcctgt cttgtctatt | 1680 |
| gtatatataa tctatatgat taaagaaaat atgcataatc agacaagctt gaatattgtt | 1740 |
| tttgcaccag acgaacagtg aggaaattcg gagctataca tatgtgcaga aggttactac | 1800 |
| ctagggttta tgcttaattt taattggagg aaatgaatgc tgattgtaac ggagttaatt | 1860 |
| ttattgataa taaattatac actatgaaac cgccattggg ctactgtaga tttgtatcct | 1920 |
| tgatgaatct ggggtttcca tcagactgaa cttacactgt atattttgca atagttacct | 1980 |
| caaggcctac tgaccaaatt gttgtgttga gatgatattt aacttttgc caaataaaat | 2040 |
| atattgattc ttttctaaaa aaaaaaaaaa aaaaaa | 2076 |

<210> SEQ ID NO 46
<211> LENGTH: 3229
<212> TYPE: DNA
<213> ORGANISM: Mus <mouse, genus>
<220> FEATURE:
<223> OTHER INFORMATION: Mouse HOX-A9 (NM_010456.3)

<400> SEQUENCE: 46

| | |
|---|---|
| gaaaaaacag aagagggaag gataccagag cggttcatac agggcccaga aactaggcga | 60 |
| ggtgaccct cagcaagaca aacacctctt gatgttgact ggcgattttc cccatctcca | 120 |
| gtctggggag cggggactagg catacagatg atggagctta gaacccgctg gctagggaat | 180 |
| aaaattcgct gggcagtttg tgctcaaaga agtgggccag ggcgcttgtg acacaatcag | 240 |

```
ggcgtttgtg acacaaaccc ttgagggttg gcagttctct ccttggcggt tgctctggtt    300
gctctgtggg gccttccctg tggagcaagg gtgatctggc cgatgtgcaa gcgcctggct    360
ggctttccag tctgactagg gtcggtagcc cattttaggt ggttgtatca tcgacggtgc    420
gtcgcgacag gggcggtggt cactctgttt gaggtggaga gagccttgta tttgactttt    480
ctaggccggc cctgggggcg cgcgcgggcg ggggctcac atctctgagg actgcaagga     540
ttatttacag ggtattcacc aaccaaacac aacagtctaa tttaaccttt ccaagtcctc    600
ataaattttt acagggagcc acagcgaggc aaacgaatct gttggtcgct cctgactttc    660
caccagcctg tgtggcttcc gaaacaataa ctccttatga aatatcataa atatagattt    720
aaatacagta gagtgagaat gcgatttggc tgctttttta tggcttcaat tattgtctaa    780
ttttatgtga gggctctgc tggccgtgct cacacgcggg acccgcgcct tcctgatggc     840
gtgattaatt gtgatataaa atagtccgct taagaagtgt gtgtgtctgg tatgtgtgtg    900
tgttgggggg gtggcaaggg agagtacaga ggcaaggcca gatttgatct tttaatcttc    960
gttggccaca attaaaacaa accagatcgt ggagctgcgc gatccctttg cataaaaaca    1020
tatgcttttt gctataaaaa ttatgactgc aaaacaccgg gccattaata gcgtgcggag    1080
tgatttacgc gttattgttc tgccgggcgg acacgtgacg cgcgtggcca atggggcgc    1140 gggcgccggc aacttattag gtgactgtac ttcacccccc cctggtgcca ccaagttgtt    1200
acatgaaatc tgcagtttca taatttcggc gggtcgggct gggccggcca ggcgcgggct    1260
actgcaatgg ccaccaccgg ggccctgggc aactactatg tggactcctt cctgctgggc    1320
gccgacgctg ctgatgagct gggtgcggga cgctacgctc cagggaccct gggtcaaccc    1380
ccaaggcagg cggcagctct ggccgaacac cccgacttca gtccttgcag cttccagtcc    1440
aaggcggcgg tgtttggtgc ctcgtggaac ccagtgcacg cggcgggcgc caatgcggtg    1500
cctgctgcag tgtatcatca ccaccaccac ccctacgtgc atcccaggc gcccgtggcg     1560 gcggcggcgc cggacggcag gtatatgcgc tcctggctgg aacccacgcc cggtgcgctc    1620
tccttcgcgg gcttaccctc cagccggcct tatggcatta aacctgaacc gctctcggcc    1680 agaagggtg actgtcccac gcttgacact cacactttgt ccctgactga ctatgcttgt     1740
ggttctcctc cagttgatag agaaaaacaa cccagcgaag gcgccttctc cgaaaacaat    1800
gccgagaatg agagcggcgg agacaagccc cccatcgatc ccaataaccc ggctgccaac    1860
tggctacatg ctcgctccac tcggaagaag cgatgccct acacaaaaca ccagacgctg      1920
gaactggaga aggagtttct gtttaacatg tacctcacac gggaccgcag gtacgaggtg    1980
gcccggctgc tcaacctcac cgaaaggcag gtcaagatct ggttccagaa ccgcaggatg    2040
aaaatgaaga aaatcaacaa ggaccgagca aaagacgagt gagcctttta ggggctcatt    2100 taaaagaga gcaagctaga aagaaaaaga aaggactgtc cgtctccctc tgtctcctct      2160
cccccaaacc cagcctccac ccgcacaaag gggctctaaa tcccaggcct catctcccca    2220
ctggcagtcc gtgctcaggc tggctcttag gcctgcggct ttgatggagg aggtattgta    2280
agctttccat tttatagaag gcacacacac acacaaggga gggcattagc gctattggct    2340
gtatgtgcta gcttgtatat atatatatat atttaaaaaa aatctacctg cttctgactt    2400
taagcaaaag gaaagaaaac tacctttttta tataatgcac aactgttgat gactggctgt    2460
atagttttta gtctctgtag ctaatttaat ttgctcttcg tgtggcagat cattctgcca    2520
aaatacttga acactgtgtt ttattgtggt aattatgttt tgtgactcaa acttctgtgc    2580
```

-continued

| | |
|---|---|
| tgggtgaagt acccattgtg attgtggaag ctagaattca atttgaactc aggttgttta | 2640 |
| tggggggaga gaagctgtgg cataatgtat agctctgtag tcttctgtgt agctagactg | 2700 |
| ttaacctacg attgtaaact agctgtaagg atttcccagt gaaatcagat ttggaaagaa | 2760 |
| aagagagata gttctccggg atgcatagat tcatgattta tctactttg aaatgtgggc | 2820 |
| ttcttcatct ttacgttcta gactccaatt ttgtccaatg tatatagaat ctccatatta | 2880 |
| aagaaatatt cataatcaga aagcttgaat attgttttg caccagagga gaagtgagga | 2940 |
| aattcggagc tatacgtgtg tgcagagggt tgctacctat gggtttacgc ttaattttaa | 3000 |
| ttgggagaaa gtgagtgctt attgtaatgg agttaatttt attgataata aattatacac | 3060 |
| catgaaactg ctcttgggct actgtagatt tgtatccttg gtgaatttgg ggttcccatc | 3120 |
| ggattgaaca tacactgtat attttgcaat agttacctca aggcctactg accaaattgt | 3180 |
| tgtgtcgaga tatttaactt ttgccaaata aaatatattg attcttta | 3229 |

<210> SEQ ID NO 47
<211> LENGTH: 3484
<212> TYPE: DNA
<213> ORGANISM: Homo sapiens
<220> FEATURE:
<223> OTHER INFORMATION: Human GATA2 (NM_001145661.1)

<400> SEQUENCE: 47

| | |
|---|---|
| actgggtcaa gcacagccct gagcggccgc gtgtccgagg cccaggtgcc ctctagagcc | 60 |
| ctgtagttcc tgcccctctc tgcccctctc ggctcctgct gttccgccgc tgtcgtccga | 120 |
| accatcccaa cccccagtcc acccagacag cgcccgagct aggggaggga acggtctggg | 180 |
| agtcggcagc tggcgccagg gcggccggag gatgccgagg ggccggagcc gggagggccc | 240 |
| gaggccgagg cgcactctac ccccagctcc taccctgtaa gccccgccag cctccggacg | 300 |
| tgctgtccct gggcccgtcg ccctcggggc tccgccgga actccttcac tctcagaggc | 360 |
| cgagtccctc ccctccccac ggctgcgtgt ggccgttgcc gtctgcaccc agaccctgag | 420 |
| ccgccgccgc cggccatgga ggtggcgccc gagcagccgc gctggatggc gcacccggcc | 480 |
| gtgctgaatg cgcagcaccc cgactcacac caccccgggcc tggcgcacaa ctacatggaa | 540 |
| cccgcgcagc tgctgcctcc agacgaggtg gacgtcttct tcaatcacct cgactcgcag | 600 |
| ggcaacccct actatgccaa ccccgctcac gcgcgggcgc gcgtctccta cagccccgcg | 660 |
| cacgcccgcc tgaccggagg ccagatgtgc cgcccacact gttgcacag cccgggtttg | 720 |
| ccctggctgg acggggcaa agcagccctc tctgccgctg cggcccacca ccacaacccc | 780 |
| tggaccgtga gccccttctc caagacgcca ctgcacccct cagctgctgg aggccctgga | 840 |
| ggcccactct ctgtgtaccc aggggctggg gtgtgggagcg ggggaggcag cgggagctca | 900 |
| gtggcctccc tcaccctac agcagcccac tctggctccc accttttcgg cttcccaccc | 960 |
| acgccaccca agaagtgtc tcctgaccct agcaccacgg gggctgcgtc tccagcctca | 1020 |
| tcttccgcgg ggggtagtgc agcccgagga gaggacaagg acgcgtcaa gtaccaggtg | 1080 |
| tcactgacgg agagcatgaa gatggaaagt ggcagtcccc tgcgcccagg cctagctact | 1140 |
| atgggcaccc agcctgctac acaccacccc atcccacct ccctcca tgtgccggcg | 1200 |
| gctgcccacg actacagcag cggactcttc caccccggag gcttcctggg ggaccggcc | 1260 |
| tccagcttca cccctaagca gcgcagcaag gctcgttcct gttcagaagg ccggagtgt | 1320 |
| gtcaactgtg gggccacagc cacccctctc tggcggcggg acggcaccgg ccactacctg | 1380 |
| tgcaatgcct gtggcctcta ccacaagatg aatgggcaga accgaccact catcaagccc | 1440 |

```
aagcgaagac tgtcggccgc cagaagagcc ggcacctgtt gtgcaaattg tcagacgaca    1500
accaccacct tatggcgccg aaacgccaac ggggaccctg tctgcaacgc ctgtggcctc    1560
tactacaagc tgcacaatgt taacaggcca ctgaccatga agaaggaagg gatccagact    1620
cggaaccgga agatgtccaa caagtccaag aagagcaaga aaggggcgga gtgcttcgag    1680
gagctgtcaa agtgcatgca ggagaagtca tcccccttca gtgcagctgc cctggctgga    1740
cacatggcac ctgtgggcca cctcccgccc ttcagccact ccggacacat cctgcccact    1800
ccgacgccca tccacccctc ctccagcctc tccttcggcc accccaccc gtccagcatg    1860 gtgaccgcca tgggctaggg aacagatgga cgtcgaggac cgggcactcc cgggatgggt    1920
ggaccaaacc cttagcagcc cagcatttcc cgaaggccga caccactcct gccagcccgg    1980
ctcggcccag caccccctct cctggagggc gcccagcagc ctgccagcag ttactgtgaa    2040
tgttccccac cgctgagagg ctgcctccgc acctgaccgc tgcccaggtg gggtttcctg    2100
catggacagt tgtttggaga acaacaagga caactttatg tagagaaaag gaggggacgg    2160
gacagacgaa ggcaaccatt tttagaagga aaaaggatta ggcaaaaata atttattttg    2220
ctcttgtttc taacaaggac ttggagactt ggtggtctga gctgtcccaa gtcctccggt    2280
tcttcctcgg gattggcggg tccacttgcc agggctctgg gggcagattt gtgggggacct   2340 cagcctgcac cctcttctcc tctggcttcc ctctctgaaa tagccgaact ccaggctggg    2400
ctgagccaaa gccagagtgg ccacggccca gggagggtga gctggtgcct gctttgacgg    2460
gccaggccct ggagggcaga gacaatcacg ggcggtcctg cacagattcc caggccaggg    2520
ctgggtcaca ggaaggaaac aacatttttct tgaaagggga aacgtctccc agatcgctcc    2580
cttggctttg aggccgaagc tgctgtgact gtgtccccctt actgagcgca agccacagcc    2640
tgtcttgtca ggtggaccct gtaaatacat cctttttctg ctaacccttc aacccctcg    2700 cctcctactc tgagacaaaa gaaaaaatat taaaaaatg cataggctta actcgctgat    2760
gagttaattg ttttatttt aaactctttt tgggtccagt tgattgtacg tagccacagg    2820
agccctgcta tgaaaggaat aaaacctaca cacaaggttg gagctttgca attcttttg    2880 gaaaagagct gggatcccac agccctagta tgaaagctgg gggtggggag gggcctttgc    2940
tgcccttggt ttctggggc tggttggcat ttgctggcct ggcagggggt gaaggcagga    3000 gttggggca ggtcaggacc aggacccagg gagaggctgt gtccctgctg gggtctcagg    3060
tccagcttta ctgtggctgt ctggatcctt cccaaggtac agctgtatat aaacgtgtcc    3120
cgagcttaga ttctgtatgc ggtgacgcg gggtgtggtg gcctgtgagg ggcccctggc    3180
ccaggaggag gattgtgctg atgtagtgac caagtgcaat atgggcgggc agtcgctgca    3240
gggagcacca cggccagaag taacttattt tgtactagtg tccgcataag aaaaagaatc    3300
ggcagtattt tctgttttta tgttttattt ggcttgtttt attttggatt agtgaactaa    3360
gttattgtta attatgtaca acatttatat attgtctgta aaaatgtat gctatcctct    3420 tattcccttta aagtgagtac tgttaagaat aataaaatac ttttgtgaa tgcccaaaaa    3480 aaaa                                                                 3484
```

<210> SEQ ID NO 48
<211> LENGTH: 3258
<212> TYPE: DNA
<213> ORGANISM: Mus <mouse, genus>
<220> FEATURE:
<223> OTHER INFORMATION: Mouse Gata2 (NM_008090.5)

<400> SEQUENCE: 48

```
gtctgtgcag gagtcggcag ctggcgccag ggcggccgga ggatgcagag gggccggagc    60
cgggcgggcc ggaggccgag acgcgcgctg tcccccaccc ctatcccgtg aatccgccgg   120
ccctggaacg cgctgtcgct gggcccgccg tacccgggct ctcctggtgt ctcttactct   180
ctactgctga gccctcccct tcccgcgccg ctgcgagtgg ccgccccacc ttcgcctggt   240
tcccaagaca cagtagtgga ccatggaggt ggcgcctgag cagcctcgct ggatggcgca   300
ccccgccgta ttgaatgcgc agcaccccga ctcgcaccat ccgggcctgg cgcataacta   360
catggagcca gcacagctgc tgcctcccga cgaggtggag gtcttcttca accatctcga   420
ctcgcagggc aacccttact acgccaaccc ggcccacgcg cgcgcgcgcg tttcctacag   480
cccggcgcat gcccgtctca ccggaggcca gatgtgccga ccacacttgt tgcacagccc   540
aggcttgccg tggctggacg ggggcaaagc agctctctct gccgccgctg cccatcacca   600
cagtccctgg accgtcagcc cgttctccaa gaccccgctg caccctcag ctgctggagc   660
acccggaggg cctctgtctg tttacccagg ggctgcgggt gggagcgggg gaggcagtgg   720
gagctccgtg gcctccctca cccccactgc agcccactcg ggctcccatc tcttcggctt   780
cccacccacg ccacccaaag aagtgtctcc agacccagc acaacaggag ctgcttcccc   840
ggcctcttct tctgcagggg gtagtgtagc ccggggtgag gacaaggatg gcgtcaagta   900
ccaagtgtca ctctccgaga gcatgaagat ggaaggcggc agtcccctgc gcccgggcct   960
agctaccatg ggcacccagc ctgcaacaca ccacccgata cccacctatc cctcctatgt  1020
gcccgccgca gctcatgact atggcagcag tctcttccat ccaggaggct tcctgggtgg  1080
ccccgcctcc agcttcaccc ctaagcagag aagcaaggct cgctcctgct cagaaggccg  1140
ggagtgtgtc aactgtggtg ccacagccac ccctctctgg cgacgagatg gcacgggcca  1200
ctacctgtgc aatgcctgtg ggctctacca caagatgaat ggacagaacc ggccgctcat  1260
caagcccaag cggaggctgt ctgctgccag aagagcgggc acctgttgtg caaattgtca  1320
gacgacaacc accaccttat ggcgccggaa cgccaacggg gaccctgtgt gcaacgcctg  1380
tggcctctac tacaagctgc acaatgttaa caggccactg accatgaaga aggaagggat  1440
ccagacccgg aatcggaaga tgtccagcaa atccaagaag agcaagaaag ggctgaatg   1500
tttcgaggag ctctccaagt gcatgcaaga gaagtcaccg cccttcagtg cggctgccct  1560
ggctggacac atggcacctg tgggacacct cccaccttt agtcactctg acacatcct  1620
acccacgccc acgcctatcc acccttcctc cagtctctct tttggccacc cccacccgtc  1680
cagcatggtg actgccatgg gctaggcaag cctcccactg gacagacatg gacatcaagg  1740
gtggtttggc agaaccagag cgaggctggg cactcccagg atgggtggaa catactcttg  1800
gctcccgccc atcccaagag acccacttcc tcctgccagc ctagcctggc cgaagccacc  1860
tctccttgga ggactcccag ccttgtgccg ccattactgt gaatatttct aactgggctg  1920
cagctcgcgt gtgcccgggg tgctgcccag aaaagtgttt tcacgagag tgtttgtttg   1980
gagagcaaaa tggacaggtt tacagattta tagcaagaag agactgggga tagaaaaatg  2040
aaaccttttt ttttcttttt ctttttttct tcttctgttt tatttttttg atggagaaag  2100
gagtaggcaa gaagaaaaat aatttatttt gctcttattt cttacaagaa cgtgaagaca  2160
tggaggcgtg tgctatttgt gttcttgggg tccttctttg ggacctcctg ccaccagtca  2220
gggctctcgg gggcagactt agaggtcctc agcctgagcc tccttcaccc cagcctgcct  2280
gcagggtagc ccctgccctg acgcagccct agagggcaga gacaattgca ggcggtcctg  2340
```

```
cgcagattcc caggccaggg ctgggtcaca ggaaggaaac attctctgga aaggggaaac    2400
gtctcccaga tcattcccct ggcttccaga ggccaaagct ggtgtgaccc aaatgggcca    2460
gagctgcagc ctgtgctcta ggccagtcgg acccctgtaa atacaaccct cttttctgct    2520
aaaccctcgg cccccctccc ctctaagata aataagaaaa tactcaaagc gaaaaccaaa    2580
ctgcataagc ttaacccgct gatgagtggt tttattttga aactcgtttt ttgggtccag    2640
tcaattgtac gttgccacag aagcccgct atggaaaaa ataaataaaa cctacaaacc    2700
aggcctgagc ttcacagtcc tttgagtggt tcttgggtcc cacagccctg cagggggct    2760 cgggacaagg gggaatctta tgctcttggt ttctgggaga cagggggcag gcaggcagtg    2820
gccctgtgat cccaggcttc tgttctgctg tggctggctg aatccttcaa ggtacagttg    2880
tacataaaaa gtgtcccaag cttcgattct gtgtgtggtg gtggcagtgg tgcagcagcc    2940 agcaagggg ccccgagtga gcccagggag acgattgtgc tgagtcaacc aagtgcaata    3000
tcggtgtcca gttgctgcag agcaccctaa ccggaagtaa cttattttgt gctagtaccc    3060
gcataagaga agaatcggca gtattttctg tttttatgtt ttgggcttgt tttattttga    3120
attagtgacc taagttattg ttaactgtgt acaacattta aatattgtct gtaaaaattg    3180
tatgctaccc tcttattcct ttaaagtgaa tactgttaaa aataataaaa tactttttgt    3240
gaaaaaaaaa aaaaaaaa                                                  3258

<210> SEQ ID NO 49
<211> LENGTH: 3198
<212> TYPE: DNA
<213> ORGANISM: Homo sapiens
<220> FEATURE:
<223> OTHER INFORMATION: Human MEIS1 (NM_002398.2)

<400> SEQUENCE: 49
atttgaggtg ttctgaccag aagaagacag agcggatgat cattcattca ccacgttgac      60
aacctcgcct gtgattgaca gctggagtgg cagaaagcca tgagatttgg tagttgggtc     120 tgagggcgc tctttttttt ccttttcttt ctttctttct tttttttttt ttaaactgat     180
ttttggggga gagaagatct gctttttttt gcccccgctg ctgtcttgga aacggagcgc     240
ttttatgctc agtgactcgg gcgctttgct tcaggtcccg tagaccgaag atctgggacc     300
agtagctcac gttgctggag acgttaaggg attttcgtc gtgcttttt ttttttttt     360 tttttttcc gggggagttt gaatatttgt ttcttttcac actggcctta agaggatat     420 attagaagtt gaagtaggaa gggagccaga gaggccgatg gcgcaaaggt acgacgatct     480
accccattac gggggcatgg atggagtagg catcccctcc acgatgtatg ggacccgca     540 tgcagccagc tccatgcagc cggtccacca cctgaaccac gggcctcctc tgcactcgca     600
tcagtacccg cacacagctc ataccaacgc catggccccc agcatgggct cctctgtcaa     660
tgacgcttta aagagagata agatgccat ttatggacac cccctcttcc ctctcttagc     720
actgattttt gagaaatgtg aattagctac ttgtaccccc cgcgagccgg gggtggcggg     780
cggggacgtc tgctcgtcag agtcattcaa tgaagatata gccgtgttcg ccaaacagat     840
tcgcgcagaa aaacctctat tttcttctaa tccagaactg gataacttga tgattcaagc     900
catacaagta ttaaggtttc atctattgga attagagaag gtacacgaat tatgtgacaa     960
tttctgccac cggtatatta gctgtttgaa agggaaaatg cctatcgatt tggtgataga    1020
cgatagagaa ggaggatcaa aatcagacag tgaagatata acaagatcag caaatctaac    1080
```

-continued

| | |
|---|---|
| tgaccagccc tcttggaaca gagatcatga tgacacggca tctactcgtt caggaggaac | 1140 |
| cccaggccct tccagcggtg gccacacgtc acacagtggg gacaacagca gtgagcaagg | 1200 |
| tgatggcttg gacaacagtg tagcttcccc cagcacaggt gacgatgatg accctgataa | 1260 |
| ggacaaaaag cgtcacaaaa agcgtggcat cttccccaaa gtagccacaa atatcatgag | 1320 |
| ggcgtggctg ttccagcatc taacacaccc ttacccttct gaagaacaga aaaagcagtt | 1380 |
| ggcacaagac acgggactca ccatccttca agtgaacaat tggtttatta atgcccggag | 1440 |
| aagaatagtg cagcccatga tagaccagtc caaccgagca gtaagtcaag gaacacctta | 1500 |
| taatcctgat ggacagccca tgggaggttt cgtaatggac ggtcagcaac atatgggaat | 1560 |
| tagagcacca ggacctatga gtggaatggg catgaatatg ggcatggagg ggcagtggca | 1620 |
| ctacatgtaa ccttcatcta gttaaccaat cgcaaagcaa gggggaaggc tgcaaagtat | 1680 |
| gccaggggag tatgtagccc gggtggtcc aatgggtgtg agtatgggac agccaagtta | 1740 |
| tacccaaccc cagatgcccc ccatcctgc tcagctgcgt catgggcccc ccatgcatac | 1800 |
| gtacattcct ggacaccctc accacccaac agtgatgatg catggaggac cgccccaccc | 1860 |
| tggaatgcca atgtcagcat caagcccac agttcttaat acaggagacc caacaatgag | 1920 |
| tggacaagtc atggacattc atgctcagta gcttaaggga atatgcattg tctgcaatgg | 1980 |
| tgactgattt caaatcatgt tttttctgca atgactgtgg agttccattc ttggcatcta | 2040 |
| ctctggacca aggagcatcc ctaattcttc atagggacct ttaaaaagca ggaaatacca | 2100 |
| actgaagtca atttggggga catgctaaat aactatataa gacattaaga gaacaaagag | 2160 |
| tgaaatattg taaatgctat tatactgtta tccatattac gttgtttctt atagatttt | 2220 |
| taaaaaaaat gtgaaatttt tccacactat gtgtgttgtt tccatagctc ttcacttcct | 2280 |
| ccagaagcct ccttacatta aaagccctta cagttatcct gcaagggaca ggaaggtctg | 2340 |
| atttgcagga tttttagagc attaaaataa ctatcaggca gaagaatctt tcttctcgcc | 2400 |
| taggatttca gccatgcgcg cgctctctct cttctctct cttttcctct ctctccctct | 2460 |
| ttctagcctg gggcttgaat ttgcatgtct aattcattta ctcaccatat ttgaattggc | 2520 |
| ctgaacagat gtaaatcggg aaggatggga aaaactgcag tcatcaacaa tgattaatca | 2580 |
| gctgttgcag gcagtgtctt aaggagactg gtaggaggag gcatggaaac caaaaggccg | 2640 |
| tgtgtttaga agcctaattg tcacatcaag catcattgtc cccatgcaac aaccaccacc | 2700 |
| ttatacatca cttcctgttt taagcagctc taaaacatag actgaagatt tattttaat | 2760 |
| atgttgactt tatttctgag caaagcatcg gtcatgtgtg tattttttca tagtcccacc | 2820 |
| ttggagcatt tatgtagaca ttgtaaataa attttgtgca aaaaggactg gaaaaatgaa | 2880 |
| ctgtattatt gcaatttttt tttgtaaaag tagcagtttg gtatgagttg gcatgcatac | 2940 |
| aagatttact aagtgggata agctaattat acttttgtt gtggataaac aaatgcttgt | 3000 |
| tgatagcctt tttctatcaa gaaaccaagg agctaattat taataacaat cattgcacac | 3060 |
| tgagtcttag cgtttctgat ggaaacagtt tggattgtat aataacgcca agcccagttg | 3120 |
| tagtcgtttg agtgcagtaa tgaaatctga atctaaaata aaaacaagat tattttttgtc | 3180 |
| aaaaaaaaaa aaaaaaaa | 3198 |

<210> SEQ ID NO 50
<211> LENGTH: 3346
<212> TYPE: DNA
<213> ORGANISM: Mus <mouse, genus>
<220> FEATURE:
<223> OTHER INFORMATION: Mouse Meis1 (NM_010789.3)

<400> SEQUENCE: 50

```
agcattctgg tcggaatcca cctctccgcc tgtgcaacac acactttaca cacgcacggc    60
gactgcaagc gggcagcatc gatcgtggct cctttaagac aaactcagac agacattttt   120
ttaaccctcc tctctaatct cccttcagtg cagcagttgc aaagagggag agagaaagag   180
aaagagagcg agagaagaga gaaactgatt aggaattagg actgattcaa ggaaagcggg   240
cgctagggct ttgtgcattt gaatattaac atttgaggtg ttctgaccag aagaagacag   300
aacggacgat cattcattca ccacgttgac aacctcgcct gtgattgaca gctggagtgg   360
cagaaagcca tgagatttgg tagttgggtc tgaggggcgc tcttttttttt tttttctttt   420
cttttctttt ctttctttttt ttttaaactg atttttttgg ggggagaga agatctgctt   480
tttttttccc ctcccactgc tgtcttggtg gaaccagagc gcttttatgc tcagcgacgc   540
gggcgccttg cttcaggtcc ggtagaccga agatctggga ccagtaattc acactgctgg   600
agacgcaaag ggatttttttt ttgttattgt tgtgctttat ttttttttcc ggggggagttt   660
gcatatttgt ttcttttcac actggcctta aagaggatat attagaagtt gaagtaggaa   720
gggagccaga gaggccgatg gcgcaaaggt acgacgacct accccattat ggggtatgg    780
atggagtagg catccctcc acgatgtatg gggacccgca tgcagccagg tccatgcaac   840
cggtccacca cctgaaccac gggcctcctc tgcactcgca tcagtacccg cacacagctc   900
acaccaacgc catggccccc agcatggggtt cctcggtcaa tgacgcttta aagagagata   960
aagatgccat ttatggacac cccctcttcc ctctcttagc actgattttt gagaaatgtg  1020
aattagctac ttgtacccccc cgcgagccgg gggtggcggg cggggacgtc tgctcgtcag  1080
agtcattcaa tgaagatata gcggtgttcg ccaaacagat tcgcgcagaa aaacctctat  1140
tctcttctaa tccagaactg gataacttga tgattcaagc catacaagtg ttaaggtttc  1200
atctgttgga attagagaag gtacacgaat tatgtgacaa tttctgccac cggtatatta  1260
gctgtttgaa agggaaaatg cctatcgatt tggtgataga tgatagagaa ggaggatcaa  1320
aatcagacag tgaagatgta acaagatcag caaatctaac tgaccagccc tcttggaata  1380
gagaccatga tgacacggca tccactcgtt caggaggaac cccgggccct tccagcggtg  1440
gccatacttc acacagtggg gataacagca gtgagcaagg tgatggcttg acaacagtg   1500
tagcttcccc cagcacaggt gacgatgatg accctgataa ggacaaaaag cgtcacaaaa  1560
agcgtggcat ctttcccaaa gtagccacca atatcatgag ggcgtggctg ttccagcatc  1620
taacacaccc ttacccttct gaagaacaga aaaagcagtt ggcacaagat acaggactta  1680
ccatccttca agtgaacaat tggtttatta atgcccggag aagaatagtg cagcccatga  1740
tagaccagtc caaccgagca gtcagccaag ggacacctta taaccctgat ggacagccaa  1800
tgggaggttt tgtaatggac ggtcagcagc acatgggcat cagagcgcca gggctgcaaa  1860
gtatgccagg ggagtatgta gcccggggtg gcccaatggg tgtgagtatg ggacagccga  1920
gttataccca agcccagatg cccccccatc ctgctcagct gcgtcatggg ccccccatgc  1980
atacgtacat tcctggacac cctcaccacc ccgcagtgat gatgcatgga ggacagcccc  2040
accctggaat gccaatgtca gcctcaagcc cctcggttct taacacagga gaccccgacaa  2100
tgagtgcaca agtcatggac attcacgctc agtagcttaa gggaatatgc gttgtctaca  2160
atggtgactg atctcgaatc aggtcttttc ctgcaaggac tatggagttc cattcttgac  2220
atctactttg gaccaaggag catccctagt tcttcatagg gactcttaaa atgcaggaga  2280
```

| | | | | |
|---|---|---|---|---|
| accatccgaa | gtcaactcgg | gggacatgca | aaaataacta | tataagacat | taaaagaaca | 2340 |
| aagagtgaaa | tattgtaaat | gctattatac | tgttatccat | attacgttgt | ttcttataga | 2400 |
| ttttttaaaa | aaaatgtgaa | attttttccac | actatgtgtg | ttgtttccat | agctgttcac | 2460 |
| ttcctccaga | agcctcctta | cattaaaaag | ccttacagtt | atcctgcaag | ggacaggaag | 2520 |
| gtctgatttg | caggattttt | agagcattaa | aataactatc | aggcagaaga | atctttcttc | 2580 |
| ttgcctagga | tttcagccat | gtgcgtgcgc | tctctctctc | tctctctctc | tctctctctc | 2640 |
| tctctctctc | tctctctctc | tctctcttct | cctccctctc | cctctttcta | gcctggggct | 2700 |
| tgaatttgca | tgtctaattc | atttactcac | catatttgaa | ttggcctgaa | cagatgtaaa | 2760 |
| tcgggaagga | tgggaaaaac | tgcagtcacc | aacaatgatt | aatcagctgt | tgcaggcagt | 2820 |
| gtcttaagga | gactggtagg | aggaggcatg | gaaacccaaa | ggccgtgtgt | gtttagaagc | 2880 |
| ctaactgtca | catcaagcat | catcgtcccc | atgcaacaac | aaccatcacc | ttatacatca | 2940 |
| cttcctgttt | tatgcagctc | aaaaaacata | gactgaagat | ttattttta | atatgttgac | 3000 |
| tttgtttctc | agcaaagcat | tggtcatgtg | tgtattttc | catagtccca | ccttggagca | 3060 |
| tttatgtaga | cattgtaaat | aaattttgtg | caaaaaggac | tggaaagatg | aactgtatta | 3120 |
| ttgcatttat | tttgttttt | tttttgtgaa | agtagcagat | tagtgcaagg | tggcatgcat | 3180 |
| ataaggttaa | ctgagtgggg | tacgctaatt | atactttttg | ttgtggataa | aaaatgcttg | 3240 |
| tcaatagcct | ttttctatca | agaaaacaag | gagctaatta | ttaataacag | tcatggcaca | 3300 |
| ctgtgtccta | tcttagcatt | taaaagtatg | caaactccag | gtccag | | 3346 |

<210> SEQ ID NO 51
<211> LENGTH: 4414
<212> TYPE: DNA
<213> ORGANISM: Homo sapiens
<220> FEATURE:
<223> OTHER INFORMATION: Human STAT5A (NM_001288718.1)

<400> SEQUENCE: 51

| | | | | | | |
|---|---|---|---|---|---|---|
| agatggccgg | agtaaaagaa | ggagggaggt | gctgcggtgg | tgggggtgat | cttggcttca | 60 |
| ctagaatccc | cagttcttcc | cctctctaca | gttttgtctc | tgaggtcaca | aaacctgtgg | 120 |
| cccccaagac | acacatgcgc | acacacgcgc | gtgcacacac | acccccaca | catttatttt | 180 |
| ttaatctagg | ggctcaaaag | atgacacgcg | ccagagctgg | aaggcgtcgc | caattggtcc | 240 |
| acttttcccct | cctcccttttt | tgcggatgag | aaaactgagg | cccaggtttg | ggatttccag | 300 |
| agcccgggat | ttcccggcaa | cgcccgacaa | ccacattccc | ccggctattc | tgacccgccc | 360 |
| cggttccggg | acgctccctg | ggagccgccg | ccgagggcct | gctgggactc | ccgggggacc | 420 |
| ccgccgtcgg | ggcagccccc | acgcccggcg | ccgcccgccg | gaacggccg | ccgctgttgc | 480 |
| gcacttgcag | gggagccggc | gactgagggc | gaggcaggga | gggagcaagc | ggggctggga | 540 |
| gggctgctgg | cgcgggctcg | cgcgctgtgt | atggtctatc | gcaggcagct | gacctttgag | 600 |
| gaggaaatcg | ctgctctccg | ctccttcctg | tagtaacagc | cgccgctgcc | gccgccgcca | 660 |
| ggaaccccgg | ccgggagcga | gagccgcggg | gcgcagagcc | ggcccggctg | ccggacggtg | 720 |
| cggccccacc | aggtgaacgg | ccatggcggg | ctggatccag | gccagcagc | tgcagggaga | 780 |
| cgcgctgcgc | cagatgcagg | tgctgtacgg | ccagcacttc | cccatcgagg | tccggcacta | 840 |
| cttggcccag | tggattgaga | gccagccatg | ggatgccatt | gacttggaca | atccccagga | 900 |
| cagagcccaa | gccacccagc | tcctgggggg | cctggtgcag | gagctgcaga | agaaggcgga | 960 |
| gcaccaggtg | ggggaagatg | ggttttttact | gaagatcaag | ctggggcact | acgccacgca | 1020 |

-continued

| | |
|---|---|
| gctccagaaa acatatgacc gctgccccct ggagctggtc cgctgcatcc ggcacattct | 1080 |
| gtacaatgaa cagaggctgg tccgagaagc caacaattgc agctctccgg ctgggatcct | 1140 |
| ggttgacgcc atgtcccaga agcaccttca gatcaaccag acatttgagg agctgcgact | 1200 |
| ggtcacgcag gacacagaga atgagctgaa gaaactgcag cagactcagg agtacttcat | 1260 |
| catccagtac caggagagcc tgaggatcca agctcagttt gcccagctgg cccagctgag | 1320 |
| cccccaggag cgtctgagcc gggagacggc cctccagcag aagcaggtgt ctctggaggc | 1380 |
| ctggttgcag cgtgaggcac agacactgca gcagtaccgc gtggagctgg ccgagaagca | 1440 |
| ccagaagacc ctgcagctgc tgcggaagca gcagaccatc atcctggatg acgagctgat | 1500 |
| ccagtggaag cggcggcagc agctggccgg gaacggcggg ccccccgagg gcagcctgga | 1560 |
| cgtgctacag tcctggtgtg agaagttggc cgagatcatc tggcagaacc ggcagcagat | 1620 |
| ccgcagggct gagcacctct gccagcagct gcccatcccc ggcccagtgg aggagatgct | 1680 |
| ggccgaggtc aacgccacca tcacggacat tatctcagcc ctggtgacca gcacattcat | 1740 |
| cattgagaag cagcctcctc aggtcctgaa gacccagacc aagtttgcag ccaccgtacg | 1800 |
| cctgctggtg ggcgggaagc tgaacgtgca catgaatccc cccaggtga aggccaccat | 1860 |
| catcagtgag cagcaggcca agtctctgct taaaaatgag aacacccgca acgagtgcag | 1920 |
| tggtgagatc ctgaacaact gctgcgtgat ggagtaccac caagccacgg gcaccctcag | 1980 |
| tgcccacttc aggaacatgt cactgaagag gatcaagcgt gctgaccggc ggggtgcaga | 2040 |
| gtccgtgaca gaggagaagt tcacagtcct gtttgagtct cagttcagtg ttggcagcaa | 2100 |
| tgagcttgtg ttccaggtga agactctgtc cctacctgtg gttgtcatcg tccacggcag | 2160 |
| ccaggaccac aatgccacgg ctactgtgct gtgggacaat gcctttgctg agccgggcag | 2220 |
| ggtgccattt gccgtgcctg acaaagtgct gtggccgcag ctgtgtgagg cgctcaacat | 2280 |
| gaaattcaag gccgaagtgc agagcaaccg gggcctgacc aaggagaacc tcgtgttcct | 2340 |
| ggcgcagaaa ctgttcaaca acagcagcag ccacctggag gactacagtg gcctgtccgt | 2400 |
| gtcctggtcc cagttcaaca gggagaactt gccgggctgg aactacacct tctggcagtg | 2460 |
| gtttgacggg gtgatggagg tgttgaagaa gcaccacaag ccccactgga atgatggggc | 2520 |
| catcctaggt tttgtgaata agcaacaggc ccacgacctg ctcatcaaca agcccgacgg | 2580 |
| gaccttcttg ttgcgcttta gtgactcaga atcgggggc atcaccatcg cctggaagtt | 2640 |
| tgactccccg gaacgcaacc tgtggaacct gaaaccattc accacgcggg atttctccat | 2700 |
| caggtccctg gctgaccggc tgggggacct gagctatctc atctatgtgt tcctgaccg | 2760 |
| ccccaaggat gaggtcttct ccaagtacta cactcctgtg ctggctaaag ctgttgatgg | 2820 |
| atatgtgaaa ccacagatca agcaagtggt ccctgagttt gtgaatgcat ctgcagatgc | 2880 |
| tgggggcagc agcgccacgt acatggacca ggccccctcc ccagctgtgt gcccccaggc | 2940 |
| tccctataac atgtacccac agaaccctga ccatgtactc gatcaggatg gagaattcga | 3000 |
| cctggatgag accatggatg tggccaggca cgtggaggaa ctcttacgcc gaccaatgga | 3060 |
| cagtcttgac tcccgcctct cgccccctgc cggtcttttc acctctgcca gaggctccct | 3120 |
| ctcatgaatg tttgaatccc acgcttctct ttggaaacaa tatgcaatgt gaagcggtcg | 3180 |
| tgttgtgagt ttagtaaggc tgtgtacact gacacctttg caggcatgca tgtgcttgtg | 3240 |
| tgtgtgtgtg tgtgtgtgtc cttgtgcatg agctacgcct gcctcccctg tgcagtcctg | 3300 |
| ggatgtggct gcagcagcgg tggcctcttt tcagatcatg gcatccaaga gtgcgccgag | 3360 |

```
tctgtctctg tcatggtaga gaccgagcct ctgtcactgc aggcactcaa tgcagccaga    3420
cctattcctc ctgggcccct catctgctca gcagctattt gaatgagatg attcagaagg    3480
ggagggggaga caggtaacgt ctgtaagctg aagtttcact ccggagtgag aagctttgcc    3540
ctcctaagag agagagacag agagacagag agagagaaag agagagtgtg tgggtctatg    3600
taaatgcatc tgtcctcatg tgttgatgta accgattcat ctctcagaag ggaggctggg    3660
gttcattttc gagtagtatt ttatacttta gtgaacgtgg actccagact ctctgtgaac    3720
cctatgagag cgcgtctggg cccggccatg tccttagcac aggggggccg ccggtttgag    3780
tgagggtttc tgagctgctc tgaattagtc cttgcttggc tgcttggcct tgggcttcat    3840
tcaagtctat gatgctgttg cccacgtttc ccgggatata tattctctcc cctccgttgg    3900
gccccagcct tctttgcttg cctctctgtt tgtaaccttg tcgacaaaga ggtagaaaag    3960
attgggtcta ggatatggtg ggtggacagg ggccccggga cttggagggt tggtcctctt    4020
gcctcctgga aaaacaaaa acaaaaaact gcagtgaaag acaagctgca aatcagccat    4080
gtgctgcgtg cctgtggaat ctggagtgag gggtaaaagc tgatctggtt tgactccgct    4140
ggaggtgggg cctggagcag gccttgcgct gttgcgtaac tggctgtgtt ctggtgaggc    4200
cttgctccca accccacacg ctcctccctc tgaggctgta ggactcgcag tcaggggcag    4260
ctgaccatgg aagattgaga gcccaaggtt taaacttctc tgaagggagg tggggatgag    4320
aagaggggtt tttttgtact ttgtacaaag accacacatt tgtgtaaaca gtgttttgga    4380
ataaaatatt tttttcataa aaaaaaaaaa aaaa                                4414

<210> SEQ ID NO 52
<211> LENGTH: 3628
<212> TYPE: DNA
<213> ORGANISM: Mus <mouse, genus>
<220> FEATURE:
<223> OTHER INFORMATION: Mouse Stat5a (NM_001164062.1)

<400> SEQUENCE: 52
taacagcctc caccgccgcc gccgtcaaga gccgtcagga gccgtcagaa gccccggcct      60
ggagcgacag ccgcaggcgc tccgcagcac caggtaaaca gccatggcgg gctggattca    120
ggcccagcag cttcagggag atgccctgcg ccagatgcaa gtgttgtatg ggcagcattt    180
ccccatcgag gtccggcact acctggccca gtggatcgag agccagccgt gggatgctat    240
tgacttggat aatccccagg accgaggtca ggccacccaa ctcctggagg gcctggtgca    300
ggagctgcag aagaaggcgg agcaccaggt ggggggaagat gggttttttgc tgaagatcaa    360
gctggggcac tatgccacac agctccagaa cacgtatgac cgctgtccca tggagctggt    420
tcgctgtatc cgtcacattc tgtacaacga acagaggctg gttcgcgaag ccaacaattg    480
cagctcccct gctggtgtcc tggttgacgc catgtcccag aagcaccttc agatcaacca    540
aaggtttgag gagctgcgcc tgatcacaca ggacacggag aacgagctga agaagctgca    600
gcagacccaa gagtacttca tcatccagta ccaggagagc ctgcggatcc aagctcagtt    660
tgcccagctg ggccagctga acccccagga gcgcatgagc agggagacgg ccctccagca    720
gaagcaagtg tccctggaga cctggctgca gcgagaggca cagacactgc agcagtaccg    780
agtggagctg gctgagaagc accagaagac cctgcagctg ctgcggaagc agcagaccat    840
catcctggac gacagctga tccagtggaa gcggagacag cagctggccg ggaacggggg    900
tccccccgag ggcagcctgg acgtgctgca gtcctggtgt gagaagctgg ccgagatcat    960
ctggcagaac cggcagcaga tccgcagggc tgagcacctg tgccagcagc tgcccatccc   1020
```

```
aggcccgtg gaggagatgc tggctgaggt caacgccacc atcacggaca tcatctcagc    1080
tctggtcacc agcacgttca tcatcgagaa gcagcctcct caggtcctga agacccagac    1140
caagtttgcg ccaccgtgc gcctgctggt gggggaaag ctgaatgtgc acatgaaccc    1200
cccgcaggtg aaggcgacca tcatcagcga gcagcaggcc aagtccctgc tcaagaatga    1260
gaacacccgc aatgagtgca gcggcgagat cctgaacaac tgttgcgtca tggagtacca    1320
ccaggccact ggcacgctca gcgcccactt cagaaacatg tcactgaaaa gaatcaagcg    1380
cgccgacagg cgtggtgcag agtcggtgac ggaggagaag ttcacagtcc tgtttgagtc    1440
tcagttcagc gttggcagca acgagctggt gttccaggtg aagaccctgt ccctccctgt    1500
ggtcgttatc gtccatggca gccaggacca caatgctact gccaccgtgc tgtgggacaa    1560
tgcctttgct gagccgggca gggtgccatt tgctgtgcct gacaaggtgc tgtggccgca    1620
gctgtgtgaa gcgctcaaca tgaaattcaa ggctgaagta cagagcaacc ggggcttgac    1680
caaagagaac ctcgtgttcc tggcacagaa actgttcaac atcagcagca accacctcga    1740
ggactacaac agcatgtctg tgtcctggtc ccagttcaac cgggagaact gcccggctg    1800 gaactacacc ttctggcagt ggttcgacgg ggtgatggag gtgctgaaga agcaccataa    1860
gccccattgg aatgatgggg ctatcctggg tttcgtgaac aagcaacagg cccacgacct    1920
gctcatcaac aagccggacg ggaccttcct gctgcgcttc agtgactcgg aaatcggggg    1980
catcaccatt gcttggaagt tgactctcc ggaccgaaac ctctggaatc tgaagccatt    2040
cacgacgcga gatttctcca ttcggtccct ggccgaccgg ctggggggacc tgaactacct    2100 tatctacgtg ttcccagacc gacccaagga cgaggtcttt gccaagtatt acactcctgt    2160
acttggttcg tcaatgcatc cacagatgcc ggagccagcg ccacctacat ggaccaggct    2220
ccttccccag tcgtgtgccc tcaacctcac tacaacatgt acccacccaa ccctgaccct    2280
gtccttgacc aagatggcga gtttgacctg gatgagagca tggatgttgc caggcacgtg    2340
gaagaacttt tacgccggcc catggacagt ctcgacgccc gcctctcccc acctgctggt    2400
ctcttcacct ccgctagaag ctccctgtcc tgaacgctgg actccatgct tctcttggaa    2460
aaccaccttc agtgtgagga gcccacgtca gttgtagtat ctctgttcat accaacaatg    2520
gctttgcacg tttcacaggg ctaccttgcc cacacagttc tgggttttgtg gctaaagcgg    2580 tggtgacctt tttgttcaga cctcaagggc ccccaggggcc tctcgtgtaa gagctgaacc    2640
tatcattgct gacaaaccta tttctccggt gtccttttc tgtccaatgg ccatttcagt    2700
gaaattctag aaaaggcagg gaggcaggtt taggcaacta agttggagtt ttactcctaa    2760
gctagaagct tcgcccagac cggtgtgctc ctgtcctcgc acaggtggaa gattggggtt    2820
catcttagta acccttata cctttgtgta tacatacggg ctgcagactt tgtgattgct    2880
cggtgtgctt aagctgttcc cttcaacaca gcagagggct gccacagccg agtgtcagtt    2940
cttgcgccag ggtggatgga cgtgagattc aagtctaacg gccttgtcca cgttcccacc    3000 atccctttc tccattcgat atcctcaccc ttccagatgg attcatcctt cttgcttttt    3060
tttttttttt tatgttttg ctttgctttt ttgagacaag gtctctccat atatcccaga    3120
ctatccatga atgatcctcc tacctgtttc tagagtgcta ggattacagg catgcatgac    3180
cacacgtggc ctcatccttt cttccttttcc tgtttgcaac cttgcttatt atatcagaaa    3240
ggaggggaat actgggggtc tgggaggagg aaacctgggg cgaaaaacct gtagcacaca    3300
aaacctgtac acactgtctg aaggaagggg gtggggagcg ctcagtctgc tccactctgc    3360
```

-continued

| | |
|---|---|
| tgggcggcaa gacctagaac gggccctgca ctgtcccacc atgggttgtg gtctcagaaa | 3420 |
| tcgcttcagc agctcttccc tggaggctgt gacagagcag ccaggaggag ccgactagga | 3480 |
| gtcctggctt ccaacctctc tgaaggaagc agagggatgc ttttttatatt ttgtacatag | 3540 |
| aactcaacat ttatgtaaac agtgtttttg aataaagttt tgttggttt ggttttttgca | 3600 |
| aatctaaaaa aaaaaaaaaa aaaaaaaa | 3628 |

<210> SEQ ID NO 53
<211> LENGTH: 8044
<212> TYPE: DNA
<213> ORGANISM: Homo sapiens
<220> FEATURE:
<223> OTHER INFORMATION: Human BCL11b (NM_138576.3)

<400> SEQUENCE: 53

| | |
|---|---|
| tgcgctttcc acctaccaga ccctgaaaga aagtgtcagg agccggtgca aacccagtt | 60 |
| taagttcaag aagacatttg caagtgcaag aggccaagca gtttgaagaa gtgtaagaga | 120 |
| tttttttttcc ttcgaaagaa tatatttttta agaaaccag ccagtccgcg aaagcaaca | 180 |
| gcagtttttt tttttttttgc ctctttttct tattttagat cgagaggttt ttcttgcttt | 240 |
| tcttcccttt tttttctttt tgcaaacaaa acaaaaaaca gcatagaaga aagagcaaaa | 300 |
| taaagaagaa gaagaggagg aagagaggga aagagaggaa gggaaaaaaa acaccaaccc | 360 |
| gggcagagga ggaggtgcgg cggcggcggc ggcggcggca gcggcggcag cggcgcggcg | 420 |
| gcggctcgga cccccctcccc cggctccccc catcagtgca gctctccggg cgatgccaga | 480 |
| atagatgccg gggcaatgtc ccgccgcaaa cagggcaacc cgcagcactt gtcccagagg | 540 |
| gagctcatca ccccagaggc tgaccatgtg gaggccgcca tcctcgaaga gacgagggt | 600 |
| ctggagatag aggagccaag tggcctgggg ctgatggtgg gtggccccga ccctgacctg | 660 |
| ctcacctgtg gccagtgtca aatgaacttc ccttggggg acatcctggt ttttatagag | 720 |
| cacaaaagga agcagtgtgg cggcagcttg ggtgcctgct atgacaaggc cctggacaag | 780 |
| gacagcccgc caccctcctc acgctccgag ctcaggaaag tgtccgagcc ggtggagatc | 840 |
| gggatccaag tcaccccga cgaagatgac caccgtgctct caccacgaa aggcatctgt | 900 |
| cccaagcagg agaacattgc agggccgtgc aggcctgccc agctgccagc ggtggccccc | 960 |
| atagctgcct cctcccaccc tcactcatcc gtgatcactt cacctctgcg tgccctgggc | 1020 |
| gctctcccgc cctgcctccc cctgccgtgc tgcagcgcgc gcccggtctc gggtgacggg | 1080 |
| actcagggtg agggtcagac ggaggctccc tttggatgcc agtgtcagtt gtcaggtaaa | 1140 |
| gatgagcctt ccagctacat ttgcacaaca tgcaagcagc ccttcaacag cgcgtggttc | 1200 |
| ctgctgcagc acgcgcagaa cacgcacggc ttccgcatct acctggagcc cgggccggcc | 1260 |
| agcagctcgc tcacgccgcg gctcaccatc ccgccgccgc tcgggccgga ggccgtggcg | 1320 |
| cagtccccgc tcatgaattt cctgggcgac agcaacccct tcaacctgct gcgcatgacg | 1380 |
| ggccccatcc tgcgggacca cccgggcttc ggcgagggcc gctgccgggg cacgccgcct | 1440 |
| ctcttcagtc cccgccgcg ccaccacctg acccgcacc gcctcagtgc cgaggagatg | 1500 |
| gggctcgtcg cccagcaccc cagtgccttc gaccgagtca tgcgcctgaa ccccatggcc | 1560 |
| atcgactcgc ccgccatgga cttctcgcgg cggctccgcg agctggcggg caacagctcc | 1620 |
| acgccgccgc ccgtgtcccc gggccgcggg aaccctatgc accggctcct gaaccccttc | 1680 |
| cagcccagcc ccaagtcccc gttcctgagc acgccgccgc tgccgccat gccccctggc | 1740 |
| ggcacgccgc cccccgcagcc gccagccaag agcaagtcgt gcgagttctg cggcaagacc | 1800 |

```
ttcaagttcc agagcaatct catcgtgcac cggcgcagtc acacgggcga agagccctac   1860
aagtgccagc tgtgcgacca cgcgtgctcg caggccagca agctcaagcg ccacatgaag   1920
acgcacatgc acaaggccgg ctcgctggcc ggccgctccg acgacgggct ctcggccgcc   1980
agctcccccg agcccggcac cagcgagctg gcgggcgagg cctcaaggc ggccgacggt    2040 gacttccgcc accacgagag cgacccgtcg ctgggccacg agccggagga ggaggacgag   2100
gaggaggagg aggaggagga ggagctgcta ctggagaacg agagccggcc cgagtcgagc   2160
ttcagcatgg actcggagct gagccgcaac cgcgagaacg cggtggtgg ggtgcccggg    2220 gtcccgggcg cggggggcgg cgcggccaag gcgctggctg acgagaaggc gctggtgctg   2280
ggcaaggtca tggagaacgt gggcctaggc gcactgccgc agtacggcga gctcctggcc   2340
gacaagcaga agcgcggcgc cttcctgaag cgtgcggcgg gcggcgggga cgcgggcgac   2400
gacgacgacg cgggcggctg cggggacgcg ggcgcgggcg gcgcggtcaa cgggcgcggg   2460
ggcggcttcg cgccaggcac cgagcccttc cccgggctct cccgcgcaa gcccgcgccg    2520 ctgcccagcc ccgggctcaa cagcgccgcc aagcgcatca aggtggagaa ggacctggag   2580
ctgccgcccg ccgcgctcat cccgtccgag aacgtgtact cgcagtggct ggtgggctac   2640
gcggcgtcgc ggcacttcat gaaggacccc ttcctgggct tcacggacgc acgacagtcg   2700
cccttcgcca cgtcgtccga gcactcgtcc gagaacggca gcctgcgctt ctccacgccg   2760
cccggggacc tgctggacgg cggcctctcg gccgcagcg gcacggccag cggaggcagc   2820
accccgcacc tgggcggccc gggccccggg cggcccagct ccaaggaggg ccgccgcagc   2880
gacacgtgcg agtactgcgg caaggtgttc aagaactgca gcaacttgac ggtgcaccgg   2940
cggagccaca ccgcggagcg gccttacaag tgcgagctgt gcaactacgc gtgcgcgcag   3000
agcagcaagc tcacgcgcca catgaagacg cacgggcaga tcggcaagga ggtgtaccgc   3060
tgcgacatct gccagatgcc cttcagcgtc tacagcaccc tggagaaaca catgaaaaag   3120
tggcacggcg agcacttgct gactaacgac gtcaaaatcg agcaggccga gaggagctaa   3180
gcgcgcgggc cccggcgccc cgcacctgta cagtggaacc gttgccaacc gagagaatgc   3240
tgacctgact tgcctccgtg tcaccgccac cccgcacccc gcgtgtcccc ggggcccagg   3300
ggaggcggca ctccaaccta acctgtgtct gcgaagtcct atggaaaccc gagggttgat   3360
taaggcagta caaattgtgg agccttttaa ctgtgcaata atttctgtat ttattgggtt   3420
ttgtaatttt tttggcatgt gcaggtactt tttattatta tttttctgt ttgaattcct    3480 ttaagagatt ttgttgggta tccatccctt ctttgttttt ttttaaccc ggtagtagcc    3540 tgagcaatga ctcgcaagca atgttagagg ggaagcatat cttttaaatt ataatttggg   3600 gggagggggtg gtgctgcttt tttgaaattt aagctaagca tgtgtaattt cttgtgaaga   3660
agccaacact caaatgactt ttaaagttgt ttacttttc attccttcct ttttttgtc     3720 ctgaaataaa aagtggcatg cagtttttt tttaattatt ttttaatttt tttttggtt    3780 tttgttttg gggtgggggg tgtggatgta cagcggataa caatctttca agtcgtagca    3840
ctttgtttca gaactggaat ggagatgtag cactcatgtc gtcccgagtc aagcggcctt   3900
ttctgtgttg atttcggctt tcatattaca taagggaaac cttgagtggt ggtgctgggg   3960
gaggcacccc acagactcag cgccgccaga gatagggttt ttggagggct cctctgggaa   4020
atggcccgac agcattctga ggttgtgcat gaccagcaga tactatcctg ttggtgtgcc   4080
ctggggtgcc atggctgcta ttcgctgtag attaggctac ataaaatggg ctgagggtac   4140
```

```
cttttttgggg agatggggtg gcctgcagtg acacagaaag gaagaaacta gcggtgttct    4200
tttaggcgtt ttctggcttg acggcttctc tctttttta aatcaccccc accacataaa    4260
tctcaaatcc tatgttgcta caaggggtca tccatcattt cccaagcaga cgaatgccct    4320
aattaattga agttagtgtt ctctcattta atgcacactg atgatattgt agggatgggt    4380
ggggtgggga tcttgcaaat ttctattctc ttttactgaa aaagcagggg atgagttcca    4440
tcagaaggtg cccagcgcta cttcccaggt ttttattttt ttttttcctat ctcattaggt    4500 tggaaggtac taaatattga actgttaaga ttagacattt gaattctgtt gacccgcact    4560
ttaaagcttt tgtttgcatt taaattaaat ggcttctaaa caagaaattg cagcatattc    4620
ttctctttgg cccagaggtg ggttaaactg taagggacag ctgagattga gtgtcagtat    4680
tgctaagcgt ggcattcaca atactggcac tataaagaac aaaataaaat aataatttat    4740
aggacagttt ttctactgcc attcaatttg atgtgagtgc cttgaaaact gatcttccta    4800
tttgagtctc ttgagacaaa tgcaaaactt tttttttgaa atgaaaagac ttttaaaaa    4860 agtaaaacaa gaaaagtaca ttctttagaa actaacaaag ccacatttac tttaagtaaa    4920
aaaaaaaaaa attctggttg aagatagagg atatgaaatg ccataagacc caatcaaatg    4980
aagaaataaa cccagcacaa ccttggacat ccattagctg aattatcctc agccccttt    5040 gttttttggga caacgctgct tagatatgga gtggaggtga tttactgctg aattaaaact    5100 caagtgcacac aagttacaag ttgatatcgt tgaatgaaaa gcaaacaaa aacaattcag    5160 gaacaacggc taattttttc taaagttaaa tttagtgcac tctgtcttaa aaatacgttt    5220
acagtattgg gtacatacaa gggtaaaaaa aaaattgtgt gtatgtgtgt tggagcgatc    5280 ttttttttc aaagtttgct taataggtta tacaaaaatg ccacagtggc cgcgtgtata    5340
ttgttttctt ttggtgacgg ggttttagta tatattatat atattaaaat ttcttgatta    5400
ctgtaaaagt ggaccagtat ttgtaataat cgagaatgcc tgggcatttt acaaaacaag    5460
aaaaaaaata ccctttttctt ttccttgaaa atgttgcagt aaaatttaaa tggtgggtct    5520
ataaatttgt tcttgttaca gtaactgtaa agtcggagtt ttagtaaatt ttttctgcc    5580 ttgggtgttg aatttttatt tcaaaaaaaa tgtatagaaa cttgtatttg gggattcaaa    5640
ggggattgct acaccatgta gaaaagtat gtagaaaaaa agtgcttaat attgttattg    5700
ctttgcagaa aaaaaaaaa tcacatttct gacctgtact tattttctc ttcccgcctc    5760 cctctggaat ggatatattg gttggttcat atgatgtagg cacttgctgt attttactg    5820 gagctcgtaa tttttaact gtaagcttgt ccttttaaag ggatttaatg tacctttttg    5880
ttagtgaatt tggaaataaa aagaaaaaaa aaacaaaaac aaacaggctg ccataatata    5940
tttttttaat ttggcaggat aaaatattgc aaaaaaaaca catttgtatg ttaagtccta    6000
ttgtacagga gaaaaagggt tgtttgacaa cctttgagaa aaagaaacaa aaggaagtag    6060
ttaaatgctt tggttcacaa atcatttagt tgtatatatt ttttgtcgga attggcctac    6120
acagagaacc gttcgtgttg ggcttctctc tgaacgcccc gaaccttgca tcaaggctcc    6180
ttggtgtggc cacagcagac cagatgggaa attatttgtg ttgagtggaa aaaaatcagt    6240
ttttgtaaag atgtcagtaa cattccacat cgtcctccct ttctctaaga ggccatctct    6300
aagatgtcag atgtagagga gagagagcga gagaacatct tccttctcta ccatcactcc    6360
tgtggcggtc accaccacca cctctcccgc ccttaccagc agaaagcaat gcaaactgag    6420
ctgctttagt ccttgagaaa ttgtgaaaca aacacaaata tcataaaagg agctggtgat    6480
tcagctgggt ccaggtgaag tgacctgctg ttgagaccgg tacaaattgg atttcaggaa    6540
```

```
ggagactcca tcacagccag gacctttcgt gccatggaga gtgttggcct cttgtctttc    6600
ttccctgctt tgctgctttg ctctctgaaa cctacattcc gtcagtttcc gaatgcgagg    6660
gcctgggatg aatttggtgc ctttccatat ctcgttctct ctccttcccc tgcgtttcct    6720
ctccatcctt catcctccat tggtcctttt tttttctttc attttttatt taatttcttt    6780
tcttcctgtc tgttcctccc ctaatcctct attttatttt tattttttgt aaagccaagt    6840
agctttaaga taaagtggtg gtcttttgga tgagggaata atgcatttt aaataaaata    6900 ccaatatcag gaagccattt tttatttcag gaaatgtaag aaaccattat ttcaggttat    6960
gaaagtataa ccaagcatcc ttttgggcaa ttccttacca aatgcagaag cttttctgtt    7020
cgatgcactc tttcctcctt gccacttacc tttgcaaagt taaaaaaaag ggggaggga    7080 atgggagaga aagctgagat ttcagtttcc tactgcagtt tcctacctgc agatccaggg    7140
gctgctgttg cctttggatg ccccactgag gtcctagagt gcctccaggg tggtcttcct    7200
gtagtcataa cagctagcca gtgctcacca gcttaccaga ttgccaggac taagccatcc    7260
caaagcacaa gcattgtgtg tctctgtgac tgcagagaag agagaatttt gcttctgttt    7320
tgtgtttaaa aaaccaacac ggaagcagat gatcccgaga gagaggcctc tagcatgggt    7380
gacccagccg acctcaggcc ggtttccgca ctgccacaac tttgttcaaa gttgccccca    7440
attggaacct gccacttggc attagagggt cttcatggg gagagaagga gactgaatta    7500
ctctaagcaa aatgtgaaaa gtaaggaaat cagcctttca tcccggtcct aagtaaccgt    7560
cagccgaagg tctcgtggaa cacaggcaaa cccgtgattt tggtgctcct tgtaactcag    7620
ccctgcaaag caaagtccca ttgatttaag ttgtttgcat ttgtactggc aaggcaaaat    7680 attttatta cctttctat tacttattgt atgagctttt gttgtttact tggaggtttt    7740
gtcttttact acaagtttgg aactattat tattgcttgg tatttgtgct ctgtttaaga    7800
aacaggcact tttttttatt atggataaaa tgttgagatg acaggaggtc atttcaatat    7860
ggcttagtaa aatatttatt gttcctttat tctctgtaca agattttggg cctcttttt    7920 tccttaatgt cacaatgttg agttcagcat gtgtctgcca tttcatttgt acgcttgttc    7980
aaaaccaagt ttgttctggt ttcaagttat aaaaataaat tggacattta acttgatctc    8040
caaa    8044
```

<210> SEQ ID NO 54
<211> LENGTH: 7922
<212> TYPE: DNA
<213> ORGANISM: Mus <mouse, genus>
<220> FEATURE:
<223> OTHER INFORMATION: Mouse Bcl11b (NM_001079883.1)

<400> SEQUENCE: 54

```
aatttatttt agccttttct ctatttaga gcaagccatc ttcctggctt tttcttcttt       60 cttttgcaa aaacaaaaac aaaaacacag cccagaagaa agagcaaaat aaagacgaag      120
aagaagaaga ggaggaggaa gaggaagaga ggaagggcag aggcaccaac ccgggcggag    180
gaggaggcgc ggcggcggcg gcggctcaga ccccctcccc ggcccgcatc tgtgcagctt    240
tccgggcgat gccagaatag atgccggggc aatgtcccgc cgcaaacagg gcaacccgca    300
gcacttgtcc cagagggaac tcatcacgcc agaggctgac catgtggagg ctaccatcct    360
cgaggaagac gagggtctgg agatagagga gcctagcagc ctggggctga tggtgggagg    420
ccccgaccct gatctactca cctgtggcca gtgtcagatg aacttcccgc tgggggacat    480
```

-continued

```
cctggttttt atagagcaca agaagaaaca gtgtggaggc ctgggcccct gctacgacaa      540
ggtcctggac aagagcagtc cacctccctc ctctcgctct gagctcagga gagtatctga      600
gccagtggag atcgggatcc aggtcacccc tgatgaagat gaccacctac tgtcacccac      660
gaaaggcatc tgtcccaagc aggagaacat tgcaggccg tgcaggcctg cccagctgcc       720
atcgatggcc cccatagctg cctcctcttc ccaccctccc acctccgtga ttacttcacc      780
tctgcgtgcc ctgggcgttc tcccaccctg tttcccgctg ccttgctgtg gtgcacgccc      840
catctcgggc gacgggactc agggtgaggg tcagatggag gctccctttg gatgccagtg      900
tgagttgtca ggtaaagatg agccttccag ctacatttgc acaacatgca agcagccctt      960
caacagcgcc tggttcctgc tgcagcacgc acagaacaca catggcttcc gaatctacct     1020
ggagcctggg ccggccagca cctcgctcac gcccaggctc accatcccgc caccgctcgg     1080
gccggagacc gtggcgcagt ccccactcat gaatttcctg ggggacagca atcctttcaa     1140
cctgctgcgc atgacgggcc ccatcctgcg ggaccaccct ggcttcggtg agggccgctt     1200
gccaggtacg ccaccgctct tcagcccacc gccacgccat cacttggacc cacaccgcct     1260
cagtgcagag gagatggggc tcgtggccca gcacccagt gccttcgacc gagtcatgcg      1320
cctgaacccc atggccatag actctcctgc catggacttc tcccggcggc tgcgagaact     1380
ggccggcaac agctccacgc cgccgcccgt gtccccaggc cgtggcaacc ctatgcaccg     1440
gctgctgaac cctttccagc ccagtcccaa gtccccgttc ctcagcacgc caccgctgcc     1500
acccatgcct gcgggcacac cgccaccgca gccgcctgcc aagagcaagt cctgtgagtt     1560
ctgcggcaag accttcaagt tccagagcaa tctcatcgtg caccggcgca gccacacggg     1620
cgagaagccc tacaagtgcc agctgtgcga ccatgcgtgc tcgcaggcga gcaagctcaa     1680
gcgccacatg aagacgcaca tgcacaaggc gggctctctg gctggccgct cagacgacgg     1740
gctctcagct gccagctccc ctgagccggg caccagcgag ctgccaggtg acctgaaagc     1800
ggccgatggc gacttccgcc accatgagag cgacccatct ctgggccccg agcctgagga     1860
cgacgaggac gaggaggagg aagaagagga gctgctgctg gagaacgaga gccggcctga     1920
gtcgagcttc agcatggact cggagctggg ccgtggccgc gagaacggag gtggcgtgcc     1980
accgggggtg gcgggcgcag gggctgcagc tgcggctctg gcggatgaga aggctctggc     2040
cctgggcaag gtgatggagg acgcagggct gggcgcactg ccgcagtatg gggagaagcg     2100
gggcgccttc ctgaagcgtg caggcgacac gggtgatgcc ggagctgttg gctgtgggga     2160
cgcgggtgca ccgggtgcag tgaacggcg cggcggggcc ttcgcgccag cgcagagcc       2220 ctttccagct ctcttcccac gcaagccagc accgctgccc agccctgggc tcggtggtcc     2280
cgcgctgcac gcggccaagc gcatcaaggt ggagaaagac ctggagctgc acctgccgc      2340 cctcatccca tctgagaacg tgtactcgca gtggctcgtg ggctacgcag catcgcgcca     2400
cttcatgaag gacccattcc tgggcttcac ggatgcgcgc cagtcgcctt tcgccacatc     2460
gtcggaacat tcctctgaga acggcagcct gcgcttctca acgccacccg ggacctgct      2520 ggacggcggg ctgtccgggc gcagtggcac ggcgagcggg gcagcacac ctcacctggg      2580 tggtccgggt cctgggaggc cgagctccaa ggagggccgc cgcagcgaca catgtgagta     2640
ctgcggcaag gtcttcaaga actgtagcaa cctgacggtg caccggagga gccacaccgg     2700
cgagcggcct acaagtgcg agctgtgcaa ctacgcgtgc gcgcagagca gcaagctcac      2760
gcgccacatg aagacgcacg gcagatcgg caaggaggtg taccgctgcg acatctgcca      2820 gatgccttc agcgtctaca gcaccctgga gaaacacatg aaaaagtggc acggtgaaca     2880
```

```
cttgctgact aatgatgtca aaatcgagca ggctgagagg agctaagcgc atacgtgggg   2940
gacactgcgt gcgtgcgtct gtacagcgtg accatcgcca accttcgcca acgggaccgg   3000
tgaccggact ggcctctgca tccccggggc ccagggaggc ggcagtccag cctaacctgt   3060
gtctgcgaag tcctatggaa acctgagggt tgattaaggc agtaaaaaat taaaaaaaaa   3120
aaaacaaaaa aacaaaaaaa tttgtggagc cttttaactg tgcaataatt tctgtattta   3180
ttgggttttg taattttttt ggcatgtacg tgcaggtacc tattattatt attatttctg   3240
tttaaattcc tttaaaagat tttgttgagt atccatccct tcattttttt ttttaataac   3300
ccagtagtag tctgagcaat gactcgcaag tgacgtagag ggaagctatc ttttaaatta   3360
taattttgtg tgtgtgtgtg gggggtgct gcttttttga aatttaagct aagcatgtgt    3420
aatttcttgt caagaagcca acacttaaat gacttttaaa gttgtttgcg ttttcatcat   3480
ttactttgtc ctgaaatgaa aagtggcatg tgggattttt ttccgggggg gagggtggc    3540 tttcaaaacc atttttttt tccgggaggt ggatgtacag cggattacaa tctttaaaat    3600
tgtagcactt tgtcttagca tcgcattgga gagttagcac tgatgtcctc ctgagccaca   3660
gaggcgtctc tgtgtggaat tcaactttca tgctatggaa ggaaaatgtt gagggggcg    3720 tggcaaacga gcctctcccc cacttgggac cccgagaatc ttttccaggg tgactctagg   3780
aacagccccc acatcctgca attgtgtgtt accaggagat atgataatgt ccttttctgg   3840
gggagcttgg cgtattggga agccgcctct gcccttgct gtagatttgg ctgcataaaa    3900
tgggccgagg atacccactg ggtagacagc tgtggcctgt agtggcggga aagaagagac   3960
taacaatgtt ctctcaggct tctcctggca agatggcttc tcttttcagc ccccagccta   4020
cagataaatc ccaggtgtcc attgctacag tggtaacttg actgtgtccc aagcagacaa   4080
ctggccctga tggtgaactg gagaagttag ctgcggggtc gctcatctca cgctgatggg   4140
cactgtaggg caaaggaatc tcacccgttc tctcttcccg gaggagctgg taagagttct   4200
gtccaaggtg ccccacgctg cttccgtttc tgtgttttgt cttttccttc ctccaattaa   4260
gttgggacat actatacatt ggacttgttg ggatttgatg tttgaattct gttgacccgc   4320
actttaaagc ttttgtttgc atttaaatta aatggcttct aaacaagaaa ttgcagcata   4380
ttcttgtctt tggcccagag gtgggttaaa ctgtaaggga cagctgagat tgagtgtcag   4440
tgttgctaag cgtggcattc acaatactgg cactataaag aacaaaatta aataatttat   4500
tggacagttt ctctactgcc attcaatttg atgtgcgtgc cttgaaaacc gatcttccta   4560
tttgagtctc ttgagacaaa tgcaaaactc tcttttttt ttgagatgaa aaaaaaaaa    4620 gacttttttaa aaagcaaaca agagaagtac attctttaga aacaaagcca catttacttt   4680
aaattaaaaa aaaaatcct ggttgaagag agaggacggg aaaatgccat aagaccagtc    4740
aaatgaagaa ataaacccag cacagccctg gacatctatt agcagaatcg ttttcagacc   4800
cccctccccc ttttttgggg caacgctgct agatatggag tggaggtgac ttactgctga   4860
attaaaactc acgtgacaca agccgatatt gttgaatgaa aaacaaaca acaacaacaa    4920 caacaaaaaa caattcagga acaatggctg atttttttt tcctcctaaa tttaaattta    4980
gtgcactctg tcttaaaaat acgtttacag tattggatac atacaagggt aaaataaatc   5040
gtgtgtatgt gtgttggagc gatctttta ttttattta ttttcaaagt ctgcttaata     5100
ggttatacag aatgccacaa tggctaggtg tatattgttc tcttttggtg atgggtttt    5160 agtatacatt atatatattg aaatttcttg attactgtca aagtggacca gtatttgtaa   5220
```

```
taattgagac tgcctgggca ttttacaaaa tgagaagaaa aaaagtcct ttttctttc      5280
cttgaaaccg ttacagtaag ttttaaatgg tgggtctata aaatctgctc tgtcacagca      5340
acctgtaaag tcggagtttt agtaaatttt tttctgcctt gggtgttgaa ttttatttt      5400
gaaaacaaaa tgtatagaaa cttgtatttg gggtttaaag ggggattgct gcaatgtgta      5460
gaaaagtat gtagagaaag tgcttaatat tgttactgct ttgcagaaga agaaaaaaaa      5520
aatcacactt ctgacctgtg cgtattttc tctcccacct ccctctggaa tggatctatt      5580
ggtcggttca tatgatgtag gctctcgctg tatttttaac tggagcttgt aattttttaa      5640
ctgtaagctt gtcctttaa agggatttaa atgtaccttt ttgttagtga atttggaaat      5700
aaaagagaa aaaaaaaca aaacaaaca ggctgccata atatatttt ttaatttggc      5760
aggataaaat attacaaaaa aaaatcccc cacaaacaa caaacaaaca aaatcccac      5820
ccacatttgt atgttaagtc ctcttgtatg gggtggggg agggttgttt gacaaccttc      5880
aagagaaaa gacacagaaa gagacatgct ttgattcaca agtcatttta gttgtatata      5940
gtctgtcaga attggcctac tcaaaaagaa ctgttggctt gggctttca ttcgaatgcc      6000
ccaactttgc atctggcctc cttggtgagg ccacagccga cttgatggca agtccttact      6060
tgtgttgagt ggagaaaaga aagcccttcc tccaagaggc agtctataag atggtagcgc      6120
ggtgagagag caagggaggt taccttctcc gctgtggcta ctgcggccac cccctccacc      6180
ccctggccac gctcaggagc agagagaatc gacagctgct tttgtccttg agcaaacctg      6240
gatggagcag cgaagcttct gagaggagca gctgggccca ggggagcctc tgccactgag      6300
actggtgcag gcgggacaga ggagagcctt gcacgcaggt cctgttccct tggaatgtct      6360
gctccatttt cccctctgt ctctctgctt ttctctgcaa ttccatccgt ttcagaccag      6420
tgaggcctgg aatgaaggaa ttctgtgcct tcccatctat gttccctccg tcctcccag      6480
gctctgccta ctctttgtgg actcctcttt aatttttcttc ctcctttgcc ccctctcccc      6540
aaaccctctt ttctcttcct ttcttctctc cttcttttct tcctcctcct cctcttttct      6600
cctcctcctc ctcctcctcc tcctcctcct cctcctcctc ttcttcttct tcttcttctt      6660
cttcttcttt ttcttcttct cctcctcctt cttcttcttt tttttttttt tgtaaagcca      6720
agtagcttta agataataaa atggttgttt attggatgag ggaataatga tacactccac      6780
aaatacctat atcaggaagc cattttttt taatttcagg aaatgtaaga aaccatcatt      6840
tcaggttatg aaagcgtgat tgtgcatctt tccaggcaga tctttactaa atgcagagtc      6900
tgtctcactg tttcccatt gacacagtta aaagatgggg gcctagtggg aggcaggcc      6960
taagtctcag tgtcctgcat gcctgcccta cggcccaggg ttaccctgcc cttttgacac      7020
cctgcctctc tgctacctgg gagcctctgt gtggttctcc tgtgctcata aaagctagcc      7080
agtgctcacc agctcaccta tcaccagaat gccaggacta agccatccta aagcacaagg      7140
acttgtgtgt ctctgtcaac tgcagagaga agaggattt tgcttctctt atcaaagaga      7200
aaaatcaacc aaccaaccta cccgaagcag gtgacccagc ctaagggctc taccgcgggt      7260
gacccagccg acctcaggtc gggttccaca ctgccacaac tttacccaaa gttgctccct      7320
attggaacct gccacttgcc attggagggt catggggggg tgggggagag ggagactgga      7380
ttactcgaag caaaatgtga accctgaagc gaacacagcc ttccacctgg ccctcccgt      7440
ccgaggtttg attccgtgat tttggtgctt tctgtgtctg ccctgcatag ccaaggcaca      7500
ttgatctctg cggtttgctt ttgtactggc aaggcggaat attttattta cctttctat      7560
tacgtatcgt atgagctttt gttgttttgcc tagagggtt gtctcttaca gcaagttgg      7620
```

| | | |
|---|---|---|
| agctatttat tattgcttgg tatttgtgct ctgcttttaa gaatgggcac ttggttttat | 7680 | |
| ttttgtttgt ttgttttttt gttgttttt aattatggat aaaatgttga gatgacaaaa | 7740 | |
| ggtcatttca atatggctta gtaaaaatat ttattgtttc ttctctgtac aagattttgg | 7800 | |
| gcctcttttt tccccttaa tgtcacaatg ttgagttcag catgtgtctg ccatttcatt | 7860 | |
| tgttcaaaac caagtttgtt ctggtttcaa gttatgaaaa taaattggga catttaactt | 7920 | |
| ga | 7922 | |

<210> SEQ ID NO 55
<211> LENGTH: 7530
<212> TYPE: DNA
<213> ORGANISM: Homo sapiens
<220> FEATURE:
<223> OTHER INFORMATION: Human NFATC2 (or NFAT1) (NM_012340.4)

<400> SEQUENCE: 55

| | |
|---|---|
| agcaggaagc tcgcgccgcc gtcgcgccg ccgctcagct tccccgggcg cgtccaggac | 60 |
| ccgctgcgcc aggcgcgccg tccccggacc cggcgtgcgt ccctacgagg aaagggaccc | 120 |
| cgccgctcga gccgcctccg ccagccccac tgcgaggggt cccagagcca gccgcgcccg | 180 |
| ccctcgcccc cggccccgca gccttcccgc cctgcgcgcc atgaacgccc ccgagcggca | 240 |
| gccccaaccc gacggcgggg acgcccagg ccacgagcct gggggcagcc ccaagacga | 300 |
| gcttgacttc tccatcctct tcgactatga gtatttgaat ccgaacgaag aagagccgaa | 360 |
| tgcacataag gtcgccagcc caccctccgg acccgcatac cccgatgatg tcctggacta | 420 |
| tggcctcaag ccatacagcc cccttgctag tctctctggc gagccccccg ccgattcgg | 480 |
| agagccggat agggtagggc cgcagaagtt tctgagcgcg gccaagccag cagggggcctc | 540 |
| gggcctgagc cctcggatcg agatcactcc gtcccacgaa ctgatccagg cagtgggggcc | 600 |
| cctccgcatg agagacgcgg gcctcctggt ggagcagccg ccctggccg gggtggccgc | 660 |
| cagcccgagg ttcaccctgc ccgtgcccgg cttcgagggc taccgcgagc cgctttgctt | 720 |
| gagccccgct agcagcggct cctctgccag cttcatttct gacaccttct cccctacac | 780 |
| ctcgccctgc gtctcgccca ataacggcgg gcccgacgac ctgtgtccgc agtttcaaaa | 840 |
| catccctgct cattattccc ccagaacctc gccataatg tcacctcgaa ccagcctcgc | 900 |
| cgaggacagc tgcctgggcc gccactcgcc cgtgccccgt ccggcctccc gctcctcatc | 960 |
| gcctggtgcc aagcggaggc attcgtgcgc cgaggccttg gttgccctgc gcccggagc | 1020 |
| ctcacccag cgctcccgga gccctcgcc gcagccctca tctcacgtgg caccccagga | 1080 |
| ccacggctcc ccggctgggt acccccctgt ggctggctct gccgtgatca tggatgccct | 1140 |
| gaacagcctc gccacggact cgccttgtgg gatccccccc aagatgtgga agaccagccc | 1200 |
| tgaccctcg ccggtgtctg ccgccccatc caaggccggc ctgcctcgcc acatctaccc | 1260 |
| ggccgtggag ttcctgggc cctgcgcagca gggcgagagg agaaactcgg ctccagaatc | 1320 |
| catcctgctg gttccgccca cttggcccaa gccgctggtg cctgccattc ccatctgcag | 1380 |
| catcccagtg actgcatccc tccctccact tgagtggccg ctgtccagtc agtcaggctc | 1440 |
| ttacgagctg cggatcgagg tgcagcccaa gccacatcac cgggcccact atgagacaga | 1500 |
| aggcagccga ggggctgtca agctccaac tggaggccac cctgtggttc agctccatgg | 1560 |
| ctacatggaa aacaagcctc tgggacttca gatcttcatt gggacagctg atgagcggat | 1620 |
| ccttaagccg cacgccttct accaggtgca ccgaatcacg gggaaaactg tcaccaccac | 1680 |

| | |
|---|---|
| cagctatgag aagatagtgg gcaacaccaa agtcctggag ataccctggg agcccaaaaa | 1740 |
| caacatgagg gcaaccatcg actgtgcggg gatcttgaag cttagaaacg ccgacattga | 1800 |
| gctgcggaaa ggcgagacgg acattggaag aaagaacacg cgggtgagac tggttttccg | 1860 |
| agttcacatc ccagagtcca gtggcagaat cgtctcttta cagactgcat ctaaccccat | 1920 |
| cgagtgctcc cagcgatctg ctcacgagct gcccatggtt gaaagacaag acacagacag | 1980 |
| ctgcctggtc tatggcggcc agcaaatgat cctcacgggg cagaacttta catccgagtc | 2040 |
| caaagttgtg tttactgaga agaccacaga tggacagcaa atttgggaga tggaagccac | 2100 |
| ggtggataag gacaagagcc agcccaacat gcttttttgtt gagatccctg aatatcggaa | 2160 |
| caagcatatc cgcacacctg taaaagtgaa cttctacgtc atcaatggga agagaaaacg | 2220 |
| aagtcagcct cagcactttta cctaccaccc agtcccagcc atcaagacgg agcccacgga | 2280 |
| tgaatatgac cccactctga tctgcagccc cacccatgga ggcctgggga gccagcctta | 2340 |
| ctaccccag cacccgatgg tggccgagtc cccctcctgc ctcgtggcca ccatggctcc | 2400 |
| ctgccagcag ttccgcacgg ggctctcatc ccctgacgcc cgctaccagc aacagaaccc | 2460 |
| agcggccgta ctctaccagc ggagcaagag cctgagcccc agcctgctgg gctatcagca | 2520 |
| gccggccctc atggccgccc cgctgtccct tgcggacgct caccgctctg tgctggtgca | 2580 |
| cgccggctcc cagggccaga gctcagcccct gctccacccc tctccgacca accagcaggc | 2640 |
| ctcgcctgtg atccactact cacccaccaa ccagcagctg cgctgcggaa gccaccagga | 2700 |
| gttccagcac atcatgtact gcgagaattt cgcaccaggc accaccagac ctggcccgcc | 2760 |
| cccggtcagt caaggtcaga ggctgagccc gggttcctac cccacagtca ttcagcagca | 2820 |
| gaatgccacg agccaaagag ccgccaaaaa cggaccccccg gtcagtgacc aaaaggaagt | 2880 |
| attacctgcg ggggtgacca ttaaacagga gcagaacttg gaccagacct acttggatga | 2940 |
| tgagctgata gacacacacc ttagctggat acaaaacata ttatgaaaca gaatgactgt | 3000 |
| gatctttgat ccgagaaatc aaagttaaag ttaatgaaat tatcaggaag gagttttcag | 3060 |
| gacctcctgc cagaaatcag acgtaaaaga agccattata gcaagacacc ttctgtatct | 3120 |
| gacccctcgg agccctccac agcccctcac cttctgtctc cttcatgtt catctcccag | 3180 |
| cccggagtcc acacgcggat caatgtatgg gcactaagcg gactctcact taaggagctc | 3240 |
| gccacctccc tctaaacacc agagagaact cttcttttcg gtttatgttt taaatcccag | 3300 |
| agagcatcct ggttgatctt aatggtgttc cgtccaaata gtaagcacct gctgaccaaa | 3360 |
| agcacattct acatgagaca ggacactgga actctcctga aacagagtg actggagctt | 3420 |
| gggggggatgg acgggggaca aagatgtggg cactgtgat taaaccccag cccttgcgtt | 3480 |
| cgttttttcca ggtcacagat acagctcctg tacctttttga aggcaaggag ttctcagagc | 3540 |
| aaccaaagga acgtgaccca agagcccagc ttacaggctg aagaaaccca aaccctcga | 3600 |
| tagagacaga aactgaactg tcagtcctta gagctcgccc agtccatgcc acaactgggc | 3660 |
| cacagctaaa gctttatttt tgaattctca ttccaaaacc aaactgtctt gcccagacaa | 3720 |
| gatcacctgt taagacttct tggcgttaag ttatgacatg tatacgcgtt tgttattatt | 3780 |
| attttttctg ctttaaaagg ctgaccaggg cacctagccc tggagctgtc ttggcgagct | 3840 |
| gttctttaac ccctgcagca cgcagtcctg ctaacacaat ttccatagac ttgggggct | 3900 |
| gacccaggct gcagagagca agcacctgtc tgctgcagct gtacaacctg atgctttgc | 3960 |
| aaggttccgc cttgctttct tcctagcagc cagagtgctt ttccgtaaag cggtggaaa | 4020 |
| tctcaagcat gtgcatttaa ttgaggaata gcagaagggc taaagcaacc aagaaaagaa | 4080 |

```
gtgtgggtat ttttgttaag taaaacagcc caagtgcttc tggaggtggg tttctaccaa    4140
gatagaggaa aagggctgaa ttccctctaa gtgggacagc cgagctcagg atgtgcttcc    4200
cagcttcact ggttaatttg acctgaacct atttaaagat cccttctgcc cctgaagacc    4260
tatccgcact caaattctaa catgaagaaa tctactcgaa tgcatccttt actttgaatg    4320
agctctattc ggttgcatgt tatatgtgat ttccttcctc ccaactgttt ccactgagcg    4380
cacccagtct cccctagtct tcctctgtgg gtgtgatttt tgtgatttt acaaacaaaa     4440 cccttgaagt tcttggcaga tgtgtttgtt tctgtttgca tgtactgcag ataccccagg    4500
acaagcgggg gattcatttt tcagccattc agttgtttcc tcaataatcc gcagcaaagt    4560
gaaaatattc ttagcactca gactgtactt agagtgtttt ctcagtccag tctgtacagt    4620
ctgtaggcag aaggcctcag aagaaagtca tggccactca gtgccactg tgggctttgt     4680 aagtcctggc tctcccgtca aggttaccca gaggtaaaag cttcctggga gtggggccag    4740
gtgtgtttgg cactccagat agaaggcaaa atgctcagat tcgggcctgt gcacttgtat    4800
gcaacctgtc ggtcgatacc tagcatttat ttttccctga caatgaacga cctttccctc    4860
acccacccta agctcaaaga gtttagcaaa attctctttt aaataaacag aatgccagta    4920
agaggttgac ccctaccatg gaacttctgg gatgctaaat acttcctcat gaacaaaata    4980
agttccttat tataagttcc ttatactagc agcttcacct aaagaatttt ctctccagca    5040
atattgactt cactggggaa aagccaagag tgtgtggtga gtgatttgtt ctcactcgac    5100
ctggctagga ctggctagga gctgtttttt gtacatgagg gaatttgggc tttcctcagt    5160
tatctgaatg ttttacccaa gtgccttcct gctattgtag caaagtagct cagcttcctt    5220
gtccacaggg tgaaaaagga ctaatgcatt ttccatcagt tttctaacta tgttagcaaa    5280
aacggcctcc tggtagctca acctcctgta cgcgtgtgtg tgtgtaatac acacacaaat    5340
aaacccctct gttttctaa gacatcttag ctggatatta taggaagcac tttcataaac      5400
aactgtaaca aatcgcaaag gaaagagaaa caaaagcatt agatttgaga cataaacagg    5460
caagagaaag tgtattagga actgacagct atcaaggaag ttttgtcagt tacaaatgct    5520
aggaggaaat tttgccaaga aggatggctc atgaaatatt tccagtacgg gaagaggcaa    5580
taagatcctc taagagaatg agaaagtagg ggtgtctaaa tggtaaagat gggtgtgttg    5640
cacgtgtgtt agaaggatct cagttgagtg aaggtttgca ctgctacatc taagttaatg    5700
taaatatgta gcactctgac aggtctaccg tgttgctgaa tgtagtatat ttccaaagtt    5760
tgcaagtctt cctgtattgt acaaagatgc tgctgcttga taatatgtat agcaatccag    5820
attagtatgt tattaaattt tattttctta cctgtatttt tatgcttttt acctgtcctc    5880
aaaatattac accctgttg gaattagatt tatatttata aatggtcaga atctttta       5940 agtgtctctt tttacacata ggttgatttt ttttcttaa gagaaatgat gtattcttga     6000
aacatttgtt actcattcca ggaaacaaaa acccatataa taaacccccc actcagagcc    6060
tgttagtcac ctctctagaa gatggcatct caggagaagg aatggctttg tggaagaagg    6120
aatcaccttt ttcttgctca agaattatgc tgacttcagc cctgagcctg gatctggtca    6180
ctgagaatca tcaagtgtct agatcctccc cccaaaataa ctaatttagt aggtgatttt    6240
gattttaaaa aattgacacc aaaaccctgc ctgcattgta atggaattcg aaaagaattc    6300
atgttcacag aactcaacgt tcaggctaat atttacagaa gggaccaaat ctaaatcctg    6360
gtagataact cctgtatgct ttatccaaag gacacccaca gttttccagc atagatataa    6420
```

```
ccaaggatga attgattcct tcaaagaact gggaggcacg gatattgcat tttttgttta    6480
catccagtag ccaagacgcc tcagtgagcc agtcttgggc agaggctgtc acatttaggc    6540
agattggaag ttggtatgtt ctaattctca ctctggacta cagtgaggct gaatttatca    6600
tgtcaaaaaa aaaaaaaaaa aaagaccttt ccaagtgctt tctattgctc agaattgaaa    6660
gaatgttttc atttcaagtt tacaagaggc atggatggag ttgtgacgtt cttgacaagc    6720
tgggctaacc tttcccgaac ttgtttcccg gaggcaaggt gctcggtgac ccagcgcatc    6780
ttaaccttgg gtctcctagg ctcgaggcta gggcattacg tttcgtggaa ccaaagcagc    6840
caattgcata gcaagtattt tcctgcattc caattaaatg cttaagaaaa agcagcatcc    6900
tataaaattg tgatcataaa catccatttc cctcagcttt tgtgagtgcc ttgacttaca    6960
gccaacatca ctgtttaact cagtctgttt aaaaacaaac ttttctggtg gttgataaca    7020
gagagttgct ccctgagcca tcagggtcct gggagctgga agtgaaaggg ttattaacat    7080
tctacctta tgcagctgtt ggctgaccag aataaactcc ctgctgagtt caagctttga    7140
atggaatgga tgcaaatgat gttgtttcca ttagagcagg tgctcacagc attctgattg    7200
gcctgagcag accgaggcta tggctgttgg gacaagctta gcatcctgga catcttgtca    7260
aagaacctca ctcacccctc tggcctctac agccctcaga ggagagaaaa ccaattctcc    7320
aacaaacagg tctctccaac atggtggtgc tggcaggctt aggtttagaa aatcctgact    7380
gttaaaggcg tttgaataca tcacattcct atgcaaatgt ttttaatctc cagtttaatg    7440
tagtttattt ttcctatatg taaagtattt ttatacggct tgtatcatga tagtttagca    7500
ataaaacagt tggaagcaac atctaaaaaa                                     7530
```

<210> SEQ ID NO 56
<211> LENGTH: 6759
<212> TYPE: DNA
<213> ORGANISM: Mus <mouse, genus>
<220> FEATURE:
<223> OTHER INFORMATION: Mouse Nfatc2 (or Nfat1) (NM_010899.3)

<400> SEQUENCE: 56

```
aggctgcaac aggtgccttg agcaggaagc tcgcgccgcc accgctcccc cggacgcgtc      60
caggacccac tgcgccgtga gccatcctcg gcctcaccgt gcgccacaga tacggtgacc     120
cctgctctgc gccccgcgac tctatacgaa cccgcatccc gaacgccccg agccatggac     180
gtcccggagc cgcagcccga ccccgatggc ggggacggcc ccggccacga gcccgggggc     240
agtccccaag acgagctgga cttttccatc ctcttcgatt atgactatct gaacccctatc     300
gaagaagaac cgatcgcaca taaggccatc agctcacccct ccggactcgc atacccggat     360
gatgtcctgg actatggcct caagccatgc aaccccttg ccagtctctc tggcgagccc     420
cctggccggt tcggagagcc ggatagtata gggttccaga actttctgag cccggtcaag     480
ccagcagggg cttcgggccc gagccctcgg atcgagatca ctccatccca cgaactgatg     540
caggcagggg gggcccctcg tgggagagac gccggcctgt cccccgagca gccggccctg     600
gccctggccg gcgtggccgc cagcccgagg ttcacactgc ccgtgccgg ctacgagggc     660
taccgcgagc gctttgctt gagccccgct agcagcggcc cctctgccag cttcatttct     720
gacaccttct cccctacac ctcgccctgc gtctcaccca taacgccgg gccgacgac       780
ctgtgtcccc agtttcaaaa catccctgct cattattccc ccagaacctc tccaataatg     840
tcacctcgaa ccagctcgc cgaggacagc tgcctgggcc gacactcgcc cgtgccccgt     900
ccggcatccc gctcctcctc acccggtgcc aagcggaggc attcgtgcgc agaggctttg     960
```

```
gttgctcctc tgcccgcagc ctcaccccag cgctcccgga gccctcgcc acagccctcg    1020 cctcacgtgg cactgcagga cgacagcatc cccgctgggt acccccccac ggccggctct    1080
gctgttctca tggatgccct caacaccctg ccaccgact cgccctgcgg gatcccctcc    1140
aagatatgga agaccagtcc tgacccgacg cctgtgtcca ccgctccgtc caaggctggc    1200
ctggcccgcc acatctaccc tactgtggag ttcctggggc catgtgagca ggaggagagg    1260
aggaattccg ctccagagtc catcctgctg gtaccaccta cttggcccaa gcagttggtg    1320
ccggccattc ccatctgcag catccctgtg actgcatccc tcccaccact cgagtggcca    1380
ctctccaatc agtcgggctc ctatgagcta cggattgagg tccaacccaa gccccatcac    1440
cgggcccact atgagacgga gggcagccgt ggcgctgtca agccccaac aggaggacac    1500 cctgtggtgc agctccacgg ctacatggag aacaagcctc tggggcttca gatcttcatt    1560
gggacagcag atgagaggat ccttaagccg cacgccttct accaagtaca caggatcact    1620
gggaaaacgg tcaccaccac gagctatgag aagatcgtag caacaccaa ggtcctggag    1680 atcccctgg agccaaagaa caacatgaga gccaccatcg actgtgcagg catcctgaag    1740
ctccgaaacg ctgacatcga gctgcggaag ggcgagacgg acatcggcag gaagaacacg    1800
cgtgtgcgcc tggtgttccg cgtgcacgtc ccagagccca gtgggcgcat cgtctccctg    1860
caggctgcgt ccaaccccat cgagtgctct cagcgctctg cccacgagct gcccatggtg    1920
gagagacaag acatggacag ctgcctggtc tacggggcc agcagatgat cctcacgggc    1980
cagaacttca gcggagtc caaggttgtg ttcatggaga agactacaga tgggcagcag    2040
atttgggaga tggaagctac ggtggataaa gacaagagcc agcctaacat gcttttgtt    2100 gagatccccg agtatcggaa caagcacatc cgcgtgcccg tgaaagtcaa cttctacgtc    2160
atcaacggaa agaggaaacg aagtcagcca cagcacttta cctaccaccc agtccctgcc    2220
atcaagacag agcccagcga tgagtatgaa ccatctttga tctgcagccc cgcccatgga    2280
ggcctgggga gccagccata ttacccacag cacccaatgc tggccgagtc ccctcctgc    2340 cttgtggcta ccatggcccc ctgccaacag ttccgctcgg ggctctcatc ccccgatgct    2400
cgctaccaac agcagagccc cgcagctgcc ctctaccaga gaagcaagag cctgagtccc    2460
ggcctgctgg gctaccagca gccgtccctc ctggcagcac ccttgggtct ggctgatgcc    2520
caccgctctg tgctggtgca tgctggtcct caggggcagg gcagggctc caccctgcca    2580 cacacatcct cggccagcca gcaggcctca cccgtgatcc actactcacc caccaaccag    2640
cagcttcgcg gtggggtca ccaggagttc cagcatatca tgtactgtga aaacttcggc    2700
cccagctctg ccaggcctgg cccgcctccc atcaaccaag gtcagaggct gagcccgggc    2760 gcctaccca cagtcatcca acaacagact gccccgagcc aaagagctgc caaaaacgga    2820
cccagtgacc agaaggaagc tctgcccacg ggagtgaccg tcaaacagga acagaacctg    2880
gaccagacct acctggatga cgttaatgaa atcatcagga aggagttttc aggacctccc    2940
tcccgaaatc agacctagaa acaaacataa tctcgcgacg ccttctactc tggaccgctt    3000
ctgtctcctc ctgccgtctg tgactggaac actgcgcatg cgcacagtgc acgcagatgg    3060
tgtcagagcc tgggagcctg ctgccgcgca acagcatct tagccgttgt ccatggtgac    3120
tggacacgaa aagcaactgc ctgctgacca aagcctcatt ctcaactcac caggatgctg    3180
aacctgagac gccaggctgc gctggcagga gaactggaga aactgcgata gcccacagac    3240
atggcttcat ttttttttgaa ttttctcttt ccaaagccaa acagccttgc cctgacagga    3300
```

```
ccacctgtcc caacttctca gccttaagtt ataacacacg tacgtgtctg ccagcttctg   3360
ggcctttgct gtgttttcct ctgcttcaaa gagccaacca aggaggccgt gggctgagag   3420
ccctctcggc cagctattcc ctaacctgct gcctacacca gactggctgg tggcatccag   3480
tcccggctgc ctgttgggaa ccctgcttct gaaggttccc ctctccaccc cctccaccca   3540
gaggtcggga gaaccttctg gatccttgca ttgactgtta aggagctaaa accaccaaac   3600
ccagtcaaaa cctacacgtg tttgtcatga ccgccaccaa acagaacaaa ggggccgaaa   3660
tctcccttty ctctgaactc aaagcaggaa agtgctggct tcaccctagt ttgttttttg   3720
tttttgttt ttaacctgaa ttcaggtaaa gcctccatag actcctgaac gctgctgtat   3780
gagctgtgac tcaggcggat ccaccccagc atatgcctta gtgtgatcaa gccctgcctg   3840
gcccggttgt gtgtcctgtg ggattctcca cacacactgc ctgctacagg cggtcctcca   3900
tggtcttcct cctggttcag ttttcttctt ccaacagcgt ttcccccaat catgtacgca   3960
agaccgtcct ctccccttgc cttcatccca gatgtctcta ttgggcatct tcttaaagtg   4020
actttctcgg ctttgtgtgc taggcagagg acccgagaag caagctacag tggctaagta   4080
cccgtggttg gtttcttacg tcctggcttt cttgtcaaag tcatctgaaa ggaaatggct   4140
ggagccgggc cagctgtcgc tggttctcct tacagagacc ccatgcccag ggttcagctt   4200
gaacatgcaa atatgacttt gtggtcagga cctagagtgt ctccccttg ctgcagccct   4260
gggctttccc tccactgacc ccatgcgtag acctgggcag aattctcgtg tgaacccaga   4320
atgtctgtaa gaagttgagc actaagccgc tatgagtcta agtacttcct gctaagcaag   4380
aaacgttctg ctggcccttt acggccagga gcttctgact ggagcaatgc cgacttctct   4440
ggggaagggt gatgagggtt cggtgagtga cagttcacac ttgccctggc tgagagccac   4500
gttttgcaca tgagggagtc aggcccttcc tcagatatct ccaagtttta cccaagtgcc   4560
ttcctgcaat tgtagtcatt gtaattgtag ctcagctgca ctgtccacag ggagacaaag   4620
ggctaactca cttcccatta gttttcatgt cagcgaaggg gttcctggta gctcagactc   4680
ctatactttc ctctgtgtgt atgtgtgcat gtgtgtgtgt gtgtgtgtgt gtgtatatac   4740
gtgtacacaa ttctcttccc tttatactat cttagccaga tagtctcaga aacttgctga   4800
taaatatccc aaacagccaa ggagagaaag cagcatctgt taccagacaa acaggccata   4860
gaaggtgtat gagcggcaga gagctatgga gaaggtttgg tcagttacag actccagggg   4920
aaacgtggcc gggagtgact gcttatcaac catttccagg atggggagat gcagtctgat   4980
cttagcgaat gagaaaagat gcccgagcag tgacgacgag tgtaccgcac gtgggttaga   5040
ggggcggaag cggaaatgtg tccttgctaa atctgtggtg tcgttccggt gacagttcca   5100
tattgctaaa tgtggcactt tctcttccaa gtccacacat ctccctgact gtacaaaggc   5160
accgctgatg gggagtatat ctatctaccc agatcagtat ggtattaaat tttatttt    5220
tatttgtatt ttgatgcttt ttatctgcct ttaaaatatc tcacccctgt tggagttaga   5280
acatatttat aaatgaccag atgtcttttt ttaagggtct atttcttttt ttaaaaaaaa   5340
tctatatctt cattttctgt aagagaaatg gtatactcct gagttttgtt ttattttgtt   5400
ttgtttgtt ttgcttttg tttctcattc tgggaaacaa atccaaagac tcacctcggg   5460
tcctatcaag acctcaggat gggagagaaa gggactttgt aggagagaac accttttta   5520
gcttgagaaa gagggcctgc tccttcagct ccatgtcagg gctgtccctg agaaccgtac   5580
gtgaaaggtt tggttggtgg tctcaatcta aagccacaga actctgcctt tccatggaca   5640
agctccttca ggcaggctga cagttgacag agccaaccac gtggagtcct cagaggtgac   5700
```

-continued

```
actgaggtgc agcatccaaa gaacagccac cttctcccca gcgcagcgta gccacggacc    5760
aagtgacctg ggataacact gttcacatgc agcagcctgg tcatccatta ccagcacca     5820 ccagccgtgg ccagccgccg gcagcactgt cacacaggga ggccagaagc cagtgtgttt    5880
taattagcac tcagaaccta taggaggctg agttggttta tcttcacacc acagtgctca    5940
gcatcaggag aaacggggc tacgtaacaa ctgtgttcat ttgccgcgct tccgaaaaga     6000
cagaggtggc caggctaggg cgagtattcc tggactcttt gccgtcaggg aaggctggag    6060
gaacccgaca catcctcacc actggcatct cccaagtttg gacaccaacc ttcatggacc    6120
caaaccaggc agctgcagag cgggaggttt ccctgcagcc cagcagttgc ttaaatgagg    6180
caacatcacc ttcacctacg accagcttac ccgtgccttg acagacatac ggccaccatc    6240
gttgtcttaa tccagtttgt ttacagctaa ctctaaatgg tgggccagga gtggtgcttc    6300
cctgagcagg acccctctga gatcacaatg aagtcctggg aactggagtc aaaagtgtta    6360
atgctttcag atgggaataa acgtcctgc cctgcctggc cctgcctggc tctgccctct      6420
caggctttag atggactggg tgcagacagt gctgttgcta tgtgagtagg aaccccagca    6480
ttctgtgaga gcatcccaga catcagacat ccccgtcccc ctgtcatttc tcagccctca    6540
tgggagcctg ctcatcgggc tctgaaggcc ggggtttggg aaaatctcca ccccactacc    6600
tgaggagtcg ggatatatca cattcctatg caaaacgatt ttaatctccg gtttcctgca    6660
gtttattttt gctatatgta aagtattttt atacggctta tatgatgaca gcttagcaat    6720
aaacagttga gagcaactct aaaaaaaaaa aaaaaaaa                            6759

<210> SEQ ID NO 57
<211> LENGTH: 2042
<212> TYPE: DNA
<213> ORGANISM: Homo sapiens
<220> FEATURE:
<223> OTHER INFORMATION: Human HOXB4 (NM_024015.4)

<400> SEQUENCE: 57
ggaaaacgag tcaggggtcg gaataaattt tagtatattt tgtgggcaat tcccagaaat      60
taatggctat gagttctttt ttgatcaact caaactatgt cgaccccaag ttccctccat     120
gcgaggaata ttcacagagc gattacctac ccagcgacca ctcgcccggg tactacgccg     180
gcggccagag gcgagagagc agcttccagc cggaggcggg cttcgggcgg cgcgcggcgt     240
gcaccgtgca gcgctacgcg gcctgccggg accctgggcc cccgccgcct ccgccaccac     300
ccccgccgcc cccgccaccg cccggtctgt ccctctcggg tcctgcgccg ccacccgccg     360
gggccctcct cccggagccc ggccagcgct gcgaggcggt cagcagcagc ccccgccgc      420 ctccctgcgc ccgaaccccc ctgcacccca gcccgtccca ctccgcgtgc aaagagcccg     480
tcgtctaccc ctggatgcgc aaagttcacg tgagcacggt aaaccccaat tacgccggcg     540
gggagcccaa gcgctctcgg accgcctaca cgcgccagca ggtcttggag ctggagaagg     600
aatttcacta caaccgctac ctgacacggc gccggagggt ggagatcgcc cacgcgctct     660
gcctctccga gcgccagatc aagatctggt tccagaaccg gcgcatgaag tggaaaaaag    720
accacaagtt gcccaacacc aagatccgct cgggtggtgc ggcaggctca gccggagggc    780
cccctggccg gcccaatgga ggcccccgcg cgctctagtg cccccgcacg cgggagccac    840
gaacctcggg gtggggtgg gcagtgagtg cagggatgg ggtgggggga caggaggggg       900
ccctggggcc tgggccccgg aaaaatctat ctgccctccc ccacacttta tatacgaata   960
```

```
aacgcagaag agggggaggg gaagctttat ttatagaaat gacaatagag ggccacgggg    1020
aggccccccc agaagcaaga ttcaaatctc ttgctttctt tcttaaaaaa aagaaaaaga    1080
aaaagcaaga agaaggaaga aagaaaaaga cagaaagaga aataggagga ggctgcagct    1140
cctcgttttc agctttggcg aagatggatc cacgtttcat ctttaatcac gccaggtcca    1200
ggcccatctg tcttgtttcc tctgccgagg agaagacggg cctcggtggc gaccattacc    1260
tcgacacccg ctaacaaatg aggcccggct cggccgcctc cgcctctgct actgccgctg    1320
ctggaagaca gcctggattt cctttctttg tcccccactc ccgatacccc gcgaaagcac    1380
cctctgactg ccagatagtg cagtgttttg gtcacggtaa cacacacaca ctctccctca    1440
tctttcgtgc ccattcactg agggccagaa tgactgctca cccacttcca ccgtgggtt    1500 gggggtgggc aacagaggag gggagcaagt agggaagggg gtggccttga caactcagga    1560
gtgagcagga aaattgagtc caaggaaaaa gagagactca gagacccggg agggccttcc    1620
tctgaaaggc caagccaagc catgcttggc agggtgaggg gccagttgag ttctgggagc    1680
tgggcactac tctgccagtc cagagttgta cagcagaagc ctctctccta gactgaaaat    1740
gaatgtgaaa ctaggaaata aaatgtgccc ctcccagtct gggaggagga tgttgcagag    1800
ccctctccca tagtttatta tgttgcatcg tttattatta ttattgataa tattattatt    1860 actattttt tgtgtcatgt gagtcctctc tccttttctc tttctgacat tccaaaacca    1920
ggccccttcc tacctctggg gctgcttgag tctagaaccc ttcgtatgtg tgaatatctg    1980
tgtgctgtac agagtgacaa tagaaataaa tgtttggttt cttgtgacca gcaaaaaaaa    2040
aa                                                                   2042

<210> SEQ ID NO 58
<211> LENGTH: 2566
<212> TYPE: DNA
<213> ORGANISM: Mus <mouse, genus>
<220> FEATURE:
<223> OTHER INFORMATION: Mouse Hoxb4 (NM_010459.7)

<400> SEQUENCE: 58
agctccctct tatcctgggg aggagatggg gccctatggg agtcagagaa aggttggtgg      60
agattaggta gggcagggggt gggggctaca cccgcagccc caacttctga gggatgcagg    120
gtttgtgctc tgcccagccc cctcacccccc aaacaggccc tccaattaac ctgctcactc    180
tttcttagtt catcaccccct ctctgttgtg gagaaagcca ggcgaggagg gggtctcccc    240
gcgggagccc tatgtaaatc ctggtgttgg gtgggtgggg aggggtagag aagggggaaat    300 aaacctcttt ggctggagta gggtccgggt gagcagattt cctatccgg gaatcgcagg     360 ccgggtggcc attggctcgg aggatcacgt gggcctctaa cttttgttcac ttgacagtaa    420 gtaggagggc tttcggaaac aggaaaacga gtcagggtc ggaataaatt ttagtatatt     480
ttgtgggcaa ttcccagaaa ttaatggcta tgagttcctt tttgatcaac tcaaactatg    540 tcgacccccaa gttccctccg tgcgaggagt attcacagag cgattaccta cccagcgacc    600
actcgcccgg gtactacgcc ggcggccaga ggcgagagag cggcttccag ccggaggcgg    660
cctttgggcg ccgggcgccg tgcactgtgc agcgctacgc ggcctgccga ccccgggc      720 ccccgccacc tccgccgccc ccgccgcccc cgccaccgcc cgggctgtcc cctcgggctc    780
cagtgcagcc aacagccggg gccctcctcc cggagcccgg gcagcgcagc gaggcggtca    840
gcagcagccc ccgccgcct ccctgcgccc agaaccccct gcatcccagc ccgtcccact    900
ccgcgtgcaa agagcccgtc gtctacccct ggatgcgcaa agttcacgtg agcacggtaa    960
```

```
acccccaatta cgccggcggg gagcccaagc gctctcggac cgcctacact cgccagcagg   1020
tcctggagtt ggagaaggag tttcactaca atcgctacct gacgcgccgc cggagggtgg   1080
agatcgccca cgcgctctgc ctgtccgagc gccagatcaa gatctggttc cagaatcggc   1140
gcatgaagtg gaaaaagac cacaagttgc caacaccaa gatccgctcg ggtggcaccg     1200
cgggcgcagc cggaggcccc cctggccggc ccaacggagg ccccccctgcg ctctagtgcc  1260 ccccaagcag gagttcgaac atgggggggt gggggggaaca gcgagcaccg aagggggtgc  1320
ggggtatggg agggtccccg ggcttgagcc cagaaaaaat ctatctaccc taccctcact   1380
ttatctataa ggaataaaca cagagaaggg gggtagggaa gccttattta tagaaaggac   1440
aataagggag ccgggtaaag tccttcggag acaagattcg agtctcttgc tttcttcctt   1500
taaaaaaaaa aagaaagaa agaaagaagg aaagaaagag agagagagaa aagaaaaaga    1560
agaaaggaag gaagcaagaa aaggaggaag aaaggaaaag acagaagaga aatggaggag   1620
tctgctgcgc ctggttttca gctttggtga agatggatcc aggcttcatc tttaatcacg   1680
ccaggcccgg gcccatctgt cttgtttact ctgccgagga gaagacgggc gagcgagctt   1740
cggtggcgac cattacctcg acacttggct aacaaatgag gccaggctcg gccgctgccg   1800
ccgcctctgc tgctgtcgct gctggatcac agcctggatt tttctttctt tgtcccctac   1860
tcctgacacc cagcgaatgc accctcagac tgccagatag cacagtgttt tggccacggt   1920
aacaaacaca cacacatata actttcctcc ctgtctgtac ccactttggg gtggggtgg    1980 gtgggaagac tgctcactcc cttccaccat agacttagaa gggggaacag aagggaattg   2040
aagggcagtc tgcacaacgt gggttcccaa atccgagccc aagaaataaa tgaaaatgaa   2100
aaaagaaagg tagcaattgg gacacccaag aaggccttct gctagaaggt ccagctaggc   2160
ctggcagggt gaggggcagt tgagttctgg gagctgggaa tgtcttctgg gcagttcaca   2220
gtagtagagt caaggccttc tcttaggtta caaatgaatg tgaaattagg aaataaaata   2280
ctgtggccct cctactctgg aaggacaatg ttgcagaacc ctctcccgtt gttatcattg   2340
ttgcatcgtt tattattatt attattatta ttattattat tattattatt attattatta   2400
ttttatgtca tgtgtgtcct ctctcctgtt ctctttctga cattccaaaa ccaggcccct   2460
tcctacctct ggggctgcct gagcctagaa ccttttgttg gtgtgaaaat ttgtgtcctg   2520
tacagagtga caacagaaat aaatgtttgg tttcttgtga ccatca                  2566
```

<210> SEQ ID NO 59
<211> LENGTH: 3014
<212> TYPE: DNA
<213> ORGANISM: Homo sapiens
<220> FEATURE:
<223> OTHER INFORMATION: Human KLF4 (NM_001314052.1)

<400> SEQUENCE: 59

```
gcagaggcgg tggcgggcgg cggcggcacc gggagccgcc gagtgaccct cccccgcccc     60 tctgccccccc cacctcccca cccgcccgtg gcccgcgccc atggccgcgc gcgctccaca   120
caactcaccg gagtccgcgc cttgcgccgc cgaccagttc gcagctccgc gccacggcag   180
ccagtctcac ctggcggcac cgcccgccca ccgcccggc cacagcccct gcgcccacgg     240
cagcactcga ggcgaccgcg acagtggtgg gggacgctgc tgagtggaag agagcgcagc   300
ccggccaccg gacctactta ctcgccttgc tgattgtcta ttttgcgtt tacaactttt    360 ctaagaactt ttgtatacaa aggaactttt taaaaaagac gcttccaagt tatatttaat    420
```

```
ccaaagaaga aggatctcgg ccaatttggg gttttgggtt ttggcttcgt ttcttctctt    480
cgttgacttt ggggttcagg tgccccagct gcttcgggct gccgaggacc ttctgggccc    540
ccacattaat gaggcagcca cctggcgagt ctgacatggc tgtcagcgac gcgctgctcc    600
catctttctc cacgttcgcg tctggcccgg cgggaaggga gaagacactg cgtcaagcag    660
gtgccccgaa taaccgctgg cgggaggagc tctcccacat gaagcgactt cccccagtgc    720
ttcccggccg cccctatgac ctggcggcg cgaccgtggc cacagacctg gagagcggcg    780
gagccggtgc ggcttgcggc ggtagcaacc tggcgcccct acctcggaga gagaccgagg    840
agttcaacga tctcctggac ctggacttta ttctctccaa ttcgctgacc catcctccgg    900
agtcagtggc cgccaccgtg tcctcgtcag cgtcagcctc ctcttcgtcg tcgccgtcga    960
gcagcggccc tgccagcgcg ccctccacct gcagcttcac ctatccgatc cgggccggga   1020
acgacccggg cgtggcgccg gcggcacgg gcggaggcct cctctatggc agggagtccg   1080 ctcccccctcc gacggctccc ttcaacctgg cggacatcaa cgacgtgagc ccctcgggcg   1140
gcttcgtggc cgagctcctg cggccagaat tggacccggt gtacattccg ccgcagcagc   1200
cgcagccgcc aggtgcgggg ctgatgggca agttcgtgct gaaggcgtcg ctgagcgccc   1260
ctggcagcga gtacggcagc ccgtcggtca tcagcgtcag caaaggcagc cctgacggca   1320
gccacccggt ggtggtggcg ccctacaacg gcgggccgcc gcgcacgtgc cccaagatca   1380
agcaggaggc ggtctcttcg tgcacccact tgggcgctgg acccctctc agcaatggcc   1440 accggccggc tgcacacgac ttcccctgg ggcggcagct ccccagcagg actaccccga   1500
ccctgggtct tgaggaagtg ctgagcagca gggactgtca ccctgccctg ccgcttcctc   1560
ccggcttcca tccccacccg ggcccaatt acccatcctt cctgcccgat cagatgcagc   1620
cgcaagtccc gccgctccat taccaaggtc agtcccgggg atttgtagct cgggctgggg   1680
agccctgtgt gtgctggccc cacttcggga cacacgggat gatgctcacc ccaccttctt   1740
cacccctaga gctcatgcca cccggttcct gcatgccaga ggagcccaag ccaaagaggg   1800
gaagacgatc gtggccccgg aaaaggaccg ccacccacac ttgtgattac gcgggctgcg   1860
gcaaaaccta cacaaagagt tcccatctca aggcacacct gcgaacccac acaggtgaga   1920
aaccttacca ctgtgactgg gacggctgtg gatggaaatt cgcccgctca gatgaactga   1980
ccaggcacta ccgtaaacac acggggcacc gcccgttcca gtgccaaaaa tgcgaccgag   2040 catttttccag gtcggaccac ctcgccttac acatgaagag gcattttaa atcccagaca   2100 gtggatatga cccacactgc cagaagagaa ttcagtattt tttacttttc acactgtctt   2160
cccgatgagg gaaggagccc agccagaaag cactacaatc atggtcaagt tcccaactga   2220
gtcatcttgt gagtggataa tcaggaaaaa tgaggaatcc aaaagacaaa aatcaaagaa   2280
cagatggggt ctgtgactgg atcttctatc attccaattc taaatccgac ttgaatattc   2340
ctggacttac aaaatgccaa gggggtgact ggaagttgtg gatatcaggg tataaattat   2400
atccgtgagt tggggagggg aagaccagaa ttcccttgaa ttgtgtattg atgcaatata   2460
agcataaaag atcaccttgt attctcttta ccttctaaaa gccattatta tgatgttaga   2520
agaagaggaa gaaattcagg tacagaaaac atgtttaaat agcctaaatg atggtgcttg   2580
gtgagtcttg gttctaaagg taccaaacaa ggaagccaaa gttttcaaac tgctgcatac   2640
tttgacaagg aaaatctata tttgtcttcc gatcaacatt tatgacctaa gtcaggtaat   2700
atacctggtt tacttcttta gcattttat gcagacagtc tgttatgcac tgtggtttca   2760
gatgtgcaat aatttgtaca atggtttatt cccaagtatg ccttaagcag aacaaatgtg   2820
```

| | |
|---|---|
| tttttctata tagttccttg ccttaataaa tatgtaatat aaatttaagc aaacgtctat | 2880 |
| tttgtatatt tgtaaactac aaagtaaaat gaacattttg tggagtttgt attttgcata | 2940 |
| ctcaaggtga gaattaagtt ttaaataaac ctataatatt ttataaaaaa aaaaaaaaaa | 3000 |
| aaaaaaaaaa aaaa | 3014 |

```
<210> SEQ ID NO 60
<211> LENGTH: 3057
<212> TYPE: DNA
<213> ORGANISM: Mus <mouse, genus>
<220> FEATURE:
<223> OTHER INFORMATION: Mouse Klf4 (NM_010637.3)

<400> SEQUENCE: 60
```

| | |
|---|---|
| agttccccgg ccaagagagc gagcgcggct ccgggcgcgc ggggagcaga ggcggtggcg | 60 |
| ggcggcggcg gcacccggag ccgccgagtg cccctccccg cccctccagc cccccaccca | 120 |
| gcaacccgcc cgtgacccgc gcccatggcc gcgcgcaccc ggcacagtcc ccaggactcc | 180 |
| gcaccccgcg ccaccgccca gctcgcagtt ccgcgccacc gcggccattc tcacctggcg | 240 |
| gcgccgcccg cccaccgccc ggaccacagc ccccgcgccg ccgacagcca cagtggccgc | 300 |
| gacaacggtg ggggacactg ctgagtccaa gagcgtgcag cctggccatc ggacctactt | 360 |
| atctgccttg ctgattgtct attttttataa gagtttacaa cttttctaag aattttttgta | 420 |
| tacaaaggaa cttttttaaa gacatcgccg gtttatattg aatccaaaga agaaggatct | 480 |
| cgggcaatct gggggttttg gtttgaggtt ttgtttctaa agttttaatt cttcgttgac | 540 |
| tttgggctc aggtaccct ctctcttctt cggactccgg aggaccttct gggcccccac | 600 |
| attaatgagg cagccacctg gcgagtctga catggctgtc agcgacgctc tgctcccgtc | 660 |
| cttctccacg ttcgcgtccg gcccggcggg aagggagaag acactgcgtc cagcaggtgc | 720 |
| cccgactaac cgttggcgtg aggaactctc tcacatgaag cgacttcccc cacttcccgg | 780 |
| ccgcccctac gacctggcgg cgacggtggc cacagacctg gagagtggcg gagctggtgc | 840 |
| agcttgcagc agtaacaacc cggcctcct agcccggagg gagaccgagg agttcaacga | 900 |
| cctcctggac ctagacttta tcctttccaa ctcgctaacc caccaggaat cggtggccgc | 960 |
| caccgtgacc acctcggcgt cagcttcatc ctcgtcttcc ccggcgagca gcggccctgc | 1020 |
| cagcgcgccc tccacctgca gcttcagcta tccgatccgg gccggggtg acccgggcgt | 1080 |
| ggctgccagc aacacaggtg agggctcct ctacagccga gaatctgcgc cacctcccac | 1140 |
| ggcccccttc aacctggcgg acatcaatga cgtgagcccc tcgggcggct tcgtggctga | 1200 |
| gctcctgcgg ccggagttgg acccagtata cattccgcca cagcagcctc agccgccagg | 1260 |
| tggcgggctg atgggcaagt ttgtgctgaa ggcgtctctg accaccctg gcagcgagta | 1320 |
| cagcagccct tcggtcatca gtgttagcaa aggaagccca gacggcagcc accccgtggt | 1380 |
| agtggcgccc tacagcggtg gcccgccgcg catgtgcccc aagattaagc aagaggcggt | 1440 |
| cccgtcctgc acggtcagcc ggtccctaga ggcccatttg agcgctggac cccagctcag | 1500 |
| caacggccac cggcccaaca cacacgactt cccctgggg cggcagctcc ccaccaggac | 1560 |
| tacccctaca ctgagtcccg aggaactgct gaacagcagg gactgtcacc ctggcctgcc | 1620 |
| tcttccccca ggattccatc ccatccggg gcccaactac cctccttcc tgccagacca | 1680 |
| gatgcagtca caagtccct ctctccatta tcaagagctc atgccaccgg ttcctgcctt | 1740 |
| gccagaggag cccaagccaa agaggggaag aaggtcgtgg ccccggaaaa gaacagccac | 1800 |

```
ccacacttgt gactatgcag gctgtggcaa aacctatacc aagagttctc atctcaaggc   1860
acacctgcga actcacacag gcgagaaacc ttaccactgt gactgggacg gctgtgggtg   1920
gaaattcgcc cgctccgatg aactgaccag gcactaccgc aaacacacag ggcaccggcc   1980
ctttcagtgc cagaagtgtg acagggcctt ttccaggtcg gaccaccttg ccttacacat   2040
gaagaggcac ttttaaatcc cacgtagtgg atgtgaccca cactgccagg agagagagtt   2100
cagtattttt ttttctaacc tttcacactg tcttcccacg aggggaggag cccagctggc   2160
aagcgctaca atcatggtca agttcccagc aagtcagctt gtgaatggat aatcaggaga   2220
aaggaagagt tcaagagaca aaacagaaat actaaaaaca aacaaacaaa aaacaaaca   2280 aaaaaaacaa gaaaaaaaaa tcacagaaca gatggggtct gatactggat ggatcttcta   2340
tcattccaat accaaatcca acttgaacat gcccggactt acaaaatgcc aaggggtgac   2400
tggaagtttg tggatatcag ggtatacact aaatcagtga gcttgggggg agggaagacc   2460
aggattccct tgaattgtgt ttcgatgatg caatacacac gtaaagatca ccttgtatgc   2520
tctttgcctt cttaaaaaaa aaaaaagcca ttattgtgtc ggaggaagag gaagcgattc   2580
aggtacagaa catgttctaa cagcctaaat gatggtgctt ggtgagtcgt ggttctaaag   2640
gtaccaaacg ggggagccaa agttctccaa ctgctgcata cttttgacaa ggaaaatcta   2700
gttttgtctt ccgatctaca ttgatgacct aagccaggta ataagcctg gtttatttct    2760 gtaacatttt tatgcagaca gtctgttatg cactgtggtt tcagatgtgc aataatttgt   2820
acaatggttt attcccaagt atgccttaa gcagaacaaa tgtgttttc tatatagttc     2880 cttgccttaa taaatatgta atataaattt aagcaaactt ctattttgta tatttgtaaa   2940
ctacaaagta aaaaaaatg aacattttgt ggagtttgta ttttgcatac tcaaggtgag   3000
aaataagttt taaataaacc tataatattt tatctgaacg acaaaaaaaa aaaaaaa      3057
```

<210> SEQ ID NO 61
<211> LENGTH: 3681
<212> TYPE: DNA
<213> ORGANISM: Homo sapiens
<220> FEATURE:
<223> OTHER INFORMATION: Human MYB (NM_001130173.1)

<400> SEQUENCE: 61

```
aatatcaacc tgtttcctcc tcctccttct cctcctcctc cgtgacctcc tcctcctctt    60
tctcctgaga aacttcgccc cagcggtgcg gagcgccgct gcgcagccgg ggagggacgc   120
aggcaggcgg cgggcagcgg gaggcggcag cccggtgcgg tccccgcggc tctcggcgga   180
gccccgcgcc cgccgcgcca tggcccgaag accccggcac agcatatata gcagtgacga   240
ggatgatgag gactttgaga tgtgtgacca tgactatgat gggctgcttc ccaagtctgg   300
aaagcgtcac ttggggaaaa caaggtggac ccgggaagag gatgaaaaac tgaagaagct   360
ggtggaacag aatggaacag atgactgaa agttattgcc aattatctcc gaatcgaac     420 agatgtgcag tgccagcacc gatggcagaa agtactaaac cctgagctca tcaagggtcc   480
ttggaccaaa gaagaagatc agagagtgat agagcttgta cagaaatacg gtccgaaacg   540
ttggtctgtt attgccaagc acttaaaggg gagaattgga aaacaatgta gggagaggtg   600
gcataaccac ttgaatccag aagttaagaa aacctcctgg acagaagagg aagacagaat   660
tatttaccag gcacacaaga gactggggaa cagatgggca gaaatcgcaa agctactgcc   720
tggacgaact gataatgcta tcaagaacca ctggaattct acaatgcgtc ggaaggtcga   780
acaggaaggt tatctgcagg agtcttcaaa agccagccag ccagcagtgg ccacaagctt   840
```

```
ccagaagaac agtcatttga tgggttttgc tcaggctccg cctacagctc aactccctgc      900
cactggccag cccactgtta acaacgacta ttcctattac acatttctg aagcacaaaa       960
tgtctccagt catgttccat accctgtagc gttacatgta aatatagtca atgtccctca     1020
gccagctgcc gcagccattc agagacacta taatgatgaa gaccctgaga aggaaaagcg     1080
aataaaggaa ttagaattgc tcctaatgtc aaccgagaat gagctaaaag gacagcaggt     1140
gctaccaaca cagaaccaca catgcagcta ccccgggtgg cacagcacca ccattgccga     1200
ccacaccaga cctcatggag acagtgcacc tgtttcctgt ttgggagaac accactccac     1260
tccatctctg ccagcggatc ctggctccct acctgaagaa agcgcctcgc cagcaaggtg     1320
catgatcgtc caccagggca ccattctgga taatgttaag aacctcttag aatttgcaga     1380
aacactccaa tttatagatt ctgattcttc atcatggtgt gatctcagca gttttgaatt     1440
cttgaagaa gcagattttt cacctagcca acatcacaca ggcaaagccc tacagcttca     1500
gcaaagagag ggcaatggga ctaaacctgc aggagaacct agcccaaggg tgaacaaacg     1560
tatgttgagt gagagttcac ttgacccacc caaggtctta cctcctgcaa ggcacagcac     1620
aattccactg gtcatccttc gaaaaaaacg gggccaggcc agcccttag ccactggaga     1680
ctgtagctcc ttcatatttg ctgacgtcag cagttcaact cccaagcgtt ccctgtcaa     1740
aagcctaccc ttctctccct cgcagttctt aaacacttcc agtaaccatg aaaactcaga     1800
cttggaaatg ccttctttaa cttccacccc cctcattggt cacaaattga ctgttacaac     1860
accatttcat agagaccaga ctgtgaaaac tcaaaaggaa aatactgttt ttagaaccc      1920
agctatcaaa aggtcaatct tagaaagctc tccaagaact cctacaccat tcaaacatgc     1980
acttgcagct caagaaatta atacggtcc cctgaagatg ctacctcaga cccctctca     2040
tctagtagaa gatctgcagg atgtgatcaa acaggaatct gatgaatctg gaattgttgc     2100
tgagtttcaa gaaaatggac caccttact gaagaaaatc aaacaagagg tggaatctcc     2160
aactgataaa tcaggaaact tcttctgctc acaccactgg gaaggggaca gtctgaatac     2220
ccaactgttc acgcagacct cgcctgtggc agatgcaccg aatattctta caagctccgt     2280
tttaatggca ccagcatcag aagatgaaga caatgttctc aaagcattta cagtacctaa     2340
aaacaggtcc ctggcgagcc ccttgcagcc ttgtagcagt acctgggaac ctgcatcctg     2400
tggaaagatg gaggagcaga tgacatcttc cagtcaagct cgtaaatacg tgaatgcatt     2460
ctcagcccgg acgctggtca tgtgagacat ttccagaaaa gcattatggt tttcagaaca     2520
cttcaagtta acttgggata tatcattcct caacatgaaa cttttcatga atgggagaag     2580
aacctatttt tgttgtggta caacagttga gagcagcacc aagtgcattt agttgaatga     2640
agtcttcttg gatttcaccc aactaaaagg atttttaaaa ataaataaca gtcttaccta     2700
aattattagg taatgaattg tagccagttg ttaatatctt aatgcagatt ttttaaaaa     2760
aaacataaaa tgatttatct gtattttaaa ggatccaaca gatcagtatt ttttcctgtg     2820
atgggttttt tgaaatttga cacattaaaa ggtactccag tatttcactt ttctcgatca     2880
ctaaacatat gcatatattt ttaaaaatca gtaaaagcat tactctaagt gtagacttaa     2940
taccatgtga catttaatcc agattgtaaa tgctcattta tggttaatga cattgaaggt     3000
acatttattg taccaaacca ttttatgagt tttctgttag cttgctttaa aaattattac     3060
tgtaagaaat agttttataa aaaattatat ttttattcag taatttaatt ttgtaaatgc     3120
caaatgaaaa acgttttttg ctgctatggt cttagcctgt agacatgctg ctagtatcag     3180
```

| | |
|---|---|
| aggggcagta gagcttggac agaaagaaaa gaaacttggt gttaggtaat tgactatgca | 3240 |
| ctagtatttc agacttttta attttatata tatatacatt ttttttcctt ctgcaataca | 3300 |
| tttgaaaact tgtttgggag actctgcatt ttttattgtg gttttttgt tattgttggt | 3360 |
| ttatacaagc atgcgttgca cttctttttt gggagatgtg tgttgttgat gttctatgtt | 3420 |
| ttgttttgag tgtagcctga ctgttttata atttgggagt tctgcatttg atccgcatcc | 3480 |
| cctgtggttt ctaagtgtat ggtctcagaa ctgttgcatg gatcctgtgt ttgcaactgg | 3540 |
| ggagacagaa actgtggttg atagccagtc actgccttaa gaacatttga tgcaagatgg | 3600 |
| ccagcactga acttttgaga tatgacggtg tacttactgc cttgtagcaa aataaagatg | 3660 |
| tgcccttatt ttacctacaa a | 3681 |

<210> SEQ ID NO 62
<211> LENGTH: 3777
<212> TYPE: DNA
<213> ORGANISM: Mus <mouse, genus>
<220> FEATURE:
<223> OTHER INFORMATION: Mouse Myb (NM_001198914.1)

<400> SEQUENCE: 62

| | |
|---|---|
| gggagtgtcc aaacctcttt gtttgatggc atctgtttac agagttacac tttaatatca | 60 |
| acctgtttcc tcctcctcct tctcctcctt ctcctcctcc tcctcggtga cctccttctc | 120 |
| ctccccttc tccggagaaa cttcgccccg gcggtgcgga gcgccgctgc gcagccgggg | 180 |
| gaggacgcag gcaaggcgga gggcagcggg aggcggcaac cggtgcggtc cccggggctc | 240 |
| ttggcggagc cccggcccgc ctcgccatgg cccggagacc ccgacacagc atctacagta | 300 |
| gcgatgaaga tgatgaagac attgagatgt gtgaccatga ctacgatggg ctgctgccca | 360 |
| aatctggaaa cgtcacttg ggaaaaacta ggtggacaag gaagaggat gagaagctga | 420 |
| agaagctggt ggaacagaac ggaacagacg actggaaagt cattgccaat tatctgccca | 480 |
| accggacaga tgtgcagtgc caacaccggt ggcagaaagt gctgaaccct gaactcatca | 540 |
| aaggtccctg gaccaaagaa gaagatcaga gagtcataga gcttgtccag aaatatggtc | 600 |
| cgaagcgttg gtctgttatt gccaagcact taaaagggag aattggaaag cagtgtcggg | 660 |
| agaggtggca aaccatttg aatccagaag ttaagaaaac ctcctggaca gaagaggagg | 720 |
| acagaatcat ttaccaggca cacaagcgtc tggggaacag atgggcagag atcgcaaagc | 780 |
| tgctgcccgg acggactgat aatgctatca agaaccactg gaattccacc atgcgtcgca | 840 |
| aggtggaaca ggaaggctac ctgcaggagc cttccaaagc cagccagacg ccagtggcca | 900 |
| cgagcttcca gaagaacaat catttgatgg ggtttgggca tgcctcacct ccatctcagc | 960 |
| tctctccaag tggccagtcc tccgtcaaca gcgaatatcc ctattaccac atcgccgaag | 1020 |
| cacaaaacat ctccagtcac gttccctatc ctgtcgcatt gcatgttaat atagtcaacg | 1080 |
| tccctcagcc ggctgcggca gccatccaga gacactataa cgacgaagac cctgagaagg | 1140 |
| aaaagcgaat aaaggagctg gagttgctcc tgatgtcaac agagaacgag ctgaagggac | 1200 |
| agcaggcatt accaacacag aaccacactt gcagctaccc cgggtggcac agcacctcca | 1260 |
| ttgtggacca gaccagacct catggggata gtgcacctgt ttcctgtttg ggagaacacc | 1320 |
| atgccacccc atctctgcct gcagatcccg gctccctacc tgaagaaagt gcctcaccag | 1380 |
| caaggtgcat gatcgtccac cagggcacca ttctggacaa tgttaagaac ctcttagaat | 1440 |
| ttgcagaaac actccagttt atagattctg attcttcgtg gtgtgatctc agcagttttg | 1500 |
| aattctctga agaagcggca gctttttcac ctagccagca gcccacaggc aaagccttcc | 1560 |

```
agcttcagca aagagagggc catgggacta gatctgcagg agagcctagc ctgagggtga    1620
ccaggcgagt gctgagcgag gcatccctcg gcccagactc accccaagcg aggcacagca    1680
aggttccgct ggtcgtccta cgaaaaaggc ggggccaggc cagcccccta gccgctggag    1740
agcctagccc ctccctcttt gctgacgtca tcagctcaac tctcaagcgt tcccctgtca    1800
aaagcctacc cttctctccc tcgcagttct tgaacacttc cagcaaccat gaaagctcgg    1860
gcttagatgc acctacctta ccctccactc ctctcattgg tcacaaactg acaccatgtc    1920
gagaccagac tgtgaaaacc cagaaggaaa attccatctt tagaactcca gctatcaaaa    1980
ggtcaatcct cgaaagctct cctcgaactc ccacaccatt caaacatgcc cttgcagctc    2040
aagaaattaa atacggtccc ctgaagatgc tacctcagac cccctcccat gcagtggagg    2100
acctacaaga tgtgattaag caggaatcgg atgaatctgg aattgtggct gagtttcaag    2160
agagtggacc accgttactg aaaaaaatca gcaggaggt ggagtcgcca actgagaaat    2220
cgggaaactt cttctgctca aaccactggg cagagaacag cctgagcacc cagctgttct    2280
cgcaggcgtc tcctgtggca gatgccccaa atattcttac aagctctgtt ttaatgacac    2340
ctgtatcaga agatgaagac aatgtcctca agcctttac cgtacctaag aacaggcccc    2400
tggtgggtcc cttgcagcca tgcagtggtg cctgggagcc agcatcctgt gggaagacag    2460
aggaccagat gacggcctcc ggtccggctc ggaaatacgt gaacgcgttc tcagctcgaa    2520
ctctggtcat gtgagacatt tccagaaaag cattatggtt ttcagaacac ttaaaagttg    2580
actttcgaca catggctcct cagcgtggag cgctccatgg ctgagagaag agcctgattt    2640
tgttgtggta caacagttga gagcagcacc aagtgcattt ttagttgctt gagatctcac    2700
ttgatttcac acaactaaaa aggattttt ttttttaaaaa taataataat gaataacagt    2760
cttacctaaa ttattaggta atgaattgtg accatttgtt aatatcataa tcagattttt    2820
taaaaaaat aaaatgattt atttgtattt tagaggatac aacagatcag tattttgac    2880
tgtggtgaat ttaaaaaaa aatttacaca agaaatatc ccagtattcc atgtatctca    2940
gtcactaaac atacagagag agattttaa aaaccaggag aagcattatt ttgaatgtta    3000
gctaaatccc aagtaatact taatgcaacc ctctaggagc tcatttgtgg ctaataatct    3060
tggaaatatc tttattatac taaaccattt catgaggaga attttgttgt cagcttgctt    3120
gaaaagttat tactgtatga aatagtttta ttgaaaaaat tatattttta ttcagtaatt    3180
taattttgta aatgccaaat ggagaaatgt gttcgctgct atggttttag cctgtagtca    3240
tgctgctagc tagtgtcagg gggcaataga gcttagatga aaaaagaga aagagactcg    3300
gtgttagata acggactatg cactagtatt ccagactttt ttatttttat atatatgtac    3360
cttttccttt tgtaattgga aaacttattt gggagaattt tgcatttgtt gtacattttt    3420
gttttttagg attttttttt tttgttgtta ttgtcgattt ataaaagcat tgcacttctt    3480
tttctttttt tgggagattt gtgttgttta tgtcatatgt tttgttttga gttcagcctg    3540
aatgttcatc cgtttgggcg ttttctgac ttggaagaac attctctgta ggtttctaag    3600
tgtacagagc cggaactgcc tcgtggttcc tgggcttcag ggaagacaaa tatgaagtc    3660
aacagccagt ttctgccttg agagcatttg caagaatgct ggcctgaat tctgaaatga    3720
cagtgtatct actgccttgt agcaaaataa agctatcctc ttatttttaca tacttcc     3777

<210> SEQ ID NO 63
<211> LENGTH: 1696
<212> TYPE: DNA
```

<213> ORGANISM: Homo sapiens
<220> FEATURE:
<223> OTHER INFORMATION: Human NFE2 (NM_006163.2)

<400> SEQUENCE: 63

```
tgttcttggg gatcctcaag catatactgt catcatcttg gaaagaaaag gctgagaacg      60
taaaactgag gacagaggag gaaagcaggg tgaccctga tgttgccta gaaaatggaa       120
aacaaaacac agcaaaacag aaaaacagaa gatctgactc tgcctttagc caggaaaaca    180
gtttggggga gtaaaaagta ttagggaaaa gagtgggcat tttgcctgga aaaaggttt    240
ctagagccat ctgggctttc cgggaacctg gaccagactc tggcccagta ggatgtcccc    300
gtgtcctccc cagcagagca ggaacagggt gatacagctg tccacttcag agctaggaga    360
gatggaactg acttggcagg agatcatgtc catcaccgag ctgcagggtc tgaatgctcc    420
aagtgagcca tcatttgagc cccaagcccc agctccatac cttggacctc caccacccac    480
aacttactgc ccctgctcaa tccacccaga ttctggcttc ccacttcctc caccacctta    540
tgagctccca gcatccacat cccatgtccc agatccccca tactcctatg gcaacatggc    600
cataccagtc tccaagccac tgagcctctc aggcctgctc agtgagccgc tccaagaccc    660
cttagccctc ctggacattg ggctgccagc agggccacct aagccccaag aagacccaga    720
atccgactca ggattatccc tcaactatag cgatgctgaa tctcttgagc tggaggggac    780
agaggctggt cggcggcgca gcgaaatatgt agagatgtac ccagtggagt accctactc    840
actcatgccc aactccttgg cccactccaa ctataccttg ccagctgctg agaccccctt    900
ggccttagag ccctcctcag gcctgtgcg ggctaagccc actgcacggg gggaggcagg    960
gagtcgggat gaacgtcggg ccttggccat gaagattcct tttcctacgg acaagattgt   1020
caacttgccg gtagatgact taatgagct attggcaagg tacccgctga cagagagcca   1080
gctagcgcta gtccgggaca tccgacgacg gggcaaaaac aaggtggcag cccagaactg   1140
ccgcaagagg aagctggaaa ccattgtgca gctggagcgg gagctggagc ggctgaccaa   1200
tgaacgggag cggcttctca gggcccgcgg ggaggcagac cggaccctgg aggtcatgcg   1260
ccaacagctg acagagctgt accgtgacat ttttccagcac cttcgggatg aatcaggcaa   1320
cagctactct cctgaagagt acgcgctgca acaggctgcc gatgggacca tcttccttgt   1380
gccccggggg accaagatgg aggccacaga ctgagctggc ccagaggggt ggaactgctg   1440
atgggatttc cttcattccc ttctgataaa ggtactcccc aaccctgagt cccagaagga   1500
gctgagttct ctagaccaga agaggatgac aatggcaaca agtgtttgga agttccaagg   1560
tgtgttcaaa gaggcttgcc ttgaggaggg ctggaatctg tcttccctga ctcggctcct   1620
caggtctttta gcctccacct tgtctaagct ttggtctata aagtgcgcta cagaaatggc   1680
aaaaaaaaaa aaaaaa                                                    1696
```

<210> SEQ ID NO 64
<211> LENGTH: 1896
<212> TYPE: DNA
<213> ORGANISM: Mus <mouse, genus>
<220> FEATURE:
<223> OTHER INFORMATION: Mouse Nfe2 (NM_001302338.1)

<400> SEQUENCE: 64

```
gatctctaag cactcacttc ttgggaagaa agggctgaaa tactaggtgt ggtggtacat      60
gcctttaatt ccagcacttg ggaggcagag gcagtcggat ctctgtgagc tagaagccag    120
cctggtctac atagcaagtt ctaggacaca gccagggaca catagcgaga ccttgtttta    180
```

```
aaaaacaaca atgaaagggt tagaccctac gctgaggaca caagaagaag gcaagggtga    240
ctcttgatgt tttcttccag aatggaaaat gaaatttcaa tccccaaacc tgagaaagac    300
tggattttgt ctctggacag gaataccatt tttagggagt aagagaaggc aacttgctga    360
gaaaaagtaa ggatacctac tctgtgtcca gaggactgac tatggtcaga tcaggtgagg    420
tagagagtac tccactgaag aaaagaacat tacagttcat agggtggttg atggcacctg    480
ttgcaggaat cctttgtgct tgtgagacc tggggccatc agctggcaca gtaggatgcc     540
cccgtgtcct cctcagcaga acaggaacag gttatcacag ctgcctgttg gggagcttgg    600
agagatggaa ctgacttggc aagagatcat gtccattact gagctgcagg gtctaaatgt    660
tccaagtgag acatcttttg agcctcaagc acccacccca taccctgggc cactgccacc    720
tccaacatat tgcccctgtt caattcatcc agatgcaggc ttctcccttc ccccaccatc    780
ttatgagctc ccagcatcta ctccccatgt cccagaacta ccatactcct atggtaatgt    840
agccatacca gtgtcaaagc cacttaccct ttcaggcctg ctcaatgagc ccctcccaga    900
ccacttagct ctcctggaca ttgggctgcc agtgggcaa cccaagcccc aagaagaccc      960
agaatctgac tcaggattat ccctcaacta cagtgatgca gaatctcttg agctagaggg   1020
tatggaggct ggcaggcgga ggagcgagta cgcggacatg tacccagtgg agtatcctta   1080
ctcacttatg cccaattctt tggcccatcc caactatact cttccaccca ctgagacacc   1140
cttggcctta gagtcatcct ccggtccagt tcgggctaag cctgctgtcc gtggggaggc   1200
agggagtcgg gacgagcggc gagccctggc catgaagatt cctttcccta cggacaagat   1260
agttaacttg ccggtagatg actttaatga gttgttggca cagtatccgc taacggagag   1320
ccagctggct ctagttcggg acatccgtcg acggggcaag aacaaggtgg cagcccaaaa   1380
ctgtcgcaag agaaaactgg aaaccattgt gcagctggag cgagagctgg agcggctgag   1440
cagtgaaagg gagcggcttc tcagagcccg aggggaggct gaccgcactc tggaggtcat   1500
gcgccaacag ctggcagagc tgtaccatga tatttccag catcttcggg atgaatctgg    1560
caacagttac tcaccagagg aatatgtact gcaacaggct gctgatggtg ccatctttct   1620
ggtaccccgt ggaaccaaaa tggaggctac agattgagct ggtctagaga gtggacactg   1680
gtgctagaga ctccctcatt cccttctgat gaaggcactt cttaatccca caagactcag   1740
agtcctccag accaaaaggc agatgtaacc atatcacctg ggagtatttg gtgaggtttg   1800
cctggaggcc aggtgttggc ttctcaggtc ctcaacccca cctcttgtcc aagctttggt   1860
tcataaagag ctgtgtggaa atagctaaaa aaaaaa                             1896
```

<210> SEQ ID NO 65
<211> LENGTH: 4093
<212> TYPE: DNA
<213> ORGANISM: Homo sapiens
<220> FEATURE:
<223> OTHER INFORMATION: Human NF-KB (NM_003998.3)

<400> SEQUENCE: 65

```
gtgagagagt gagcgagaca gaaagagaga gaagtgcacc agcgagccgg ggcaggaaga     60
ggaggtttcg ccaccggagc ggcccggcga cgcgctgaca gcttccctg ccctcccgt    120 cggtcgggcc gccagccgcc gcagccctcg gcctgcacgc agccaccggc cccgctcccg    180
gagcccagcg ccgccgaggc cgcagccgcc cggccagtaa ggcggcgccg ccgcccggcc    240
accgcgcgcc ctgcgcttcc ctccgcccgc gctgcggcca tggcgcggcg ctgactggcc    300
```

```
tggcccggcc ccgccgcgct cccgctcgcc ccgacccgca ctcgggcccg cccgggctcc      360
ggcctgccgc cgcctcttcc ttctccagcc ggcaggcccg cgccgcttag gagggagagc      420
ccacccgcgc caggaggccg aacgcggact cgccacccgg cttcagaatg cagaagatg       480
atccatattt gggaaggcct gaacaaatgt tcatttggga tccttctttg actcatacaa     540
tatttaatcc agaagtattt caaccacaga tggcactgcc aacagcagat ggcccatacc     600
ttcaaatatt agagcaacct aaacagagag gatttcgttt ccgttatgta tgtgaaggcc    660
catcccatgg tggactacct ggtgcctcta gtgaaaagaa caagaagtct taccctcagg     720
tcaaaatctg caactatgtg ggaccagcaa aggttattgt tcagttggtc acaaatggaa    780
aaaatatcca cctgcatgcc cacagcctgg tgggaaaaca ctgtgaggat gggatctgca    840
ctgtaactgc tggacccaag gacatggtgg tcggcttcgc aaacctgggt atacttcatg     900
tgacaaagaa aaaagtattt gaaacactgg aagcacgaat gacagaggcg tgtataaggg    960
gctataatcc tggactcttg gtgcaccctg accttgccta tttgcaagca gaaggtggag   1020
gggaccggca gctgggagat cgggaaaaag agctaatccg ccaagcagct ctgcagcaga   1080
ccaaggagat ggacctcagc gtggtgcggc tcatgtttac agcttttctt ccggatagca   1140
ctggcagctt cacaaggcgc ctggaacccg tggtatcaga cgccatctat gacagtaaag   1200
cccccaatgc atccaacttg aaaattgtaa gaatggacag gacagctgga tgtgtgactg   1260
gaggggagga aatttatctt ctttgtgaca agttcagaa agatgacatc cagattcgat    1320
tttatgaaga ggaagaaaat ggtggagtct gggaaggatt tggagatttt tcccccacag   1380
atgttcatag acaatttgcc attgtcttca aaactccaaa gtataaagat attaatatta   1440
caaaaccagc ctctgtgttt gtccagcttc ggaggaaatc tgacttggaa actagtgaac   1500
caaaacctt cctctactat cctgaaatca agataaaga agaagtgcag aggaaacgtc     1560
agaagctcat gcccaatttt tcggatagtt tcggcggtgg tagtggtgct ggagctggag   1620
gcggaggcat gtttggtagt ggcggtggag gaggggcac tggaagtaca ggtccagggt    1680
atagcttccc acactatgga tttcctactt atggtgggat tactttccat cctggaacta   1740
ctaaatctaa tgctgggatg aagcatggaa ccatggacac tgaatctaaa aaggaccctg   1800
aaggttgtga caaaagtgat gacaaaaaca ctgtaaacct ctttgggaaa gttattgaaa    1860
ccacagagca agatcaggag cccagcgagg ccaccgttgg gaatggtgag gtcactctaa   1920
cgtatgcaac aggaacaaaa gaagagagtg ctggagttca ggataacctc tttctagaga   1980
aggctatgca gcttgcaaag aggcatgcca atgccctttt cgactacgcg gtgacaggag   2040
acgtgaagat gctgctggcc gtccagcgcc atctcactgc tgtgcaggat gagaatgggg   2100
acagtgtctt acacttagca atcatccacc ttcattctca acttgtgagg gatctactag   2160
aagtcacatc tggtttgatt tctgatgaca ttatcaacat gagaaatgat ctgtaccaga   2220
cgcccttgca cttggcagtg atcactaagc aggaagatgt ggtggaggat ttgctgaggg   2280
ctggggccga cctgagcctt ctggaccgct tgggtaactc tgtttttgcac ctagctgcca   2340
aagaaggaca tgataaagtt ctcagtatct tactcaagca caaaaggca gcactacttc    2400
ttgaccaccc caacgggac ggtctgaatg ccattcatct agccatgatg agcaatagcc    2460
tgccatgttt gctgctgctg gtggccgctg ggctgacgt caatgctcag gagcagaagt    2520
ccgggcgcac agcactgcac ctggctgtgg agcacgacaa catctcattg gcaggctgcc   2580
tgctcctgga gggtgatgcc catgtggaca gtactaccta cgatgaacc acaccctgc     2640
atatagcagc tgggagaggg tccaccaggc tggcagctct tctcaaagca gcaggagcag   2700
```

| | |
|---|---|
| atcccctggt ggagaacttt gagcctctct atgacctgga tgactcttgg gaaaatgcag | 2760 |
| gagaggatga aggagttgtg cctggaacca cgcctctaga tatggccacc agctggcagg | 2820 |
| tatttgacat attaaatggg aaaccatatg agccagagtt tacatctgat gatttactag | 2880 |
| cacaaggaga catgaaacag ctggctgaag atgtgaagct gcagctgtat aagttactag | 2940 |
| aaattcctga tccagacaaa aactgggcta ctctggcgca gaaattaggt ctggggatac | 3000 |
| ttaataatgc cttccggctg agtcctgctc cttccaaaac acttatggac aactatgagg | 3060 |
| tctctggggg tacagtcaga gagctggtgg aggccctgag acaaatgggc tacaccgaag | 3120 |
| caattgaagt gatccaggca gcctccagcc cagtgaagac cacctctcag cccactcgc | 3180 |
| tgcctctctc gcctgcctcc acaaggcagc aaatagacga gctccgagac agtgacagtg | 3240 |
| tctgcgacag cggcgtggag catccttcc gcaaactcag ctttaccgag tctctgacca | 3300 |
| gtggtgcctc actgctaact ctcaacaaaa tgccccatga ttatgggcag gaaggacctc | 3360 |
| tagaaggcaa aatttagcct gctgacaatt cccacaccg tgtaaaccaa agccctaaaa | 3420 |
| ttccactgcg ttgtccacaa gacagaagct gaagtgcatc caaaggtgct cagagagccg | 3480 |
| gcccgcctga atcattctcg atttaactcg agacctttc aacttggctt cctttcttgg | 3540 |
| ttcataaatg aattttagtt tggttcactt acagatagta tctagcaatc acaacactgg | 3600 |
| ctgagcggat gcatctgggg atgaggttgc ttactaagct ttgccagctg ctgctggatc | 3660 |
| acagctgctt tctgttgtca ttgctgttgt ccctctgcta cgttcctatt gtcattaaag | 3720 |
| gtatcacggt cgccacctgg cattccttct gaccacagca tcattttgca ttcaaattaa | 3780 |
| gggttaagaa aagagatatt ttaaaatgag agtcacttga tgtgccattt taaaaaaaaa | 3840 |
| ggcatattgc ttttctaat gtggttattt ctctgatttg caaaaaaaaa aaaaaaaaaa | 3900 |
| atacttgtca atatttaaac atggttacaa tcattgctga aaatggtatt ttccccttt | 3960 |
| tctgcatttt gctattgtaa atatgttttt tagatcaaat actttaaagg aaaaaatgtt | 4020 |
| ggatttataa atgctatttt ttattttact tttataataa aaggaaaagc aaattgatga | 4080 |
| cctcaaaaaa aaa | 4093 |

<210> SEQ ID NO 66
<211> LENGTH: 4128
<212> TYPE: DNA
<213> ORGANISM: Mus <mouse, genus>
<220> FEATURE:
<223> OTHER INFORMATION: Mouse Nf-kb (NM_008689.2)

<400> SEQUENCE: 66

| | |
|---|---|
| gtccgtctgt ctgctctctc tcgacgtcag tgggaatttc cagccaggaa gtgagagagt | 60 |
| gagcgagaga ggacgagaga gaagtaccga ggcgagccgg gcaggaagag gaggtttcgc | 120 |
| caccccgagca gcccggctgc gcgctgacgg cttcccgtgc cctgcgcgcc cccggcctgc | 180 |
| cgccgccgcc gccgccgccg ccgccctcgg cctgctcgcg ggccggctct agcagcgcag | 240 |
| gccggagctc agggccccgc cgcgcccggc ccgccccgcg cttctccgcc cgcgccgcag | 300 |
| ccatggcgcg ccgctgagcc gcccgcccgc ccgcccgcgc ccgaccccgg ctcgggctcc | 360 |
| cgccggtccg cgccgctccg cagcgggagc ccgcaggcga ggagaggccg cgccgcatct | 420 |
| ccagggtacc ctcagaggcc agaagagggt gtcagagccc ttgtaactgg agtttgacgg | 480 |
| tcgtgagctg cgcatcttca ccatggcaga cgatgatccc tacggaactg gcaaatgtt | 540 |
| tcatttgaac actgctttga ctcactcaat atttaatgca gaattatatt caccagaaat | 600 |

```
accactgtca acagatggcc catacottca aatattagag caaccaaaac agaggggatt      660
tcgattccgc tatgtgtgtg aaggcccatc acacggaggg cttccggag cctctagtga      720 gaagaacaag aaatcctacc cacaggtcaa aatttgcaac tatgtggggc ctgcaaaggt     780
tatcgttcag ttggtcacaa atggaaaaaa catccacctg cacgcccaca gcctggtggg     840
caagcactgt gaggacgggg tatgcaccgt aacagcagga cccaaggaca tggtggttgg     900
ctttgcaaac ctgggaatac ttcatgtgac taagaaaaag gtatttgaaa cactggaagc     960
acggatgaca gaggcgtgta ttaggggcta taatcctgga cttctggtgc attctgacct    1020
tgcctatcta caagcagaag gcggaggaga ccggcaactc acagacagag agaaggagat    1080
catccgccag gcagccgtgc agcagaccaa ggagatggac ctgagcgtgg tgcgcctcat    1140
gttcacagcc ttcctccctg acagcactgg cagcttcact cggagactgg agcctgtggt    1200
gtcagacgcc atctatgata gcaaagcccc gaatgcatcc aacctgaaaa tcgtgagaat    1260
ggacagaaca gcaggatgtg tgacgggagg ggaggagatt taccttctct gtgacaaggt    1320
tcagaaagat gacatccaga ttcggtttta tgaagaggaa gaaaatggcg gagtttggga    1380
aggatttggg gacttttccc ccacagatgt tcatagacag tttgccattg tcttcaaaac    1440
gccaaagtat aaggatgtca acattacaaa gccagcttcc gtgtttgttc agcttcggag    1500
gaaatcagac ctggaaacta gtgaaccgaa accctttctc tactaccctg aaatcaaaga    1560
caaagaggaa gtgcaaagga acgccagaa gcttatgccg aacttctcgg acagcttcgg    1620
tggcggcagt ggagcgggag ccggtggtgg aggcatgttc ggtagtggcg gtggcggagg    1680
gagtaccgga agccctggcc cagggtatgg ctactcgaac tacggattc ctccctacgg    1740 tgggattaca ttccatcccg gagtcacgaa atccaacgca ggggtcaccc atggcaccat    1800
aaacaccaaa tttaaaaatg gccctaaaga ttgtgccaag agtgatgacg aggagagtct    1860
gactctccct gagaaggaaa ctgaaggtga agggcccagc ctgcccatgg cctgcaccaa    1920
gacggaaccc atcgccttgg catccaccat ggaagacaag gagcaggaca tgggatttca    1980
ggataacctc tttcttgaga aggctctgca gctcgccagg cgacacgcca acgccctttt    2040
cgactacgca gtgacggggg atgtgaagat gttgctggcc gtgcaacgcc atctcaccgc    2100
cgtgcaggat gagaatgggg acagtgtctt acacttagcc atcatccacc tccacgctca    2160
gcttgtgagg gatctgctgg aagtcacatc tggtttgatc tctgatgaca tcatcaacat    2220
gagaaatgac ctgtatcaga cacctctgca cttggccgtg atcaccaagc aggaagatgt    2280
agtagaggat ttgctgaggg ttggggctga cctgagcctt ctggaccgct ggggcaactc    2340
tgtcctgcac ctagctgcca agaaggaca cgacagaatc ctcagcatcc tgctcaagag    2400
cagaaaagca gcgccccta tcgaccaccc caatggggaa ggtctaaatg ccatccacat    2460
agctgtgatg agcaatagcc tgccatgtct gctgctgctg gtggctgccg gggcagaagt    2520
caatgctcag gagcagaagt ctgggcgcac agcgctgcac ctggccgtgg agtacgacaa    2580
catctccttg gctggctgcc tgcttctgga gggtgatgcc cacgtggaca gtaccaccta    2640
tgatgggact acacctctgc atatagcggc cggaagaggg tccaccagac tggcagctct    2700
tctcaaagca gcaggagcag accccctggt ggagaacttt gagcctctct atgacctgga    2760
cgactcttgg gagaaggctg gagaagatga gggagtggtg ccaggtacca caccctgga    2820 catggctgcc aactggcagg tatttgacat actaaatggg aaaccgtatg agcctgtgtt    2880
cacatctgat gatatactac cacaaggga catgaagcag ctgacagaag acacgaggct    2940
acaactctgc aaactgctgg aaattcctga tccagacaaa actgggccaa ctctggcaca    3000
```

```
gaagttgggt ctggggatac tgaacaatgc cttccggctg agtcctgctc cttctaaaac    3060
tctcatggac aactatgagg tctctggggg taccatcaaa gagctgatgg aggccctgca    3120
acagatgggc tacacagagg ccattgaagt gatccaggca gccttccgca ccccggcaac    3180
cacagcctcc agccccgtga ccactgctca ggtccactgt ctgcctctct cgtcttcctc    3240
cacgaggcag cacatagatg aactccggga tagtgacagc gtctgtgaca gtggtgtgga    3300
gacatccttc cgcaaactca gctttacaga gtctcttact ggagacagcc cactgctatc    3360
tctgaacaaa atgccccacg gttatgggca ggaaggacct attgaaggca aaatttagcc    3420
tgctggccgt tcccccacac tgtgtaaacc aaagccctga cagtccattg catcgtccca    3480
aaggaggaag gcaaagcgaa tccaaaggtg ctggagaatc gccggcctgc agggtcactc    3540
gatttcattc aaggccttcc gaatttggcg tcctttcttg gttctgaaat gaatgtagt    3600 tgccacgcac agacggtgtc tagcaatcat ggcgctcgct cgctcagctg cactctatgg    3660
ctcaggtgca gtgtcttgag ctttctctgc tgctactgga tcacatttgc tttgtgttgt    3720
tactgctgtc cctccgctgg gttcctgctg tcattaaaag gtgtcgctgt ccccacccgg    3780
tgtcctttct agccatctac tgtaagttgt gcattcaaat taagattaag gaaaaacata    3840
tttttaaatg agtaccttga tgcgcaataa aaaaagaca tttctttttt taatgtggtt    3900
tatctgtgat ttaaaaataa aaaacacatg aacttacaat atttaaaaca tgctacaatc    3960
agtgctgaaa atagtatttt ccccgtttta tgcatttac tattgtaaat atgttttcta    4020
aatcaaatac tttaaaagaa gaatgttga atttataaat gctatttact ttttattt    4080 acttttataa taaaagtaca agcacattgt tgacctaaaa aaaaaaaa              4128
```

<210> SEQ ID NO 67
<211> LENGTH: 127
<212> TYPE: PRT
<213> ORGANISM: Homo sapiens
<220> FEATURE:
<223> OTHER INFORMATION: Human BATF3

<400> SEQUENCE: 67

Met Ser Gln Gly Leu Pro Ala Ala Gly Ser Val Leu Gln Arg Ser Val
1               5                   10                  15

Ala Ala Pro Gly Asn Gln Pro Gln Pro Gln Pro Gln Gln Gln Ser Pro
            20                  25                  30

Glu Asp Asp Asp Arg Lys Val Arg Arg Arg Glu Lys Asn Arg Val Ala
        35                  40                  45

Ala Gln Arg Ser Arg Lys Lys Gln Thr Gln Lys Ala Asp Lys Leu His
    50                  55                  60

Glu Glu Tyr Glu Ser Leu Glu Gln Glu Asn Thr Met Leu Arg Arg Glu
65                  70                  75                  80

Ile Gly Lys Leu Thr Glu Glu Leu Lys His Leu Thr Glu Ala Leu Lys
                85                  90                  95

Glu His Glu Lys Met Cys Pro Leu Leu Leu Cys Pro Met Asn Phe Val
            100                 105                 110

Pro Val Pro Pro Arg Pro Asp Pro Val Ala Gly Cys Leu Pro Arg
        115                 120                 125

<210> SEQ ID NO 68
<211> LENGTH: 118
<212> TYPE: PRT
<213> ORGANISM: Mus musculus
<220> FEATURE:

<223> OTHER INFORMATION: Mouse BATF3

<400> SEQUENCE: 68

```
Met Ser Gln Gly Pro Pro Ala Val Ser Val Leu Gln Arg Ser Val Asp
1               5                   10                  15

Ala Pro Gly Asn Gln Pro Gln Ser Pro Lys Asp Asp Arg Lys Val
                20                  25                  30

Arg Arg Arg Glu Lys Asn Arg Val Ala Ala Gln Arg Ser Arg Lys Lys
            35                  40                  45

Gln Thr Gln Lys Ala Asp Lys Leu His Glu Glu His Glu Ser Leu Glu
    50                  55                  60

Gln Glu Asn Ser Val Leu Arg Arg Glu Ile Ser Lys Leu Lys Glu Glu
65                  70                  75                  80

Leu Arg His Leu Ser Glu Val Leu Lys Glu His Glu Lys Met Cys Pro
                85                  90                  95

Leu Leu Leu Cys Pro Met Asn Phe Val Gln Leu Arg Ser Asp Pro Val
                100                 105                 110

Ala Ser Cys Leu Pro Arg
            115
```

<210> SEQ ID NO 69
<211> LENGTH: 426
<212> TYPE: PRT
<213> ORGANISM: Homo sapiens
<220> FEATURE:
<223> OTHER INFORMATION: Human IRF8

<400> SEQUENCE: 69

```
Met Cys Asp Arg Asn Gly Gly Arg Arg Leu Arg Gln Trp Leu Ile Glu
1               5                   10                  15

Gln Ile Asp Ser Ser Met Tyr Pro Gly Leu Ile Trp Glu Asn Glu Glu
                20                  25                  30

Lys Ser Met Phe Arg Ile Pro Trp Lys His Ala Gly Lys Gln Asp Tyr
            35                  40                  45

Asn Gln Glu Val Asp Ala Ser Ile Phe Lys Ala Trp Ala Val Phe Lys
    50                  55                  60

Gly Lys Phe Lys Glu Gly Asp Lys Ala Glu Pro Ala Thr Trp Lys Thr
65                  70                  75                  80

Arg Leu Arg Cys Ala Leu Asn Lys Ser Pro Asp Phe Glu Glu Val Thr
                85                  90                  95

Asp Arg Ser Gln Leu Asp Ile Ser Glu Pro Tyr Lys Val Tyr Arg Ile
                100                 105                 110

Val Pro Glu Glu Glu Gln Lys Cys Lys Leu Gly Val Ala Thr Ala Gly
            115                 120                 125

Cys Val Asn Glu Val Thr Glu Met Glu Cys Gly Arg Ser Glu Ile Asp
        130                 135                 140

Glu Leu Ile Lys Glu Pro Ser Val Asp Asp Tyr Met Gly Met Ile Lys
145                 150                 155                 160

Arg Ser Pro Ser Pro Pro Glu Ala Cys Arg Ser Gln Leu Leu Pro Asp
                165                 170                 175

Trp Trp Ala Gln Gln Pro Ser Thr Gly Val Pro Leu Val Thr Gly Tyr
                180                 185                 190

Thr Thr Tyr Asp Ala His His Ser Ala Phe Ser Gln Met Val Ile Ser
            195                 200                 205

Phe Tyr Tyr Gly Gly Lys Leu Val Gly Gln Ala Thr Thr Thr Cys Pro
        210                 215                 220
```

Glu Gly Cys Arg Leu Ser Leu Ser Gln Pro Gly Leu Pro Gly Thr Lys
225                 230                 235                 240

Leu Tyr Gly Pro Glu Gly Leu Glu Leu Val Arg Phe Pro Pro Ala Asp
            245                 250                 255

Ala Ile Pro Ser Glu Arg Gln Arg Gln Val Thr Arg Lys Leu Phe Gly
        260                 265                 270

His Leu Glu Arg Gly Val Leu Leu His Ser Ser Arg Gln Gly Val Phe
    275                 280                 285

Val Lys Arg Leu Cys Gln Gly Arg Val Phe Cys Ser Gly Asn Ala Val
290                 295                 300

Val Cys Lys Gly Arg Pro Asn Lys Leu Glu Arg Asp Glu Val Val Gln
305                 310                 315                 320

Val Phe Asp Thr Ser Gln Phe Phe Arg Glu Leu Gln Gln Phe Tyr Asn
                325                 330                 335

Ser Gln Gly Arg Leu Pro Asp Gly Arg Val Val Leu Cys Phe Gly Glu
            340                 345                 350

Glu Phe Pro Asp Met Ala Pro Leu Arg Ser Lys Leu Ile Leu Val Gln
        355                 360                 365

Ile Glu Gln Leu Tyr Val Arg Gln Leu Ala Glu Ala Gly Lys Ser
    370                 375                 380

Cys Gly Ala Gly Ser Val Met Gln Ala Pro Glu Glu Pro Pro Asp
385                 390                 395                 400

Gln Val Phe Arg Met Phe Pro Asp Ile Cys Ala Ser His Gln Arg Ser
                405                 410                 415

Phe Phe Arg Glu Asn Gln Gln Ile Thr Val
            420                 425

<210> SEQ ID NO 70
<211> LENGTH: 424
<212> TYPE: PRT
<213> ORGANISM: Mus musculus
<220> FEATURE:
<223> OTHER INFORMATION: Mouse IRF8

<400> SEQUENCE: 70

Met Cys Asp Arg Asn Gly Gly Arg Arg Leu Arg Gln Trp Leu Ile Glu
1                   5                   10                  15

Gln Ile Asp Ser Ser Met Tyr Pro Gly Leu Ile Trp Glu Asn Asp Glu
            20                  25                  30

Lys Thr Met Phe Arg Ile Pro Trp Lys His Ala Gly Lys Gln Asp Tyr
        35                  40                  45

Asn Gln Glu Val Asp Ala Ser Ile Phe Lys Ala Trp Ala Val Phe Lys
50                  55                  60

Gly Lys Phe Lys Glu Gly Asp Lys Ala Glu Pro Ala Thr Trp Lys Thr
65                  70                  75                  80

Arg Leu Arg Cys Ala Leu Asn Lys Ser Pro Asp Phe Glu Glu Val Thr
                85                  90                  95

Asp Arg Ser Gln Leu Asp Ile Ser Glu Pro Tyr Lys Val Tyr Arg Ile
            100                 105                 110

Val Pro Glu Glu Glu Gln Lys Cys Lys Leu Gly Val Ala Pro Ala Gly
        115                 120                 125

Cys Met Ser Glu Val Pro Glu Met Glu Cys Gly Arg Ser Glu Ile Glu
    130                 135                 140

Glu Leu Ile Lys Glu Pro Ser Val Asp Glu Tyr Met Gly Met Thr Lys
145                 150                 155                 160

```
Arg Ser Pro Ser Pro Glu Ala Cys Arg Ser Gln Ile Leu Pro Asp
            165                 170                 175

Trp Trp Val Gln Gln Pro Ser Ala Gly Leu Pro Leu Val Thr Gly Tyr
            180                 185                 190

Ala Ala Tyr Asp Thr His His Ser Ala Phe Ser Gln Met Val Ile Ser
            195                 200                 205

Phe Tyr Tyr Gly Gly Lys Leu Val Gly Gln Ala Thr Thr Thr Cys Leu
        210                 215                 220

Glu Gly Cys Arg Leu Ser Leu Ser Gln Pro Gly Leu Pro Lys Leu Tyr
225                 230                 235                 240

Gly Pro Asp Gly Leu Glu Pro Val Cys Phe Pro Thr Ala Asp Thr Ile
                245                 250                 255

Pro Ser Glu Arg Gln Arg Gln Val Thr Arg Lys Leu Phe Gly His Leu
                260                 265                 270

Glu Arg Gly Val Leu Leu His Ser Asn Arg Lys Gly Val Phe Val Lys
            275                 280                 285

Arg Leu Cys Gln Gly Arg Val Phe Cys Ser Gly Asn Ala Val Val Cys
        290                 295                 300

Lys Gly Arg Pro Asn Lys Leu Glu Arg Asp Glu Val Val Gln Val Phe
305                 310                 315                 320

Asp Thr Asn Gln Phe Ile Arg Glu Leu Gln Gln Phe Tyr Ala Thr Gln
                325                 330                 335

Ser Arg Leu Pro Asp Ser Arg Val Val Leu Cys Phe Gly Glu Glu Phe
            340                 345                 350

Pro Asp Thr Val Pro Leu Arg Ser Lys Leu Ile Leu Val Gln Val Glu
            355                 360                 365

Gln Leu Tyr Ala Arg Gln Leu Val Glu Ala Gly Lys Ser Cys Gly
        370                 375                 380

Ala Gly Ser Leu Met Pro Ala Leu Glu Glu Pro Gln Pro Asp Gln Ala
385                 390                 395                 400

Phe Arg Met Phe Pro Asp Ile Cys Thr Ser His Gln Arg Pro Phe Phe
                405                 410                 415

Arg Glu Asn Gln Gln Ile Thr Val
            420

<210> SEQ ID NO 71
<211> LENGTH: 271
<212> TYPE: PRT
<213> ORGANISM: Homo sapiens
<220> FEATURE:
<223> OTHER INFORMATION: Human PU.1

<400> SEQUENCE: 71

Met Leu Gln Ala Cys Lys Met Glu Gly Phe Pro Leu Val Pro Pro Gln
1               5                   10                  15

Pro Ser Glu Asp Leu Val Pro Tyr Asp Thr Asp Leu Tyr Gln Arg Gln
            20                  25                  30

Thr His Glu Tyr Tyr Pro Tyr Leu Ser Ser Asp Gly Glu Ser His Ser
        35                  40                  45

Asp His Tyr Trp Asp Phe His Pro His His Val His Ser Glu Phe Glu
    50                  55                  60

Ser Phe Ala Glu Asn Asn Phe Thr Glu Leu Gln Ser Val Gln Pro Pro
65                  70                  75                  80

Gln Leu Gln Gln Leu Tyr Arg His Met Glu Leu Glu Gln Met His Val
            85                  90                  95
```

```
Leu Asp Thr Pro Met Val Pro Pro His Pro Ser Leu Gly His Gln Val
                100                 105                 110

Ser Tyr Leu Pro Arg Met Cys Leu Gln Tyr Pro Ser Leu Ser Pro Ala
            115                 120                 125

Gln Pro Ser Ser Asp Glu Glu Gly Glu Arg Gln Ser Pro Pro Leu
130                 135                 140

Glu Val Ser Asp Gly Glu Ala Asp Gly Leu Glu Pro Gly Pro Gly Leu
145                 150                 155                 160

Leu Pro Gly Glu Thr Gly Ser Lys Lys Ile Arg Leu Tyr Gln Phe
                165                 170                 175

Leu Leu Asp Leu Leu Arg Ser Gly Asp Met Lys Asp Ser Ile Trp Trp
            180                 185                 190

Val Asp Lys Asp Lys Gly Thr Phe Gln Phe Ser Ser Lys His Lys Glu
        195                 200                 205

Ala Leu Ala His Arg Trp Gly Ile Gln Lys Gly Asn Arg Lys Lys Met
        210                 215                 220

Thr Tyr Gln Lys Met Ala Arg Ala Leu Arg Asn Tyr Gly Lys Thr Gly
225                 230                 235                 240

Glu Val Lys Lys Val Lys Lys Lys Leu Thr Tyr Gln Phe Ser Gly Glu
                245                 250                 255

Val Leu Gly Arg Gly Gly Leu Ala Glu Arg Arg His Pro Pro His
            260                 265                 270

<210> SEQ ID NO 72
<211> LENGTH: 272
<212> TYPE: PRT
<213> ORGANISM: Mus musculus
<220> FEATURE:
<223> OTHER INFORMATION: Mouse PU.1

<400> SEQUENCE: 72

Met Leu Gln Ala Cys Lys Met Glu Gly Phe Ser Leu Thr Ala Pro Pro
1               5                   10                  15

Ser Asp Asp Leu Val Thr Tyr Asp Ser Glu Leu Tyr Gln Arg Pro Met
                20                  25                  30

His Asp Tyr Tyr Ser Phe Val Gly Ser Asp Gly Glu Ser His Ser Asp
            35                  40                  45

His Tyr Trp Asp Phe Ser Ala His His Val His Asn Asn Glu Phe Glu
        50                  55                  60

Asn Phe Pro Glu Asn His Phe Thr Glu Leu Gln Ser Val Gln Pro Pro
65                  70                  75                  80

Gln Leu Gln Gln Leu Tyr Arg His Met Glu Leu Glu Gln Met His Val
                85                  90                  95

Leu Asp Thr Pro Met Val Pro Pro His Thr Gly Leu Ser His Gln Val
                100                 105                 110

Ser Tyr Met Pro Arg Met Cys Phe Pro Tyr Gln Thr Leu Ser Pro Ala
            115                 120                 125

His Gln Gln Ser Ser Asp Glu Glu Gly Glu Arg Gln Ser Pro Pro
130                 135                 140

Leu Glu Val Ser Asp Gly Glu Ala Asp Gly Leu Glu Pro Gly Pro Gly
145                 150                 155                 160

Leu Leu His Gly Glu Thr Gly Ser Lys Lys Lys Ile Arg Leu Tyr Gln
                165                 170                 175

Phe Leu Leu Asp Leu Leu Arg Ser Gly Asp Met Lys Asp Ser Ile Trp
            180                 185                 190
```

-continued

```
Trp Val Asp Lys Asp Lys Gly Thr Phe Gln Phe Ser Ser Lys His Lys
        195                 200                 205

Glu Ala Leu Ala His Arg Trp Gly Ile Gln Lys Gly Asn Arg Lys Lys
    210                 215                 220

Met Thr Tyr Gln Lys Met Ala Arg Ala Leu Arg Asn Tyr Gly Lys Thr
225                 230                 235                 240

Gly Glu Val Lys Lys Val Lys Lys Leu Thr Tyr Gln Phe Ser Gly
                245                 250                 255

Glu Val Leu Gly Arg Gly Gly Leu Ala Glu Arg Leu Pro Pro His
        260                 265                 270
```

<210> SEQ ID NO 73
<211> LENGTH: 671
<212> TYPE: PRT
<213> ORGANISM: Homo sapiens
<220> FEATURE:
<223> OTHER INFORMATION: Human TCF4

<400> SEQUENCE: 73

```
Met His His Gln Gln Arg Met Ala Ala Leu Gly Thr Asp Lys Glu Leu
1               5                   10                  15

Ser Asp Leu Leu Asp Phe Ser Ala Met Phe Ser Pro Pro Val Ser Ser
            20                  25                  30

Gly Lys Asn Gly Pro Thr Ser Leu Ala Ser Gly His Phe Thr Gly Ser
        35                  40                  45

Asn Val Glu Asp Arg Ser Ser Ser Gly Ser Trp Gly Asn Gly Gly His
    50                  55                  60

Pro Ser Pro Ser Arg Asn Tyr Gly Asp Gly Thr Pro Tyr Asp His Met
65                  70                  75                  80

Thr Ser Arg Asp Leu Gly Ser His Asp Asn Leu Ser Pro Pro Phe Val
                85                  90                  95

Asn Ser Arg Ile Gln Ser Lys Thr Glu Arg Gly Ser Tyr Ser Ser Tyr
            100                 105                 110

Gly Arg Glu Ser Asn Leu Gln Gly Cys His Gln Gln Ser Leu Leu Gly
        115                 120                 125

Gly Asp Met Asp Met Gly Asn Pro Gly Thr Leu Ser Pro Thr Lys Pro
    130                 135                 140

Gly Ser Gln Tyr Tyr Gln Tyr Ser Ser Asn Asn Pro Arg Arg Arg Pro
145                 150                 155                 160

Leu His Ser Ser Ala Met Glu Val Gln Thr Lys Lys Val Arg Lys Val
                165                 170                 175

Pro Pro Gly Leu Pro Ser Ser Val Tyr Ala Pro Ser Ala Ser Thr Ala
            180                 185                 190

Asp Tyr Asn Arg Asp Ser Pro Gly Tyr Pro Ser Ser Lys Pro Ala Thr
        195                 200                 205

Ser Thr Phe Pro Ser Ser Phe Phe Met Gln Asp Gly His His Ser Ser
    210                 215                 220

Asp Pro Trp Ser Ser Ser Gly Met Asn Gln Pro Gly Tyr Ala Gly
225                 230                 235                 240

Met Leu Gly Asn Ser Ser His Ile Pro Gln Ser Ser Tyr Cys Ser
                245                 250                 255

Leu His Pro His Glu Arg Leu Ser Tyr Pro Ser His Ser Ser Ala Asp
            260                 265                 270

Ile Asn Ser Ser Leu Pro Pro Met Ser Thr Phe His Arg Ser Gly Thr
        275                 280                 285
```

```
Asn His Tyr Ser Thr Ser Ser Cys Thr Pro Ala Asn Gly Thr Asp
        290                 295                 300

Ser Ile Met Ala Asn Arg Gly Ser Gly Ala Ala Gly Ser Ser Gln Thr
305                 310                 315                 320

Gly Asp Ala Leu Gly Lys Ala Leu Ala Ser Ile Tyr Ser Pro Asp His
                325                 330                 335

Thr Asn Asn Ser Phe Ser Ser Asn Pro Ser Thr Pro Val Gly Ser Pro
            340                 345                 350

Pro Ser Leu Ser Ala Gly Thr Ala Val Trp Ser Arg Asn Gly Gly Gln
        355                 360                 365

Ala Ser Ser Ser Pro Asn Tyr Glu Gly Pro Leu His Ser Leu Gln Ser
370                 375                 380

Arg Ile Glu Asp Arg Leu Glu Arg Leu Asp Asp Ala Ile His Val Leu
385                 390                 395                 400

Arg Asn His Ala Val Gly Pro Ser Thr Ala Met Pro Gly Gly His Gly
                405                 410                 415

Asp Met His Gly Ile Ile Gly Pro Ser His Asn Gly Ala Met Gly Gly
            420                 425                 430

Leu Gly Ser Gly Tyr Gly Thr Gly Leu Leu Ser Ala Asn Arg His Ser
        435                 440                 445

Leu Met Val Gly Thr His Arg Glu Asp Gly Val Ala Leu Arg Gly Ser
450                 455                 460

His Ser Leu Leu Pro Asn Gln Val Pro Val Pro Gln Leu Pro Val Gln
465                 470                 475                 480

Ser Ala Thr Ser Pro Asp Leu Asn Pro Pro Gln Asp Pro Tyr Arg Gly
                485                 490                 495

Met Pro Pro Gly Leu Gln Gly Gln Ser Val Ser Ser Gly Ser Ser Glu
            500                 505                 510

Ile Lys Ser Asp Asp Glu Gly Asp Glu Asn Leu Gln Asp Thr Lys Ser
        515                 520                 525

Ser Glu Asp Lys Lys Leu Asp Asp Lys Lys Asp Ile Lys Ser Ile
530                 535                 540

Thr Arg Ser Arg Ser Ser Asn Asn Asp Asp Glu Asp Leu Thr Pro Glu
545                 550                 555                 560

Gln Lys Ala Glu Arg Glu Lys Glu Arg Arg Met Ala Asn Asn Ala Arg
                565                 570                 575

Glu Arg Leu Arg Val Arg Asp Ile Asn Glu Ala Phe Lys Glu Leu Gly
            580                 585                 590

Arg Met Val Gln Leu His Leu Lys Ser Asp Lys Pro Gln Thr Lys Leu
        595                 600                 605

Leu Ile Leu His Gln Ala Val Ala Val Ile Leu Ser Leu Glu Gln Gln
610                 615                 620

Val Arg Glu Arg Asn Leu Asn Pro Lys Ala Ala Cys Leu Lys Arg Arg
625                 630                 635                 640

Glu Glu Glu Lys Val Ser Ser Glu Pro Pro Leu Ser Leu Ala Gly
                645                 650                 655

Pro His Pro Gly Met Gly Asp Ala Ser Asn His Met Gly Gln Met
            660                 665                 670

<210> SEQ ID NO 74
<211> LENGTH: 670
<212> TYPE: PRT
<213> ORGANISM: Mus musculus
<220> FEATURE:
```

<223> OTHER INFORMATION: Mouse TCF4

<400> SEQUENCE: 74

```
Met His His Gln Gln Arg Met Ala Ala Leu Gly Thr Asp Lys Glu Leu
1               5                   10                  15

Ser Asp Leu Leu Asp Phe Ser Ala Met Phe Ser Pro Pro Val Ser Ser
            20                  25                  30

Gly Lys Asn Gly Pro Thr Ser Leu Ala Ser Gly His Phe Thr Gly Ser
        35                  40                  45

Asn Val Glu Asp Arg Ser Ser Gly Ser Trp Gly Thr Gly Gly His
    50                  55                  60

Pro Ser Pro Ser Arg Asn Tyr Gly Asp Gly Thr Pro Tyr Asp His Met
65                  70                  75                  80

Thr Ser Arg Asp Leu Gly Ser His Asp Asn Leu Ser Pro Pro Phe Val
                85                  90                  95

Asn Ser Arg Ile Gln Ser Lys Thr Glu Arg Gly Ser Tyr Ser Ser Tyr
            100                 105                 110

Gly Arg Glu Asn Val Gln Gly Cys His Gln Gln Ser Leu Leu Gly Gly
        115                 120                 125

Asp Met Asp Met Gly Asn Pro Gly Thr Leu Ser Pro Thr Lys Pro Gly
    130                 135                 140

Ser Gln Tyr Tyr Gln Tyr Ser Ser Asn Asn Ala Arg Arg Arg Pro Leu
145                 150                 155                 160

His Ser Ser Ala Met Glu Val Gln Thr Lys Lys Val Arg Lys Val Pro
                165                 170                 175

Pro Gly Leu Pro Ser Ser Val Tyr Ala Pro Ser Ala Ser Thr Ala Asp
            180                 185                 190

Tyr Asn Arg Asp Ser Pro Gly Tyr Pro Ser Ser Lys Pro Ala Ala Ser
        195                 200                 205

Thr Phe Pro Ser Ser Phe Phe Met Gln Asp Gly His His Ser Ser Asp
    210                 215                 220

Pro Trp Ser Ser Ser Ser Gly Met Asn Gln Pro Gly Tyr Gly Gly Met
225                 230                 235                 240

Leu Gly Asn Ser Ser His Ile Pro Gln Ser Ser Tyr Cys Ser Leu
                245                 250                 255

His Pro His Glu Arg Leu Ser Tyr Pro Ser His Ser Ser Ala Asp Ile
            260                 265                 270

Asn Ser Ser Leu Pro Pro Met Ser Thr Phe His Arg Ser Gly Thr Asn
        275                 280                 285

His Tyr Ser Thr Ser Ser Cys Thr Pro Pro Ala Asn Gly Thr Asp Ser
    290                 295                 300

Ile Met Ala Asn Arg Gly Thr Gly Ala Ala Gly Ser Ser Gln Thr Gly
305                 310                 315                 320

Asp Ala Leu Gly Lys Ala Leu Ala Ser Ile Tyr Ser Pro Asp His Thr
                325                 330                 335

Asn Asn Ser Phe Ser Ser Asn Pro Ser Thr Pro Val Gly Ser Pro Pro
            340                 345                 350

Ser Leu Ser Ala Gly Thr Ala Val Trp Ser Arg Asn Gly Gly Gln Ala
        355                 360                 365

Ser Ser Ser Pro Asn Tyr Glu Gly Pro Leu His Ser Leu Gln Ser Arg
    370                 375                 380

Ile Glu Asp Arg Leu Glu Arg Leu Asp Asp Ala Ile His Val Leu Arg
385                 390                 395                 400
```

```
Asn His Ala Val Gly Pro Ser Thr Ala Val Pro Gly Gly His Gly Asp
                405                 410                 415
Met His Gly Ile Met Gly Pro Ser His Asn Gly Ala Met Gly Ser Leu
            420                 425                 430
Gly Ser Gly Tyr Gly Thr Ser Leu Leu Ser Ala Asn Arg His Ser Leu
            435                 440                 445
Met Val Gly Ala His Arg Glu Asp Gly Val Ala Leu Arg Gly Ser His
    450                 455                 460
Ser Leu Leu Pro Asn Gln Val Pro Val Pro Gln Leu Pro Val Gln Ser
465                 470                 475                 480
Ala Thr Ser Pro Asp Leu Asn Pro Pro Gln Asp Pro Tyr Arg Gly Met
            485                 490                 495
Pro Pro Gly Leu Gln Gly Gln Ser Val Ser Ser Gly Ser Ser Glu Ile
            500                 505                 510
Lys Ser Asp Asp Glu Gly Asp Glu Asn Leu Gln Asp Thr Lys Ser Ser
            515                 520                 525
Glu Asp Lys Lys Leu Asp Asp Lys Lys Asp Ile Lys Ser Ile Thr
    530                 535                 540
Arg Ser Arg Ser Ser Asn Asn Asp Asp Glu Asp Leu Thr Pro Glu Gln
545                 550                 555                 560
Lys Ala Glu Arg Glu Lys Glu Arg Arg Met Ala Asn Asn Ala Arg Glu
                565                 570                 575
Arg Leu Arg Val Arg Asp Ile Asn Glu Ala Phe Lys Glu Leu Gly Arg
            580                 585                 590
Met Val Gln Leu His Leu Lys Ser Asp Lys Pro Gln Thr Lys Leu Leu
        595                 600                 605
Ile Leu His Gln Ala Val Ala Val Ile Leu Ser Leu Glu Gln Gln Val
        610                 615                 620
Arg Glu Arg Asn Leu Asn Pro Lys Ala Ala Cys Leu Lys Arg Arg Glu
625                 630                 635                 640
Glu Glu Lys Val Ser Ser Glu Pro Pro Leu Ser Leu Ala Gly Pro
                645                 650                 655
His Pro Gly Met Gly Asp Ala Ala Asn His Met Gly Gln Met
            660                 665                 670
```

COMPOSITIONS FOR REPROGRAMMING CELLS INTO DENDRITIC CELLS OR ANTIGEN PRESENTING CELLS, METHODS AND USES THEREOF

TECHNICAL FIELD

The present disclosure relates to the development of methods for making dendritic cells or antigen presenting cells with antigen presenting capacity from differentiated, multipotent or pluripotent stem cells by introducing and expressing isolated transcription factors. More particularly, the disclosure provides methods for redirecting differentiated, multipotent or pluripotent stem cells to a dendritic cell or antigen presenting cell state by direct cellular reprogramming with a surprisingly use of combinations of transcription factors.

BACKGROUND

Cellular reprogramming relies on rewiring the epigenetic and transcriptional network of one cell state to that of a different cell type. Transcription factor (TF)-transduction experiments have highlighted the plasticity of adult somatic or differentiated cells, providing new technologies to generate any desired cell type. Through forced expression of TFs, it is possible to reprogram somatic or differentiated cells into induced pluripotent stem cells (iPSCs) that are remarkably similar to embryonic stem cells (1, 2). Alternatively, a somatic cell can also be converted into another specialized cell type (3). Direct lineage conversion has proven successful to reprogram mouse and human fibroblasts into several cell types, such as neurons, cardiomyocytes and hepatocytes, using TFs specifying the target-cell identity (4). Lineage conversions were also demonstrated in the hematopoietic system, where forced expression of TFs induced a macrophage fate in B cells and fibroblasts (5) and the direct reprogramming of mouse fibroblasts into clonogenic hematopoietic progenitors is achieved with Gata2, Gfi1b, cFos and Etv6 (6). These four TFs induce a dynamic, multi-stage hemogenic process that progresses through an endothelial-like intermediate, recapitulating developmental hematopoiesis in vitro (7).

Reprogrammed cells are very promising therapeutic tools for regenerative medicine, and cells obtained by differentiation of iPSCs are already being tested in clinical studies. For hematopoietic regeneration, however, approaches to generate mature blood cells from iPSCs are still lacking. Therefore, alternative strategies are needed to generate patient-specific definitive hematopoietic cells that can be used as blood products. Given the opportunity of direct cell reprogramming mediated by TFs, one can envision the generation of antigen-presenting cells (APCs) of the immune system such as Dendritic Cells (DCs).

DCs are professional APCs capable of activating T cell responses by displaying peptide antigens complexed with the major histocompatibility complex (MHC) on the surface, together with all of the necessary soluble and membrane associated co-stimulatory molecules. DCs induce primary immune responses, potentiate the effector functions of previously primed T-lymphocytes, and orchestrate communication between innate and adaptive immunity. DCs are found in most tissues, where they continuously sample the antigenic environment and use several types of receptors to monitor for invading pathogens. In steady state, and at an increased rate upon detection of pathogens, sentinel DC in non-lymphoid tissues migrate to the lymphoid organs where they present to T cells the antigens they have collected and processed. The phenotype acquired by the T cell depends on the context in which the DC presents its antigen. If the antigen is derived from a pathogen, or damaged self, DC receive danger signals, become activated and the T cells are then stimulated to become effectors, necessary to provide protective immunity.

The ability of DCs to induce adaptive immunity has boosted research on DC-vaccine strategies for bacterial, viral and parasitic pathogens and cancer immunotherapy. In fact, clinical trials are ongoing utilizing DC-mediated immunotherapy for several tumor types, including solid and hematological tumors (8). However, the clinical outcome has been inconsistent, probably associated with variable efficiency in generating DCs in vitro: autologous monocytes give origin to less-efficient DCs, and hematopoietic progenitors are isolated in very low numbers. In addition, these precursor cells are commonly compromised in cancer-bearing patients, resulting in the generation of dysfunctional DCs (8, 9). Cancer evasion mechanisms also may be underlying the lack of consistent therapeutic advantages in DC-based immunotherapies. During tumor progression cancer cells exploit several immunological processes to escape immune surveillance. These adaptations, together with cancer antigen heterogeneity, prevent the recognition of tumor antigens by the immune system and are consequently responsible for the reduced immunogenicity of tumor cells and current immunotherapies.

The generation of APCs by direct reprogramming opens new opportunities to a better understanding of DC specification and cellular identity, contributing to a more efficient control of immune responses using autologous-engineered cells.

These facts are disclosed in order to illustrate the technical problem addressed by the present disclosure.

GENERAL DESCRIPTION

The present subject matter identifies several isolated transcription factors that surprisingly reprogram or induce differentiated cell, multipotent or pluripotent stem cell into dendritic cell, in vitro, ex vivo or in vivo.

Surprisingly the induced Dendritic Cells generated by reprogramming as described in the present disclosure, are intrinsically more mature than splenic DCs (natural DCs) and are less dependent on exogenous activation stimuli for antigen presentation.

DCs are professional APCs located throughout the body functioning at the interface of the innate and adaptive immune system. DCs are able to provide a crucial link between the external environment and the adaptive immune system through their ability to capture, process and present antigens to T cells, targeting them to different types of immune responses or to tolerance. Firstly, DCs have to capture antigens and process them through major histocompatibility complex (MHC) class I and MHC class II. Following their activation, DCs are able to migrate towards the local draining lymph nodes priming multiple B cell and T cell responses, a key feature of adaptive immunity. The early protective efficacy is primarily conferred by the induction of antigen-specific antibodies produced by B lymphocytes. The long-term protection against specific antigens requires the persistence of specific antibodies and the generation of immunological memory that could provide a rapid and efficient response after subsequent antigen exposure. DCs, as professional APCs, have the ability to cross-present antigens, meaning that, in addition to its classical ability to present exogenous antigens on MHC class II and endogenous antigens on MHC class I, they are also able to present exogenous antigens on MHC class I, a critical step for the generation of Cytotoxic T Lymphocyte responses (CTL).

The ontogeny and/or microenvironment in which DC are positioned may result in the expression of distinct combinations of surface receptors by DCs. For example, phenotypic criteria alone allow the classification of mouse DCs into different subpopulations. Of these, conventional DC (cDC) in lymphoid tissues are traditionally sub-divided into cDC1 and cDC2 subpopulations. It has been argued that different DC subsets may be involved in specific recognition of certain pathogens and/or regulate different immune responses, e.g. Th1 or Th2 (immunity) or regulatory T cells (tolerance). However, the phenotype and functional behavior of DCs is also significantly conditioned by external activating stimuli, denoting significant plasticity. cDC1 and cDC2 subsets differentially prime Th1 and Th2 responses in vivo. Immune therapy for cancer relies on using DCs to prime Th1 or cytotoxic T lymphocyte responses to promote tumor clearance.

Currently, DC-based immunotherapies rely on autologous DC precursors: either monocytes, which are associated with the production of less-efficient DCs, or hematopoietic progenitors, which are isolated in very low numbers. In addition, these precursor cells are commonly compromised in cancer-bearing patients, resulting in the generation of dysfunctional DCs. In contrast, non-hematopoietic cell-types such as fibroblasts are usually not affected. Human Dermal Fibroblasts (HDFs) also exhibit other competitive advantages, namely are easily obtained from a small skin punch biopsy, are easily expanded in vitro for several passages (15-20 million cells after 4 weeks) and can be conserved frozen and used on-demand. Given the fundamental role of DCs as APCs functioning at the interface of the innate and adaptive immune system, there remains a clinical need to find alternative strategies to generate functional DCs to prime antigen-specific immune responses.

An aspect of the present disclosure relates to compositions comprising the combination of at least two isolated transcription factors
encoded by a sequence 90% identical to a sequence from a list consisting of: BATF3 (SEQ. ID. 1 or SEQ. ID. 2), IRF8 (SEQ. ID. 5, SEQ. ID. 6), PU.1 (SEQ. ID. 7, SEQ. ID. 8), TCF4 (SEQ. ID. 13, SEQ. ID. 14);
as a reprogramming or inducing factor of a cell selected from a list consisting of: stem cell or a differentiated cell, or mixtures thereof,
into dendritic cell or antigen presenting cell in vitro, ex vivo or in vivo.

In some embodiments, polypeptide variants or family members having the same or a similar activity as the reference polypeptide encoded by the sequences provided in the sequence listing can be used in the compositions, methods, and kits described herein. Generally, variants of a particular polypeptide encoding a DC inducing factor for use in the compositions, methods, and kits described herein will have at least about 90%, at least about 91%, at least about 92%, at least about 93%, at least about 94%, at least about 95%, at least about 96%, at least about 97%, at least about 98%, at least about 99% or more sequence identity to that particular reference polynucleotide or polypeptide as determined by sequence alignment programs and parameters described herein and known to those skilled in the art.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (over the whole the sequence) alignment of two sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information (NCBI). Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences). Minor manual editing may be performed to optimise alignment between conserved motifs, as would be apparent to a person skilled in the art. The sequence identity values, which are indicated in the present subject-matter as a percentage were determined over the entire amino acid sequence, using BLAST with default parameters.

In an embodiment for better results, the combination of isolated transcription factor may be:
BATF3 (SEQ. ID. 1 or SEQ. ID. 2) and IRF8 (SEQ. ID. 5, SEQ. ID. 6); or BATF3 (SEQ. ID. 1, SEQ. ID. 2) and PU.1 (SEQ. ID. 7, SEQ. ID. 8); or IRF8 (SEQ. ID. 5, SEQ. ID. 6) and PU.1 (SEQ. ID. 7, SEQ. ID. 8); or TCF4 (SEQ. ID. 13, SEQ. ID. 14) and BATF3 (SEQ. ID. 1, SEQ. ID. 2); or TCF4 (SEQ. ID. 13, SEQ. ID. 14) and IRF8 (SEQ. ID. 5, SEQ. ID. 6); or TCF4 (SEQ. ID. 13, SEQ. ID. 14) and PU.1 (SEQ. ID. 7, SEQ. ID. 8); or BATF3 (SEQ. ID. 1, SEQ. ID. 2), IRF8 (SEQ. ID. 5, SEQ. ID. 6) and PU.1 (SEQ. ID. 7, SEQ. ID. 8); or TCF4 (SEQ. ID. 13, SEQ. ID. 14) BATF3 (SEQ. ID. 1, SEQ. ID. 2) and IRF8 (SEQ. ID. 5, SEQ. ID. 6); or TCF4 (SEQ. ID. 13, SEQ. ID. 14), IRF8 (SEQ. ID. 5, SEQ. ID. 6) and PU.1 (SEQ. ID. 7, SEQ. ID. 8); or TCF4 (SEQ. ID. 13, SEQ. ID. 14), BATF3 (SEQ. ID. 1, SEQ. ID. 2), IRF8 (SEQ. ID. 5, SEQ. ID. 6) and PU.1 (SEQ. ID. 7, SEQ. ID. 8).

In an embodiment, the isolated transcription factor of the present disclosure may be used in veterinary or human medicine, in particular in immunotherapy, or in neurodegenerative diseases, or in cancer or in infectious diseases.

In an embodiment for better results the cell may be selected from a list consisting of: pluripotent stem cell, multipotent stem cell, differentiated cell, tumor cell, cancer cell, and mixtures thereof. In particular mammalian cell, more in particular a mouse or a human cell.

In an embodiment for better results, the isolated transcription factor of the present disclosure may be use as a reprogramming or inducing factor of a cell selected from a list consisting of: pluripotent stem cell, or multipotent stem cell, or differentiated cell, and mixtures thereof into dendritic cell.

In an embodiment for better results, the isolated transcription factor of the present disclosure may be use a reprogramming or inducing factor of a cell selected from a list consisting of: tumor cell, cancer cell, and mixtures thereof, into antigen presenting cell.

Another aspect of the present disclosure is the use of a combination of at least two sequences at least 90% identical, preferably at least 91%, 92%, 93%, 94%, 95%, 96%, 97%, 98%, 99%, or identical, to a sequence from a list consisting of: BATF3 (SEQ. ID. 1 or SEQ. ID. 2), IRF8 (SEQ. ID. 5, SEQ. ID. 6), PU.1 (SEQ. ID. 7, SEQ. ID. 8), TCF4 (SEQ. ID. 13, SEQ. ID. 14), and mixtures thereof;

as a reprogramming or inducing factor of a cell selected from a list consisting of: stem cell or a differentiated cell, or mixtures thereof,
into dendritic cell or antigen presenting cell in vitro, ex vivo or in vivo.

Preferably the combination may be selected from a list consisting of: BATF3 (SEQ. ID. 1 or SEQ. ID. 2), IRF8 (SEQ. ID. 5, SEQ. ID. 6), PU.1 (SEQ. ID. 7, SEQ. ID. 8), TCF4 (SEQ. ID. 13, SEQ. ID. 14), and mixtures thereof. More preferably, the isolated transcription may include the following combination: BATF3 (SEQ. ID. 1 or SEQ. ID. 2) and IRF8 (SEQ. ID. 5, SEQ. ID. 6); or BATF3 (SEQ. ID. 1, SEQ. ID. 2) and PU.1 (SEQ. ID. 7, SEQ. ID. 8); or IRF8 (SEQ. ID. 5, SEQ. ID. 6) and PU.1 (SEQ. ID. 7, SEQ. ID. 8); or TCF4 (SEQ. ID. 13, SEQ. ID. 14) and BATF3 (SEQ. ID. 1, SEQ. ID. 2); or TCF4 (SEQ. ID. 13, SEQ. ID. 14) and IRF8 (SEQ. ID. 5, SEQ. ID. 6); or TCF4 (SEQ. ID. 13, SEQ. ID. 14) and PU.1 (SEQ. ID. 7, SEQ. ID. 8); or BATF3 (SEQ. ID. 1, SEQ. ID. 2), IRF8 (SEQ. ID. 5, SEQ. ID. 6) and PU.1 (SEQ. ID. 7, SEQ. ID. 8); or TCF4 (SEQ. ID. 13, SEQ. ID. 14), BATF3 (SEQ. ID. 1, SEQ. ID. 2) and IRF8 (SEQ. ID. 5, SEQ. ID. 6); or TCF4 (SEQ. ID. 13, SEQ. ID. 14), IRF8 (SEQ. ID. 5, SEQ. ID. 6) and PU.1 (SEQ. ID. 7, SEQ. ID. 8); or TCF4 (SEQ. ID. 13, SEQ. ID. 14), BATF3 (SEQ. ID. 1, SEQ. ID. 2), IRF8 (SEQ. ID. 5, SEQ. ID. 6) and PU.1 (SEQ. ID. 7, SEQ. ID. 8).

Another aspect of the present disclosure relates to a construct or a vector encoding at least one isolated transcription factor described in the present subject-matter.

In an embodiment for better results, the construct or the vector may be the combination of three isolated transcription factors is in the following sequential order from 5' to 3': PU.1 (SEQ. ID. 7, SEQ. ID. 8), IRF8 (SEQ. ID. 5, SEQ. ID. 6), BATF3 (SEQ. ID. 1, SEQ. ID. 2); or IRF8 (SEQ. ID. 5, SEQ. ID. 6), PU.1 (SEQ. ID. 7, SEQ. ID. 8), BATF3 (SEQ. ID. 1, SEQ. ID. 2).

In an embodiment, the vector is a viral vector; in particular a retrovirus, a adenovirus, a lentivirus, a herpes virus, a pox virus, or adeno-associated virus vectors.

In an embodiment for better results, the transducing step further comprises at least one vector selected from a list consisting of: a nucleic acid sequence encoding IL12; nucleic acid sequence encoding GM-CSF; nucleic acid sequence encoding IL-7; nucleic acid sequence encoding siRNA targeting IL-10 RNA, and mixtures thereof.

In an embodiment for better results the transducing of step further comprises at least one vector comprising nucleic acids encoding immunostimulatory cytokines.

Another aspect of the present disclosure relates to a method for programming or inducing a stem cell or a differentiated cell into a dendritic cell or antigen presenting cell, comprising the following step:
  transducing a cell selected from a list consisting of: a stem cell or a differentiated cell, and mixtures thereof,
  with one or more vectors comprising at least two nucleic acid sequence encoding a sequence at least 90% identical to a sequence from a list consisting of: BATF3 (SEQ. ID. 1, SEQ. ID. 2), IRF8 (SEQ. ID. 5, SEQ. ID. 6), PU.1 (SEQ. ID. 7, SEQ. ID. 8), TCF4 (SEQ. ID. 13, SEQ. ID. 14), and mixtures thereof; preferably at least 91%, 92%, 93%, 94%, 95%, 96%, 97%, 98%, 99%, or identical;
  culturing the transduced somatic cell in a cell media that supports growth of dendritic cells or antigen presenting cells.

Preferably for better results, wherein the combination of isolated transcription factors is selected from the following encoded combinations: BATF3 (SEQ. ID. 1 or SEQ. ID. 2) and IRF8 (SEQ. ID. 5, SEQ. ID. 6); or BATF3 (SEQ. ID. 1, SEQ. ID. 2) and PU.1 (SEQ. ID. 7, SEQ. ID. 8); or IRF8 (SEQ. ID. 5, SEQ. ID. 6) and PU.1 (SEQ. ID. 7, SEQ. ID. 8); or TCF4 (SEQ. ID. 13, SEQ. ID. 14) and BATF3 (SEQ. ID. 1, SEQ. ID. 2); or TCF4 (SEQ. ID. 13, SEQ. ID. 14) and IRF8 (SEQ. ID. 5, SEQ. ID. 6); or TCF4 (SEQ. ID. 13, SEQ. ID. 14) and PU.1 (SEQ. ID. 7, SEQ. ID. 8); or BATF3 (SEQ. ID. 1, SEQ. ID. 2), IRF8 (SEQ. ID. 5, SEQ. ID. 6) and PU.1 (SEQ. ID. 7, SEQ. ID. 8); or TCF4 (SEQ. ID. 13, SEQ. ID. 14) BATF3 (SEQ. ID. 1, SEQ. ID. 2) and IRF8 (SEQ. ID. 5, SEQ. ID. 6); or TCF4 (SEQ. ID. 13, SEQ. ID. 14), IRF8 (SEQ. ID. 5, SEQ. ID. 6) and PU.1 (SEQ. ID. 7, SEQ. ID. 8); or TCF4 (SEQ. ID. 13, SEQ. ID. 14), BATF3 (SEQ. ID. 1, SEQ. ID. 2), IRF8 (SEQ. ID. 5, SEQ. ID. 6) and PU.1 (SEQ. ID. 7, SEQ. ID. 8).

In an embodiment for better results, the construct or the vector may be the combination of at least three isolated transcription factors in the following sequential order from 5' to 3': PU.1 (SEQ. ID. 7, SEQ. ID. 8), IRF8 (SEQ. ID. 5, SEQ. ID. 6), BATF3 (SEQ. ID. 1, SEQ. ID. 2); or IRF8 (SEQ. ID. 5, SEQ. ID. 6), PU.1 (SEQ. ID. 7, SEQ. ID. 8), BATF3 (SEQ. ID. 1, SEQ. ID. 2).

In an embodiment for better results, cells may be transduced with a plurality of isolated transcription factors and cultured during at least 2 days, preferably at least 5 days, more preferably at least 8 days, even more preferably 9 days.

In an embodiment for better results, the transducing step may further comprise at least one vector selected from a list consisting of: a nucleic acid sequence encoding IL-12; nucleic acid sequence encoding GM-CSF; nucleic acid sequence encoding IL-7; nucleic acid sequence encoding siRNA targeting IL-10 RNA, and mixtures thereof.

In an embodiment for better results, the cell may be selected from the group consisting of pluripotent stem cell, or multipotent stem cell, differentiated cell, and mixtures thereof. In particular an endoderm derived cell, a mesoderm derived cell, or an ectoderm derived cell, a multipotent stem cell including mesenchymal stem cell, a hematopoietic stem cell, intestinal stem cell, a pluripotent stem cell, a tumor or cancer cell and cell lines.

In an embodiment for better results, the cell may be a non-human cell, preferably a mouse or a human cell, more preferably cell is a human or mouse fibroblast, or a mammal umbilical cord blood stem cell.

Another aspect of the present disclosure relates to induced dendritic cell or antigen presenting cell obtained by the method described in the present disclosure.

Another aspect of the present disclosure relates to induced antigen presenting cell obtained by the method described in the present disclosure. In particular, an induced antigen presenting cell capable to present a cancer antigen, a self-antigen, an allergen, an antigen from a pathogenic and/or infectious organism.

Another aspect of the present disclosure relates to composition comprising at least one isolated transcription factor as described in the present disclosure, or an induced dendritic cell as described in the present disclosure, or an induced antigen presenting cell as described in the present disclosure, or mixtures thereof, in a therapeutically effective amount and a pharmaceutically acceptable excipient.

In a preferably embodiment, the composition may be use in veterinary or human medicine, in particular in immunotherapy, or in neurodegenerative diseases, or in cancer or in infectious diseases.

In a preferably embodiment, the composition may further comprise an anti-viral, an analgesic, an anti-inflammatory agent, a chemotherapy agent, a radiotherapy agent, an antibiotic, a diuretic, or mixtures thereof.

In a preferably embodiment, the composition may further comprise a filler, a binder, a disintegrant, or a lubricant, or mixtures thereof.

In a preferably embodiment, the composition may be use in intradermal and transdermal therapies.

In a preferably embodiment, the composition may be use as an injectable formulation, in particular an in-situ injection.

In a preferably embodiment, the composition may be use in veterinary or human medicine, in particular in immunotherapy, or in the treatment or therapy neurodegenerative diseases, or in the treatment or therapy of cancer or in the treatment or therapy of an infectious diseases.

In a preferably embodiment, the composition may be use in the treatment, therapy or diagnostic of a central and peripheral nervous system disorder.

In a preferably embodiment, the composition may be use in the treatment therapy or diagnostic of neoplasia in particular cancer, namely solid or hematological tumors.

In a preferably embodiment, the composition may be use in the treatment, diagnostic or therapy of benign tumor, malignant tumor, early cancer, basal cell carcinoma, cervical dysplasia, soft tissue sarcoma, germ cell tumor, retinoblastoma, age-related macular degeneration, Hodgkin's lymphoma, blood cancer, prostate cancer, ovarian cancer, cervix cancer, uterus cancer, vaginal cancer, breast cancer, nasopharynx cancer, trachea cancer, larynx cancer, bronchi cancer, bronchioles cancer, lung cancer, hollow organs cancer, esophagus cancer, stomach cancer, bile duct cancer, intestine cancer, colon cancer, colorectum cancer, rectum cancer, bladder cancer, ureter cancer, kidney cancer, liver cancer, gall bladder cancer, spleen cancer, brain cancer, lymphatic system cancer, bone cancer, pancreatic cancer, leukemia, skin cancer, or myeloma.

In a preferably embodiment, the composition may be use in the treatment, therapy or diagnostic of a fungal, viral, chlamydial, bacterial, nanobacterial or parasitic infectious disease.

In a preferably embodiment, the composition may be use in therapy or diagnostic of HIV, infection with SARS coronavirus, Asian flu virus, herpes simplex, herpes zoster, hepatitis, or viral hepatitis.

In a preferably embodiment, the composition may be use in the treatment, therapy or diagnostic of an amyloid disease in particular Amyloid A (AA) amyloidosis, Alzheimer's disease, Light-Chain (AL) amyloidosis, Type-2 Diabetes, Medullary Carcinoma of the Thyroid, Parkinson's disease, Polyneuropathy, or Spongiform Encephalopathy—Creutzfeldt Jakob disease.

Another aspect of the present disclosure relates to a vaccine for cancer comprising to compositions comprising at least one isolated transcription factor as described in the present disclosure, or an induced dendritic cell as described in the present disclosure, or an induced antigen presenting cell as described in the present disclosure, or mixtures thereof.

A kit comprising at least one of the following components: a composition comprising at least one isolated transcription factor as described in the present disclosure, or an induced dendritic cell as described in the present disclosure, or a induced antigen presenting cell as described in the present disclosure, a composition as described in the present disclosure, or a vector as described in the present disclosure, or a construct as described in the present disclosure or mixtures thereof.

An aspect of the present disclosure relates to compositions, methods, and kits for dendritic cell induction or for reprogramming cells to antigen-presenting dendritic cells (DC). In some embodiments, the compositions comprise at least one DC inducing factor. Such compositions, methods and kits can be used for inducing dendritic cells in vitro, ex vivo, or in vivo, as described herein, and these induced dendritic cells (iDCs) can be used in immunotherapies.

The compositions, methods, and kits for dendritic cell induction or for reprogramming cells to dendritic cells of the present disclosure are based, in part, in the use of a novel combination of transcription factors that permit direct reprogramming of differentiated cells to the dendritic cell state. Such compositions, nucleic acid constructs, methods and kits can be used for inducing dendritic cells in vitro, ex vivo, or in vivo, as described herein, and these induced dendritic cells can be used in immunotherapies.

In an embodiment, the present disclosure relates to the regulation of the immune system, and in particular to the use of reprogrammed dendritic cells to prime immune responses to target antigens.

In an embodiment, the resulting dendritic cell is an antigen presenting cell which activates T cells against MHC class I-antigen targets. Cancer, viral, bacterial and parasitic infections are all ameliorated by the reprogrammed dendritic cells. As reprogrammed dendritic cells are capable of cross-presenting extracellular antigens via the MHC class I pathway, they are particularly suitable for generation of cytotoxic T lymphocyte responses.

In an embodiment isolated transcription factor (or exogenous transcription factor) selected from a list consisting of: BATF3 (SEQ. ID. 1, SEQ. ID. 2), IRF8 (SEQ. ID. 5, SEQ. ID. 6), PU.1 (SEQ. ID. 7, SEQ. ID. 8), TCF4 (SEQ. ID. 13, SEQ. ID. 14), and mixtures thereof, upon forced expression in fibroblasts induce activation of the Clec9a DC-specific reporter, DC morphology and a conventional DC type 1 (cDC1) transcriptional program. Induced Dendritic Cells (iDCs) express cDC1 markers, major histocompatibility complex (MHC)-I and II at the cell surface and the co-stimulatory molecules CD80, CD86 and CD40. iDCs are able to engulf particles and upon challenge with LPS or poly I:C secrete inflammatory cytokines. iDCs present antigens to CD4+ T cells and cross-present antigens to CD8+ T cells. In an embodiment isolated transcription factor (or exogenous transcription factor) selected from a list consisting of: BATF3 (SEQ. ID. 1, SEQ. ID. 2), IRF8 (SEQ. ID. 5, SEQ. ID. 6), PU.1 (SEQ. ID. 7, SEQ. ID. 8), upon forced expression in fibroblasts induce expression of CLEC9A and HLA-DR, typical DC markers, and DC morphology. Induced Dendritic Cells (iDCs) are able to engulf particles and soluble protein. This disclosure provides powerful new treatments for cancers and cellular infections, as well as a variety of diagnostic and cell screening assays. In an embodiment, isolated transcription factor (or exogenous transcription factor) selected from a list consisting of: BATF3 (SEQ. ID. 1, SEQ. ID. 2), IRF8 (SEQ. ID. 5, SEQ. ID. 6), PU.1 (SEQ. ID. 7, SEQ. ID. 8), upon forced expression in cancer cell lines induce expression of CLEC9A and MHC-II at the cell surface.

In an embodiment, CLEC9A is preferentially expressed on the subset cDC1 of dendritic cells. This is an important cell type because it is capable of processing antigens derived from outside the cell and presenting them to T cells via MHC class I molecules. This is in contrast to most antigen presenting cells, which present extracellularly-derived antigens via MHC class II molecules. Consequently, this mechanism of antigen presentation is sometimes referred to as "cross-presentation". These cells therefore play an important role in the generation and stimulation of CTL responses, which are an essential part of the immune response against intracellular pathogens, e.g. viruses and cancers.

In an embodiment, immune responses stimulated via iDCs involve proliferation of T cells, which may be CTL or helper T cells. Antigen presenting cells (and in particular iDCs) can induce proliferation of both CD8+ T cells and CD4+ T cells, and may stimulate proliferation of both types of T cells in any given immune response.

In an embodiment, iDCs may be implicated in at least Th1, Th2, and Th17-type immune responses. Thus, the methods of the invention may be applied to stimulation of various types of immune response against any antigen. However, these cells are believed to be particularly important in the generation of CTL responses, so the immune response to be stimulated is preferably a CTL response. The method may comprise determining production and/or proliferation of CTLs, which are typically T cells expressing CD8 and are capable of cytotoxic activity against cells displaying their cognate antigen in the context of MHC class I molecules.

It will therefore be further understood that iDCs may be used for the prophylaxis and/or treatment of any condition in which it is desirable to induce a CTL response, such as cancer, or infection by an intracellular parasite or pathogen, such as a viral infection.

Nevertheless, if modified, iDCs can result in proliferation of helper T cells as well as, or instead of, CTLs. Thus, the method may additionally or alternatively comprise determining production and/or proliferation of helper T cells. The helper T cells may be CD4+ T cells, and may be of Th1, Th2, Th17 or Treg type.

Under certain conditions, it is believed that iDCs may be capable of stimulating regulatory T cell (Treg) proliferation. Treg cells are characterised by the expression of the Foxp3 (Forkhead box p3) transcription factor. Most Treg cells are CD4+ and CD25+, and can be regarded as a subset of helper T cells, although a small population may be CD8+. Thus, the immune response, which is to be stimulated by a method of the present disclosure, may comprise inducing proliferation of Treg cells in response to an antigen. Given that Treg cells may be capable of modulating the response of other cells of the immune system against an antigen in other ways, e.g. inhibiting or suppressing their activity, the effect on the immune system as a whole may be to modulate (e.g. suppress or inhibit) the response against that antigen. Thus, the methods of this aspect of the invention can equally be referred to as methods of modulating (e.g. inhibiting or suppressing) an immune response against an antigen. This may be particularly useful (for example) in the treatment of autoimmune disease.

iDCs will promote antigen-specific responses. The antigen may be any protein or fragment thereof against which it is desirable to raise an immune response, in particular a CTL response, but also a Th17 response or a Treg response. These may include antigens associated with, expressed by, displayed on, or secreted by cells against which it is desirable to stimulate a CTL response, including cancer cells and cells containing intracellular pathogens or parasites. For example, the antigen may be, or may comprise, an epitope peptide from a protein expressed by an intracellular pathogen or parasite (such as a viral protein) or from a protein expressed by a cancer or tumor cell. Thus, the antigen may be a tumor-specific antigen. The term "tumor-specific" antigen should not be interpreted as being restricted to antigens from solid tumors, but to encompass antigens expressed specifically by any cancerous, transformed or malignant cell.

The invention therefore provides a primed antigen presenting cell or population thereof. By "primed" is meant that the cell has been contacted with an antigen, is presenting that antigen or an epitope thereof in the context of MHC molecules, preferably MHC I molecules, and is capable of activating or stimulating T cells to proliferate and differentiate into effector cells in response thereof.

The term "antigen" is well understood in the art and includes immunogenic substances as well as antigenic epitopes. It will be appreciated that the use of any antigen is envisioned for use in the present invention and thus includes, but is not limited to, a self-antigen (whether normal or disease-related), an infectious antigen (e.g., a microbial antigen, viral antigen, etc.), or some other foreign antigen (e.g., a food component, pollen, etc.). Loading the antigen-presenting cells with an antigen can be accomplished utilizing standard methods, for example, pulsing, transducing, transfecting, and/or electrofusing. It is envisioned that the antigen can be nucleic acids (DNA or RNA), proteins, protein lysate, whole cell lysate, or antigen proteins linked to other proteins, i.e., heat shock proteins. The antigens can be derived or isolated from a pathogenic microorganism such as viruses including HIV, influenza, Herpes simplex, human papilloma virus, Hepatitis B, Hepatitis C, EBV, Cytomegalovirus (CMV) and the like. The antigen may be derived or isolated from pathogenic bacteria such as from *Chlamydia, Mycobacteria, Legionella*, Meningiococcus, Group A *Streptococcus, Salmonella, Listeria, Hemophilus influenzae*, and the like. Still further, the antigen may be derived or isolated from pathogenic yeast including *Aspergillus*, invasive *Candida, Nocardia*, Histoplasmosis, Cryptosporidia and the like. The antigen may be derived or isolated from a pathogenic protozoan and pathogenic parasites including, but not limited to *Pneumocystis carinii, Trypanosoma, Leishmania, Plasmodium* and *Toxoplasma gondii*. In certain embodiments, the antigen includes an antigen associated with a preneoplastic or hyperplastic state. Antigens may also be associated with, or causative of cancer. Such antigens are tumor specific antigen, tumor associated antigen (TAA) or tissue specific antigen, epitope thereof, and epitope agonist thereof. Such antigens include but are not limited to carcinoembryonic antigen (CEA) and epitopes thereof such as CAP-1, CAP-1-6D, MART-1, MAGE-1, MAGE-3, GAGE, GP-100, MUC-1, MUC-2, point mutated ras oncogene, normal and point mutated p53 oncogenes, PSMA, tyrosinase, TRP-1 (gp75), NY-ESO-1, TRP-2, TAG72, KSA, CA-125, PSA, HER-2/neu/c-erb/B2, BRC-I, BRC-II, bcr-abl, pax3-fkhr, ews-fli-1, modifications of TAAs and tissue specific antigen, splice variants of TAAs, epitope agonists, and the like.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent or fragment thereof, can be any protein of interest, for example, but not limited to; mutated proteins; therapeutic proteins; truncated proteins, wherein the protein is normally absent or expressed at lower levels in the cell. Proteins of interest can be selected from a group comprising; mutated proteins, genetically engineered proteins, peptides, synthetic peptides, recombinant proteins, chimeric proteins, antibodies, humanized proteins, humanized antibodies, chimeric antibodies, modified proteins and fragments thereof.

As used herein, the term "transcription factor" or "TF" refers to a protein that binds to specific parts of DNA using DNA binding domains and is part of the system that controls the transcription of genetic information from DNA to RNA.

The term "DC inducing factor," as used herein, refers to a developmental potential altering factor, as that term is defined herein, such as a protein, RNA, or small molecule, the expression of which contributes to the reprogramming of a cell, e.g. a somatic cell, to the DC state. A DC inducing factor can be, for example, transcription factors that can reprogram cells to the DC state, such as PU.1, IRF8, BATF3 and TCF4, and the like, including any gene, protein, RNA or small molecule that can substitute for one or more of these factors in a method of making iDCs in vitro. In some embodiments, exogenous expression of a DC inducing factor induces endogenous expression of one or more DC inducing factors, such that exogenous expression of the one or more DC inducing factor is no longer required for stable maintenance of the cell in the iDC state.

The term "an antigen-presenting cell" (APC) as used herein, refers to a cell that displays antigen complexed with major histocompatibility complexes (MHCs) on their surfaces; this process is known as antigen presentation. T cells may recognize these complexes using their T cell receptors (TCRs). These cells process antigens and present them to T-cells.

The term "a somatic cell" used herein, refers to any biological cell forming the body of an organism; that is, in a multicellular organism, any cell other than a gamete, germ cell, gametocyte or undifferentiated stem cell.

The expression of endogenous DC inducing factors can be induced by the use of DNA targeting systems able to modulate mammalian gene expression in a cell with or without the use of chromatin modifying drugs. In some embodiments, the DNA targeting system may comprise a Clustered Regularly Interspaced Short Palindromic Repeats (CRISPR)/CRISPR-associated (Cas) 9-based system (as described in WO2014197748 A2) that may include any modified protein, isolated polynucleotide or vector contacted with the cell and at least one guide RNA targeting a promoter region of at least one gene selected from the group consisting of PU.1, IRF8, BATF3 and TCF4. The DNA targeting system may comprise dCas9-VP64. In some embodiments, the DNA targeting system may comprise two or more transcription activator-like effector transcription factors (as described in US20140309177 A1) that bind to different target regions of at least one gene selected from the group consisting of PU.1, IRF8, BATF3 and TCF4.

In an embodiment, iDCs can be used as immunotherapy to induce specific immune responses in patients with cancer, such as melanoma, prostate cancer, glioblastoma, acute myeloid leukemia, among others.

In an embodiment, iDCs can also be used to treat infections caused by viral, bacterial and parasitic pathogens.

In an embodiment, iDCs can also be used as in vitro tools for vaccine immunogenicity testing.

The pluripotent stem cells used in the present disclosure are obtained without having to recur to a method necessarily involving the destruction of human embryos, namely with the use of induced pluripotent stem cells. Induced pluripotent stem cells (also known as iPS cells or iPSCs) are a type of pluripotent stem cell that can be generated directly from adult cells by cellular reprogramming.

The induced Dendritic Cells (iDCs) obtainable by this method express MHC-I and II at the cell surface and the co-stimulatory molecules CD80, CD86 and CD40.

In some embodiments, the composition may comprises the isolated transcription factor discloses in the present subject-matter, in an amount effective to improve the immunotherapy by at least 5%, at least 10%, at least 15%, at least 20%, at least 25%, at least 30%, at least 40%, at least 50%, at least 60%, at least 70%, at least 75%, at least 80%, at least 90%, at least 95%, at least 95.7%, at least 98%, or at least 99% in the subject.

In some embodiments, the composition may comprise the induced dendritic cells disclosure in the present subject-matter, in an amount effective to improve the immunotherapy by at least 5%, at least 10%, at least 15%, at least 20%, at least 25%, at least 30%, at least 40%, at least 50%, at least 60%, at least 70%, at least 75%, at least 80%, at least 90%, at least 95%, at least 95.7%, at least 98%, or at least 99% in the subject.

DC inducing factors of the present disclosure can be delivered to induce reprogramming in vitro, ex vivo or in vivo.

Differentiated cells of the present disclosure can be isolated from a subject in need, DC inducing factors can be introduced to induce reprogramming into iDCs. Generated iDCs can be infused back to the patient.

Alternatively, DC inducing factors can be delivered to induce reprogramming in vivo of, for example, cancer cells into iDC with ability to present cancer antigens.

Preferred routes of administration include but are not limited to oral, parenteral, intramuscular, intravenous, in situ injection, intranasal, sublingual, intratracheal, and inhalation.

In some embodiments, the dose or dosage form is administered to the subject once a day, twice a day, or three times a day. In other embodiments, the dose is administered to the subject once a week, once a month, once every two months, four times a year, three times a year, twice a year, or once a year.

The embodiments of the invention provide multiple applications, including kits for research use and methods for generation of cells useful for conducting small molecule screens for immune disorders. In addition, the invention provides commercially and medically useful methods to produce autologous dendritic cells and give them back to a patient in need.

For example, the methods described herein can be used to produce dendritic cells to treat diseases including hyperproliferative diseases, which can also be further defined as cancer. In still further embodiments, the cancer is melanoma, non-small cell lung, small-cell lung, lung, hepatocarcinoma, leukemia, retinoblastoma, astrocytoma, glioblastoma, gum, tongue, neuroblastoma, head, neck, breast, pancreatic, prostate, colorectal, Esophageal, Non-Hodgkin lymphoma, uterine, liver, thyroid, renal, skin, bone, testicular, ovarian, mesothelioma, cervical, gastrointestinal, lymphoma, brain, colon, sarcoma or bladder. The cancer may include a tumor comprised of tumor cells. For example, tumor cells may include, but are not limited to melanoma cell, a bladder cancer cell, a breast cancer cell, a lung cancer cell, a colon cancer cell, a prostate cancer cell, a liver cancer cell, a pancreatic cancer cell, a stomach cancer cell, a testicular cancer cell, a brain cancer cell, an ovarian cancer cell, a lymphatic cancer cell, a skin cancer cell, a brain cancer cell, a bone cancer cell, or a soft tissue cancer cell. In other embodiments, the hyperproliferative disease is rheumatoid arthritis, inflammatory bowel disease, osteoarthritis, leiomyomas, adenomas, lipomas, hemangiomas, fibromas, vascular occlusion, restenosis, atherosclerosis, pre-neoplastic lesions (such as adenomatous hyperplasia and prostatic intraepithelial neoplasia), carcinoma in situ, oral hairy leukoplakia, or psoriasis.

Accordingly, provided herein, in an embodiment are dendritic cell (DC) inducing composition comprising one or more expression vectors encoding at least two, three, four, or more DC inducing factors selected from: BATF3 (SEQ. ID. 1, SEQ. ID. 2), IRF8 (SEQ. ID. 5, SEQ. ID. 6), PU.1 (SEQ. ID. 7, SEQ. ID. 8), TCF4 (SEQ. ID. 13, SEQ. ID. 14), or mixtures thereof. In a particular embodiment, the addition of increases the efficiency in at least 8%.

In some embodiments of these aspects and all such aspects described herein, the one or more expression vectors are retroviral vectors.

In some embodiments of these aspects and all such aspects described herein, the one or more expression vectors are lentiviral vectors. In some embodiments, the lentiviral vectors are inducible lentiviral vectors.

Also provided herein, in some aspects, are dendritic cell (DC) inducing compositions comprising modified mRNA sequences encoding at least two, three, four, DC inducing factors selected from BATF3 (SEQ. ID. 1, SEQ. ID. 2), IRF8 (SEQ. ID. 5, SEQ. ID. 6), PU.1 (SEQ. ID. 7, SEQ. ID. 8), TCF4 (SEQ. ID. 13, SEQ. ID. 14), or mixtures thereof, wherein each cytosine of each said modified mRNA sequence is a modified cytosine, each uracil of each said modified mRNA sequence is a modified uracil, or a combination thereof.

Provided herein, in some aspects, are dendritic cell (DC) inducing compositions comprising at least two sequences selected from TCF4 (SEQ. ID. 13, SEQ. ID. 14), BATF3 (SEQ. ID. 1, SEQ. ID. 2), IRF8 (SEQ. ID. 5, SEQ. ID. 6), PU.1 (SEQ. ID. 7, SEQ. ID. 8), or mixtures thereof, wherein each cytosine of each said modified mRNA sequence is a modified cytosine, each uracil of each said modified mRNA sequence is a modified uracil, or a combination thereof.

In some embodiments of these aspects and all such aspects described herein, the modified cytosine is 5-methylcytosine and the modified uracil is pseudouracil.

Also provided herein in some aspects, are methods for preparing an induced dendritic cell (iDC) from a somatic cell comprising:
  transducing the somatic cell with one or more vectors comprising a nucleic acid sequence encoding PU.1 (SEQ. ID. 7, SEQ. ID. 8), a nucleic acid sequence encoding IRF8 (SEQ. ID. 5, SEQ. ID. 6); a nucleic acid sequence encoding BATF3 (SEQ. ID. 1, SEQ. ID. 2); wherein each said nucleic acid sequence is operably linked to a promoter; and
  culturing the transduced somatic cell in a cell media that supports growth of dendritic cells, thereby preparing an iDC.

In some embodiments of these aspects and all such aspects described herein, the transducing step further comprises one or more vectors comprising one or more of: a nucleic acid sequence encoding TCF4 (SEQ. ID. 13, SEQ. ID. 14); a nucleic acid sequence encoding IL12; nucleic acid sequence encoding GM-CSF; nucleic acid sequence encoding IL-7; nucleic acid sequence encoding siRNA targeting IL-10 RNA.

In some embodiments of these aspects and all such aspects described herein, the transducing step further comprises one or more vectors comprising nucleic acids encoding immunostimulatory cytokines. Preferably, the cytokine is one of the interleukins (e.g., IL-1α, IL-1β, IL-2, IL-3, IL-4, IL-6, IL-7, IL-8, IL-9, IL-10, IL-12, IL-18, IL-19, IL-20), interferons (e.g., IFN-α, IFN-β, IFN-γ, tumor necrosis factor (TNF), transforming growth factor-β (TGF-β), granulocyte colony stimulating factors (G-CSF), macrophage colony stimulating factor (M-CSF), granulocyte-macrophage colony stimulating factor (GM-CSF), Flt-3 ligand or kit ligand. The amino acid sequences of these cytokines are well known in the art. In the case of heterodimeric immunostimulatory cytokines (e.g., IL-12), induced dendritic cells (iDCs) shall be genetically modified to express both subunits of the cytokine molecule.

The additional vectors may also comprise nucleic acids encoding variants of these cytokines. For example, for those cytokines having both pro-forms and mature forms (e.g., before and after cleavage of a signal peptide, or before and after limited proteolysis to yield an active fragment), the APCs of the invention may be genetically modified to express either the pro- or mature form. Other variants, such as fusion proteins between an active fragment of a cytokine and a heterologous sequence (e.g., a heterologous signal peptide), may also be employed. Species variants may also be employed to the extent that they retain activity in a human subject. Thus, for example, human APCs may be genetically modified to express a murine, bovine, equine, ovine, feline, canine, non-human primate or other mammalian variant of a human cytokine if these species variants retain activity substantially similar to their human homologues.

It may be desirable also to administer further immunostimulatory agents in order to achieve maximal CTL stimulation and proliferation, and/or stimulation and proliferation of other T cell types. These may include agents capable of activating dendritic cells and stimulating their ability to promote T cell activation. Such an agent may be referred to as an adjuvant. The adjuvant may comprise an agonist for CD40 (such as soluble CD40 ligand, or an agonist antibody specific for CD40), an agonist of CD28, CD27 or OX40 (e.g. an agonist antibody specific for one of those molecules), a CTLA-4 antagonist (e.g. a blocking antibody specific for CTLA-4), and/or a Toll-like receptor (TLR) agonist, and/or any other agent capable of inducing dendritic cell activation. A TLR agonist is a substance that activates a Toll-like receptor. Preferably, the TLR agonist is an activator of TLR3, TLR4, TLR5, TLR7 or TLR9. A suitable TLR agonist is MPL (monophosphoryl lipid A), which binds TLR4. Other TLR agonists which may be used are LTA (lipoteichoic acid, which binds TLR2; Poly I:C (polyinosine-polycytidylic acid), which binds TLR3; flagellin, which binds TLR5; imiquimod or polyU RNA (1-(2-methylpropyl)-1H-imidazo (4,5-c)quinolin-4-amine), which binds TLR7 and CpG (DNA CpG motifs), which binds TLR9; or any other component which binds to and activates a TLR. For more details, see Reis e Sousa, Toll-like receptors and dendritic cells. Seminars in Immunology 16:27, 2004. Adjuvants which may not work via TLRs include 5' triphosphate RNA, poly I:C, and β-glucans such as curdlan (β-1,3-glucan).

In some embodiments of these aspects and all such aspects described herein, the culturing step further comprises the use of cell media that supports growth of dendritic cells or antigen presenting cells supplemented with at least one immunostimulatory recombinant cytokine selected from the group consisting of interleukins (e.g., IL-1α, IL-1β, IL-2, IL-3, IL-4, IL-6, IL-7, IL-8, IL-9, IL-10, IL-12, IL-18, IL-19, IL-20), interferons (e.g., IFN-α, IFN-β, IFN-γ), tumor necrosis factor (TNF), transforming growth factor-β (TGF-β), granulocyte colony stimulating factors (G-CSF), macrophage colony stimulating factor (M-CSF), granulocyte-macrophage colony stimulating factor (GM-CSF), Flt-3 ligand or kit ligand. In the case of heterodimeric immunostimulatory cytokines (e.g., IL-12), induced dendritic cells (iDCs) shall be cultured with both subunits of the cytokine molecule. Other pro-inflammatory cytokines may also be used as adjuvants.

In some embodiments of these aspects and all such aspects described herein, the somatic cell is a fibroblast cell.

In some embodiments of these aspects and all such aspects described herein, the somatic cell is a hematopoietic lineage cell.

In some embodiments of these aspects and all such aspects described herein, the hematopoietic lineage cell is selected from promyelocytes, neutrophils, eosinophils, basophils, reticulocytes, erythrocytes, mast cells, osteoclasts, megakaryoblasts, platelet producing megakaryocytes, platelets, monocytes, macrophages, lymphocytes, NK cells, NKT cells, innate lymphocytes, multipotent hematopoietic stem and progenitor cells, oligopotent hematopoietic progenitor cells, lineage restricted hematopoietic progenitors.

In some embodiments of these aspects and all such aspects described herein, the hematopoietic lineage cell is selected from a multi-potent progenitor cell (MPP), common myeloid progenitor cell (CMP), granulocyte-monocyte progenitor cells (GMP), common lymphoid progenitor cell (CLP), and pre-megakaryocyte-erythrocyte progenitor cell.

In some embodiments of these aspects and all such aspects described herein, the hematopoietic lineage cell is selected from a megakaryocyte-erythrocyte progenitor cell (MEP), a ProB cell, a PreB cell, a PreProB cell, a ProT cell, a double-negative T cell, a pro-NK cell, a pre-dendritic cell (pre-DC), pre-granulocyte/macrophage cell, a granulocyte/macrophage progenitor (GMP) cell, and a pro-mast cell (ProMC).

Also provided herein, in some aspects, are kits for making induced dendritic cells (iDC), the kits comprising any of the DC inducing compositions comprising one or more expression vector components described herein.

Provided herein, in some aspects, are kits for making induced dendritic cells (iDC), the kits comprising any of the DC inducing compositions comprising modified mRNA sequence components described herein.

In some embodiments of these aspects and all such aspects described herein, the one or more expression vectors are lentiviral vectors. In some embodiments, the lentiviral vectors are inducible lentiviral vectors. In some embodiments, the lentiviral vectors are polycistronic inducible lentiviral vectors. In some embodiments, the polycistronic inducible lentiviral vectors express three or more nucleic acid sequences. In some embodiments, each of the nucleic acid sequences of the polycistronic inducible lentiviral vectors are separated by 2A peptide sequences.

The use of polycistronic viral expression systems can increase the in vivo reprogramming efficiency of somatic cells to iDCs. Accordingly, in some embodiments of the aspects described herein, a polycistronic lentiviral vector is used. In such embodiments, sequences encoding two or more of the DC inducing factors described herein, are expressed from a single promoter, as a polycistronic transcript. 2A peptide strategy can be used to make polycistronic vectors (see, e.g., Expert Opin Biol Ther. 2005 May; 5(5): 627-38). Polycistronic expression vector systems can also use internal ribosome entry sites (IRES) elements to create multigene, or polycistronic, messages. IRES elements are able to bypass the ribosome scanning model of 5'-methylated Cap dependent translation and begin translation at internal sites (Pelletier and Sonenberg, 1988). IRES elements can be linked to heterologous open reading frames. Multiple open reading frames can be transcribed together, each separated by an IRES, thus creating polycistronic messages. By virtue of the IRES element, each open reading frame is accessible to ribosomes for efficient translation. Multiple genes can be efficiently expressed using a single promoter/enhancer to transcribe a single message. See, for example, U.S. Pat. Nos. 4,980,285; 5,925,565; 5,631,150; 5,707,828; 5,759,828; 5,888,783; 5,919,670; and 5,935,819; and Sambrook et al., Molecular Cloning: A Laboratory Manual, 2nd Ed., Cold Spring Harbor Press (1989).

BRIEF DESCRIPTION OF THE DRAWINGS

The following figures provide preferred embodiments for illustrating the description and should not be seen as limiting the scope of invention.

Figure 17:
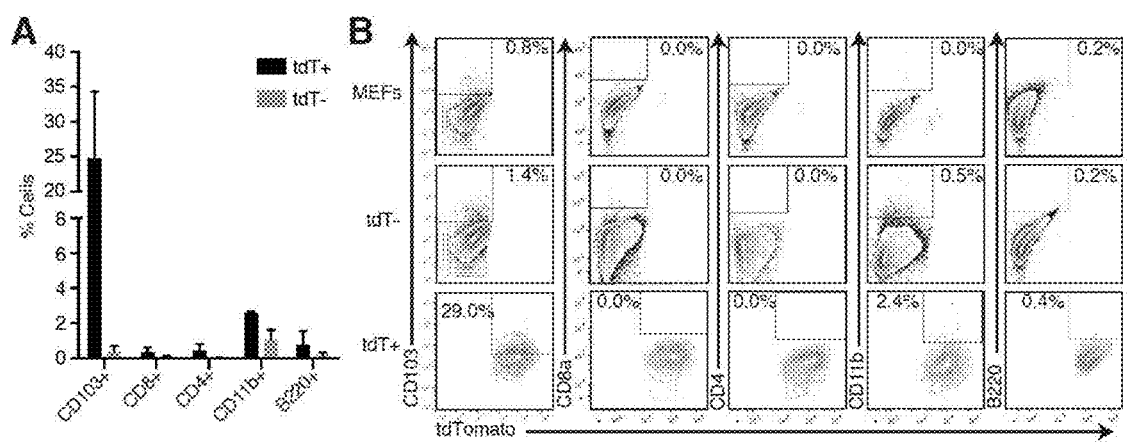

Heat map showing increased expression of Clec9a, PU.1, IRF8 and BATF3 in CD103+ DCs (highlighted in red) belonging to cDC1 subset when compared to other DC subsets and several hematopoietic cell lineages available in the Immunological Genome Project (www.immgen.org). Gene expression data were analyzed by Cluster 3.0 and displayed by Treeview. Red indicates increased expression, whereas blue indicates decreased expression over the mean FIG. 17. Induced DCs express cDC1 markers at cell surface. (A) Flow cytometry analysis of surface phenotype of MEFs transduced with PIB 8 days after the addition of Dox. Quantification of CD103, CD8a, CD4, C11b and B220 expression in tdT+ and tdT− populations. (B) Representative flow cytometry plots.

Figure 18:
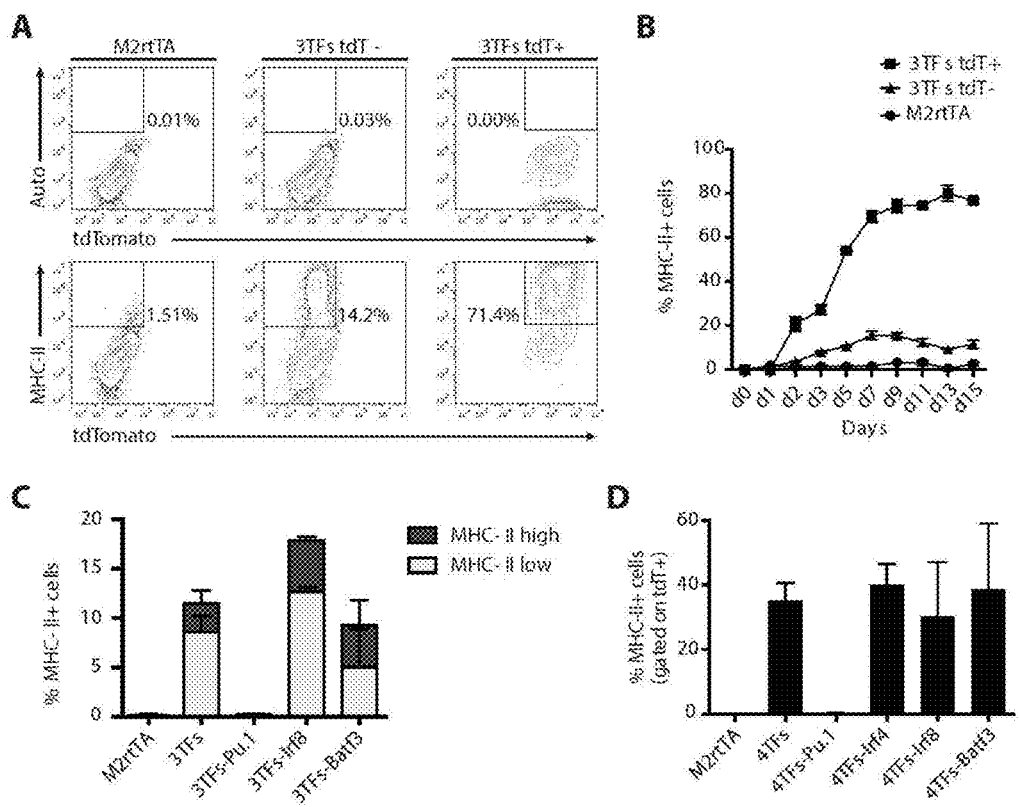

FIG. 18. Induced DCs express antigen-presenting machinery at the cell surface (A) Flow cytometry analysis of MHC-II expression in MEFs transduced with M2rtTA (as control) and PIB (PU.1, IRF8 and BATF3) 7 days after addition of Dox. TdTomato+ and tdTomato-populations are shown. (B) Kinetics of MHC-II surface expression in M2rtTA and PIB transduced cells. MEFs were analysed by flow cytometry from day 1 to 15 after addition of Dox. (C) Quantification of the percentage of cells expressing MHC-II in high and low levels in bulk cultures after removal of individual TF from the pool of PIB, at day 5 after addition of Dox. (D) Quantification of MHC-II+ cells at day 5 within tdTomato+ population after transduction with 4TFs or upon their individual removal.

Figure 19:
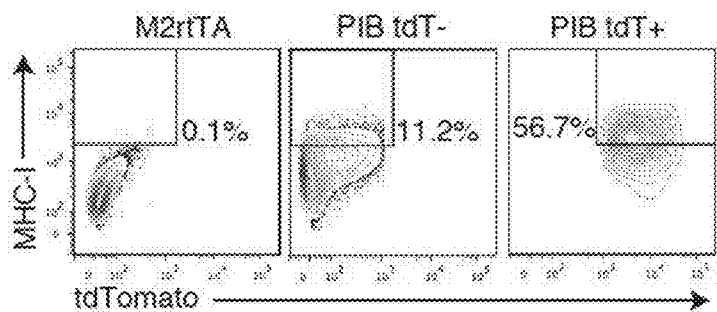

FIG. 19. Induced DCs express MHC-I at cell surface. Flow cytometry analysis of MHC-I expression in MEFs transduced with M2rtTA and PIB at day 7 after the addition of Dox.

Figure 20:
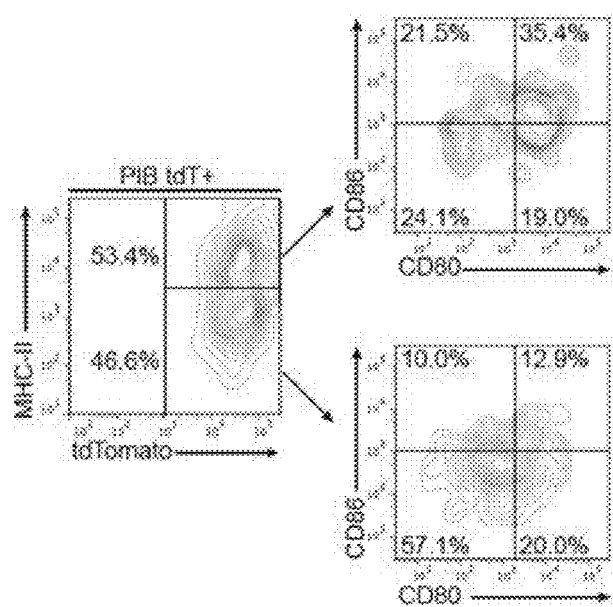
Figure 21:
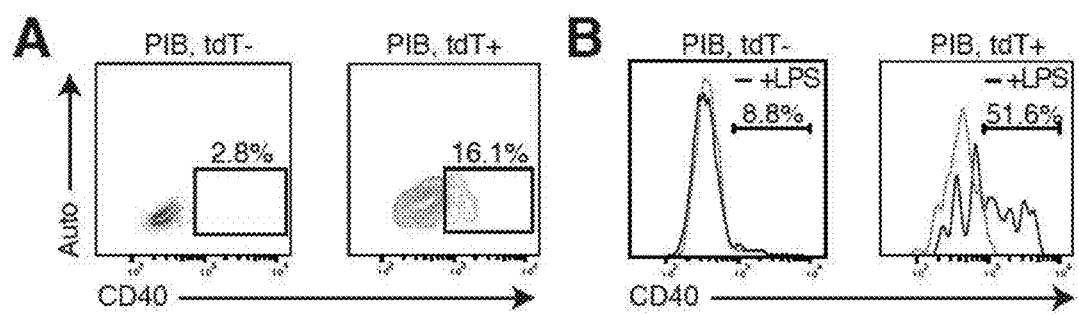

FIG. 20. Induced DCs express co-stimulatory molecules at cell surface. Flow cytometry analysis of co-stimulatory molecules (CD80 and CD86) at cell surface of tdTomato+ population in PIB (PU.1, IRF8 and BATF3) transduced MEFs 5 days after addition of Dox. MHC-II+ and MHC-II− populations are shown FIG. 21. Induced DCs up-regulate CD40 expression upon LPS stimuli. (A) Flow cytometry analysis of CD40 expression in tdTomato− and tdTomato+ population in PIB-transduced MEFs at day 8. (B) Histograms show expression of CD40 with or without overnight LPS stimulation at day 13.

Figure 22:
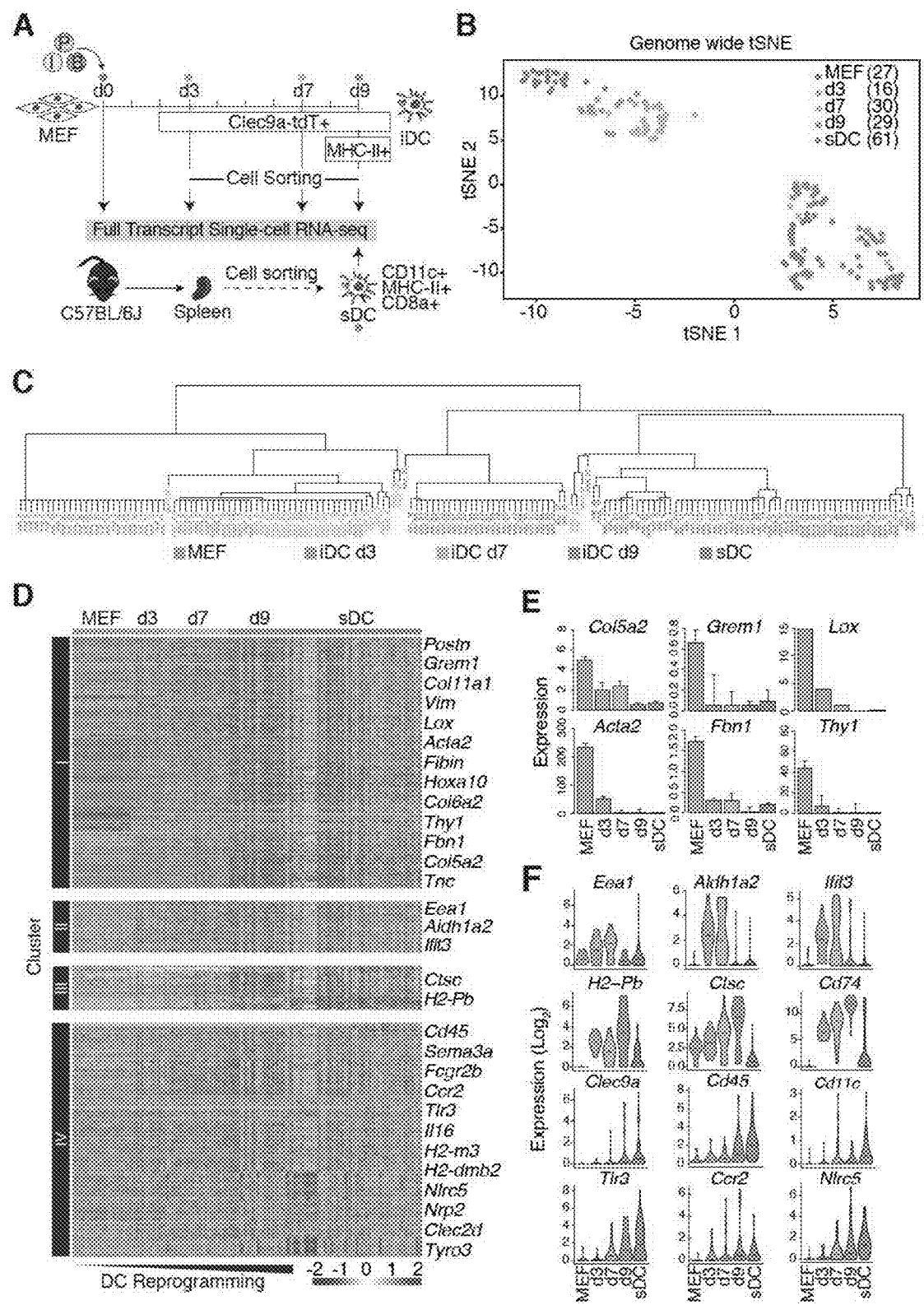

FIG. 22. PIB factors program global dendritic cell gene expression program in fibroblasts. (A) Clec9a reporter MEFs were transduced with Pu.1 (P), Irf8 (I) and Batf3 (B) to generate iDCs. Transduced cells were sorted by FACS and sampled using full-transcript single-cell RNA-seq using Fluidigm C1 system, at day 3 (d3, 20 Clec9a-tdTomato+ cells), day 7 (d7, 40 Clec9a-tdTomato+ cells) and day 9 (d9, 36 Clec9a-tdTomato+ MHC-II+ cells). Non-transduced MEFs at day 0 (30 cells) and splenic DCs (sDCs, 66 CD11c+ MHC-II+CD8a+ cells) isolated from C57Bl/6 animals were used as controls. (B) t-distributed stochastic linear embedding (tSNE) analysis of genome-wide transcriptomes showing clustering of 163 single cells. Each dot represents an individual cell. The number of cells from each sample group is depicted inside brackets. (C) Complete•linkage hierarchical clustering of the consensus matrix obtained by the SC3 clustering algorithm. (D) Heatmap showing expression of the 6525 most variable genes across the 5 different biological sample groups (columns, MEFs, d3, d7, d9 and sDCs). 4 clusters of genes are shown: Cluster I (3014 genes), II (530 genes), III (347 genes) and IV (2634 genes). Color scheme is based on z-score distribution, from −2 (blue) to 2 (red). Examples of genes from each cluster are shown (right panel). (E) Expression levels of fibroblast genes are shown as Census counts median values ±95% confidence interval. (F) Expression levels of genes in Cluster II (Eea1, Aldh1a2, Ifit3), Cluster III (H2-Pb, Ctsc, Cd74) and Cluster IV (Clec9a, Cd45, Cd11c, Tlr3, Ccr2, Nlrc5), presented as violin plots (height, gene expression; width, abundance of cells expressing the gene). Log values of Census counts are shown, horizontal lines corresponding to median values.

Figure 23:
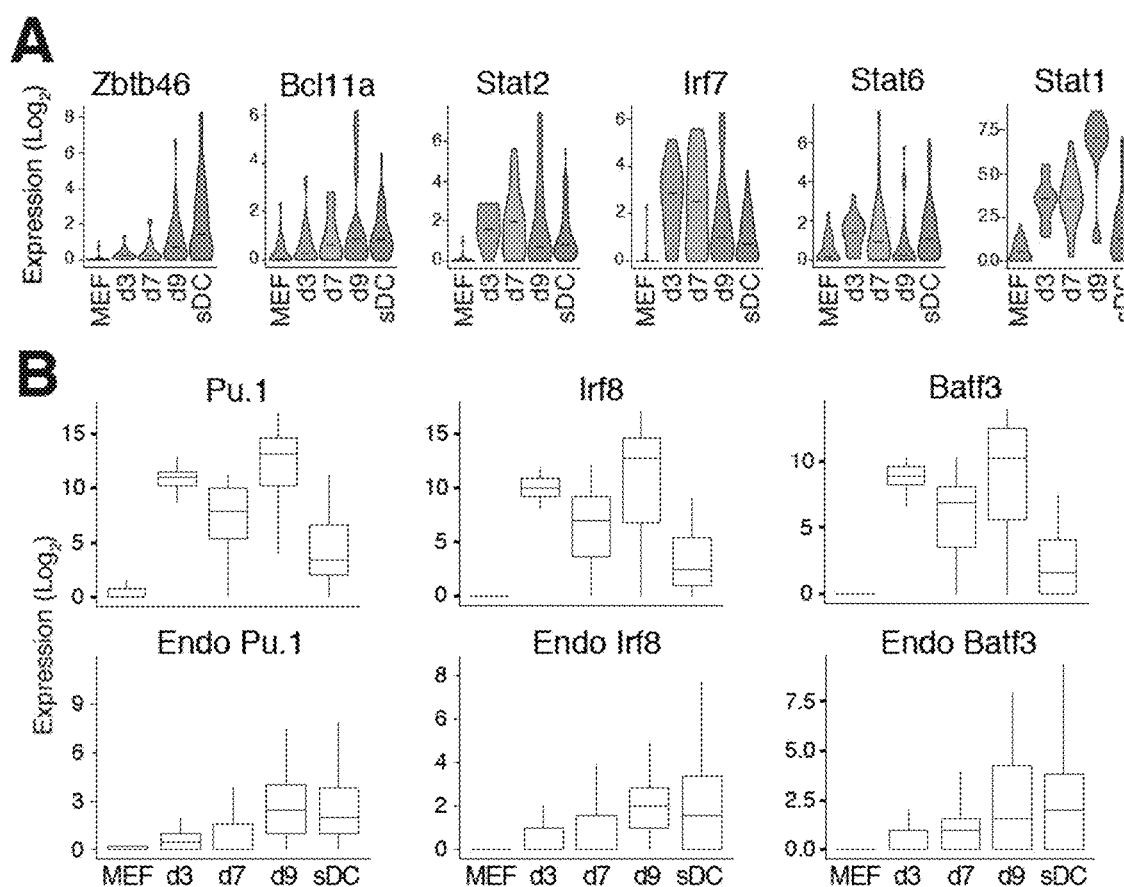

FIG. 23. PIB factors induce expression of DC transcriptional regulators, including endogenous Pu.1, Irf8 and Batf3. (A) Violin plots showing the expression levels of the DC transcriptional regulators Zbtb46, Bcl11a, Stat2, Irf7, Stat6 and Stat1. (B) Expression levels of Pu.1, Irf8 and Batf3 genes are shown as Log counts presented as box plot with whiskers extending to ±1.5× interquartile range. Total (left panel) and endogenous transcript (right panel) levels are displayed.

Figure 24:
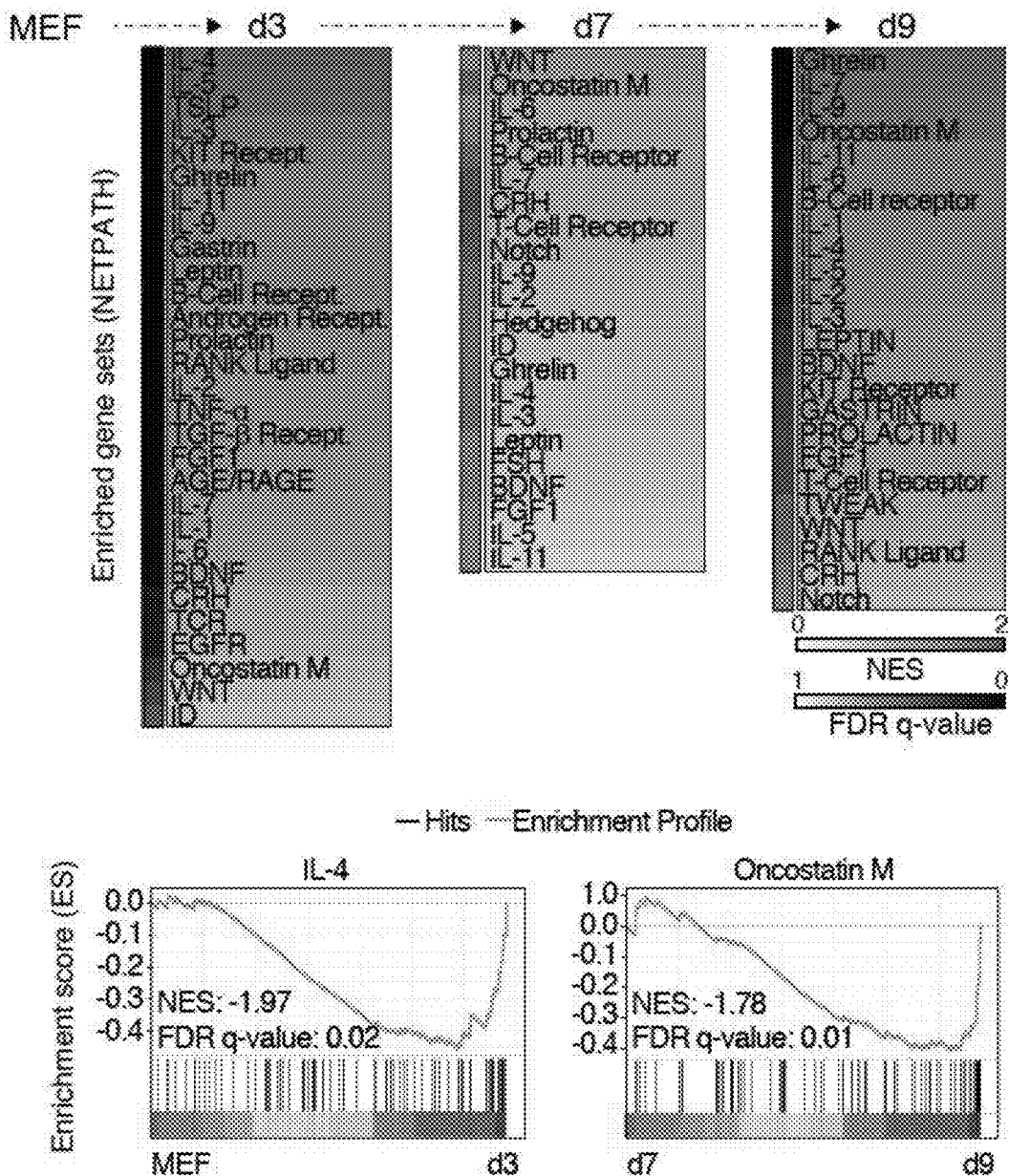

FIG. 24. Pathway enrichment for step-wise transitions during iDC reprogramming. (A) Gene set enrichment analysis (GSEA) for step-wise iDC reprogramming was performed using annotated gene sets from NetPath-annotated signaling pathways. Day 3 refers to the pathways upregulated at day 3 versus MEFs, day 7 refers to the pathways upregulated at day 7 versus day 3 and day 9 refers to the upregulated pathways at day 9 versus day 7. Datasets were ordered according to the normalized enrichment score (NES) and the False Discovery Rate (FDR) q-value is shown. The bottom panel shows the enrichment plots for the IL-4 (day 3) and Oncostatin M (day 9) gene sets.

Figure 25:
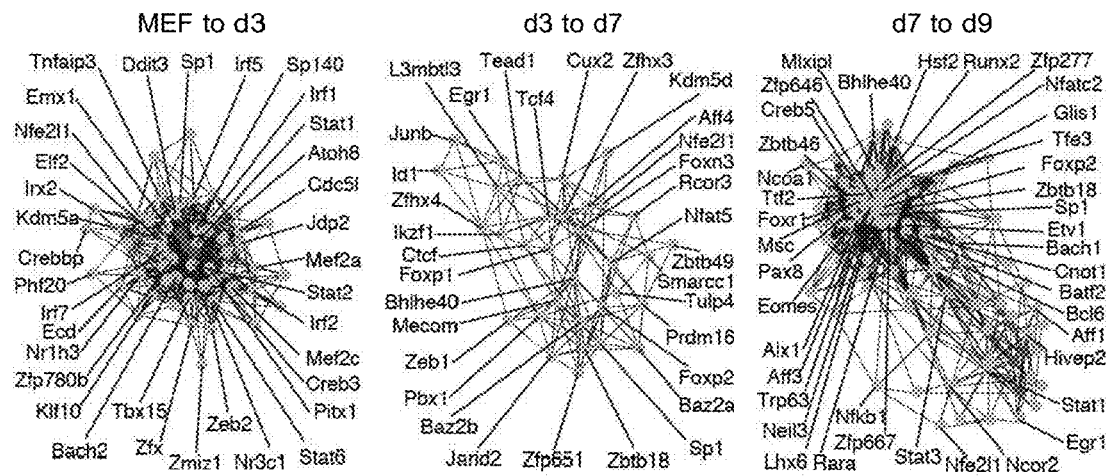
Figure 25:
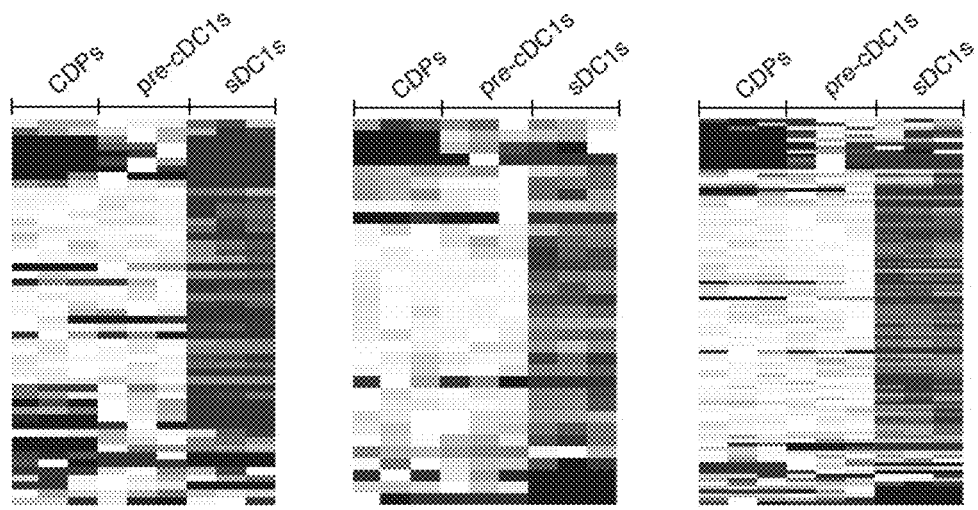
Figure 25:
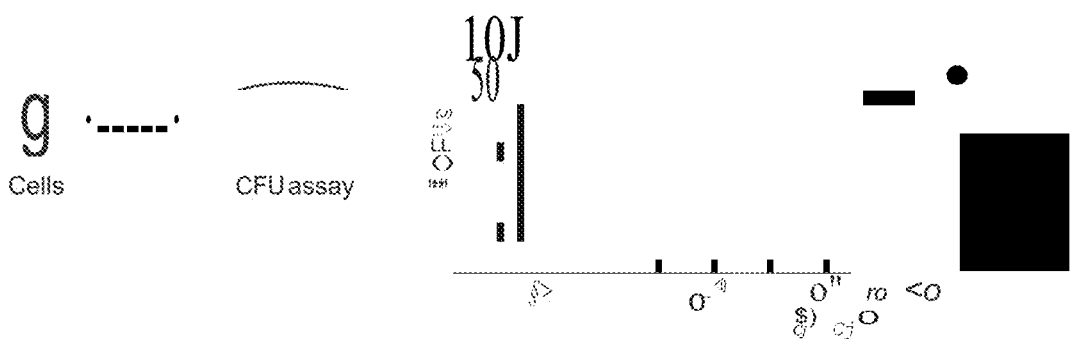

FIG. 25. Transcriptional networks for step-wise transitions during iDC reprogramming. (A) Transcription factor covariance networks during iDC reprogramming for each step-wise transition. Shown are transcriptional regulators with more than five edges, with each edge reflecting a correlation >0.35 between connected transcriptional regulators. The transcription factors PU.1, IRF8 and BATF3 are highlighted in red. (B) Heat maps showing expression of transcriptional regulators shown in panel A in DC precursors (CDPs and pre-DC1) and mature cells (cDC1) from bone marrow (GSE60782). Gene expression data were analyzed by Cluster 3.0 and displayed by Treeview. Red indicates increased expression, whereas blue indicates decreased expression over the mean. (C) PIB-transduced MEFs at day 3, 5, 7, 10 and 25 after addition of Dox were assayed for hematopoietic colony formation (mean±SD, n=2). Sorted sDC1s and unsorted splenocytes and bone marrow cells were included as controls.

Figure 26:
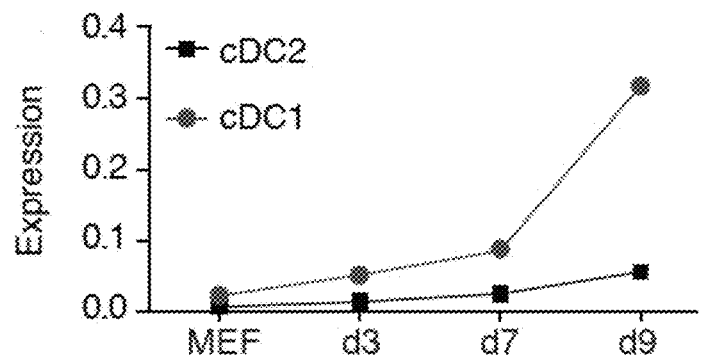

FIG. 26. PIB factors induce transcriptional reprogramming towards cDC1 expression program. cDC1 and cDC2 gene expression signatures were generated by analyzing the datasets from Schlitzer et al. (11) (GSE60783). Cumulative median expression levels of cDC1 and cDC2 gene signatures during reprogramming.

Figure 27:
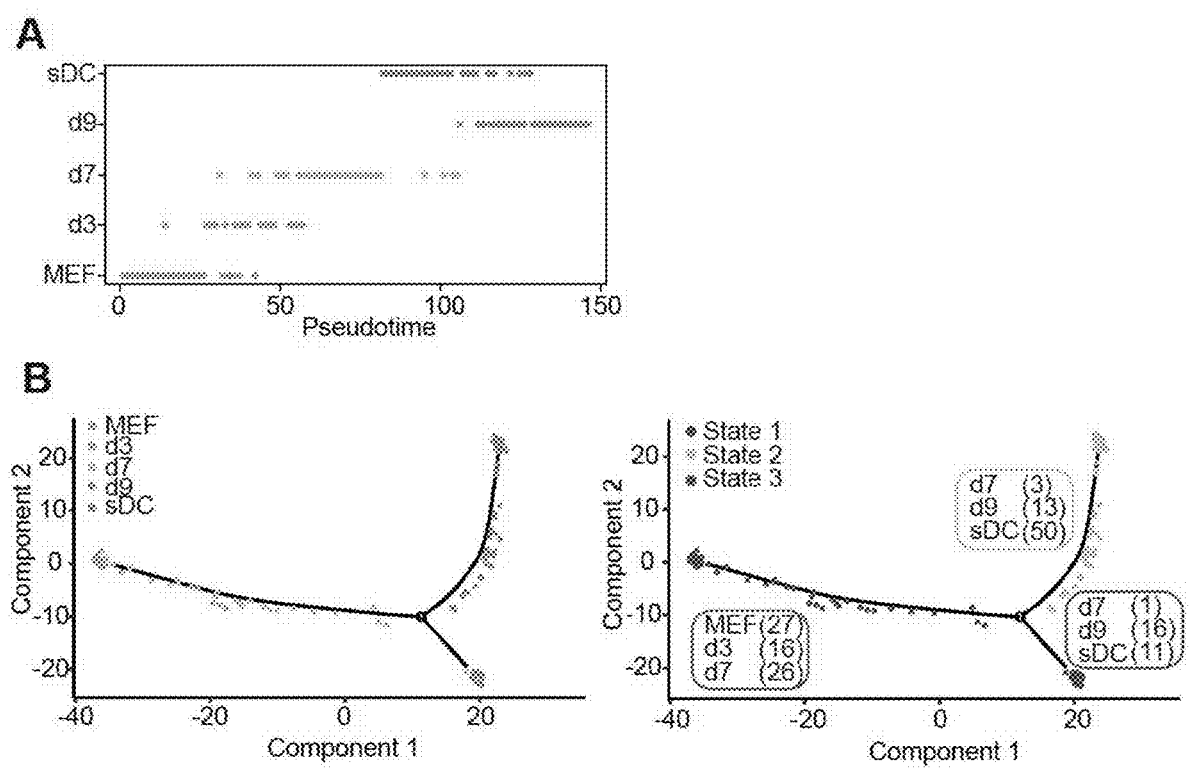

FIG. 27. Reconstruction of single cell reprogramming trajectory. (A) Genome wide transcriptomes of single cells were ordered with TSCAN software (Pseudo-time). Ordering of non-transduced MEFs, induced DCs (iDCs) Clec9a-tdTomato+ at day 3 (d3), day 7 (d7), Clec9a-tdTomato+ MHC-II+ day 9 (d9) and splenic DCs (sDCs, CD11c+ MHC-II+ CD8a+) are shown. Each dot represents an individual cell. (B) Cell expression profiles in a two-dimensional independent component space according to predicted trajectory. Solid black line shows pseudo-time ordering constructed by Monocle2. Each dot represents an individual cell, colored according to biological sample groups (left panel) or cell state (right panel). The number of cells from each sample group assigned to each cell state is depicted inside brackets.

Figure 28:
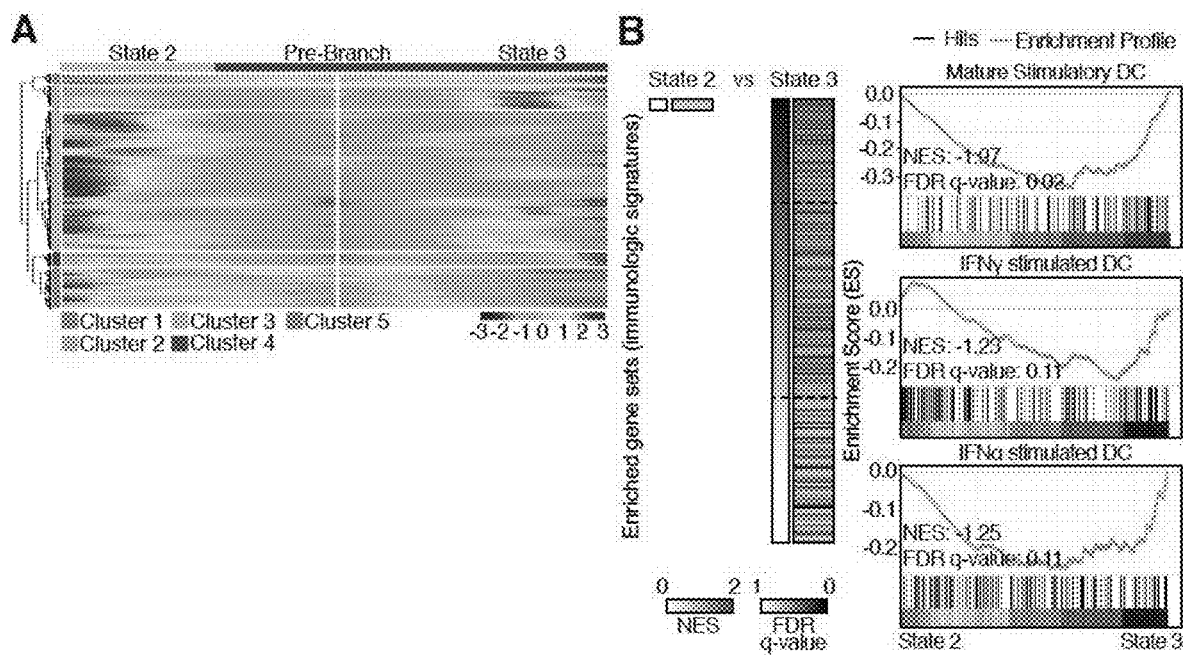

FIG. 28. Reconstruction of single cell reprogramming trajectory highlights different maturation states of iDCs. (A) Five kinetic clusters of branch-dependent genes identified by BEAM. (B) Gene set enrichment analysis (GSEA) between cell state 2 and cell state 3 was performed using gene sets present in the Immunologic signatures collection (4,872 gene sets, FDR<0.02 or maximum of 200 genes per gene set). Gene sets were ordered according to the normalized enrichment score (NES) and the False Discovery Rate (FDR) q-value is shown. Black lines represent DC gene sets. The right panel shows enrichment plots for Mature Stimulatory DC, IFNγ stimulated DC and IFNα stimulated DC gene sets (all enriched in State 3).

Figure 29:
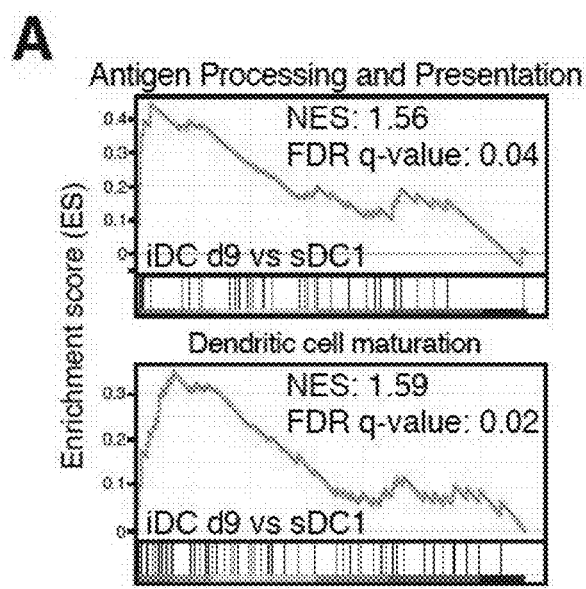

FIG. 29. PIB factors induce high levels of expression of genes associated with DC maturation. (A) GSEA for day 9 iDCs and sDCIs showing the enrichment for 2 MSigDB gene sets (left). Violin plots (right) show expression distribution of day 9 enriched genes.

Figure 30:
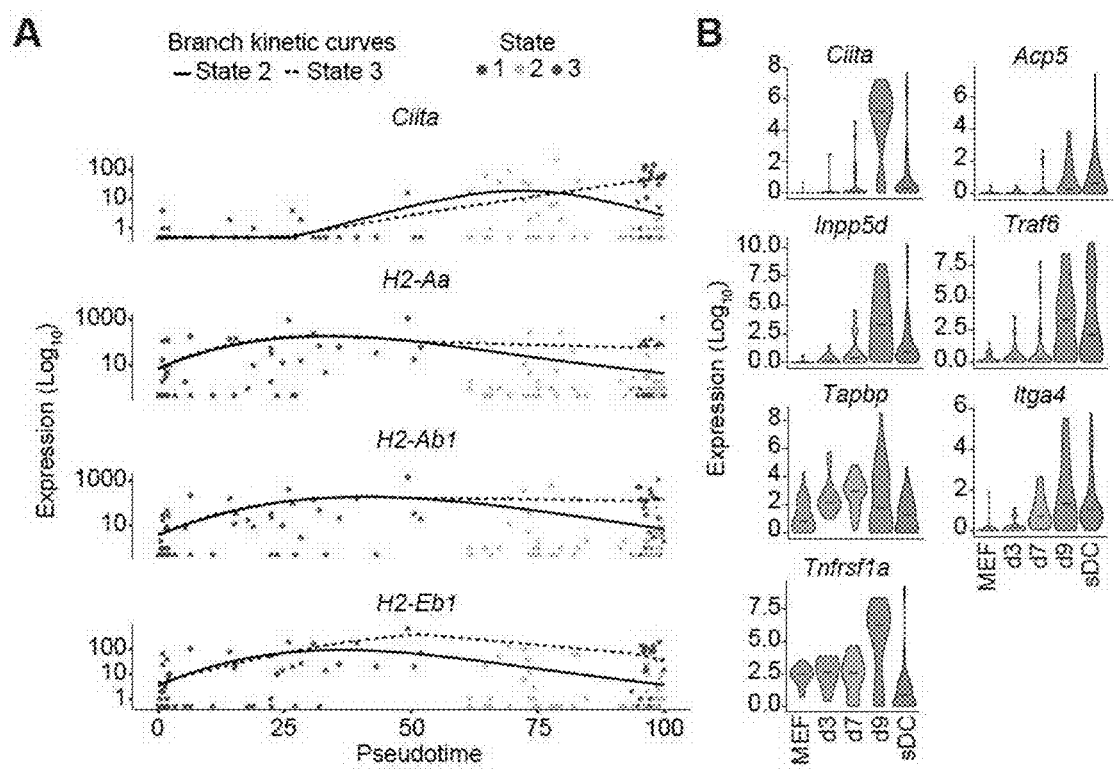

FIG. 30. PIB factors induce high levels of expression of genes associated with DC maturation. (A) Expression levels of Ciita, H2-Aa, H2-Ab1 and H2-Eb1 genes in single cells from State 1, 2 and 3 ordered with Monocle2 (Pseudo-time). Each dot represents relative expression values for individual cells. Lines represent branch kinetics curves for State 2 (solid line) and State 3 (dashed line). (B) Violin plots showing the expression levels of Ciita, Acp5, Tnfrsf1a, Tapbp, Inpp5d, Traf6 and Itga4 genes. Log values of Census counts are shown, horizontal lines corresponding to median values.

Figure 31:
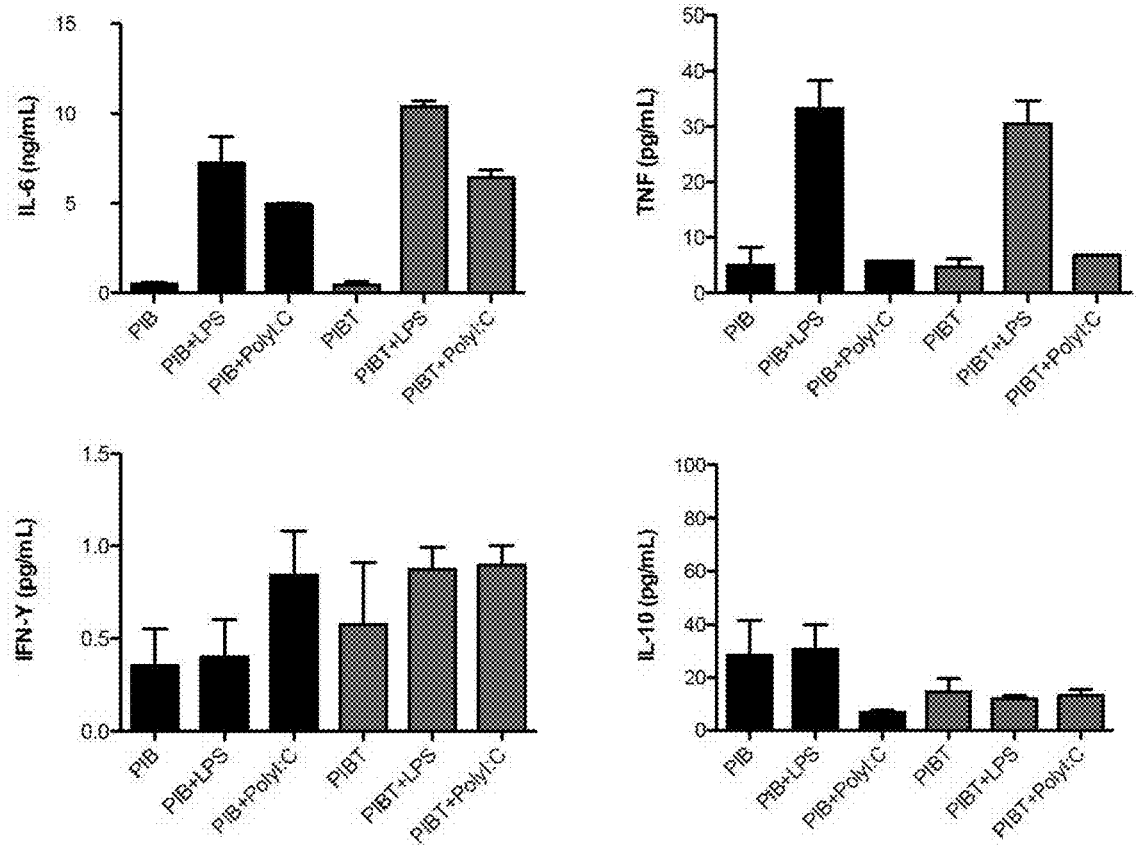

FIG. 31. Induced DCs secrete inflammatory cytokines upon TLR stimuli. (A) Secretion of cytokines by MEFs transduced with PIB (PU.1, IRF8 and BATF3) or PIBT (PU.1, IRF8, BATF3 and TCF4) with or without TLR4 (LPS) or TLR3 (PolyI:C) stimuli overnight. Supernatants of MEFs transduced with PIB or PIBT factors were collected at day 10 after addition of Dox and analysed for cytokine concentration using BD Cytometric Bead Array Mouse Inflammation Kit. Cytokine levels for untreated, 100 ng/mL LPS or 25 ag/mL of PolyI:C-treated cells overnight are shown; black or grey bars represent PIB or PIBT-transduced MEFs, respectively.

Figure 32:
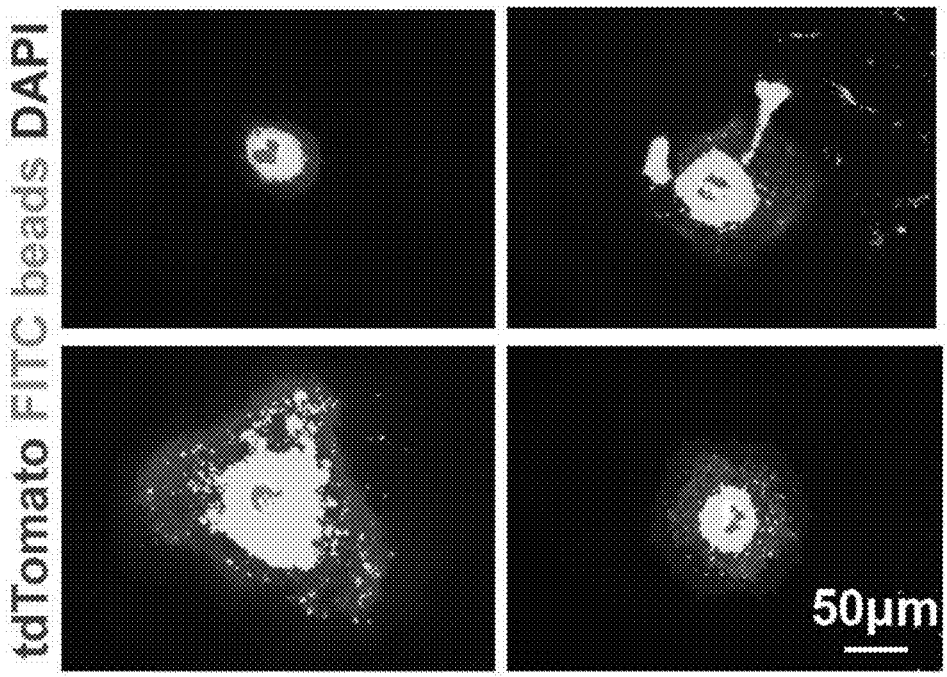

FIG. 32. Induced DCs are able to engulf small particles. MEFs transduced with PIB (PU.1, IRF8 and BATF3) were incubated overnight with FITC-labelled latex beads (1 μm) and analysed by fluorescent microscopy at day 7 after addition of Dox.

Figure 33:
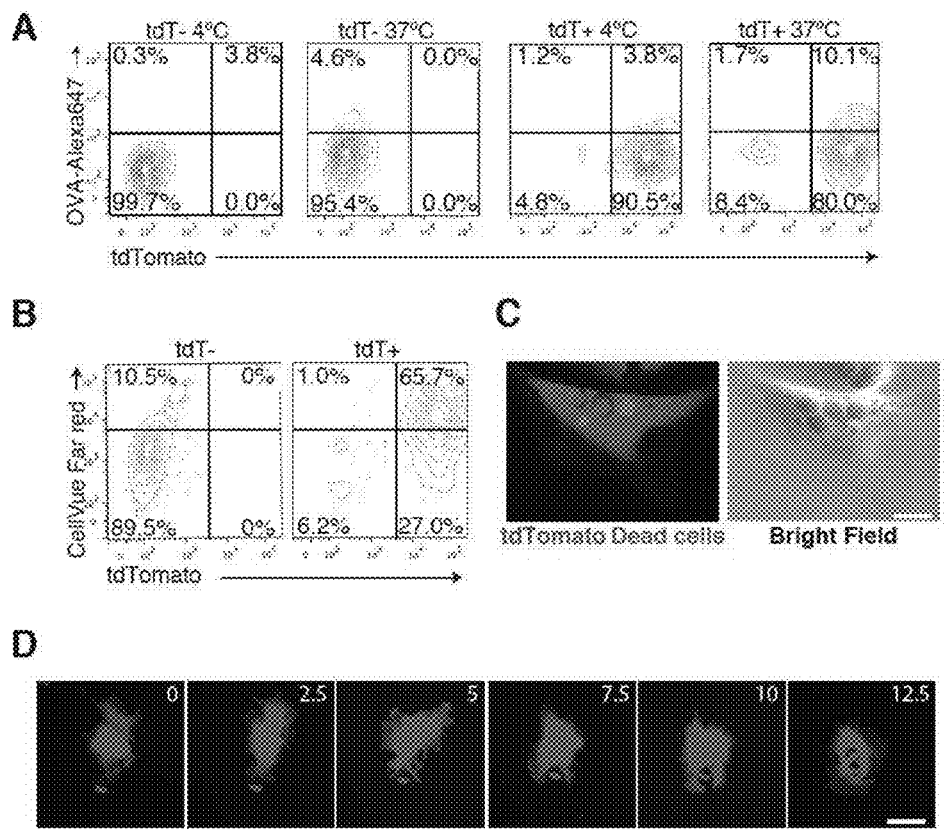

FIG. 33. Induced DCs are able to engulf proteins and dead cells. (A) PIB-transduced MEFs were FACS sorted and tdTomato- and tdTomato+(iDCs) populations were incubated with AlexaFluor647-labelled Ovalbumin (OVA-Alexa647) at 37° C. at day 11 and analysed by flow cytometry. Controls were kept on ice (4° C.). (B) Sorted tdTomato- and tdTomato+(iDCs) populations at day 11 were incubated overnight with dead cells labeled with CellVue Claret Far Red membrane staining and analyzed by flow cytometry. (C, D) iDCs at day 11 were incubated overnight with dead cells labelled with DAPI and analysed by fluorescent or (D) time-lapse microscopy.

Figure 34:
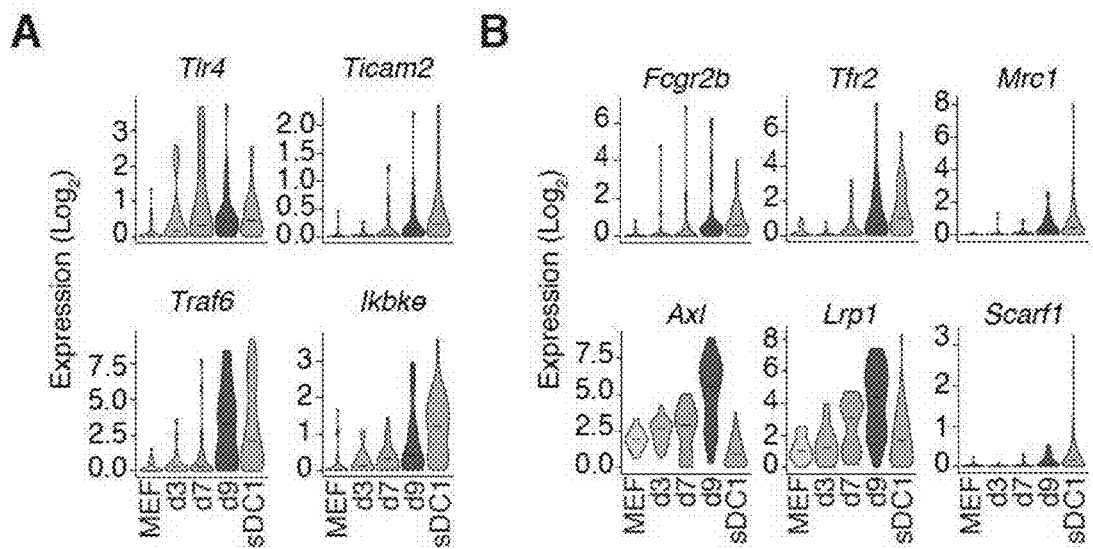

FIG. 34. Induced DCs express genes involved in TLR signalling and endocytic pathway. Violin plots for genes regulating (A) TLR signalling and (B) incorporation of antigens.

Figure 35:
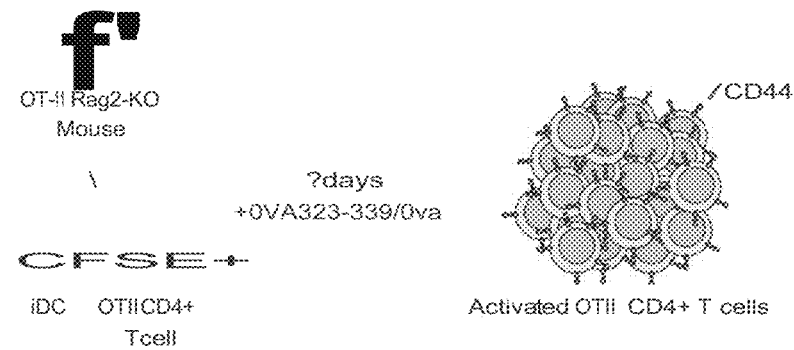
Figure 35:
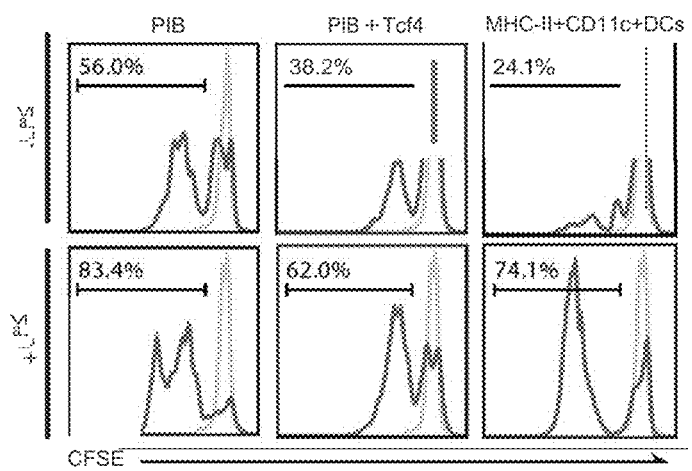
Figure 35:
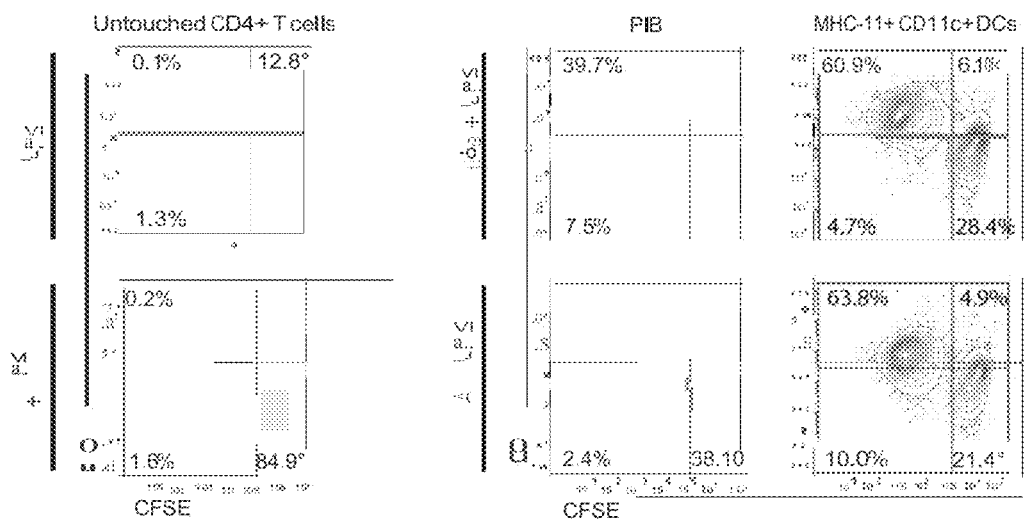

FIG. 35. Induced DCs capture and present antigens to CD4+ T cells. (A) Schematic representation of antigen presenting assay. iDCs at day 8 after addition of Dox were co-cultured with OT-II CD4+ T cells isolated from OT-II Rag2KO mice and labelled with CFSE in the presence of Ovalbumin (OVA) or OVA peptide 323-339. After 7 days, activation of CD4+ T cells was evaluated by CFSE dilution and expression of T cell activation marker CD44. (B) Flow cytometry plots of CFSE-labelled CD4+ T cells co-cultured with MEFs transduced with PIB or PIB plus TCF4, in the presence of OVA, stimulated or not with LPS. CD4+ T cells co-cultured with splenic MHC-II+CD11c+ DCs were included as controls. Grey lines correspond to untouched CD4+ T cells. (C) Flow cytometry plots showing CD44 expression of CFSE-labelled CD4+ T cells co-cultured with MEFs transduced with PIB, in the presence of LPS and OVA or OVA peptide.

Figure 36:
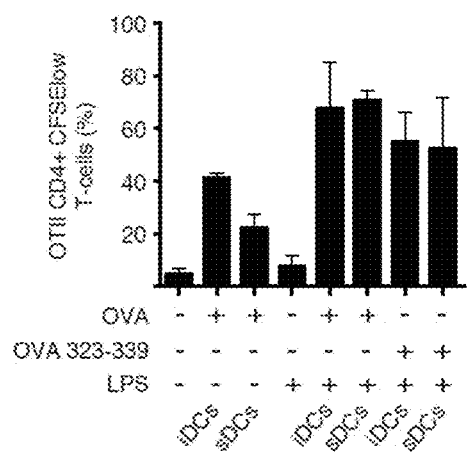

FIG. 36. Induced DCs capture and present antigens to CD4+ T cells. Quantification of the percentage of CFSElow CD4+ T-cells co-cultured with MEFs transduced with PIB (iDCs), in the presence of LPS and OVA or OVA peptide. Splenic DCs were included as control.

Figure 37:
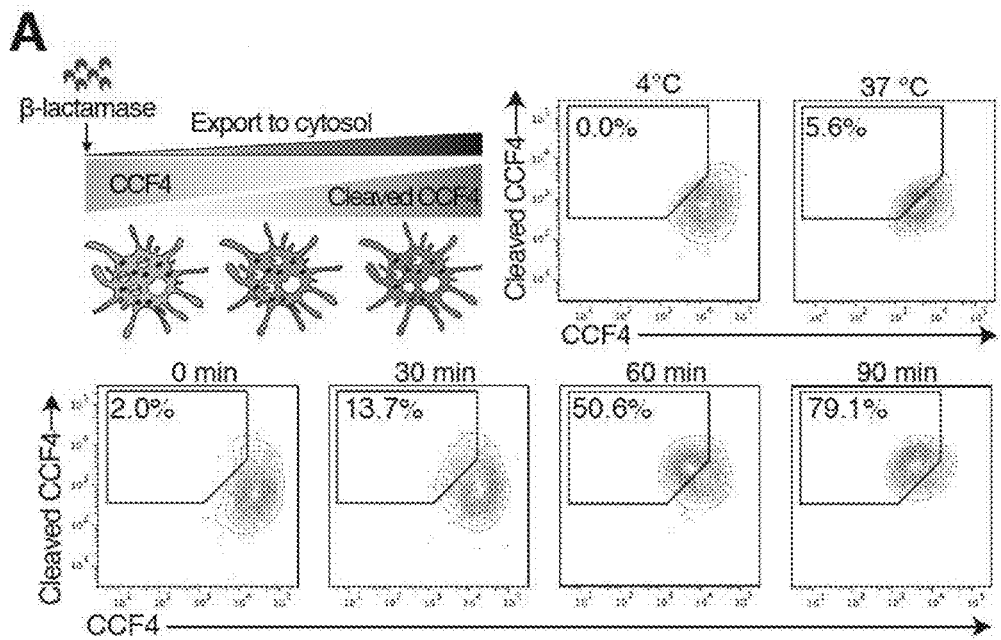
Figure 37:
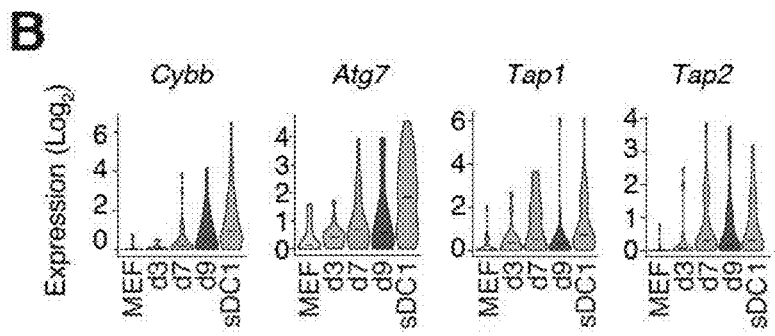

FIG. 37. Induced DCs efficiently export endocytic cargo into the cytoplasm and express cross-presentation genes. (A) iDCs at day 16 were loaded with a FRET-sensitive cytosolic substrate of β-lactamase, CCF4, followed by incubation with β-lactamase. Kinetics of β-lactamase's export to cytosol was measured as CCF4 cleavage by flow cytometry. (B) Violin plots for genes regulating cross-presentation.

Figure 38:
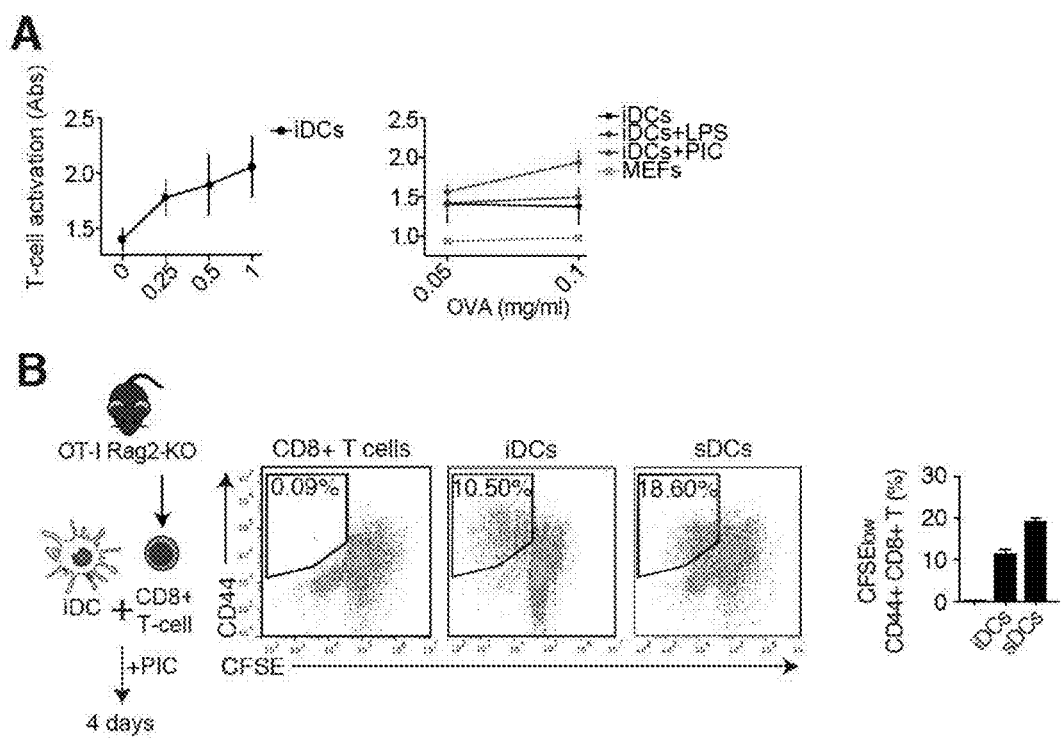

FIG. 38 Induced DCs capture and cross-present exogenous antigens to CD8+ T cells. (A) iDCs at day 16 were co-incubated with B3Z T-cell hybridomas for 16 h and increasing concentrations of soluble OVA protein in the absence (left panel) or presence of LPS or poly-I:C (PIC) stimulation (right panel). T-cell activation was measured as upregulation of β-galactosidase expression in B3Zs (driven by the IL-2 promoter) and quantified using a colorimetric substrate, CPRG. (B) Schematic representation of cross-presentation assay (left panel). iDCs at day 8 after addition of Dox were co-cultured with OT-1 CD8+ T cells isolated from OT-1 Rag2KO mice and labelled with CFSE in the presence of Ovalbumin (OVA) or OVA 257-264 peptide. After 4 days, activation of CD4+ T cells was evaluated by CFSE dilution and expression of the T cell activation marker CD44. Flow cytometry plots showing CD44 expression of CFSE-labelled CD8+ T cells co-cultured with MEFs transduced with PIB or PIB plus TCF4, in the presence of OVA. CD8+ T cells co-cultured with splenic MHC-II+CD11c+ DCs were included as controls (middle panel), and respective quantification (right panel).

Figure 39:
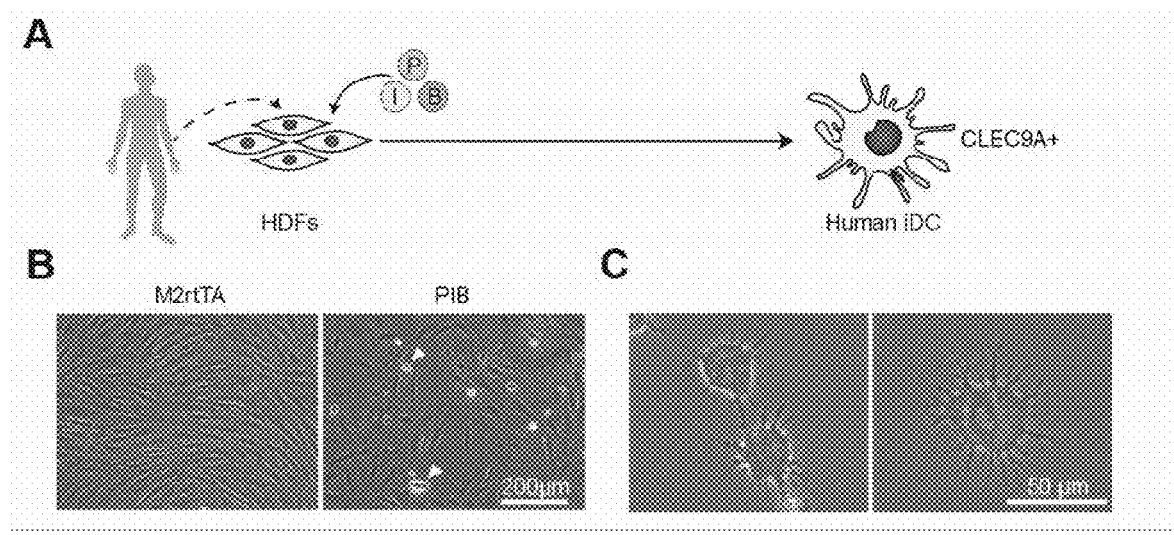

FIG. 39. PU.1, IRF8 and BATF3 induce DC-like morphology in human fibroblasts. (A) Human Dermal Fibroblasts (HDFs) were transduced with PIB (PU.1, IRF8, BATF3) and cultured in the presence of Dox. (B) Bright field images of HDFs transduced with PIB at day 3 after addition of Dox. White arrowheads mark cells with typical DC-like morphology. M2rtTA transduced HDFs are shown as control. (C) Higher magnification of bright field images of PIB-transduced HDFs with DC-like morphology.

Figure 40:
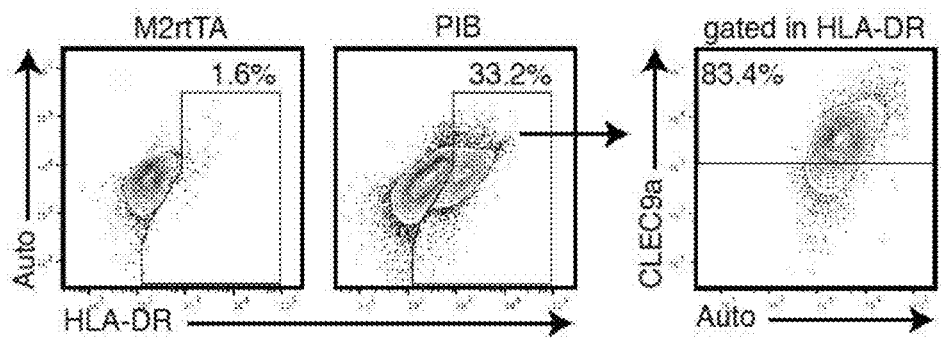

FIG. 40. PU.1, IRF8 and BATF3 induce expression of HLA-DR and CLEC9A in human fibroblasts. Flow cytometry analysis of HLA-DR and CLEC9A expression in PIB-transduced human fibroblasts at day 9 after addition of Dox.

Figure 41:
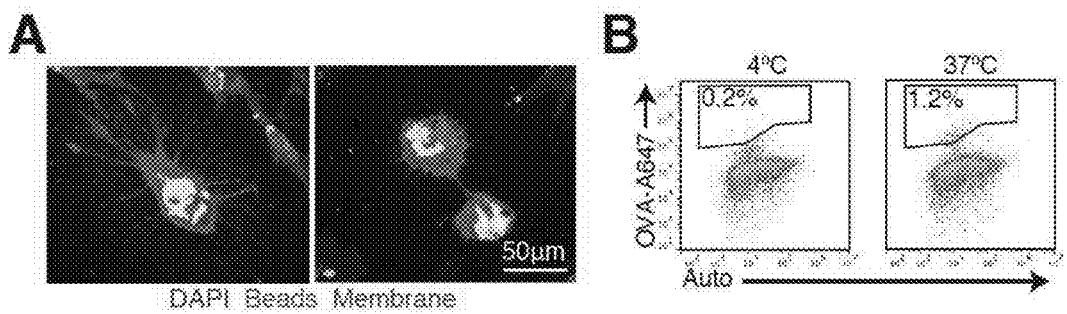

FIG. 41. PU.1, IRF8 and BATF3 induce ability to capture beads and proteins in human fibroblasts. (A) HDFs transduced with PIB were incubated overnight with FITC-labelled latex beads (1 μm) and analysed by fluorescent microscopy at day 7 after addition of Dox. CellVue Claret Far Red and DAPI were used to stain cellular membranes and nuclei, respectively. (B) Flow cytometry analysis of PIB-transduced HDFs after incubation with Ovalbumine- AlexaFluor647 for 20 minutes at 37° C. at day 7 after addition of Dox. Controls were kept on ice (4° C.).

Figure 42:
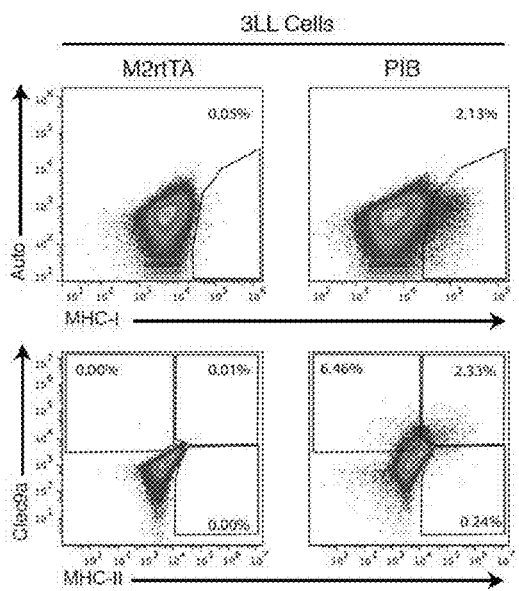

FIG. 42. PIB factors induce Clec9a and MHC-II expression in lung cancer cells. Flow cytometry analysis of Clec9a and MHC-II expression in PIB-transduced 3LL cells at day 8 after addition of Dox. M2rtTA-transduced cells are included as control.

Figure 43:
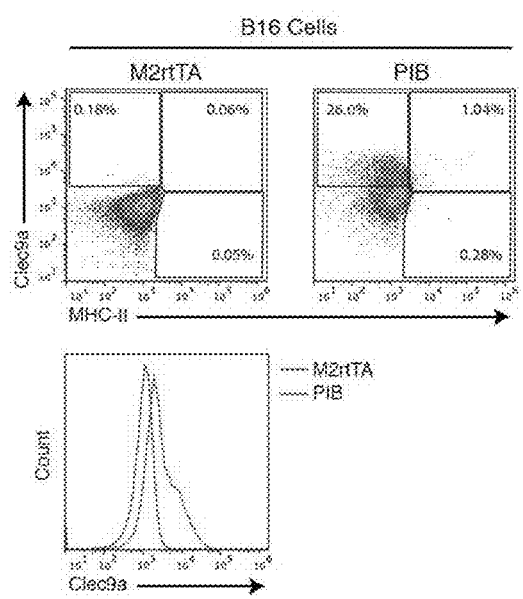

FIG. 43. PIB factors induce CLec9a and MHC-II expression in melanoma cells. Flow cytometry analysis of Clec9a and MHC-II expression in PIB-transduced B16 cells at day 8 after addition of Dox. M2rtTA-transduced cells are included as control.

Figure 44:
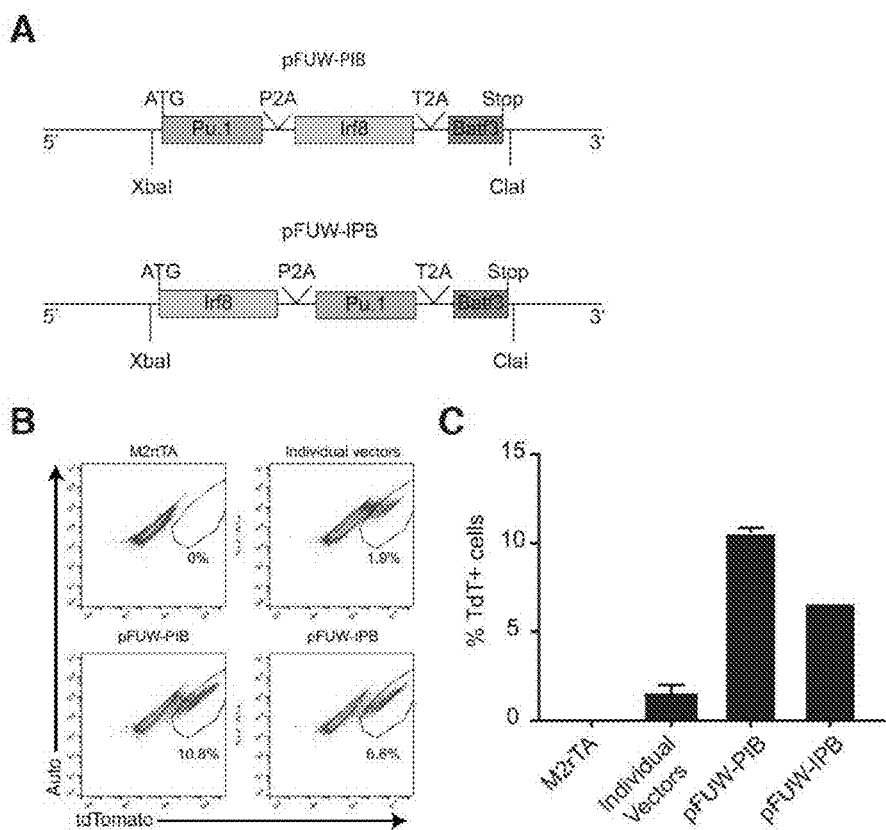

FIG. 44. Delivery of PIB factors in a polycistronic vector increases reprogramming efficiency. (A) Schematic representation of polycistronic regions encoding either Pu.1, Irf8 and Batf3 (PIB) or Irf8, Pu.1 and Batf3 (IPB) separated by 2A-like sequences. (B) Flow cytometry analysis of Clec9a reporter activation in MEFs transduced with Pu.1, Irf8 and Batf3 in individual vectors (top, right panel) or polycistronic vectors (PIB and IPB) at day 7 after addition of Dox. M2rtTA-transduced cells are included as control. (C) Quantification of tdTomato+ cells after transduction with PIB factors in individual or polycistronic vectors at day 7.

DETAILED DESCRIPTION

The present disclosure relates to compositions, nucleic acid constructs, methods and kits thereof for cell induction or reprogramming cell to the dendritic cell state or antigen presenting cell state, based, in part, on the surprisingly effect described herein of novel use and combinations of transcription factors that permit induction or reprogramming of differentiated or undifferentiated cells into dendritic cells or antigen presenting cells. Such compositions, nucleic acid constructs, methods and kits can be used for inducing dendritic cells in vitro, ex vivo, or in vivo, and these induced dendritic cells or antigen presenting cells can be used for immunotherapy applications.

Natural DCs are bone marrow-derived cells that are seeded in all tissues. DCs are poised to sample the environment and to transmit the gathered information to cells of the adaptive immune system (T cells and B cells). Upon antigen engulfment, DCs initiate an immune response by presenting the processed antigen, which is in the form of peptide-major histocompatibility complex (MHC) molecule complexes, to naive (that is, antigen inexperienced) T cells in lymphoid tissues. After activation, DCs typically overexpress co-stimulatory and MHC molecules in addition to secrete various cytokines responsible for initiating and/or enhancing many T and B lymphocyte responses, i.e. type I interferon, tumor necrosis factor (TNF)-α, IFN-γ, IL-12 and IL-6. Thus, DCs are generally identified by their high expression of major histocompatibility complex class II molecules (MHC-II), co-stimulatory molecules, such as CD80/86 and CD40, and integrin CD11c, as well as their superior capacity to secrete inflammatory cytokines and to migrate from non-lymphoid to lymphoid organs and stimulate naive T cells. In mice and humans, distinct subsets of DCs can be variably defined by phenotype, ontogeny, and function. They include the conventional DC subset 1 (cDC1, also kwon as CD8a+ DC subset) found in mouse lymphoid organs and the related CD103+DC subset in non-lymphoid tissues. Cells bearing a similar phenotype have recently been described in humans, humanized mice, and sheep, indicating cross-species conservation of the cDC1 family. This extended family has distinct functional properties, most notably a remarkable efficiency at capturing material from dead or dying cells, as well as processing exogenous antigens for cross-presentation on MHC class I. These two features allow cDC1 DCs to cross-present cell-associated antigens and trigger CTL responses against infectious agents or tumors. In addition to priming CD8+ T cells, cDC1+ DCs have been implicated in the establishment of cross-tolerance to tissue-specific cell-associated antigens. The ability of cDC1 DCs to either cross-prime or cross-tolerize CD8+ T cells against cell-associated antigens implies that they can decode the context in which they encounter dead cells. DNGR-1, also known as CLEC9A, is a receptor for necrotic cells that favors cross-priming of CTLs to dead cell-associated antigens in mice. DNGR-1 is selectively expressed at high levels by mouse cDC1 DCs, CD103+ DCs and by their human equivalents, being responsible for recognizing an intracellular ligand exposed after cell death. Recently, expression of Clec9a was shown to allow the identification of DC precursors (CDPs) committed to the conventional DC lineage and their progeny in lymphoid tissues (10).

The successful identification of DC inducing factors capable of reprogramming differentiated cells to induced DCs, as described herein, can advance our basic understanding of DC biology in a number of ways. This work will provide thorough insight into DC minimal transcriptional networks. In addition, the identification of DC inducing factors offer unprecedented opportunities to understand how DC state is established and how key regulatory machinery is put into place.

Figure 1:
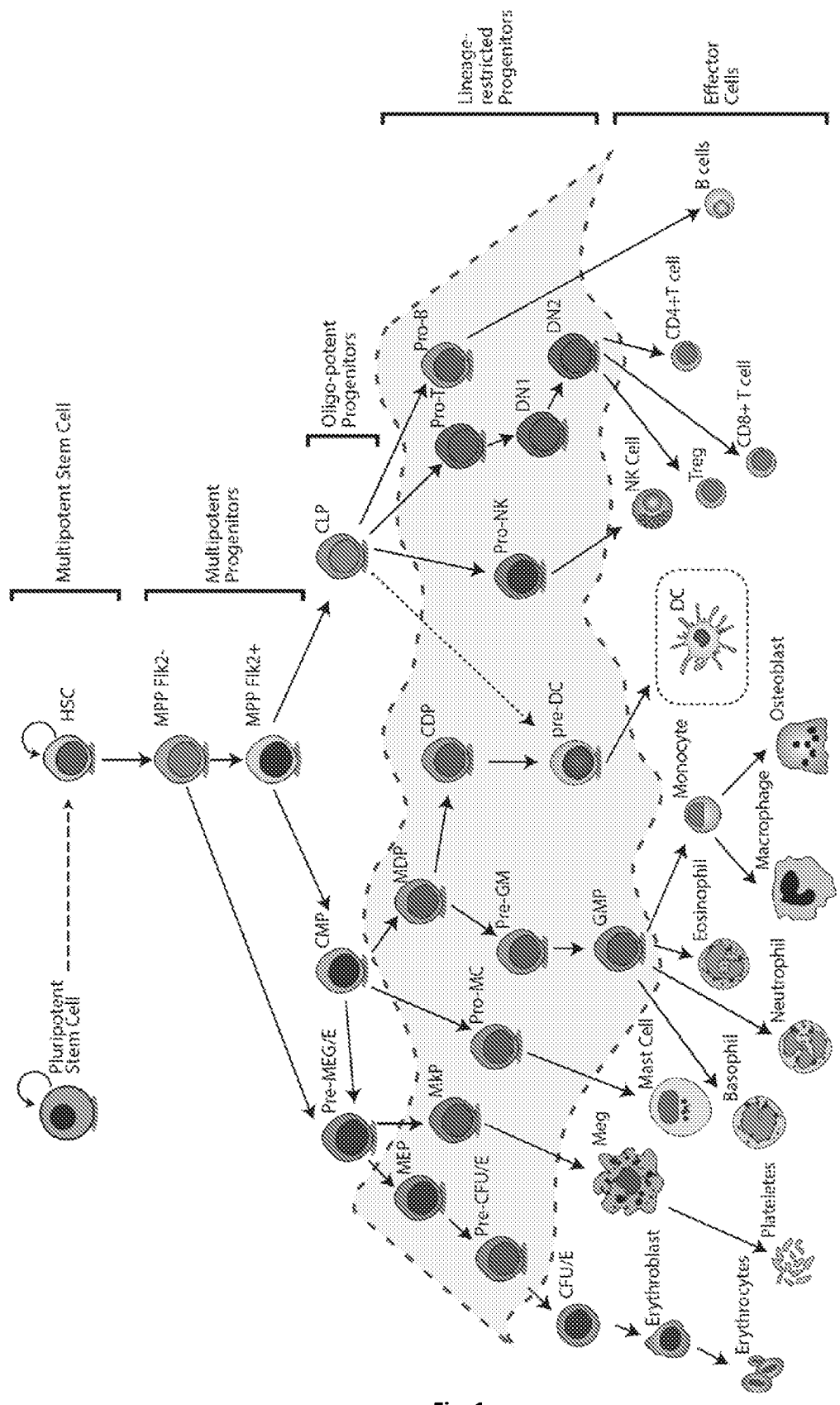
FIG. 1. Schematic representation of hematopoietic differentiation. Whereas hematopoietic differentiation normally proceeds from hematopoietic stem cells (HSCs) through progressively more-restricted progenitors into differentiated blood effector cells, such as dendritic cells (DCs) (highlighted with dashed-line box), the results described herein aim to utilize DC-enriched transcription factors to reprogram somatic differentiated cells from other lineages into the dendritic cell fate with antigen-presenting capacity. Multipotent progenitor cells (MPPs), common myeloid progenitor cells (CMPs), common lymphoid progenitor cells (CLPs), granulocyte-monocyte progenitor cells (GMPs), pre-megakaryocyte-erythrocyte (pre-MEG/E) progenitor cell, megakaryocyte-erythrocyte progenitor cells (MEP), colony forming unit-erythroid (CFU-E), megakaryocytic progenitor MkP, pro-mast cells (ProMCs), Monocyte DC progenitors (MDP), Common Dendritic Cell Precursors (CDP), pre-dendritic cell (pre-DC), double negative T lineage precursors (DN1, DN2).

Transcription factors play a critical role in the specification of all cell types during development. The success of direct reprogramming strategies using transcription factor-mediated reprogramming indicates that it is equally plausible to direct the differentiation of pluripotent ES/iPS cells or multipotent stem cells to specific fates using such factors. Accordingly, using the DC inducing factors identified herein, directed differentiation of ES/iPS cells to a definitive DC fate by expression of the DC-enriched transcription factors can be achieved. Additionally, using the DC inducing factors identified herein, directed differentiation of multipotent hematopoietic stem and progenitor cells to a definitive DC fate by expression of the DC-enriched transcription factors can be achieved (forcing differentiation along the hematopoietic tree depicted in FIG. 1).

Figure 2:
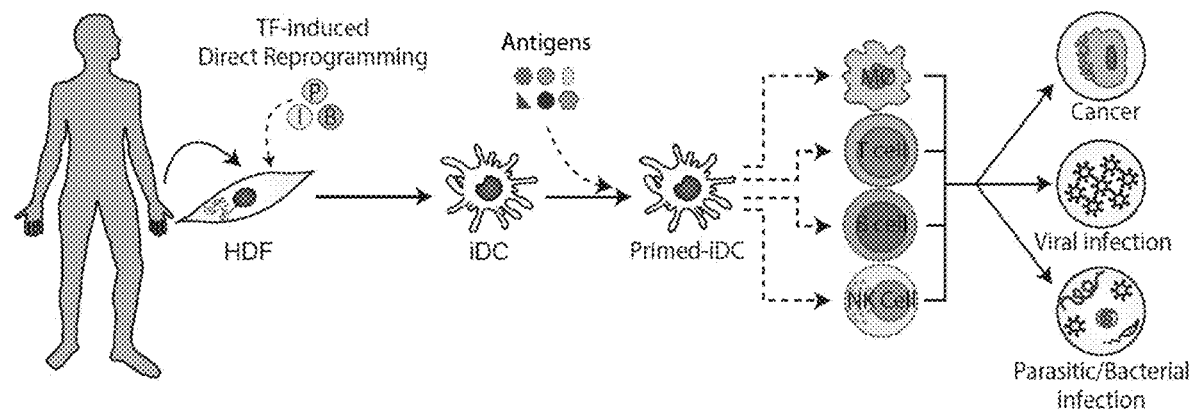
FIG. 2. Generating Antigen Presenting Cells by Direct Cellular Reprogramming. Observation of the effect of the TF combination disclosure in the present subject-matter for the induction of dendritic cells (iDCs) from mouse and human fibroblasts. Induced DCs can be applied to generate a personalized immunotherapy after loading with cell extracts or defined antigens (Primed-iDC). DCs are specialized in antigen presentation to Macrophages (MO), T, B and NK cells. Induced DCs stimulate antigen-specific immune responses against cancer, viral, parasitic or bacterial infections.

Typically, nucleic acids encoding the DC inducing factors, e.g., DNA or RNA, or constructs thereof, are introduced into a cell, using viral vectors or without viral vectors, via one or repeated transfections, and the expression of the gene products and/or translation of the RNA molecules result in cells that are morphologically, biochemically, and functionally similar to DCs, as described herein. These induced DCs (iDCs) after priming with the adequate antigens have the ability to capture, process and present them to effectors cells of the immune system (macrophages, T-cells, B-cells, NK cells) eliciting antigen-specific immune responses against cancer, viral and parasitic/bacterial infections (FIG. 2).

Figure 3:
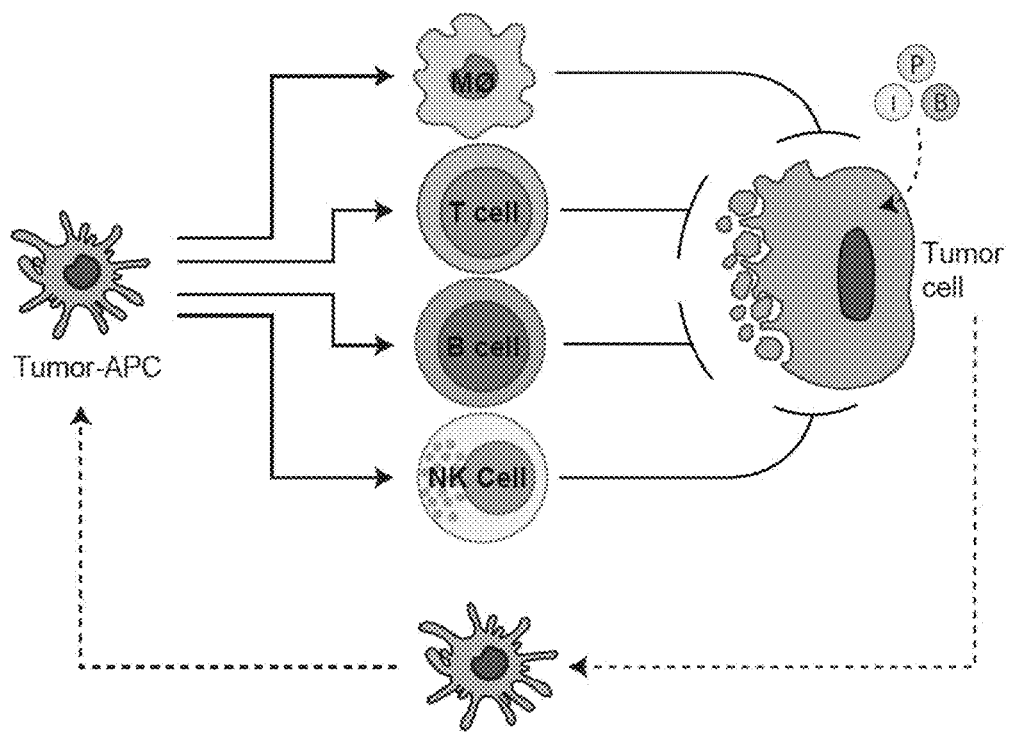
FIG. 3. In situ or ex vivo direct reprogramming of cancer cells to stimulate antigen-specific immune responses. Effect of TF combination (PIB) for the induction of DC fate and antigen presenting capacity, when this cocktail is introduced directly into cancer cells in vivo or in situ or, ex vivo or in vitro. This strategy enables tumor cells to present their specific antigens (Tumor-APC) to CD4+ and CD8+ T-cells, triggering a targeted immune response against the tumor.

An aspect of the present disclosure is the use of TFs or the use of a combination of TFs in cancer cells (in situ or ex vivo) to force them to present their own antigens to immune cells (FIG. 3). This method represents a feasible strategy to increase the clinical outcome of anticancer immunotherapies as it bypasses cancer evasion mechanisms and increases tumor immunogenicity.

Figure 4:
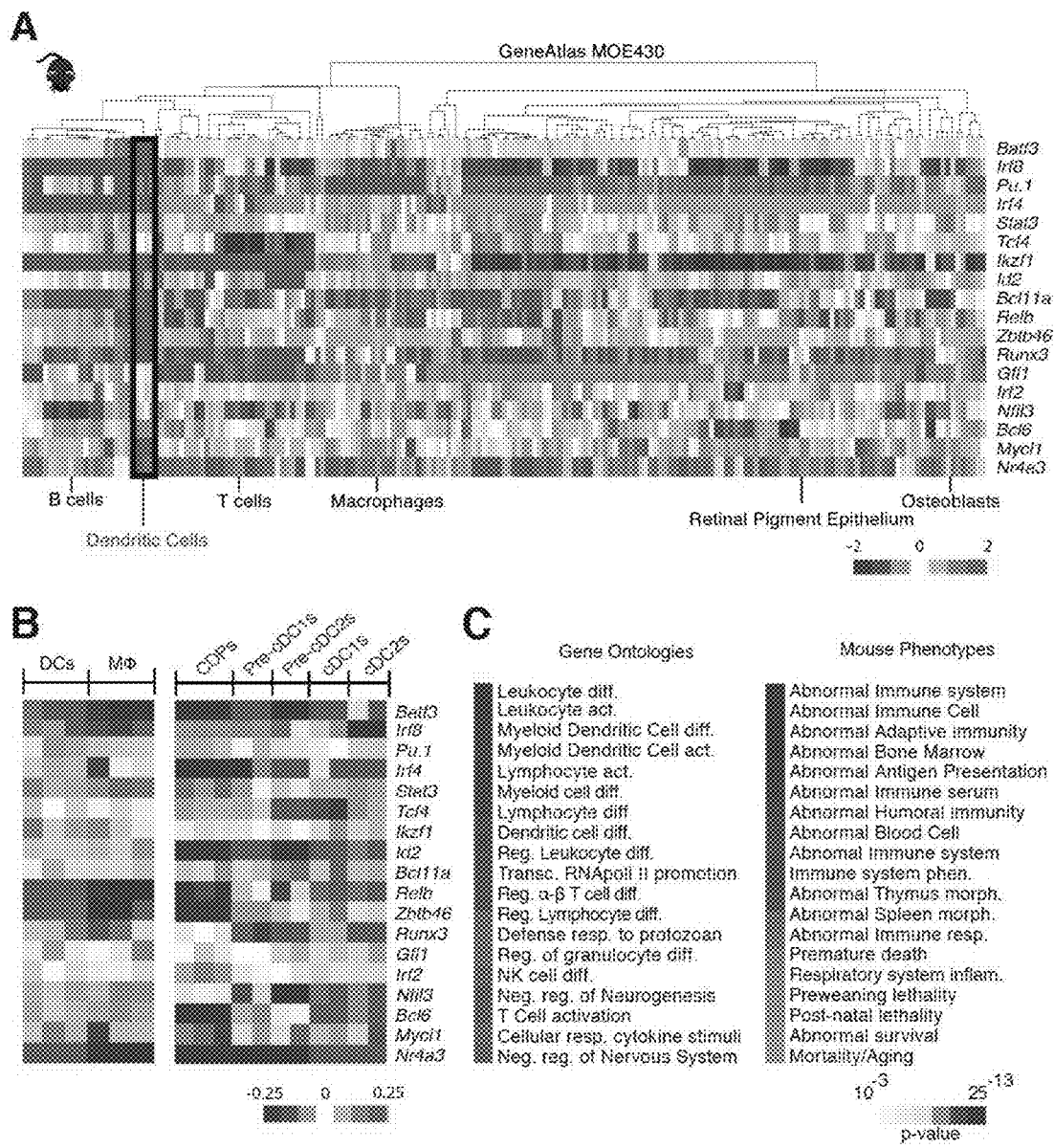
FIG. 4. 18 TF candidates for the direct reprogramming of DCs. (A) Heat map showing gene expression of the 18 candidate factors across multiple mouse tissues (GeneAtlas MOE430). The majority of the 18 factors are specifically enriched in DCs (black box) but not in other tissues (right). (B) Heat maps showing increased gene expression of the 18 factors in mouse DCs when compared with macrophages (Mcp) derived from bone marrow cultures (left panel, GSE62361). Heat maps displaying gene expression of the 18 TFs in common dendritic cell precursors (CDP), Pre-conventional DCs (Pre-cDC1 and Pre-cDC2) and conventional DCs (cDC1 and cDC2) (right panel, GSE66565). Gene expression data were analyzed by Cluster 3.0 and displayed by Treeview. Red indicates increased expression, whereas blue indicates decreased expression over the mean. (C) Gene ontology biological process (left) and mouse loss-of-function mutant phenotype (right) enrichment analysis was performed for the candidate 18 TFs using Enrichr (http://amp.pharm.mssm.edu/Enrichr/). Lists show the most enriched terms (top 19) and left columns show respective p-values. Top enriched biological processes enriched are leucocyte differentiation (p=2.51E-12), leucocyte activation (p=1.02E-11), DC differentiation (p=9.58E-12) and DC activation (p=6.31E-11), whilst mutant phenotypes include abnormal adaptive immunity (p=1.19E-04) and abnormal antigen presentation (p=1.25E-03).

In an embodiment, 18 candidate TFs were selected due to their specifically enriched gene expression in DCs (FIG. 4A), enriched in DCs when compared to macrophages, which are less efficient APCs (FIG. 4B, left panel) (20) and during DC ontogeny (FIG. 4B, right panel). Gene ontology (GO) enrichment analysis for the 18 TFs highlighted their fundamental role on leucocyte and DC differentiation (p=2.51E-12 and p=9.58E-12, respectively) and activation (p=1.02E-11 and p=6.31E-11, whilst mouse mutant phenotype enrichment analysis confirmed that genetic perturbations in those genes cause largely hematopoietic phenotypes, in particular abnormal adaptive immunity (p=1.19E-04) and abnormal antigen presentation (p=1.25E-03) (FIG. 4C). 18 candidate TFs were cloned individually in a reprogramming proven Doxycycline (Dox)-inducible lentiviral vector (6).

Figure 5:
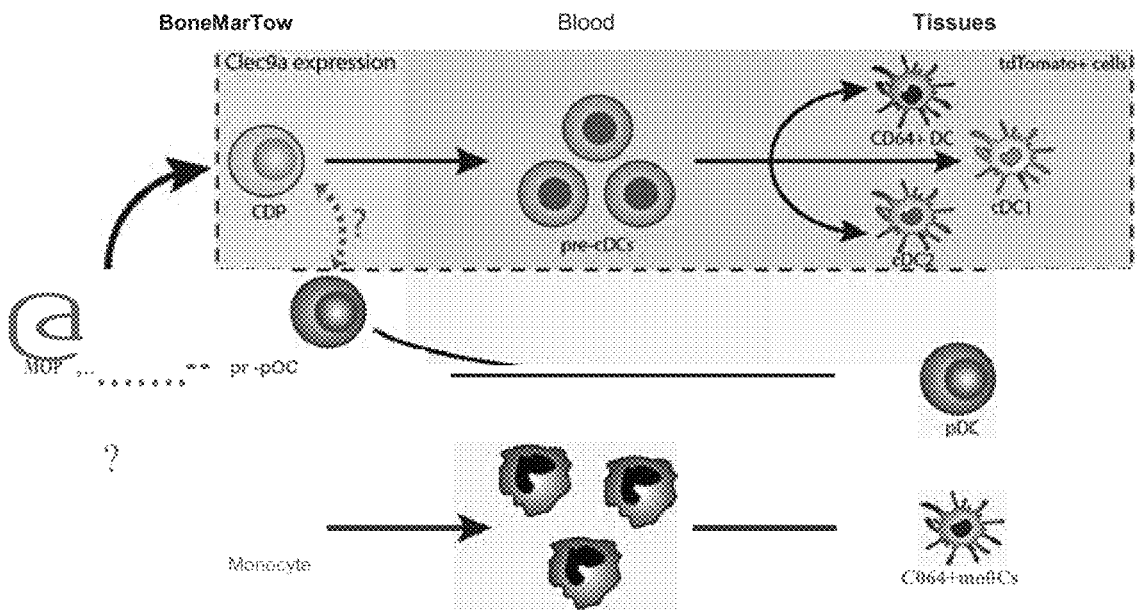
FIG. 5. Expression of Clec9a is specifically restricted to the conventional DC-lineage. (A) Clec9a-Cre X R26-stop-Tomato double transgenic mouse enables identification of conventional DCs and their committed precursors (CDP, Common Dendritic Cell Precursors), but not other leukocytes, due to restricted tdTomato expression. (B) Expression profile of Clec9a in DCs and several hematopoietic cell lineages obtained from data available in Immunological Genome Project (www.immgen.org). (C) Gene expression of the Clec9a gene in Monocyte DC progenitors (MDPs) and DC-committed precursors (CDPs and pre-DCs) at the single cell level (GSE60783).
Figure 5:
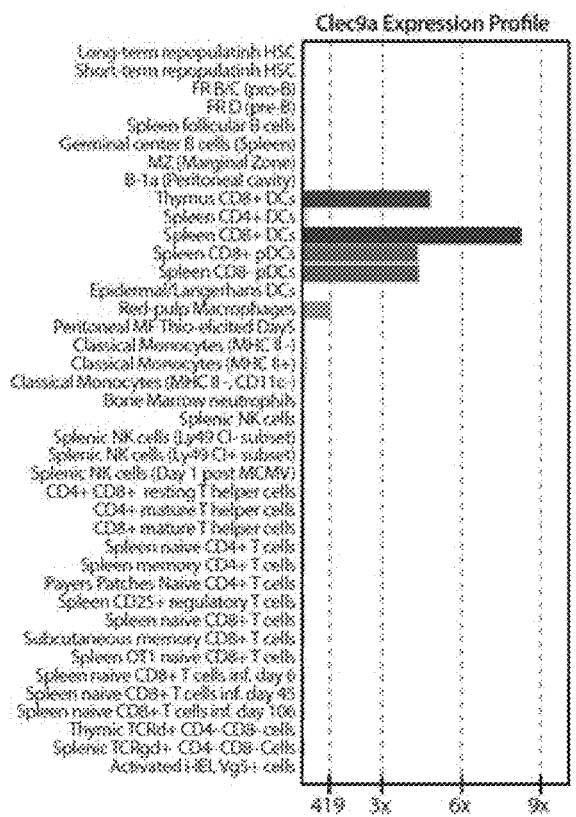
Figure 5:
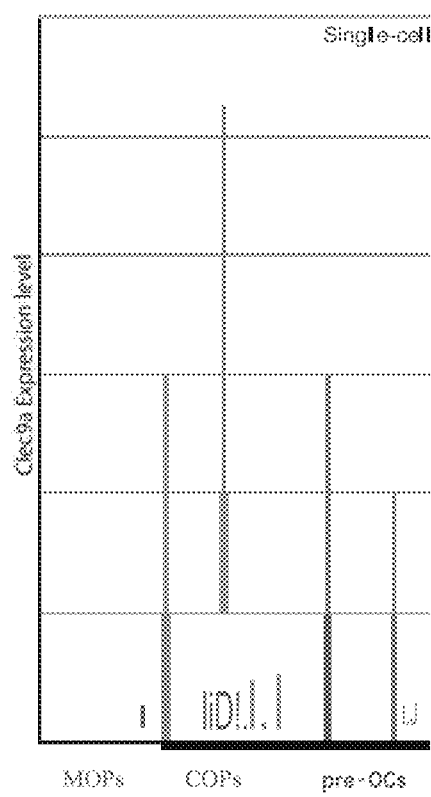
Figure 6:
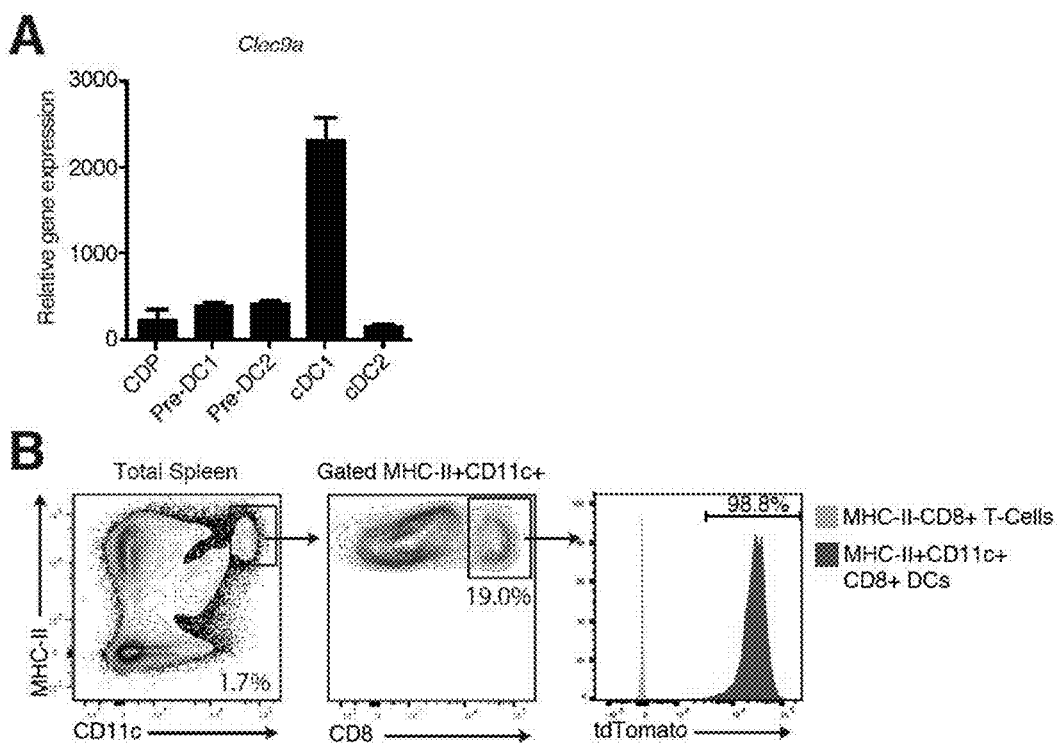
FIG. 6. Clec9a is highly expressed in mature cDC1s. (A) Gene expression of Clec9a in DC precursors (CDPs, pre-DC1 and pre-DC2) and mature cells (cDC1 and cDC2) (GSE60782). (B) Confirmation of Clec9a-tdTomato on splenic cDC1 (MHC-II+CD11c+CD8+ cells) isolated from double transgenic C9a-tdT animals. CD8+ T-cells that do not express Clec9a were included as control.

In an embodiment, for screening the effect of the new dendritic cell-inducing TFs and DC-inducing TF combinations by cellular reprogramming, it has started with Mouse Embryonic Fibroblasts (MEFs) harboring a DC-specific reporter (Clec9a-Cre X R26-stop-tdTomato) and used the activation of the reporter to shown DC-inducing TFs. In Clec9a-tomato reporter mouse, the tdTomato fluorescent protein is expressed exclusively by CDPs, pre-DCs and in cDCs (10). Macrophages, other immune lineages or monocyte-derived DCs in culture do not express Clec9a and therefore the tdTomato protein (FIG. 5A). Within the immune system Clec9a gene expression is selectively restricted to CDPs and their progeny (pre-cDCs and cDCs) (FIG. 5B). Results from gene expression analysis of cDC and precursors also highlighted that Clec9a expression is acquired after commitment to cDC lineage in CDPs and pre-DCs and not before in Monocyte DC progenitors (MDPs) (FIG. 5C) (11). Clec9a is expressed in CDPs, both pre-DCs and cDC subset, reaching high levels in the cDC1 subset (FIG. 6A) (21). Spleen cells isolated from Clec9a reporter mice were analysed, confirming that 98.8% of cDC1 cells (gated in MHC-II+CD11c+CD8a+) express the tdTomato fluorescent protein (FIG. 6B).

Figure 7:
FIG. 7. Isolation and purification of Clec9a reporter MEFs to screen candidate TFs. (A) Double transgenic (Clec9a-Cre X R26-stop-Tomato) pregnant females were used to isolate MEFs at embryonic day E13.5. After removal of the head, fetal liver and internal organs, MEFs were cultured until confluency. MEFs were sorted to remove residual CD45+ and tdTomato+ cells that could represent cells with hematopoietic potential. (B) Gating strategy to remove residual CD45+ and tdTomato+ cells. Double negative MEFs, approximately 97% of the population, were sorted. (C) Purity confirmation of the sorted population.
Figure 7:
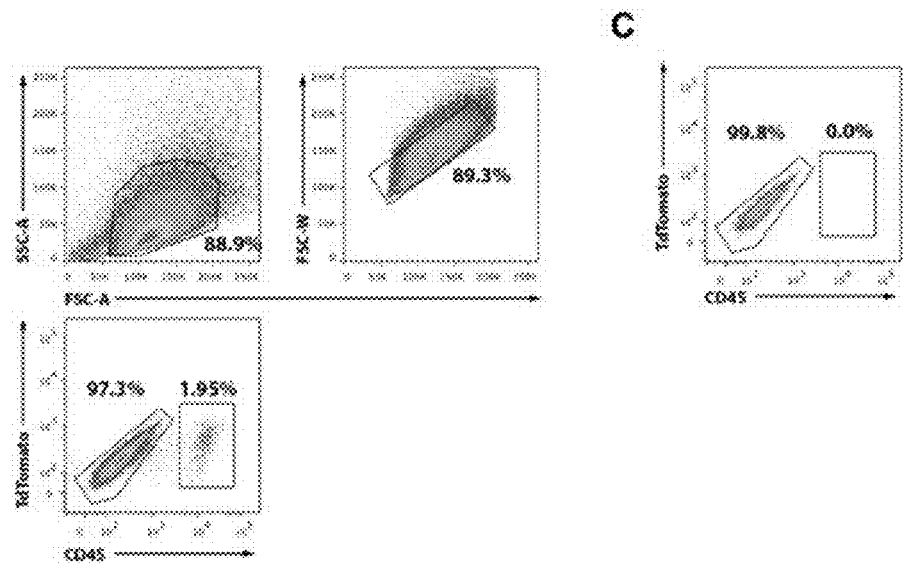

Double transgenic Clec9a-tdTomato reporter MEFs were isolated from E13.5 embryos and excluded from any contaminating tdTomato+ or CD45+ cell that could be already committed to the hematopoietic lineage (FIGS. 7A and 7B) by Fluorescent-Activated Cell Sorting (FACS). MEFs used for screening and in the following experiments were tdTomato– CD45– with a purity of 99.8% (FIG. 7C).

In an embodiment, PU.1, IRF8 and BATF3 are sufficient for Clec9a activation and to impose dendritic cell morphology.

Figure 8:
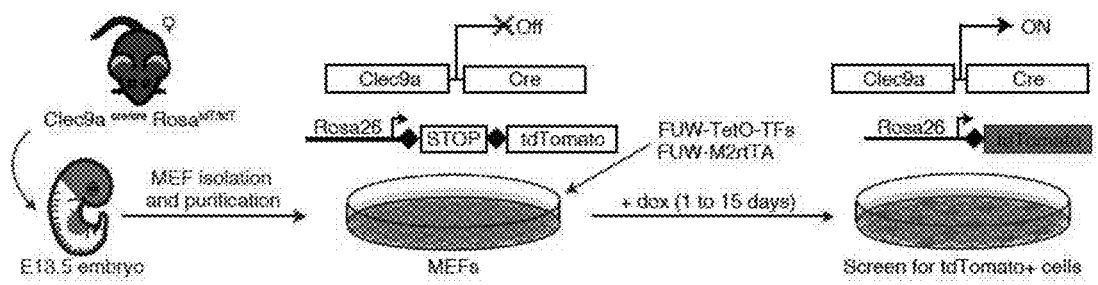
FIG. 8. Experimental design to screen candidate TFs' ability to activate Clec9a reporter MEFs. Purified MEFs were transduced with different pools of inducible lentiviral vectors encoding DC-specific TFs. MEFs were cultured in the presence of Dox to induce expression of the TFs and monitored from day 1 to 15 for tdTomato expression. Activation of Clec9a promoter induces expression of Cre recombinase, which mediates excision of the Stop codon and consequent expression of tdTomato.
Figure 9:
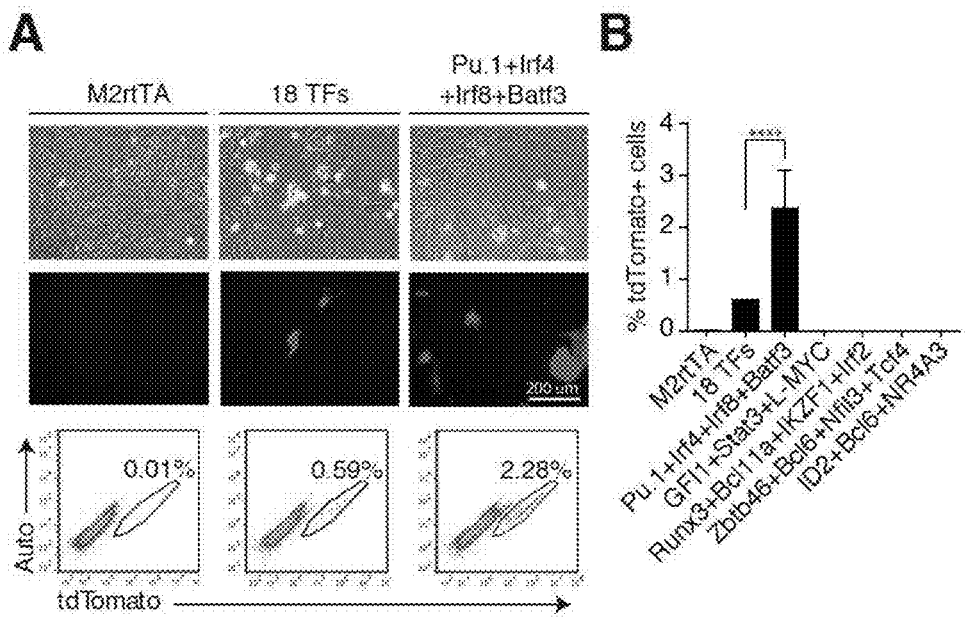
FIG. 9. Combinations of candidate DC-inducing TFs induce activation of the Clec9a-tdTomato reporter. (A) MEFs were transduced with M2rtTA (as control), all 18 candidate TFs and pools of 3-4 TFs and analyzed by fluorescent microscopy and flow cytometry 5 days after addition of Dox. (B) Quantification of tdT+ cells after transduction with M2rtTA, all 18 TFs or smaller pools at day 8. Mean±SD, n=2. (C) Quantification of tdT+ cells after removal of individual TFs from the pool of 4 TFs or their individual expression at day 8. Mean±SD, n=2.
Figure 9:
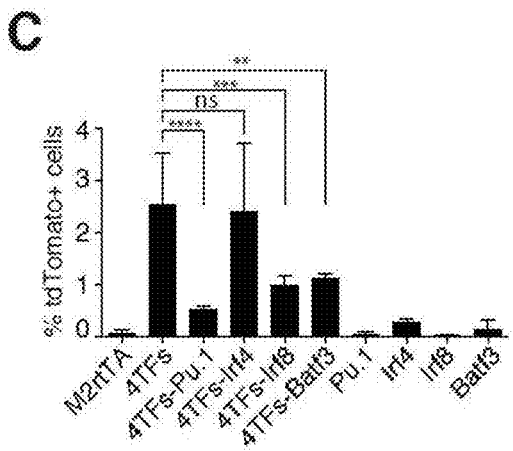

In an embodiment, Clec9a reporter MEFs were transduced with combinations of candidate TFs and evaluated for tdTomato expression (FIG. 8). After transduction with the 18 candidate TFs or one of the pools of 4 TFs, we observed the emergence of tdTomato+ cells 5 days after adding Dox (FIG. 9A, FIG. 9B). The pool comprising of Pu.1, Irf4, Irf8 and Batf3 generated more tdTomato+ cells than 18 TFs (2.36% versus 0.59%, respectively) suggesting that the minimal combination of factors required to induced reporter activation is contained within this pool. TdTomato+ cells were not detected after transduction with control M2rtTA vector. We then removed each of the factors individually (FIG. 9C). Pu.1, Irf8 and Batf3 (PIB) removal reduced reporter activation while removal of Irf4 did not have an impact. These results suggest that PIB are essential for DC reprogramming.

Figure 10:
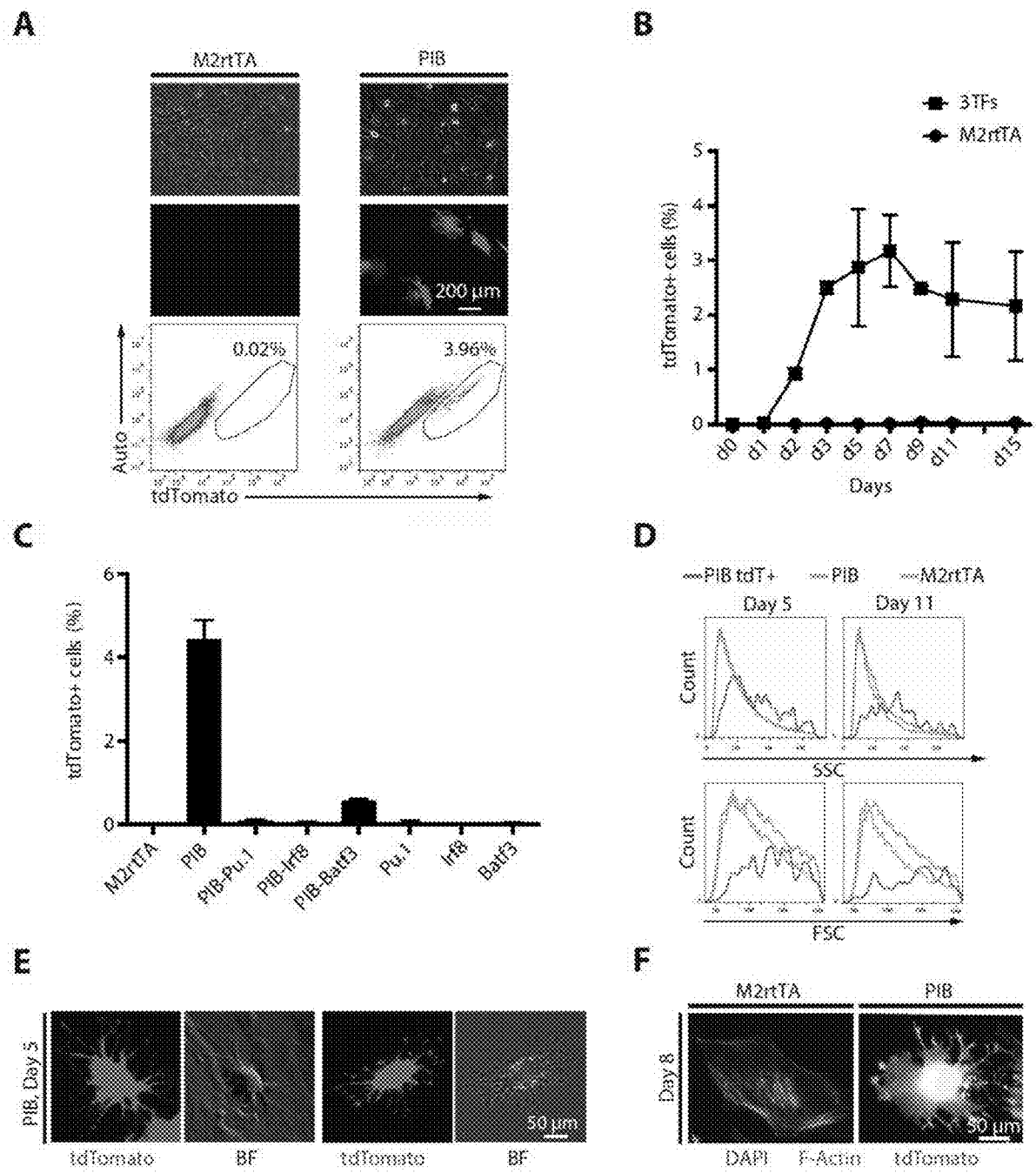
FIG. 10. Minimal transcription factor network activates Clec9a reporter and induce DC morphology in mouse fibroblasts. (A) MEFs were transduced with M2rtTA (as control) or PU.1, IRF8 and BATF3 (PIB—mixture of the 3 TF) and analysed by fluorescent microscopy and flow cytometry 5 days after addition of Dox. (B) Kinetics of Clec9a-tdTomato reporter activation analysed by flow cytometry. (C) Quantification of tdTomato+ cells after removal of individual TFs from the pool of PIB or their individual expression at day 5 after addition of Dox. (D) Flow cytometry histograms showing size (FSC) and complexity (SSC) in PIB transduced cells (gated in tdTomato+ or total population) and M2rtTA transduced cells. (E) Morphology of tdTomato+ cells at day 5 after the addition of Dox. (F) Immunofluorescence for F-actin at day 8 after addition of Dox.
Figure 11:
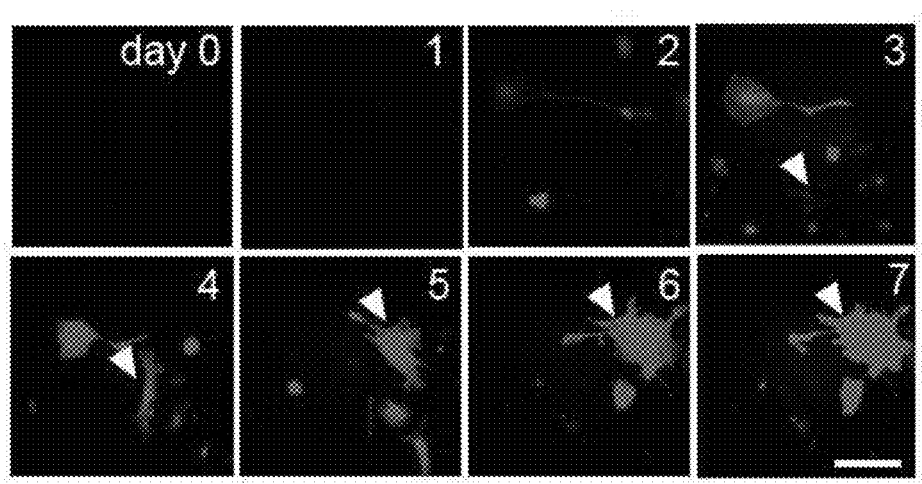
FIG. 11. Kinetics of Clec9a reporter activation analyzed by time-lapse microscopy from day 0 to day 7. Scale bars represent 200 µm.
Figure 12:
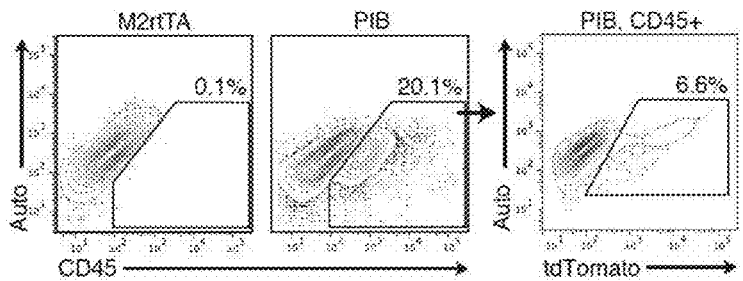
FIG. 12. Minimal transcription factor network induces expression of the pan-hematopoietic marker CD45. Flow cytometry analysis at day 8 for expression of CD45 and tdTomato in PIB-transduced MEFs.

In an embodiment when the combination of PU.1, IRF8 or BATF3 (PIB) was expressed in MEFs the Clec9-reporter is activated with an increased efficiency (approx. 3.96%, FIG. 10A). In an embodiment was then evaluated the kinetics of reporter activation (FIG. 10B). TdTomato+ cells start to be detected between day 1 and day 2 and peak between day 5 and day 7 (FIG. 10B). In an embodiment removal of PU.1, IRF8 or BATF3 completely abolished reporter activation whereas their individual expression was not sufficient to generate tdTomato+ cells (FIG. 10C). These data suggest that in this embodiment PIB constitute the minimal combination of TFs for Clec9a activation and induced Dendritic Cell (iDC) generation. Importantly, tdTomato+ cells display increased size and complexity (FIG. 10D), consistent with the observed stellate morphology and the establishment of dendrites characteristic of DCs (FIG. 10E, FIG. 10F). It has been confirmed that reporter activation occurs around 30 hours by time-lapse microscopy and observed that tdTomato+ cells exhibited morphology changes, migration capacity and dendrites gradually being established within 6 days (FIG. 11). The pan-hematopoietic marker CD45 is expressed in approximately 20% of PIB-transduced MEFs, with approximately 6.6% of tdT+ cells included in this population (FIG. 12).

Figure 13:
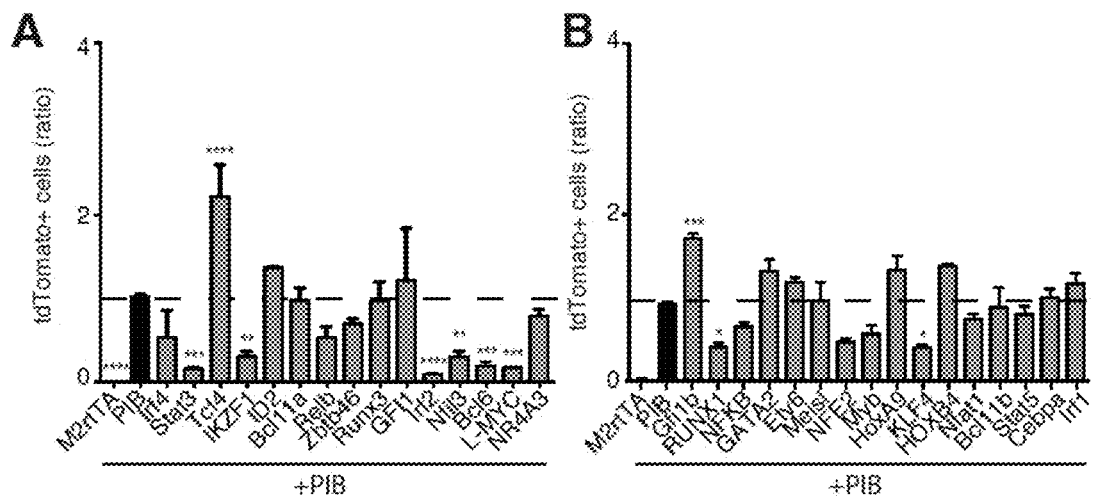
FIG. 13. TCF4 increases the efficiency of Clec9a reporter activation. (A) MEFs were transduced with PU.1, IRF8 and BATF3, PIB (black bar) or PIB combined with individual TFs from the 18 candidates (grey bars). tdTomato+ cells were quantified at day 8. M2rtTA transduction was included as control. Mean±SD, n=2-6. (B) MEFs were transduced with PIB (black bar) or PIB combined with individual hematopoietic TFs (grey bars). tdTomato+ cells were quantified at day 8. Mean±SD, n=2-6.

In an embodiment was evaluated the impact of expressing additional factors to PIB. It was assessed the individual impact of each of the TFs from the candidate pool of 18 TFs (FIG. 13A) as well as other hematopoietic TFs (FIG. 13B). From the 31 TFs tested it was observed that STAT3, IKZF1, IRF2, NFIL3, BCL6, L-MYC, RUNX1 and KLF4 negatively impact the numbers of tdTomato+ cells generated. The addition of TCF4 and Gfi1b showed a 2.2-fold and 1.9-fold increase in reporter activation, respectively.

Figure 14:
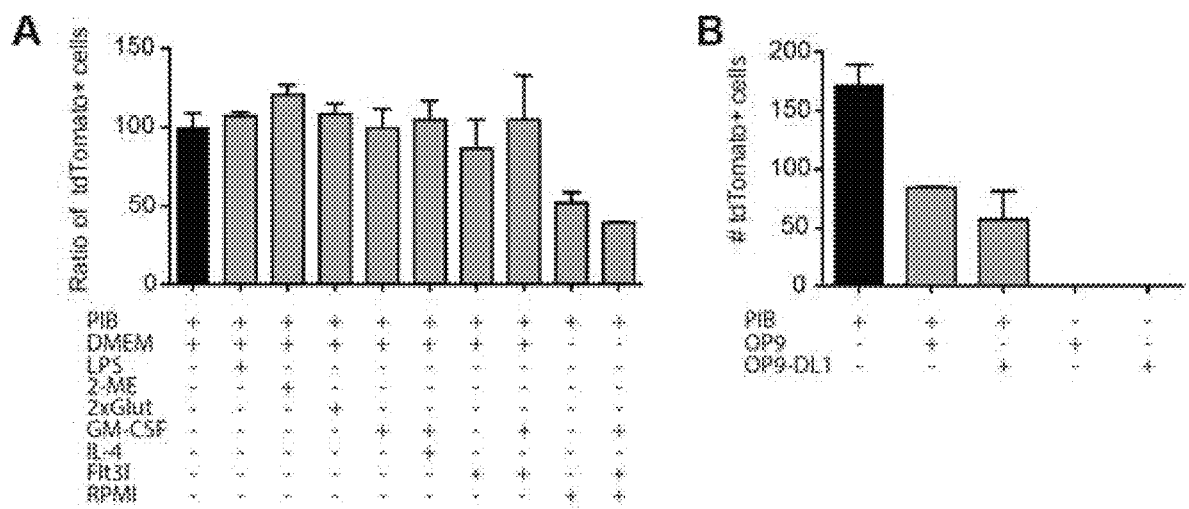
FIG. 14. Optimal culture conditions to induce the activation of the Clec9a reporter. (A) Quantification of tdTomato+ cells in MEFs transduced with PIB (PU.1, IRF8 and BATF3) and cultured in different conditions at day 10 after addition of Dox. (B) Absolute numbers of tdTomato+ cells in MEFs transduced with PIB (black bar) and co-cultured with OP9 and OP9-DL1 cells at day 10 after addition of Dox. OP9 and OP9-DL1 cultures were included as controls.

In an effort to optimize the culture conditions for iDC generation it was tested the addition of the cytokines Granulocyte-macrophage colony-stimulating factor (GM-CSF), IL-4 and FMS-like tyrosine kinase 3 ligand (Flt3l) during the induction (FIG. 14A) because of their important role during DC specification (12). It was also tested adding lipopolysaccharides (LPS), different media compositions (RPMI, 2-mercaptoethanol (2-ME) and 4 mM L-Glutamine (2×Glut) and co-culture with the stromal cells OP-9 and OP9-DL1 (FIG. 14B) (13). These culture modifications did not increase the number of induced tdTomato+ cells.

Figure 15:
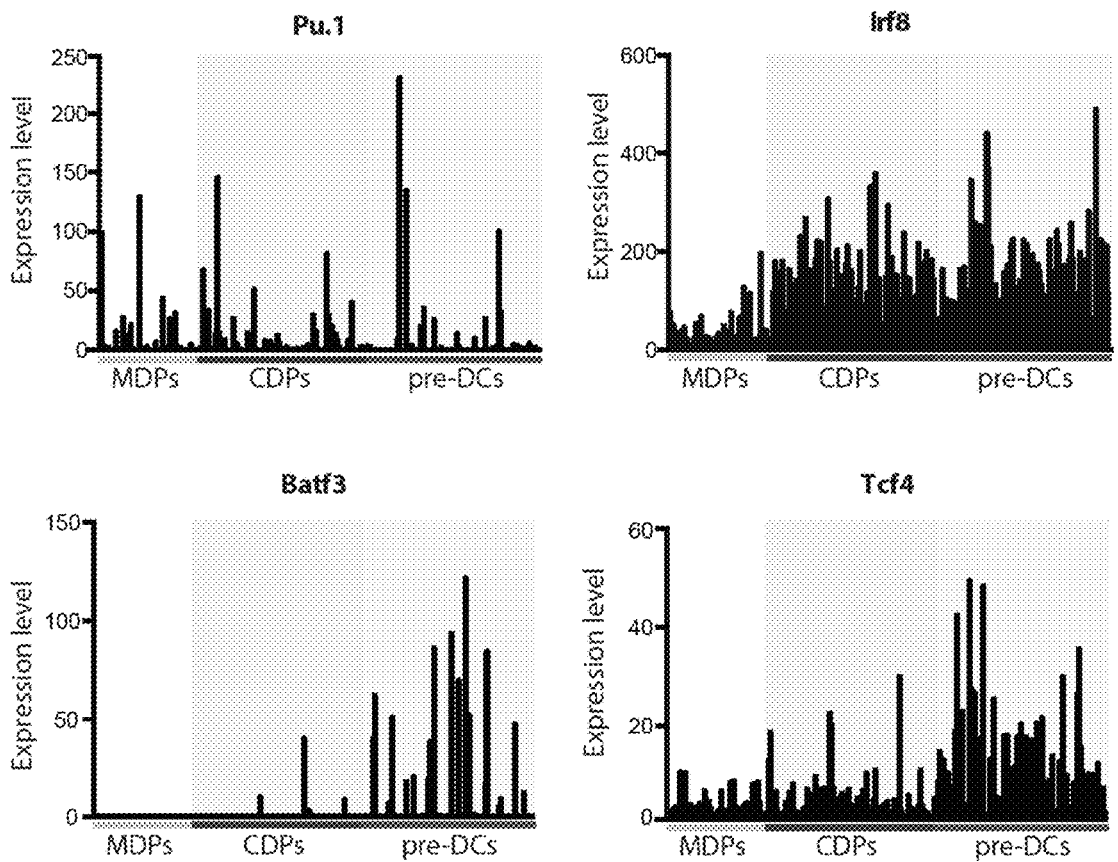
FIG. 15. Expression profiles of PU.1, IRF8, BATF3 and TCF4 at the single cell level. Gene expression of PU.1, IRF8, BATF3 and TCF4 in single monocyte-dendritic cells precursors (MDPs) and restricted DC precursor cells (CDPs, and pre-DCs) (GSE60783). Gene expression level is shown in reads per kilobase of exon model per million mapped reads (RPKM) values.
Figure 16:
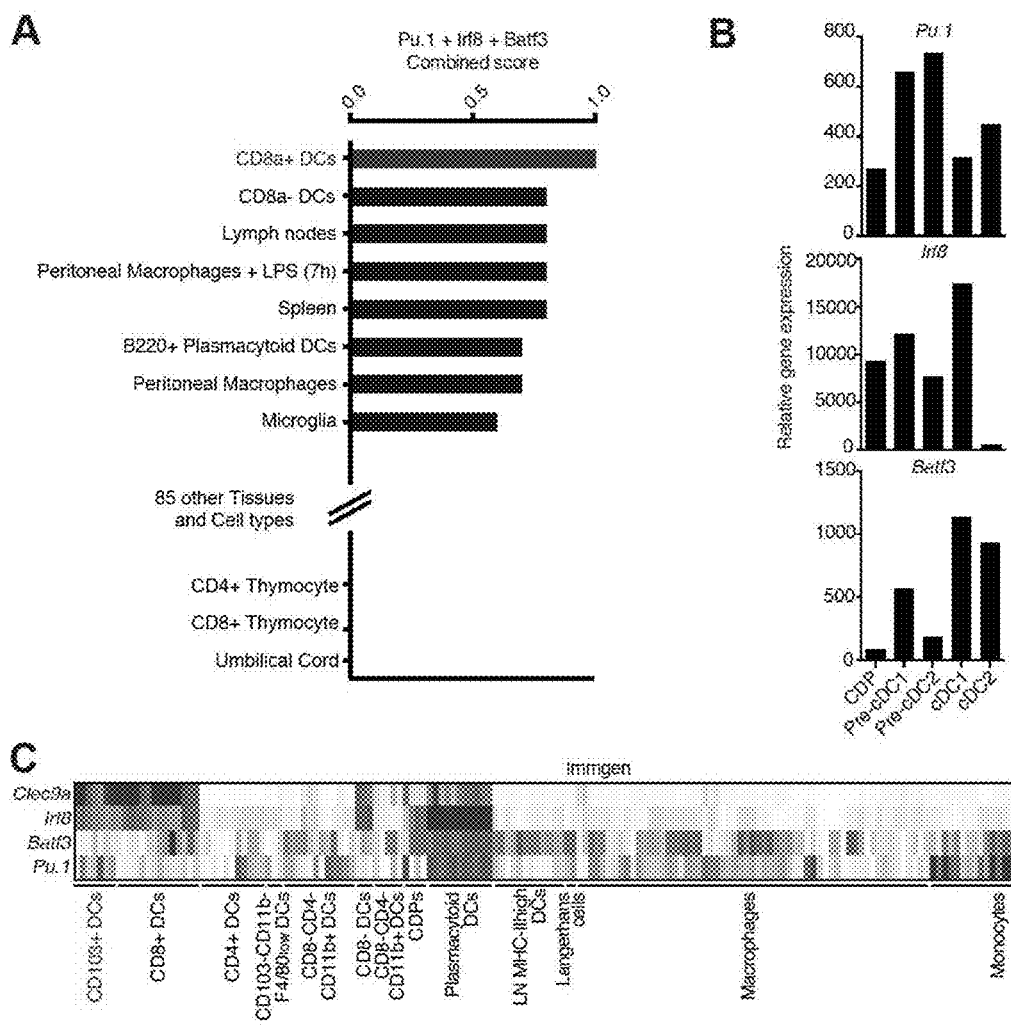
FIG. 16. Analysis of PU.1, IRF8, BATF3 factors expression in mouse cells/tissues. (A) Combined gene expression levels of Pu.1+Irf8+Batf3 across 96 tissues and cell-types. Gene expression data from different mouse tissues and cell-types, were obtained from the GeneAtlas MOE430 database. The "GPSforGenes" program was written and used to classify the tissues where combinations of TFs were most enriched (best fit=1). (B) Gene expression of Pu.1, Irf8 and Batf3 in DC precursors (CDPs, pre-DC1 and pre-DC2) and mature cells (cDC1 and cDC2) (GSE60782). Gene expression level is shown in relative gene expression. (C)

In an embodiment, the in vivo expression patterns of the PIB and TCF4 were analysed. PU.1, IRF8, BATF3 and TCF4 transcripts are expressed in single DC precursor cells (FIG. 15). While Pu.1 is equally expressed in MDPs, CDPs and Pre-DCs, IRF8 expression markedly increases in CDPs and is maintained in pre-DCs. BATF3 and TCF4 are only up-regulated at a later stage, in pre-DCs. Moreover, the combined expression of PU.1+IRF8+BATF3 is mostly enriched in CD8a+ DCs among 96 cells and tissues (FIG. 16A). Importantly, Pu.1 levels are higher in both pre-DC stages, while Irf8 and Batf3 are specifically enriched in pre-cDC1 and cDC1 subsets (FIG. 16B). When compared to other DC subsets and several hematopoietic cell lineages, Clec9a, Pu.1, Irf8 and Batf3 display increased expression of in CD103+ DCs belonging to cDC1 subset (FIG. 16C).

In an embodiment, it was evaluated whether the activation of the C9a-tdTomato reporter was reflected in the expression of DC markers, such as typical surface markers used to discriminate between conventional cDC and pDC subsets (FIG. 17A, FIG. 17B). Interestingly, the cDC1 marker CD103 is expressed in 25±13.65% of tdTomato+ cells in contrast to undetectable levels in tdTomato– cells suggesting the specification of a non-lymphoid migratory cDC1 program. Moreover, we could detect only residual expression of cDC2 and pDC markers (0.41±0.58% CD4+, 2.56±0.18% CD11b+, 0.77±1.09% B220+ cells, respectively).

In an embodiment was evaluated, if the activation of the Clec9a-tdTomato reporter was reflected in the expression of key components of the antigen presentation machinery at the cell surface. Remarkably it was observed that 71.4% of tdTomato+ cells at day 7 expressed MHC-II at the surface (FIG. 18A), a key molecule for the establishment of APC functionality. The expression of MHC-II is gradually acquired starting between day 1 and day 2 and peak between day 7 and day 11 (FIG. 18B). The kinetics of MHC-II activation resembles the activation of the Clec9a reporter (FIG. 10B). At day 7 the tdTomato-compartment contained a lower percentage of MHC-II+ cells (14.2%) (FIG. 18A). It was then addressed whether expression of MHC-II was controlled directly by PIB factors. By excluding each of the factors individually it was observed that PU.1 expression, but not IRF8 or BATF3 expression, is important for MHC-II activation (FIG. 18C), consistent with the described Pu.1 role in regulating Class II Transactivator (CIITA) through its promoter I (CIITApI) (14, 15). CIITA is known as the master regulator of MHC Class II genes' expression, determining cell-type-specific, cytokine-induced and developmental-derived modulation of MHC-II expression through the differential usage of CIITA promoters (16). In conventional DCs, CIITApI has been associated with regulation of MHC-II genes.

In an embodiment, due to the described involvement of IRF4 in inducing MHC-II expression through interaction with CIITA (17), it was evaluated whether IRF4 could compensate for Pu.1 in the generation of MHC-II+ cells within the tdTomato+ population. It was therefore assessed the expression of MHC-II in tdTomato+ cells generated by 4TFs (including IRF4) or their individual exclusion (FIG. 18D). Inclusion of IRF4 in the pool did not increase MHC-II expression on tdTomato+ cells and IRF4 could not substitute for the loss of Pu.1. Accordingly, IRF4 and PU.1 were found to synergistically promote MHC-II expression through CIITA promoter III in B cells but not DCs (17). During reprogramming to iDCs, no synergism with PU.1 was observed, which was strictly required for MHC-II expression in tdTomato+ cells.

In an embodiment, it was evaluated the expression of MHC class I molecules, key molecules for the establishment of APC functionality. 56.7% of tdTomato+ cells at day 7 expressed MHC-I at the surface (FIG. 19). At day 7 the tdT– compartment contained a lower percentage of MHC-I+ cells (11.2%) (FIG. 19).

In an embodiment, it was evaluated the expression the co-stimulatory molecules CD80 and CD86, required for efficient antigen presentation (FIG. 20). CD80 and CD86 are expressed in 35.2% of tdTomato+ MHC-II+ cells in contrast to only 12.9% of tdTomato+ MHC-II– cells. This characterization of the expression of MHC-II, CD80 and CD86 at the cell surface of iDCs suggests that a cohort of tdTomato+ MHC-II+ cells would be competent in antigen presentation. An additional co-stimulatory molecule, CD40, is expressed in 16.1% of tdTomato+ cells, comparing to only 2.8% of tdTomato– cells (FIG. 21A). Resting cDCs, in particular cDC1 subset, have been described to respond to microbial stimulation up-regulating the expression of co-stimulatory molecules and becoming more effective APCs (25). Accordingly, tdTomato+ cells up-regulate the expression of CD40 (4-fold increase) at cell surface after toll-like receptor TLR4 stimulation (LPS) (FIG. 21B).

In an embodiment, in order to define the extent of transcriptional changes during iDC reprogramming, it was measured the full-length single-cell transcriptomes after transduction with PIB (FIG. 22A). 192 cells were initially profiled from nontransduced MEFs, sorted day 3 Clec9a-tdTomato+, day 7 Clec9a-tdTomato+, day 9 Clec9-tdTomato+ MHC-II+ cells and freshly isolated CD11c+ MHC-II+CD8a+ splenic DCs (sDCs). From these, 163 individual cells passed quality control filters and were used for analysis. After alignment of reads at individual gene loci, it has used the Census algorithm to convert relative RNAseq expression levels (transcript per million, TPM) into relative transcript counts (Census counts) without the need for experimental spike-in controls and improving the accuracy of differential expression analysis. It was first employed t-distributed stochastic linear embedding (tSNE) algorithm to perform clustering analysis of the genome-wide transcriptomes (FIG. 22B) and observed two main clusters of cells. IDCs at day 3 and the majority of day 7 cells map close to MEFs, whilst the remaining day 7 and all day 9 iDCs cluster together with sDCs. It was performed unsupervised clustering using Single-Cell Consensus Clustering (SC3), confirming the global similarity of sDCs with the group of day 9 and some of the day 7 iDCs (FIG. 22C). Moreover, the timing of global transcriptome reprogramming correlates well with the peak generation of Clec9a-tdTomato+ MHC-II+ cells between days 7 and 15 (FIG. 18B). TdTomato+ cells show time-dependent transcriptional changes starting as early as day 3; by day 9 iDCs are remarkably similar to bona fide DCs. This analysis suggests that PIB factors induce global transcription reprogramming towards the DC fate. It was extracted the 6525 most variable genes across the dataset, which after clustering could be organized in 4 groups (FIG. 22D). Cluster I comprises highly expressed genes in MEFs, which are silenced during DC reprogramming. These include typical fibroblast markers, such as Col5a2, Grem1, Lox, Acta2 and Thy1 (FIG. 22E). Cluster II includes transcripts enriched at day 3 and day 7, suggesting activation during the initial stages of reprogramming. This cluster comprises genes such as Eea1 and Aldh1a2 that are associated with intracellular trafficking and metabolism as well as type I interferon (IFN) signaling (Ifit3) (FIG. 22F). In contrast, Cluster III encompasses genes enriched at day 9 (FIG. 22D). Interestingly, MHC-II related genes (such as H2-Pb) as well as genes regulating cross-presentation in DCs (such as the cathepsin Ctsc and Cd74) are enriched in this cluster (FIG. 22F). Finally, Cluster IV includes genes enriched in sDCIs and reprogrammed iDCs (FIG. 22D), such as the pan-hematopoietic marker Cd45 and the general DC marker Cd11c (FIG. 22F). Importantly, cDC1-restricted genes were also upregulated, such as the Clec9a gene and Tlr3 (22), and the key regulator of MHC class I-dependent immune responses (Nlrc5) necessary for antigen cross-presentation, a key feature of cDCIs (23). Indeed, we have detected a robust increase in cDC1-signature genes during the reprogramming process when compared to cDC2-signature genes (FIG. 26) (11). Collectively, these data suggest complete DC reprogramming favoring the cDC1 subset. Accordingly GO analysis showed that categories related to antigen processing and presentation (p-value=3.34E-08, 1.80E-06, 3.53E-06, 4.03E-06) where enriched top biological process and pathways (Table 1). Top cellular component GO categories include lysosome (p-value=1.31E-07) and lytic vacuole (p-value=1.44E-07), concordant with the described role of lysosome signaling in coordinating antigen processing and migration of DCs (24). MicroRNA (miRNA) target prediction showed highest enrichment of miR-155 (p-value=1.41E-11) and miR-124 (p-value=1.00E-10) targets (Table 2), that have been implicated in DC function and specification, respectively (25,26).

TABLE 1

Top 5 gene ontology biological process (left) and cellular component (right) enriched in Cluster I to IV.

|  | GO Biological Processes | P-value | GO Cellular Processes | P-value |
|---|---|---|---|---|
| Cluster I | Translation | 1.06E−81 | Ribonucleoprotein complex | 1.46E−96 |
|  | Generation of metabolites and energy | 1.50E−34 | Ribosome | 1.75E−90 |
|  | Electron transport chain | 2.58E−26 | Mitochondrion | 6.32E−72 |
|  | Intracellular transport | 1.52E−24 | Mitochondrial part | 7.38E−50 |
|  | Establishment of protein localization | 3.61E−19 | Ribosomal subunit | 6.27E−37 |
| Cluster II | Chromatin modification | 2.74E−05 | Membrane-enclosed lumen | 2.96E−06 |
|  | Protein transport | 1.07E−04 |  |  |
|  | Establishment of protein localization | 1.22E−04 | Intracellular organelle lumen | 5.10E−06 |
|  | Macromolecule catabolic process | 1.54E−04 | Organelle lumen | 5.53E−06 |
|  |  |  | Endoplasmatic reticulum | 9.61E−06 |
|  | Protein catabolic process | 1.54E−04 | Non-membrane bound organelle | 9.98E−05 |
| Cluster III | Antigen presentation of exogenous antigen | 3.34E−08 | Vacuole | 1.38E−08 |
|  |  |  | Lysosome | 1.31E−07 |
|  | Antigen presentation of exogenous peptide | 1.80E−06 | Lytic vacuole | 1.44E−07 |
|  |  |  | Cytosol | 3.08E−05 |
|  | Actin cytoskeleton organization | 2.71E−06 | Endoplasmatic reticulum | 4.19E−05 |
|  | Antigen presentation of peptide antigen | 3.53E−06 |  |  |
|  | Antigen processing and presentation | 4.03E−06 |  |  |
| Cluster IV | Chromosome organization | 3.28E−09 | Cytoskeleton | 2.51E−11 |
|  | Cell cycle | 5.10E−09 | Non-membrane bound organelle | 1.24E−09 |
|  | Regulation of GTPase-mediated signaling | 9.30E−09 | Intracellular organelle | 1.24E−09 |
|  | DNA metabolic process | 2.64E−08 | Endomembrane system | 3.39E−09 |
|  | Regulation Ras protein signal transduction | 1.20E−07 | Microtubule cytoskeleton | 2.31E−08 |

TABLE 2

Gene ontology mouse loss-of-function mutant phenotype (top panel), KEGG pathways (middle panel) and microRNA target interactions (bottom panel) enrichment analysis was performed on the 4 clusters of genes identified using the 6,525 most variable genes across the 5 sample groups (relative to FIG. 22). The lists show the most enriched terms and the right columns show respective p-values by fold change in relation to the top enriched term.

|  | Cluster I | P-value | Cluster II | P-value | Cluster III |
|---|---|---|---|---|---|
| Mouse Phenotypes | Abnormal cell death | 2.36E−11 | Abnormal response to infection | 4.25E−06 | Abnormal adaptive immunity |
|  | Abnormal cell physiology | 3.44E−12 | Abnormal embryonic tissue | 3.87E−06 | Abnormal innate immunity |
|  | Premature death | 1.10E−12 | Abnormal development patterning | 2.68E−06 | Abnormal immune physiology |
|  | Abnormal extraembryonic tissue | 5.36E−13 | Abnormal extraembryonic tissue | 1.00E−06 | Mammalian phenotype |
|  | Abnormal embryonic tissue | 1.86E−13 | Abnormal embryo size | 5.38E−07 | Prenatal lethality |
|  | Abnormal cell proliferation | 7.69E−14 | Abnormal immune system | 1.38E−07 | Abnormal bone marrow |
|  | Abnormal embryo size | 2.25E−14 | Abnormal adaptive immunity | 4.15E−08 | Abnormal immune cell |
|  | Cellular phenotype | 7.15E−19 | Abnormal immune cell | 3.61E−08 | Premature death |
|  | Mammalian phenotype | 8.04E−29 | Mammalian phenotype | 5.99E−09 | Abnormal blood cell |
|  | Prenatal Lethality | 8.24E−50 | Prenatal Lethality | 5.05E−10 | Abnormal immune system |
| Pathways | Citrate cycle (TCA cycle) | 2.06E−05 | Endocytosis | 8.69E−02 | Endometrial cancer |
|  | Ubiquitin mediated proteolysis | 1.51E−05 | Apoptosis | 8.01E−02 | Thyroid cancer |
|  | Nucleotide excision repair | 8.73E−06 | Vesicular transport | 7.84E−02 | Glioma |
|  | Spliceosome | 9.90E−11 | Lysosome | 3.79E−02 | Prostate cancer |
|  | Proteasome | 1.01E−14 | Galactose metabolism | 3.35E−02 | Chronic myeloid leukemia |
|  | Alzheimer's disease | 2.76E−20 | RIG-I-like receptor signaling | 3.35E−02 | Chemokine signaling |
|  | Parkinson's disease | 3.04E−31 | Antigen processing/presentation | 3.30E−02 | B cell receptor signaling |
|  | Huntington's disease | 1.33E−32 | Cytosolic DNA-sensing | 1.47E−02 | Leukocyte migration |
|  | Oxidative phosphorylation | 3.72E−34 | Toll-like receptor signaling | 4.50E−03 | Antigen presentation |
|  | Ribosome | 2.32E−53 | Ubiquitin mediated proteolysis | 3.09E−03 | Lysosome |
| MicroRNAs | miR-1-3p | 9.67E−17 | miR-100-5p | 3.85E−05 | miR-15b-5p |
|  | Let-7b-5p | 1.91E−17 | miR-7b-5p | 2.78E−05 | miR-30a-5p |
|  | miR-320a | 1.08E−18 | miR-425-5p | 2.63E−05 | miR-19a-3p |
|  | miR-484 | 1.72E−19 | miR-19b-3p | 2.07E−05 | miR-93-5p |
|  | miR-92a-3p | 7.25E−20 | miR-98-5p | 1.93E−05 | miR-34a-5p |
|  | miR-100-5p | 1.84E−20 | Let-106b-5p | 4.53E−06 | miR-17-5p |
|  | miR-186-5p | 1.80E−20 | miR-93-5p | 4.39E−06 | miR-16-5p |
|  | miR-30a-5p | 7.02E−21 | miR-215-5p | 3.24E−06 | miR-1-3p |
|  | miR-615-3p | 1.11E−26 | miR-21-5p | 3.01E−06 | miR-124-3p |

TABLE 2-continued

Gene ontology mouse loss-of-function mutant phenotype (top panel), KEGG pathways (middle panel) and microRNA target interactions (bottom panel) enrichment analysis was performed on the 4 clusters of genes identified using the 6,525 most variable genes across the 5 sample groups (relative to FIG. 22). The lists show the most enriched terms and the right columns show respective p-values by fold change in relation to the top enriched term.

| | miR-16-5p | 6.33E−40 | miR-192-5p | 2.43E−06 miR-155-5p |
|---|---|---|---|---|
| | | P-value | Cluster IV | P-value |
| Mouse Phenotypes | | 6.36E−11 | Abnormal morphology | 3.90E−15 |
| | | 3.22E−11 | Cellular phenotype | 2.36E−15 |
| | | 2.73E−11 | Premature death | 1.73E−16 |
| | | 6.53E−12 | Abnormal brain morphology | 1.48E−16 |
| | | 4.54E−12 | Pre-natal lethality | 4.28E−19 |
| | | 2.92E−12 | Preweaning lethality | 1.80E−20 |
| | | 5.46E−13 | Post-natal lethality | 1.64E−20 |
| | | 4.15E−13 | Abnormal survival | 1.70E−22 |
| | | 1.40E−15 | Mortality/aging | 7.48E−23 |
| | | 9.50E−17 | Mammalian phenotype | 8.97E−38 |
| Pathways | | 6.38E−04 | Endometrial cancer | 3.56E−03 |
| | | 6.09E−04 | Adherent junction | 3.32E−03 |
| | | 5.83E−04 | Pancreatic cancer | 1.80E−03 |
| | | 5.06E−04 | Pathways in cancer | 1.08E−03 |
| | | 5.02E−04 | Long-term depression | 6.48E−04 |
| | | 4.48E−04 | Prostate cancer | 6.44E−04 |
| | | 1.77E−04 | Insulin signaling | 1.90E−04 |
| | | 1.33E−04 | Inositol metabolism | 1.59E−04 |
| | | 3.02E−05 | Acute myeloid leukemia | 9.09E−05 |
| | | 2.08E−09 | Phosphatidylinositol signal. | 1.16E−05 |
| MicroRNAs | | 2.92E−07 | miR-425-5p | 1.64E−06 |
| | | 2.76E−07 | miR-484 | 9.27E−07 |
| | | 1.15E−07 | miR-21-5p | 7.15E−07 |
| | | 5.32E−08 | miR-223-3p | 3.97E−07 |
| | | 4.41E−08 | miR-181a-5p | 8.57E−08 |
| | | 1.54E−08 | miR-9-5p | 1.12E−08 |
| | | 7.27E−09 | miR-149-5p | 7.37E−10 |
| | | 4.60E−09 | miR-218-5p | 1.85E−10 |
| | | 1.00E−10 | miR-340-5p | 1.25E−10 |
| | | 1.41E−11 | miR-324-3p | 1.11E−12 |

This analysis also revealed activation of DC transcriptional regulators, including Zbtb46 and Bcl11a, which were originally included in our candidate TF list (FIG. 23A). Several members of the interferon-regulatory factors IFN and signal transducer and activator of transcription (STAT) protein families were also identified. For example, Stat2 and Irf7, key mediators of TLR-Induced DC activation and type I IFN responses, respectively, are detected in high levels at day 3 and 7. Stat6 also display high median expression values for day 3 and day 7, whilst Stat1 expression increases at day 9 to levels 128-fold higher than splenic DCs. DC maturation has been reported to be accompanied by a change from STAT6 to STAT1 utilization, which suggests that Pu.1, Irf8 and Batf3 overexpression may also induce DC maturation. It was observed high levels of expression of Pu.1, Irf8 and Batf3 at day 3, day 7 and day 9 when compared to sDCs, consistently with the lentiviral-mediated expression of the 3 TFs (FIG. 23B, top panel). Since our lentiviral vectors encode the coding sequences without UTRs, it was quantified the expression levels of the endogenous transcripts using the reads at the 3'- and 5'-UTRs. Importantly, it was observed the expression of endogenous Pu.1, Irf8 and Batf3 starting at day 3 (FIG. 23B, bottom panel). At day 9 of reprogramming, endogenous expression levels are comparable to splenic DCs.

In order to further characterize the dynamic nature of the transcriptional reprogramming, gene set enrichment analysis (GSEA) was performed using NetPath gene sets to compare the transitions between day 0, 3, 7 and 9 (FIG. 24, top panel). It was observed that several immune-related gene sets were highly enriched in day 3 compared with MEFs. Interestingly, IL-4 used for in vitro differentiation of DCs ranked on top (NES: 1.97, FDR q-value: 0.02) (FIG. 24, bottom left panel). Some gene sets were also enriched on day 7, although with smaller NES values, suggesting that more subtle transitions might occur during this phase. In contrast, several gene sets were highly enriched in day 9 compared with day 7, including interleukin pathways and Oncostatin M, previously associated with DC maturation (FIG. 24, bottom right panel).

In an embodiment, the transcriptional networks for stepwise transitions during iDC reprogramming were evaluated (FIG. 25A). It was observed that the transition of MEFs to day 3 was associated with the expression of a dense TF network that highly connected to the PIB reprogramming factors; the transition of day 3 to day 7 was softer, characterized by a less dense TF network, which do not include the PIB factors; and the transition of day 7 to day 9, characterized by a dense TF network which can be divided in 2 clusters of TFs, one denser that includes the cDC marker Zbtb46, and one composed by fewer TFs including the PIB factors. This reinforces the idea that a subtler transition might occur between day 3 and day 7, and suggests that day 9 iDCs might have acquired a stable cell fate. Importantly, all these transcriptional regulators are enriched in mature DCs and not in DC progenitors, irrespective of the day that are activated, suggesting that the reprogramming process do not pass through an intermediate progenitor state (FIG. 25B). Moreover, the absence of intermediate progenitor cells in the iDC reprogramming process was further validated by performing hematopoietic colony formation assays with PIB-transduced MEFs at day 3, 5, 7, 10 and 25 after addition of Dox, including sorted sDCIs and unsorted splenocytes and bone marrow cells as controls (FIG. 25C). No colonies were observed in iDCs or sDC1 cultures whereas, as expected, unsorted splenocytes and bone marrow cells in culture gave origin to colonies. This supports the idea that the reprogramming process is direct and do not transit through intermediate progenitor cells.

In an embodiment, it was set out to reconstruct the DC reprogramming path by establishing a pseudo-temporal order based on the gradual transition of cell transcriptomes (FIG. 27A). Using pseudo-Time reconstruction in Single-Cell RNA-seq Analysis (TSCAN) software, it was observed that the order is consistent with the temporal reprogramming events, with MEFs being followed by day 3 iDCs and subsequently by the majority of day 7 iDCs. Interestingly, 4 individual day 7 and some day 9 iDCs are positioned in line with sDCs in the pseudotime ordering, suggesting that the transcriptome reprogramming was complete. However, the remaining day 9 iDCs seem to be further away from the initial timepoint than the splenic DCs. In order to confirm the robustness of these results, it was performed pseudo-time ordering using Monocle2, an alternative algorithm for delineating differentiation paths. This reconstruction positioned biological sample groups along 3 branches of pseudo-time ordering (FIG. 27B, left panel). MEFs, d3 iDCs and 26 day 7 iDCs were placed along the first branch, considered cell state 1 (FIG. 27B, right panel), which then reaches a branching point and divides into State 2 and State 3. State 2 includes 82% of sDCs as well as 3 day 7 and 13 day 9 iDCs. However, 55% of day 9 iDCs as well as 11 sDCs are placed within State 3, which is consistent with TSCAN results. To understand the transcriptional differences between these 2 states, GO enrichment analysis was performed using the differentially expressed genes (Table 3), which showed that top biological processes and pathways in State 3 include type I and type II (IFN-γ) IFN signaling, known inflammatory mediators of DC activation and maturation (38, 39). Genetic perturbations for State 3 enriched genes highlighted corresponding immune phenotypes, such as abnormal APC and abnormal immune system. Consistently, BEAM analysis revealed 2 kinetic clusters of branch-dependent genes upregulated in State 3 (cluster 2 and 4) functionally enriched for antigen presentation and other immune-related processes (FIG. 28A and Table 4).

TABLE 3

Top 5 gene ontology biological process, mouse phenotypes and wiki pathways enrichment analysis of genes differentially expressed between State 2 and State 3. Relative to FIG. 27.

| | State 2 | P-Value | State 3 | P-Value |
|---|---|---|---|---|
| GO Biological processes | Phosphatidylinositol dephosphorylation | 5.90E−04 | IFNγ signaling | 2.58E−06 |
| | | | Response to IFNγ | 6.98E−06 |
| | Regulation of error-prone translesion synthesis | 6.50E−04 | Cellular response to IFNγ | 7.39E−06 |
| | | | Neutrophil degranulation | 2.21E−05 |
| | Actin filament capping | 1.05E−03 | | |
| | Actin filament reorganization | 1.19E−03 | Type I interferon signaling | 2.24E−05 |
| | Peptidyl-serine autophosphorylation | 2.13E−03 | | |
| Phenotypes | Lethality at weaning | 2.56E−06 | Abnormal antigen presenting cell | 1.00E−09 |
| | Premature death | 9.47E−05 | | |
| | Abnormal mineral homeostasis | 1.25E−03 | Abnormal immune system | 8.88E−08 |
| | Mammalian phenotype | 9.44E−04 | Abnormal blood cell | 1.34E−07 |
| | Abnormal startle reflex | 3.40E−03 | Abnormal response to infection | 1.40E−07 |
| | | | Abnormal bone marrow | 1.79E−07 |
| Pathways | Estrogen signaling pathway | 7.03E−03 | IFNγ signaling | 9.80E−07 |
| | Regulation of actin cytoskeleton | 9.07E−03 | G13 Signaling | 3.09E−06 |
| | | | Alzheimers Disease | 5.68E−06 |
| | Breast cancer | 9.50E−03 | Heart Hypertrophy | 1.52E−05 |
| | MAPK signaling | 1.06E−02 | IL-3 Signaling Pathway | 1.94E−05 |
| | Gastric cancer | 1.06E−02 | | |

TABLE 4

Top 5 gene ontology biological process and mouse loss-of-function mutant phenotype enrichment analysis of genes in Cluster 1 to 5. Relative to FIG. 28.

| | GO Biological processes | P-value | Mouse Phenotypes | P-value |
|---|---|---|---|---|
| Cluster 1 | Translation | 6.97E−05 | Abnormal cell death | 8.32E−04 |
| | DNA packaging | 5.26E−03 | Abnormal lacrimal gland | 1.25E−03 |
| | Nucleosome assembly | 1.41E−02 | Abnormal sex gland | 2.11E−03 |
| | Chromatin assembly | 1.51E−02 | Abnormal hormone levels | 3.18E−03 |
| | Protein-DNA assembly | 1.57E−02 | Abnormal muscle contractility | 4.46E−03 |
| Cluster 2 | Negative regulation signal transduction | 7.46E−03 | Abnormal blood cell | 2.33E−06 |
| | | | Abnormal immune system | 2.52E−05 |
| | Negative regulation cell communication | 1.20E−02 | Abnormal immune cell | 7.16E−04 |
| | | | Perinatal lethality | 9.04E−04 |

TABLE 4-continued

Top 5 gene ontology biological process and mouse loss-of-function mutant phenotype enrichment analysis of genes in Cluster 1 to 5. Relative to FIG. 28.

|  | GO Biological processes | P-value | Mouse Phenotypes | P-value |
|---|---|---|---|---|
|  | Regulation of cell killing | 1.29E-02 | Abnormal adaptive immunity | 6.72E-04 |
|  | Regulation leukocyte cytotoxicity | 1.29E-02 |  |  |
|  | Regulation lymphocyte immunity | 2.23E-02 |  |  |
| Cluster 3 | Sensory perception chemical stimulus | 9.34E-23 | Mammalian phenotype Abnormal blood homeostasis | 3.04E-14 9.59E-09 |
|  | Neurological system process | 1.04E-22 |  |  |
|  | Sensory perception | 1.67E-22 | Abnormal hormone levels | 9.62E-09 |
|  | Sensory perception smell | 6.48E-22 | Abnormal nervous system | 7.57E-08 |
|  | Cognition | 2.96E-21 | Abnormal neuron morphology | 6.91E-08 |
| Cluster 4 | Antigen presentation of exogenous peptide | 1.94E-05 | Abnormal blood cell Abnormal Immune system | 1.81E-09 5.66E-08 |
|  | Antigen presentation via MHC-II | 1.94E-05 | Abnormal antigen presenting cell | 1.77E-07 |
|  | Polysaccharide antigen presentation | 4.03E-05 | Abnormal immune cell | 8.54E-07 |
|  | Positive regulation leukocyte activation | 8.20E-05 | Abnormal bone marrow | 1.87E-06 |
|  | Exogenous antigen presentation | 8.91E-05 |  |  |
| Cluster 5 | Protein-DNA complex assembly | 4.71E-03 | Mammalian phenotype | 4.93E-05 |
|  | Chromosome organization | 7.89E-03 | No abnormal phenotype | 4.81E-04 |
|  | Chromatin | 1.01E-02 | Normal phenotype | 5.16E-04 |
|  | Lens development in eye | 1.34E-02 | Metabolism phenotype | 1.54E-03 |
|  | Positive regulation of secretion | 1.47E-02 | Abnormal Social interaction | 5.30E-03 |

In an embodiment, GSEA also showed that 4705 vs 167 gene sets for immunological signatures were upregulated on State 3 when compared with State 2, such as Mature Stimulatory DC, IFNγ and IFNα stimulated DC gene sets (FIG. 28B). As State 3 contained the majority of day 9 iDCs, it was sought to confirm that similar maturation trait was observed when comparing sDC1s (naive) with day 9 iDCs. GSEA showed that antigen processing and presentation and DC maturation gene sets are enriched at day 9 iDCs (FIG. 29A). Interestingly, Stat6, which is associated with immature DCs, was up regulated in sDC1s, whilst Stat1, described to increase with maturation, was up regulated in day 9 iDCs (FIG. 23A).

In an embodiment, given that it was previously observed that iDCs express high levels of MHC-II molecules, which is reported to be associated with maturation of DCs (FIG. 18), it was sought to investigate if the observed pseudotime trajectories were indicative of different maturation states. It was observed that the branch kinetic curves reflect a continuous upregulation of Ciita, the known master regulator of MHC-II genes' expression, and several MHC-II genes (H2-Aa, H2-Ab1 and H2-Eb1) towards State 3 as compared with State 2 (FIG. 30A). Consistently, expression of Ciita and genes associated with mouse (Tnfrs1a, Tapbp, Inpp5d and Traf6) and human (Acp5 and Itag4) DC maturation were enriched at day 9 iDCs (FIG. 30B). These data suggest that iDCs are intrinsically more mature than sDCs and may be less dependent on exogenous activation stimuli for antigen presentation.

In an embodiment, the induced dendritic cells in some aspects of all the embodiments of disclosure, while similar in functional characteristics, differ in their gene expression from the naturally occurring endogenous dendritic cells (Table 5).

TABLE 5

Top 500 differentially expressed genes between day 9 iDCs and sDC1 cells ordered by fold change.

| Day 9 up (vs sDC1) | Fold change | Day9 Down (vs sDC1) | Fold Change |
|---|---|---|---|
| Cd74 | 8.378400519 | AY036118 | 3.630967107 |
| Ucp2 | 7.999114666 | Sfi1 | 3.546674749 |
| Grn | 7.650480054 | Gprc5c | 3.440084658 |
| Cdkn1a | 7.079169574 | Olfr648 | 3.00881167 |
| S100a11 | 7.048233116 | Rsph9 | 2.959047864 |
| Gapdh | 6.979316778 | Tmsb4x | 2.890522248 |
| Cct8 | 6.923788452 | Mtmr1 | 2.654214297 |
| Ly6e | 6.336631107 | Il15 | 2.574244187 |
| Ubb | 6.19368097 | Fanci | 2.24583185 |
| B2m | 6.151779369 | Ptprk | 2.113646962 |
| Mir6240 | 6.053040315 | Cnot6l | 2.002604494 |
| Irf8 | 5.725731065 | Bdkrb1 | 1.987001179 |
| Mir6236 | 5.674808976 | Pdgfb | 1.930540437 |
| Spi1 | 5.640038385 | Letm1 | 1.915941208 |
| Cd81 | 5.563653083 | Abca3 | 1.880254741 |
| Ctsa | 5.501860486 | Plpp5 | 1.867877278 |
| Rnf13 | 5.457727173 | 1700095J03Rik | 1.847936727 |
| Ifitm3 | 5.400810698 | Dcun1d4 | 1.788829125 |
| Samhd1 | 5.263523757 | Lrif1 | 1.769132531 |
| Pgam1-ps2 | 5.203763065 | Fus | 1.758030571 |
| Prkar1a | 5.192511183 | Ltbp1 | 1.719160475 |
| Gns | 5.151976827 | Prr15l | 1.702342332 |
| Gdi2 | 5.020765205 | Rps20 | 1.686771039 |
| mt-Nd5 | 4.991318969 | Fam92a | 1.682146576 |
| Usp14 | 4.895884787 | Rpl32 | 1.661123211 |
| Eif2ak3 | 4.883252352 | Clstn3 | 1.658201639 |
| mt-Tm | 4.874702287 | Usp10 | 1.651957116 |
| Med21 | 4.82652063 | 2900009J06Rik | 1.642513164 |
| Shisa5 | 4.762756365 | 4930553I04Rik | 1.639560609 |
| Stat1 | 4.717469627 | Nceh1 | 1.633238968 |
| Scpep1 | 4.654917481 | Kdelr1 | 1.623624988 |
| Tmem59 | 4.630781554 | Amdhd2 | 1.620291498 |
| Drg1 | 4.622644784 | Snhg14 | 1.60518724 |
| Pttg1ip | 4.613419142 | Ppcdc | 1.593210807 |
| Batf3 | 4.567419599 | Cit | 1.571609014 |
| Grina | 4.563608382 | Lef1 | 1.571116453 |

TABLE 5-continued

Top 500 differentially expressed genes between day 9 iDCs and sDC1 cells ordered by fold change.

| Day 9 up (vs sDC1) | Fold change | Day9 Down (vs sDC1) | Fold Change |
|---|---|---|---|
| Ctsc | 4.562081251 | Cinp | 1.555760027 |
| Calm2 | 4.5319627 | Cep290 | 1.542877805 |
| Ifi44 | 4.526513658 | Eya4 | 1.542329932 |
| Arhgdib | 4.448903084 | Ssbp2 | 1.541337751 |
| Ifitm2 | 4.43505433 | Stard3nl | 1.53918705 |
| Itm2b | 4.41388282 | Ppp2r5a | 1.529811517 |
| Sbds | 4.328188964 | Rps27 | 1.514118829 |
| Bst1 | 4.322914109 | Rpain | 1.512378029 |
| Nnat | 4.253027937 | Rps15a | 1.503115843 |
| Sulf2 | 4.233589183 | Ushbp1 | 1.489434725 |
| Lgals3bp | 4.212602771 | Caprin2 | 1.48766573 |
| Dazap2 | 4.138256756 | Glis1 | 1.468306086 |
| Slc30a9 | 4.045135818 | Rpl24 | 1.455561714 |
| Rbms1 | 4.026259385 | Rgs1 | 1.452134922 |
| Ftl1 | 4.022138158 | Lsp1 | 1.445858249 |
| Eif3a | 4.002306157 | Malat1 | 1.441188932 |
| Axl | 3.997197448 | Kctd19 | 1.439866506 |
| Cited2 | 3.993185485 | Sfxn5 | 1.438464054 |
| Lars2 | 3.932022979 | Brca2 | 1.429734511 |
| Cfl1 | 3.902855666 | Fgd4 | 1.429251043 |
| Pfn1 | 3.862256545 | Mir762 | 1.42527755 |
| Ate1 | 3.846471162 | Rabgap1 | 1.418468643 |
| Myadm | 3.828349737 | Notch1 | 1.417303263 |
| Bgn | 3.827554891 | Anapc5 | 1.415567561 |
| Ywhab | 3.794470188 | Slc6a17 | 1.412700849 |
| mt-Rnr1 | 3.783136169 | Ncapd2 | 1.407349715 |
| Tnfrsf1a | 3.708506639 | Ccdc40 | 1.382403998 |
| Tmbim6 | 3.677054824 | 4930519L02Rik | 1.382401843 |
| Ppp3r1 | 3.659734805 | Aacs | 1.378156309 |
| Cap1 | 3.650896891 | Arhgef40 | 1.377963701 |
| Sparc | 3.634708576 | Olfr986 | 1.376630166 |
| Tgtp2 | 3.628901251 | Dnm1 | 1.369144578 |
| Chordc1 | 3.627931997 | Adgrv1 | 1.36678555 |
| Mir8114 | 3.606630393 | Reg2 | 1.36266606 |
| Tma7 | 3.600667604 | Kif24 | 1.360757058 |
| Slc25a3 | 3.59553779 | Khk | 1.354650399 |
| Unc93b1 | 3.541471457 | Camk2d | 1.353347692 |
| Mapk1 | 3.539792266 | Disp1 | 1.337935937 |
| Spp1 | 3.53813155 | Msh3 | 1.330172804 |
| Trim25 | 3.537049716 | Pmfl | 1.328658766 |
| Ywhaz | 3.533742941 | Mrpl48 | 1.320851411 |
| Pla2g7 | 3.518104367 | Fry | 1.318521603 |
| Cyfip1 | 3.485665307 | Adgra3 | 1.315125368 |
| Ncoa4 | 3.473391046 | Tssc1 | 1.313253438 |
| Tgtp1 | 3.454518062 | Fbf1 | 1.312311242 |
| Pros1 | 3.417372505 | Hsd3b2 | 1.311309901 |
| Dda1 | 3.40525625 | Snord57 | 1.309355259 |
| Cmtr1 | 3.387409585 | Adsl | 1.308071098 |
| Stt3a | 3.385900731 | Banp | 1.307751088 |
| mt-Cytb | 3.381159175 | Diexf | 1.303869281 |
| Edem1 | 3.367122678 | Ctage5 | 1.296409102 |
| Lgmn | 3.355164538 | Olfr1089 | 1.295835162 |
| Serinc3 | 3.35283067 | Arhgef19 | 1.293919043 |
| Plbd2 | 3.337813415 | Trpm4 | 1.291888876 |
| Slfn5 | 3.330993072 | Olfr980 | 1.290974033 |
| Rab1b | 3.324732402 | Ap3b2 | 1.290262191 |
| Ap3d1 | 3.315238282 | Ndufs1 | 1.282010137 |
| Icam1 | 3.293730801 | Prob1 | 1.279252518 |
| Mdh1 | 3.270873537 | Tox | 1.277128111 |
| Hsp90aa1 | 3.26235373 | Tnk2 | 1.275196071 |
| Zmpste24 | 3.256672868 | Pcdh15 | 1.274945531 |
| mt-Rnr2 | 3.227837673 | Use1 | 1.273360442 |
| Sp100 | 3.20878081 | Znrf1 | 1.273285759 |
| Surf4 | 3.208326066 | Il16 | 1.265024831 |
| Pkm | 3.190910497 | Gsn | 1.264820606 |
| Ciita | 3.181654915 | Tyrobp | 1.254979854 |
| Glul | 3.165849559 | Zfp57 | 1.25469807 |
| Cmc4 | 3.145763373 | Dnm3 | 1.249092237 |
| Ifit2 | 3.140223266 | Btbd19 | 1.246939299 |
| AA474408 | 3.12954966 | Tmeff2 | 1.244721598 |
| Pigt | 3.127377903 | Pde1c | 1.241625438 |
| Serinc1 | 3.116484011 | Slc16a14 | 1.241236737 |
| Lyn | 3.111346193 | Herc4 | 1.240940968 |
| Tnfaip1 | 3.108541206 | Pdzd2 | 1.240932703 |
| Rnf145 | 3.108426516 | Cenpu | 1.239620462 |
| Ubl5 | 3.09022469 | Ccdc9 | 1.237773411 |
| Map2k4 | 3.089586057 | Cd63 | 1.235857882 |
| Hmga1 | 3.069250123 | Scrib | 1.229623359 |
| Cox6a1 | 3.069034679 | Lats2 | 1.222817428 |
| Laptm4a | 3.060750646 | Plbd1 | 1.220326423 |
| Psmc5 | 3.047865774 | 1700030K09Rik | 1.212538771 |
| Plekho2 | 3.039215546 | Gpsm3 | 1.212322462 |
| Lgals9 | 3.035253178 | Rasa4 | 1.212195177 |
| Mlxip | 3.031480133 | Jade1 | 1.211805352 |
| Fos | 2.995472377 | Astn1 | 1.206888241 |
| Fkbp10 | 2.995150234 | Abca2 | 1.205733273 |
| Gps2 | 2.993152938 | Ptpn5 | 1.2051801 |
| Tecr | 2.987574318 | Tpk1 | 1.201688574 |
| Mbnl1 | 2.96248689 | Kantr | 1.201432145 |
| Sez6l | 2.951436702 | Slc15a2 | 1.199012945 |
| Sh3bp2 | 2.949222732 | Fgfl | 1.196064338 |
| Mov10 | 2.935927814 | 4930511M06Rik | 1.193287597 |
| Fam167a | 2.91423349 | A430010J10Rik | 1.193177327 |
| Asns | 2.907465523 | Pde4c | 1.186996538 |
| C530025M09Rik | 2.889428766 | 2610203C20Rik | 1.183842191 |
| Zdhhc5 | 2.875076576 | Cep85 | 1.182775307 |
| Rpl38 | 2.871058843 | Auts2 | 1.181857217 |
| Tmod3 | 2.869947135 | Pld1 | 1.179419755 |
| Tspan9 | 2.868408159 | Lsamp | 1.179262613 |
| Arhgap1 | 2.861787688 | Ercc5 | 1.174619478 |
| Rn7s1 | 2.857560775 | B230216N24Rik | 1.172531942 |
| Rn7s2 | 2.857560775 | Cdkal1 | 1.172233483 |
| St3gal5 | 2.850664779 | Plb1 | 1.170618218 |
| Lamp2 | 2.838622934 | Ttc3 | 1.169286246 |
| Zfp36l1 | 2.828619356 | Smarcad1 | 1.1661693 |
| Qsox1 | 2.816348613 | B130055M24Rik | 1.164407791 |
| Nubp2 | 2.801535041 | Glrb | 1.162769632 |
| Dap | 2.798447222 | Fam71e1 | 1.161503582 |
| H2-Eb1 | 2.790275212 | Actr1b | 1.160650079 |
| Trpc4ap | 2.790223774 | Fam120c | 1.159839707 |
| Ptk2 | 2.774986716 | Lamb3 | 1.1544153 |
| Litaf | 2.76910688 | Rpl18 | 1.147822978 |
| Samd12 | 2.756415888 | B430219N15Rik | 1.147593372 |
| Hspa8 | 2.738492847 | Pnpla7 | 1.146410398 |
| Psap | 2.725482169 | Myo1b | 1.145796458 |
| Rap1b | 2.708283782 | Tmcc1 | 1.145088425 |
| Rab11b | 2.707195739 | Mxd1 | 1.142557058 |
| Kdm5c | 2.659888994 | Gtpbp4 | 1.140348186 |
| Atp6v0c | 2.652904455 | Mbtd1 | 1.139896426 |
| Pnkp | 2.627212937 | Mir101c | 1.139676828 |
| Atp1b3 | 2.57433971 | Srcin1 | 1.138957445 |
| Plin2 | 2.569589842 | C130026I21Rik | 1.13879651 |
| Dusp1 | 2.564304737 | Qrich1 | 1.135006953 |
| Dennd6a | 2.55766128 | Snora7a | 1.129825352 |
| Syt9 | 2.54591498 | P2ry2 | 1.12826657 |
| Park7 | 2.538892352 | Tle6 | 1.127997617 |
| Thbs1 | 2.526658864 | Gstt2 | 1.127976061 |
| Ndel1 | 2.520436416 | Rnf214 | 1.125647634 |
| Eif2s2 | 2.517791626 | Mier2 | 1.125490293 |
| Degs1 | 2.516228756 | Rad52 | 1.123514249 |
| Pcsk6 | 2.508442547 | Tsfm | 1.121124616 |
| Washc4 | 2.501207547 | Rpl34 | 1.118504821 |
| H2-Pb | 2.494182352 | Ampd2 | 1.118010861 |
| Gins4 | 2.480528831 | Col6a6 | 1.11565181 |
| Ap2m1 | 2.479969608 | 6820408C15Rik | 1.11415417 |
| Stam | 2.460346325 | Plekha7 | 1.11413288 |
| Calm1 | 2.459547652 | Kifc1 | 1.113349023 |
| Cd47 | 2.452322667 | Entpd8 | 1.11138608 |
| Arhgap5 | 2.436336219 | Trmu | 1.111070484 |
| Msn | 2.427359 | Dhx30 | 1.110688069 |
| Arhgef2 | 2.424471636 | Becn1 | 1.108510602 |
| Rnps1 | 2.421957675 | Gtf2h1 | 1.107621797 |
| Agpat3 | 2.420651749 | Dennd2d | 1.107444842 |
| Hexb | 2.406950442 | St14 | 1.10685259 |
| Jmjd1c | 2.403960577 | Sema6c | 1.105449952 |
| Uba7 | 2.393024725 | Olfr1321 | 1.105249776 |
| Stat3 | 2.392854797 | Nin | 1.104494546 |
| Aqr | 2.390209543 | 2900076A07Rik | 1.103729098 |

TABLE 5-continued

Top 500 differentially expressed genes between
day 9 iDCs and sDC1 cells ordered by fold change.

| Day 9 up (vs sDC1) | Fold change | Day9 Down (vs sDC1) | Fold Change |
|---|---|---|---|
| Rasgrp3 | 2.389626162 | Alg13 | 1.102785341 |
| Ifi207 | 2.378045514 | Rapgef3 | 1.101622786 |
| Tcn2 | 2.366636661 | Trps1 | 1.101516996 |
| Jkamp | 2.362648719 | Morc2a | 1.100797248 |
| Xpnpep2 | 2.36068485 | Myo15b | 1.097398552 |
| Pld4 | 2.345478622 | Dlg1 | 1.096480818 |
| Csnk1a1 | 2.333344842 | Pus7 | 1.092393911 |
| Cmklr1 | 2.331529539 | H2afz | 1.091796066 |
| mt-Co1 | 2.330383946 | Cacna1f | 1.091419504 |
| Commd7 | 2.308633577 | Rps7 | 1.091078821 |
| Gabarap | 2.303502443 | Kctd15 | 1.087832781 |
| Aes | 2.298975567 | Slc22a15 | 1.083405985 |
| Nfe2l1 | 2.296002657 | Nbr1 | 1.082686573 |
| Sgpl1 | 2.2917436 | Cd27 | 1.081589891 |
| Gbf1 | 2.287585646 | Itga2b | 1.080996825 |
| Gstm1 | 2.280980951 | Eci2 | 1.080130803 |
| Mtcl1 | 2.275467469 | Cd6 | 1.080089799 |
| Vcl | 2.249503311 | Mical1 | 1.080032007 |
| Slc25a5 | 2.249170226 | Serpina6 | 1.079365549 |
| 2610507B11Rik | 2.249033444 | Cadm2 | 1.079157707 |
| Tmem248 | 2.243289507 | Kmt5b | 1.075999202 |
| Chd9 | 2.24028321 | Scn8a | 1.075722849 |
| B4galt5 | 2.23488477 | Zfp239 | 1.075383073 |
| Rictor | 2.234163721 | Ap1s1 | 1.075103048 |
| Srrm2 | 2.233556776 | Erdr1 | 1.071138918 |
| Sh3bgrl | 2.232075277 | Cacna1a | 1.069720493 |
| Cdc42se1 | 2.209710506 | Ivns1abp | 1.067892703 |
| Lrp1 | 2.208956871 | Dhodh | 1.067584269 |
| Ipo9 | 2.195716865 | Ttn | 1.067147365 |
| Tcp1 | 2.194202192 | Ddx19a | 1.066321446 |
| Ppp1cb | 2.188862064 | Stx4a | 1.064577603 |
| Pgam1 | 2.187328026 | Safb2 | 1.063265347 |
| Atp6v0e | 2.185473454 | Aloxe3 | 1.063249994 |
| Pik3r1 | 2.177807689 | Stx18 | 1.062644106 |
| mt-Nd4l | 2.170033442 | Notch4 | 1.062408256 |
| Ddx5 | 2.1526024 | Vars2 | 1.06236208 |
| n-R5-8s1 | 2.137222743 | Ces5a | 1.06224942 |
| Ddost | 2.137080797 | Fxyd2 | 1.061290421 |
| Btf3 | 2.136870648 | Olfr539 | 1.061124921 |
| Pitpna | 2.130897293 | Ubl4a | 1.06102377 |
| Zfp451 | 2.121640696 | Plxnc1 | 1.059510561 |
| Msrb3 | 2.108023782 | Tars2 | 1.059081003 |
| Tram1 | 2.103942132 | A430073D23Rik | 1.058179534 |
| Gpx1 | 2.092125019 | Brpf1 | 1.058170111 |
| Rab3il1 | 2.091780481 | E2f6 | 1.05716641 |
| Anxa3 | 2.082860042 | Gle1 | 1.055917907 |
| Prkaa1 | 2.07920508 | Clca3a2 | 1.053662602 |
| Rab8b | 2.076542275 | Mir99ahg | 1.052669091 |
| Srpr | 2.060721132 | Grk2 | 1.052345211 |
| Ncstn | 2.048033241 | Firre | 1.052005979 |
| mt-Nd2 | 2.046373118 | Cp | 1.049988888 |
| Sf3b1 | 2.044486528 | Cacna2d4 | 1.04830389 |
| H2-Ab1 | 2.037298163 | Isy1 | 1.046348457 |
| Plp2 | 2.021912335 | 4930402H24Rik | 1.046335717 |
| Dnm1l | 2.011874745 | D430042O09Rik | 1.045493524 |
| Nptx1 | 2.007694218 | Pax6 | 1.043231341 |
| Clec16a | 1.998844774 | Rcbtb2 | 1.042445583 |
| Uggt1 | 1.98850241 | Wapl | 1.042368448 |
| Pxk | 1.982701164 | Rab14 | 1.040736807 |
| Tiparp | 1.982534756 | Magi3 | 1.038947888 |
| Impad1 | 1.982393464 | Ctbp2 | 1.037976024 |
| Gpcpd1 | 1.979316308 | Prpf4b | 1.037971623 |
| Tmem214 | 1.973030883 | Csmd2 | 1.037185914 |
| Coro1b | 1.970528885 | Btbd11 | 1.036685875 |
| Naaa | 1.968987323 | Vwf | 1.036683252 |
| Snx12 | 1.960818344 | Cdh4 | 1.036640143 |
| Anpep | 1.959292302 | Apbb1 | 1.036638533 |
| Ptk2b | 1.94897573 | Ccdc162 | 1.0359892 |
| Gusb | 1.944307923 | Sipa1l3 | 1.035923762 |
| Ccnd3 | 1.940195368 | Slc35a3 | 1.035192913 |
| Syf2 | 1.939540412 | Ahrr | 1.034311688 |
| Tubb5 | 1.927300046 | Opcml | 1.034020412 |
| Ap2b1 | 1.927092864 | Sirt5 | 1.032682041 |
| Col4a1 | 1.92298865 | Nox4 | 1.032270813 |
| Myl12b | 1.918466916 | Spint2 | 1.031953157 |
| Ccnd1 | 1.912610788 | Aebp2 | 1.031681705 |
| Sfxn3 | 1.906741793 | Dtnbp1 | 1.030548993 |
| Timp2 | 1.906668629 | Iqca | 1.030543359 |
| B230219D22Rik | 1.902284133 | Lbp | 1.029703558 |
| Rhog | 1.887582293 | Kcnj16 | 1.029523684 |
| Scap | 1.88592784 | Gtf2ird1 | 1.028843965 |
| Qk | 1.88561085 | Aldoa | 1.026887502 |
| Bfar | 1.882090302 | Pfdn5 | 1.026732581 |
| Slfn5os | 1.880082558 | Mtx3 | 1.026090598 |
| Lipa | 1.879981666 | Zfp950 | 1.025199024 |
| Plekha1 | 1.876160326 | Rasgrp4 | 1.024647963 |
| Errfi1 | 1.86913871 | Lmf1 | 1.024604555 |
| Ccnd2 | 1.866791989 | Smc3 | 1.024558747 |
| Snhg4 | 1.85926484 | Fam118b | 1.024505164 |
| Zmat3 | 1.858777231 | Kif15 | 1.023953631 |
| Ptpn9 | 1.856452888 | Cpeb3 | 1.023923019 |
| Egr1 | 1.853897687 | Adgra1 | 1.023026376 |
| Dnajc10 | 1.852044296 | Safb | 1.022908183 |
| A630033H20Rik | 1.851287962 | Psmb3 | 1.022863235 |
| Ctsb | 1.832770858 | Dhtkd1 | 1.022813101 |
| Sgsh | 1.831682811 | Bmpr1b | 1.02276876 |
| Ctnna1 | 1.825509641 | Cdk14 | 1.022075321 |
| Gng12 | 1.823669353 | Abcd3 | 1.020692022 |
| Tmem176b | 1.82285949 | A530040E14Rik | 1.019535471 |
| Atp6v0a2 | 1.820322631 | Phf24 | 1.018368684 |
| Dmd | 1.814015876 | Frmd5 | 1.017848005 |
| Ssbp4 | 1.808520665 | Cldn34c1 | 1.017608358 |
| Dck | 1.807120995 | Mfap4 | 1.017464779 |
| Tmed10 | 1.804630829 | Lgi1 | 1.016790218 |
| Plekha2 | 1.788241201 | Fgfr2 | 1.016403211 |
| Ywhae | 1.787342486 | Espn | 1.015617966 |
| Prdx6 | 1.782181966 | Olfr90 | 1.015595827 |
| Cpne8 | 1.780683612 | Ahcyl2 | 1.015502202 |
| Pan3 | 1.76632335 | Zbtb46 | 1.015224258 |
| Tsn | 1.765727062 | Ghrhr | 1.013691524 |
| Postn | 1.760918581 | Slu7 | 1.013465906 |
| 5031439G07Rik | 1.754798139 | Rgs6 | 1.011093407 |
| Tcf25 | 1.751773197 | Hacl1 | 1.010778823 |
| Capza2 | 1.748806651 | Myo1g | 1.01023387 |
| Ssr3 | 1.745487096 | Tsen54 | 1.00985654 |
| Pafah1b1 | 1.741737246 | Tdo2 | 1.006294884 |
| Sbf2 | 1.740917993 | Mrgprc2-ps | 1.006158745 |
| Ubc | 1.738762972 | Sez6 | 1.005579581 |
| Rnpep | 1.733612821 | Fmr1 | 1.004972266 |
| Tnpo1 | 1.73276259 | Olfr295 | 1.004922065 |
| 1110037F02Rik | 1.731726851 | Stard10 | 1.004561273 |
| Ogt | 1.722820519 | Ikzf3 | 1.003969279 |
| Nras | 1.722695811 | Mad1l1 | 1.003331901 |
| Ddx39b | 1.722321035 | Sun2 | 1.002634026 |
| Elovl5 | 1.716649083 | Zfp532 | 1.001725437 |
| Inpp5d | 1.708655113 | C2cd3 | 1.001540813 |
| Stx7 | 1.705989329 | Gpr89 | 1.001332809 |
| Klf3 | 1.704318719 | C920009B18Rik | 1.001138066 |
| Sdc3 | 1.691630397 | Itsn1 | 1.001091655 |
| Pltp | 1.689657257 | BC034090 | 1.000446333 |
| Gnai2 | 1.686128128 | Gripap1 | 0.999489556 |
| Nfib | 1.677548572 | Lmo7 | 0.998665132 |
| Eef1a1 | 1.666817084 | Cep250 | 0.99700681 |
| Sval2 | 1.654461632 | Mkln1 | 0.996736898 |
| Cxcl16 | 1.653930195 | 9030624J02Rik | 0.996673208 |
| Gpr108 | 1.649897733 | C2cd5 | 0.994435489 |
| Atp5h | 1.648363833 | Racgap1 | 0.994262554 |
| Ppp1ca | 1.648036693 | Epb41 | 0.993574572 |
| Amfr | 1.646430431 | Rgs3 | 0.9935682 |
| 2310014F06Rik | 1.642609288 | Map2k2 | 0.991526748 |
| mt-Tl1 | 1.638589779 | Zfp369 | 0.990602507 |
| Twsg1 | 1.636545598 | Zcchc4 | 0.990232518 |
| Magt1 | 1.631891466 | Celf3 | 0.989871179 |
| Gria3 | 1.614777482 | Nfrkb | 0.988761687 |
| Gna12 | 1.611782252 | 1500012K07Rik | 0.987475187 |
| Ppp4r1l-ps | 1.611024994 | Csnk1g1 | 0.987302343 |
| Mfge8 | 1.606938172 | Tbk1 | 0.987242185 |
| Lasp1 | 1.606641944 | Ube2e2 | 0.986976054 |

TABLE 5-continued

Top 500 differentially expressed genes between
day 9 iDCs and sDC1 cells ordered by fold change.

| Day 9 up (vs sDC1) | Fold change | Day9 Down (vs sDC1) | Fold Change |
|---|---|---|---|
| Gstp1 | 1.60150536 | C2cd2l | 0.986252848 |
| Sh3pxd2b | 1.598640187 | Nlgn1 | 0.985395138 |
| Coq10b | 1.597748785 | Atad3aos | 0.98523759 |
| Cdk1 | 1.590738694 | Lair1 | 0.98518503 |
| Wnk1 | 1.589077278 | Lamtor3 | 0.983751037 |
| Calm3 | 1.575849963 | Man2c1 | 0.98191137 |
| Rad23b | 1.575037653 | Phc2 | 0.981299938 |
| Naa20 | 1.570197421 | Rnf123 | 0.980776141 |
| Nkx2-2 | 1.566605188 | Rgs11 | 0.980226854 |
| Nfix | 1.555019024 | Fbxo18 | 0.980008734 |
| Nans | 1.547167513 | Plxna3 | 0.979857188 |
| Sidt2 | 1.545962364 | Adam23 | 0.979186928 |
| Oasl2 | 1.532383232 | Thsd7a | 0.979160545 |
| Cyb561a3 | 1.53078711 | Pde4d | 0.979053978 |
| Rasal2 | 1.530399343 | Smim1 | 0.977702838 |
| Flt4 | 1.527570552 | Pum2 | 0.977669452 |
| 2810474O19Rik | 1.526141876 | Dlec1 | 0.977609037 |
| 3222401L13Rik | 1.520827618 | Arhgef4 | 0.977585828 |
| Fyttd1 | 1.520231944 | Zbtb49 | 0.977502295 |
| Iigp1 | 1.515968737 | Senp3 | 0.977451995 |
| Atp6v1a | 1.514613918 | Trpm2 | 0.976880999 |
| Lrrc42 | 1.513457922 | 1810032O08Rik | 0.976754675 |
| Trim16 | 1.513078049 | Gramd1c | 0.976420001 |
| Tmub2 | 1.511718079 | Zfp13 | 0.975991964 |
| Slc25a12 | 1.511137106 | Ppp4r1 | 0.975773873 |
| Oasl1 | 1.509642511 | Proser2 | 0.975505959 |
| Rpph1 | 1.507834495 | Nek10 | 0.975435395 |
| Crtc3 | 1.506271977 | Mcf2l | 0.974595726 |
| Rnf44 | 1.502558854 | Cald1 | 0.974287067 |
| Rab43 | 1.4997319 | Homez | 0.973060396 |
| Lrch4 | 1.494344133 | Plcg1 | 0.972958606 |
| Trim35 | 1.493644106 | Pkp4 | 0.972945011 |
| Slit2 | 1.489830377 | Hnrnpk | 0.972631359 |
| Cyp2f2 | 1.488373517 | Ppp2r1a | 0.97246017 |
| Snx3 | 1.481595088 | Trmt1 | 0.972303044 |
| Etv5 | 1.479921021 | Rab3gap1 | 0.972187837 |
| Oas2 | 1.473261403 | 4930431F12Rik | 0.972082764 |
| Psme1 | 1.470561263 | Tcte2 | 0.97206615 |
| Lsm12 | 1.468223249 | Aoah | 0.9714557 |
| Impact | 1.466855064 | 1700110I01Rik | 0.970367518 |
| Dcakd | 1.465419814 | 4933427J07Rik | 0.970106045 |
| Tbp | 1.463219259 | Polrmt | 0.969835731 |
| Alg8 | 1.463180722 | Plekhg3 | 0.969499396 |
| Csrp1 | 1.460388067 | Chrna9 | 0.969212179 |
| Znfx1 | 1.459793233 | Fgfr1op2 | 0.969013346 |
| Ctps | 1.457382832 | Olfr889 | 0.968607339 |
| Zc3h14 | 1.456860742 | Gnas | 0.968283741 |
| Nisch | 1.454173681 | Egflam | 0.967634053 |
| Polr2a | 1.45089857 | Clk4 | 0.966015603 |
| Hectd1 | 1.443602365 | Metap1d | 0.965868178 |
| Mir195b | 1.442373355 | Rap1gap | 0.965285567 |
| Rnf139 | 1.439425895 | Inpp5f | 0.965246376 |
| Hist1h4m | 1.436213948 | Olfr509 | 0.964350171 |
| Yap1 | 1.436000261 | Trpm1 | 0.964078371 |
| Csel1 | 1.432919664 | Palm | 0.963865503 |
| Hist1h4n | 1.420524579 | Capn10 | 0.96369017 |
| Lhx9 | 1.412383525 | Acad10 | 0.962450168 |
| Plekhn1 | 1.410987625 | Xndc1 | 0.962213076 |
| Arpc4 | 1.404917958 | Tesk2 | 0.961846014 |
| Vamp3 | 1.404006857 | Acox2 | 0.961694735 |
| Phkb | 1.402306049 | Ptpn3 | 0.960945148 |
| Atp1a1 | 1.398979263 | Slf1 | 0.960893662 |
| Scamp2 | 1.393517046 | Rpl23 | 0.95970086 |
| Rnf213 | 1.392440751 | Hdac7 | 0.959267451 |
| Grb10 | 1.389174904 | Prkcb | 0.958836304 |
| Znrf2 | 1.388534731 | Bcas3 | 0.958813276 |
| Hspa5 | 1.385032431 | Rpl19-ps10 | 0.958779312 |
| Dnase2a | 1.37456459 | Efcab7 | 0.958287456 |
| Cyr61 | 1.371301936 | Pabpc1 | 0.95824206 |
| Cystm1 | 1.370152464 | Rassf8 | 0.95818526 |
| Hnrnpl | 1.35916454 | Lrmp | 0.957724619 |
| Ppia | 1.357022789 | 1700034P13Rik | 0.957400444 |
| Pptc7 | 1.353998906 | Rspry1 | 0.95567678 |
| Fxr1 | 1.347297931 | Sorbs2 | 0.955664718 |
| Kif1c | 1.345550329 | Rtel1 | 0.955325539 |
| Ctsd | 1.339661798 | Snph | 0.955256444 |
| Tgoln1 | 1.338617781 | Clk1 | 0.952095381 |
| Fam65a | 1.336440467 | Tdh | 0.951361116 |
| Synpo | 1.335052229 | 4930571N24Rik | 0.95129822 |
| Fbrs | 1.332797189 | Frmd4b | 0.951044409 |
| Abcc1 | 1.330281279 | Txnrd2 | 0.950976492 |
| Ranbp2 | 1.330010856 | D10Wsu102e | 0.950757437 |
| Ubr4 | 1.327808199 | Stxbp2 | 0.950655783 |
| Sel11 | 1.325945409 | Mum1 | 0.950334319 |
| Tsg101 | 1.322854408 | Adam12 | 0.949845685 |
| Bag1 | 1.32115605 | Gramd1b | 0.949409727 |
| Cmtm3 | 1.319131098 | Duxbl1 | 0.94925517 |
| Rsu1 | 1.318682847 | Pmaip1 | 0.949000209 |
| Il6st | 1.318295734 | Fance | 0.948894855 |
| Gng2 | 1.315481592 | Prosc | 0.948788392 |
| Tmem184b | 1.31525017 | Lima1 | 0.948520832 |
| Gatm | 1.314698511 | Aen | 0.94849098 |
| Mir1193 | 1.31441673 | Prdm16 | 0.948418105 |
| Pias1 | 1.314346226 | Pcca | 0.948384277 |
| Elk3 | 1.309805838 | 4933411E06Rik | 0.948034366 |
| Rnf130 | 1.301482051 | Slc26a4 | 0.947701486 |
| Rpl13 | 1.300399066 | Dgkd | 0.946864762 |
| Lpp | 1.296602519 | Csnk1e | 0.945641621 |
| Mrpl45 | 1.296477005 | Katnal2 | 0.945160424 |
| Cyb5r3 | 1.296253036 | Vcam1 | 0.944460807 |
| Shprh | 1.289669952 | Tmem200a | 0.944191277 |
| Cpt1c | 1.289477514 | Chek2 | 0.943761214 |
| Ptpn1 | 1.282425471 | Sgk2 | 0.943639303 |
| Fam160a2 | 1.279579655 | Nsun5 | 0.943217275 |
| Cfh | 1.26988982 | Tcf7l1 | 0.941235147 |
| Hnrnpul1 | 1.266397252 | Uckl1 | 0.941137918 |
| Txndc12 | 1.266168771 | Rasgrp2 | 0.941009198 |
| Eri3 | 1.264671312 | Smarcd2 | 0.940938344 |
| Gsk3b | 1.256436011 | Epha7 | 0.939472345 |
| Rnh1 | 1.255232223 | Armc6 | 0.938877158 |
| Man1b1 | 1.250578892 | Ptpn22 | 0.938849214 |
| Fkbp1a | 1.245105748 | Fev | 0.938824194 |
| Mia3 | 1.244304037 | Serpinb6a | 0.938234426 |
| Ruvbl2 | 1.239887848 | Mier1 | 0.938199749 |
| Adam10 | 1.233094367 | 4930567H12Rik | 0.938007376 |
| Mfap5 | 1.232219563 | Sgsm1 | 0.936969063 |
| Trim56 | 1.226423401 | Csn1s1 | 0.936473012 |
| Aaed1 | 1.225534965 | Herpud1 | 0.936370431 |
| Mapre1 | 1.223804151 | Braf | 0.936045549 |
| Laptm5 | 1.223212463 | Npsr1 | 0.935924917 |
| Glipr2 | 1.21815041 | Cox6b1 | 0.935454199 |
| Dock10 | 1.213163554 | Dpm1 | 0.935059488 |
| Tmx2 | 1.211625711 | Rhoa | 0.935000601 |
| Tor1aip2 | 1.210578968 | Chrnb3 | 0.934196093 |
| Etv6 | 1.208482154 | Cobl | 0.934107222 |
| Vmn1r70 | 1.208124474 | Al838599 | 0.933705762 |
| Anxa5 | 1.205547419 | Vars | 0.932030709 |
| Cuta | 1.203534407 | Clspn | 0.931082728 |
| Larp1 | 1.202436659 | Dvl2 | 0.930782278 |
| Tapbp | 1.19794257 | Dync1h1 | 0.930369494 |
| Ddx6 | 1.193876061 | Luc7l2 | 0.930153333 |
| Mbnl2 | 1.186460159 | Rell2 | 0.929377802 |
| Ncoa3 | 1.179909627 | Zfp260 | 0.929183972 |
| Tpm3 | 1.179006377 | Dock3 | 0.929117216 |
| Dok1 | 1.178638573 | Bace1 | 0.928792603 |
| Per1 | 1.177725503 | Sh3gl2 | 0.927925558 |
| Prrc2b | 1.177576351 | Pde1a | 0.927007191 |
| Memo1 | 1.173534294 | Zfyve1 | 0.925770343 |
| Pcbp1 | 1.173138043 | Tacc2 | 0.925762625 |
| Ccs | 1.172429114 | Col16a1 | 0.925278858 |
| F11r | 1.168823701 | Urod | 0.924496139 |
| Mmp23 | 1.167621462 | Kntc1 | 0.924441575 |
| Ssr2 | 1.167292126 | Tprn | 0.92401978 |
| Pmpcb | 1.16244984 | Ipmk | 0.923602568 |
| Mtmr2 | 1.161744403 | Tns4 | 0.923451301 |
| Atxn10 | 1.15851223 | Zfp512b | 0.923242144 |
| Glg1 | 1.156216287 | Rnf10 | 0.922947177 |
| Fndc3a | 1.156036991 | Pus10 | 0.922597079 |

TABLE 5-continued

Top 500 differentially expressed genes between
day 9 iDCs and sDC1 cells ordered by fold change.

| Day 9 up (vs sDC1) | Fold change | Day9 Down (vs sDC1) | Fold Change |
|---|---|---|---|
| Zdhhc13 | 1.153699404 | Slc39a9 | 0.922555226 |
| Mef2c | 1.150436919 | Arhgap22 | 0.921849391 |
| Mir8116 | 1.144949195 | Mknk1 | 0.921395425 |
| Slc6a6 | 1.143929269 | 1810059H22Rik | 0.921384279 |
| Dmpk | 1.143512387 | Ttc29 | 0.921368016 |
| Prr32 | 1.137396445 | Grip1 | 0.921036891 |
| Zcchc6 | 1.136983879 | Nudt16 | 0.920946667 |
| Pfkp | 1.136528919 | Sf3b5 | 0.920695962 |
| 1600014C10Rik | 1.134651281 | Sbno1 | 0.920236532 |
| Pdhb | 1.13293917 | 4933407L21Rik | 0.92002246 |
| Elk4 | 1.130558075 | Bend5 | 0.919256559 |
| Casp3 | 1.129817521 | Pard3 | 0.918710037 |
| Gskip | 1.129732393 | Fam81a | 0.918653108 |
| Dnase1l3 | 1.127323549 | Abcg2 | 0.918618185 |
| Pde4b | 1.124393895 | Flt3 | 0.917955107 |
| B4galt1 | 1.124344501 | Nebl | 0.917936388 |
| Ube2v1 | 1.120565671 | Ddc | 0.917229801 |
| Ifi213 | 1.120530139 | Lrrc8d | 0.916139547 |
| Cops8 | 1.119841447 | Focad | 0.915711203 |
| Sf3a2 | 1.118870719 | Tlk2 | 0.915663628 |

In an embodiment, in addition to the membrane associated co-stimulatory molecules, mature DCs express cytokines with a pro-inflammatory function that are important for the development of T-cell responses. These responses can be initiated by the triggering of at least 11 different Toll-like receptors (TLRs), allowing the specific recognition of distinct conserved microbial or viral structures. It was asked whether iDCs secrete cytokines to the media when challenged with TLR3 (using Polyinosinic-polycytidylic acid (poly-I:C)) or TLR4 (Lipopolysaccharides (LPS)) stimulation (FIG. 31). Upon LPS or polyI:C challenge of iDCs it was observed an increase in the secretion of IL-6 (14- or 10-fold, respectively). An increase in the secretion of tumor necrosis factor TNF (7-fold) and interferon IFN-γ (2-fold) was also observed after LPS stimulation or polyI:C, respectively. Cells transduced with PIB plus TCF4 (PIBT) respond equivalently to stimulation displaying increased secretion of IL-6, TNF and IFN-γ. Importantly, upon stimulation of iDCs it was not observed increase in the secretion of the anti-inflammatory cytokine IL-10. These results suggest that iDCs underwent maturation towards a proinflammatory profile.

In an embodiment, it was evaluated the capacity of iDCs to mount an antigen-specific immune response. First it was evaluated whether iDCs would be able to engulf particles by incubation with 1 μm FITC-labeled latex beads. After incubation tdTomato+ cells contained numerous fluorescent beads in the cytoplasm (FIG. 32), suggesting that iDCs have established the competence for phagocytosis.

Then, we evaluated the ability of iDCs to capture soluble proteins. Remarkably, 13.8% of tdTomato+ cells were able to actively uptake soluble protein after incubation at 37-C for 20 minutes in contrast to only 5.6% when incubated at 4° C. (FIG. 33A), further suggesting that iDCs have established the competence for phagocytosis/endocytosis. In contrast, only 4.6% of tdTomato– cells showed similar ability. Next, we evaluated whether iDCs were able to internalize dead cell material in vitro (FIG. 33B-D). This unique ability has been shown to be associated with cDC1 DC subtypes to cross-present cell-associated antigens on MHC-I (27). After overnight incubation with labeled dead cells, 65.7% of purified tdTomato+ cells have incorporated dead cell material in contrast to only 10.5% of tdTomato-(FIG. 33B). Uptake of dead cells was further analysed by live imaging and it was observed that tdTomato+ cells avidly accumulated dead cell material in the cytoplasm (FIG. 33C). TdTomato+ cells move actively and, upon encountering a dead cell, projected cellular protrusions to incorporate and engulf it (FIG. 33D).

Moreover, we have confirmed that iDCs express genes encoding TLR (Tlr3 and Tlr4) and other mediators of TLR signaling, including MyD88-dependent (TRAM (encoded by Ticam2), and Traf6) and independent (IKKE) pathways (FIG. 34A). Also, we have confirmed that iDCs express key mediators of receptor-mediated endocytosis (Fcgr2b, Tfr2 and Mrc1) and macropinocytosis of dead cells (Axl, Lrp1 and Scarf1), further suggesting that iDCs have acquired the ability for sense and incorporate antigens (FIG. 34B).

In an embodiment, it was evaluated the functional capacity of iDCs to promote antigen-specific proliferation of CD4 T-cells (FIG. 35A). For this it was employed MHC class II-restricted ovalbumin-specific T cells (OT-Ill cells) isolated from lymph nodes and spleen of OT-II Rag2 KO mice (18). In this model T cells respond to the processed antigenic peptide (OVA 323-339) when shown in the context of MHC-I of DCs. Therefore OT-II CD4 T-cells were co-cultured with iDCs when given the Ovalbumin protein (OVA) or pre-processed antigenic peptide (OVA 323-339). Functional DCs are able to capture the protein, process and present the processed antigenic peptide in the context of MHC-II. Induced CD4+ T cell proliferation was measured by CFSE dilution and the activation of the T-cell activation marker CD44 after 7 days of co-culture. Remarkably, 56% of CD4+ T cells diluted CFSE when co-cultured with PIB-generated iDCs in the presence of OVA protein (FIG. 35B). When co-cultured with MEFs transduced with PIB+ TCF4, 38.2% of CD4+ T cells diluted CFSE content, which suggests that inclusion of TCF4 in the reprogramming pool does not increase the stimulatory ability of iDCs. Splenic MHC-II+CD11c+ DCs were used as controls and generated 24.1% of proliferative T-cells. Importantly, addition of LPS stimuli, which is commonly employed to induce DC "maturation", increased the antigen-specific stimulatory ability of MEFs transduced with PIB (1.5-fold) or PIB+TCF4 (2-fold) and also splenic DCs (3-fold) (FIG. 35B and FIG. 36). As expected, T-cells that were not co-cultured did not proliferate with or without LPS stimuli. To further assess the stimulatory ability of iDCs, it was evaluated if they were able to induce expression of T-cell activation markers, such as CD44. When given the pre-processed antigen, OT-Ill CD4 T cells diluted CFSE and upregulated the expression of CD44 when co-cultured with both PIB-generated iDCs and splenic MHC-II+CD11c+ DCs (FIG. 35C). Importantly, when given OVA protein, iDCs display comparable ability to induce CD44 expression in OT-II T cells when compared with splenic DCs (52.2% versus 63.8%). This data supports iDCs' functional ability to incorporate and process OVA protein followed by presentation of processed Ovalbumin peptides in MHC-II complexes at cell surface. Collectively, these results highlight the functional capacity of iDCs and support the feasibility of using directly reprogrammed fibroblast to present antigens and inducing antigen-specific adaptive immune responses.

In an embodiment, it was evaluated if iDCs acquire ability to export antigens to cytosol and express key genes essential for cross-presentation ability. Cross-presentation via the cytosolic pathway involves antigen export from endocytic compartments to the cytosol. Thus, the ability of iDCs to perform antigen export was evaluated using a cytofluorimetry-based assay (FIG. 37A). Remarkably, after 90-minute incubation with b-lactamase, approximately 80% of CCF4-loaded iDCs expressed cleaved CCF4. Thus, iDCs were able to uptake b-lactamase and efficiently export it into the cytoplasm, leading to the generation of cleaved CCF4. It was also confirmed that iDCs express genes involved in cross-presentation pathway, such as Cybb, Atg7, Tap1 and Tap2 (FIG. 37B).

In an embodiment, it was evaluated if iDCs were able to cross-present antigens to CD8+ T-cells. For this, cross-presentation of OVA at MHC-I molecules was evaluated by co-culturing iDCs with B3Z T-cell hybridoma cells that express β-galactosidase under the control of IL-2 promoter (FIG. 38A, left panel). It was observed that iDCs were able to induce antigen-specific T-cell activation in a concentration-dependent manner. Moreover, it was observed an increase of activation of B3Z T-cells after TLR3 stimulation with polyI:C and not with LPS (FIG. 38A, right panel). Accordingly, it has been described that maturation of cDC1s with polyI:C enhances the MHC-I cross-presentation process (28). Moreover, cross-presentation was also evaluated employing MHC class I-restricted ovalbumin-specific T cells (OT-I cells) isolated from lymph nodes and spleen of OT-I Rag2 KO mice (19). In this model T-cells respond to the processed antigenic peptide (OVA 257-264) when shown in the context of MHC-I of DCs. Therefore OT-I CD8 T-cells were co-cultured with iDCs in the presence of the Ovalbumin protein (OVA) and polyI:C stimulation (FIG. 38B). Functional DCs are able to capture the exogenous protein, process and perform cross-presentation of the processed antigenic peptide in the context of MHC-I, inducing activation of CD8+ T cells. Induced CD8+ T cell proliferation was measured by CFSE dilution and the activation of the T-cell activation marker CD44 after 4 days of co-culture. Remarkably, in the presence of OVA protein, 11.3±1.13% of CD8+ T cells diluted CFSE and up-regulated CD44 expression when co-cultured with iDCs, respectively (FIG. 38B). Splenic MHC-II+CD11c+ DCs were used as controls and generated 18.05±0.78% of proliferative and CD44+ T-cells.

In an embodiment, Human Dermal Fibroblasts (HDFs) were transduced with PIB (FIG. 39A). Importantly, it was observed morphologic alterations when PIB TFs were introduced in HDFs. Three days after transduction it was observed that HDFs lost the characteristic bipolar and elongated shapes and acquired a stellate DC-like morphology (FIGS. 39B and 39C). Moreover, it was evaluated the expression of typical DC surface markers. Human foreskin fibroblasts BJs transduced with PIB express HLA-DR molecules and CLEC9A, known specific human DC markers (FIG. 40), suggesting that PIB combination of DC-inducing factors is conserved between the mouse and human and is sufficient to generate human iDCs.

In an embodiment, it was evaluated whether human iDCs would be able to engulf particles by incubation with 1 μm FITC-labeled latex beads. After incubation PIB-transduced HDFs contained numerous fluorescent beads in the cytoplasm (FIG. 41A), suggesting that iDCs have established the competence for phagocytosis. Additionally, the ability to incorporate proteins was evaluated by incubating iDCs with AlexaFluor647-labelled ovalbumine (FIG. 41B). After incubation at 37° C., 1.2% of PIB-transduced HDFs contained labelled protein, suggesting that iDCs are able to actively engulf proteins.

In an embodiment, it was evaluated whether cancer cells would acquire DC phenotypic traits after transduction with PU.1, IRF8 and BATF3. Remarkably, 2.13% of PIB-transduced lung cancer cells (3LL cell line) expressed MHC-I molecules and 2.33% co-expressed MHC-II and CLEC9A at cell surface 8 days after addition of Dox (FIG. 42). Similarly, 26% of PIB-transduced B16 melanoma cancer cells expressed CLEC9A, whilst 1.04% of cells co-expressed it with MHC-II molecules (FIG. 43). These results suggest that it is possible to induce DC phenotype in cancer cells using PIB factors.

In an embodiment, coding regions of PU.1, IRF8 and BATF3 were cloned into polycistronic inducible lentiviral vectors that express the three nucleic acid sequences, each of them separated by 2A peptide sequences (FIG. 44A). The 3 TFs were included in different orders, PU.1, IRF8 and BATF3 (PIB) or IRF8, PU.1 and BATF3 (IPB). Impressively, Clec9a reporter activation was observed in 10.8% and 6.6% of MEFs transduced with the polycistronic vectors (PIB and IPB, respectively). In contrast, only 1.9% of tdTomato+ cells were observed in MEFs transduced with lentiviral vectors encoding individual factors (FIGS. 44B and 44C). As expected, delivery of PIB factors in polycistronic vectors increased reprogramming efficiency up to 6-fold.

In an embodiment, coding regions of each candidate TF were individually cloned into an inducible lentiviral pFUW-TetO vector (6) in which the expression of the TFs is under the control of the tetracycline operator and a minimal CMV promoter. A previously described lentiviral vector containing the reverse tetracycline transactivator M2rtTA under the control of a constitutively active human ubiquitin C promoter (FUW-M2rtTA) was used in combination. Human Embryonic Kidney (HEK) 293T cells were transfected with a mixture of TF-encoding plasmids, packaging constructs and the VSV-G envelope protein. Viral supernatants were harvested after 36, 48 and 60 hours, filtered (0.45 μm, Corning) and used fresh or concentrated 40-fold with Amicon ultra centrifugal filters (Millipore).

In some embodiments, polypeptide variants or family members having the same or a similar activity as the reference polypeptide encoded by the sequences provided in the sequence list can be used in the compositions, methods, and kits described herein. Generally, variants of a particular polypeptide encoding a DC inducing factor for use in the compositions, methods, and kits described herein will have at least about 95%, at least about 96%, at least about 97%, at least about 98%, at least about 99% or more sequence identity to that particular reference polynucleotide or polypeptide as determined by sequence alignment programs and parameters described herein and known to those skilled in the art.

*Homo sapiens* Basic Leucine Zipper ATF-Like Transcription Factor (BATF3), mRNA (SEQ. ID. 1) and a codon optimized, or different codons encoding the same amino acids, are naturally also contemplated to be covered by the reference to the nucleic acid as set forth herein.

*Homo sapiens* Spi-1 proto-oncogene (PU.1), mRNA (SEQ. ID. 7) and a codon optimized, or different codons encoding the same amino acids, are naturally also contemplated to be covered by the reference to the nucleic acid as set forth herein.

*Homo sapiens* Interferon Regulatory Factor 8 (IRF8), mRNA (SEQ. ID. 5) and a codon optimized, or different codons encoding the same amino acids, are naturally also contemplated to be covered by the reference to the nucleic acid as set forth herein.

*Homo sapiens* Transcription factor 4 (TCF4), mRNA (SEQ. ID. 13) and a codon optimized, or different codons encoding the same amino acids, are naturally also contemplated to be covered by the reference to the nucleic acid as set forth herein.

In some embodiments of the compositions, methods, and kids provided herein, the number of DC inducing factors used or selected to generate iDCs from a starting somatic cell, such as a fibroblast cell or hematopoietic lineage cell, a multipotent stem cell, an induced pluripotent stem cell, a cancer or tumor cell is at least three. In some embodiments, the number of DC inducing factors used or selected is at least four, at least five, at least six, at least seven, at least eight, at least nine, at least ten, at least eleven, at least twelve, at least thirteen, at least fourteen, at least fifteen, at least sixteen, at least seventeen, at least eighteen, at least nineteen, at least twenty, at least thirty, at least thirty three, at least thirty five, at least forty, or more.

Also provided herein, in various aspects of the compositions, methods, and kits, are isolated amino acid sequences, and isolated DNA or RNA nucleic acid sequences encoding one or more DC inducing factors for use in making iDCs.

In some embodiments of the compositions, methods, and kits described herein, the nucleic acid sequence or construct encoding the DC inducing factor(s), such as PU.1, IRF8, BATF3 and TCF4, is inserted or operably linked into a suitable expression vector for transfection of cells using standard molecular biology techniques. As used herein, a "vector" refers to a nucleic acid molecule, such as a dsDNA molecule that provides a useful biological or biochemical property to an inserted nucleotide sequence, such as the nucleic acid constructs or replacement cassettes described herein. Examples include plasmids, phages, autonomously replicating sequences (ARS), centromeres, and other sequences that are able to replicate or be replicated in vitro or in a host cell, or to convey a desired nucleic acid segment to a desired location within a host cell. A vector can have one or more restriction endonuclease recognition sites (whether type I, II or IIs) at which the sequences can be cut in a determinable fashion without loss of an essential biological function of the vector, and into which a nucleic acid fragment can be spliced or inserted in order to bring about its replication and cloning. Vectors can also comprise one or more recombination sites that permit exchange of nucleic acid sequences between two nucleic acid molecules. Vectors can further provide primer sites, e.g., for PCR, transcriptional and/or translational initiation and/or regulation sites, recombination signals, replicons, additional selectable markers, etc. A vector can further comprise one or more selectable markers suitable for use in the identification of cells transformed with the vector.

In some embodiments of the compositions, methods, and kits described herein, the expression vector is a viral vector. Some viral-mediated expression methods employ retrovirus, adenovirus, lentivirus, herpes virus, pox virus, and adeno-associated virus (AAV) vectors, and such expression methods have been used in gene delivery and are well known in the art.

In some embodiments of the compositions, methods, and kits described herein, the viral vector is a retrovirus. Retroviruses provide a convenient platform for gene delivery. A selected gene can be inserted into a vector and packaged in retroviral particles using techniques known in the art. The recombinant virus can then be isolated and delivered to target cells of the subject either in vivo or ex vivo. A number of retroviral systems have been described. See, e.g., U.S. Pat. No. 5,219,740; Miller and Rosman (1989) BioTechniques 7:980-90; Miller, A. D. (1990) Human Gene Therapy 1:5-14; Scarpa et al. (1991) Virology 180:849-52; Burns et al. (1993) Proc. Natl. Acad. Sci. USA 90:8033-37; Boris-Lawrie and Temin (1993) Curr. Opin. Genet. Develop. 3:102-09. In some embodiments of the compositions, methods, and kits described herein, the retrovirus is replication deficient. Retroviral vector systems exploit the fact that a minimal vector containing the 5' and 3' LTRs and the packaging signal are sufficient to allow vector packaging, infection and integration into target cells, provided that the viral structural proteins are supplied in trans in the packaging cell line. Fundamental advantages of retroviral vectors for gene transfer include efficient infection and gene expression in most cell types, precise single copy vector integration into target cell chromosomal DNA and ease of manipulation of the retroviral genome.

In some embodiments of the compositions, methods, and kits described herein, the viral vector is an adenovirus-based expression vector. Unlike retroviruses, which integrate into the host genome, adenoviruses persist extrachromosomally, thus minimizing the risks associated with insertional mutagenesis (Haj-Ahmad and Graham (1986) J. Virol. 57:267-74; Bett et al. (1993) J. Virol. 67:5911-21; Mittereder et al. (1994) Human Gene Therapy 5:717-29; Seth et al. (1994) J. Virol. 68:933-40; Barr et al. (1994) Gene Therapy 1:51-58; Berkner, K. L. (1988) BioTechniques 6:616-29; and Rich et al. (1993) Human Gene Therapy 4:461-76). Adenoviral vectors infect a wide variety of cells, have a broad host-range, exhibit high efficiencies of infectivity, direct expression of heterologous genes at high levels, and achieve long-term expression of those genes in vivo. The virus is fully infective as a cell-free virion so injection of producer cell lines is not necessary. With regard to safety, adenovirus is not associated with severe human pathology, and the recombinant vectors derived from the virus can be rendered replication defective by deletions in the early-region 1 ("E1") of the viral genome. Adenovirus can also be produced in large quantities with relative ease. Adenoviral vectors for use in the compositions, methods, and kits described herein can be derived from any of the various adenoviral serotypes, including, without limitation, any of the over 40 serotype strains of adenovirus, such as serotypes 2, 5, 12, 40, and 41. The adenoviral vectors used herein are preferably replication-deficient and contain the DC inducing factor of interest operably linked to a suitable promoter.

In some embodiments of the compositions, methods, and kits described herein, the nucleic acid sequences encoding the DC inducing factor(s), such as, PU.1, IRF8, BATF3 and TCF4 are introduced or delivered using one or more inducible lentiviral vectors. Control of expression of DC inducing factors delivered using one or more inducible lentiviral vectors can be achieved, in some embodiments, by contacting a cell having at least one DC inducing factor in an expression vector under the control of or operably linked to an inducible promoter, with a regulatory agent (e.g., doxycycline) or other inducing agent. When using some types of inducible lentiviral vectors, contacting such a cell with an inducing agent induces expression of the DC inducing factors, while withdrawal of the regulatory agent inhibits expression. When using other types of inducible lentiviral vectors, the presence of the regulatory agent inhibits expression, while removal of the regulatory agent permits expression. As used herein, the term "induction of expression" refers to the expression of a gene, such as a DC inducing factor encoded by an inducible viral vector, in the presence of an inducing agent, for example, or in the presence of one or more agents or factors that cause endogenous expression of the gene in a cell.

In some embodiments of the aspects described herein, a doxycycline (Dox) inducible lentiviral system is used. Unlike retroviruses, lentiviruses are able to transduce quiescent cells making them amenable for transducing a wider variety of hematopoietic cell types. For example, the pFUW-tetO lentivirus system has been shown to transduce primary hematopoietic progenitor cells with high efficiency.

In some embodiments of the methods described herein, the nucleic acid sequences encoding the DC inducing factor(s), such as PU.1 (SEQ. ID. 7, SEQ. ID. 8), IRF8 (SEQ. ID. 5, SEQ. ID. 6), BATF3 (SEQ. ID. 1, SEQ. ID. 2) and/or TCF4 (SEQ. ID. 13, SEQ. ID. 14), are introduced or delivered using a non-integrating vector (e.g., adenovirus). While integrating vectors, such as retroviral vectors, incorporate into the host cell genome and can potentially disrupt normal gene function, non-integrating vectors control expression of a gene product by extra-chromosomal transcription. Since non-integrating vectors do not become part of the host genome, non-integrating vectors tend to express a nucleic acid transiently in a cell population. This is due in part to the fact that the non-integrating vectors are often rendered replication deficient. Thus, non-integrating vectors have several advantages over retroviral vectors including, but not limited to: (1) no disruption of the host genome, and (2) transient expression, and (3) no remaining viral integration products. Some non-limiting examples of non-integrating vectors for use with the methods described herein include adenovirus, baculovirus, alphavirus, picornavirus, and vaccinia virus. In some embodiments of the methods described herein, the non-integrating viral vector is an adenovirus. Other advantages of non-integrating viral vectors include the ability to produce them in high titers, their stability in vivo, and their efficient infection of host cells.

Nucleic acid constructs and vectors for use in generating iDCs in the compositions, methods, and kits described herein can further comprise, in some embodiments, one or more sequences encoding selection markers for positive and negative selection of cells. Such selection marker sequences can typically provide properties of resistance or sensitivity to antibiotics that are not normally found in the cells in the absence of introduction of the nucleic acid construct. A selectable marker can be used in conjunction with a selection agent, such as an antibiotic, to select in culture for cells expressing the inserted nucleic acid construct. Sequences encoding positive selection markers typically provide antibiotic resistance, i.e., when the positive selection marker sequence is present in the genome of a cell, the cell is sensitive to the antibiotic or agent. Sequences encoding negative selection markers typically provide sensitivity to an antibiotic or agent, i.e., when the negative selection marker is present in the genome of a cell, the cell is sensitive to the antibiotic or agent.

Nucleic acid constructs and vectors for use in making iDCs in the compositions, methods, and kits thereof described herein can further comprise, in some embodiments, other nucleic acid elements for the regulation, expression, stabilization of the construct or of other vector genetic elements, for example, promoters, enhancers, TATA-box, ribosome binding sites, IRES, as known to one of ordinary skill in the art.

In some embodiments of the compositions, methods, and kits described herein, the DC inducing factor(s), such as PU.1 (SEQ. ID. 7, SEQ. ID. 8), IRF8 (SEQ. ID. 5, SEQ. ID. 6), BATF3 (SEQ. ID. 1, SEQ. ID. 2) and/or TCF4 (SEQ. ID. 13, SEQ. ID. 14), are provided as synthetic, modified RNAs, or introduced or delivered into a cell as a synthetic, modified RNA, as described in US Patent Publication 2012-0046346-A1, the contents of which are herein incorporated by reference in their entireties. In those embodiments where synthetic, modified RNAs are used to reprogram cells to iDCs according to the methods described herein, the methods can involve repeated contacting of the cells or involve repeated transfections of the synthetic, modified RNAs encoding DC inducing factors, such as for example, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, or more transfections.

In addition to one or more modified nucleosides, the modified mRNAs for use in the compositions, methods, and kits described herein can comprise any additional modifications known to one of skill in the art and as described in US Patent Publications 2012-0046346-A1 and 20120251618A1, and PCT Publication WO 2012/019168. Such other components include, for example, a 5' cap (e.g., the Anti-Reverse Cap Analog (ARCA) cap, which contains a 5'-5'-triphosphate guanine-guanine linkage where one guanine contains an N7 methyl group as well as a 3'-O-methyl group; caps created using recombinant Vaccinia Virus Capping Enzyme and recombinant 2'-O-methyltransferase enzyme, which can create a canonical 5'-5'-triphosphate linkage between the 5'-most nucleotide of an mRNA and a guanine nucleotide where the guanine contains an N7 methylation and the ultimate 5'-nucleotide contains a 2'-O-methyl generating the Cap1 structure); a poly(A) tail (e.g., a poly-A tail greater than 30 nucleotides in length, greater than 35 nucleotides in length, at least 40 nucleotides, at least 45 nucleotides, at least 55 nucleotides, at least 60 nucleotide, at least 70 nucleotides, at least 80 nucleotides, at least 90 nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900 nucleotides, at least 1000 nucleotides, or more); a Kozak sequence; a 3' untranslated region (3' UTR); a 5' untranslated region (5' UTR); one or more intronic nucleotide sequences capable of being excised from the nucleic acid, or any combination thereof.

The modified mRNAs for use in the compositions, methods, and kits described herein can further comprise an internal ribosome entry site (IRES). An IRES can act as the sole ribosome binding site, or can serve as one of multiple ribosome binding sites of an mRNA. An mRNA containing more than one functional ribosome binding site can encode several peptides or polypeptides, such as the DC inducing factors described herein, that are translated independently by the ribosomes ("multicistronic mRNA"). When nucleic acids are provided with an IRES, further optionally provided is a second translatable region. Examples of IRES sequences that can be used according to the invention include without limitation, those from picornaviruses (e.g. FMDV), pest viruses (CFFV), polio viruses (PV), encephalomyocarditis viruses (ECMV), foot-and-mouth disease viruses (FMDV), hepatitis C viruses (HCV), classical swine fever viruses (CSFV), murine leukemia virus (MLV), simian immune deficiency viruses (SW) or cricket paralysis viruses (CrPV).

In some embodiments of the compositions, methods, and kits described herein, the synthetic, modified RNA molecule comprises at least one modified nucleoside. In some embodiments of the compositions, methods, and kits described herein, the synthetic, modified RNA molecule comprises at least two modified nucleosides.

In some embodiments of the compositions, methods, and kits described herein, the modified nucleosides are selected from the group consisting of 5-methylcytosine (5mC), N6-methyladenosine (m6A), 3,2'-O-dimethyluridine (m4U), 2-thiouridine (s2U), 2' fluorouridine, pseudouridine, 2'-O-methyluridine (Um), 2'deoxy uridine (2' dU), 4-thiouridine (s4U), 5-methyluridine (m5U), 2'-O-methyladenosine (m6A), N6,2'-O-dimethyladenosine (m6Am), N6,N6,2'-O-trimethyladenosine (m62Am), 2'-O-methylcytidine (Cm), 7-methylguanosine (m7G), 2'-O-methylguanosine (Gm), N2,7-dimethylguanosine (m2,7G), N2,N2,7-trimethylguanosine (m2,2,7G), and inosine (I). In some embodiments, the modified nucleosides are 5-methylcytosine (5mC), pseudouracil, or a combination thereof.

Modified mRNAs need not be uniformly modified along the entire length of the molecule. Different nucleotide modifications and/or backbone structures can exist at various positions in the nucleic acid. One of ordinary skill in the art will appreciate that the nucleotide analogs or other modification(s) can be located at any position(s) of a nucleic acid such that the function of the nucleic acid is not substantially decreased. A modification can also be a 5' or 3' terminal modification. The nucleic acids can contain at a minimum one and at maximum 100% modified nucleotides, or any intervening percentage, such as at least 50% modified nucleotides, at least 80% modified nucleotides, or at least 90% modified nucleotides.

In some embodiments, it is preferred, but not absolutely necessary, that each occurrence of a given nucleoside in a molecule is modified (e.g., each cytosine is a modified cytosine e.g., 5-methylcytosine, each uracil is a modified uracil, e.g., pseudouracil, etc.). For example, the modified mRNAs can comprise a modified pyrimidine such as uracil or cytosine. In some embodiments, at least 25%, at least 50%, at least 80%, at least 90% or 100% of the uracil in the nucleic acid are replaced with a modified uracil. It is also contemplated that different occurrences of the same nucleoside can be modified in a different way in a given synthetic, modified RNA molecule. The modified uracil can be replaced by a compound having a single unique structure, or can be replaced by a plurality of compounds having different structures (e.g., 2, 3, 4 or more unique structures). In some embodiments, at least 25%, at least 50%, at least 80%, at least 90% or 100% of the cytosine in the nucleic acid may be replaced with a modified cytosine. The modified cytosine can be replaced by a compound having a single unique structure, or can be replaced by a plurality of compounds having different structures (e.g., 2, 3, 4 or more unique structures) (e.g., some cytosines modified as 5mC, others modified as 2'-O-methylcytosine or other cytosine analog). Such multi-modified synthetic RNA molecules can be produced by using a ribonucleoside blend or mixture comprising all the desired modified nucleosides, such that when the RNA molecules are being synthesized, only the desired modified nucleosides are incorporated into the resulting RNA molecule encoding the DC inducing factor.

In certain embodiments it is desirable to intracellularly degrade a modified nucleic acid introduced into the cell, for example if precise timing of protein production is desired. Thus, in some embodiments of the compositions, methods, and kits described herein, provided herein are modified nucleic acids comprising a degradation domain, which is capable of being acted on in a directed manner within a cell.

While it is understood that iDCs can be generated by delivery of DC inducing factors in the form of nucleic acid (DNA or RNA) or amino acid sequences, in some embodiments of the compositions, methods, and kits described herein, iDC induction can be induced using other methods, such as, for example, by treatment of cells with an agent, such as a small molecule or cocktail of small molecules, that induce expression one or more of the DC inducing factors.

Detection of expression of DC inducing factors introduced into cells or induced in a cell population using the compositions, methods, and kits described herein, can be achieved by any of several techniques known to those of skill in the art including, for example, Western blot analysis, immunocytochemistry, and fluorescence-mediated detection.

In order to distinguish whether a given combination of DC inducing factors has generated iDCs, one or more DC activities or parameters can be measured, such as, in some embodiments, differential expression of surface antigens. The generation of induced DCs using the compositions, methods, and kits described herein preferably causes the appearance of the cell surface phenotype characteristic of endogenous DCs, such as CLEC9A, MHC-I, MHC-II, CD40, CD80, CD86, CD103, for example.

DCs are most reliably distinguished from other immune cells by their functional behavior. Functional aspects of DC phenotypes, or dendritic cell activities, such as the ability of a dendritic cell to induce antigen specific T cell responses, can be easily determined by one of skill in the art using routine methods known in the art, and as described herein, for example, in the Drawings, i.e., FIGS. 1-44. In some embodiments of the aspects described herein, functional assays to identify reprogramming factors can be used. For example, in some embodiments, antigen presentation and antigen cross-presentation assays can be used to confirm antigen-specific induction of T cell responses (antigen presentation potential) of iDCs generated using the compositions, methods, and kits thereof. Cytokine secretion can be used to confirm immune-modulatory properties of iDCs generated using the compositions, methods, and kits described herein. Ability to engulf particles, proteins and dead cells of iDCs generated using the compositions, methods, and kits described herein can be evaluated by culturing transduced cells in the presence of labelled beads, ovalbumine or dead cells, followed by flow cytometry analysis, respectively.

As used herein, "cellular parameter," "DC parameter," or "antigen presentation activity" refer to measureable components or qualities of endogenous or natural DCs, particularly components that can be accurately measured. A cellular parameter can be any measurable parameter related to a phenotype, function, or behavior of a cell. Such cellular parameters include, changes in characteristics and markers of a DC or DC population, including but not limited to changes in viability, cell growth, expression of one or more or a combination of markers, such as cell surface determinants, such as receptors, proteins, including conformational or posttranslational modification thereof, lipids, carbohydrates, organic or inorganic molecules, nucleic acids, e.g. mRNA, DNA, global gene expression patterns, etc. Such cellular parameters can be measured using any of a variety of assays known to one of skill in the art. For example, viability and cell growth can be measured by assays such as Trypan blue exclusion, CFSE dilution, and 3H-thymidine incorporation. Expression of protein or polypeptide markers can be measured, for example, using flow cytometric assays, Western blot techniques, or microscopy methods. Gene expression profiles can be assayed, for example, using RNA-sequencing methodologies and quantitative or semi-quantitative real-time PCR assays. A cellular parameter can also refer to a functional parameter or functional activity. While most cellular parameters will provide a quantitative readout, in some instances a semi-quantitative or qualitative result can be acceptable. Readouts can include a single determined value, or can include mean, median value or the variance, etc. Characteristically a range of parameter readout values can be obtained for each parameter from a multiplicity of the same assays. Variability is expected and a range of values for each of the set of test parameters will be obtained using standard statistical methods with a common statistical method used to provide single values.

In some embodiments of the compositions, methods, and kits described herein, additional factors and agents can be used to enhance iDC reprogramming. For example, factors and agents that modify epigenetic pathways can be used to facilitate reprogramming into iDCs.

Essentially any primary somatic cell type can be used for producing iDCs or reprogramming somatic cells to iDCs according to the presently described compositions, methods, and kits. Such primary somatic cell types also include other stem cell types, including pluripotent stem cells, such as induced pluripotent stem cells (iPS cells); other multipotent stem cells; oligopotent stem cells; and (5) unipotent stem cells. Some non-limiting examples of primary somatic cells useful in the various aspects and embodiments of the methods described herein include, but are not limited to, fibroblast, epithelial, endothelial, neuronal, adipose, cardiac, skeletal muscle, hematopoietic or immune cells, hepatic, splenic, lung, circulating blood cells, gastrointestinal, renal, bone marrow, and pancreatic cells, as well as stem cells from which those cells are derived. The cell can be a primary cell isolated from any somatic tissue including, but not limited to, spleen, bone marrow, blood, brain, liver, lung, gut, stomach, intestine, fat, muscle, uterus, skin, spleen, endocrine organ, bone, etc. The term "somatic cell" further encompasses, in some embodiments, primary cells grown in culture, provided that the somatic cells are not immortalized. Where the cell is maintained under in vitro conditions, conventional tissue culture conditions and methods can be used, and are known to those of skill in the art. Isolation and culture methods for various primary somatic cells are well within the abilities of one skilled in the art.

In some embodiments of these aspects and all such aspects described herein, the somatic cell is a fibroblast cell.

In some embodiments of these aspects and all such aspects described herein, the somatic cell can be a hematopoietic lineage cell.

In some embodiments of these aspects and all such aspects described herein, the somatic cell can be a cancer cell or a tumor cell.

In some embodiments of the compositions, methods, and kits described herein, a somatic cell to be reprogrammed or made into an iDC cell is a cell of hematopoietic origin. As used herein, the terms "hematopoietic-derived cell," "hematopoietic-derived differentiated cell," "hematopoietic lineage cell," and "cell of hematopoietic origin" refer to cells derived or differentiated from a multipotent hematopoietic stem cell (HSC). Accordingly, hematopoietic lineage cells for use with the compositions, methods, and kits described herein include multipotent, oligopotent, and lineage-restricted hematopoietic progenitor cells, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, and lymphocytes (e.g., T-lymphocytes, which carry T-cell receptors (TCRs), B-lymphocytes or B cells, which express immunoglobulin and produce antibodies, NK cells, NKT cells, and innate lymphocytes). As used herein, the term "hematopoietic progenitor cells" refer to multipotent, oligopotent, and lineage-restricted hematopoietic cells capable of differentiating into two or more cell types of the hematopoietic system, including, but not limited to, granulocytes, monocytes, erythrocytes, megakaryocytes, and lymphocytes B-cells and T-cells. Hematopoietic progenitor cells encompass multi-potent progenitor cells (MPPs), common myeloid progenitor cells (CMPs), common lymphoid progenitor cells (CLPs), granulocyte-monocyte progenitor cells (GMPs), and pre-megakaryocyte-erythrocyte progenitor cell. Lineage-restricted hematopoietic progenitor cells include megakaryocyte-erythrocyte progenitor cells (MEP), ProB cells, PreB cells, PreProB cells, ProT cells, double-negative T cells, pro-NK cells, pre-granulocyte/macrophage cells, granulocyte/macrophage progenitor (GMP) cells, and pro-mast cells (ProMCs). A differentiation chart of the hematopoietic lineage is provided at FIG. 1.

Cells of hematopoietic origin for use in the compositions, methods, and kits described herein can be obtained from any source known to comprise these cells, such as fetal tissues, umbilical cord blood, bone marrow, peripheral blood, mobilized peripheral blood, spleen, liver, thymus, lymph, etc. Cells obtained from these sources can be expanded ex vivo using any method acceptable to those skilled in the art prior to use in with the compositions, methods, and kits for making iDCs described herein. For example, cells can be sorted, fractionated, treated to remove specific cell types, or otherwise manipulated to obtain a population of cells for use in the methods described herein using any procedure acceptable to those skilled in the art. Mononuclear lymphocytes may be collected, for example, by repeated lymphocytophereses using a continuous flow cell separator as described in U.S. Pat. No. 4,690,915, or isolated using an affinity purification step of CLP method, such as flow-cytometry using a cytometer, magnetic separation, using antibody or protein coated beads, affinity chromatography, or solid-support affinity separation where cells are retained on a substrate according to their expression or lack of expression of a specific protein or type of protein, or batch purification using one or more antibodies against one or more surface antigens specifically expressed by the cell type of interest. Cells of hematopoietic origin can also be obtained from peripheral blood. Prior to harvest of the cells from peripheral blood, the subject can be treated with a cytokine, such as e.g., granulocyte-colony stimulating factor, to promote cell migration from the bone marrow to the blood compartment and/or promote activation and/or proliferation of the population of interest. Any method suitable for identifying surface proteins, for example, can be employed to isolate cells of hematopoietic origin from a heterogeneous population. In some embodiments, a clonal population of cells of hematopoietic origin, such as lymphocytes, is obtained. In some embodiments, the cells of hematopoietic origin are not a clonal population.

Further, in regard to the various aspects and embodiments of the compositions, methods, and kits described herein, a somatic cell can be obtained from any mammalian species, with non-limiting examples including a murine, bovine, simian, porcine, equine, ovine, or human cell. In some embodiments, the somatic cell is a human cell. In some embodiments, the cell is from a non-human organism, such as a non-human mammal.

In general, the methods for making iDCs described herein involve culturing or expanding somatic cells, such as cells of hematopoietic origin, in any culture medium that is available and well-known to one of ordinary skill in the art. Such media include, but are not limited to, Dulbecco's Modified Eagle's Medium® (DMEM), DMEM F12 Medium®, Eagle's Minimum Essential Medium®, F-12K Medium®, Iscove's Modified Dulbecco's Medium®, RPMI-1640 Medium®, and serum-free medium for culture and expansion of DCs. Many media are also available as low-glucose formulations, with or without sodium. The medium used with the methods described herein can, in some embodiments, be supplemented with one or more immunostimulatory cytokine. Commonly used growth factors include, but are not limited to, G-CSF, GM-CSF, TNF-α, IL-4, the Flt-3 ligand and the kit ligand. In addition, in preferred embodiments, the immunostimulatory cytokine is selected from the group consisting of the interleukins (e.g., IL-1α, IL-1β, IL-2, IL-3, IL-4, IL-6, IL-8, IL-9, IL-10, IL-12, IL-18, IL-19, IL-20), the interferons (e.g., IFN-α, IFN-β, IFN-γ), tumor necrosis factor (TNF), transforming growth factor-β (TGF-β), granulocyte colony stimulating factor (G-CSF), macrophage colony stimulating factor (M-CSF), granulocyte-macrophage colony stimulating factor (GM-CSF), the Flt-3 ligand and the kit ligand.

Cells in culture can be maintained either in suspension or attached to a solid support, such as extracellular matrix components or plating on feeder cells, for example. Cells being used in the methods described herein can require additional factors that encourage their attachment to a solid support, in some embodiments, such as type I and type II collagen, chondroitin sulfate, fibronectin, "superfibronectin" and fibronectin-like polymers, gelatin, poly-D and poly-L-lysine, thrombospondin and vitronectin. In some embodiments, the cells are suitable for growth in suspension cultures. Suspension-competent host cells are generally monodisperse or grow in loose aggregates without substantial aggregation. Suspension-competent host cells include cells that are suitable for suspension culture without adaptation or manipulation (e.g., cells of hematopoietic origin, such as lymphoid cells) and cells that have been made suspension-competent by modification or adaptation of attachment-dependent cells (e.g., epithelial cells, fibroblasts).

In some embodiments of these aspects and all such aspects described herein, the isolated induced dendritic cells (iDCs) further comprise a pharmaceutically acceptable carrier for administration to a subject in need.

Also provided herein, in some aspects, are methods of treating a subject in need of treatment to induce antigen-specific immune responses to eliminate cancer cells or infectious agents using the DC inducing compositions and methods of preparing iDCs described herein, or using the isolated induced dendritic cells (iDCs) and cell clones thereof produced using any of the combinations of DC inducing factors, DC inducing compositions, or methods of preparing iDCs described herein. In such methods of treatment, somatic cells, such as fibroblast cells or hematopoietic lineage cells, can first be isolated from the subject, and the isolated cells transduced or transfected, as described herein with a DC inducing composition comprising expression vectors or synthetic mRNAs, respectively. The isolated induced dendritic cells (iDCs) produced using any of the combinations of DC inducing factors, DC inducing compositions, or methods of preparing iDCs described herein, can then be administered to the subject, such as via systemic injection of the iDCs to the subject.

Also provided herein, in some aspects, are methods of treating a subject in need of treatment to induce antigen-specific immune responses to eliminate cancer cells or infectious agents using the DC inducing compositions and any of the combinations of DC inducing factors described herein. In such methods of treatment, cancer cells are transduced, as described herein with a DC inducing composition comprising expression vectors. Cancer cells can be first isolated from the subject, transduced with a DC inducing composition comprising expression vectors and then administered to the subject, such as via systemic injection. Alternatively, cancers cells can be transduced in situ or in vivo with DC inducing composition comprising viral expression vectors. The modified cancer cell acquires antigen presentation ability, presenting their tumor antigens to T cells and eliciting cytotoxic responses against themselves.

The reprogrammed iDCs generated using the compositions, methods, and kits described herein can, in some embodiments of the methods of treatment described herein, be used directly or administered to subjects in need of immunotherapies. Accordingly, various embodiments of the methods described herein involve administration of an effective amount of a iDC or a population of iDCs, generated using any of the compositions, methods, and kits described herein, to an individual or subject in need of a cellular therapy. The cell or population of cells being administered can be an autologous population, or be derived from one or more heterologous sources. Further, such iDCs can be administered in a manner that permits them to migrate to lymph node and activate effector T cells.

A variety of means for administering cells to subjects are known to those of skill in the art. Such methods can include systemic injection, for example, i.v. injection, or implantation of cells into a target site in a subject. Cells may be inserted into a delivery device which facilitates introduction by injection or implantation into the subject. Such delivery devices can include tubes, e.g., catheters, for injecting cells and fluids into the body of a recipient subject. In one preferred embodiment, the tubes additionally have a needle, e.g., through which the cells can be introduced into the subject at a desired location. The cells can be prepared for delivery in a variety of different forms. For example, the cells can be suspended in a solution or gel or embedded in a support matrix when contained in such a delivery device. Cells can be mixed with a pharmaceutically acceptable carrier or diluent in which the cells remain viable.

Accordingly, the cells produced by the methods described herein can be used to prepare cells to treat or alleviate several cancers and tumors including, but not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like.

In addition to the above, the methods of the invention can be used to prevent or eliminate infection by pathogens known to predispose to certain cancers. Pathogens of particular interest for use in the cancer vaccines provided herein include the hepatitis B virus (hepatocellular carcinoma), hepatitis C virus (heptomas), Epstein Barr virus (EBV) (Burkitt lymphoma, nasopharynx cancer, PTLD in immunosuppressed individuals), HTLVL (adult T cell leukemia), oncogenic human papilloma viruses types 16, 18, 33, 45 (adult cervical cancer), and the bacterium *Helicobacter pylori* (B cell gastric lymphoma). Other medically relevant microorganisms that may serve as antigens in mammals and more particularly humans are described extensively in the literature, e.g., C. G. A Thomas, Medical Microbiology, Bailliere Tindall, (1983).

In addition to the above, the methods of the invention can be used for viral infections. Exemplary viral pathogens include, but are not limited to, infectious virus that infect mammals, and more particularly humans. Examples of infectious virus include, but are not limited to: Retroviridae (e.g., human immunodeficiency viruses, such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses such as the SARS coronavirus); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Bir-naviridae; Hepadnaviridae (Hepatitis B virus); Parvovirida (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; P. oxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class I=internally transmitted; class 2=parenterally transmitted (i.e. Hepatitis C); Norwalk and related viruses, and astro viruses).

In addition to the above, the methods of the invention can be used to target gram negative and gram positive bacteria in vertebrate animals. Such gram positive bacteria include, but are not limited to *Pasteurella* sp., Staphylococci sp., and *Streptococcus* sp. Gram negative bacteria include, but are not limited to, *Escherichia coli*, *Pseudomonas* sp., and *Salmonella* sp. Specific examples of infectious bacteria include but are not limited to: *Helicobacter pyloris, Borella burgdorferi, Legionella pneumophilia, Mycobacteria* sp. (e.g. *M. tuberculosis, M. avium, M. intracellulare, M. kansaii, M. gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae*, pathogenic *Campylobacter* sp., *Enterococcus* sp., *Haemophilus infuenzae, Bacillus antracis, Corynebacterium diphtheriae, Corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Rickettsia*, and *Actinomyces israelii*.

In addition to the above, the methods of the invention can be used to target pathogens that include, but are not limited to, infectious fungi and parasites that infect mammals, and more particularly humans. Examples of infectious fungi include, but are not limited to: *Cryptococcus neoformans, Histoplasma capsulatum, Coccidioides immitis, Blastomyces dermatitidis, Chlamydia trachomatis*, and *Candida albicans*.

In addition to the above, the methods of the invention can be used to target parasites such as intracellular parasites and obligate intracellular parasites. Examples of parasites include but are not limited to *Plasmodium-falciparum, Plasmodium ovale, Plasmodium malariae, Plasmdodium vivax, Plasmodium knowlesi, Babesia microti, Babesia divergens, Trypanosoma cruzi, Toxoplasma gondii, Trichinella spiralis, Leishmania major, Leishmania donovani, Leishmania braziliensis, Leishmania tropica, Trypanosoma gambiense, Trypanosoma rhodesiense, Wuchereria bancrofti, Brugia malayi, Brugia timori, Ascaris lumbricoides, Onchocerca volvulus* and *Schistosoma mansoni*.

If modified induced dendritic cells can be used to induce a tolerogenic response including the suppression of a future or existing immune response, to one or more target antigens. Thus, induce DCs are useful for treating or preventing an undesirable immune response including, for example, transplant rejection, graft versus host disease, allergies, parasitic diseases, inflammatory diseases and autoimmune diseases. Examples of transplant rejection, which can be treated or prevented in accordance with the present invention, include rejections associated with transplantation of bone marrow and of organs such as heart, liver, pancreas, kidney, lung, eye, skin etc. Examples of allergies include seasonal respiratory allergies; allergy to aeroallergens such as hayfever; allergy treatable by reducing serum IgE and eosinophilia; asthma; eczema; animal allergies, food allergies; latex allergies; dermatitis; or allergies treatable by allergic desensitisation. Autoimmune diseases that can be treated or prevented by the present invention include, for example, psoriasis, systemic lupus erythematosus, myasthenia gravis, stiff-man syndrome, thyroiditis, Sydenham chorea, rheumatoid arthritis, diabetes and multiple sclerosis. Examples of inflammatory disease include Crohn's disease, chronic inflammatory eye diseases, chronic inflammatory lung diseases and chronic inflammatory liver diseases, autoimmune haemolytic anaemia, idiopathic leucopoenia, ulcerative colitis, dermatomyositis, scleroderma, mixed connective tissue disease, irritable bowel syndrome, systemic lupus erythromatosus (SLE), multiple sclerosis, myasthenia gravis, Guillain-Barre syndrome (antiphospholipid syndrome), primary myxoedema, thyrotoxicosis, pernicious anaemia, autoimmune atrophic gastris, Addison's disease, insulin-dependent diabetes mellitus (IDDM), Goodpasture's syndrome, Behcet's syndrome, Sjogren's syndrome, rheumatoid arthritis, sympathetic ophthalmia, Hashimoto's disease/hypothyroiditis, celiac disease/dermatitis herpetiformis, and demyelinating disease primary biliary cirrhosis, mixed connective tissue disease, chronic active hepatitis, Graves' disease/hyperthyroiditis, scleroderma, chronic idiopathic thrombocytopenic purpura, diabetic neuropathy and septic shock.

Pharmaceutically acceptable carriers and diluents include saline, aqueous buffer solutions, solvents and/or dispersion media. The use of such carriers and diluents is well known in the art. The solution is preferably sterile and fluid. Preferably, prior to the introduction of cells, the solution is stable under the conditions of manufacture and storage and preserved against the contaminating action of microorganisms such as bacteria and fungi through the use of, for example, parabens, chlorobutanol, phenol, ascorbic acid, thimerosal, and the like.

It is preferred that the mode of cell administration is relatively non-invasive, for example by intravenous injection, pulmonary delivery through inhalation, topical, or intranasal administration. However, the route of cell administration will depend on the tissue to be treated and may include implantation. Methods for cell delivery are known to those of skill in the art and can be extrapolated by one skilled in the art of medicine for use with the methods and compositions described herein.

Also provided herein, in some aspects, are kits for making induced dendritic cells (iDCs), the kits comprising any of the DC inducing compositions comprising one or more expression vector components described herein.

Also provided herein, in some aspects, are kits comprising one or more of the DC inducing factors described herein as components for the methods of making the induced dendritic cells described herein.

Accordingly, in some aspects, provided herein, are kits for preparing induced dendritic cells comprising the following components: (a) one or more expression vectors encoding at least one, two, three, four, five, six, seven, eight, or more DC inducing factors selected from: BATF3 (SEQ. ID. 1, SEQ. ID. 2), SPIB (SEQ. ID. 3, SEQ. ID. 4), IRF8 (SEQ. ID. 5, SEQ. ID. 6), PU.1 (SEQ. ID. 7, SEQ. ID. 8), STAT3 (SEQ. ID. 11, SEQ. ID. 12), TCF4 (SEQ. ID. 13, SEQ. ID. 14), IKZF1 (SEQ. ID. 15, SEQ. ID. 16), ID2 (SEQ. ID. 17, SEQ. ID. 18), BCL11A (SEQ. ID. 19, SEQ. ID. 20), RELB (SEQ. ID. 21, SEQ. ID. 22), ZBTB46 (SEQ. ID. 23, SEQ. ID. 24), RUNX3 (SEQ. ID. 25, SEQ: ID. 26), GFI1 (SEQ. ID. 27, SEQ. ID. 28), IRF2 (SEQ. ID. 29, SEQ. ID. 30), NFIL3 (SEQ. ID. 31, SEQ. ID. 32), BCL6 (SEQ. ID. 33, SEQ. ID. 34), L-MYC (SEQ. ID. 35, SEQ. ID. 36), NR4A3 (SEQ. ID. 37, SEQ. ID. 38), and (b) packaging and instructions therefor.

The kits described herein, in some embodiments, can further provide the synthetic mRNAs or the one or more expression vectors encoding DC inducing factors in an admixture or as separate aliquots.

In some embodiments, the kits can further comprise an agent to enhance efficiency of reprogramming. In some embodiments, the kits can further comprise one or more antibodies or primer reagents to detect a cell-type specific marker to identify cells induced to the dendritic cell state.

In some embodiments, the kits can further comprise a buffer. In some such embodiments, the buffer is RNase-free TE buffer at pH 7.0. In some embodiments, the kit further comprises a container with cell culture medium.

All kits described herein can further comprise a buffer, a cell culture medium, a transduction or transfection medium and/or a media supplement. In preferred embodiments, the buffers, cell culture mediums, transfection mediums, and/or media supplements are DNAse and RNase-free. In some embodiments, the synthetic, modified RNAs provided in the kits can be in a non-solution form of specific quantity or mass, e.g., 20 ag, such as a lyophilized powder form, such that the end-user adds a suitable amount of buffer or medium to bring the components to a desired concentration, e.g., 100 ng/l.

All kits described herein can further comprise devices to facilitate single-administration or repeated or frequent infusions of the cells generated using the kits components described herein, such as a non-implantable delivery device, e.g., needle, syringe, pen device, or an implantatable delivery device, e.g., a pump, a semi-permanent stent (e.g., intravenous, intraperitoneal, intracisternal or intracapsular), or a reservoir. In some such embodiments, the delivery device can include a mechanism to dispense a unit dose of a pharmaceutical composition comprising the iDCs. In some embodiments, the device releases the composition continuously, e.g., by diffusion. In some embodiments, the device can include a sensor that monitors a parameter within a subject. For example, the device can include pump, e.g., and, optionally, associated electronics.

In an embodiment, induced dendritic cells are made by the hand of man by, e.g., modifying the gene expression of at least one of the factors disclosed herein of a somatic cell, a pluripotent cell, a progenitor cell or a stem cell, or by exposing any one of these cell types to at least one protein or RNA that produces at least one protein as disclosed herein. The cells can further be made by exposing them to small molecules that turn on at least one of the factors disclosed herein. In some aspects at least two, three, four, five, six, seven, or eight factors are used to make the induced dendritic cells.

In an embodiment, the induced dendritic cells in some aspects of all the embodiments of disclosure, while similar in functional characteristics, differ significantly in their gene expression from the naturally occurring endogenous dendritic cells.

In an embodiment, the induced dendritic cells as described herein differ from naturally occurring dendritic cells by both their posttranslational modification signatures and their gene expression signatures.

In an embodiment, the induced dendritic cells as described herein differ from naturally occurring dendritic cells by their ability to growth in vitro as adherent cultures and to survive in culture for more than one month.

In an embodiment, induced dendritic cell is also defined as comprising a gene expression signature that differs from naturally occurring dendritic cells. One can experimentally show the difference by comparing the gene expression pattern of a naturally occurring dendritic cell to that of the induced dendritic cells. Therefore, in some aspects of all the embodiments of the invention, the induced dendritic cells comprise an expression signature that is about 1-5%, 5-10%, 5-15%, or 5-20% different from the expression signature of about 1-5%, 2-5%, 3-5%, up to 50%, up to 40%, up to 30%, up to 25%, up to 20%, up to 15%, or up to 10% of specific genes. For example, expression levels of DC inducing factor(s), such as PU.1, IRF8, BATF3 and TCF4, in iDCs are higher than in naturally occurring DCs as the DC inducing factors are being overexpressed.

In an embodiment, mouse Embryonic Fibroblasts (MEFs) were isolated and purified in the following way: Clec9aCre/Cre animals (10) were crossed with Rosa26-stopflox-tdTomato reporter mice (The Jackson Laboratory) to generate double homozygous $Clec9a^{Cre/Cre}$ $Rosa^{tdTomato/tdTomato}$ (C9A-tdTomato) mice. C57BL/6 mice, Rag2 constitutive knock-out (KO)/OT-II random transgenic (Rag2KO/OT-II) mice and Rag2KO/OT-I random transgenic mice were acquired from Charles River and Taconic, respectively (17-

19). All animals were housed under controlled temperature (23±2° C.), subject to a fixed 12-h light/dark cycle, with free access to food and water.

In an embodiment, primary cultures of MEFs were isolated from E13.5 embryos of C9A-tdTomato or C57BL/6 mice (6, 10). Head, fetal liver and all internal organs were removed and the remaining tissue was mechanically dissociated. Dissected tissue was enzymatic digested using 0.12% trypsin/0.1 mM Ethylenediaminetetraacetic acid (EDTA) solution (3 mL per embryo), and incubation at 37° C. for 15 min. Additional 3 mL of same solution per embryo were added, followed by another 15 min incubation period. A single cell suspension was obtained and plated in 0.1% gelatin-coated 10-cm tissue culture dishes in growth media. Cells were grown for 2-3 days until confluence, dissociated with Tryple Express and frozen in Fetal Bovine Serum (FBS) 10% dimethyl sulfoxide (DMSO). Before plating for lentiviral transduction, MEFs were sorted to remove residual CD45+ and tdTomato+ cells that could represent cells with hematopoietic potential. MEFs used for screening and in the following experiments were tdTomato− CD45− with a purity of 99.8% and expanded up to 4 passages.

In an embodiment, HEK293T cells, MEFs and Human Dermal Fibroblasts (HDFs, ScienCell) were maintained in growth medium [Dulbecco's modified eagle medium (DMEM) supplemented with 10% (v/v) FBS, 2 mM L-Glutamine and antibiotics (10 µg/ml Penicillin and Streptomycin)], OP-9 and OP-9-DL1 cell lines were cultured in Minimum Essential Medium (MEM) Alpha containing 20% FBS, 1 mM L-Glutamine and penicillin/streptomycin (10 µg/ml). OP-9 and OP-9-DL1 were routinely passaged at 80% confluency. All cells were maintained at 37° C. and 5% (v/v) CO2. All tissue culture reagents were from Thermo Fisher Scientific unless stated otherwise.

In an embodiment, viral transduction and reprogramming experiments were performed in the following way: C9A-tdTomato MEFs were seeded at a density of 40,000 cells per well on 0.1% gelatin coated 6-well plates. Cells were incubated overnight with a ratio of 1:1 FUW-TetO-TFs and FUW-M2rtTA lentiviral particles in growth media supplemented with 8 µg/mL polybrene. When testing combinations of TFs, equal MOIs of each individual viral particles were applied. Cells were transduced twice in consecutive days and after overnight incubation, media was replaced with fresh growth media. After the second transduction, growth media was supplemented with Doxycycline (1 µg/mL)—day 0. Media was changed every 2-3 days for the duration of the cultures. Emerging tdTomato+ cells were analyzed 1-15 days post-transduction. When stated, variations of culture conditions were applied, namely RPMI-1640, Lipopolysaccharide (LPS, 100 ng/ml, Sigma), 2-Mercaptoethanol (1×104 µM; 2-ME), L-glutamine (2 µmol/ml), GM-CSF (10 ng/ml, STEMCELL Technologies), IL-4 (20 ng/ml, STEMCELL Technologies) and Flt31 (100 ng/ml, STEMCELL Technologies).

In an embodiment, fluorescent microscopy and immunofluorescence was evaluated in the following way: C9A-driven tdTomato in MEFs and transduced HDFs were visualized directly on 6-well plates under an inverted microscope (Zeiss AxioVert 200M) and images processed with AxioVision and Adobe Photoshop software. DAPI (4',6-diamidino-2-phenylindole, 1 µg/mL, Sigma) and Phalloidin (50 µg/ml, Sigma) were used to stain nuclei and F-actin, respectively. For time-lapse microscopy fluorescent pictures were acquired after adding Dox every 1 hour for 6 days and 4 hours using an INCELL Analyzer 2200 (GE Healthcare). Movies were generated with ImageJ software (NIH).

In an embodiment, flow cytometry analysis was performed in the following way: Transduced C9A-tdTomato MEFs or transduced human fibroblasts were dissociated with TrypLE Express, resuspended in 200 µL PBS 5% FBS and kept at 4° C. prior analysis in BD Accuri C6 Flow Cytometer (BD Biosciences). Sample acquisition was performed with the configuration 3-blue-1-red (533/30 filter in FL1; 585/40 in FL2, 670 LP in FL3 and 675/25 in FL4). tdTomato fluorescence was analyzed in the FL2 channel. For the analysis of CD45 or MHC-II cell surface marker expression, dissociated cells were incubated with APC-Cy7 rat anti-mouse CD45 antibody or Alexa Fluor 647 rat anti-mouse I-A/I-E diluted in PBS 5% FBS at 4° C. for 30 minutes in the presence of rat serum (1/100, GeneTex) to block unspecific binding. Cells were washed with PBS 5% FBS, resuspended in PBS 5% FBS and analyzed in a BD Accuri C6 Flow cytometer. CD45 APC-Cy7 and I-A/I-E Alexa Fluor 647 fluorescence were analyzed in FL4 channel. For the combined analysis of MHCII, CD80 and CD86 cell surface expression, dissociated cells were stained with Alexa Fluor 647 rat anti-mouse I-A/I-E, BV650 rat anti-mouse CD80 and PE-CY7 rat anti-mouse CD86 and analyzed in BD FACSAria III (BD Biosciences). For the analysis of transduced HDFs, dissociated cells were stained with APC mouse anti-human CLEC9A and FITC mouse anti-human HLA-DR. To assess CD4+ and CD8+ T cell proliferation and activation after 7 days of co-culture with APCs, carboxyfluorescein succinimidyl ester (CFSE)-labeled T cells were incubated with PE rat anti-mouse CD44 and analyzed in BD Accuri C6. Flow cytometry data were analyzed using FlowJo software (FLOWJO, LLC, version 7.6).

In an embodiment, fluorescence activated cell sorting (FACS) was performed in the following way: To purify C9A-tdTomato MEFs, cells were incubated at 4° C. for 30 minutes with APC-Cy7 anti-CD45 antibody diluted in PBS 5% FBS. Subsequently, MEFs were washed with PBS 5% FBS, resuspended in PBS 5% FBS and tdTomato− CD45− MEFs were purified in BD FACSAria III. When described tdTomato+ cells were purified using BD FACSAria III and cultured in the absence or presence of doxycycline. For the isolation of splenic DCs, splenic cells were incubated with Alexa Fluor 647 rat anti-mouse I-A/I-E, FITC rat anti-mouse CD11c and APC-Cy7 rat anti-mouse CD8a. CD11c+ MHCII+CD8a+ splenic DCs were purified in BD FACSAria III (BD Biosciences). FACS data was processed in FlowJo software.

In an embodiment, GPSforGenes software was used to calculate the specificity of Pu.1, Irf8 and Batf3 combination for the DC lineage. Gene expression data was downloaded from BioGPS database (GeneAtlas MOE430), transformed to log-space and normalized to bring the expression values to 0-1 range for each gene across different samples. The resulting data was then searched for samples with the highest averaged expression for Pu.1+Irf8+Batf3.

In an embodiment, Single cell mRNAseq analysis was performed in the following way: Single-end reads were mapped to the mm10 mouse genome (Ensembl annotation, release 89) using Salmon v0.8.1 with k=21. The resulting TPM were imported into R using tximport library and converted into mRNA counts using the Census algorithm implemented in monocle library. Scatter library was used to discard cells and genes that didn't pass quality control threshold. The following QC criteria were used: 1) library size per cell; 2) number of genes detected in each single cell;

3) percentage of counts in mitochondrial genes. From the 192 cells initially profiled, 163 individual cells passed quality control filters and were used for analysis. Custom R scripts were used to perform t-distributed stochastic neighbor embedding (tSNE) (Monocle and scatter package), principal component analysis (PCA) (Monocle and scatter package), hierarchical clustering (SC3 package), variance analysis and to construct heat maps, box plots, scatter plots, violin plots, dendrograms, bar graphs, and histograms. Generally, ggplot2, gplots, graphics and pheatmap packages were used to generate data graphs.

In an embodiment, differential expression analysis was performed using Monocle package, and selecting genes with BH-corrected p-value less than 0.05. The resulting genes were next filtered by variance (genes with variance >=1 across all conditions were selected). Finally, the resulting 6,525 genes were grouped into 4 distinct clusters based on hierarchical clustering.

In an embodiment, endogenous expression of genes was determined using STAR v2.5.3a with default settings. A window was defined based on −10 kb, start of the gene and end of the gene, +10 kb, which correspond to 5' and 3' untranslated regions (UTRs) and used to calculate the number of reads in the UTRs using multicov from bedtools v2.27.0.

In an embodiment, DC lineage of iDCs was determined by using cDC1 and cDC2 gene signatures from Schlitzer (11). The majority of genes were highly expressed in MEF, and across all our condition. These genes were discarded. Moreover, as sDC cells were purified for the cDC1 markers CD11c, MHC-II and CD8a, genes that were expressed in sDC but at the same time were found in cDC2 signature list were discarded. cDC1/cDC2 gene lists were then used to performed hierarchical clustering. Next, only clusters in which median expression of genes in MEF cells were significantly lower compared to day3, day7 and day9 were selected. Besides that, for cDC2 gene list, in addition to procedure described above, gene clusters with median expression of genes in sDC cells significantly higher compared to day3, day7 and day9 were also discarded. Next, the median of gene expression across each selected gene was calculated from each particular condition. Finally, the median of gene expression across all pre-sorted cDC1 and cDC2 gene signatures defined by Schlitzer and colleagues, was calculated.

In an embodiment, the Monocle package, an algorithm that uses independent component analysis with minimal spanning tree to connect cells along a pseudotemporally ordered path, was used to order cells on a pseudo-time course during MEF to iDC cell reprogramming. Monocle analysis was performed based on cDC1 and cDC2 genes from Schlitzer, 2015 (11) as genes, which define a cell's progress, as this was an alternative approach to prove that day9 are cDC1-like cells. The resulting trajectories were visualized using Monocle functions. Since single-cell trajectories included branches, branched expression analysis modeling (BEAM) was used, a special statistical test implemented in Monocle package in order to find differentially expressed genes between the branches. As an alternative approach to Monocle branching algorithm, TSCAN was used, which combines clustering with pseudotime analysis, by building a minimum-spanning tree to connect the clusters. TSCAN, in contrast to Monocle, can use all genes to order the cells.

In an embodiment, gene ontology (biological process, cellular component and KEGG pathway) was performed using Enrichr (http://amp.pharm.mssm.edu/Enrichr/) and Database for Annotation, Visualization and Integrated Discovery (DAVID) clustered functional analysis (david.ncifcrf.gov/).

In an embodiment, microRNA target interaction analysis was performed using miRTarBase 2017, Enrichr website (http://amp.pharm.mssm.edu/Enrichr/).

In an embodiment, Mouse phenotype analysis was performed using Network2canvas (http://www.maayanlab.net/2C/#.rWmRvOjLc8yk).

In an embodiment, gene set enrichment analysis (GSEA) between all possible conditions and states were performed against C7: immunologic signatures from Molecular Signatures Database (MSigDB) and NetPath.

In an embodiment, TF network analysis was computed by pairwise correlation matrix using Pearson correlation. TFs were selected based on DBD: Transcription factor prediction database (http://www.transcriptionfactor.org/) in mouse. As the objective was to investigate the switch between condition from mef to day9, 3 lists were created corresponding to switch from mef to day3; day3 to day7; day7 to day9 and included only those TF which have log FC=0.5 for pair of conditions. Next, out of TFs defined based on log FC for 3 pair of conditions TFs were selected with a Pearson correlation of greater than 0.35 with at least five other TFs. Taking into consideration the fact that those results could be obtained by chance, permutations were used in order to determine the probability of TFs passing this threshold by chance. 100 permutations were performed and all of them resulted in 0 TFs that pass this threshold. The function graph.adjacency( ) of igraph R package was used, which took Pearson pairwise correlation matrix for the selected TFs for 3 pair of conditions.

In an embodiment, Methylcellulose clonogenic assays were performed in the fallowing way: PIB-transduced MEFs at day 3, 5, 7, 10 and 25 after addition of Dox were assayed in 1% methylcellulose media (Methocult M3434, Stem Cell Technologies). Sorted sDC1 (MHC-II+CD11c+CD8a+) as well as unsorted splenocytes and bone marrow cells were used as control. Hematopoietic colonies were scored and counted after 7-10 days of culture in 5% $CO_2$ at 37° C.

In an embodiment, bead incorporation assay was evaluated in the following way: transduced C9A-tdTomato MEF or transduced HDF cultures were incubated with 2.5% yellow-green fluorescent-coupled solid latex beads (carboxylate-modified polystyrene, Sigma) at 1:1000 ratio in growth medium. Sixteen hours later, cells were washed twice in PBS 5% FBS and analyzed under an inverted microscope. DAPI (1 g/mL, Sigma) was used for nuclear staining.

In an embodiment, incorporation of labelled ovalbumin was evaluated in the following way: transduced MEFs and human fibroblast cultures were incubated with Alexa647-labelled ovalbumin (Life Technologies) for 20 minutes at 37° C. or 4° C. After washing with PBS 5% FBS, cells were analysed in BD Accuri C6.

In an embodiment, incorporation of dead cells was evaluated in the following way: HEK293T cells were exposed to ultra-violet (UV) irradiation to induce cell death and labelled with CellVue® Claret Far Red Fluorescent Cell Linker Kit (Sigma), according to manufacturer's instructions. Transduced MEFs were incubated with Far red-labelled dead cells overnight, and analysed in BD Accuri C6.

In an embodiment, inflammatory cytokine assay was performed in the following way: Levels of the cytokines interleukin-6 (IL-6), interleukin-10 (IL-10), interleukin-12p70 (IL-12p70), interferon-γ (IFN-γ) and tumor necrosis factor (TNF) were assessed in supernatants of iDCs cultures 10 days after Dox supplementation. At day 9, 100 ng/mL LPS or 25 µg/mL of Polyinosinic-polycytidylic acid (PolyI:C) (Invivogen) were added for overnight stimulation. 50 µL of culture supernatants from a 6-well plate well were collected and analyzed by CBA Mouse Inflammation Kit (BD Biosciences), according to manufacturer's instructions. Acquisition was performed with a BD Accuri C6 and data were analyzed using FCAP array software, version 3.0 (BD Biosciences). The limit of detection in CBA was: IL-6, 20.91 pg/ml; IL-10, 10.55 pg/ml; IFN-γ, 18.2 pg/ml; TNF, 18.13 pg/ml; IL-12p70, 20.05 pg/ml.

In an embodiment, splenic DC isolation was evaluated in the following way: Freshly isolated spleens were homogenized using the frosted ends of 2 sterile slides. Cells were harvested in PBS supplemented with 2% FBS and filtered through a 70 µm cell strainers (BD Biosciences). Red blood cells were lysed with BD Pharm Lyse (BD Biosciences) for 8 min at room temperature. MHC-II+CD11c+ DCs were purified by FACS (BD FACSAria III, BD Biosciences) and immediately used for antigen presenting assays.

In an embodiment, CD4+ T cell isolation and antigen presenting assays was evaluated in the following way: CD4+ T cells from spleen of Rag2KO/OT-II mice were enriched using Dynabeads Untouched Mouse CD4 Cells Kit (BD Biosciences), according to manufacturer's instructions. Enriched CD4+ T cells were labeled with CFSE 5 µM at room temperature for 10 min, washed, and counted before cultured with APCs. iDCs cultures at day 8 after the addition of Dox or splenic CD11c+ MHC-II+ DCs cells were incubated with OVA protein (10 µg/mL) or OVA323-339 peptide (10 µg/mL) in the presence or absence of 100 ng/mL of LPS and co-cultured with untouched CFSE-labeled OT-II CD4+ T cells. iDC cultures (20000 cells) or 20000 splenic CD11c+ MHC-II+ DCs were incubated with 20000 CFSE-labeled CD4+ T cells in 96-well round-bottom tissue culture plates. T cell proliferation (dilution of CFSE staining) and activation (CD44 expression) were assessed by flow cytometry after 7 days of co-culture.

In an embodiment, CD8+ T cell isolation and antigen cross-presentation was evaluated in the following way: CD8+ T cells from spleen of Rag2KO/OT-I mice were enriched using Dynabeads Untouched Mouse CD8 Cells Kit (BD Biosciences), according to manufacturer's instructions. Enriched CD8+ T cells were labelled with CFSE 5 µM at room temperature for 10 min, washed, and counted before cultured with APCs. iDCs cultures at day 8 after the addition of Dox or splenic CD11c+ MHC-II+ DCs cells were incubated with OVA protein (10 µg/mL) in the presence of 25 µg/mL of polyI:C and co-cultured with untouched CFSE-labelled OT-I CD8+ T cells. iDC cultures (20000 cells) or 20000 splenic CD11c+ MHC-II+ DCs were incubated with 20000 CFSE-labelled CD8+ T cells in 96-well round-bottom tissue culture plates. T cell proliferation (dilution of CFSE staining) and activation (CD44 expression) were assessed by flow cytometry after 4 days of co-culture.

In an embodiment, hybridoma cross-presentation assays were performed in the following way: PIB-transduced Clec9a-tdTomato MEFs at day 16 after addition of Dox were dissociated with TrypLE Express, resuspended in growth media and incubated for 4 hours with different concentrations of OVA protein. After being extensively washed, PIB-transduced MEFs (100,000 cells) were co-cultured with 100,000 B3Z cells in 96-well round-bottom tissue culture plates in the presence or absence of 100 ng/mL LPS or 25 µg/mL PIC. After 18 h, cells were lysed in a buffer containing 0.125% Nonidet P-40 (substitute), 9 mM MgCl2, and a colorimetric CPRG β-galactosidase substrate. β-galactosidase activity was measured on MicroPlate Reader as optical density at 590 nm.

In an embodiment, the efficiency of antigen export to the cytosol by Clec9a-tdTomato+ cells were analyzed by cytofluorimetry-based assay. Briefly, PIB-transduced MEFs at day 16 after addition of Dox were dissociated with TrypLE Express, resuspended in loading buffer and loaded with 1 µM CCF4-AM for 30 min at room temperature. Cells were then washed and incubated with 2 mg/mL β-lactamase at 37° C. for 30, 60 and 90 minutes. To stop the reaction, cells were transferred to ice cold PBS. Immediately before flow cytometry analysis in a BD FACSAriaIII, the cells were stained with Fixable Viability Dye eFluor 780 (eBioscience). The percentage of live Clec9a-tdTomato+ cells with a high blue-to-green (V450/V500) fluorescence ratio was used as a measure of the efficiency of antigen export into the cytosol.

In an embodiment, comparisons among groups were performed by one-way ANOVA followed by Bonferroni's multiple comparison test with GraphPad Prism 5 software. P-values are shown when relevant (*$p<0.05$; $p<0.01$, *$p<0.001$, ****$p<0.0001$).

TABLE 6

Primary Antibodies Used in the analysis

| Antibody/Antigen | Specie | Clone | Conjugate | Source |
|---|---|---|---|---|
| CD45 | Mouse | 30-F11 | PE | BD Pharmingen |
| CD4 | Mouse | GK1.5 | PE-CY7 | eBioscience |
| CD8α | Mouse | 53-6.7 | APC-Cy7 | Biolegend |
| CD44 | Mouse | IM7 | PE | BD Pharmingen |
| CD103 | Mouse | 2E7 | APC-Cy7 | Biolegend |
| MHC Class II (I-A/I-E) | Mouse | M5/114.15.2 | Alexa Fluor 647 | BD Pharmingen |
| MHC Class I (H-2Kb) | Mouse | AF6-88.5.5.3 | FITC | eBioscience |
| CD80 (B7 1) | Mouse | 16-101A | BV650 | BD Horizon |
| CD86 (B7 2) | Mouse | GL1 | PE-CY7 | eBioscience |
| CD40 | Mouse | HM40-3 | eFluor450 | eBioscience |
| B220 | Mouse | RA3-6B2 | FITC | eBioscience |
| CD11b | Mouse | M1/70 | AlexaFluor700 | eBioscience |
| CD11c | Mouse | N418 | FITC | Biolegend |
| HLA-DR | Human | L243 | FITC | Biolegend |
| CLEC9A | Human | 8F9 | APC | Biolegend |

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

Where singular forms of elements or features are used in the specification of the claims, the plural form is also included, and vice versa, if not specifically excluded. For example, the term "a cell" or "the cell" also includes the plural forms "cells" or "the cells," and vice versa. In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

The above described embodiments are combinable.

The following claims further set out particular embodiments of the present disclosure.

All references recited in this document are incorporated herein in their entirety by reference, as if each and every reference had been incorporated by reference individually.

REFERENCES

1. Takahashi K, Tanabe K, Ohnuki M, Narita M, Ichisaka T, Tomoda K, et al. Induction of pluripotent stem cells from adult human fibroblasts by defined factors. Cell. 2007; 131(5):861-72. Epub 2007/11/24. doi: 10.1016/j.cell.2007.11.019. PubMed PMID: 18035408.
2. Takahashi K, Yamanaka S. Induction of pluripotent stem cells from mouse embryonic and adult fibroblast cultures by defined factors. Cell. 2006; 126(4):663-76. Epub 2006/08/15. doi: 10.1016/j.cell.2006.07.024. PubMed PMID: 16904174.
3. Pereira C F, Lemischka I R, Moore K. Reprogramming cell fates: insights from combinatorial approaches. Ann N Y Acad Sci. 2012; 1266:7-17. Epub 2012/08/21. doi: 10.1111/j.1749-6632.2012.06508.x. PubMed PMID: 22901251.
4. Xu J, Du Y, Deng H. Direct lineage reprogramming: strategies, mechanisms, and applications. Cell Stem Cell. 2015; 16(2):119-34. Epub 2015/02/07. doi: 10.1016/j.stem.2015.01.013. PubMed PMID: 25658369.
5. Xie H, Ye M, Feng R, Graf T. Stepwise reprogramming of B cells into macrophages. Cell. 2004; 117(5):663-76. Epub 2004/05/28. PubMed PMID: 15163413.
6. Pereira C F, Chang B, Qiu J, Niu X, Papatsenko D, Hendry C E, et al. Induction of a hemogenic program in mouse fibroblasts. Cell Stem Cell. 2013; 13(2):205-18. Epub 2013/06/19. doi: 10.1016/j.stem.2013.05.024. PubMed PMID: 23770078; PubMed Central PMCID: PMCPMC3735774.
7. Pereira C F, Chang B, Gomes A, Bernitz J, Papatsenko D, Niu X, et al. Hematopoietic Reprogramming In Vitro Informs In Vivo Identification of Hemogenic Precursors to Definitive Hematopoietic Stem Cells. Dev Cell. 2016; 36(5):525-39. Epub 2016/03/10. doi: 10.1016/j.devcel.2016.02.011. PubMed PMID: 26954547; PubMed Central PMCID: PMCPMC4785845.
8. Datta J, Terhune J H, Lowenfeld L, Cintolo J A, Xu S, Roses R E, et al. Optimizing dendritic cell-based approaches for cancer immunotherapy. Yale J Biol Med. 2014; 87(4):491-518. Epub 2014/12/17. PubMed PMID: 25506283; PubMed Central PMCID: PMCPMC4257036.
9. Subklewe M, Geiger C, Lichtenegger F S, Javorovic M, Kvalheim G, Schendel D J, et al. New generation dendritic cell vaccine for immunotherapy of acute myeloid leukemia. Cancer Immunol Immunother. 2014; 63(10): 1093-103. Epub 2014/09/05. doi: 10.1007/s00262-014-1600-5. PubMed PMID: 25186611.
10. Schraml B U, van Blijswijk J, Zelenay S, Whitney P G, Filby A, Acton S E, et al. Genetic tracing via DNGR-1 expression history defines dendritic cells as a hematopoietic lineage. Cell. 2013; 154(4):843-58. Epub 2013/08/21. doi: 10.1016/j.cell.2013.07.014. PubMed PMID: 23953115.
11. Schlitzer A, Sivakamasundari V, Chen J, Sumatoh H R, Schreuder J, Lum J, et al. Identification of cDC1- and cDC2-committed DC progenitors reveals early lineage priming at the common DC progenitor stage in the bone marrow. Nat Immunol. 2015; 16(7):718-28. Epub 2015/06/10. doi: 10.1038/ni.3200. PubMed PMID: 26054720.
12. Merad M, Sathe P, Helft J, Miller J, Mortha A. The dendritic cell lineage: ontogeny and function of dendritic cells and their subsets in the steady state and the inflamed setting. Annu Rev Immunol. 2013; 31:563-604. Epub 2013/03/23. doi: 10.1146/annurev-immunol-020711-074950. PubMed PMID: 23516985; PubMed Central PMCID: PMCPMC3853342.
13. Senju S, Hirata S, Matsuyoshi H, Masuda M, Uemura Y, Araki K, et al. Generation and genetic modification of dendritic cells derived from mouse embryonic stem cells. Blood. 2003; 101(9):3501-8. Epub 2002/10/31. doi: 10.1182/blood-2002-07-2254. PubMed PMID: 12406878.
14. Kitamura N, Yokoyama H, Yashiro T, Nakano N, Nishiyama M, Kanada S, et al. Role of PU.1 in MHC class II expression through transcriptional regulation of class II transactivator pl in dendritic cells. J Allergy Clin Immunol. 2012; 129(3):814-24 e6. Epub 2011/11/25. doi: 10.1016/j.jaci.2011.10.019. PubMed PMID: 22112519.
15. Smith M A, Wright G, Wu J, Tailor P, Ozato K, Chen X, et al. Positive regulatory domain I (PRDM1) and IRF8/

PU.1 counter-regulate MHC class II transactivator (CIITA) expression during dendritic cell maturation. J Biol Chem. 2011; 286(10):7893-904. Epub 2011/01/11. doi: 10.1074/jbc.M110.165431. PubMed PMID: 21216962; PubMed Central PMCID: PMCPMC3048676.

16. Reith W, LeibundGut-Landmann S, Waldburger J M. Regulation of MHC class II gene expression by the class II transactivator. Nat Rev Immunol. 2005; 5(10):793-806. Epub 2005/10/04. doi: 10.1038/nri1708. PubMed PMID: 16200082.

17. van der Stoep N, Quinten E, Marcondes Rezende M, van den Elsen P J. E47, IRF-4, and PU.1 synergize to induce B-cell-specific activation of the class II transactivator promoter III (CIITA-PIII). Blood. 2004; 104(9):2849-57. Epub 2004/07/10. doi: 10.1182/blood-2004-03-0790. PubMed PMID: 15242870.

18. Shinkai Y, Rathbun G, Lam K P, Oltz E M, Stewart V, Mendelsohn M, et al. RAG-2-deficient mice lack mature lymphocytes owing to inability to initiate V(D)J rearrangement. Cell. 1992; 68(5):855-67. Epub 1992/03/06. PubMed PMID: 1547487.

19. Hogquist K A, Jameson S C, Heath W R, Howard J L, Bevan M J, Carbone F R. T cell receptor antagonist peptides induce positive selection. Cell. 1994; 76(1):17-27. Epub 1994/01/14. PubMed PMID: 8287475.

20. J. Helft et al., GM-CSF Mouse Bone Marrow Cultures Comprise a Heterogeneous Population of CD11c(+) MHCII(+) Macrophages and Dendritic Cells. Immunity 42, 1197 (Jun. 16, 2015).

21. G. E. Grajales-Reyes et al., Batf3 maintains autoactivation of Irf8 for commitment of a CD8alpha(+) conventional DC clonogenic progenitor. Nat Immunol 16, 708 (July, 2015).

22. B. T. Edelson et al., Peripheral CD103$^+$ dendritic cells form a unified subset developmentally related to CD8a$^+$ conventional dendritic cells. The Journal of Experimental Medicine 207, 823 (2010).

23. K. S. Kobayashi, P. J. van den Elsen, NLRC5: a key regulator of MHC class I-dependent immune responses. Nat Rev Immunol 12, 813 (12/print, 2012).

24. M. Bretou et al., Lysosome signaling controls the migration of dendritic cells. Science Immunology, (2017).

25. S. M. Han et al., TCF4-Targeting miR-124 is Differentially Expressed amongst Dendritic Cell Subsets. Immune Network 16, 61 (2016).

26. I. Dunand-Sauthier et al., Silencing of c-Fos expression by microRNA-155 is critical for dendritic cell maturation and function. Blood 117, 4490 (2011).

27. O. Schulz, C. Reis e Sousa, Cross-presentation of cell-associated antigens by CD8alpha+ dendritic cells is attributable to their ability to internalize dead cells. Immunology 107, 183 (2002).

28. L. Delamarre, H. Holcombe, I. Mellman, Presentation of Exogenous Antigens on Major Histocompatibility Complex (MHC) Class I and MHC Class II Molecules Is Differentially Regulated during Dendritic Cell Maturation. The Journal of Experimental Medicine 198, 111 (2003).

The invention claimed is:

1. A method for reprogramming or inducing a cell into a dendritic cell or antigen presenting cell, comprising the following steps:
transducing a cell with one or more vectors encoding at least three transcription factors, wherein said at least three transcription factors individually comprise a sequence at least 90% identical to a sequence selected from the group consisting of BATF3 as set forth in SEQ. ID. 67 or SEQ. ID. 68, IRF8 as set forth in SEQ. ID. 69 or SEQ. ID. 70, PU.1 as set forth in SEQ. ID. 71 or SEQ. ID. 72.

2. The method according to claim 1, wherein the cell is selected from the group consisting of: a pluripotent stem cell, a multipotent stem cell, a human or murine differentiated cell, a tumour cell, a cancer cell, a human or mouse fibroblast, a mammalian hematopoietic lineage cell, including monocytes or hematopoietic stem and progenitor cells and mesenchymal stem cells, and mixtures thereof.

3. The method according to claim 1, wherein the antigen of the antigen presenting cell is selected from the group consisting of: a cancer antigen, a self-antigen, an allergen, an antigen from a pathogenic and/or infectious organism.

4. The method according to claim 1, wherein the vector encodes a combination of three isolated transcription factors in the following sequential order from 5' to 3':
PU.1, IRF8, BATF3; or
IRF8, PU.1, BATF3.

5. The method according to claim 1, wherein said vector or a second vector comprises a nucleic acid sequence selected from the group consisting of: a nucleic acid sequence encoding IL12; nucleic acid sequence encoding GM-CSF; nucleic acid sequence encoding IL-4; nucleic acid sequence encoding IFN-α; nucleic acid sequence encoding IFN-β; nucleic acid sequence encoding IFN-γ; nucleic acid sequence encoding TNF; nucleic acid sequence encoding siRNA targeting IL-10 RNA, and mixtures thereof.

6. The method according to claim 1, wherein the transducing step further comprises at least one vector comprising polynucleotide sequences encoding one or more immunostimulatory cytokines.

* * * * *